US011299484B2

(12) United States Patent
Martin et al.

(10) Patent No.: US 11,299,484 B2
(45) Date of Patent: Apr. 12, 2022

(54) INHIBITING FATTY ACID SYNTHASE (FASN)

(71) Applicant: FORMA Therapeutics, Inc., Watertown, MA (US)

(72) Inventors: Matthew W. Martin, Arlington, MA (US); Mary-Margaret Zablocki, Revere, MA (US); Scot Mente, Watertown, MA (US); Christopher Dinsmore, Newton, MA (US); Zhongguo Wang, Lexington, MA (US); Xiaozhang Zheng, Lexington, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/021,759

(22) Filed: Sep. 15, 2020

(65) Prior Publication Data

US 2021/0024508 A1 Jan. 28, 2021

Related U.S. Application Data

(63) Continuation of application No. 16/598,481, filed on Oct. 10, 2019, now Pat. No. 10,875,848.

(60) Provisional application No. 62/744,071, filed on Oct. 10, 2018.

(30) Foreign Application Priority Data

Oct. 9, 2019 (TW) ................. 108136774

(51) Int. Cl.
*C07D 405/14* (2006.01)
*C07D 221/20* (2006.01)
*C07D 409/14* (2006.01)
*C07D 413/14* (2006.01)
*C07D 405/06* (2006.01)

(52) U.S. Cl.
CPC ......... *C07D 405/14* (2013.01); *C07D 221/20* (2013.01); *C07D 405/06* (2013.01); *C07D 409/14* (2013.01); *C07D 413/14* (2013.01)

(58) Field of Classification Search
CPC ............... C07D 405/14; C07D 221/20; C07D 409/14; C07D 413/14; C07D 405/06
See application file for complete search history.

(56) References Cited

U.S. PATENT DOCUMENTS

| 4,888,268 A | 12/1989 | Itoh et al. |
| 9,718,807 B2 | 8/2017 | Scott et al. |
| 2004/0067972 A1 | 4/2004 | Boyle et al. |
| 2004/0180906 A1 | 8/2004 | Flynn et al. |
| 2010/0113465 A1 | 5/2010 | Long et al. |
| 2010/0130477 A1 | 5/2010 | Bernstein et al. |
| 2014/0194415 A1 | 7/2014 | Ghergurovich et al. |
| 2015/0166890 A1 | 6/2015 | Archetti et al. |
| 2016/0002188 A1 | 1/2016 | Bair et al. |
| 2016/0046863 A1 | 2/2016 | Archetti et al. |
| 2017/0002267 A1 | 1/2017 | Lee et al. |
| 2017/0186964 A1 | 6/2017 | Cho et al. |
| 2017/0216262 A1 | 8/2017 | Bair et al. |
| 2017/0244043 A1 | 8/2017 | Kim et al. |
| 2018/0130964 A1 | 5/2018 | Kim et al. |

FOREIGN PATENT DOCUMENTS

| CA | 2260767 A1 | 1/1998 |
| CA | 2492225 A1 | 1/2004 |
| CA | 2609957 A1 | 1/2007 |
| CA | 2634250 A1 | 7/2007 |
| CA | 2634847 A1 | 7/2007 |
| CA | 2637717 A1 | 8/2007 |
| CA | 2668094 A1 | 5/2008 |
| CA | 2696053 A1 | 9/2008 |
| CA | 2759098 A1 | 10/2010 |
| CA | 2764526 A1 | 12/2010 |
| CA | 2778990 A1 | 5/2011 |
| CN | 101384553 A | 3/2009 |
| CN | 101400682 A | 4/2009 |
| CN | 101426777 A | 5/2009 |
| CN | 101668520 A | 3/2010 |
| CN | 102372698 A | 3/2012 |
| CN | 102627610 A | 8/2012 |
| CN | 103420890 A | 12/2013 |
| CN | 104371744 A | 2/2015 |
| CN | 104876912 A | 9/2015 |
| CN | 104876912 B | 7/2017 |
| EP | 1073891 A2 | 2/2001 |

(Continued)

OTHER PUBLICATIONS

Wu, W.-L.,"Design and synthesis of orally efficacious benzimidazoles as melanin-concentrating hormone receptor 1 antagonists." Bioorganic & medicinal chemistry letters 16.14 (2006): 3674-3678.*
Gansler et al., "Increased Expression of Fatty Acid Synthase (OA-519) in Ovarian Neoplasms Predicts Shorter Survival," Human Pathology, vol. 28, No. 6 (Jun. 1997), pp. 686-692.
Aicher et al., "Secondary Amides of ®-3,3,3-Trifluoro-2-hydroxy-2-methylpropionic Acid as Inhibitors of Pyruvate Dehydrogenase Kinase," J. Med. Chem. 43, (2000), pp. 236-249.
Clayden et al., "Summary: the three major approaches to the synthesis of aromatic heterocycles," Organic Chemistry, (2001), pp. 1214-1215.

(Continued)

*Primary Examiner* — John M Mauro
(74) *Attorney, Agent, or Firm* — Barnes & Thornburg LLP

(57) ABSTRACT

The present disclosure is directed to inhibitors of FASN. The compounds can be useful in the treatment of disease or disorders associated with the inhibition of FASN. For instance, the disclosure is concerned with compounds and compositions for inhibition of FASN, methods of treating, preventing, or ameliorating diseases or disorders associated with the inhibition of FASN, and methods of synthesis of these compounds.

22 Claims, 269 Drawing Sheets

(56) References Cited

FOREIGN PATENT DOCUMENTS

| | | |
|---|---|---|
| EP | 1164374 A1 | 12/2001 |
| EP | 1255567 | 11/2002 |
| EP | 1290446 | 3/2003 |
| EP | 1397360 | 3/2004 |
| EP | 1401469 | 3/2004 |
| EP | 0922099 A1 | 9/2004 |
| EP | 0922099 B1 | 9/2004 |
| EP | 1465631 | 10/2004 |
| EP | 1534074 | 6/2005 |
| EP | 1545572 | 6/2005 |
| EP | 1073891 B1 | 8/2006 |
| EP | 1751131 | 2/2007 |
| EP | 1764616 A2 | 3/2007 |
| EP | 1807102 | 7/2007 |
| EP | 1831209 | 9/2007 |
| EP | 1884513 A1 | 2/2008 |
| EP | 1896453 | 3/2008 |
| EP | 1482924 B1 | 5/2008 |
| EP | 1926721 | 6/2008 |
| EP | 1814879 B1 | 9/2008 |
| EP | 1966143 | 9/2008 |
| EP | 1976848 | 10/2008 |
| EP | 1976854 | 10/2008 |
| EP | 1981341 | 10/2008 |
| EP | 1751131 B1 | 11/2008 |
| EP | 2019091 A1 | 1/2009 |
| EP | 2074103 | 7/2009 |
| EP | 2076494 | 7/2009 |
| EP | 1831209 B1 | 8/2009 |
| EP | 2091951 | 8/2009 |
| EP | 1896453 B1 | 12/2009 |
| EP | 2139877 | 1/2010 |
| EP | 1465631 B1 | 2/2010 |
| EP | 2170802 | 4/2010 |
| EP | 2076494 B1 | 7/2010 |
| EP | 2233486 A1 | 9/2010 |
| EP | 2274288 | 1/2011 |
| EP | 2274288 A2 | 1/2011 |
| EP | 2144604 B1 | 9/2011 |
| EP | 2142533 | 11/2011 |
| EP | 2445506 B1 | 5/2012 |
| EP | 2485728 | 8/2012 |
| EP | 2493310 | 9/2012 |
| EP | 2493910 | 9/2012 |
| EP | 2503890 | 10/2012 |
| EP | 2485728 B1 | 7/2013 |
| EP | 2483277 B1 | 12/2015 |
| EP | 1926721 B1 | 5/2016 |
| EP | 2091951 B1 | 2/2018 |
| FR | 2829766 A1 | 3/2003 |
| GB | 2450771 A | 1/2009 |
| JP | 2002201193 A | 7/2002 |
| JP | 2004082438 A | 3/2004 |
| JP | 2012123282 A | 6/2012 |
| JP | 2014118368 A | 6/2014 |
| KR | 1006379551 B1 | 10/2006 |
| WO | 1993000313 A2 | 1/1993 |
| WO | 19942466 A1 | 2/1994 |
| WO | 199630343 A1 | 10/1996 |
| WO | 19983648 A1 | 1/1998 |
| WO | 199916751 A1 | 4/1999 |
| WO | 199954728 A1 | 10/1999 |
| WO | 1999064446 A1 | 12/1999 |
| WO | 200022909 A2 | 4/2000 |
| WO | 2000021959 A1 | 4/2000 |
| WO | 200078309 A1 | 12/2000 |
| WO | 200078310 A1 | 12/2000 |
| WO | 2000078317 A1 | 12/2000 |
| WO | 200114363 A1 | 3/2001 |
| WO | 200114364 A1 | 3/2001 |
| WO | 200117942 A1 | 3/2001 |
| WO | 2001014362 A1 | 3/2001 |
| WO | 20013752 A2 | 5/2001 |
| WO | 200130775 A1 | 5/2001 |
| WO | 200136003 A2 | 5/2001 |
| WO | 200190099 A1 | 11/2001 |
| WO | 200196873 A2 | 12/2001 |
| WO | 200200620 A1 | 1/2002 |
| WO | 200200646 A1 | 1/2002 |
| WO | 200200647 A1 | 1/2002 |
| WO | 200202119 A1 | 1/2002 |
| WO | 2002009651 A2 | 2/2002 |
| WO | 2002009688 A1 | 2/2002 |
| WO | 2002024197 A1 | 3/2002 |
| WO | 2002026745 A1 | 4/2002 |
| WO | 2002055661 A2 | 7/2002 |
| WO | 2002080952 A2 | 10/2002 |
| WO | 2002083071 A2 | 10/2002 |
| WO | 2002095007 A2 | 11/2002 |
| WO | 2003000688 A1 | 1/2003 |
| WO | 2003024956 A1 | 3/2003 |
| WO | 2003049736 A1 | 6/2003 |
| WO | 2003084948 A1 | 10/2003 |
| WO | 2004009015 A2 | 1/2004 |
| WO | 2004014370 A2 | 2/2004 |
| WO | 2004024705 A1 | 3/2004 |
| WO | 2004030637 A2 | 4/2004 |
| WO | 2004037800 A1 | 5/2004 |
| WO | 2004050022 A2 | 6/2004 |
| WO | 2004067008 A1 | 8/2004 |
| WO | 2004110350 A2 | 12/2004 |
| WO | 2004110368 A2 | 12/2004 |
| WO | 2004110375 A2 | 12/2004 |
| WO | 2005000217 A2 | 1/2005 |
| WO | 2005009950 A2 | 2/2005 |
| WO | 2005016344 A1 | 2/2005 |
| WO | 2005021528 A1 | 3/2005 |
| WO | 2005033090 A1 | 4/2005 |
| WO | 2005035534 A1 | 4/2005 |
| WO | 2005044787 A1 | 5/2005 |
| WO | 2005044797 A1 | 5/2005 |
| WO | 2005046685 A1 | 5/2005 |
| WO | 2005073186 A1 | 8/2005 |
| WO | 2005085226 A1 | 9/2005 |
| WO | 2005097740 A1 | 10/2005 |
| WO | 2005097746 A2 | 10/2005 |
| WO | 2005097750 A1 | 10/2005 |
| WO | 2005110413 A2 | 11/2005 |
| WO | 2005116006 A1 | 12/2005 |
| WO | 2005116009 A1 | 12/2005 |
| WO | 2006006490 A1 | 1/2006 |
| WO | 2006021801 A1 | 3/2006 |
| WO | 2006032322 A1 | 3/2006 |
| WO | 2006034341 A2 | 3/2006 |
| WO | 2006049933 A2 | 5/2006 |
| WO | 2006051202 A1 | 5/2006 |
| WO | 2006058905 A1 | 6/2006 |
| WO | 2006060461 A1 | 6/2006 |
| WO | 2006061094 A1 | 6/2006 |
| WO | 2006067311 A2 | 6/2006 |
| WO | 2006123257 A2 | 11/2006 |
| WO | 2006129199 A1 | 12/2006 |
| WO | 2007002057 A1 | 1/2007 |
| WO | 2007003962 A2 | 1/2007 |
| WO | 2007029035 A2 | 3/2007 |
| WO | 2007033175 A2 | 3/2007 |
| WO | 2007038669 A2 | 4/2007 |
| WO | 2007049532 A1 | 5/2007 |
| WO | 2007068620 A1 | 6/2007 |
| WO | 2007068641 A1 | 6/2007 |
| WO | 2007073405 A1 | 6/2007 |
| WO | 2007075629 A2 | 7/2007 |
| WO | 2007075688 A2 | 7/2007 |
| WO | 2007080140 A1 | 7/2007 |
| WO | 2007082840 A1 | 7/2007 |
| WO | 2007087204 A2 | 8/2007 |
| WO | 2007089634 A2 | 8/2007 |
| WO | 2007092065 A2 | 8/2007 |
| WO | 2007130468 A2 | 11/2007 |
| WO | 2007137955 A1 | 12/2007 |
| WO | 2007138351 A2 | 12/2007 |
| WO | 2007138355 A1 | 12/2007 |
| WO | 2008011453 A2 | 1/2008 |

(56) References Cited

FOREIGN PATENT DOCUMENTS

| | | |
|---|---|---|
| WO | 2008023720 A1 | 2/2008 |
| WO | 2008030891 A2 | 3/2008 |
| WO | 2008052658 A1 | 5/2008 |
| WO | 2008059214 A1 | 5/2008 |
| WO | 2008061399 A1 | 5/2008 |
| WO | 2008066789 A2 | 6/2008 |
| WO | 2008073825 A1 | 6/2008 |
| WO | 2008075064 A1 | 6/2008 |
| WO | 2008075070 A1 | 6/2008 |
| WO | 2008075077 A1 | 6/2008 |
| WO | 2008077597 A1 | 7/2008 |
| WO | 2008080455 A1 | 7/2008 |
| WO | 2008099000 A2 | 8/2008 |
| WO | 2008106166 A2 | 9/2008 |
| WO | 2008106167 A1 | 9/2008 |
| WO | 2008106202 A1 | 9/2008 |
| WO | 2008109175 A1 | 9/2008 |
| WO | 2008133273 A1 | 11/2008 |
| WO | 2008133955 A1 | 11/2008 |
| WO | 2008157751 A2 | 12/2008 |
| WO | 2009000864 A1 | 12/2008 |
| WO | 2009004356 A1 | 1/2009 |
| WO | 2009030318 A1 | 3/2009 |
| WO | 2009058314 A1 | 5/2009 |
| WO | 2009064927 A2 | 5/2009 |
| WO | 2009099736 A2 | 8/2009 |
| WO | 2009117676 A2 | 9/2009 |
| WO | 2009143404 A1 | 11/2009 |
| WO | 2009151910 A2 | 12/2009 |
| WO | 2010017055 A2 | 2/2010 |
| WO | 2010056309 A2 | 5/2010 |
| WO | 2010056631 A1 | 5/2010 |
| WO | 2010072302 A1 | 7/2010 |
| WO | 2010075273 A1 | 7/2010 |
| WO | 2010077915 A1 | 7/2010 |
| WO | 2010089092 A1 | 8/2010 |
| WO | 2010092181 A1 | 8/2010 |
| WO | 2010114957 A1 | 10/2010 |
| WO | 2010115688 A1 | 10/2010 |
| WO | 2010120262 A1 | 10/2010 |
| WO | 2010129053 A2 | 11/2010 |
| WO | 2010138589 A1 | 12/2010 |
| WO | 2010150100 A1 | 12/2010 |
| WO | 2011024953 A1 | 3/2011 |
| WO | 2011035018 A2 | 3/2011 |
| WO | 2011036284 A1 | 3/2011 |
| WO | 2011042145 A1 | 4/2011 |
| WO | 2011043994 A1 | 4/2011 |
| WO | 2011053821 A1 | 5/2011 |
| WO | 2011056635 A1 | 5/2011 |
| WO | 2011066211 A1 | 6/2011 |
| WO | 2011097300 A1 | 8/2011 |
| WO | 2011098433 A1 | 8/2011 |
| WO | 2011103546 A1 | 8/2011 |
| WO | 2011123681 A1 | 10/2011 |
| WO | 2011140190 A1 | 11/2011 |
| WO | 2011140296 A1 | 11/2011 |
| WO | 2011146401 A1 | 11/2011 |
| WO | 2011163612 A1 | 12/2011 |
| WO | 2011163619 A1 | 12/2011 |
| WO | 2012016133 A2 | 2/2012 |
| WO | 2012016217 A1 | 2/2012 |
| WO | 2012019430 A1 | 2/2012 |
| WO | 2012037298 A1 | 3/2012 |
| WO | 2012037299 A2 | 3/2012 |
| WO | 2012041158 A1 | 4/2012 |
| WO | 2012064632 A1 | 5/2012 |
| WO | 2012064642 A1 | 5/2012 |
| WO | 2012071562 A2 | 5/2012 |
| WO | 2012083048 A2 | 6/2012 |
| WO | 2012083059 A1 | 6/2012 |
| WO | 2012083061 A2 | 6/2012 |
| WO | 2012092442 A1 | 7/2012 |
| WO | 2012096928 A2 | 7/2012 |
| WO | 2012101013 A1 | 8/2012 |
| WO | 2012110518 A1 | 8/2012 |
| WO | 2012110519 A1 | 8/2012 |
| WO | 2012122391 A1 | 9/2012 |
| WO | 2012125521 A1 | 9/2012 |
| WO | 2012126562 A1 | 9/2012 |
| WO | 2012129562 A2 | 9/2012 |
| WO | 2012130166 A1 | 10/2012 |
| WO | 2012130380 A1 | 10/2012 |
| WO | 2012151451 A1 | 11/2012 |
| WO | 2012151452 A1 | 11/2012 |
| WO | 2012160015 A1 | 11/2012 |
| WO | 2013004372 A1 | 1/2013 |
| WO | 2013017600 A1 | 2/2013 |
| WO | 2013022605 A1 | 2/2013 |
| WO | 2013025733 A1 | 2/2013 |
| WO | 2013028445 A1 | 2/2013 |
| WO | 2013028495 A1 | 2/2013 |
| WO | 2013033068 A1 | 3/2013 |
| WO | 2013045413 A1 | 4/2013 |
| WO | 2013060636 A1 | 5/2013 |
| WO | 2013064083 A1 | 5/2013 |
| WO | 2013078771 A1 | 6/2013 |
| WO | 2013124040 A1 | 8/2013 |
| WO | 2013156608 A1 | 10/2013 |
| WO | 2013157021 A1 | 10/2013 |
| WO | 2013178816 A1 | 12/2013 |
| WO | 2014028946 A2 | 2/2014 |
| WO | 2014039769 A1 | 3/2014 |
| WO | 2014044356 A1 | 3/2014 |
| WO | 2014090362 A1 | 6/2014 |
| WO | 2014146747 A1 | 9/2014 |
| WO | 2014164749 A1 | 10/2014 |
| WO | 2014164767 A1 | 10/2014 |
| WO | 2014166584 A1 | 10/2014 |
| WO | 2014166586 A1 | 10/2014 |
| WO | 2015014446 A1 | 2/2015 |
| WO | 2015046827 A1 | 4/2015 |
| WO | 2015084606 A1 | 6/2015 |
| WO | 2015103583 A1 | 7/2015 |
| WO | 2015154022 A1 | 10/2015 |
| WO | 2015154039 A2 | 10/2015 |
| WO | 2015173225 A1 | 11/2015 |
| WO | 2015175171 A1 | 11/2015 |
| WO | 2016005577 A1 | 1/2016 |
| WO | 2016034262 A1 | 3/2016 |
| WO | 2016040449 A1 | 3/2016 |
| WO | 2016118638 A1 | 7/2016 |
| WO | 2016205590 A1 | 12/2016 |
| WO | 2016205633 A1 | 12/2016 |
| WO | 2017019817 A1 | 2/2017 |
| WO | 2017019822 A1 | 2/2017 |
| WO | 2017033175 A1 | 3/2017 |
| WO | 2017041893 A1 | 3/2017 |
| WO | 2017066705 A1 | 4/2017 |
| WO | 2017109830 A1 | 6/2017 |
| WO | 2017161028 A1 | 9/2017 |
| WO | 2017189613 A1 | 11/2017 |
| WO | 2017197240 A1 | 11/2017 |
| WO | 2018089904 A1 | 5/2018 |
| WO | 2018106818 A1 | 6/2018 |
| WO | 2018106820 A1 | 6/2018 |
| WO | 2018112204 A1 | 6/2018 |
| WO | 2009098282 A1 | 8/2019 |
| WO | 2009132202 A2 | 10/2019 |

OTHER PUBLICATIONS

Deschrijver et al., "RNA Interference-mediated Silencing of the Fatty Acid Synthase Gene Attenuates Growth and Induces Morphological Changes and Apoptosis of LNCaP Prostate Cancer Cells," Cancer Research 63, (Jul. 2003), pp. 3799-3804.

Harrison et al., "Orlistat in the Treatment of NASH: A Case Series," The American Journal of Gastroenterology, vol. 98, No. 4, (2003), pp. 926-930.

Harrison et al., "A pilot study of orlistat treatment in obese, non-alcoholic steatohepatitis patients," Aliment Pharmacol Ther, 20: (2004), pp. 623-628.

(56) References Cited

OTHER PUBLICATIONS

Kridel et al., "Orlistat Is a Novel Inhibitor of Fatty Acid Synthase with Antitumor Activity," Cancer Research 64, (Mar. 2004), pp. 2070-2075.
Li et al., "Fatty Acid Synthase Expression Is Induced by the Epstein-Barr Virus Immediate-Early Protein BRLF1 and Is Required for Lytic Viral Gene Expression," Journal of Virology, vol. 78, No. 8, (Apr. 2004), pp. 4197-4206.
Kuhajda, Francis P., "Fatty Acid Synthase and Cancer: New Application of an Old Pathway," Cancer Res 66: (12), (Jun. 2006), pp. 5977-5980.
Database Reg. Chemical Abstracts RN 927570-20-5 (Mar. 20, 2007).
Hunt et al., "mRNA Stability and Overexpression of Fatty Acid Synthase in Human Breast Cancer Cell Lines," Anticancer Research, 27: (2007), pp. 27-34.
Menendez, Javier A. and Lupu, Ruth, "Fatty acid synthase and the lipogenic phenotype in cancer pathogenesis," Nature Reviews, vol. 7, (Oct. 2007), pp. 763-777.
Rassmann et al., "The human fatty acid synthase: A new therapeutic target for coxsackievirus B3-induced diseases?," Aniviral Research 76 (2007) pp. 150-158.
Menear et al., "4-[3-(4-Cyclopropanecarbonylpiperazine-1-fluorobenzyl]-2H-phthalazin-1-one: A Novel Bioavailable Inhibitor of Poly (ADP-ribose) Polymerase-1," J. Med. Chem. 51, (2008), pp. 6581-6591.
Munger et al., "Systems-level metabolic flux profiling identifies fatty acid synthesis as a target for antiviral therapy," Nature Biotechnology, vol. 26, No. 10, (Oct. 2008), pp. 1179-1186.
Vazquez et al., "Discovery of GSK837149A, an inhibitor of human fatty acid synthase targeting the –ketoacyl reductase reaction", FEBS Journal 275 (2008), pp. 1556-1567.
Yang et al., "Fatty Acid Synthase Is Upregulated during HCV Infection and Regulates HCV Entry and Production," Hepatology, 48(5) (Nov. 2008), pp. 1396-1403.
Zhang et al., "–Lactam congeners of orlistat as inhibitors of fatty acid synthase", Bioorganic & Medicinal Chemistry Letters, (2008), 18, pp. 2491-2494.
Montgomery et al., "Discovery and SAR of benzyl phenyl ethers as inhibitors of bacterial phenylalanyl-tRNA synthetase," Bioorganic & Medicinal Chemistry Letters, 19 (2009), pp. 665-669.
Samsa et al., "Dengue Virus Capsid Protein Usurps Lipid Droplets for Viral Particle Formation", PLOS Pathogens, vol. 5, Iss. 10, (Oct. 2009), pp. 1-14.
Ferrigno et al., "Development of substituted 6 [4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells," Bioorganic & Medicinal Chemistry Letters 20 (2010), pp. 1100-1105).
Flavin et al., "Fatty acid synthase as a potential therapeutic target in cancer," Future Oncol., 6(4), (Apr. 2010), pp. 551-562.
Heaton, et al., "Dengue virus nonstructural protein 3 redistributes fatty acid synthase to sites of viral replication and increases cellular fatty acid synthesis," PNAS, vol. 107, No. 40, (Oct. 2010), pp. 17345-17350.
Oliveras et al., "Novel anti-fatty acid synthase compounds with anti-cancer activity in HER2+ breast cancer," Ann. N.Y. Acad. Sci. 1210 (2010), pp. 86-93.
Rhee et al., "Synthesis and cytotoxicity of 2-phenylquinazolin-4(3H)-one derivatives," European Journal of Medicinal Chemistry, 46 (2011), pp. 3900-3908.
Fatima, Sabiha; Bathini, Raju; Sivan, Sree Kanth; and Manga, Vijjulatha, "Molecular docking and 3D-QSAR studies on inhibitors of DNA damage signaling enzyme human PARP-1," Journal of Receptors and Signal Transduction, (2012), pp. 1-11.
Kant et al., "Myelopoietic Efficacy of Orlistat in Murine Hosts Bearing T Cell Lymphoma: Implication in Macrophage Differentiation and Activation," PLOS ONE, vol. 8, Issue 12, (Dec. 2013), pp. 1-14.
Tu et al., "Medicinal chemistry design principles for liver targeting through OATP transporters", Curr. Top. Med. Chem. (2013), 13(7), pp. 857-866.
Berod et al., "De novo fatty acid synthesis controls the fate between regulatory T and T helper 17 cells," Nature Medicine, vol. 20, No. 11, (Nov. 2014), pp. 1327-1337.
Fako, Valerie E.; Zhang, Jian-Ting; and Liu, Jing-Yuan, "Mechanism of Orlistat Hydrolysis by the Thioesterase of Human Fatty Acid Synthase," ACS Catal. 4, (2014), pp. 3444-3453.
International Search Report for PCT/US14/23388, dated Aug. 18, 2014, 4 pages.
Endo et al., "Obesity Drives Th17 Cell Differentiation by Inducing the Lipid Metabolic Kinase, ACC1," Cell Reports, 12, (Aug. 2015), pp. 1042-1055.
Jones, Suzanne F. and Infante, Jeffrey R., "Molecular Pathways: Fatty Acid Synthase," Clinical Cancer Research, (Dec. 2015), pp. 1-14.
Smagris et al., "pnpla3I148M Knockin Mice Accumulate PNPLA3 on Lipid Droplets and Develop Hepatic Steatosis," Hepatology, vol. 61, No. 1, (2015), pp. 108-118.
Xenical (orlistat) Highlights of Prescribing Information (Aug. 2015), Reference ID: 3803457.
Harriman et al., "Acetyl-CoA carboxylase inhibition by ND-630 reduces hepatic steatosis, improves insulin sensitivity, and modulates dyslipidemia in rats," PNAS Early Edition (2016), pp. 1-15.
Paglialunga, Sabina and Dehn, Clayton A., "Clinical assessment of hepatic de novo lipogenesis in non-alcoholic fatty liver disease", Lipids in Health and Disease, 15:159, (2016), pp. 1-10.
Filozof et al., "Clinical Endpoints and Adaptive Clinical Trials in Precirrhotic Nonalcoholic Steatohepatitis: Facilitating Development Approaches for an Emerging Epidemic", Hepatology Communications, vol. 1, No. 7, (2017), pp. 577-585.
International Search Report for PCT/US17/29469, dated Oct. 2, 2017, 4 pages.
Konerman, Monica A., Jones, Jacob C., and Harrison, Stephen A., "Pharmacotherapy for NASH: Current and Emerging", Journal of Hepatology (2017), pp. 1-15.
Written Opinion of the ISA for PCT/US17/29469, dated Oct. 2, 2017, 19 pages.
Lawitz et al., "Acetyl-CoA Carboxylase Inhibitor GS-0976 for 12 Weeks Reduces Hepatic De Novo Lipogenesis and Steatosis in Patients With Nonalcoholic Steatohepatitis", Clinical Gastroenterology and Hepatology (May 31, 2018) pp. 1-12.
Loomba et al., "GS-0976 Reduces Hepatic Steatosis and Fibrosis Markers in Patients With Nonalcoholic Fatty Liver Disease", Gastroenterology (Nov. 2018), 155: pp. 1463-1473.
Esler, William P. and Bence, Kendra K., "Metabolic Targets in Nonalcoholic Fatter Liver Disease", Cellular and Molecular Gastroenterology and Hepatology, (2019), pp. 1-21.
Martin et al., "Discovery and optimization of novel piperazines as potent inhibitors of fatty acid synthase (FASN)", Bioorg Med Chem Lett. (Apr. 2019), 29, Iss. 8, pp. 1001-1006.
Wu et al., "Design and synthesis of orally efficacious benzimidazoles as melanin-concentrating hormone receptor 1 antagonist", Bioorg. Med. Chem. Lett. 16 (2006) pp. 3674-3678.
Invitation to Pay Additional Fees and, Where Applicable, Protest Fee for PCT/US2019/055603, dated Nov. 21, 2019.
International Search Report and the Written Opinion for International Application No. PCT/US2019/055603, dated Feb. 5, 2020, 12 pgs.

* cited by examiner

| Comp. No. | IC$_{50}$ | Peak elution | Chemical Name | MS m/z [M+H]$^+$ | $^1$H NMR |
|---|---|---|---|---|---|
| 1 | B | 1st eluting isomer | (1-(4-(6-fluorobenzo[d]oxazol-2-yl)phenyl)-6-azaspiro[2.5]octan-6-yl)(1-hydroxycyclopropyl)methanone | 407 | 1H-NMR (400 MHz, DMSO-d6) δ (ppm): 8.09 (d, J = 8.4 Hz, 2H), 7.84-7.78 (m, 2H), 7.50 (d, J = 8.0 Hz, 2H), 7.33-7.26 (m, 1H), 6.25 (s, 1H), 3.92-2.98 (m, 4H), 2.19-2.16 (m, 1H), 1.61-1.50 (m, 2H), 1.32-1.19 (m, 2H), 1.16-1.06 (m, 1H), 0.98-0.94 (m, 1H), 0.91-0.84 (m, 2H), 0.78-0.67 (m, 2H). |
| 2 | A | 2nd eluting isomer | (1-(4-(6-fluorobenzo[d]oxazol-2-yl)phenyl)-6-azaspiro[2.5]octan-6-yl)(1-hydroxycyclopropyl)methanone | 407 | 1H-NMR (400 MHz, DMSO-d6) δ (ppm): 8.09 (d, J = 8.4 Hz, 2H), 7.84-7.78 (m, 2H), 7.50 (d, J = 8.0 Hz, 2H), 7.32-7.26 (m, 1H), 6.25 (s, 1H), 3.91-3.00 (m, 4H), 2.19-2.16 (m, 1H), 1.62-1.51 (m, 2H), 1.32-1.21 (m, 2H), 1.17-1.08 (m, 1H), 0.98-0.96 (m, 1H), 0.90-0.84 (m, 2H), 0.75-0.67 (m, 2H). |
| 3 | B | | (1-chloro-2-(4-(6-fluorobenzo[d]oxazol-2-yl)phenyl)-6-azaspiro[2.5]octan-6-yl)(1-hydroxycyclopropyl)methanone | 441, 443 | 1H-NMR (400 MHz, DMSO-d6) δ (ppm): 8.13 (d, J = 8.0 Hz, 2H), 7.85-7.72 (m, 2H), 7.54 (d, J = 8.0 Hz, 2H), 7.32-7.27 (m, 1H), 6.32 (s, 1H), 4.40-3.96 (m, 2H), 3.78 (d, J = 7.6 Hz, 1H), 3.29-2.91 (m, 2H), 2.41 (d, J = 7.6 Hz, 1H), 2.03-1.90 (m, 1H), 1.84-1.75 (m, 1H), 1.37-1.31 (m, 2H), 0.99-0.90 (m, 2H), 0.80-0.74 (m, 2H). |

Figure 2-1

| | | | | 1H-NMR (400 MHz, DMSO-d6) δ (ppm) |
|---|---|---|---|---|
| 4 | C | 1st eluting isomer | | 1H-NMR (400 MHz, DMSO-d6) δ (ppm): 8.16 (d, J = 8.0 Hz, 2H), 7.86-7.80 (m, 2H), 7.58 (d, J = 8.0 Hz, 2H), 7.33-7.28 (m, 1H), 6.32 (s, 1H), 4.12-3.40 (m, 4H), 3.10-3.06 (m, 1H), 1.92-1.79 (m, 2H), 1.51-1.38 (m, 2H), 0.95-0.90 (m, 2H), 0.76-0.70 (m, 2H). |
| 5 | A | 2nd eluting isomer | 1-[1,1-difluoro-2-[4-(6-fluoro-1,3-benzoxazol-2-yl)phenyl]-6-azaspiro[2.5]octane-6-carbonyl]cyclopropan-1-ol | 443 |
| | | | | 1H-NMR (400 MHz, DMSO-d6) δ (ppm): 8.15 (d, J = 8.0 Hz, 2H), 7.86-7.80 (m, 2H), 7.57 (d, J = 8.0 Hz, 2H), 7.33-7.28 (m, 1H), 6.32 (s, 1H), 4.15-3.40 (m, 4H), 3.10-3.06 (m, 1H), 1.91-1.79 (m, 2H), 1.51-1.40 (m, 2H), 0.95-0.90 (m, 2H), 0.76-0.70 (m, 2H). |
| 6 | A | 1st eluting isomer | (1-hydroxycyclopropyl)(1-(4-(1-methyl-1H-benzo[d]imidazol-5-yl)phenyl)-6-azaspiro[2.5]octan-6-yl)methanone | 402 |
| | | | | 1H-NMR (400 MHz, DMSO-d6) δ (ppm): 8.21 (s, 1H), 7.90 (s, 1H), 7.65-7.57 (m, 4H), 7.33 (d, J = 7.6 Hz, 2H), 6.25 (s, 1H), 3.87 (s, 3H), 3.82-3.40 (m, 4H), 2.11-2.05 (m, 1H), 1.59-1.50 (m, 2H), 1.29-1.21 (m, 1H), 1.18-1.10 (m, 2H), 0.91-0.84 (m, 3H), 0.79-0.69 (m, 2H). |
| 7 | B | 2nd eluting isomer | | 402 |
| | | | | 1H-NMR (400 MHz, DMSO-d6) δ (ppm): 8.21 (s, 1H), 7.90 (s, 1H), 7.65-7.57 (m, 4H), 7.33 (d, J = 8.0 Hz, 2H), 6.25 (s, 1H), 3.87 (s, 3H), 3.82-3.40 (m, 4H), 2.11-2.05 (m, 1H), 1.59-1.50 (m, 2H), 1.29-1.21 (m, 1H), 1.18-1.07 (m, 2H), 0.91-0.84 (m, 3H), 0.79-0.69 (m, 2H). |

Figure 2-2

| | | | | |
|---|---|---|---|---|
| 8 | C | 1st eluting isomer | (1,1-difluoro-2-(4-(1-methyl-1H-benzo[d]imidazol-5-yl)phenyl)-6-azaspiro[2.5]octan-6-yl)(1-hydroxycyclopropyl)methanone | 438 | 1H-NMR (400 MHz, CD3OD) δ (ppm): 8.16 (s, 1H), 7.90 (s, 1H), 7.67-7.64 (m, 4H), 7.43 (d, J = 7.6 Hz 2H), 4.25-3.40 (m, 7H), 2.79 (d, J = 15.2 Hz, 1H), 2.07-1.92 (m, 2H), 1.66-1.50 (m, 2H), 1.08-1.01 (m, 2H), 0.90-0.84 (m, 2H). LCMS (ES, m/z): 438 [M+H]+. |
| 9 | A | 2nd eluting isomer | | 438 | 1H-NMR (400 MHz, CD3OD) δ (ppm): 8.17 (s, 1H), 7.90 (s, 1H), 7.67-7.64 (m, 4H), 7.44 (d, J = 7.6 Hz 2H), 4.30-3.40 (m, 7H), 2.80 (d, J = 14.8 Hz, 1H), 2.07-1.92 (m, 2H), 1.66-1.50 (m, 2H), 1.08-1.01 (m, 2H), 0.90-0.84 (m, 2H). |
| 10 | D | 1st eluting isomer | 4'-(6-(1-hydroxycyclopropane-1-carbonyl)-6-azaspiro[2.5]octan-1-yl)-[1,1'-biphenyl]-3-carboxylic acid | 392 | 1H-NMR (DMSO-d6, 400 MHz) δ (ppm): 13.08 (s, 1H), 8.17 (s, 1H), 7.92 (d, J = 7.2 Hz, 2H), 7.64-7.57 (m, 3H), 7.37 (d, J = 8.0 Hz, 2H), 6.25 (s, 1H), 3.84-3.07 (m, 4H), 2.12-2.08 (m, 1H), 1.58-1.51 (m, 2H), 1.28-1.20 (m, 1H), 1.16-1.11 (m, 2H), 0.92-0.86 (m, 3H), 0.74-0.69 (m, 2H). |
| 11 | B | 2nd eluting isomer | | 392 | 1H-NMR (DMSO-d6, 400 MHz) δ (ppm): 13.13 (brs, 1H), 8.17 (s, 1H), 7.92-7.92-7.89 (m, 2H), 7.63 (d, J = 8.4 Hz, 2H), 7.59-7.55 (m, 1H), 7.36 (d, J = 8.0 Hz, 2H), 6.25 (s, 1H), 3.89-3.25 (m, 4H), 2.12-2.08 (m, 1H), 1.59-1.51 (m, 2H), 1.27-1.21 (m, 1H), 1.17-1.11 (m, 2H), 0.92-0.86 (m, 3H), 0.74-0.70 (m, 2H). |

Figure 2-3

| | | | | |
|---|---|---|---|---|
| 12 | B | 1st eluting isomer | 4'-(6-((R)-tetrahydrofuran-2-carbonyl)-6-azaspiro[2.5]octan-1-yl)-[1,1'-biphenyl]-3-carboxylic acid | 406 | 1H-NMR (DMSO-d6, 400 MHz) δ (ppm): 13.07 (brs, 1H), 8.12 (s, 1H), 7.92 (d, J =8.0 Hz, 2H), 7.64-7.58 (m, 3H), 7.37 (d, J = 8.0 Hz, 2H), 4.70-4.57 (m, 1H), 3.78-3.51 (m, 4H), 3.35-3.15 (m, 2H), 2.15-2.07 (m, 1H), 2.02-1.90 (m, 2H), 1.85-1.70 (m, 2H), 1.60-1.45 (m, 2H), 1.32-0.98 (m, 3H), 0.92-0.88 (m, 1H). |
| 13 | D | 2nd eluting isomer | | 406 | 1H-NMR (DMSO-d6, 400 MHz) δ (ppm): 13.08 (brs, 1H), 8.17 (s, 1H), 7.93-7.91 (m, 2H), 7.64-7.57 (m, 3H), 7.36 (d, J = 8.0 Hz, 2H), 4.72-4.56 (m, 1H), 3.78-3.55 (m, 4H), 3.27-3.08 (m, 2H), 2.13-2.08 (m, 1H), 2.04-1.91 (m, 2H), 1.86-1.72 (m, 2H), 1.62-1.53 (m, 1H), 1.51-1.47 (m, 1H), 1.25-1.05 (m, 3H), 0.92-0.87 (m, 1H). |
| 14 | D | 1st eluting isomer | 4'-(6-(1-hydroxycyclopropane-1-carbonyl)-6-azaspiro[2.5]octan-1-yl)-[1,1'-biphenyl]-4-carboxylic acid | 392 | 1H-NMR (400 MHz, CD3OD) δ (ppm): 8.11 (d, J = 8.0 Hz, 2H), 7.75 (d, J = 8.0 Hz, 2H), 7.64 (d, J = 8.0 Hz, 2H), 7.37 (d, J = 8.0 Hz, 2H), 4.19-3.40 (m, 4H), 2.18-2.15 (m, 1H), 1.70-1.60 (m, 2H), 1.41-1.29 (m, 2H), 1.17-1.12 (m, 1H), 1.02-0.96 (m, 3H), 0.92-0.81(m,2H). |

Figure 2-4

| | | | | |
|---|---|---|---|---|
| 15 | A | | 2nd eluting isomer | 392 | 1H-NMR (400 MHz, CD3OD) δ (ppm): 8.11 (d, J = 8.0 Hz, 2H), 7.75 (d, J = 8.0 Hz, 2H), 7.64 (d, J = 8.0 Hz, 2H), 7.37 (d, J = 8.0 Hz, 2H), 4.15-3.40 (m, 4H), 2.18-2.14 (m, 1H), 1.67-1.61 (m, 2H), 1.35-1.28 (m, 2H), 1.16-1.13 (m, 1H), 1.02-0.96 (m, 3H), 0.87-0.81 (m, 2H). |
| 16 | A | 4'-((S)-6-((R)-tetrahydrofuran-2-carbonyl)-6-azaspiro[2.5]octan-1-yl)-[1,1'-biphenyl]-4-carboxylic acid | 1st eluting isomer | 406 | 1H-NMR (400 MHz, CD3OD) δ (ppm): 8.11 (d, J = 8.0 Hz, 2H), 7.74 (d, J = 8.0 Hz, 2H), 7.64 (d, J = 8.0 Hz, 2H), 7.38-7.36 (m, 2H), 4.79-4.67 (m, 1H), 3.97-3.65 (m, 4H), 3.49-3.33 (m, 1H), 3.31-3.28 (m, 1H), 2.18-1.89 (m, 5H), 1.75-1.55 (m, 2H), 1.45-1.25 (m, 2H), 1.16-1.13 (m,1H), 0.99-0.96 (m, 1H). |
| 17 | C | 4'-((R)-6-((R)-tetrahydrofuran-2-carbonyl)-6-azaspiro[2.5]octan-1-yl)-[1,1'-biphenyl]-4-carboxylic acid | 2nd eluting isomer | 406 | 1H-NMR (400 MHz, CD3OD) δ (ppm): 8.11 (d, J = 8.0 Hz, 2H), 7.74 (d, J = 8.0 Hz, 2H), 7.64 (d, J = 8.0 Hz, 2H), 7.37 (d, J = 8.0 Hz, 2H), 4.79-4.65 (m, 1H), 3.95-3.68 (m, 4H), 3.55-3.26 (m, 2H), 2.26-2.14 (m, 2H), 2.05-1.92 (m, 3H), 1.72-1.60 (m, 2H), 1.32-1.22 (m, 2H), 1.16-1.14 (m, 1H), 0.99-0.96 (m,1H). |

Figure 2-5

| | | | | |
|---|---|---|---|---|
| 18 | B | 1st eluting isomer | 4-{4-[2,2-difluoro-6-[(2R)-oxolane-2-carbonyl]-6-azaspiro[2.5]octan-1-yl]phenyl}benzoic acid | 442 | 1H-NMR (d6-DMSO, 400 MHz) δ (ppm): 13.03(br, 1H), 8.02 (d, J= 8.4 Hz, 2H), 7.80 (d, J= 8.4 Hz, 2H), 7.73 (d, J= 7.6 Hz, 2H), 7.45 (d, J= 7.6 Hz, 2H), 4.78-4.50 (m, 1H), 3.96-3.65 (m, 3H), 3.63-3.39 (m, 2H), 3.28-3.05 (m, 1H), 3.04-2.91 (m, 1H), 2.11-1.66 (m, 6H), 1.56-1.23 (m, 2H). |
| 19 | D | 2nd eluting isomer | | 442 | 1H-NMR (d6-DMSO, 400 MHz) δ (ppm): 13.05 (br, 1H), 8.02 (d, J= 8.4 Hz, 2H), 7.80 (d, J= 8.0 Hz, 2H), 7.73 (d, J= 7.6 Hz, 2H), 7.45 (d, J= 8.0 Hz, 2H), 4.79-4.51 (m, 1H), 3.98-3.61 (m, 3H), 3.58-3.42 (m, 2H), 3.28-3.12 (m, 1H), 3.02-2.91 (m, 1H), 2.11-1.91 (m, 2H), 1.91-1.70 (m, 4H), 1.56-1.25 (m, 2H). |
| 20 | D | 1st eluting isomer | 4'-(2,2-difluoro-6-((R)-tetrahydrofuran-2-carbonyl)-6-azaspiro[2.5]octan-1-yl)-6-fluoro-[1,1'-biphenyl]-3-carboxylic acid | 460 | 1H-NMR (400 MHz, CD3OD) δ (ppm): 8.18-8.15 (m, 1H), 8.08-8.04 (m, 1H), 7.58 (d, J = 8.0 Hz, 2H), 7.49-7.46 (m, 2H), 7.34-7.29 (m, 1H), 4.80-4.70 (m, 1H), 4.14-3.82 (m, 3H), 3.74-3.67 (m, 1H), 3.64-3.35 (m, 2H), 2.83 (d, J = 14.8 Hz, 1H), 2.27-1.83 (m, 6H), 1.70-1.48 (m, 2H). |

Figure 2-6

| 21 | B | 2nd eluting isomer | | 460 | 1H NMR (400 MHz, CD$_3$OD) δ (ppm): 8.16 (d, J = 7.6 Hz, 1H), 8.08-8.04 (m, 1H), 7.58 (d, J = 8.0 Hz, 2H), 7.49-7.46 (m, 2H), 7.34-7.29 (m, 1H), 4.80-4.70 (m, 1H), 4.00-3.81 (m, 3H), 3.62-3.38 (m, 2H), 3.30-3.12 (m, 1H), 2.86-2.80 (m, 1H), 2.26-1.87 (m, 6H), 1.60-1.41 (m, 2H). |
|---|---|---|---|---|---|
| 22 | C | 1st eluting isomer | 6-fluoro-4'-(6-(1-hydroxycyclopropane-1-carbonyl)-6-azaspiro[2.5]octan-1-yl)-[1,1'-biphenyl]-3-carboxylic acid | 410 | 1H-NMR (400 MHz, CD$_3$OD) δ (ppm): 8.18-8.15 (m, 1H), 8.06-8.02 (m, 1H), 7.52 (d, J = 7.2 Hz, 2H), 7.38 (d, J = 8.0 Hz, 2H), 7.33-7.28 (m, 1H), 4.11-3.40 (m, 4H), 2.19-2.16 (m, 1H), 1.71-1.60 (m, 2H), 1.41-1.29 (m, 2H), 1.18-1.15 (m, 1H), 1.02-0.94 (m, 3H), 0.90-0.81 (m, 2H). |
| 23 | B | 2nd eluting isomer | | 410 | 1H-NMR (CD$_3$OD, 400 MHz) δ (ppm): 8.18-8.14 (m, 1H), 8.06-8.03 (m, 1H), 7.52 (d, J = 7.2 Hz, 2H), 7.38 (d, J = 8.0 Hz, 2H), 7.33-7.28 (m, 1H), 4.14-3.40 (m, 4H), 2.19-2.16 (m, 1H), 1.71-1.60 (m, 2H), 1.39-1.26 (m, 2H), 1.18-1.15 (m, 1H), 1.02-0.97 (m, 3H), 0.90-0.85 (m, 2H). |

Figure 2-7

| | | | | 1H-NMR (CD₃OD, 400 MHz) δ (ppm): 8.17-8.15 (m, 1H), 8.05-8.02 (m, 1H), 7.52 (d, J = 7.2 Hz, 2H), 7.40-7.36 (m, 2H), 7.33-7.28 (m, 1H), 4.78-4.67 (m, 1H), 3.94-3.63 (m, 4H), 3.51-3.30 (m, 2H), 2.24-2.10 (m, 2H), 2.05-1.91 (m, 3H), 1.75-1.58 (m, 2H), 1.45-1.26 (m, 2H), 1.20-1.13 (m, 1H), 1.10-0.96 (m, 1H). |
|---|---|---|---|---|
| 24 | B | 1st eluting isomer | 424 | |
| 25 | D | 2nd eluting isomer | 4-fluoro-3-{4-[6-[(2R)-oxolane-2-carbonyl]-6-azaspiro[2.5]octan-1-yl]phenyl}benzoic acid | 424 | 1H-NMR (CD₃OD, 400 MHz) δ (ppm): 8.17-8.15 (m, 1H), 8.05-8.02 (m, 1H), 7.52 (d, J = 7.2 Hz, 2H), 7.38 (d, J = 8.0 Hz, 2H), 7.31-7.28 (m, 1H), 4.78-4.66 (m, 1H), 3.95-3.68 (m, 4H), 3.54-3.35 (m, 2H), 2.27-2.16 (m, 2H), 2.10-1.92 (m, 3H), 1.74-1.58 (m, 2H), 1.35-1.21 (m, 2H), 1.17-1.15 (m, 1H), 1.00-0.96 (m, 1H). |
| 26 | D | 1st eluting isomer | 4'-(2,2-difluoro-6-(1-hydroxycyclopropane-1-carbonyl)-6-azaspiro[2.5]octan-1-yl)-[1,1'-biphenyl]-3-carboxylic acid | 428 | 1H-NMR (400 MHz, CD₃OD) δ (ppm): 8.28 (s, 1H), 8.02 (d, J = 7.6 Hz, 1H), 7.88 (d, J = 7.6 Hz, 1H), 7.66 (d, J = 8.4 Hz, 2H), 7.59-7.55 (m, 1H), 7.46 (d, J = 8.0 Hz, 2H), 4.29-3.35 (m, 4H), 2.81 (d, J = 15.2 Hz, 1H), 2.04-1.87 (m, 2H), 1.65-1.49 (m, 2H), 1.07-1.05 (m, 2H), 0.92-0.87 (m, 2H). |

Figure 2-8

| 27 | B | 2nd eluting isomer | | 428 | 1H NMR (400 MHz, CD₃OD) δ (ppm): 8.28 (s, 1H), 8.02 (d, J = 8.0 Hz, 1H), 7.88 (d, J = 7.6 Hz, 1H), 7.67 (d, J = 8.4 Hz, 2H), 7.59-7.55 (m, 1H), 7.47 (d, J = 8.0 Hz, 2H), 4.31-3.33 (m, 4H), 2.81 (d, J = 15.2 Hz, 1H), 2.03-1.88 (m, 2H), 1.65-1.49 (m, 2H), 1.07-1.04 (m, 2H), 0.91-0.88 (m, 2H). |
|---|---|---|---|---|---|
| 28 | D | 1st eluting isomer | 4'-(2,2-difluoro-6-(1-hydroxycyclopropane-1-carbonyl)-6-azaspiro[2.5]octan-1-yl)-6-fluoro-hexahydro-[1,1'-biphenyl]-3-carboxylic acid | 446 | 1H-NMR (CD₃OD, 400 MHz) δ (ppm): 8.18-8.15 (m, 1H), 8.08-8.04 (m, 1H), 7.58 (d, J = 7.6 Hz, 2H), 7.48 (d, J = 8.0 Hz, 2H), 7.34-7.29 (m, 1H), 4.32-3.39 (m, 4H), 2.83 (d, J = 15.2 Hz, H), 2.04-1.88 (m, 2H), 1.66-1.50 (m, 2H), 1.07-1.04 (m, 2H), 0.91-0.88 (m, 2H). |
| 29 | A | 2nd eluting isomer | | 446 | 1H-NMR (CD₃OD,, 400 MHz) δ (ppm): 8.18-8.15 (m, 1H), 8.08-8.04 (m, 1H), 7.58 (d, J = 7.6 Hz, 2H), 7.48 (d, J = 8.0 Hz, 2H), 7.34-7.29 (m, 1H), 4.28-3.40 (m, 4H), 2.83 (d, J = 14.8 Hz, H), 2.04-1.88 (m, 2H), 1.67-1.50 (m, 2H), 1.07-1.04 (m, 2H), 0.91-0.88 (m, 2H). |

Figure 2-9

| 30 | D | 1st eluting isomer | 4'-(2,2-difluoro-6-((R)-tetrahydrofuran-2-carbonyl)-6-azaspiro[2.5]octan-1-yl)-[1,1'-biphenyl]-3-carboxylic acid | 442 | 1H-NMR (CD₃OD, 400 MHz) δ (ppm): 8.28 (s, 1H), 8.02 (d, J = 7.6 Hz, 1H), 7.87 (d, J = 7.6 Hz, 1H), 7.66 (d, J = 7.2 Hz, 2H), 7.59-7.55 (m, 1H), 7.48-7.43 (m, 2H), 4.80-4.68 (m, 1H), 4.12-3.83 (m, 3H), 3.72-3.58 (m, 2H), 3.43-3.36 (m, 1H), 2.81 (d, J = 15.2 Hz, 1H), 2.27-1.84 (m, 6H), 1.69-1.45 (m, 2H). |
|---|---|---|---|---|---|
| 31 | B | 2nd eluting isomer | 4'-(2,2-difluoro-6-((R)-tetrahydrofuran-2-carbonyl)-6-azaspiro[2.5]octan-1-yl)-[1,1'-biphenyl]-3-carboxylic acid | 442 | 1H-NMR (CD₃OD, 400 MHz) δ (ppm): 8.28 (s, 1H), 8.02 (d, J = 7.6 Hz, 1H), 7.87 (d, J = 8.0 Hz, 1H), 7.66 (d, J = 7.6 Hz, 2H), 7.59-7.55 (m, 1H), 7.48-7.44 (m, 2H), 4.80-4.68 (m, 1H), 4.00-3.83 (m, 3H), 3.60-3.38 (m, 2H), 3.21-3.14 (m, 1H), 2.85-2.77 (m, 1H), 2.24-1.88 (m, 6H), 1.60-1.43 (m, 2H). |
| 32 | D | 1st eluting isomer | 4'-(2,2-difluoro-6-(1-hydroxycyclopropane-1-carbonyl)-6-azaspiro[2.5]octan-1-yl)-[1,1'-biphenyl]-4-carboxylic acid | 428 | 1H-NMR (CD₃OD, 400 MHz) δ (ppm): 8.11 (d, J = 8.0 Hz, 2H), 7.76 (d, J = 7.6Hz, 2H), 7.70 (d, J = 7.6Hz, 2H), 7.47 (d, J = 8.0 Hz, 2H), 4.59-3.40 (m, 4H), 2.92-2.63 (m, 1H), 2.20-1.79 (m, 2H), 1.79-1.37 (m, 2H) CD₃OD, 1.19-1.00 (m, 2H), 0.99-0.79 (m, 2H) |

Figure 2-10

| | | | | |
|---|---|---|---|---|
| 33 | A | 2nd eluting isomer | | 428 | 1H-NMR (CD₃OD, 400 MHz) δ (ppm): 8.11 (d, J= 8.0 Hz, 2H), 7.75 (d, J= 8.4 Hz, 2H), 7.70 (d, J= 8.4 Hz, 2H), 7.47 (d, J= 8.0 Hz, 2H), 4.50-3.40 (m, 4H), 2.91-2.71 (m, 1H), 2.24-1.75 (m, 2H), 1.75-1.36 (m, 2H), 1.22-1.00 (m, 2H), 0.99-0.85 (m, 2H) |
| 34 | D | 1st eluting isomer | (1,1-difluoro-2-(2'-fluoro-5'-(1H-tetrazol-5-yl)-[1,1'-biphenyl]-4-yl)-6-azaspiro[2.5]octan-6-yl)((R)-tetrahydrofuran-2-yl)methanone | 484 | 1H-NMR (d6-DMSO, 400 MHz) δ (ppm): 8.20 (d, J= 7.6 Hz, 1H), 8.15-8.02 (m, 1H), 7.75-7.54 (m, 3H), 7.49 (d, J= 8.0 Hz, 2H), 4.84-4.41 (m, 1H), 4.06-3.66 (m, 3H), 3.62-3.45 (m, 2H), 3.30-3.21 (m, 1H), 3.11-2.91 (m, 1H), 2.15-1.92 (m, 2H), 1.92-1.69 (m, 4H), 1.60-1.30 (m, 2H). |
| 35 | B | 2nd eluting isomer | | 484 | 1H-NMR (d6-DMSO, 400 MHz) δ (ppm): 8.21 (d, J= 7.6 Hz, 1H), 8.15-8.02 (m, 1H), 7.73-7.55 (m, 3H), 7.49 (d, J= 8.0 Hz, 2H), 4.78-4.60 (m, 1H), 3.91-3.81 (m, 1H), 3.81-3.68 (m, 2H), 3.68-3.49 (m, 1H), 3.49-3.40 (m, 1H), 3.28-3.08 (m, 1H), 3.07-2.95 (m, 1H), 2.15-1.70 (m, 6H), 1.59-1.29 (m, 2H). |

Figure 2-11

| | | | | 1H-NMR (d6-DMSO, 400 MHz) δ (ppm) |
|---|---|---|---|---|
| 36 | C | 1st eluting isomer | ((R)-1-(2'-fluoro-5'-(1H-tetrazol-5-yl)-[1,1'-biphenyl]-4-yl)-6-azaspiro[2.5]octan-6-yl)((R)-tetrahydrofuran-2-yl)methanone | 448 | 1H-NMR (d6-DMSO, 400 MHz) δ (ppm): 8.35-8.11 (m, 1H), 8.10-7.98 (m, 1H), 7.69-7.50 (m, 3H), 7.42 (d, J=8.0 Hz, 2H), 4.80-4.41 (m, 1H), 3.85-3.65 (m, 2H), 3.64-3.55 (m, 2H), 3.40-3.35 (m, 1H), 3.26-3.11 (m, 1H), 2.25-2.11 (m, 1H), 2.10-1.92 (m, 2H), 1.91-1.69 (m, 2H), 1.62-1.45 (m, 2H), 1.32-1.08 (m, 3H), 0.98-0.86 (m, 1H). |
| 37 | A | 2nd eluting isomer | ((S)-1-(2'-fluoro-5'-(1H-tetrazol-5-yl)-[1,1'-biphenyl]-4-yl)-6-azaspiro[2.5]octan-6-yl)((R)-tetrahydrofuran-2-yl)methanone | 448 | 1H-NMR (d6-DMSO, 400 MHz) δ (ppm): 8.27-8.16 (m, 1H), 8.16-7.97 (m, 1H), 7.81-7.50 (m, 3H), 7.42 (d, J=8.4 Hz, 2H), 4.80-4.52 (m, 1H), 3.83-3.53 (m, 4H), 3.48-3.38 (m, 1H), 3.29-3.15 (m, 1H), 2.11-2.08 (m, 1H), 2.07-1.92 (m, 2H), 1.90-1.68 (m, 2H), 1.66-1.53 (m, 1H), 1.51-1.40 (m, 1H), 1.20-1.07 (m, 3H), 0.97-0.83 (m, 1H). |
| 38 | D | 1st eluting isomer | (2-(4'-(2H-tetrazol-5-yl)-[1,1'-biphenyl]-4-yl)-1,1-difluoro-6-azaspiro[2.5]octan-6-yl)((R)-tetrahydrofuran-2-yl)methanone | 466 | 1H-NMR (d6-DMSO, 400 MHz) δ (ppm): 8.13 (d, J= 8.4 Hz, 2H), 7.92 (d, J= 8.4 Hz, 2H), 7.77 (d, J= 8.0 Hz, 2H), 7.46 (d, J= 8.4 Hz, 2H), 4.85-4.50 (m, 1H), 3.99-3.68 (m, 3H), 3.59-3.48 (m, 2H), 3.28-3.10 (m, 1H), 3.04-2.91 (m, 1H), 2.09-1.92 (m, 2H), 1.92-1.69(m, 4H), 1.57-1.30 (m, 2H). |

Figure 2-12

| 39 | B | 2nd eluting isomer | | 466 | 1H-NMR (DMSO, 400 MHz) δ (ppm): 8.13 (d, J= 8.0 Hz, 2H), 7.93 (d, J= 8.0 Hz, 2H), 7.77 (d, J= 7.2 Hz, 2H), 7.46 (d, J= 8.0 Hz, 2H), 4.81-4.53 (m, 1H), 3.93-3.82 (m, 1H), 3.82-3.68 (m, 2H), 3.68-3.42 (m, 2H), 3.18-2.91 (m, 2H), 2.09-1.92 (m, 2H), 1.92-1.69(m, 4H), 1.59-1.28 (m, 2H). |
|---|---|---|---|---|---|
| 40 | D | 1st eluting isomer | 4'-(6-(1-hydroxycyclopropane-1-carbonyl)-6-azaspiro[2.5]octan-1-yl)-6-methoxy-[1,1'-biphenyl]-3-carboxylic acid | 422 | 1H-NMR (CD₃OD, 400 MHz) δ (ppm): 8.04-8.01 (m, 1H), 7.96 (s, 1H), 7.45 (d, J = 8.4 Hz, 2H), 7.30 (d, J = 8.4 Hz, 2H), 7.16 (d, J = 8.4 Hz, 1H), 4.22-3.40 (m, 7H), 2.17-2.13 (m, 1H), 1.71-1.60 (m, 2H), 1.39-1.30 (m, 2H), 1.15-1.13 (m, 1H), 1.06-1.01 (m, 2H), 0.97-0.94 (m, 1H), 0.90-0.85 (m, 2H). |
| 41 | B | 2nd eluting isomer | | 422 | 1H-NMR (CD₃OD, 400 MHz) δ (ppm): 8.02 (d, J = 7.2 Hz, 1H), 7.96 (s, 1H), 7.45 (d, J = 8.0 Hz, 2H), 7.30 (d, J = 8.0 Hz, 2H), 7.16 (d, J = 8.8 Hz, 1H), 4.12-3.40 (m, 7H), 2.18-2.13 (m, 1H), 1.70-1.61 (m, 2H), 1.38-1.27 (m, 2H), 1.14-1.11 (m, 1H), 1.06-1.00 (m, 2H), 0.97-0.94 (m, 1H), 0.90-0.85 (m, 2H). |

Figure 2-13

| | | | | |
|---|---|---|---|---|
| 42 | D | 1st eluting isomer | 466 | 1H-NMR (DMSO, 400 MHz) δ (ppm): 8.33 (s, 1H), 8.05 (d, J= 7.6 Hz, 1H), 7.90 (d, J= 8.0 Hz, 1H), 7.85-7.75 (m, 2H), 7.74-7.65 (m, 1H), 7.48 (d, J= 8.0 Hz, 2H), 4.81-4.49 (m, 1H), 4.00-3.68 (m, 2H), 3.61-3.41 (m, 2H), 3.31-3.11 (m, 1H), 3.09-2.88 (m, 1H), 2.08-1.92 (m, 2H), 1.91-1.68 (m, 4H), 1.59-1.22 (m, 2H). |
| 43 | B | 1,1-difluoro-6-[(2R)-oxolane-2-carbonyl]-2-{4-[3-(2H-1,2,3,4-tetrazol-5-yl)phenyl]phenyl}-6-azaspiro[2.5]octane 2nd eluting isomer | 466 | 1H-NMR (DMSO, 400 MHz) δ (ppm): 8.33 (s, 1H), 8.05 (d, J= 7.6 Hz, 2H), 7.89 (d, J= 7.6 Hz, 2H), 7.85-7.75 (m, 2H), 7.74-7.65 (m, 1H), 7.48 (d, J= 7.6 Hz, 2H), 4.81-4.49 (m, 1H), 3.96-3.80 (m, 1H), 3.80-3.68 (m, 1H), 3.68-3.40 (m, 2H), 3.29-3.08 (m, 1H), 3.08-2.91 (m, 1H), 2.16-1.89 (m, 3H),1.88-1.61 (m, 4H), 1.60-1.28 (m, 2H). |
| 44 | A | 4-{4-[(1S)-6-(1-hydroxycyclopropanecarbonyl)-6-azaspiro[2.5]octan-1-yl]phenyl}-3-methylbenzoic acid* 1st eluting isomer | 406 | 1H-NMR (CD3OD, 400 MHz) δ (ppm): 7.95 (s, 1H), 7.89 (d, J= 8.0 Hz, 1H), 7.44-7.20 (m, 5H), 4.20-3.38 (m, 4H), 2.32 (s, 3H), 2.23-2.04 (m, 1H), 1.89-1.51 (m, 2H), 1.41-1.25 (m, 2H), 1.21-1.09 (m, 1H), 1.08-0.95 (m, 3H), 0.93-0.79 (m, 2H). |

Figure 2-14

| | | | | |
|---|---|---|---|---|
| 45 | C | 2nd eluting isomer | 4-{4-[(1R)-6-(1-hydroxycyclopropanecarbonyl)-6-azaspiro[2.5]octan-1-yl]phenyl}-3-methylbenzoic acid | 406 | 1H-NMR (CD₃OD, 400 MHz) δ (ppm): 7.95 (s, 1H), 7.89 (d, J = 8.0 Hz, 1H), 7.40-7.20 (m, 5H), 4.18-3.39 (m, 4H), 2.32 (s, 3H), 2.23-2.10 (m, 1H), 1.85-1.48 (m, 2H), 1.47-1.22 (m, 2H), 1.20-1.10 (m, 1H), 1.09-0.95 (m, 3H), 0.94-0.69 (m, 2H). |
| 46 | A | 1st eluting isomer | 4'-(6-(1-hydroxycyclopropane-1-carbonyl)-6-azaspiro[2.5]octan-1-yl)-2-methoxy-[1,1'-biphenyl]-4-carboxylic acid | 422 | 1H-NMR (CD₃OD, 400 MHz) δ (ppm): 7.70 (s, 2H), 7.50-7.45 (m, 2H), 7.42-7.37 (m, 1H), 7.31-7.26 (m, 2H), 4.08-3.41 (m, 7H), 2.17-2.10 (m, 1H), 1.70-1.60 (m, 2H), 1.40-1.30 (m, 2H), 1.15-0.85 (m, 6H). |
| 47 | C | 2nd eluting isomer | 4'-(6-(1-hydroxycyclopropane-1-carbonyl)-6-azaspiro[2.5]octan-1-yl)-2-methoxy-[1,1'-biphenyl]-4-carboxylic acid | 422 | 1H-NMR (CD₃OD, 400 MHz) δ (ppm): 7.72-7.70 (m, 2H), 7.50-7.48 (m, 2H), 7.42-7.40 (m, 1H), 7.30 (d, J = 8.0 Hz, 2H), 4.12-3.40 (m, 7H), 2.17-2.10 (m, 1H), 1.70-1.60 (m, 2H), 1.40-1.26 (m, 2H), 1.15-1.10 (m, 1H), 1.06-0.82 (m, 5H). |
| 48 | C | 1st eluting isomer | (R)-4'-(6-(1-hydroxycyclopropane-1-carbonyl)-6-azaspiro[2.5]octan-1-yl)-6-methyl-[1,1'-biphenyl]-3-carboxylic acid | 406 | 1H-NMR (400 MHz, DMSO-d6) δ (ppm): 12.97 (brs, 1H), 7.84-7.81 (m, 1H), 7.74 (d, J = 1.6Hz, 1H), 7.42 (d, J = 8.0 Hz, 2H), 7.34-7.28 (m, 4H), 6.26 (s, 1H), 3.95-3.30 (m, 4H), 2.30 (s, 3H), 2.13-2.09 (m, 1H), 1.58-1.47 (m, 2H), 1.30-1.11 (m, 3H), 0.93-0.83 (m, 3H), 0.78-0.67 (m, 2H). |

Figure 2-15

| | | | | |
|---|---|---|---|---|
| 49 | B | 2nd eluting isomer | (S)-4'-(6-(1-hydroxycyclopropane-1-carbonyl)-6-azaspiro[2.5]octan-1-yl)-6-methyl-[1,1'-biphenyl]-3-carboxylic acid | 406 | 1H-NMR (400 MHz, DMSO-d6) δ (ppm): 7.83-7.81 (m, 1H), 7.74 (d, J = 1.6 Hz, 1H), 7.42 (d, J = 8.0 Hz, 1H), 7.38-7.22 (m, 4H), 6.26 (s, 1H), 3.98-3.45 (m, 4H), 2.30 (s, 3H), 2.13-2.09 (m, 1H), 1.60-1.47 (m, 2H), 1.32-1.10 (m, 3H), 0.93-0.80 (m, 3H), 0.75-0.63 (m, 2H). |
| 50 | D | 1st eluting isomer | ((R)-1-(3'-(2H-tetrazol-5-yl)-[1,1'-biphenyl]-4-yl)-6-azaspiro[2.5]octan-6-yl)((R)-tetrahydrofuran-2-yl)methanone | 430 | 1H-NMR (400 MHz, CD3OD) δ (ppm): 8.32 (s, 1H), 8.01 (d, J = 8.0 Hz, 1H), 7.84-7.82 (m, 1H), 7.69-7.63 (m, 3H), 7.39 (d, J = 8.0 Hz, 2H), 4.80-4.66 (m, 1H), 3.99-3.65 (m, 4H), 3.57-3.33 (m, 2H), 2.27-2.16 (m, 2H), 2.07-1.89 (m, 3H), 1.73-1.60 (m, 2H), 1.37-1.24 (m, 2H), 1.18-1.15 (m, 1H), 1.00-0.97 (m, 1H). |
| 51 | A | 2nd eluting isomer | ((S)-1-(3'-(2H-tetrazol-5-yl)-[1,1'-biphenyl]-4-yl)-6-azaspiro[2.5]octan-6-yl)((R)-tetrahydrofuran-2-yl)methanone | 430 | 1H-NMR (400 MHz, CD3OD) δ (ppm): 8.32 (s, 1H), 8.00 (d, J = 7.6 Hz, 1H), 7.86 (d, J = 7.6 Hz, 1H), 7.69-7.63 (m, 3H), 7.42-7.37 (m, 2H), 4.80-4.66 (m, 1H), 3.99-3.65 (m, 4H), 3.51-3.35 (m, 2H), 2.26-2.09 (m, 2H), 2.06-1.87 (m, 3H), 1.75-1.56 (m, 2H), 1.44-1.24 (m, 2H), 1.18-1.13 (m ,1H), 1.00-0.96 (m, 1H). |

Figure 2-16

| 52 | A | 1st eluting isomer | ((S)-1-(4'-(2H-tetrazol-5-yl)-[1,1'-biphenyl]-4-yl)-6-azaspiro[2.5]octan-6-yl)((R)-tetrahydrofuran-2-yl)methanone | 430 | 1H NMR (400 MHz, CD3OD) δ (ppm): 8.12 (d, J = 8.0 Hz, 2H), 7.86 (d, J = 8.0 Hz, 2H), 7.67 (d, J = 8.4 Hz, 2H), 7.39 (d, J = 8.0 Hz, 2H), 4.80-4.66 (m, 1H), 3.99-3.92 (m, 1H), 3.89-3.63 (m, 3H), 3.51-3.35 (m, 2H), 2.25-2.13 (m, 2H), 2.05-1.87 (m, 3H), 1.73-1.57 (m, 2H), 1.36-1.25 (m, 2H), 1.18-1.14 (m, 1H), 1.00-0.97 (m, 1H). |
| 53 | D | 2nd eluting isomer | ((1R)-1-(4'-(1l2-tetrazolidin-5-yl)-[1,1'-biphenyl]-4-yl)-6-azaspiro[2.5]octan-6-yl)((R)-tetrahydrofuran-2-yl)methanone | 430 | 1H NMR (400 MHz, CD3OD) δ (ppm): 8.12 (d, J = 8.0 Hz 2H), δ 7.86 (d, J = 8.0 Hz, 2H), 7.67 (d, J = 8.0 Hz 2H), 7.39 (d, J = 8.0 Hz, 2H), 4.91-4.66 (m, 1H), 3.97-3.65 (m, 4H), 3.51-3.37 (m, 2H), 2.22-2.13 (m, 2H), 2.06-1.92 (m, 3H), 1.73-1.61 (m, 2H), 1.33-1.25 (m, 2H), 1.17-1.15 (m,1H), 1.00-0.97 (m, 1H). |
| 54 | A | 1st eluting isomer | 1-methyl-6-(4-(6-((R)-tetrahydrofuran-2-carbonyl)-6-azaspiro[2.5]octan-1-yl)phenyl)-1H-indole-2-carboxylic acid | 459 | 1H-NMR (CD3OD, 400 MHz) δ (ppm): 7.72-7.62 (m, 4H), 7.42 (d, J = 8.0 Hz, 1H), 7.36-7.31 (m, 2H), 7.30-7.28 (m, 1H), 4.78-4.62 (m, 1H), 4.14 (s, 3H), 3.97-3.83 (m, 2H), 3.70-3.50 (m, 2H), 3.47-3.32 (m, 2H), 2.25-2.10 (m, 2H), 2.00-1.89 (m, 3H), 1.72-1.54 (m, 2H), 1.47-1.28 (m, 2H), 1.16-1.13 (m, 1H), 0.96-0.95 (m, 1H). |

Figure 2-17

| 55 | C | 2nd eluting isomer | | 459 | 1H-NMR (CD₃OD, 400 MHz) δ (ppm): 7.72-7.66 (m, 4H), 7.42 (d, J = 8.0 Hz, 1H), 7.36-7.34 (m, 2H), 7.30 (s, 1H), 4.78-4.63 (m, 1H), 4.13 (s, 3H), 3.97-3.81 (m, 2H), 3.78-3.60 (m, 2H), 3.56-3.32 (m, 2H), 2.26-2.14 (m, 2H), 2.03-1.90 (m, 3H), 1.78-1.59 (m, 2H), 1.32-1.23 (m, 2H), 1.15-1.13 (m, 1H), 0.98-0.95 (m, 1H). |
|---|---|---|---|---|---|
| 56 | D | 1st eluting isomer | 3-(4-((R)-6-((R)-tetrahydrofuran-2-carbonyl)-6-azaspiro[2.5]octan-1-yl)phenyl)quinoline-8-carboxylic acid | 457 | 1H-NMR (CD₃OD, 400 MHz) δ (ppm): 9.39 (s, 1H), 8.86 (s, 1H), 7.70 (d, J = 6.8 Hz, 1H), 7.38 (d, J= 7.6 Hz, 1H), 7.92-7.73 (m, 3H), 7.48 (d, J= 8.0 Hz, 2H), 4.82-4.61 (m, 1H), 4.02-3.68 (m, 4H), 3.60-3.48 (m, 1H), 3.47-3.40 (m, 1H), 2.35-2.11 (m, 2H), 2.10-1.85(m, 3H), 1.79-1.55 (m, 2H), 1.43-1.25 (m, 2H), 1.24-1.10 (m, 1H), 1.05-0.91 (m, 1H). |
| 57 | A | 2nd eluting isomer | 3-(4-((S)-6-((R)-tetrahydrofuran-2-carbonyl)-6-azaspiro[2.5]octan-1-yl)phenyl)quinoline-8-carboxylic acid | 457 | 1H-NMR (CD₃OD, 400 MHz) δ (ppm): 9.38 (s, 1H), 8.85 (s, 1H), 7.69 (d, J = 7.2 Hz, 1H), 7.37 (d, J=7.2 Hz, 1H), 7.97-7.69 (m, 3H), 7.47 (s, 2H), 4.82-4.64 (m, 1H), 4.05-3.61 (m, 4H), 3.60-3.38 (m, 2H), 2.32-1.81 (m, 5H), 1.79-1.57 (m, 2H), 1.52-1.12 (m, 3H), 1.09-0.91 (m, 1H). |

Figure 2-18

| 58 | A | 1st eluting isomer | 6-methyl-4'-(6-((R)-tetrahydrofuran-2-carbonyl)-6-azaspiro[2.5]octan-1-yl)-[1,1'-biphenyl]-3-carboxylic acid | 420 | 1H-NMR (CD₃OD, 400 MHz) δ (ppm): 7.98-7.89 (m, 1H), 7.89-7.80 (m, 1H), 7.50-7.31 (m, 3H), 7.31-7.23 (m, 2H), 4.81-4.62 (m, 1H), 4.04-3.92 (m, 1H), 3.92-3.59 (m, 3H), 3.56-3.40 (m, 2H), 2.33 (s, 3H), 2.30-2.12 (m, 2H), 2.12-1.84 (m, 3H), 1.83-1.25 (m, 4H), 1.21-1.09 (m, 1H), 1.03-0.92 (m, 1H). |
| --- | --- | --- | --- | --- | --- |
| 59 | C | 2nd eluting isomer | | 420 | 1H-NMR (CD3OD, 400 MHz) δ (ppm): 7.99-7.79 (m, 2H), 7.48-7.18 (m, 5H), 4.85-4.61 (m, 1H), 4.06-3.61 (m, 4H), 3.61-3.40 (m, 2H), 2.33 (s, 3H), 2.29-2.12 (m, 2H), 2.12-1.81 (m, 3H), 1.71-1.50 (m, 2H), 1.44-1.22 (m, 2H), 1.20-1.09 (m, 1H), 1.08-0.82 (m, 1H). |
| 60 | A | 1st eluting isomer | 2-chloro-4'-(6-((R)-tetrahydrofuran-2-carbonyl)-6-azaspiro[2.5]octan-1-yl)-[1,1'-biphenyl]-4-carboxylic acid | 440, 442 | 1H-NMR (CD₃OD, 400 MHz) δ (ppm): 8.11 (s, 1H), 7.98 (d, J=8.0 Hz, 1H), 7.49-7.31 (m, 5H), 4.82-4.65 (m, 1H), 4.03-3.91 (m, 1H), 3.90-3.63 (m, 3H), 3.54-3.41 (m, 2H), 2.30-2.11 (m, 2H), 2.10-1.89 (m, 3H), 1.78-1.56 (m, 2H), 1.47-1.22 (m, 2H), 1.19-1.12 (m, 1H), 1.01-0.94 (m, 1H). |

Figure 2-19

| # | | | Name | Mass | 1H-NMR |
|---|---|---|---|---|---|
| 61 | C | 2nd eluting isomer | | 440, 442 | 1H-NMR (CD₃OD, 400 MHz) δ (ppm): 8.11 (s, 1H), 7.99 (d, J=8.0 Hz, 1H), 7.51-7.31 (m, 5H), 4.84-4.61 (m, 1H), 4.02-3.91 (m, 1H), 3.90-3.65 (m, 3H), 3.58-3.39 (m, 2H), 2.32-2.11 (m, 2H), 2.10-1.89 (m, 3H), 1.78-1.53 (m, 2H), 1.42-1.21 (m, 2H), 1.19-1.13 (m, 1H), 1.01-0.95 (m, 1H). |
| 62 | A | 1st eluting isomer | 6-chloro-4'-(6-((R)-tetrahydrofuran-2-carbonyl)-6-azaspiro[2.5]octan-1-yl)-[1,1'-biphenyl]-3-carboxylic acid | 440 | 1H-NMR (CD₃OD, 400 MHz) δ (ppm): 8.04-7.87 (m, 2H), 7.71-7.56(m, 1H), 7.44-7.30 (m, 4H), 4.84-4.62(m, 1H), 4.07-3.91(m, 1H), 3.91-3.55(m, 3H), 3.53-3.39(m, 2H), 2.34-2.09(m, 2H), 2.09-1.82 (m, 3H), 1.82-1.55 (m, 2H), 1.51-1.22 (m, 2H), 1.22-1.08 (m, 1H), 1.03-0.93 (m, 1H). |
| 63 | C | 2nd eluting isomer | | 440 | 1H-NMR (CD₃OD, 400 MHz) δ (ppm): 8.09-7.88 (m, 2H), 7.71-7.54(m, 1H), 7.47-7.27 (m, 4H), 4.83-4.58(m, 1H), 4.04-3.49(m, 5H), 3.47-3.37(m, 1H), 2.33-2.12(m, 2H), 2.12-1.82 (m, 3H), 1.79-1.53 (m, 2H), 1.42-1.20 (m, 2H), 1.20-1.03 (m, 1H), 1.03-0.87 (m, 1H). |
| 64 | A | 1st eluting isomer | 2-methyl-4'-(6-((R)-tetrahydrofuran-2-carbonyl)-6-azaspiro[2.5]octan-1-yl)-[1,1'-biphenyl]-4-carboxylic acid | 420 | 1H-NMR (CD₃OD, 400 MHz) δ (ppm): 7.95 (s, 1H), 7.89 (d, J = 8.0 Hz, 1H), 7.36-7.28 (m, 5H), 4.80-4.68 (m, 1H), 3.99-3.63 (m, 4H), 3.51-3.36 (m, 2H), 2.32 (s, 3H), 2.26-2.13 (m, 2H), 2.07-1.89 (m, 3H), 1.76-1.58 (m, 2H), 1.43-1.26 (m, 2H), 1.16-1.12 (m, 1H), 0.99-0.96 (m, 1H). |

Figure 2-20

| | | | | | |
|---|---|---|---|---|---|
| 65 | C | 2nd eluting isomer | | 420 | 1H-NMR (CD3OD, 400 MHz) δ (ppm): 7.95 (s, 1H), 7.89 (d, J = 8.0 Hz, 1H), 7.36-7.28 (m, 5H), 4.80-4.67 (m, 1H), 3.99-3.67 (m, 4H), 3.54-3.40 (m, 2H), 2.32 (s, 3H), 2.26-2.14 (m, 2H), 2.07-1.91 (m, 3H), 1.75-1.56 (m, 2H), 1.41-1.25 (m, 2H), 1.16-1.13 (m, 1H), 0.99-0.96 (m, 1H). |
| 66 | A | 1st eluting isomer | 3-methoxy-4-{4-[6-[(2R)-oxolane-2-carbonyl]-6-azaspiro[2.5]octan-1-yl]phenyl}benzoic acid | 436 | 1H-NMR (CD3OD, 400 MHz) δ (ppm): 7.72-7.68 (m, 2H), 7.50-7.44 (m, 2H), 7.41-7.36 (m, 1H), 7.31-7.23 (m, 2H), 4.79-4.61 (m, 1H), 3.99-3.65 (m, 7H), 3.47-3.23 (m, 2H), 2.24-1.85 (m, 5H), 1.72-1.54 (m, 2H), 1.41-1.22 (m, 2H), 1.15-1.06 (m, 1H), 0.97-0.90 (m, 1H). |
| 67 | C | 2nd eluting isomer | | 436 | 1H-NMR (CD3OD, 400 MHz) δ (ppm): 7.72-7.69 (m, 2H), 7.50-7.46 (m, 2H), 7.42-7.39 (m, 1H), 7.31-7.27 (m, 2H), 4.80-4.64 (m, 1H), 3.99-3.82 (m, 5H), 3.76-3.67 (m, 2H), 3.55-3.37 (m, 2H), 2.26-2.11 (m, 2H), 2.06-1.90 (m, 3H), 1.74-1.57 (m, 2H), 1.37-1.24 (m, 2H), 1.14-1.12 (m, 1H), 0.97-0.94 (m, 1H). |

Figure 2-21

| 68 | A | 1st eluting isomer | 4-methoxy-3-{4-[(1S)-6-[(2R)-oxolane-2-carbonyl]-6-azaspiro[2.5]octan-1-yl]phenyl}benzoic acid | 420 | 1H-NMR (CD₃OD, 400 MHz) δ (ppm): 7.98-7.89 (m, 1H), 7.89-7.80 (m, 1H), 7.50-7.31 (m, 3H), 7.31-7.23 (m, 2H), 4.81-4.62 (m, 1H), 4.04-3.92 (m, 1H), 3.92-3.59 (m, 3H), 3.56-3.40 (m, 2H), 2.33 (s, 3H), 2.30-2.12 (m, 2H), 2.12-1.84 (m, 3H), 1.83-1.25 (m, 4H), 1.21-1.09 (m, 1H), 1.03-0.92 (m, 1H). |
|---|---|---|---|---|---|
| 69 | D | 2nd eluting isomer | 4-methoxy-3-{4-[(1R)-6-[(2R)-oxolane-2-carbonyl]-6-azaspiro[2.5]octan-1-yl]phenyl}benzoic acid | 420 | 1H-NMR (CD₃OD, 400 MHz) δ (ppm): 7.99-7.79 (m, 2H), 7.48-7.18 (m, 5H), 4.85-4.61 (m, 1H), 4.06-3.61 (m, 4H), 3.61-3.40 (m, 2H), 2.33 (s, 3H), 2.29-2.12 (m, 2H), 2.12-1.81 (m, 3H), 1.71-1.50 (m, 2H) 1.44-1.22 (m, 2H), 1.20-1.09 (m, 1H), 1.08-0.82 (m, 1H). |
| 70 | B | 1st eluting isomer | 4-chloro-4'-(6-((R)-tetrahydrofuran-2-carbonyl)-6-azaspiro[2.5]octan-1-yl)-[1,1'-biphenyl]-3-carboxylic acid | 440 | 1H-NMR (CD₃OD, 400 MHz) δ (ppm): 8.06-8.02 (m, 1H), 7.78-7.73 (m, 1H), 7.63-7.54 (m, 3H), 7.38-7.33 (m, 2H), 4.84-4.66 (m, 1H), 4.02-3.92 (m, 1H), 3.91-3.60 (m, 3H), 3.50-3.21(m,2H), 2.30-2.15(m, 2H), 2.10-1.85(m, 3H), 1.80-1.61(m, 2H), 1.41-1.23(m, 2H), 1.18-1.11(m,1H), 1.00-0.91(m, 1H). |

Figure 2-22

| | | | | |
|---|---|---|---|---|
| 71 | C | 2nd eluting isomer | 440 | 1H-NMR (CD3OD, 400 MHz) δ (ppm): 8.06-8.02 (m, 1H), 7.78-7.73 (m, 1H), 7.63-7.54 (m, 3H), 7.36 (d, J=8.0 Hz, 2H), 4.84-4.65 (m, 1H), 4.01-3.92 (m, 1H), 3.92-3.60 (m, 3H), 3.50-3.25 (m, 2H), 2.29-2.12 (m, 2H), 2.10-1.87 (m, 3H), 1.82-1.56 (m, 2H), 1.39-1.18 (m, 2H), 1.15-1.05(m, 1H), 1.00-0.92 (m, 1H). |
| 72 | A | 1st eluting isomer | 475 | 1H NMR (CD3OD, 400 MHz) δ (ppm): 9.39 (s, 1H), 9.01 (s, 1H), 8.32 (s, 1H), 8.20-8.15 (m, 1H), 8.04-8.01 (m, 1H), 7.66-7.57 (m, 2H), 7.35-7.34 (m, 1H), 4.85-4.67 (m, 1H), 4.02--3.48 (m, 5H), 3.47-3.21 (m, 1H), 2.26-1.88 (m, 5H), 1.80-1.60 (m, 2H), 1.30-1.20 (m, 3H), 1.07-1.03 (m, 1H). |
| 73 | B | 2nd eluting isomer | 7-(3-fluoro-4-(6-((R)-tetrahydrofuran-2-carbonyl)-6-azaspiro[2.5]octan-1-yl)phenyl)quinoline-3-carboxylic acid | 475 | 1H NMR (CD3OD, 400 MHz) δ (ppm): 9.40 (s, 1H), 9.01 (s, 1H), 8.32 (s, 1H), 8.20-8.15 (m, 1H), 8.04-8.01 (m, 1H), 7.66-7.57 (m, 2H), 7.54-7.24 (m, 1H), 4.85-4.66 (m, 1H), 3.99-3.48 (m, 5H), 3.51-3.40 (m, 1H), 2.28-1.12 (m, 2H), 2.10-1.88 (m, 3H), 1.70-1.61 (m, 1H), 1.35-1.29 (m, 3H), 1.24-1.19 (m, 1H), 1.09-1.04 (m, 1H). |

Figure 2-23

| | | | | |
|---|---|---|---|---|
| 74 | B | 1st eluting isomer | 1-methyl-6-(4-(6-((R)-tetrahydrofuran-2-carbonyl)-6-azaspiro[2.5]octan-1-yl)cyclohexyl)-1H-indazole-3-carboxylic acid | 460 | 1H-NMR (CD3OD, 400 MHz) δ (ppm): 8.33 (s, 1H), 7.78-7.75 (m, 1H), 7.71-7.69(m,1 H), 7.61 (d, J=8.0 Hz, 2H), 7.33 (d, J=8.0 Hz, 2H), 4.94-4.63 (m,1H), 4.19 (s, 3H), 3.95-3.92 (m, 1H), 3.88-3.80 (m, 1H), 3.74-3.65 (m, 2H), 3.41-3.34 (m, 1H), 3.33-3.25 (m, 1H), 2.15-2.11 (m, 2H), 1.99-1.87 (m, 3H), 1.60-1.51 (m, 2H), 1.35-1.28 (m, 2H), 1.21-1.11 (m, 1H), 0.96-0.91 (m, 1H) |
| 75 | A | 2nd eluting isomer | | 460 | 1H-NMR (CD3OD, 400 MHz) δ (ppm): 8.33 (s, 1H), 7.79-7.72 (m, 2H), 7.64-7.62(m, 2 H), 7.50-7.25 (m, 2H), 4.89-4.66 (m, 1H), 4.21 (s, 3H), 3.99-3.61 (m, 4H), 3.53-3.35 (m, 2H), 2.24-1.80 (m, 5H), 1.79-1.51 (m, 2H), 1.48-1.17 (m, 2H), 1.15-0.85 (m, 2H). |
| 76 | A | 1st eluting isomer | 5-(4-(6-((R)-tetrahydrofuran-2-carbonyl)-6-azaspiro[2.5]octan-1-yl)phenyl)thiophene-3-carboxylic acid | 412 | 1H-NMR (400 MHz, CD3OD) δ (ppm): 8.13 (s, 1H), 7.71 (s, 1H), 7.59 (d, J = 8.0 Hz, 2H), 7.32-7.29 (m, 2H), 4.77-4.67 (m, 1H), 4.01-3.91 (m, 1H), 3.90-3.70 (m, 2H), 3.69-3.60 (m, 1H), 3.50-3.40 (m, 1H), 3.32-3.22 (m, 1H), 2.29-2.10 (m, 2H), 2.06-1.82 (m, 3H), 1.74-1.50 (m, 2H), 1.42-1.21 (m, 2H), 1.20-1.08 (m, 1H), 1.00-092 (m, 1H). |

Figure 2-24

| | | | | |
|---|---|---|---|---|
| 77 | C | 2nd eluting isomer | | 412 | 1H-NMR (400 MHz, CD3OD) δ (ppm): 8.13 (s, 2H), 7.71 (s, 1H), 7.59 (d, J = 8.0 Hz, 2H), 7.31 (d, J = 8.0 Hz, 2H), 4.77-4.65 (m, 1H), 3.98-3.79 (m, 2H), 3.75-3.62 (m, 2H), 3.55-3.24 (m, 2H), 2.29-2.10 (m, 2H), 2.09-1.85 (m, 3H), 1.75-1.53 (m, 2H), 1.37-1.17 (m, 2H), 1.15-1.09 (m, 1H), 1.01-0.93 (m, 1H). |
| 78 | D | 1st eluting isomer | 5-(4-(6-((R)-tetrahydrofuran-2-carbonyl)-6-azaspiro[2.5]octan-1-yl)phenyl)thiophene-2-carboxylic acid | 412 | 1H-NMR (d6-DMSO, 400 MHz) δ (ppm): 13.14 (br, 1H), 7.69 (d, J=4.0 Hz, 1H), 7.65 (d, J=4.0 Hz, 2H), 7.54 (d, J=8.0 Hz, 1H), 7.33 (d, J=7.6 Hz, 2H), 4.80-4.45 (m, 1H), 3.88-3.62 (m, 2H), 3.62-3.48 (m, 2H), 3.48-3.38 (m, 1H), 3.22-3.00 (m, 1H), 2.19-2.08 (m, 1H), 2.08-1.91 (m, 2H), 1.89-1.67 (m, 2H), 1.66-1.30 (m, 2H), 1.29-0.97 (m, 3H), 0.96-0.80 (m, 1H). |
| 79 | A | 2nd eluting isomer | | 412 | 1H-NMR (d6-DMSO, 400 MHz) δ (ppm): 13.12 (br, 1H), 7.69 (d, J=3.6 Hz, 1H), 7.65 (d, J=8.0 Hz, 2H), 7.55 (d, J=3.6 Hz, 1H), 7.35 (d, J=8.0 Hz, 2H), 4.76-4.46 (m, 1H), 3.89-3.67 (m, 2H), 3.65-3.45 (m, 2H), 3.44-3.35 (m, 1H), 3.20-3.00 (m, 1H), 2.18-2.09 (m, 1H), 2.08-1.89 (m, 2H), 1.88-1.68 (m, 2H), 1.62-1.35 (m, 2H), 1.34-1.02 (m, 3H), 1.00-0.75 (m, 1H). |

Figure 2-25

| | | | | |
|---|---|---|---|---|
| 80 | D | 1st eluting isomer | 406 | 1H-NMR (CD₃OD, 400 MHz) δ (ppm): 8.09 (d, J = 8.0 Hz, 2H), 7.74 (d, J = 8.0 Hz, 2H), 7.64 (d, J = 7.6 Hz, 2H), 7.36 (d, J = 4.4 Hz, 2H), 4.79-4.61 (m, 1H), 3.96-3.59 (m, 4H), 3.52-3.20 (m, 2H), 2.21-1.82 (m, 5H), 1.78-1.59 (m, 2H), 1.57-1.22 (m, 2H), 1.19-1.11 (m, 1H), 0.98-0.92 (m,1H). |
| 81 | B | 2nd eluting isomer | 406 | 1H-NMR (CD₃OD, 400 MHz) δ (ppm): 8.09-8.07 (d, J = 8.0 Hz, 2H), 7.74 (d, J = 6.8 Hz, 2H), 7.63(d, J = 8.0 Hz, 2H), 7.37 (d, J = 8.0 Hz, 2H), 4.85-4.62 (m, 2H), 3.99-3.61 (m, 4H), 3.60-3.38 (m, 1H), 2.38-2.11 (m, 2H), 2.09-1.81(m, 3H), 1.80-1.55(m, 2H), 1.35-1.13 (m, 3H), 0.98-0.91 (m,1H). |
| 82 | D | 1st eluting isomer | 447 | 1H-NMR (CD₃OD, 400 MHz) δ (ppm): 8.21 (s, 1H), 8.31-8.04 (m, 3H), 7.84-7.63(m, 1H), 7.57-7.28 (m, 2H), 4.83-4.49(m, 1H), 4.07-3.61(m, 4H), 3.61-3.15(m, 2H), 2.37-2.09(m, 2H), 2.09-1.80 (m, 3H), 1.80-1.47 (m, 2H), 1.39-1.13 (m, 4H). |
| 83 | B | 2nd eluting isomer | 447 | 1H-NMR (CD₃OD, 400 MHz) δ (ppm): 8.39 (s, 1H), 8.29-8.04 (m, 3H), 7.86-7.68(m, 1H), 7.57-7.38 (m, 2H), 4.86-4.55(m, 1H), 4.07-3.57(m, 4H), 3.52-3.32(m, 2H), 2.28-1.84(m, 5H), 1.82-1.52 (m, 2H), 1.51-1.20 (m, 4H). |

Compound 80/81: 4-{4-[6-[(2S)-oxolane-2-carbonyl]-6-azaspiro[2.5]octan-1-yl]phenyl}benzoic acid Compound 82/83: 2-(4-(6-((R)-tetrahydrofuran-2-carbonyl)-6-azaspiro[2.5]octan-1-yl)phenyl)benzo[d]oxazole-5-carboxylic acid

Figure 2-26

| 84 | B | 1st eluting isomer | 7-(4-(6-((R)-tetrahydrofuran-2-carbonyl)-6-azaspiro[2.5]octan-1-yl)cyclohexan-1-yl)quinoline-3-carboxylic acid | 457 | 1H-NMR (DMSO-d6, 400 MHz) δ (ppm): 9.35 (s, 1H), 8.93 (s, 1H), 8.32 (s, 1H), 8.24 (d, J = 8.4 Hz, 1H), 8.04 (d, J = 8.4 Hz, 1H), 7.82 (d, J = 8.0 Hz, 2H), 7.41 (d, J = 8.0 Hz, 2H), 4.74-4.52 (m, 1H), 3.83-3.52 (m, 2H), 3.47-3.05 (m, 3H), 2.17-2.08 (m, 1H), 2.08-1.87 (m, 2H), 1.85-1.72 (m, 2H), 1.64-1.46 (m, 2H), 1.32-1.21 (m, 1H), 1.20-1.05 (m, 2H), 1.04 (d, J = 6.0 Hz, 1H), 0.96-0.87 (m, 1H) |
|---|---|---|---|---|---|
| 85 | B | 2nd eluting isomer | | 457 | 1H-NMR (DMSO-d6, 400 MHz) δ (ppm): 9.34 (s, 1H), 8.73 (s, 1H), 8.26 (s, 1H), 8.13 (d, J = 8.4 Hz, 1H), 7.95 (d, J = 8.8Hz, 1H), 7.80 (d, J = 8.0 Hz, 2H), 7.40 (d, J = 8.4 Hz, 2H), 4.73-4.55(m, 1H), 3.82-3.62 (m, 3H), 3.62-3.56 (m, 2H), 3.26-3.13 (m, 1H), 2.16-2.11 (m, 1H), 2.09-1.92 (m, 2H), 1.88-1.70 (m, 2H), 1.65-1.48 (m, 2H), 1.32-1.07 (m, 3H), 0.95-0.89 (m, 1H). |
| 86 | C | 1st eluting isomer | 2-(4-(6-(1-hydroxycyclopropane-1-carbonyl)-6-azaspiro[2.5]octan-1-yl)cyclohexyl)benzo[d]oxazole-5-carboxylic acid | 433 | 1H-NMR (CD3OD, 400 MHz) δ (ppm): 8.41 (s, 1H), 8.27-7.98 (m, 3H), 7.82-7.69(m, 1H), 7.58-7.38 (m, 2H), 4.23-3.39(m, 4H), 2.37-2.12(m, 1H), 1.84-1.48 (m, 2H), 1.48-1.29 (m, 2H), 1.29-1.19 (m, 1H), 1.09-0.93 (m, 3H), 0.93-0.73 (m, 2H). |

Figure 2-27

| | | | | |
|---|---|---|---|---|
| 87 | A | 2nd eluting isomer | | 433 | 1H-NMR (CD₃OD, 400 MHz) δ (ppm): 8.41 (s, 1H), 8.31-8.03 (m, 3H), 7.84-7.67(m, 1H), 7.55-7.37 (m, 2H), 4.28-3.39(m, 4H), 2.33-2.12(m, 1H), 1.84-1.53 (m, 2H), 1.47-1.30 (m, 2H), 1.30-1.19 (m, 1H), 1.09-0.98 (m, 3H), 0.98-0.69 (m, 2H). |
| 88 | B | 1st eluting isomer | 6-(4-(6-((R)-tetrahydrofuran-2-carbonyl)-6-azaspiro[2.5]octan-1-yl)phenyl)-1H-indazole-3-carboxylic acid | 445.51 | 1H-NMR (CD₃OD, 400 MHz) δ (ppm): 8.22 (d, J=8.0 Hz, 1H), 7.80 (s, 1H), 7.66 (d, J=7.6 Hz, 2H), 7.61 (d, J=8.0 Hz, 1H), 7.42-7.34 (m, 2H), 4.81-4.62 (m, 1H), 4.01-3.91 (m, 1H), 3.90-3.74 (m, 2H), 3.72-3.61 (m, 1H), 3.53-3.39 (m, 2H), 2.30-2.10 (m, 2H), 2.09-1.81 (m, 3H), 1.80-1.52 (m, 2H), 1.49-1.24 (m, 2H), 1.23-1.09 (m, 1H), 1.02-0.91 (m, 1H). |
| 89 | D | 2nd eluting isomer | | 445.51 | 1H-NMR (CD₃OD, 400 MHz) δ (ppm): 8.22 (d, J=8.0 Hz, 1H), 7.79 (s, 1H), 7.66 (d, J=8.0 Hz, 2H), 7.61 (d, J=8.8 Hz, 1H), 7.37 (d, J=8.0 Hz, 2H), 4.81-4.63 (m, 1H), 4.10-3.80 (m, 2H), 3.79-3.62 (m, 2H), 3.61-3.49 (m, 1H), 3.47-3.39 (m, 1H), 2.41-2.11 (m, 2H), 2.10-1.84 (m, 3H), 1.80-1.54 (m, 2H), 1.48-1.19 (m, 2H), 1.21-1.08 (m, 1H), 1.01-0.91 (m, 1H). |

Figure 2-28

| | | | | |
|---|---|---|---|---|
| 90 | D | 1st eluting isomer | | 440, 442 | 1H-NMR (CD3OD, 400 MHz) δ (ppm): 8.15-8.08 (m, 2H), 7.77-7.76 (m, 3H), 7.60 (d, J = 8.0 Hz, 1H), 7.30 (d, J = 8.0 Hz, 1H), 4.82-4.65 (m, 1H), 4.11-3.78 (m, 3H), 3.73-3.47 (m, 2H), 2.30-2.10 (m, 2H), 2.08-1.78 (m, 4H), 1.71-1.48 (m, 1H), 1.44-0.88 (m, 5H). |
| 91 | B | 2nd eluting isomer | 4-{3-chloro-4-[6-[(2R)-oxolane-2-carbonyl]-6-azaspiro[2.5]octan-1-yl]phenyl}benzoic acid | 440, 442 | 1H-NMR (CD3OD, 400 MHz) δ (ppm): 8.15-8.07 (m, 2H), 7.80-7.72 (m, 3H), 7.60 (d, J = 8.0 Hz, 1H), 7.30 (d, J = 8.0 Hz, 1H), 4.81-4.65 (m, 1H), 4.14-3.78 (m, 3H), 3.70-3.48 (m, 1H), 3.42-3.38 (m, 1H), 2.29-1.74 (m, 5H), 1.63-1.51 (m, 1H), 1.38-1.12 (m, 4H), 1.08-1.00 (m, 1H), 0.96-0.88 (m, 1H). |
| 92 | D | 1st eluting isomer | 4'-(6-(1-aminocyclopropane-1-carbonyl)-6-azaspiro[2.5]octan-1-yl)-[1,1'-biphenyl]-3-carboxylic acid | 391 | 1H NMR (DMSO-d6, 400 MHz) δ (ppm): 8.20-8.13 (m, 2H), 7.99-7.90 (m, 2H), 7.71-7.55 (m, 3H), 7.37 (d, J = 8.0 Hz, 2H), 7.25-6.35 (m, 1H), 3.74-3.56 (m, 2H), 3.50-3.42 (m, 1H), 3.28-3.19 (m, 1H), 2.14-2.06 (m, 1H), 1.58-1.49 (m, 2H), 1.33-1.21 (m, 1H), 1.17-1.08 (m, 2H), 0.93-0.86 (m, 1H), 0.84-0.77 (m, 2H), 0.66-0.59 (m, 2H). |

Figure 2-29

| | | | | |
|---|---|---|---|---|
| 93 | B | 2nd eluting isomer | | 391 | 1H NMR (DMSO-d6, 400 MHz) δ (ppm): 8.21-8.15 (m, 2H), 7.93-9.90 (m, 2H), 7.64-7.57 (m, 3H), 7.41-7.35 (m, 2H), 7.28-5.99 (m, 1H), 3.75-3.42 (m, 4H), 2.18-2.08 (m, 1H), 1.58-1.50 (m, 2H), 1.31-1.20 (m, 1H), 1.17-1.10 (m, 2H), 0.93-0.87 (m, 1H), 0.84-0.76 (m, 2H), 0.67-0.57 (m, 2H). |
| 94 | D | 1st eluting isomer | 3'-chloro-4'-(6-(1-hydroxycyclopropane-1-carbonyl)-6-azaspiro[2.5]octan-1-yl)-[1,1'-biphenyl]-4-carboxylic acid | 426, 428 | 1H NMR (400 MHz, CD$_3$OD) δ (ppm): 8.11 (d, J= 8.0 Hz, 2H), 7.76-7.74 (m, 3H), 7.60 (d, J= 7.2 Hz, 1H), 7.31 (d, J= 8.0 Hz, 1H), 4.27-3.43 (m, 4H), 2.25-2.18 (m, 1H), 1.92-1.84 (m, 1H), 1.65-1.56 (m, 1H), 1.37-1.26 (m, 1H), 1.22-0.98 (m, 5H), 0.89-1.82 (m, 2H) |
| 95 | B | 2nd eluting isomer | | 426, 428 | 1H NMR (400 MHz, CD$_3$OD) δ (ppm): 8.11 (d, J= 8.0 Hz, 2H), 7.76-7.74 (m, 3H), 7.60 (d, J= 7.2 Hz, 1H), 7.31 (d, J= 7.6 Hz, 1H), 4.26-3.43 (m, 4H), 2.23-2.19 (m, 1H), 1.92-1.84 (m, 1H), 1.67-1.56 (m, 1H), 1.37-1.25 (m, 1H), 1.23-0.98 (m, 5H), 0.89-1.83 (m, 2H). |
| 96 | A | 1st eluting isomer | 2'-chloro-4'-(6-((R)-tetrahydrofuran-2-carbonyl)-6-azaspiro[2.5]octan-1-yl)-[1,1'-biphenyl]-4-carboxylic acid | 440 | 1H-NMR (CD$_3$OD, 400 MHz) δ (ppm): 8.09 (d, J = 8.0 Hz, 2H), 7.54 (d, J = 8.0 Hz, 2H), 7.41-7.23 (m, 3H), 4.85-4.68 (m, 1H), 3.97-3.63(m, 4H), 3.56-3.35(m, 2H), 2.32-1.88 (m, 5H), 1.80-1.31 (m, 4H), 1.20-0.99 (m, 2H). |

Figure 2-30

| | | | | |
|---|---|---|---|---|
| 97 | C | 2nd eluting isomer | | 440 | 1H-NMR (CD₃OD, 400 MHz) δ (ppm): 8.09 (d, J = 8.0 Hz, 2H), 7.55 (d, J = 8.0 Hz, 2H), 7.42-7.28 (m, 3H), 4.79-4.67 (m, 1H), 3.97-3.63(m, 4H), 3.58-3.35(m, 2H), 2.31-1.89 (m, 5H), 1.72-1.21 (m, 4H), 1.15-0.95 (m, 2H). |
| 98 | B | 1st eluting isomer | 2-(4-(6-((R)-tetrahydrofuran-2-carbonyl)-6-azaspiro[2.5]octan-1-yl)cyclohexan-1-yl)-3H-113-benzo[d]oxazole-6-carboxylic acid | 447 | 1H-NMR (CD₃OD, 400 MHz) δ (ppm): 8.31 (s, 1H), 8.21 (d, J=8.0 Hz, 2H), 8.11 (d, J=8.0 Hz, 2H), 7.76 (d, J=7.6 Hz, 2H), 7.50 (d, J=7.6 Hz, 2H), 4.82-4.63 (m,1H), 4.02-3.62 (m, 4H), 3.49-3.36 (m,2H), 2.28-1.82 (m, 5H),1.80-1.61(m, 2H), 1.45-1.22(m, 3H), 1.09-1.02 (m,1H). |
| 99 | C | 2nd eluting isomer | | 447 | 1H-NMR (CD₃OD, 400 MHz) δ (ppm): 8.31 (s, 1H), 8.21 (d, J=7.6 Hz, 2H), 8.12 (d, J=8.8 Hz, 2H), 7.76 (d, J=8.4Hz, 2H), 7.52-7.45 (m, 2H), 4.85-4.62(m, 1H), 4.02-3.62 (m, 4H), 3.49-3.36 (m, 2H), 2.32-1.87 (m, 5H), 1.80-1.59(m, 2H), 1.52-1.21 (m, 3H), 1.09-1.01 (m,1H). |
| 100 | D | 1st eluting isomer | 2-chloro-5-{4-[6-(1-hydroxycyclopropanecarbonyl)-6-azaspiro[2.5]octan-1-yl]phenyl}benzoic acid | 426 | 1H NMR (400 MHz, CD₃OD) δ (ppm): 8.08 (d, J = 2.3 Hz, 1H), 7.76 (d, J = 8.4 Hz, 1H), 7.63-7.53 (m, 3H), 7.36 (d, J = 7.6 Hz, 2H), 4.13-3.40 (m, 4H), 2.17-2.13 (m, 1H), 1.72-1.58 (s, 2H), 1.40-1.25 (m, 2H), 1.16-1.13 (m, 1H), 1.09-0.98 (m, 3H), 0.89-0.82 (m, 2H). LCMS (ES, m/z): 426 [M+H]+. |

Figure 2-31

| | | | | |
|---|---|---|---|---|
| 101 | B | 2nd eluting isomer | | 426 | 1H NMR (400 MHz, CD3OD) δ (ppm): 8.07 (s, 1H), 7.74 (d, J = 8.4 Hz, 1H), 7.62-7.54 (m, 3H), 7.35 (d, J = 7.8 Hz, 2H), 4.15-3.40 (m, 4H), 2.17-2.10 (m, 1H), 1.71-1.59 (m, 2H), 1.41-1.22 (m, 2H), 1.15-1.11 (m, 1H), 1.09-0.91 (m, 3H), 0.90-0.82 (m, 2H). LCMS (ES, m/z): 426 [M+H]+ |
| 102 | C | 1st eluting isomer | 7-(3-fluoro-4-(6-(1-hydroxycyclopropane-1-carbonyl)-6-azaspiro[2.5]octan-1-yl)phenyl)quinoline-3-carboxylic acid | 461 | 1H NMR (DMSO-d6, 400 MHz) δ (ppm):13.55 (br, 1H), 9.34 (s, 1H), 9.01 (s, 1H), 8.43-8.35 (m, 1H), 8.31-8.28 (m, 1H), 8.13-8.04 (m, 1H), 7.85-7.64 (m, 2H), 7.37-7.30 (m, 1H), 6.50-6.05 (m, 1H), 3.97-3.58 (m, 4H), 2.13-2.05 (m, 1H), 1.59-1.51 (m, 2H), 1.28-1.06 (m, 3H), 1.00-0.65 (m, 5H). |
| 103 | A | 2nd eluting isomer | | 461 | 1H NMR (DMSO-d6, 400 MHz) δ (ppm):13.55 (br, 1H), 9.34 (s, 1H), 9.01 (s, 1H), 8.41-8.36 (m, 1H), 8.31-8.28 (m, 1H), 8.13-8.06 (m, 1H), 7.81-7.68 (m, 2H), 7.37-7.32 (m, 1H), 6.33-6.17 (m, 1H), 3.95-3.42 (m, 4H), 2.10-2.07 (m, 1H), 1.59-1.51 (m, 2H), 1.28-1.09 (m, 3H), 1.02-0.96 (m, 1H), 0.94-0.83 (m, 2H), 0.81-0.67 (m, 2H). |

Figure 2-32

| | | | | 1H-NMR (CD3OD, 400 MHz) δ (ppm) |
|---|---|---|---|---|
| 104 | D | 1st eluting isomer | 6-(6-((R)-tetrahydrofuran-2-carbonyl)-6-azaspiro[2.5]octan-1-yl)-2-naphthoic acid | 380 | 1H-NMR (CD3OD, 400 MHz) δ (ppm): 8.58 (s, 1H), 8.02 (d, J= 8.4 Hz, 1H), 7.98-7.84 (m, 2H), 7.71 (s, 1H), 7.56 (d, J= 8.0 Hz, 1H), 4.8-4.58 (m, 1H), 4.01-3.65 (m, 4H), 3.54-3.42 (m, 1H), 3.28-3.16 (m, 1H), 2.39-2.10 (m, 2H), 2.10-1.83 (m, 3H), 1.83-1.52 (m, 2H), 1.39-1.18 (m, 3H), 1.09-0.98 (m, 1H). |
| 105 | B | 2nd eluting isomer | | 380 | 1H-NMR (CD3OD, 400 MHz) δ (ppm): 8.58 (s, 1H), 8.03 (d, J= 7.6 Hz, 1H), 7.99-7.81 (m, 2H), 7.71 (s, 1H), 7.61-7.45 (m, 1H), 4.81-4.56 (m, 1H), 4.01-3.57 (m, 4H), 3.51-3.34 (m, 1H), 3.28-3.08 (m, 1H), 2.38-2.24 (m, 1H), 2.24-1.81 (m, 4H), 1.81-1.53 (m, 2H), 1.47-1.18 (m, 3H), 1.09-0.99 (m, 1H). |
| 106 | D | 1st eluting isomer | 2'-chloro-4'-(6-(1-hydroxycyclopropane-1-carbonyl)-6-azaspiro[2.5]octan-1-yl)-[1,1'-biphenyl]-4-carboxylic acid | 426 | 1H-NMR (CD3OD, 400 MHz) δ (ppm): 8.10 (d, J = 8.0 Hz, 2H), 7.55 (d, J = 8.0 Hz, 2H), 7.42-7.28 (m, 3H), 4.31-3.35 (m, 4H), 2.18-2.09 (m, 1H), 1.77-1.58 (m, 2H), 1.45-1.38 (m, 2H), 1.23-1.11 (m, 1H), 1.09-0.96 (m, 3H), 0.92-0.81 (m, 2H). |
| 107 | A | 2nd eluting isomer | | 426 | 1H-NMR (CD3OD, 400 MHz) δ (ppm): 8.09 (d, J = 8.4 Hz, 2H), 7.56 (d, J = 8.4 Hz, 2H), 7.46-7.22 (m, 3H), 4.28-3.35 (m, 4H), 2.18-2.10 (m, 1H), 1.80-1.59 (m, 2H), 1.40-1.27(m, 2H), 1.19-1.12(m, 1H), 1.08-0.97 (m, 3H), 0.95-0.82 (m, 2H). |

Figure 2-33

| | | | | 1H-NMR (CD₃OD, 400 MHz) δ (ppm): 8.31 (s, 1H), 8.23 (d, J=8.4 Hz, 2H), 8.13 (d, J=8.4 Hz, 1H), 7.79 (d, J=8.0 Hz, 1H), 7.51 (d, J=8.0 Hz, 2H), 4.21-3.35 (m, 4H), 2.27-2.22 (m, 1H), 1.85-1.51 (m, 2H), 1.43-1.24 (m, 3H), 1.13-0.99 (m, 3H), 0.98-0.77 (m, 2H). | 433 |
|---|---|---|---|---|---|
| 108 | D | 1st eluting isomer | 2-(4-(6-(1-hydroxycyclopropane-1-carbonyl)-6-azaspiro[2.5]octan-1-yl)phenyl)benzo[d]oxazole-6-carboxylic acid | | |
| 109 | B | 2nd eluting isomer | | 1H-NMR (CD₃OD, 400 MHz) δ (ppm): 8.32 (s, 1H), 8.23 (d, J=8.4 Hz, 2H), 8.14 (d, J=8.0 Hz, 1H), 7.81 (d, J=8.4 Hz, 1H), 7.51 (d, J=8.4 Hz, 2H), 4.20-3.38 (m, 4H), 2.29-2.19 (m, 1H), 1.82-1.55 (m, 2H), 1.41-1.25 (m, 3H), 1.10-0.95 (m, 3H), 0.95-0.75 (m, 2H). | 433 |
| 110 | B | 1st eluting isomer | (R)-7-(4-(6-(1-hydroxycyclopropane-1-carbonyl)-6-azaspiro[2.5]octan-1-yl)phenyl)quinoline-3-carboxylic acid | 1H NMR (400 MHz, CD₃OD) δ (ppm): 9.38 (s, 1H), 9.01 (s, 1H), 8.32 (s, 1H), 8.18 (d, J = 8.4 Hz, 1H), 8.05-8.03 (m, 1H), 7.79 (d, J = 8.0 Hz, 2H), 7.44 (d, J = 8.0 Hz, 2H), 4.24-3.41 (m, 4H), 2.21-2.17 (m, 1H), 1.75-1.60 (m, 2H), 1.42-1.29 (m, 2H), 1.20-1.17 (m, 1H), 1.07-0.99 (m, 3H), 0.92-0.83 (m, 2H). | 443 |

Figure 2-34

| 111 | A | 2nd eluting isomer | (S)-7-(4-(6-(1-hydroxycyclopropane-1-carbonyl)-6-azaspiro[2.5]octan-1-yl)phenyl)quinoline-3-carboxylic acid | 443 | 1H-NMR (400 MHz, CD3OD) δ (ppm): 9.39 (s,1H), 9.00 (s, 1H), 8.32 (s, 1H), 8.17 (d, J = 8.4 Hz, 1H), 8.04 (d, J = 8.8 Hz, 1H), 7.79 (d, J = 8.4 Hz, 2H), 7.44 (d, J = 8.0 Hz, 2H), 4.20-3.41 (m, 4H), 2.22-2.18 (m, 1H), 1.73-1.62 (m, 2H), 1.41-1.30 (m, 2H), 1.20-1.17 (m, 1H), 1.02-0.99 (m, 3H), 0.90-0.87 (m, 2H). |
| --- | --- | --- | --- | --- | --- |
| 112 | C | 1st eluting isomer | 5-(4-(6-(1-hydroxycyclopropane-1-carbonyl)-6-azaspiro[2.5]octan-1-yl)cyclohexyl)thiophene-3-carboxylic acid | 398 | 1H-NMR (400 MHz, CD3OD) δ (ppm): 8.10 (d, J = 1.6 Hz, 1H), 7.91 (d, J = 1.6 Hz, 1H), 7.62 (d, J = 8.0 Hz, 2H), 7.32 (d, J = 8.0 Hz, 2H), 4.15-3.40 (m, 4H), 2.15-2.11 (m, 1H), 1.70-1.60 (m, 2H), 1.41-1.19 (m, 2H), 1.14-1.11 (m, 1H), 1.06-0.92 (m, 3H), 0.90-0.81 (m, 2H). |
| 113 | A | 2nd eluting isomer | | 398 | 1H-NMR (400 MHz, CD3OD) δ (ppm): 8.10 (d, J = 1.6 Hz, 1H), 7.91 (d, J = 1.6 Hz, 1H), 7.62 (d, J = 8.0 Hz, 2H), 7.32 (d, J = 8.0 Hz, 2H), 4.10-3.40 (m, 4H), 2.15-2.11 (m, 1H), 1.70-1.60 (m, 2H), 1.40-1.23 (m, 2H), 1.18-1.12 (m, 1H), 1.05-0.93 (m, 3H), 0.90-0.84 (m, 2H). |

Figure 2-35

| 114 | C | 1st eluting isomer | 4'-((5S)-6-(1-hydroxycyclopropane-1-carbonyl)-5-methyl-6-azaspiro[2.5]octan-1-yl)-[1,1'-biphenyl]-4-carboxylic acid | 406 | 1HNMR (CD₃OD, 400 MHz) δ (ppm): 8.09 (d, J=8.0 Hz, 2H), 7.73 (d, J=8.0 Hz, 2H), 7.61 (d, J=8.4 Hz, 2H), 7.30 (d, J=8.0 Hz, 2H), 4.59-4.15 (m, 1H), 3.29-2.85 (m, 1H), 2.45-2.15 (m, 1H), 2.08-1.89 (m, 1H), 1.61-1.33 (m, 4H), 1.32-1.18 (m, 3H), 1.17-0.70 (m, 6H). |
| 115 | B | 2nd eluting isomer | | 406 | 1HNMR (CD₃OD, 400 MHz) δ (ppm): 8.09 (d, J=8.0 Hz, 2H), 7.73 (d, J=7.6 Hz, 2H), 7.62 (d, J=8.0 Hz, 2H), 7.30 (d, J=8.0 Hz, 2H), 4.59-4.23 (m, 1H), 3.28-2.82 (m, 1H), 2.29-2.00 (m, 1H), 2.00-1.82 (m, 1H), 1.78-1.55 (m, 1H), 1.54-1.26 (m, 4H), 1.25-1.02 (m, 4H), 1.00-0.71 (m, 4H). |
| 116 | D | 1st eluting isomer | 4'-((5S)-5-methyl-6-((R)-tetrahydrofuran-2-carbonyl)-6-azaspiro[2.5]octan-1-yl)-[1,1'-biphenyl]-4-carboxylic acid | 420 | 1H-NMR (CD₃OD, 400 MHz) δ (ppm): 8.08 (d, J=7.6 Hz, 2H), 7.73 (d, J=8.4 Hz, 2H), 7.62 (d, J=8.0 Hz, 2H), 7.30 (d, J=7.6 Hz, 2H), 4.79-4.59 (m, 1H), 4.48-4.27 (m, 1H), 4.03-3.87 (m, 1H), 3.86-3.72 (m, 1H), 3.41-3.35 (m, 1H), 2.40-2.22 (m, 1H), 2.21-2.10 (m, 1H), 2.90-1.80 (m, 4H), 1.69-1.42 (m, 2H), 1.40-1.20 (m, 5H), 1.18-1.05 (m, 1H), 0.95-0.78 (m, 1H). |

Figure 2-36

| | | | | |
|---|---|---|---|---|
| 117 | B | 2nd eluting isomer | | 420 | 1H-NMR (CD₃OD, 400 MHz) δ (ppm): 8.09 (d, J=7.6 Hz, 2H), 7.73 (d, J=8.4 Hz, 2H), 7.62 (d, J=8.0 Hz, 2H), 7.31 (d, J=8.0Hz, 2H), 4.85-4.60 (m, 2H), 4.59-4.23 (m, 1H), 4.09-3.79 (m, 2H), 3.52-3.35 (m, 1H), 2.30-1.81 (m, 6H), 1.71-1.51 (m, 1H), 1.48-1.09 (m, 6H), 0.92-0.72 (m, 1H). |
| 118 | B | 1st eluting isomer | 4'-(6-((R)-tetrahydrofuran-2-carbonyl)-2-azaspiro[2.5]octan-1-yl)-[1,1'-biphenyl]-4-carboxylic acid | 474 | 1H NMR (400 MHz, DMSO-d6) δ (ppm): 8.28 (s, 1H), 8.22 (d, J = 8.0 Hz, 1H), 7.58-7.54 (m, 1H), 7.36-7.33 (m, 2H), 7.28-7.25 (m, 2H), 4.70-4.58 (m, 1H), 3.83-3.49 (m, 4H), 3.27-3.15 (m, 2H), 2.12-1.77 (m, 5H), 1.64-1.42 (m, 2H), 1.33-1.00 (m, 3H), 0.97-0.82 (m, 1H). |
| 119 | D | 2nd eluting isomer | | 474 | 1H NMR (400 MHz, DMSO-d6) (ppm): 13.55 (br, 1H), 8.24 (s, 1H), 8.23-8.21 (m, 1H), 7.57 (d, J = 8.0 Hz, 1H), 7.36-7.33 (m, 2H), 7.28-7.25 (m, 2H), 4.70-4.58 (m, 1H), 3.78-3.53 (m, 4H), 3.25-3.07 (m, 2H), 2.13-1.76 (m, 5H), 1.57-1.44 (m, 2H), 1.23-1.00 (m, 3H), 0.92-0.87 (m, 1H). |
| 120 | C | 1st eluting isomer | 3-(4-(6-((R)-tetrahydrofuran-2-carbonyl)-6-azaspiro[2.5]octan-1-yl)phenyl)quinoline-7-carboxylic acid | 457 | 1H NMR (400 MHz, DMSO-d6) δ (ppm): 13.30 (br, 1H), 9.39-9.38 (m, 1H), 8.74 (s, 1H), 8.60 (s, 1H), 8.15-8.08 (m, 2H), 7.86 (d, J=8.4 Hz, 2H), 7.45 (d, J=8.4 Hz, 2H), 4.72-4.55 (m, 1H), 3.78-3.59 (m, 6H), 2.15-2.10 (m, 1H), 2.04-1.73 (m, 4H), 1.68-1.42 (m, 2H), 1.28-0.88 (m, 4H). |

Figure 2-37

| | | | | 1H NMR |
|---|---|---|---|---|
| 121 | A | 2nd eluting isomer | | 457 | 1H NMR (400 MHz, DMSO-d6) δ (ppm): 13.33 (br, 1H), 9.39 (s, 1H), 8.76 (s, 1H), 8.60 (s, 1H), 8.17-8.09 (m, 2H), 7.87 (d, J=8.0 Hz, 2H), 7.45 (d, J=8.4 Hz, 2H), 4.70-4.58 (m, 1H), 3.78-3.61 (m, 4H), 3.27-3.18 (m, 2H), 2.16-1.71 (m, 5H), 1.68-1.47 (m, 2H), 1.28-0.90 (m, 4H). |
| 122 | D | 1st eluting isomer | 4'-((5R)-6-(1-hydroxycyclopropane-1-carbonyl)-5-methyl-6-azaspiro[2.5]octan-1-yl)-[1,1'-biphenyl]-4-carboxylic acid | 406 | 1H NMR (DMSO-d6, 400 MHz) δ (ppm): 12.96 (br, 1H), 8.01 (d, J = 8.4 Hz, 2H), 7.86-7.76 (m, 2H), 7.65 (d, J = 8.0 Hz, 2H), 7.30 (d, J = 8.0 Hz, 2H), 6.27 (s, 1H), 4.95-4.32 (m, 2H), 3.38-3.32(m, 1H), 1.92-1.86 (m, 3H), 1.54-1.47 (m, 1H), 1.32-1.23 (m, 2H), 1.21-1.06 (m, 3H), 0.97-0.91 (m, 1H), 0.85-0.74 (m, 1H), 0.75-0.66 (m, 3H). |
| 123 | B | 2nd eluting isomer | | 406 | 1H NMR (DMSO-d6, 400 MHz) δ (ppm): 12.96 (br, 1H), 8.01 (d, J = 8.4 Hz, 2H), 7.79 (d, J = 8.4 Hz, 2H), 7.65 (d, J = 8.0 Hz, 2H), 7.30 (d, J = 8.0 Hz, 2H), 6.25 (s, 1H), 4.89-4.71 (m, 1H), 4.35-4.20 (m, 1H), 3.20-2.90 (m, 1H), 2.19-2.10 (m, 1H), 1.92-1.86 (m, 2H), 1.35-1.20 (m, 5H), 1.17-1.12 (m, 1H), 1.08-1.03 (m, 1H), 0.93-0.65 (m, 5H). |

Figure 2-38

| | | | | |
|---|---|---|---|---|
| 124 | D | 1st eluting isomer | 4'-((5R)-5-methyl-6-((R)-tetrahydrofuran-2-carbonyl)-6-azaspiro[2.5]octan-1-yl)-[1,1'-biphenyl]-4-carboxylic acid | 420 | 1H NMR (DMSO-d6, 400 MHz) δ (ppm): 12.96 (br, 1H), 8.04-7.98 (m, 2H), 7.82-7.75 (m, 2H), 7.64 (d, J = 8.4 Hz, 2H), 7.30 (d, J = 8.0 Hz, 2H), 4.76-3.58 (m, 5H), 2.91-2.84 (m, 1H), 2.08-1.72 (m, 6H), 1.57-1.39 (m, 1H), 1.32-1.02 (m, 6H), 0.74-0.65 (m, 1H). |
| 125 | B | 2nd eluting isomer | | 420 | 1H NMR (DMSO-d6, 400 MHz) δ (ppm): 12.97 (br, 1H), 8.04-7.98 (m, 2H), 7.82-7.75 (m, 2H), 7.64 (d, J = 8.4 Hz, 2H), 7.28 (d, J = 8.0 Hz, 2H), 4.78-3.61 (m, 5H), 3.26-2.74 (m, 1H), 2.27-1.66 (m, 6H), 1.39-1.07 (m, 6H), 1.07-0.96 (m, 1H), 0.88-0.68 (m, 1H). |
| 126 | A | 1st eluting isomer | 4'-(6-(1-hydroxycyclopropane-1-carbonyl)-6-azaspiro[2.5]octan-1-yl)-2-(trifluoromethyl)-[1,1'-biphenyl]-4-carboxylic acid | 460 | 1H-NMR (CD3OD, 400 MHz) δ (ppm): 8.41 (s, 1H), 8.26-8.17 (m, 1H), 7.49-7.41 (m, 1H), 7.38-7.22 (m, 4H), 4.35-3.35 (m, 4H), 2.23-2.12 (m, 1H), 1.74-1.58 (m, 2H), 1.41-1.22 (m, 2H), 1.19-1.11 (m, 1H), 1.05-0.92 (m, 3H), 0.91-0.84 (m, 1H). |
| 127 | D | 2nd eluting isomer | | 460 | 1H-NMR (CD3OD, 400 MHz) δ (ppm): 8.42 (s,1H), 8.27-8.12 (m, 1H), 7.45-7.20 (m, 5H), 4.21-3.35 (m, 4H), 2.26-2.12 (m, 1H), 1.79-1.60(m, 2H), 1.48-1.22 (m, 2H), 1.18-1.12 (m, 1H), 1.07-0.98 (m, 3H), 0.92-0.85 (m, 1H). |

Figure 2-39

| 128 | D | 1st eluting isomer | 7-(4-(6-((R)-tetrahydrofuran-2-carbonyl)-6-azaspiro[2.5]octan-1-yl)phenyl)quinoline-4-carboxylic acid | 457 | 1H-NMR (CD3OD, 400 MHz) δ (ppm): 9.00 (d, J = 4.8 Hz, 1H), 8.90 (d, J = 8.8 Hz, 1H), 8.32 (s, 1H), 8.07-8.03 (m, 1H), 7.99 (d, J = 4.8 Hz, 1H), 7.78 (d, J = 8.4 Hz, 2H), 7.42 (d, J = 8.0 Hz, 2H), 4.85-4.67 (m, 1H), 4.01-3.66 (m, 4H), 3.64-3.25 (m, 2H), 2.31-2.18 (m, 2H), 2.16-1.81 (m, 3H), 1.64-1.61 (m, 2H), 1.35-1.30 (m, 2H),1.18-1.16 (m, 1H), 1.10-0.97 (m, 1H). |
| 129 | B | 2nd eluting isomer | | 457 | 1H-NMR (CD3OD, 400 MHz) δ (ppm): 8.95 (d, J = 4.8 Hz, 1H), 8.79 (d, J = 8.4 Hz, 1H), 8.29 (s, 1H), 7.99 (d, J = 4.8 Hz, 1H), 7.87 (d, J = 4.4 Hz, 1H), 7.76 (d, J = 7.2 Hz, 2H), 7.42-7.39 (m, 2H), 4.83-4.64 (m, 1H), 4.08-3.61 (m, 4H), 3.67-3.20 (m, 2H), 2.28-2.11 (m, 2H), 2.10-1.82 (m, 3H), 1.80-1.53 (m, 2H), 1.48-1.25 (m, 2H), 1.21-1.13 (m, 1H), 1.02-0.94 (m, 1H). |
| 130 | C | 1st eluting isomer | 3-(4-(6-((R)-tetrahydrofuran-2-carbonyl)-6-azaspiro[2.5]octan-1-yl)phenyl)quinoline-6-carboxylic acid | 457 | 1H-NMR (400 MHz, CD3OD) δ (ppm): 9.25 (s, 1H), 8.76 (s, 1H), 8.68 (s, 1H), 8.32 (d, J = 8.8 Hz, 2H), 8.12 (d, J = 8.8 Hz,1H), 7.78-7.76 (m, 2H), 7.43 (d, J = 8.0 Hz, 2H), 4.79-4.65 (m, 1H), 3.97-3.64 (m, 4H), 3.58-3.25 (m, 2H), 2.23-2.16 (m, 2H), 2.07-1.86 (m, 3H), 1.78-1.61 (m, 2H), 1.38-1.20 (m, 2H), 1.19-1.16 (m, 1H), 1.01-0.98 (m, 1H). |

Figure 2-40

| | | | | |
|---|---|---|---|---|
| 131 | A | 2nd eluting isomer | 457 | 1H-NMR (400 MHz, CD$_3$OD) δ (ppm): 9.27 (s, 1H), 8.77 (s, 1H), 8.72 (s, 1H), 8.33 (d, J = 8.4 Hz, 1H) 8.13 (d, J = 8.8 Hz,1H), 7.80 (d, J = 8.0 Hz, 2H), 7.47-7.44 (m, 2H), 4.80-4.67 (m, 1H), 3.95-3.66 (m, 4H), 3.48-3.26 (m, 2H), 2.22-2.08 (m, 2H), 2.02-1.86 (m, 3H), 1.78-1.61 (m, 2H), 1.47-1.24 (m, 2H), 1.21-1.17 (m, 1H), 1.02-0.99 (m, 1H). |
| 132 | B | 1st eluting isomer | 3'-fluoro-2-methyl-4'-(6-((R)-tetrahydrofuran-2-carbonyl)-6-azaspiro[2.5]octan-1-yl)-[1,1'-biphenyl]-4-carboxylic acid | 438 | 1H NMR (400 MHz, DMSO-d6) δ (ppm):12.95 (br, 1H), 7.88 (s, 1H), 7.83-7.79 (m, 1H), 7.39-7.30 (m, 1H), 7.29-7.19 (m, 2H), 7.15-7.13 (m, 1H), 4.75-4.56 (m, 1H), 3.80-3.51 (m, 4H), 3.26-3.22 (m, 2H), 2.30 (s, 3H), 2.10-1.90 (m, 3H), 1.89-1.72 (m, 2H), 1.70-1.48 (m, 2H), 1.14-1.03 (m, 3H), 0.99-0.92 (m, 1H). |
| 133 | C | 2nd eluting isomer | | 438 | 1H NMR (400 MHz, DMSO-d6) δ (ppm):12.96 (br, 1H), 7.83 (s, 1H), 7.83-7.80 (m, 1H), 7.38-7.33 (m, 1H), 7.31-7.21 (m, 2H), 7.15-7.13 (m, 1H), 4.75-4.54 (m, 1H), 3.82-3.51 (m, 4H), 3.26-3.23 (m, 2H), 2.30 (s, 3H), 2.08-1.90 (m, 3H), 1.89-1.72 (m, 2H), 1.70-1.48 (m, 2H), 1.14-1.03 (m, 3H), 1.00-0.92 (m, 1H). |

Figure 2-41

| | | | | |
|---|---|---|---|---|
| 134 | B | 1st eluting isomer | 3-methyl-4-{4-[6-(1,3-oxazole-2-carbonyl)-6-azaspiro[2.5]octan-1-yl]phenyl}benzoic acid | 417 | 1H-NMR (CD₃OD, 400 MHz) δ (ppm): 8.12-8.02 (m, 1H),8.01-7.92 (m, 1H), 7.92-7.82(m, 1H), 7.43-7.23 (m, 6H), 4.21-4.05(m, 1H), 3.98-3.44(m, 3H), 2.31(s, 3H), 2.26-2.12 (m, 1H), 1.88-1.63 (m, 2H), 1.45-1.33 (m, 2H), 1.21-1.12 (m, 1H), 1.05-0.97 (m, 1H). |
| 135 | D | 2nd eluting isomer | | 417 | 1H-NMR (CD₃OD, 400 MHz) δ (ppm): 8.12-8.02 (m, 1H),7.99-7.92 (m, 1H), 7.92-7.82(m, 1H), 7.42-7.22 (m, 6H), 4.21-4.03(m, 1H), 4.03-3.73(m, 2H), 3.73-3.50(m, 1H), 2.32(s, 3H), 2.26-2.12 (m, 1H), 1.83-1.63 (m, 2H), 1.47-1.31 (m, 2H), 1.24-1.12 (m, 1H), 1.07-0.95 (m, 1H). |
| 136 | A | 1st eluting isomer | 6-(4-(6-(1-hydroxycyclopropane-1-carbonyl)-6-azaspiro[2.5]octan-1-yl)phenyl)-1H-indazole-3-carboxylic acid | 432 | 1H-NMR (CD₃OD, 400 MHz) δ (ppm): 8.24 (d, J = 8.4 Hz, 1H), 7.79(s, 1H) 7.66 (d, J=8.0 Hz, 2H), 7.60 (d, J=8.8 Hz, 1H), 7.38 (d, J=8.0 Hz, 2H), 4.90-3.46 (m, 3H), 2.18-2.05 (m, 1H), 1.85-1.55 (s, 2H), 1.42-1.27 (m, 3H), 1.10-1.05 (m, 1H), 1.05-0.97 (m, 3H), 0.97-0.87 (m, 2H) |
| 137 | C | 2nd eluting isomer | | 432 | 1H-NMR (CD₃OD, 400 MHz) δ (ppm): 8.23 (m, J = 8.0 Hz, 1H), 7.79(s, 1H) 7.66 (d, J=8.0 Hz, 2H), 7.59 (d, J=8.8 Hz, 1H), 7.38 (d, J=8.0 Hz, 2H), 4.15-3.55 (m, 3H), 2.35-2.05 (m, 1H), 1.85-1.55 (s, 2H), 1.33-1.27 (m, 3H), 1.10-1.05 (m, 1H), 1.05-0.97 (m, 3H), 0.97-0.78 (m, 2H). |

Figure 2-42

| 138 | C | 1st eluting isomer | 4'-(6-acetyl-6-azaspiro[2.5]octan-1-yl)-2-methyl-[1,1'-biphenyl]-4-carboxylic acid | 364 | 1H-NMR (CD₃OD, 400 MHz) δ (ppm): 7.95 (s, 1H), 7.94-7.87 (m, 1H), 7.39-7.21(m, 5H), 3.83-3.61 (m, 2H), 3.59-3.35 (m, 2H), 2.32 (s, 3H), 2.18-2.04 (m, 4H), 1.75-1.56 (m, 2H), 1.41-1.23 (m, 2H)1.21-1.10 (m,1H), 0.99-0.92 (m,1H). |
|---|---|---|---|---|---|
| 139 | D | 2nd eluting isomer | | 364 | 1H-NMR (CD₃OD, 400 MHz) δ (ppm): 7.95 (s, 1H), 7.90-7.87 (m, 1H), 7.35-7.27 (m, 5H), 3.74-3.3.65 (m, 2H), 3.49-3.32 (m, 2H), 2.32 (s, 3H), 2.18-2.07 (m, 4H), 1.67-1.56 (m, 2H), 1.35-1.21 (m, 2H), 1.18-1.10 (m,1H), 1.00-0.91 (m, 1H). |
| 140 | A | 1st eluting isomer | 3-methyl-4-{4-[6-propanoyl-6-azaspiro[2.5]octan-1-yl]phenyl}benzoic acid | 378 | 1H-NMR (CD₃OD, 400 MHz) δ (ppm): 7.95 (s, 1H), 7.89 (d, J=8.0 Hz, 1H), 7.39-7.25 (m, 5H), 3.83-3.58 (m, 2H), 3.54-3.35 (m, 2H), 2.50-2.42 (m, 1H), 2.42-2.34 (m, 1H), 2.34-2.28 (m, 3H), 2.20-2.10 (m, 1H), 1.73-1.53 (m, 2H), 1.39-1.21 (m, 2H), 1.19-1.05 (m, 4H), 1.01-0.92 (m, 1H). |
| 141 | D | 2nd eluting isomer | | 378 | 1H-NMR (CD₃OD, 400 MHz) δ (ppm): 7.97 (s, 1H), 7.89 (d, J=8.0 Hz, 1H), 7.42-7.21 (m, 5H), 3.83-3.58 (m, 2H), 3.53-3.33 (m, 2H), 2.51-2.42 (m, 1H), 2.42-2.33 (m, 1H), 2.33-2.28 (m, 3H), 2.22-2.11 (m, 1H), 1.71-1.54 (m, 2H), 1.38-1.21 (m, 2H), 1.21-1.07 (m, 4H), 1.06-0.91 (m, 1H). |

Figure 2-43

| | | | | |
|---|---|---|---|---|
| 142 | B | 1st eluting isomer | 417 | 1H-NMR (CD₃OD, 400 MHz) δ (ppm): 8.41-8.01 (m, 1H), 8.01-7.93 (m, 1H), 7.93-7.75(m, 1H), 7.49-7.18(m, 5H), 4.21-4.02(m, 1H), 4.02-3.83(m, 1H), 3.83-3.48(m, 2H), 2.31(s, 3H), 2.26-2.12 (m, 1H), 1.88-1.63 (m, 2H), 1.45-1.33 (m, 2H), 1.21-1.12 (m, 1H), 1.05-0.97 (m, 1H). |
| 143 | D | 2nd eluting isomer | 417 | 1H-NMR (CD₃OD, 400 MHz) δ (ppm): 8.38-8.02 (m, 1H), 8.02-7.93 (m, 1H), 7.93-7.76(m, 1H), 7.49-7.17(m, 5H), 4.21-4.02(m, 1H), 4.02-3.85(m, 1H), 3.85-3.70(m, 1H), 3.70-3.50(m, 1H), 2.32(s, 3H), 2.22-2.06 (m, 1H), 1.82-1.61 (m, 2H), 1.49-1.31 (m, 2H), 1.27-1.08 (m, 1H), 1.08-0.88 (m, 1H). |
| | | | | 4'-(6-(2,3-dihydro-1H-1,2,3-triazole-4-carbonyl)-6-azaspiro[2.5]octan-1-yl)-2-methyl-[1,1'-biphenyl]-4-carboxylic acid |
| 144 | D | 1st eluting isomer | 380 | 1H NMR (400 MHz, DMSO-d6) δ (ppm): 12.70 (br, 1H), 7.97-7.90 (m, 1H), 7.85-7.79 (m, 1H), 7.42 (d, J=8.0 Hz, 2H), 7.33-7.26 (m, 2H), 7.23-7.20 (m, 2H), 3.85 (s, 3H), 3.61-3.45 (m, 2H), 3.31-3.07 (m, 2H), 2.13-2.04 (m, 1H), 1.94 (s, 3H), 1.55-1.46 (m, 2H), 1.29-1.03 (m, 3H), 0.92-0.82 (m, 1H). |

Note: rows 143 and 144 additionally labeled: "4'-(6-acetyl-6-azaspiro[2.5]octan-1-yl)-6-methoxy-[1,1'-biphenyl]-3-carboxylic acid" for row 144.

Figure 2-44

| | | | | |
|---|---|---|---|---|
| 145 | B | 2nd eluting isomer | 380 | 1H NMR (400 MHz, DMSO-d6) δ 12.70 (br, 1H), 8.01-7.89 (m, 1H), 7.86-7.77 (m, 1H), 7.42 (d, J=8.0 Hz, 2H), 7.34-7.27 (m, 2H), 7.28-7.20 (m, 1H), 3.85 (s, 3H), 3.65-3.44 (m, 2H), 3.34-3.13 (m, 2H), 2.13-2.04 (m, 1H), 1.94 (s, 3H), 1.56-1.44 (m, 2H), 1.27-1.03 (m, 3H), 0.89-0.86 (m, 1H). |
| 146 | D | 1st eluting isomer | 394 | 1H NMR (400 MHz, DMSO-d6) δ 12.72 (br, 1H), 7.95-7.91 (m, 1H), 7.83 (s, 1H), 7.42 (d, J = 8.0 Hz, 2H), 7.32-7.26 (m, 2H), 7.21 (d, J = 8.8 Hz, 1H), 3.85 (s, 3H), 3.59-3.51 (m, 2H), 3.29-3.17 (m, 2H), 2.35-2.22 (m, 2H), 2.08-2.03 (m, 1H), 1.56-1.41(m, 2H), 1.25-1.06 (m, 3H), 1.02-0.94 (m, 3H), 0.88-0.82 (m, 1H). |
| 147 | B | 2nd eluting isomer | 4'-(6-acetyl-6-azaspiro[2.5]octan-1-yl)-6-methoxy-[1,1'-biphenyl]-3-carboxylic acid | 394 | 1H NMR (400 MHz, DMSO-d6) δ 12.72 (br, 1H), 7.95-7.91 (m, 1H), 7.83 (s, 1H), 7.42 (d, J = 8.0 Hz, 2H), 7.32-7.26 (m, 2H), 7.21 (d, J = 8.8 Hz, 1H), 3.85 (s, 3H), 3.61-3.51 (m, 2H), 3.27-3.14 (m, 2H), 2.35-2.22 (m, 2H), 2.08-2.03 (m, 1H), 1.55-1.43 (m, 2H), 1.25-1.06 (m, 3H), 1.02-0.93 (m, 3H), 0.89-0.82 (m, 1H). |

Figure 2-45

| | | | | |
|---|---|---|---|---|
| 148 | D | 1st eluting isomer | 4'-(6-(cyclopropanecarbonyl)-6-azaspiro[2.5]octan-1-yl)-6-methoxy-[1,1'-biphenyl]-3-carboxylic acid | 406 | 1H NMR (CD3OD, 400 MHz) δ (ppm): 8.03-8.00 (m, 1H), 7.95 (s, 1H), 7.48-7.45 (m, 2H), 7.31-7.26 (m, 2H), 7.16-7.13 (m, 1H), 3.92-3.87 (m, 4H), 3.83-3.59 (m, 2H), 3.55-3.50 (m, 1H), 2.16-2.13 (m, 1H), 2.07-1.83 (m, 1H), 1.69-1.59 (m, 2H), 1.36-1.26 (m, 2H), 1.13-1.12 (m, 1H), 0.95 (s, 1H), 0.87-0.76 (m, 4H). |
| 149 | B | 2nd eluting isomer | | 406 | 1H NMR (CD3OD, 400 MHz) δ (ppm): 8.03-8.00 (m, 1H), 7.95 (s, 1H), 7.48-7.45 (m, 2H), 7.31-7.26 (m, 2H), 7.16-7.13 (m, 1H), 3.95-3.83 (m, 4H), 3.80-3.60 (m, 2H), 3.52-3.50 (m, 1H), 2.17-2.13 (m, 1H), 2.01-1.90 (m, 1H), 1.69-1.59 (m, 2H), 1.37-1.27 (m, 2H), 1.15-1.12 (m, 1H), 0.97-0.94 (m, 1H), 0.91-0.73 (m, 4H). |
| 150 | B | 1st eluting isomer | 4-methoxy-4'-(6-((R)-tetrahydrofuran-2-carbonyl)-6-azaspiro[2.5]octan-1-yl)-[1,1'-biphenyl]-3-carboxylic acid | 436 | 1H-NMR (CD3OD, 400 MHz) δ (ppm): 8.08 (s, 1H), 7.82 (d, J= 8.4 Hz, 1H), 7.54 (d, J= 8.0 Hz, 2H), 7.37-7.32 (m, 2H), 7.23 (d, J= 8.8 Hz, 1H), 4.81-4.62 (m, 1H), 3.97 (s, 3H), 3.95-3.60 (m, 4H), 3.52-3.35 (m, 1H), 3.33-3.19 (m, 1H), 2.30-2.11 (m, 2H), 2.10-1.82 (m, 3H), 1.78-1.52 (m, 2H), 1.46-1.22 (m, 2H), 1.18-1.14 (m, 1H), 1.00-0.95 (m, 1H). |

Figure 2-46

| | | | | 1H-NMR (CD3OD, 400 MHz) δ (ppm): |
|---|---|---|---|---|
| 151 | C | 2nd eluting isomer | 436 | 1H-NMR (CD3OD, 400 MHz) δ (ppm): 8.08 (s, 1H), 7.82 (d, J= 8.4 Hz, 1H), 7.54 (d, J= 8.4 Hz, 2H), 7.33 (d, J= 8.4 Hz, 2H), 7.23 (d, J= 8.8 Hz, 1H), 4.82-4.61 (m, 1H), 3.97 (s, 3H), 3.95-3.61 (m, 4H), 3.59-3.35 (m, 1H), 3.33-3.21 (m, 1H), 2.30-2.11 (m, 2H), 2.10-1.85 (m, 3H), 1.79-1.52 (m, 2H), 1.47-1.25 (m, 2H), 1.15-1.08 (m, 1H), 0.98-0.92 (m, 1H). |
| 152 | B | 1st eluting isomer | 2-methyl-4'-(6-((R)-tetrahydrofuran-2-carbonyl)-6-azaspiro[2.5]octan-1-yl)-[1,1'-biphenyl]-3-carboxylic acid | 420 | 1H-NMR (CD3OD, 400 MHz) δ (ppm): 7.81 (d, J = 7.6 Hz, 1H), 7.35-7.31 (m, 4H), 7.31-7.21 (m, 2H), 4.91-4.68 (m, 1H), 3.97-3.73 (m, 4H), 3.46-3.32 (m, 2H), 2.40 (s, 3H), 2.18-2.09 (m, 2H), 2.07-1.83 (m, 3H), 1.78-1.54 (m, 2H), 1.45-1.25 (m, 2H), 1.18-1.11 (m, 1H), 0.10-0.95 (m, 1H). |
| 153 | D | 2nd eluting isomer | 420 | 1H-NMR (CD3OD, 400 MHz) δ (ppm): 7.81 (d, J = 7.2 Hz, 1H), 7.35-7.32 (m, 4H), 7.30-7.22 (m, 2H), 4.91-4.68 (m, 1H), 3.96-3.70 (m, 4H), 3.46-3.34 (m, 2H), 2.39 (s, 3H), 2.32-2.11(m, 2H), 2.15-1.94 (m, 3H), 1.92-1.63 (m, 2H), 1.35-1.28 (m, 2H), 1.45-1.20 (m, 1H), 0.98-0.92 (m, 1H). |

Figure 2-47

| 154 | B | 1st eluting isomer | 5-(4-(6-((R)-tetrahydrofuran-2-carbonyl)-6-azaspiro[2.5]octan-1-yl)phenyl)nicotinic acid | 407 | 1H-NMR (400 MHz, CD3OD) δ (ppm): 9.09 (s, 1H), 9.01(s, 1H), 8.60 (d, J = 2.0 Hz, 1H), 7.68 (d, J = 8.0 Hz, 2H), 7.44-7.42 (m, 2H), 4.80-4.65 (m, 1H), 3.97-3.65 (m, 4H), 3.50-3.42 (m, 1H), 3.28-3.20 (m, 1H), 2.25-2.10 (m, 2H), 2.05-1.88 (m, 3H), 1.75-1.55 (m, 2H), 1.45-1.22 (m, 2H), 1.18-1.14 (m, 1H), 1.00-0.95 (m, 1H). |
| 155 | D | 2nd eluting isomer | 5-(4-(6-((R)-tetrahydrofuran-2-carbonyl)-6-azaspiro[2.5]octan-1-yl)phenyl)nicotinic acid | 407 | 1H-NMR (400 MHz, CD3OD) δ (ppm): 9.09 (s, 1H), 9.00 (s, 1H), 8.60 (d, J = 2.4 Hz, 1H), 7.67 (d, J = 8.0 Hz, 2H), 7.44-7.42 (m, 2H), 4.80-4.65 (m, 1H), 3.97-3.65 (m, 4H), 3.54-3.20 (m, 2H), 2.25-2.10 (m, 2H), 2.05-1.88 (m, 3H), 1.75-1.55 (m, 2H), 1.38-1.22 (m, 2H), 1.18-1.14 (m, 1H), 1.00-0.97 (m, 1H). |
| 156 | A | 1st eluting isomer | 6-(4-(6-((R)-tetrahydrofuran-2-carbonyl)-6-azaspiro[2.5]octan-1-yl)cyclohexyl)-1-naphthoic acid | 456 | 1H-NMR (CD3OD, 400 MHz) δ (ppm): 9.00 (d, J = 8.0 Hz, 1H), 8.22-8.15 (m, 3H), 7.92 (d, J = 9.2 Hz, 1H), 7.74 (d, J = 8.0 Hz, 1H), 7.58 (t, J = 7.6 Hz, 1H), 7.49-7.37 (m, 2H), 4.89-4.78 (m, 1H), 3.97-3.67 (m, 4H), 3.62-3.32(m, 2H), 2.17-1.92 (m, 5H), 1.81-1.29 (m, 4H), 1.28-0.96 (m, 2H). |

Figure 2-48

| | | | | |
|---|---|---|---|---|
| 157 | C | 2nd eluting isomer | 456 | 1H-NMR (CD₃OD, 400 MHz) δ (ppm): 9.00 (d, J = 8.0 Hz, 1H), 8.22-8.15 (m, 3H), 7.92 (d, J = 8.8 Hz, 1H), 7.74 (d, J = 8.0 Hz, 1H), 7.58 (d, J = 8.0 Hz, 1H), 7.55-7.38 (m, 2H), 4.85-4.68 (m, 1H), 3.97-3.74 (m, 4H), 3.69-3.32(m, 2H), 2.23-1.92 (m, 5H), 1.92-1.29 (m, 4H), 1.28-0.98 (m, 2H). |
| 158 | B | 1st eluting isomer | 420 | 1H NMR (CD₃OD, 400 MHz) δ (ppm): 8.04-8.01 (m, 1H), 7.96-7.94 (m, 1H), 7.44 (d, J= 8.4 Hz, 2H), 7.38 (d, J= 6.8 Hz, 2H), 7.16 (d, J= 8.8 Hz, 1H), 3.90 (s, 3H), 3.79-3.66 (m, 1H), 3.58-3.37 (m, 3H), 3.30-3.16 (m, 1H), 2.29-1.93 (m, 6H), 1.89-1.76 (m, 1H), 1.62-1.57 (m, 2H), 1.31-1.26 (m, 2H), 1.12-1.06 (m, 1H), 0.93-0.88 (m, 1H). |
| 159 | D | 2nd eluting isomer | 4'-(6-(cyclobutanecarbonyl)-6-azaspiro[2.5]octan-1-yl)-6-methoxy-[1,1'-biphenyl]-3-carboxylic acid | 420 | 1H-NMR (400 MHz, CD₃OD) δ (ppm): 8.04(d, J=2.4 Hz, 1H), 8.03(d, J= 2.0 Hz, 1H), 7.44 (d, J= 8.4 Hz, 2H), 7.28 (d, J=7.2 Hz, 2H), 7.15(d, J= 8.8 Hz, 1H), 3.89 (s, 3H), 3.82-3.63 (m, 1H), 3.47-3.45 (m, 1H), 3.33-3.32 (m, 1H), 3.32-3.24 (m, 1H), 3.24-3.16 (m, 1H), 2.30-2.22 (m, 3H), 2.21-2.15 (m, 2H), 2.13-2.10 (m, 1H), 2.10-1.61 (m, 1H), 1.61-1.57 (m, 2H), 1.29-1.26 (m, 2H), 1.12-1.09 (m, 1H), 0.95-0.92 (m, 1H). |

Figure 2-49

| | | | | 1H-NMR |
|---|---|---|---|---|
| 160 | A | 1st eluting isomer | 5-methyl-4'-(6-((R)-tetrahydrofuran-2-carbonyl)-6-azaspiro[2.5]octan-1-yl)-[1,1'-biphenyl]-3-carboxylic acid | 420 | 1H-NMR (CD₃OD, 400 MHz) δ (ppm): 8.07 (s, 1H), 7.82 (s, 1H), 7.71-7.65(m,1 H), 7.59 (d, J=8.0 Hz, 2H), 7.38-7.32 (m, 2H), 4.82-4.66 (m,1H), 4.03-3.61 (m, 4H), 3.49-3.25 (m, 2H), 2.48 (s, 3H), 2.28-2.10 (m, 2H), 2.08-1.82 (m, 3H), 1.80-1.52 (m, 2H), 1.49-1.27 (m, 2H), 1.25-1.11 (m, 2H), 1.01-0.92 (m, 1H). |
| 161 | C | 2nd eluting isomer | 5-methyl-4'-(6-((R)-tetrahydrofuran-2-carbonyl)-6-azaspiro[2.5]octan-1-yl)-[1,1'-biphenyl]-3-carboxylic acid | 420 | 1H-NMR (CD₃OD, 400 MHz) δ (ppm): 8.07 (s, 1H), 7.82 (s, 1H), 7.69-7.64(m, 1H), 7.59 (d, J=8.0 Hz, 2H), 7.38-7.31 (m, 2H), 4.81-4.62 (m,1H), 4.05-3.79 (m, 2H), 3.77-3.61 (m, 2H), 3.58-3.25 (m, 2H), 2.48 (s, 3H), 2.27-2.12 (m, 2H), 2.10-1.86 (m, 3H), 1.84-1.55 (m, 2H), 1.48-1.22 (m, 2H), 1.21-1.13 (m, 1H), 0.97-0.91 (m, 1H). |
| 162 | A | 1st eluting isomer | 5-methoxy-4'-(6-((R)-tetrahydrofuran-2-carbonyl)-6-azaspiro[2.5]octan-1-yl)-[1,1'-biphenyl]-3-carboxylic acid | 436 | 1H-NMR (CD₃OD, 400 MHz) δ (ppm):7.87 (s, 1H), 7.60 (d, J=8.0 Hz, 2H), 7.54 (s, 1H), 7.41-7.26 (m, 3H), 4.85-4.61 (m, 1H), 4.01-3.89 (m, 4H), 3.89-3.62 (m, 3H), 3.52-3.41 (m, 1H), 3.31-3.21 (m, 1H), 2.35-2.09 (m, 2H), 2.09-1.81 (m, 3H), 1.81-1.52 (m, 2H), 1.45-1.21 (m, 2H), 1.21-1.09 (m, 1H), 1.02-0.91 (m, 1H). |

Figure 2-50

| | | | |
|---|---|---|---|
| 163 | C | 2nd eluting isomer | 436 | 1H-NMR (CD3OD, 400 MHz) δ (ppm):7.87 (s, 1H), 7.60 (d, J=8.0 Hz, 2H), 7.54 (s, 1H), 7.41-7.31 (m, 3H), 4.81-4.60 (m, 1H), 4.02-3.81 (m, 5H), 3.81-3.62 (m, 2H), 3.54-3.47 (m, 1H), 3.31-3.23 (m, 1H), 2.35-2.11 (m, 2H), 2.11-1.82 (m, 3H), 1.82-1.57 (m, 2H), 1.45-1.19 (m, 2H), 1.19-1.09 (m, 1H), 1.02-0.91 (m, 1H). |
| 164 | A | 1st eluting isomer | 5-fluoro-4'-(6-((R)-tetrahydrofuran-2-carbonyl)-6-azaspiro[2.5]octan-1-yl)-[1,1'-biphenyl]-3-carboxylic acid | 424 | 1H NMR (400 MHz, DMSO-d6) δ (ppm): 13.42 (br, 1H), 8.03 (s, 1H), 7.86-7.79 (m, 1H), 7.72-7.59 (m, 3H), 7.37 (d, J = 8.0 Hz, 2H), 4.76-4.51 (m, 1H), 3.81-3.52 (m, 4H), 3.25-3.14 (m, 2H), 2.15-1.88 (m, 3H), 1.87-1.67 (m, 2H), 1.59-1.47 (m, 2H), 1.28-1.03 (m, 3H), 0.94-0.88 (m, 1H). |
| 165 | D | 2nd eluting isomer | 424 | 1H NMR (400 MHz, DMSO-d6) δ (ppm):13.40 (br, 1H), 8.03 (s, 1H), 7.86-7.78 (m, 1H), 7.73-7.58 (m, 3H), 7.37 (d, J = 8.0 Hz, 2H), 4.75-4.51 (m, 1H), 3.80-3.55 (m, 4H), 3.27-3.10 (m, 2H), 2.14-1.90 (m, 3H), 1.87-1.69 (m, 2H), 1.63-1.47 (m, 2H), 1.25-1.06 (m, 3H), 0.93-0.88 (m, 1H). |

Figure 2-51

| | | | | |
|---|---|---|---|---|
| 166 | B | 1st eluting isomer | 2-methoxy-4'-(6-((R)-tetrahydrofuran-2-carbonyl)-6-azaspiro[2.5]octan-1-yl)-[1,1'-biphenyl]-3-carboxylic acid | 436 | 1H-NMR (CD₃OD, 400 MHz) δ (ppm): 7.68-7.62 (m, 1H), 7.50 (d, J = 8.0 Hz, 2H), 7.49-7.41 (m, 1H), 7.33 (d, J = 8.0 Hz, 2H), 7.22 (t, J = 7.6 Hz, 1H), 4.85-4.63 (m, 1H), 4.03-3.59 (m, 4H), 3.49 (s, 3H), 3.48-3.26 (m, 2H), 2.30-1.81 (m, 5H), 1.76-1.50 (m, 2H), 1.44-1.20 (m, 2H), 1.18-1.11 (m, 1H), 1.02-0.92 (m, 1H). |
| 167 | D | 2nd eluting isomer | 2-methoxy-4'-(6-((R)-tetrahydrofuran-2-carbonyl)-6-azaspiro[2.5]octan-1-yl)-[1,1'-biphenyl]-3-carboxylic acid | 436 | 1H-NMR (CD₃OD, 400 MHz) δ (ppm): 7.75 (d, J = 8.0 Hz, 1H), 7.56-7.47 (m, 3H), 7.34 (d, J = 8.4 Hz, 2H), 7.26 (t, J = 7.6 Hz, 1H), 4.82-4.63 (m, 1H), 4.02-3.63 (m, 4H), 3.47 (s, 3H), 3.43-3.25 (m, 2H), 2.30-1.83 (m, 5H), 1.79-1.52 (m, 2H), 1.42-1.20 (m, 2H), 1.18-1.12 (m, 1H), 1.01-0.93 (m, 1H). |
| 168 | B | 1st eluting isomer | 2-fluoro-4'-(6-((R)-tetrahydrofuran-2-carbonyl)-6-azaspiro[2.5]octan-1-yl)-[1,1'-biphenyl]-3-carboxylic acid | 424 | 1H NMR (CD₃OD, 400 MHz) δ (ppm): 7.92-7.88 (m, 1H), 7.69-7.65(m, 1H), 7.48 (d, J=7.6 Hz, 2H), 7.37-7.30 (m, 3H), 4.89-4.60 (m, 1H), 4.01-3.57 (m, 4H), 3.52-3.40 (m, 1H), 3.32-3.23 (m, 1H), 2.33-1.78 (m, 5H), 1.78-1.50 (m, 2H), 1.45-1.21 (m, 2H), 1.15-1.13 (m, 1H), 0.98-0.95 (m, 1H). |

Figure 2-52

| 169 | D | 2nd eluting isomer | | 424 | 1H NMR (CD3OD, 400 MHz) δ (ppm): 7.92-7.87 (m, 1H), 7.68-7.66 (m, 1H), 7.56-7.43 (m, 2H), 7.42-7.25 (m, 3H), 4.89-4.72 (m, 1H), 4.03-3.63 (m, 4H), 3.59-3.34 (m, 2H), 2.26-2.13 (m, 2H), 2.05-1.85 (m, 3H), 1.76-1.50 (m, 2H), 1.39-1.20 (m, 2H), 1.16-1.13 (m, 1H), 0.99-0.95 (m, 1H). |
|---|---|---|---|---|---|
| 170 | C | 1st eluting isomer | 5-chloro-6-methoxy-4'-((R)-6-((R)-tetrahydrofuran-2-carbonyl)-6-azaspiro[2.5]octan-1-yl)-[1,1'-biphenyl]-3-carboxylic acid | 470 | 1H-NMR (CD3OD, 400 MHz) δ (ppm): 8.10-7.96 (m, 1H), 7.95-7.68 (m, 1H), 7.51 (d, J=8.0 Hz, 2H), 7.40-7.19 (m, 2H), 4.81-4.53 (m, 1H), 4.10-3.60 (m, 4H), 3.58-3.49 (m, 3H), 3.40-3.35 (m, 2H), 2.31-2.10 (m, 2H), 2.05-1.83 (m, 3H), 1.78-1.51 (m, 2H), 1.41-1.19 (m, 2H), 1.18-1.03 (m, 1H), 1.02-0.82 (m, 1H). |
| 171 | A | 2nd eluting isomer | 5-chloro-6-methoxy-4'-((S)-6-((R)-tetrahydrofuran-2-carbonyl)-6-azaspiro[2.5]octan-1-yl)-[1,1'-biphenyl]-3-carboxylic acid | 470 | 1HNMR (CD3OD, 400 MHz) δ (ppm): 8.10-8.01 (m, 1H), 8.00-7.88 (m, 1H), 7.51 (d, J=8.4 Hz, 2H), 7.48-7.25 (m, 2H), 4.80-4.62 (m, 1H), 4.02-3.60 (m, 4H), 3.58-3.52 (m, 3H), 3.50-3.39 (m, 2H), 2.32-2.10 (m, 2H), 2.05-1.85 (m, 3H), 1.78-1.52 (m, 2H), 1.50-1.21 (m, 2H), 1.20-1.11 (m, 1H), 1.08-0.90 (m, 1H). |

Figure 2-53

| | | | | |
|---|---|---|---|---|
| 172 | A | 1st eluting isomer | 5-fluoro-6-methoxy-4'-(6-((R)-tetrahydrofuran-2-carbonyl)-6-azaspiro[2.5]octan-1-yl)-[1,1'-biphenyl]-3-carboxylic acid | 454 | 1HNMR (CD$_3$OD, 400 MHz) δ (ppm): 7.82 (s, 1H), 7.79-7.70 (m, 1H), 7.48 (d, J=8.0 Hz, 2H), 7.41-7.28 (m, 2H), 4.82-4.62 (m, 1H), 4.00-3.90 (m, 1H), 3.90-3.61(m, 6H), 3.53-3.38(m, 1H), 3.30-3.24(m, 1H), 2.30-2.09 (m, 2H), 2.09-1.81 (m, 3H), 1.78-1.52 (m, 2H), 1.48-1.22 (m, 2H), 1.22-1.09 (m, 1H), 1.03-0.90 (m, 1H). |
| 173 | D | 2nd eluting isomer | | 454 | 1HNMR (CD$_3$OD, 400 MHz) δ (ppm): 7.82 (s, 1H), 7.79-7.70 (m, 1H), 7.48 (d, J=8.0 Hz, 2H), 7.35 (d, J=8.4 Hz, 2H), 4.82-4.62 (m, 1H), 4.00-3.78 (m, 5H), 3.78-3.61 (m, 2H), 3.58-3.48 (m, 1H), 3.48-3.38 (m, 1H), 2.32-2.11 (m, 2H), 2.11-1.83 (m, 3H), 1.80-1.53 (m, 2H), 1.41-1.20 (m, 2H), 1.20-1.11 (m, 1H), 1.02-0.90 (m, 1H) |
| 174 | B | 1st eluting isomer | 4'-(6-((R)-tetrahydrofuran-2-carbonyl)-6-azaspiro[2.5]octan-1-yl)-6-(trifluoromethoxy)-[1,1'-biphenyl]-3-carboxylic acid | 490 | 1H-NMR (CD$_3$OD, 400 MHz) δ (ppm): 8.27-7.98 (m, 2H), 7.50 (d, J = 8.4 Hz, 1H), 7.46-7.33 (m, 4H), 4.81-4.63 (m, 1H), 4.00-3.60 (m, 4H), 3.53-3.30 (m, 2H), 2.29-1.83 (m, 5H), 1.80-1.53 (m, 2H), 1.41-1.22 (m, 2H), 1.20-1.14 (m, 1H), 0.99-0.91 (m, 1H). |

Figure 2-54

| | | | | |
|---|---|---|---|---|
| 175 | D | 2nd eluting isomer | | 490 | 1H-NMR (CD₃OD, 400 MHz) δ (ppm): 8.21-8.05 (m, 2H), 7.50 (d, J = 8.4 Hz, 1H), 7.45-7.32 (m, 4H), 4.82-4.65 (m, 1H), 4.01-3.62 (m, 4H), 3.59-3.25 (m, 2H), 2.29-2.11 (m, 2H), 2.09-1.85 (m, 3H), 1.79-1.51 (m, 2H), 1.40-1.17 (m, 2H), 1.15-1.10 (m, 1H), 1.02-0.98 (m, 1H). |
| 176 | A | 1st eluting isomer | 4'-(6-((R)-tetrahydrofuran-2-carbonyl)-6-azaspiro[2.5]octan-1-yl)-6-(trifluoromethyl)-[1,1'-biphenyl]-3-carboxylic acid | 474 | 1H NMR (CD₃OD, 400 MHz) δ (ppm): 8.14 (d, J=8.8 Hz, 1H), 7.96-7.86 (m, 2H), 7.34-7.26 (m, 4H), 4.80 – 4.64 (m, 1H), 4.00-3.55 (m, 4H), 3.52-3.36 (m, 2H), 2.24-1.83 (m, 5H), 1.80-1.49 (m, 2H), 1.42-0.88 (m, 4H). |
| 177 | C | 2nd eluting isomer | | 474 | 1H NMR (CD₃OD, 400 MHz) δ (ppm): 8.10 (d, J = 8.0 Hz, 1H), 7.94 (d, J = 4.4 Hz, 1H), 7.83 (d, J = 8.0 Hz, 1H), 7.32-7.25 (m, 4H), 4.80-4.67 (m, 1H), 3.98-3.65 (m, 4H), 3.56-3.37 (m, 2H), 2.28-2.12 (m, 2H), 2.09-1.83 (m, 3H), 1.74-1.55 (m, 2H), 1.38-1.20 (m, 2H), 1.16-1.12 (m, 1H), 0.99-0.94 (m, 1H). |
| 178 | B | 1st eluting isomer | 6-(4-(6-((R)-tetrahydrofuran-2-carbonyl)-6-azaspiro[2.5]octan-1-yl)phenyl)picolinic acid | 407 | 1H-NMR (400 MHz, CD₃OD) δ (ppm): 8.10-8.01(m, 5H), 7.40-7.38 (m, 2H), 4.80-4.65 (m, 1H), 3.97-3.89 (m, 1H), 3.87-3.81 (m, 1H), 3.78-3.65 (m, 2H), 3.50-3.20 (m, 2H), 2.25-2.10 (m, 2H), 2.05-1.88 (m, 3H), 1.75-1.55 (m, 2H), 1.45-1.22 (m, 2H), 1.18-1.14 (m, 1H), 1.00-0.95 (m, 1H). |

Figure 2-55

| 179 | D | 2nd eluting isomer | | 407 | 1H-NMR (400 MHz, CD3OD) δ (ppm): 8.10-8.01 (m, 5H), 7.40-7.38 (m, 2H), 4.80-4.65 (m, 1H), 3.97-3.62 (m, 4H), 3.55-3.20 (m, 2H), 2.25-2.10 (m, 2H), 2.05-1.88 (m, 3H), 1.75-1.55 (m, 2H), 1.45-1.22 (m, 2H), 1.18-1.14 (m, 1H), 1.00-0.95 (m, 1H). |
|---|---|---|---|---|---|
| 180 | A | 1st eluting isomer | ((S)-1-(2'-methoxy-4'-(2H-tetrazol-5-yl)-1',2',3',4',5',6'-hexahydro-[1,1'-biphenyl]-4-yl)-6-azaspiro[2.5]octan-6-yl)((R)-tetrahydrofuran-2-yl)methanone | 460 | 1H-NMR (CD3OD, 400 MHz) δ (ppm): 7.75 (s, 1H), 7.69 (d, J = 8.0 Hz, 1H), 7.52-7.50 (m, 3H), 7.32-7.29 (m, 2H), 4.78-4.68 (m, 1H), 3.97 (s, 3H), 3.95-3.82 (m, 1H), 3.86-3.45 (m, 4H), 3.34-3.12 (m, 1H),2.32-2.11 (m, 2H), 2.10-1.93(m, 3H), 1.92-1.52 (m, 2H), 1.35-1.28 (m, 2H), 1.18-1.10 (m, 1H), 0.99-0.85 (m, 1H). |
| 181 | C | 2nd eluting isomer | ((R)-1-(2'-methoxy-4'-(2H-tetrazol-5-yl)-1',2',3',4',5',6'-hexahydro-[1,1'-biphenyl]-4-yl)-6-azaspiro[2.5]octan-6-yl)((R)-tetrahydrofuran-2-yl)methanone | 460 | 1H-NMR (CD3OD, 400 MHz) δ (ppm): 7.78(s, 1H), 7.69(d, J = 7.6 Hz, 1H), 7.53-7.44 (m, 3H), 7.32-7.23 (m, 2H), 4.80-4.66 (m, 1H), 3.97 (s, 3H), 3.95-3.80 (m, 2H), 3.76-3.62 (m, 2H), 3.60-3.32 (m, 2H), 2.30-1.92(m, 5H), 1.79-1.58 (m, 2H), 1.39-1.16 (m, 2H), 1.17-1.11 (m, 1H), 0.97-0.89 (m, 1H). |

Figure 2-56

| 182 | A | 1st eluting isomer | (1-(3'-(2H-tetrazol-5-yl)-[1,1'-biphenyl]-4-yl)-6-azaspiro[2.5]octan-6-yl)(cyclopropyl)methanone | 400 | 1H NMR (CD₃OD, 400 MHz) δ (ppm): 8.31 (s, 1H), 8.00 (d, J = 7.6 Hz, 1H), 7.87 (d, J = 8.0 Hz, 1H), 7.80-7.62 (m, 3H), 7.45-7.33 (m, 2H), 3.92-3.85 (m, 1H), 3.78-3.73 (m, 2H), 3.59-3.45 (m, 1H), 2.18-2.12 (m, 1H), 2.11-1.80 (m, 1H), 1.74-1.50 (m, 2H), 1.44-1.21 (m, 2H), 1.17-1.12 (m, 1H), 1.01-0.93 (m, 1H), 0.91-0.68 (m, 4H). |
| 183 | C | 2nd eluting isomer | | 400 | 1H NMR (CD3OD, 400 MHz) δ (ppm): 8.31 (s, 1H), 8.00 (d, J = 8.0 Hz, 1H), 7.87 (d, J = 8.0 Hz, 1H), 7.70-7.61 (m, 3H), 7.45-7.33 (m, 2H), 3.94-3.88 (m, 1H), 3.82-3.60 (m, 2H), 3.59-3.43 (m, 1H), 2.19-2.16 (m, 1H), 2.07-1.81 (m, 1H), 1.72-1.59 (m, 2H), 1.45-1.23 (m, 2H), 1.19-1.11 (m, 1H), 1.00-0.98 (m, 1H), 0.94-0.67 (m, 4H). |
| 184 | B | 1st eluting isomer | 2-(4-(6-((R)-tetrahydrofuran-2-carbonyl)-6-azaspiro[2.5]octan-1-yl)phenyl)quinoline-5-carboxylic acid | 457 | 1H NMR (CD₃OD, 400 MHz) δ (ppm): 9.47 (d, J = 8.8 Hz, 1H), 8.32 (m, 2H), 8.15-8.10 (m, 3H), 7.83 (t, J = 8.0 Hz, 1H), 7.47-7.44 (m, 2H), 4.88-4.77 (m, 1H), 3.95-3.69 (m, 4H), 3.46-3.34(m, 1H), 3.33-3.32 (m, 1H), 2.23-1.92 (m, 5H), 1.68-1.66 (m, 2H), 1.30-1.28 (m, 2H), 1.22-1.20 (m, 1H), 1.03-1.00 (m, 1H). |

Figure 2-57

| 185 | C | 2nd eluting isomer | | 457 | 1H NMR (CD3OD, 400 MHz) δ(ppm): 9.47 (d, J = 8.8 Hz, 1H), 8.31 (d, J = 8.0 Hz, 2H), 8.15-8.10 (m, 3H), 7.83 (t, J = 8.0 Hz, 1H), 7.46 (d, J = 8.0 Hz, 2H), 4.88-4.77 (m, 1H), 3.96-3.69 (m, 4H), 3.46-3.34(m, 1H), 3.33–3.32 (m, 1H), 2.23-1.92 (m, 5H), 1.68-1.66 (m, 2H), 1.30-1.28 (m, 2H), 1.22-1.20 (m, 1H), 1.03-1.00 (m, 1H). |
|---|---|---|---|---|---|
| 186 | A | 1st eluting isomer | 5-chloro-4'-(6-((R)-tetrahydrofuran-2-carbonyl)-6-azaspiro[2.5]octan-1-yl)-[1,1'-biphenyl]-3-carboxylic acid | 440 | 1H NMR (400 MHz, CD3OD) δ (ppm): 8.18 (d, J = 1.8 Hz, 1H), 7.95 (s, 1H), 7.86 (s, 1H), 7.65-7.48 (m, 2H), 7.41-7.35 (m, 2H), 4.79-4.64 (m, 1H), 4.01-3.65 (m, 4H), 3.51-3.19 (m, 2H), 2.23-1.82 (m, 5H), 1.78-1.52 (m, 2H), 1.47-1.05 (m, 3H), 0.97-0.91 (m, 1H). |
| 187 | C | 2nd eluting isomer | | 440 | 1H-NMR (400 MHz, CD3OD) δ (ppm): 8.18 (d, J = 2.1 Hz, 1H), 7.98 (s, 1H), 7.86 (s, 1H), 7.62-7.56 (m, 2H), 7.41-7.35 (m, 2H), 4.78-4.62 (m, 1H), 4.01-3.81 (m, 2H), 3.77-3.58 (m, 2H), 3.56-3.25 (m, 2H), 2.29-2.12 (m, 2H), 2.10-1.89 (m, 3H), 1.75-1.52 (m, 2H), 1.36-1.11 (m, 3H), 0.99-0.96 (m, 1H). |

Figure 2-58

| | | | | |
|---|---|---|---|---|
| 188 | A | 1st eluting isomer | 3'-fluoro-6-methoxy-4'-(6-((R)-tetrahydrofuran-2-carbonyl)-6-azaspiro[2.5]octan-1-yl)-[1,1'-biphenyl]-3-carboxylic acid | 454, 456 | 1H NMR (400 MHz, DMSO-d6) δ 12.74 (br, 1H), 7.99-7.94 (m, 1H), 7.85 (s, 1H), 7.35-7.20 (m, 4H), 4.74-4.56 (m, 1H), 3.87 (s, 3H), 3.81-3.51 (m, 4H), 3.44-3.36 (m, 1H), 3.29-3.16 (m, 1H), 2.15-1.91 (m, 3H), 1.88-1.71 (m, 2H), 1.69-1.45 (m, 2H), 1.3-1.02 (m, 3H), 0.99-0.91 (m, 1H). |
| 189 | D | 2nd eluting isomer | 3'-fluoro-6-methoxy-4'-(6-((R)-tetrahydrofuran-2-carbonyl)-6-azaspiro[2.5]octan-1-yl)-[1,1'-biphenyl]-3-carboxylic acid | 454, 456 | 1H NMR (400 MHz, DMSO-d6) δ 12.74 (br, 1H), 8.0-7.93 (m, 1H), 7.86-7.84 (m, 1H), 7.43-7.19 (m, 4H), 4.74-4.55 (m, 1H), 3.87 (s, 3H), 3.80-3.46 (m, 4H), 3.42-3.37 (m, 1H), 3.27-3.12 (m, 1H), 2.08-1.92 (m, 3H), 1.85-1.76 (m, 2H), 1.60-1.45 (m, 2H), 1.39-1.12 (m, 3H), 0.95-0.90 (m, 1H). |
| 190 | B | 1st eluting isomer | 6-(difluoromethyl)-4'-(6-((R)-tetrahydrofuran-2-carbonyl)-6-azaspiro[2.5]octan-1-yl)-[1,1'-biphenyl]-3-carboxylic acid | 456 | 1H-NMR (CD3OD, 400 MHz) δ (ppm): 8.16 (d, J = 8.0 Hz, 1H), 7.99 (s, 1H), 7.87 (d, J = 8.0 Hz, 1H), 7.43-7.26 (m, 4H), 6.81-6.50 (m, 1H), 4.85-4.68 (m, 1H), 3.98-3.90 (m, 1H), 3.89-3.62 (m, 3H), 3.53-3.36 (m, 2H), 2.26-2.12 (m, 2H), 2.10-1.85 (m, 3H), 1.82-1.50 (m, 2H), 1.46-1.21 (m, 2H), 1.19-1.11 (m, 1H), 1.02-0.92 (m, 1H). |

Figure 2-59

| | | | | | |
|---|---|---|---|---|---|
| 191 | D | 2nd eluting isomer | | 456 | 1H-NMR (CD₃OD, 400 MHz) δ (ppm): 8.15 (d, J = 8.0 Hz, 1H), 8.00 (s, 1H), 7.87 (d, J = 8.4 Hz, 1H), 7.42-7.27 (m, 4H), 6.81-6.60 (m, 1H), 4.85-4.68 (m, 1H), 3.99-3.64 (m, 4H), 3.55-3.35 (m, 2H), 2.28-2.12 (m, 2H), 2.10-1.85 (m, 3H), 1.76-1.55 (m, 2H), 1.52-1.22 (m, 2H), 1.20-1.12 (m, 1H), 1.09-0.98 (m, 1H). |
| 192 | D | 1st eluting isomer | 4-(4-(6-((R)-tetrahydrofuran-2-carbonyl)-6-azaspiro[2.5]octan-1-yl)phenyl)picolinic acid | 407 | 1H-NMR (CD₃OD, 400 MHz) δ (ppm): 8.70 (d, J = 5.2 Hz, 1H), 8.49 (s, 1H), 8.02 – 8.01 (m, 1H), 7.81 (d, J = 8.0 Hz, 2H), 7.46 (d, J = 8.4 Hz, 2H), 4.90-4.67 (m, 1H), 3.95-3.72 (m, 4H), 3.57-3.39 (m, 1H), 3.33-3.32 (m, 1H), 2.21-2.18 (m, 2H), 1.99-1.91 (m, 3H), 1.65-1.30 (m, 2H), 1.26-1.19 (m, 3H), 1.03-1.00 (m, 1H). |
| 193 | B | 2nd eluting isomer | | 407 | 1H-NMR (CD₃OD, 400 MHz) δ (ppm): 8.70 (d, J = 5.2 Hz, 1H), 8.50 (s, 1H), 8.02 (d, J = 5.2 Hz, 1H), 7.81 (d, J = 7.6 Hz, 2H), 7.48-7.45 (m, 2H), 4.90-4.78 (m, 1H), 3.97-3.93 (m, 1H), 3.88-3.81 (m, 2H), 3.71-3.57 (m, 1H), 3.45-3.42 (m, 1H), 3.30 (s, 1H), 2.22-2.17 (m, 2H), 2.14-1.85 (m, 3H), 1.81-1.35 (m, 3H), 1.30-1.26 (m, 1H), 1.25-1.19 (m, 1H), 1.03-0.98 (m, 1H). |

Figure 2-60

| | | | | 1H-NMR (CD3OD, 400 MHz) δ (ppm): |
|---|---|---|---|---|
| 194 | C | 1st eluting isomer | 4'-(6-(1H-pyrazole-5-carbonyl)-6-azaspiro[2.5]octan-1-yl)-6-methoxy-1,2,3,4,5,6-hexahydro-[1,1'-biphenyl]-3-carboxylic acid | 432 | 1H-NMR (CD3OD, 400 MHz) δ (ppm): 8.10-7.89 (m, 2H), 7.82-7.62 (m, 1H), 7.62-7.39 (m, 2H), 7.39-7.23 (m, 2H), 7.16 (d, J = 8.0 Hz, 1H), 6.72-6.26 (m, 1H), 4.09-3.80 (m, 5H), 3.80-3.40(m, 2H), 2.25-2.05 (m, 1H), 1.91-1.60 (m, 2H), 1.48-1.28 (m, 2H), 1.22-1.07 (m, 1H), 1.07-0.85 (m, 1H). |
| 195 | B | 2nd eluting isomer | | 432 | 8.11-7.89 (m, 2H), 7.78-7.58 (m, 1H), 7.52-7.40 (m, 2H), 7.40-7.23 (m, 2H), 7.16 (d, J = 7.2 Hz, 1H), 6.72-6.49 (m, 1H), 4.09-3.78 (m, 5H), 3.78-3.43(m, 2H), 2.28-2.05 (m, 1H), 1.80-1.55 (m, 2H), 1.46-1.23 (m, 2H), 1.19-1.08 (m, 1H), 1.08-0.88(m, 1H). |
| 196 | D | 1st eluting isomer | 4'-(6-(1H-1,2,3-triazole-5-carbonyl)-6-azaspiro[2.5]octan-1-yl)-6-methoxy-[1,1'-biphenyl]-3-carboxylic acid | 433 | 1H-NMR (CD3OD, 400 MHz) δ (ppm): 8.78-8.19 (m, 1H), 8.09-7.98 (m, 1H), 7.98-7.91 (m, 1H), 7.51-7.41 (m, 2H), 7.41-7.26 (m, 2H), 7.26-7.06 (m, 1H), 4.01-3.84 (m, 5H), 3.77-3.61 (m, 1H), 3.61-3.47 (m, 1H), 2.24-2.09 (m, 1H), 1.79-1.61 (m, 2H), 1.49-1.31 (m, 2H), 1.24-1.08 (m, 1H), 1.08-0.91 (m, 1H). |

Figure 2-61

| 197 | B | 2nd eluting isomer | | 433 | 1H-NMR (CD3OD, 400 MHz) δ (ppm): 8.67-8.32 (m, 1H), 8.07-7.99 (m, 1H), 7.99-7.91 (m, 1H), 7.51-7.39 (m, 2H), 7.39-7.24 (m, 2H), 7.24-7.02 (m, 1H), 4.01-3.81 (m, 5H), 3.77-3.63 (m, 1H),3.63-3.47 (m, 1H), 2.22-2.11 (m, 1H), 1.79-1.64 (m, 2H), 1.49-1.29 (m, 2H), 1.19-1.08 (m, 1H), 1.08-0.91 (m, 1H). |
|---|---|---|---|---|---|
| 198 | A | 1st eluting isomer | (1-(2'-methyl-4'-(1H2,2H4-tetrazol-5-yl)-[1,1'-biphenyl]-4-yl)-6-azaspiro[2.5]octan-6-yl)((R)-tetrahydrofuran-2-yl)methanone | 444 | 1H-NMR (CD3OD, 400 MHz) δ (ppm): 7.97 (s, 1H), 7.90 (d, J= 8.0 Hz, 1H), 7.42 (d, J=8.0 Hz, 1H), 7.42-7.35 (m, 4H), 4.84-4.65 (m, 1H), 4.10-3.98 (m, 1H), 3.92-3.80 (m, 1H), 3.80-3.60 (m, 2H), 3.55-3.45 (m, 2H), 2.38 (s, 3H), 2.31-2.10 (m, 2H), 2.10-1.88 (m, 3H), 1.85-1.57 (m, 2H), 1.45-1.21 (m, 2H), 1.19-1.11 (m, 1H), 0.99-0.90 (m, 1H). |
| 199 | C | 2nd eluting isomer | | 444 | 1H-NMR (CD3OD, 400 MHz) δ (ppm): 7.97 (s, 1H), 7.90 (d, J= 8.0 Hz, 1H), 7.42 (d, J=7.6 Hz, 1H), 7.39-7.24 (m, 4H), 4.85-4.61 (m, 1H), 4.08-3.60 (m, 4H), 3.55-3.33 (m, 2H), 2.38 (s, 3H), 2.30-2.10 (m, 2H), 2.10-1.85 (m, 3H), 1.80-1.53 (m, 2H), 1.45-1.22 (m, 2H), 1.19-1.12 (m, 1H), 1.01-0.92 (m, 1H). |

Figure 2-62

| | | | | 1H-NMR (CD₃OD, 400 MHz) δ (ppm) |
|---|---|---|---|---|
| 200 | A | 1st eluting isomer | (1-(5'-(1,3-dihydro-2l2-tetrazol-5-yl)-2'-methyl-[1,1'-biphenyl]-4-yl)-6-azaspiro[2.5]octan-6-yl)((R)-tetrahydrofuran-2-yl)methanone | 444 | 1H-NMR (CD₃OD, 400 MHz) δ (ppm): 7.98-7.81 (m, 2H), 7.50 (d, J = 7.6 Hz, 1H), 7.43-7.19 (m, 4H), 4.90-4.74 (m, 1H), 3.98-3.74 (s, 4H), 3.46 (s, 2H), 2.35 (s, 3H), 2.24-1.83 (m, 5H), 1.78-1.52 (m, 2H), 1.47-1.21 (m, 2H), 1.18-1.12 (m, 1H), 1.02-0.95 (m, 1H). |
| 201 | C | 2nd eluting isomer | | 444 | 1H-NMR (CD₃OD, 400 MHz) δ (ppm): 7.85-7.83 (m, 2H), 7.50 (d, J = 8.0 Hz, 1H), 7.38-7.27 (m, 4H), 4.90-4.69 (m, 1H), 4.03-3.64 (m, 4H), 3.43-3.32 (m, 2H), 2.35 (s, 3H), 2.18-2.00 (m, 2H), 1.99-1.93 (m, 3H), 1.80-1.47 (m, 2H), 1.47-1.21 (m, 2H), 1.17-1.14 (m, 1H), 1.01-0.94 (m, 1H). |
| 202 | A | 1st eluting isomer | 1-(1-(4'-(2H-tetrazol-5-yl)-[1,1'-biphenyl]-4-yl)-6-azaspiro[2.5]octan-6-yl)propan-1-one | 388 | 1H-NMR (CD₃OD, 400 MHz) δ (ppm): 8.09 (d, J=8.0 Hz, 2H), 7.85 (d, J=8.0 Hz, 2H), 7.65 (d, J=7.2 Hz, 2H), 7.39-7.32 (m, 2H), 3.82-3.63 (m, 2H), 3.52-3.24 (m, 1H), 3.36-3.31 (m, 1H), 2.52-2.41 (m, 1H), 2.39-2.32 (m, 1H), 2.19-2.11 (m, 1H), 1.69-1.61 (m, 1H), 1.59-1.54 (m, 1H), 1.40-1.25 (m, 2H), 1.20-1.06 (m, 4H), 0.99-0.91 (m, 1H). |

Figure 2-63

| | | | | |
|---|---|---|---|---|
| 203 | C | 2nd eluting isomer | | 388 | 1H-NMR (CD₃OD, 400 MHz) δ (ppm): 8.15-8.03 (m, 2H), 7.89-7.81 (m, 2H), 7.68-7.60 (m, 2H), 7.41-7.32 (m, 2H), 3.85-3.63 (m, 2H), 3.56-3.22 (m, 2H), 2.51-2.32 (m, 2H), 2.19-2.09 (m, 1H), 1.71-1.58 (m, 2H), 1.49-1.20 (m, 2H), 1.19-1.03 (m, 4H), 0.99-0.91 (m, 1H). |
| 204 | A | 1st eluting isomer | 1-(1-(3'-(2H-tetrazol-5-yl)-1,2,3,4-tetrahydro-[1,1'-biphenyl]-4-yl)-6-azaspiro[2.5]octan-6-yl)propan-1-one | 388 | 1H-NMR (400 MHz, CD₃OD) δ (ppm): 8.31 (s, 1H), 8.00 (d, J = 6.8 Hz, 1H), 7.87 (d, J = 7.2 Hz, 1H), 7.69-7.63 (m, 3H), 7.39 (d, J = 6.8 Hz, 2H), 3.76-3.66 (m, 2H), 3.55-3.35 (m, 2H), 2.50-2.43 (m, 1H), 2.38-2.31 (m, 1H), 2.20-2.15 (m, 1H), 1.70-1.58 (m, 2H), 1.41-1.20 (m, 2H), 1.19-1.05 (m, 4H), 1.02-0.95 (m, 1H). |
| 205 | B | 2nd eluting isomer | | 388 | 1H-NMR (400 MHz, CD₃OD) δ (ppm): 8.31 (s, 1H), 8.00 (d, J = 6.8 Hz, 1H), 7.87 (d, J = 7.2 Hz, 1H), 7.69-7.63 (m, 3H), 7.39 (d, J = 6.8 Hz, 2H), 3.80-3.66 (m, 2H), 3.55-3.35 (m, 1H), 2.50-2.43 (m, 1H), 2.38-2.31 (m, 1H), 2.20-2.15 (m, 1H), 1.70-1.65 (m, 1H), 1.64-1.60 (m, 1H), 1.41-1.20 (m, 1H), 1.19-1.05 (m, 4H), 1.02-0.95 (m, 1H). |

Figure 2-64

| 206 | A | 1st eluting isomer | (1-(2'-chloro-4'-(2H-tetrazol-5-yl)-[1,1'-biphenyl]-4-yl)-6-azaspiro[2.5]octan-6-yl)((R)-tetrahydrofuran-2-yl)methanone | 464 | 1H-NMR (d6-DMSO, 400 MHz) δ (ppm): 8.21 (s, 1H), 8.08 (d, J = 8.4 Hz, 1H), 7.67 (d, J = 5.6 Hz, 1H), 7.52-7.37 (m, 4H), 4.85-4.50 (m, 1H), 3.80-3.50 (m, 4H), 3.27-3.17 (m, 2H), 2.19-1.89 (m, 3H), 1.89-1.7 (m, 2H), 1.7-1.47 (m, 2H), 1.20-1.09 (m, 2H), 0.99-0.86 (m, 1H). |
| --- | --- | --- | --- | --- | --- |
| 207 | C | 2nd eluting isomer | (1-(2'-chloro-4'-(2H-tetrazol-5-yl)-[1,1'-biphenyl]-4-yl)-6-azaspiro[2.5]octan-6-yl)((R)-tetrahydrofuran-2-yl)methanone | 464 | 1H-NMR (d6-DMSO, 400 MHz) δ (ppm): 8.25 (s, 1H), 8.08 (d, J = 8.0 Hz, 1H), 7.67 (d, J = 8.0 Hz, 1H), 7.53-7.32 (m, 4H), 4.85-4.40 (m, 1H), 3.95-3.55 (m, 4H), 3.55-3.45 (m, 1H), 3.20-3.10 (m, 1H), 2.20-2.05 (m, 1H), 2.10-1.87 (m, 2H), 1.87-1.65 (m, 2H), 1.63-1.42 (m, 2H), 1.25-1.09 (m, 3H), 0.95-0.87 (m, 1H). |
| 208 | A | 1st eluting isomer | (1-(2'-chloro-5'-(1,3-dihydro-2l2-tetrazol-5-yl)-[1,1'-biphenyl]-4-yl)-6-azaspiro[2.5]octan-6-yl)((R)-tetrahydrofuran-2-yl)methanone | 464 | 1H-NMR (400 MHz, CD3OD) δ (ppm): 8.06 (s, 1H), 8.01 (d, J = 8.0 Hz, 1H), 7.74 (d, J = 8.0 Hz, 1H), 7.48-7.45 (m, 2H), 7.44-7.41 (m, 2H), 4.78-4.65 (m, 1H), 4.02-3.58 (m, 4H), 3.52-3.35 (m, 2H), 2.30-1.86 (m, 5H), 1.83-1.52 (m, 2H), 1.50-1.06 (m, 3H), 1.03-0.78 (m, 1H). |

Figure 2-65

| 209 | B | 2nd eluting isomer | | 464 | 1H-NMR (400 MHz, CD3OD) δ (ppm): 8.07 (s, 1H), 8.00 (d, J = 8.4 Hz, 1H), 7.68 (d, J = 8.4 Hz, 1H), 7.46 (d, J = 8.4 Hz, 2H), 7.38 (d, J = 8.4 Hz, 2H), 4.78-4.62 (m, 1H), 4.02-3.65 (m, 4H), 3.58-3.36 (m, 2H), 2.30-2.15 (m, 2H), 2.10-1.88 (m, 3H), 1.80-1.57 (m, 2H), 1.36-1.29 (m, 2H), 1.21-1.18 (m, 1H), 1.02-0.95 (m, 1H). |
|---|---|---|---|---|---|
| 210 | D | 1st eluting isomer | 4'-(6-(1-aminocyclopropane-1-carbonyl)-6-azaspiro[2.5]octan-1-yl)-[1,1'-biphenyl]-4-carboxylic acid | 390 | 1H-NMR (400 MHz, CD3OD) δ (ppm): 8.10 (d, J=8.4 Hz, 2H), 7.74 (d, J=8.4 Hz, 2H), 7.64 (d, J= 8.0 Hz, 2H), 7.38 (d, J=8.4 Hz, 2H), 3.87-3.50 (m, 2H), 3.45-3.40 (m, 1H), 3.34-3.32 (m, 1H), 2.21-2.17 (m, 1H), 1.70-1.68 (m, 2H), 1.41-1.29 (m, 2H), 1.19-1.16 (m, 3H), 1.16-0.99 (m, 3H). |
| 211 | B | 2nd eluting isomer | | 391 | 1H NMR (CD3OD, 400 MHz) δ (ppm): 8.10 (d, J = 8.4 Hz, 2H), 7.74 (d, J = 8.0 Hz, 2H), 7.65 (d, J = 8.4 Hz, 2H), 7.38 (d, J = 8.0 Hz, 2H), 3.84-3.59 (m, 2H), 3.57-3.54 (m, 1H), 3.45-3.32 (m, 1H), 2.20-2.17 (m, 1H), 1.70-1.68 (m, 2H), 1.38-1.30 (m, 2H), 1.19-1.05 (m, 3H), 1.01-0.96 (m, 3H). |

Figure 2-66

| | | | | |
|---|---|---|---|---|
| 212 | A | 1st eluting isomer | 3-(4-(6-((R)-tetrahydrofuran-2-carbonyl)-6-azaspiro[2.5]octan-1-yl)phenyl)isoquinoline-8-carboxylic acid | 457 | 1H NMR (400 MHz, DMSO-d6) δ (ppm):13.56 (br, 1H), 10.24 (s, 1H), 8.50 (s, 1H), 8.27-8.15 (m, 4H), 7.86 (t, J = 7.6 Hz, 1H), 7.41 (d, J = 8.0 Hz, 2H), 4.69-4.56 (m, 1H), 3.82-3.49 (m, 4H), 3.45-3.38 (m, 1H), 3.20-3.17 (m, 1H), 2.13-2.10 (m, 1H), 2.08-1.69 (m, 4H), 1.59-1.46 (m, 2H), 1.37-1.02 (m, 3H), 0.93-0.89 (m, 1H). |
| 213 | C | 2nd eluting isomer | | 457 | 1H NMR (400 MHz, DMSO-d6) δ (ppm):13.56 (br, 1H), 10.24 (s, 1H), 8.50 (s, 1H), 8.29-8.14 (m, 4H), 7.86 (t, J = 7.6 Hz, 1H), 7.41 (d, J = 8.0 Hz, 2H), 4.68-4.56 (m, 1H), 3.82-3.55 (m, 4H), 3.43-3.39 (m, 1H), 3.24-3.03 (m, 1H), 2.13-2.10 (m, 1H), 2.08-1.70 (m, 4H), 1.65-1.47 (m, 2H), 1.32-1.03 (m, 3H), 0.93-0.89 (m, 1H). |
| 214 | C | 1st eluting isomer | 1-methyl-2-(4-(6-((R)-tetrahydrofuran-2-carbonyl)-6-azaspiro[2.5]octan-1-yl)phenyl)-1H-indole-6-carboxylic acid | 459 | 1H NMR (CD3OD, 400 MHz) δ (ppm): 8.18 (s, 1H), 7.78 (d, J = 8.4 Hz, 1H), 7.62 (d, J = 8.4 Hz, 1H), 7.53 (d, J = 8.0 Hz, 2H), 7.41 (d, J = 8.0 Hz, 2H), 6.60 (s, 1H), 4.80-4.66 (m, 1H), 4.02- 3.93 (m, 1H), 3.88-3.82 (m, 4H), 3.73-3.70 (m, 2H), 3.57-3.49 (m, 1H), 3.43-3.40 (m, 1H), 2.28-2.13 (m, 2H), 2.09-1.85 (m, 3H), 1.75-1.57 (m, 2H), 1.36-1.31 (m, 2H), 1.19-1.62 (m, 1H), 1.02-0.98 (m, 1H). |

Figure 2-67

| | | | | |
|---|---|---|---|---|
| 215 | A | 2nd eluting isomer | | 459 | 1H NMR (CD3OD, 400 MHz) δ (ppm): 8.18 (s, 1H), 7.79 (d, J = 8.4 Hz, 1H), 7.61 (d, J = 8.4 Hz, 1H), 7.53 (d, J = 8.0 Hz, 2H), 7.42-7.39 (m, 2H), 6.60 (s, 1H), 4.78-4.67 (m, 1H), 3.97-3.81(m, 5H), 3.79-3.73 (m, 2H), 3.46-3.44 (m, 1H), 3.33-3.32 (m, 1H), 2.21-2.19 (m, 2H), 2.09-1.85 (m, 3H), 1.80-1.55 (m, 2H), 1.44-1.28 (m, 2H) 1.18-1.17 (m, 1H), 1.02-0.98 (m, 1H). |
| 216 | A | 1st eluting isomer | 4-hydroxy-6-methoxy-4'-(6-((R)-tetrahydrofuran-2-carbonyl)-6-azaspiro[2.5]octan-1-yl)-[1,1'-biphenyl]-3-carboxylic acid | 452 | 1H-NMR (CD3OD, 400 MHz) δ (ppm): 7.74 (s, 1H), 7.37(d, J=7.6 Hz, 2H), 7.24 (d, J= 7.6 Hz, 2H), 6.60 (s, 1H), 4.90-4.65 (m, 1H), 3.97-3.87(m, 1H), 3.82-3.65 (m, 6H), 3.45-3.32(m, 1H), 3.29- 3.29(m, 1H), 2.16-2.04 (m, 2H), 2.11-1.89 (m, 3H), 1.89-1.55(m, 2H), 1.36-1.25 (m, 2H), 1.11-1.07(m, 1H), 0.99-0.91(m, 1H). |
| 217 | B | 2nd eluting isomer | | 452 | 1H-NMR (CD3OD, 400 MHz) δ (ppm): 7.75 (s, 1H), 7.37 (d, J = 8.0 Hz, 2H), 7.25 (d, J = 8.0 Hz, 2H), 6.60 (s, 1H), 4.80-4.62 (m, 1H), 4.05-3.91 (m, 1H), 3.89-3.80 (m, 4H), 3.78-3.61 (m, 2H), 3.58-3.25 (m, 2H), 2.28-2.05 (m, 2H), 2.04-1.86 (m, 3H), 1.76-1.49 (m, 2H), 1.38-1.28 (m, 2H), 1.16-1.10 (m, 1H), 0.95-0.88 (m, 1H). |

Figure 2-68

| | | | | |
|---|---|---|---|---|
| 218 | A | 1st eluting isomer | 6-chloro-5-methyl-4'-(6-((R)-tetrahydrofuran-2-carbonyl)-6-azaspiro[2.5]octan-1-yl)-[1,1'-biphenyl]-3-carboxylic acid | 454, 456 | 1H NMR (400 MHz, DMSO-d6) δ 12.74 (br, 1H), 7.99-7.94 (m, 1H), 7.85 (s, 1H), 7.35-7.20 (m, 4H), 4.74-4.56 (m, 1H), 3.87 (s, 3H), 3.81-3.51 (m, 4H), 3.44-3.36 (m, 1H), 3.29-3.16 (m, 1H), 2.15-1.91 (m, 3H), 1.88-1.71 (m, 2H), 1.69-1.45 (m, 2H), 1.3-1.02 (m, 3H), 0.99-0.91 (m, 1H). |
| 219 | C | 2nd eluting isomer | 6-chloro-5-methyl-4'-(6-((R)-tetrahydrofuran-2-carbonyl)-6-azaspiro[2.5]octan-1-yl)-[1,1'-biphenyl]-3-carboxylic acid | 454, 456 | 1H NMR (400 MHz, DMSO-d6) δ 12.74 (br, 1H), 8.0-7.93 (m, 1H), 7.86-7.84 (m, 1H), 7.43-7.19 (m, 4H), 4.74-4.55 (m, 1H), 3.87 (s, 3H), 3.80-3.46 (m, 4H), 3.42-3.37 (m, 1H), 3.27-3.12 (m, 1H), 2.08-1.92 (m, 3H), 1.85-1.76 (m, 2H), 1.60-1.45 (m, 2H), 1.39-1.12 (m, 3H), 0.95-0.90 (m, 1H). |
| 220 | A | 1st eluting isomer | 6-fluoro-5-methyl-4'-(6-((R)-tetrahydrofuran-2-carbonyl)-6-azaspiro[2.5]octan-1-yl)-[1,1'-biphenyl]-3-carboxylic acid | 438 | 1HNMR (CD3OD, 400 MHz) δ (ppm): 8.10-7.69 (m, 2H), 7.65-7.15 (m, 4H), 4.85-4.55 (m, 1H), 4.00-3.55 (m, 4H), 3.54-3.34 (m, 2H), 2.39 (s, 3H), 2.38-1.80 (m, 5H), 1.78-1.47 (m, 2H), 1.46-1.19 (m, 2H), 1.18-0.80 (m, 2H). |
| 221 | C | 2nd eluting isomer | 6-fluoro-5-methyl-4'-(6-((R)-tetrahydrofuran-2-carbonyl)-6-azaspiro[2.5]octan-1-yl)-[1,1'-biphenyl]-3-carboxylic acid | 438 | 1HNMR (CD3OD, 400 MHz) δ (ppm): 8.05-7.80 (m, 2H), 7.60-7.42 (m, 2H), 7.41-7.21 (m, 2H), 4.81-4.52 (m, 1H), 4.05-3.82 (m, 2H), 3.80-3.58 (m, 2H), 3.57-3.35 (m, 5H), 2.39 (s, 3H), 2.38-1.80 (m, 5H), 1.79-1.41 (m, 2H), 1.40-1.20 (m, 2H), 1.19-0.80 (m, 2H). |

Figure 2-69

| | | | | |
|---|---|---|---|---|
| 222 | NT | 1st eluting isomer | 6-chloro-5-methoxy-4'-(6-((R)-tetrahydrofuran-2-carbonyl)-6-azaspiro[2.5]octan-1-yl)-[1,1'-biphenyl]-3-carboxylic acid | 470 | 1H-NMR (CD$_3$OD, 400 MHz) δ (ppm): 7.68 (s, 1H), 7.61 (s, 1H), 7.42-7.25(m, 4H), 4.85-3.67 (m, 1H), 3.97 (s, 3H), 3.96-3.91 (m, 1H), 3.90-3.69(m, 3H), 3.58-3.35(m, 2H), 2.28-2.11 (m, 2H), 2.10-1.85(m, 3H),1.80-1.49 (m, 2H), 1.42-1.22(m, 2H), 1.20-1.05,(m, 1H), 1.01-0.92 (m,1H). |
| 223 | A | 2nd eluting isomer | 6-chloro-5-methoxy-4'-(6-((R)-tetrahydrofuran-2-carbonyl)-6-azaspiro[2.5]octan-1-yl)-[1,1'-biphenyl]-3-carboxylic acid | 470 | 1H-NMR (CD$_3$OD, 400 MHz) δ (ppm): 7.70 (s, 1H), 7.60 (s, 1H), 7.41-7.25(m, 4H), 4.82-4.67 (m, 1H), 3.98 (s, 3H), 3.97-3.90 (m, 1H), 3.90-3.60 (m, 3H), 3.58-3.35 (m, 2H), 2.28-2.10 (m, 2H), 2.10-1.8 5(m, 3H), 1.80-1.49 (m, 2H), 1.42-1.22 (m, 2H), 1.19-1.05 (m, 1H), 1.02-0.92 (m, 1H). |
| 224 | D | 1st eluting isomer | 6-fluoro-5-methoxy-4'-(6-((R)-tetrahydrofuran-2-carbonyl)-6-azaspiro[2.5]octan-1-yl)-[1,1'-biphenyl]-3-carboxylic acid | 454 | 1H-NMR (CD$_3$OD, 400 MHz) δ (ppm): 7.88-7.65 (m, 2H), 7.50 (d, J=7.6 Hz, 2H), 7.37 (d, J=8.0 Hz, 2H), 4.81-4.58 (m, 1H), 3.98 (s, 3H), 3.97-3.65 (m, 4H), 3.59-3.34 (m, 2H), 2.39-1.81 (m, 5H), 1.81-1.57 (m, 2H), 1.48-1.21 (m, 2H), 1.21-1.09 (m, 1H), 1.01-0.88 (m, 1H). |

Figure 2-70

| | | | | |
|---|---|---|---|---|
| 225 | B | 2nd eluting isomer | 454 | 1H-NMR (CD₃OD, 400 MHz) δ (ppm): 7.91-7.61 (m, 2H), 7.50 (d, J=7.2 Hz, 2H), 7.43-7.25 (m, 2H), 4.81-4.61 (m, 1H), 3.98 (s, 3H), 3.97-3.58 (m, 4H), 3.48-3.41 (m, 1H), 3.31-3.23 (m, 1H), 2.35-1.89 (m, 5H), 1.82-1.51 (m, 2H), 1.49-1.21 (m, 2H), 1.19-1.13 (m, 1H), 1.01-0.91 (m, 1H). |
| 226 | C | 1st eluting isomer | 460 | 1H-NMR (CD₃OD, 400 MHz) δ (ppm): 8.01-7.98 (m, 2H), 7.51 (d, J = 8.0 Hz, 2H), 7.33-7.18 (m, 3H), 4.78-4.66 (m, 1H), 3.99-3.97 (m, 4H), 3.96-3.88 (m, 1H), 3.76-3.72 (m , 2H), 3.60-3.50 (m, 1H), 3.41 (s, 1H), 2.31-2.14 (m, 2H), 2.14-1.92 (m, 3H),1.80-1.61(m, 2H),1.42-1.22(m, 2H), 1.15-1.12(m, 1H), 0.98-0.95 (m, 1H). |
| 227 | A | 2nd eluting isomer | ((1-(2'-methoxy-5'-(2H-tetrazol-5-yl)-[1,1'-biphenyl]-4-yl)-6-azaspiro[2.5]octan-6-yl)((R)-tetrahydrofuran-2-yl)methanone | 460 | 1H-NMR (CD₃OD, 400 MHz) δ (ppm): 8.02-7.98 (m ,2H), 7.52 (d, J = 7.2 Hz, 2H), 7.34-7.29 (m, 3H), 4.89-4.69 (m, 1H), 3.98-3.93 (m, 4H), 3.89-3.69 (m, 3H), 3.69-3.45 (m, 2H), 2.31-2.18 (m, 2H), 2.16-1.94 (m, 3H), 1.80-1.55 (m, 2H), 1.50-1.30 (m, 2H), 1.15-1.14 (m, 1H), 0.97-0.95 (m, 1H). |

Figure 2-71

| 228 | A | 1st eluting isomer | (1-(4'-(2H-tetrazol-5-yl)-[1,1'-biphenyl]-4-yl)-6-azaspiro[2.5]octan-6-yl)(cyclopropyl)methanone | 400 | 1H-NMR (CD₃OD, 400 MHz) δ (ppm): 8.11 (d, J=8.4 Hz, 2H), 7.86 (d, J=8.4 Hz, 2H), 7.67 (d, J=7.6 Hz, 2H), 7.39 (d, J=7.2 Hz, 2H), 3.99-3.91 (m, 1H), 3.82-3.61 (m,1H), 3.60-3.35 (m, 2H), 2.24-2.12 (m, 1H), 2.08-1.91 (m, 1H), 1.79-1.67 (m, 1H), 1.65-1.52 (m, 1H), 1.48-1.23 (m, 2H), 1.22-1.14 (m, 1H), 1.02-0.94 (m, 1H), 0.91-0.76 (m, 4H). |
|---|---|---|---|---|---|
| 229 | C | 2nd eluting isomer | | 400 | 1H-NMR (CD₃OD, 400 MHz) δ (ppm): 8.11 (d, J=8.4 Hz, 2H), 7.87 (d, J=8.4 Hz, 2H), 7.67 (d, J=6.8 Hz, 2H), 7.42-7.33 (m, 2H), 3.95-3.86 (m, 1H), 3.84-3.69 (m,1H), 3.67-3.35 (m, 2H), 2.21-2.14 (m, 1H), 2.07-1.84 (m, 1H),1.75-1.56 (m, 2H), 1.54-1.22 (m, 2H), 1.21-1.12 (m,1H), 1.04-0.98 (m, 1H), 0.91-0.73 (m, 4H). |
| 230 | B | 1st eluting isomer | 2-(1-methyl-1H-pyrazol-4-yl)-5-{4-[(6-[(2R)-oxolane-2-carbonyl]-6-azaspiro[2.5]octan-1-yl]phenyl}benzoic acid | 486 | 1H-NMR (400 MHz, CD₃OD) δ (ppm): 7.96 (s, 1H), 7.82 (s, 1H), 7.77 (d, J = 6.0 Hz, 1H), 7.65 (s, 1H), 7.61 (d, J = 7.2 Hz, 2H), 7.54 (d, J= 8.0 Hz, 1H), 7.37-7.34 (m, 2H), 4.78-4.65 (m, 1H), 3.98-3.90 (m, 4H), 3.89-3.62 (m, 3H), 3.49-3.25 (m, 2H), 2.25-2.10 (m, 2H), 2.05-1.88 (m, 3H), 1.72-1.55 (m, 2H), 1.42-1.21 (m, 2H), 1.16-1.12 (m, 1H), 0.98-0.94 (m, 1H). |

Figure 2-72

| | | | | |
|---|---|---|---|---|
| 231 | D | 2nd eluting isomer | | 486 | 1H-NMR (400 MHz, CD3OD) δ (ppm): 7.96 (s, 1H), 7.82 (s, 1H), 7.78-7.75 (m, 1H), 7.65 (s, 1H), 7.61 (d, J = 7.2 Hz, 2H), 7.53 (d, J = 8.0 Hz, 1H), 7.37-7.34 (m, 2H), 4.76-4.65 (m, 1H), 3.98-3.90 (m, 4H), 3.89-3.81 (m, 1H), 3.80-3.61(m, 2H), 3.55-3.24 (m, 2H), 2.25-2.10 (m, 2H), 2.05-1.88 (m, 3H), 1.72-1.55 (m, 2H), 1.34-1.21 (m, 2H), 1.16-1.12 (m, 1H), 0.98-0.94 (m, 1H). |
| 232 | B | 1st eluting isomer | 6-{4-[6-(1-hydroxycyclopropanecarbonyl)-6-azaspiro[2.5]octan-1-yl]phenyl}-1-methyl-1H-indazole-3-carboxylic acid | 446 | 1H NMR (400 MHz, CD3OD -d4) δ(ppm): 8.37 (s, 1H), 7.82-7.79 (m, 1H), 7.74-7.72 (m, 1H), 7.65-7.63 (d, J = 8 Hz, 2H), 7.38-7.36 (d, J = 8 Hz, 2H), 4.21 (s, 3H), 4.03-3.50 (m, 4H), 2.11-2.04 (m, 1H), 1.72-1.63 (s, 2H), 1.39-1.28 (s, 2H), 1.21-1.15 (m, 1H), 1.12-0.99 (m, 3H), 0.95-0.82 (s, 2H). |
| 233 | A | 2nd eluting isomer | | 446 | 1H NMR (400 MHz, CD3OD -d4) δ(ppm): 8.37 (s, 1H), 7.82-7.80 (m, 1H), 7.75-7.71 (m, 1H), 7.63 (d, J=8.0 Hz, 2H), 7.37 (d, J=8.4 Hz, 2H), 4.21 (s, 3H), 4.21-3.41 (m, 4H), 2.18-2.06 (m, 1H), 1.67-1.50 (m, 2H), 1.34-1.31 (m, 2H), 1.22-1.14 (m, 1H), 1.06-0.95 (m, 3H), 0.92-0.81 (m, 2H). |

Figure 2-73

| | | | | |
|---|---|---|---|---|
| 234 | B | 1st eluting isomer | 5-{4-[6-(1-hydroxycyclopropanecarbonyl)-6-azaspiro[2.5]octan-1-yl]phenyl}thiophene-2-carboxylic acid | 398 | 1HNMR (CD$_3$OD, 400 MHz) δ (ppm): 7.74 (d, J=4.0 Hz, 1H), 7.65 (d, J=8.4 Hz, 2H), 7.41 (d, J=3.6 Hz, 1H), 7.33 (d, J=8.4 Hz, 2H), 4.29-3.35 (m, 4H), 2.21-2.00 (m, 1H), 1.80-1.52 (m, 2H), 1.40-1.25 (m, 2H), 1.20-1.09 (m, 1H), 1.08-0.92 (m, 3H), 0.91-0.78 (m, 2H). |
| 235 | C | 2nd eluting isomer | | 398 | 1HNMR (CD$_3$OD, 400 MHz) δ (ppm): 7.74 (d, J=4.0 Hz, 1H), 7.65 (d, J=8.0 Hz, 2H), 7.41 (d, J=3.6 Hz, 1H), 7.33 (d, J=8.4 Hz, 2H), 4.19-3.39 (m, 4H), 2.20-2.09 (m, 1H), 1.80-1.49 (m, 2H), 1.42-1.21 (m, 2H), 1.20-1.11 (m, 1H), 1.08-0.92 (m, 3H), 0.89-0.78 (m, 2H). |
| 236 | A | 1st eluting isomer | 3-{4-[6-[(2R)-oxolane-2-carbonyl]-6-azaspiro[2.5]octan-1-yl]phenyl}-8-(2H-1,2,3,4-tetrazol-5-yl)quinoline | 481 | 1H NMR (DMSO-d6, 400 MHz) δ (ppm): 9.71 (s, 1H), 9.12-8.73 (m, 2H), 8.32-8.16 (m, 1H), 7.89-7.67 (m, 3H), 7.49 (d, J = 6.0 Hz, 2H), 4.76-4.52 (m, 1H), 3.82-3.51 (m, 4H), 3.41-3.12 (m, 2H), 2.17-2.11 (m, 1H), 2.09-1.88 (m, 2H), 1.86-1.72 (m, 2H), 1.66-1.47 (m, 2H), 1.35-1.04 (m, 3H), 0.95-0.87 (m, 1H). |

Figure 2-74

| | | | | |
|---|---|---|---|---|
| 237 | C | 2nd eluting isomer | 481 | 1H NMR (DMSO-d6, 400 MHz) δ (ppm): 9.70 (s, 1H), 9.13-8.65 (m, 2H), 8.32-8.16 (m, 1H), 7.95-7.67 (m, 3H), 7.55-7.41 (m, 2H), 4.72-4.51 (m, 1H), 3.82-3.52 (m, 4H), 3.22 – 3.05 (m, 2H), 2.18-2.12 (m, 1H), 2.08-1.89 (m, 2H), 1.86-1.69 (m, 2H), 1.68-1.46 (m, 2H), 1.31-1.02 (m, 3H), 0.97-0.84 (m, 1H). |
| 238 | A | 1st eluting isomer | 481 | 1H NMR (400 MHz, DMSO-d6) δ 9.32 (s, 1H), 8.67 (d, J = 7.6 Hz, 2H), 8.29 (d, J = 8.4 Hz, 1H), 8.16 (d, J = 8.4 Hz, 1H), 7.85 (d, J = 8.0 Hz, 2H), 7.75-7.56 (m, 2H), 4.64-4.54 (m, 1H), 3.83-3.58 (m, 4H), 3.23-3.15 (m, 2H), 2.17-2.12 (m, 1H), 2.09-1.88 (m, 2H), 1.86-1.68 (m, 2H), 1.63-1.51 (m, 2H), 1.35-1.05 (m, 3H), 0.95-0.88 (m, 1H). |
| 239 | C | (1-(4-(7-(2H-tetrazol-5-yl)quinolin-3-yl)phenyl)-6-azaspiro[2.5]octan-6-yl)((R)-tetrahydrofuran-2-yl)methanone<br>2nd eluting isomer | 481 | 1H NMR (400 MHz, DMSO-d6) δ9.32 (d, J = 2.3 Hz, 1H), 8.70 – 8.63 (m, 2H), 8.29 (m, 1H), 8.16 (d, J = 8.6 Hz, 1H), 7.85 (d, J = 7.9 Hz, 2H), 7.44 (d, J = 8.0 Hz, 2H), 4.75-4.56 (m, 1H), 3.85-3.59 (m, 4H), 3.33-3.13 (m, 2H), 2.16-2.12 (m, 1H), 2.09-1.91 (m, 2H), 1.87-1.71 (m, 2H), 1.68-1.47 (m, 2H), 1.28-1.05 (m, 3H), 0.93-0.88 (m, 1H). |

Figure 2-75

| | | | | |
|---|---|---|---|---|
| 240 | A | 1st eluting isomer | (1-(4-(1-methyl-3-(2H-tetrazol-5-yl)-1H-indazol-6-yl)phenyl)-6-azaspiro[2.5]octan-6-yl)((R)-tetrahydrofuran-2-yl)methanone | 484 | 1H NMR (400 MHz, DMSO-d6) δ 8.36 (d, J = 8.4 Hz, 1H), 7.99 (s, 1H), 7.76 (d, J = 8.0 Hz, 2H), 7.61 (d, J = 8.4 Hz, 1H), 7.39 (d, J = 8.0 Hz, 2H), 4.73-4.64 (m, 1H), 4.21 (s, 3H), 3.86-3.63 (m, 4H), 3.33-3.12 (m, 2H), 2.19-1.67 (m, 5H), 1.62-1.45 (m, 2H), 1.32-1.09 (m, 3H), 0.92-0.86 (m, 1H). |
| 241 | D | 2nd eluting isomer | (1-(4-(1-methyl-3-(2H-tetrazol-5-yl)-1H-indazol-6-yl)phenyl)-6-azaspiro[2.5]octan-6-yl)((R)-tetrahydrofuran-2-yl)methanone | 484 | 1H NMR (400 MHz, DMSO-d6) δ 8.36 (d, J = 8.4 Hz, 1H), 8.00 (s, 1H), 7.76 (d, J = 8.0 Hz, 2H), 7.62 (d, J = 8.8 Hz, 1H), 7.39 (d, J = 8.0 Hz, 2H), 4.73-4.52 (m, 1H), 4.21 (s, 3H), 3.82-3.56 (m, 4H), 3.33-3.09 (m, 2H), 2.16-2.12 (m, 1H), 2.09-1.89 (m, 2H), 1.87-1.68 (m, 2H), 1.65-1.45 (m, 2H), 1.37-1.03 (m, 3H), 0.93-0.87 (m, 1H). |
| 242 | D | 1st eluting isomer | ((S)-1-(4-(5-(2H-tetrazol-5-yl)benzo[d]oxazol-2-yl)phenyl)-6-azaspiro[2.5]octan-6-yl)((R)-tetrahydrofuran-2-yl)methanone | 471 | 1H NMR (400 MHz, CD3OD-d4) δ(ppm): 8.40 (s, 1H), 8.22 (d, J = 8.4 Hz, 2H), 8.14 (d, J = 8.4 Hz, 1H), 7.87 (d, J = 8.4 Hz, 1H), 7.50 (d, J = 8.0 Hz, 2H), 4.85-4.64 (m, 1H), 4.01-3.65 (m, 4H), 3.62-3.33 (m, 2H), 2.28-2.11 (m, 2H), 2.09-1.86 (m, 3H), 1.79-1.54 (m, 2H), 1.42-1.23 (m, 3H), 1.08-1.00 (m, 1H). |
| 243 | B | Racemate | 6-propionyl-1-(4-(quinolin-7-yl)phenyl)-6-azaspiro[2.5]octane-1-carboxylic acid | 415 | |

Figure 2-76

| 244 | C | Racemate | (S)-1-(4-(quinolin-7-yl)phenyl)-6-((R)-tetrahydrofuran-2-carbonyl)-6-azaspiro[2.5]octane-1-carboxylic acid | 457 | |
|---|---|---|---|---|---|
| 245 | B | 1st eluting isomer | 6-propionyl-1-(4-(quinolin-7-yl)phenyl)-6-azaspiro[2.5]octane-1-carboxylic acid | 415 | 1H-NMR (CD3OD, 400 MHz) δ (ppm): 9.01- 8.82 (m, 1H), 8.51-8.34 (m, 1H), 8.33-8.19 (m, 1H), 8.11-8.00 (m, 1H), 8.00-7.91 (m, 1H), 7.83-7.72 (m, 2H), 7.63-7.46 (m, 3H), 4.44 - 4.10 (m, 1H), 4.01-3.62(m, 1H), 3.49-3.17 (m, 1H), 3.17-2.88 (m, 1H), 2.56-2.28 (m, 2H), 2.02-1.71 (m, 3H), 1.69-1.43 (m, 1H), 1.43-1.33 (m, 1H), 1.21-1.01(m, 3H), 0.89-0.71 (m, 1H). LCMS (ES, m/z):415 [M+H]+. |
| 246 | C | 2nd eluting isomer | | 415 | 1H-NMR (CD3OD, 400 MHz) δ (ppm): 8.95-8.81 (m, 1H), 8.51-8.32 (m, 1H), 8.29-8.21 (m, 1H), 8.11-8.01(m, 1H), 8.01-7.91 (m, 1H), 7.83-7.71 (m, 2H), 7.66-7.48 (m, 3H), 4.42-4.09 (m, 1H), 4.00-3.69 (m, 1H), 3.47-3.18 (m, 1H), 3.18-2.82 (m, 1H), 2.54-2.26(m, 2H), 2.01-1.69 (m, 3H), 1.69-1.42(m, 1H), 1.40-1.30 (m, 1H), 1.22-1.02(m, 3H), 0.91 - 0.68 (m, 1H). LCMS (ES, m/z):415 [M+H]+. |

Figure 2-77

| | | | | |
|---|---|---|---|---|
| 247 | C | 1st eluting isomer | 6-(1-hydroxycyclopropane-1-carbonyl)-1-(4-(1-methyl-1H-benzo[d]imidazol-5-yl)phenyl)-6-azaspiro[2.5]octane-1-carboxylic acid | 446 | 1H-NMR (CD3OD, 400 MHz) δ (ppm): 8.20 (s, 1H), 7.91 (s, 1H), 7.70-7.58 (m, 4H), 7.56-7.49 (m, 2H), 4.58-4.01 (m, 2H), 3.95 (s, 3H), 3.70-3.33 (m, 1H), 3.30-2.81(m, 1H), 2.04-1.87 (m, 1H), 1.86-1.79 (m, 1H), 1.78-1.72 (m, 1H), 1.70-1.55 (m, 1H), 1.45-1.26 (m, 1H), 1.12-0.99 (m, 2H), 0.98-0.75 (m, 3H). LCMS (ES, m/z):466[M+H]+ |
| 248 | B | 2nd eluting isomer | | 446 | 1H-NMR (CD3OD, 400 MHz) δ (ppm): 8.21 (s, 1H), 7.91 (s, 1H), 7.75-7.59 (m, 4H), 7.58-7.49 (m, 2H), 4.75-4.01 (m, 2H), 3.96 (s, 3H), 3.88-3.41 (m, 1H), 3.30-2.72 (m, 1H), 2.04-1.87 (m, 1H), 1.86-1.78 (m, 1H), 1.77-1.73 (m, 1H), 1.71-1.55 (m, 1H), 1.45-1.26 (m, 1H), 1.12-0.98 (m, 2H), 0.96-0.77(m, 3H). LCMS (ES, m/z):466[M+H]+ |
| 249 | B | 1st eluting isomer | 6-(1-hydroxycyclopropane-1-carbonyl)-1-(3'-sulfamoyl-[1,1'-biphenyl]-4-yl)-6-azaspiro[2.5]octane-1-carboxylic acid | 471 | 1H-NMR (CD3OD, 400 MHz) δ (ppm): 8.18 (s, 1H), 7.91-7.85 (m, 2H), 7.68-7.60 (m, 3H), 7.59-7.52 (m, 2H), 4.73-3.78 (m, 2H), 3.72-3.35 (m, 1H), 3.30-2.80 (m, 1H), 2.04-1.86 (m, 1H), 1.86-1.75 (m,1H), 1.74-1.70 (m, 1H), 1.69-1.48 (m, 1H), 1.46-1.36 (m, 1H), 1.12-0.99 (m, 2H), 0.96-0.85 (m, 2H), 0.84-0.72 (m, 1H). LCMS (ES, m/z):471 [M+H]+. |

Figure 2-78

| | | | | |
|---|---|---|---|---|
| 250 | D | 2nd eluting isomer | 471 | 1H-NMR (CD3OD, 400 MHz) δ (ppm): 8.18 (s, 1H), 7.91-7.84 (m, 2H), 7.71-7.61 (m, 3H), 7.60-7.52 (m, 2H), 4.78-3.82 (m, 2H), 3.70-3.38 (m, 1H), 3.29-2.55 (m,1H), 2.06-1.76 (m, 3H), 1.74-1.48 (m, 1H), 1.48-1.36 (m, 1H), 1.18-0.99 (m, 2H), 0.98-0.81 (m, 2H), 0.80-0.72 (m, 1H). LCMS (ES, m/z):471 [M+H]+. |
| 251 | A | 1st eluting isomer | 6-(1-hydroxycyclopropane-1-carbonyl)-1-(4-(quinolin-7-yl)phenyl)-6-azaspiro[2.5]octane-1-carboxylic acid | 443 | 1H-NMR (CD3OD, 400 MHz) δ (ppm): 8.99-8.81 (m, 1H), 8.51-8.31 (m, 1H), 8.31-8.17 (m, 1H), 8.11-7.88 (m, 2H), 7.82-7.63 (m, 2H), 7.63-7.42 (m, 3H), 4.68-3.87 (m, 2H), 3.72-3.39 (m, 1H), 3.25- 2.89 (m, 1H), 2.14-1.76 (m, 3H), 1.74-1.52 (m, 1H), 1.45-1.33 (m, 1H), 1.12-0.97 (m, 2H), 0.97- 0.77(m, 3H). LCMS (ES, m/z):443 [M+H]+. |
| 252 | B | 2nd eluting isomer | | 443 | 1H-NMR (CD3OD, 400 MHz) δ (ppm): 8.99- 8.81 (m, 1H), 8.51-8.31 (m, 1H), 8.31-8.17 (m, 1H), 8.09-8.02 (m, 1H), 8.02-7.86 (m, 1H), 7.83-7.69 (m, 2H), 7.66-7.44 (m, 3H), 4.62-4.02 (m, 2H), 3.67-3.42 (m, 1H), 3.29-2.91 (m, 1H), 2.08-1.91 (m, 1H), 1.91-1.72 (m, 2H), 1.72-1.52 (m, 1H), 1.46-1.37 (m, 1H), 1.18-0.99 (m, 2H), 0.99-0.78 (m, 3H). LCMS (ES, m/z):443 [M+H]+. |

Figure 2-79

| | | | | |
|---|---|---|---|---|
| 253 | A | 1st eluting isomer | 6-propionyl-1-(4-(quinolin-3-yl)phenyl)-6-azaspiro[2.5]octane-1-carboxylic acid | 415 | 1H-NMR (CD3OD, 400 MHz) δ (ppm): 9.18 (s, 1H), 8.61 (s, 1H), 8.12-8.01 (m, 2H), 7.85-7.77 (m, 3H), 7.72-7.54 (m, 3H), 4.57-4.13 (m, 1H), 4.02-3.72 (m, 1H), 3.45-2.90 (m, 2H), 2.55-2.32 (m, 2H), 2.02-1.75 (m, 3H), 1.70-1.48 (m, 1H), 1.45-1.35 (m, 1H), 1.21-1.06 (m, 3H), 0.85-0.71 (m, 1H). LCMS (ES, m/z): 415[M+H]+. |
| 254 | D | 2nd eluting isomer | | 415 | 1H-NMR (CD3OD, 400 MHz) δ (ppm): 9.18 (s, 1H), 8.61 (s, 1H), 8.12-8.00 (m, 2H), 7.86-7.75 (m, 3H), 7.73-7.56 (m, 3H), 4.57-4.11 (m, 1H), 4.02-3.72 (m, 1H), 3.46-2.89 (m, 2H), 2.51-2.32 (m, 2H), 2.00-1.76 (m, 3H), 1.72-1.48 (m, 1H), 1.45-1.34 (m, 1H), 1.19-1.08 (m, 3H), 0.93-0.72 (m, 1H). LCMS (ES, m/z): 415[M+H]+. |
| 255 | B | 1st eluting isomer | 1-(2-fluoro-4-(1-methyl-1H-benzo[d]imidazol-5-yl)phenyl)-6-(1-hydroxycyclopropane-1-carbonyl)-6-azaspiro[2.5]octane-1-carboxylic acid | 464 | 1H-NMR (CD3OD, 400 MHz) δ (ppm): 8.20 (s, 1H), 7.93 (s, 1H), 7.66 (s, 2H), 7.51-7.35 (m, 3H), 4.88-4.06 (m, 2H), 3.96 (s, 3H), 3.25-2.83 (m, 2H), 2.12-1.78 (m, 4H), 1.47-1.35 (m, 1H), 1.15-0.98 (m, 2H), 0.92-0.76 (m, 3H). LCMS (ES, m/z): 464 [M+H]+. |

Figure 2-80

| | | | | |
|---|---|---|---|---|
| 256 | A | 2nd eluting isomer | | 464 | 1H-NMR (CD3OD, 400 MHz) δ (ppm): 8.20 (s, 1H), 7.92 (s, 1H), 7.66 (s, 2H), 7.48-7.32 (m, 3H), 4.81-4.07 (m, 2H), 3.96 (s, 3H), 3.33-2.73 (m, 2H), 2.14-1.75 (m, 4H), 1.45-1.38 (m, 1H), 1.12-1.00 (m, 2H), 0.97-0.77 (m, 3H). LCMS (ES, m/z): 464 [M+H]+. |
| 257 | A | 1st eluting isomer | 6-(1-hydroxycyclopropane-1-carbonyl)-1-(4-(quinolin-3-yl)phenyl)-6-azaspiro[2.5]octane-1-carboxylic acid | 443 | 1H-NMR (CD3OD, 400 MHz) δ (ppm): 9.18 (s, 1H), 8.62 (s, 1H), 8.12-8.00 (m, 2H), 7.85-7.76 (m, 3H), 7.72-7.62 (m, 3H), 4.51-4.02 (m, 2H), 3.26-3.01 (m, 1H), 2.04-1.50 (m, 4H), 1.46-1.22 (m, 2H), 1.11-0.97 (m, 2H), 0.97-0.73 (m, 3H). LCMS (ES, m/z): 443 [M+H]+. |
| 258 | C | 2nd eluting isomer | | 443 | 1H-NMR (CD3OD, 400 MHz) δ (ppm): 9.18 (s, 1H), 8.62 (s, 1H), 8.12-7.96 (m, 2H), 7.86-7.74 (m, 3H), 7.72-7.63 (m, 3H), 4.51-4.05 (m, 2H), 3.26-3.10 (m, 1H), 2.02-1.54 (m, 4H), 1.45-1.36 (m, 1H), 1.35-1.22 (m, 2H), 1.21-1.13 (m, 1H), 0.96-0.75 (m, 3H). LCMS (ES, m/z): 443 [M+H]+. |

Figure 2-81

| | | | | |
|---|---|---|---|---|
| 259 | B | 1st eluting isomer | 1-(4-(1-methyl-1H-benzo[d]imidazol-5-yl)phenyl)-6-propionyl-6-azaspiro[2.5]octane-1-carboxylic acid | 418 | 1H-NMR (CD3OD, 400 MHz) δ (ppm): 8.21 (s, 1H), 7.90 (s, 1H), 7.71-7.58 (m, 4H), 7.55-7.48 (m, 2H), 4.35-4.12 (m, 1H), 3.96 (s, 3H), 3.97-3.75 (m, 1H), 3.42-2.83 (m, 2H), 2.53-2.42 (m, 2H), 2.0-1.72 (m, 3H), 1.65-1.46 (m, 1H), 1.38-1.32 (m, 1H), 1.18-1.05 (m, 3H), 0.91-0.73 (m, 1H). LCMS (ES, m/z):418[M+H]+ |
| 260 | D | 2nd eluting isomer | 1-(4-(1-methyl-1H-benzo[d]imidazol-5-yl)phenyl)-6-propionyl-6-azaspiro[2.5]octane-1-carboxylic acid | 418 | 1H-NMR (CD3OD, 400 MHz) δ (ppm): 8.23 (s, 1H), 7.90 (s, 1H), 7.71-7.60 (m, 4H), 7.56-7.46 (m, 2H), 4.35-4.11 (m, 1H), 3.96 (s, 3H), 3.95-3.71 (m, 1H), 3.45-2.88 (m, 2H), 2.51-2.32 (m, 2H), 1.99-1.71 (m, 3H), 1.67-1.43 (m, 1H), 1.37-1.31 (m, 1H), 1.17-1.04 (m, 3H), 0.89-0.72 (m, 1H). LCMS (ES, m/z):418[M+H]+ |
| 261 | B | 1st eluting isomer | 1-(2-fluoro-4-(1-methyl-1H-benzo[d]imidazol-5-yl)phenyl)-6-propionyl-6-azaspiro[2.5]octane-1-carboxylic acid | 436 | 1H NMR (400 MHz, CD3OD-d4) δ(ppm): 8.20 (s, 1H), 7.92 (s, 1H), 7.65 (s, 2H), 7.51-7.32 (m, 3H), 4.55-4.27 (m, 1H), 4.03-3.81 (m, 4H), 3.24-3.12 (m, 1H), 3.02-2.73 (m, 1H), 2.52-2.35 (m, 2H), 2.16-2.01 (m, 1H), 2.00-1.64 (m, 3H), 1.48-1.35 (m, 1H), 1.18-1.07 (m, 3H), 0.87-0.73 (m,1H). LCMS (ES, m/z): 436 [M+H]+ |

Figure 2-82

| | | | | |
|---|---|---|---|---|
| 262 | C | 2nd eluting isomer | 436 | 1H-NMR (CD3OD-d4, 400 MHz) δ (ppm): 8.20 (s, 1H), 7.92 (s, 1H), 7.65 (s, 2H), 7.49-7.31 (m, 3H), 4.53-4.28 (m, 1H), 4.05-3.81 (m, 4H), 3.22-3.11 (m, 1H), 3.05-2.71 (m, 1H), 2.55-2.31 (m, 2H), 2.16-2.02 (m, 1H), 2.00-1.65 (m, 3H), 1.42-1.36 (m, 1H), 1.19-1.08 (m, 3H), 0.86-0.72 (m,1H). LCMS (ES, m/z): 436 [M+H]+. |
| 263 | D | 1st eluting isomer | 1-(4-(1-methyl-1H-indazol-6-yl)phenyl)-6-propionyl-6-azaspiro[2.5]octane-1-carboxylic acid | 418 | 1H-NMR (CD3OD, 400 MHz) δ (ppm): 8.05 (s, 1H), 7.85-7.80 (m, 1H), 7.79-7.73 (m, 1H), 7.73-7.68 (m, 2H), 7.58-7.51 (m, 2H), 7.50-7.42 (m, 1H), 4.39-4.19 (m,1H), 4.18-4.13 (m, 3H), 4.01-3.72 (m, 1H), 3.55-2.92 (m, 2H), 2.55-2.35 (m, 2H), 2.01-1.75 (m, 3H),1.69-1.45(m, 1H), 1.45-1.35 (m, 1H), 1.20-1.07 (m, 3H), 0.95-0.75 (m, 1H). LCMS (ES, m/z):418[M+H]+ |
| 264 | B | 2nd eluting isomer | 418 | 1H-NMR (CD3OD, 400 MHz) δ (ppm): 8.05 (s, 1H), 7.85-7.79 (m, 1H), 7.78-7.73 (m, 1H), 7.73-7.68 (m, 2H), 7.58-7.51 (m, 2H), 7.50-7.45 (m, 1H), 4.40-4.18 (m, 1H), 4.17-4.09 (m, 3H), 4.01-3.72 (m, 1H), 3.50-2.89 (m, 2H), 2.55-2.34 (m, 2H), 1.99-1.75 (m, 3H), 1.69-1.45 (m, 1H), 1.45-1.35 (m, 1H), 1.20-1.07 (m, 3H), 0.95-0.74 (m, 1H). LCMS (ES, m/z):418[M+H]+ |

Figure 2-83

| | | | | |
|---|---|---|---|---|
| 265 | C | 1st eluting isomer | 6-(1-hydroxycyclopropane-1-carbonyl)-1-(4-(1-methyl-1H-indazol-6-yl)phenyl)-6-azaspiro[2.5]octane-1-carboxylic acid | 446 | 1H-NMR (CD3OD, 400 MHz) δ (ppm): 8.05 (s, 1H), 7.85-7.80 (m, 1H), 7.79-7.73 (m, 1H), 7.73-7.68 (m, 2H), 7.58-7.51 (m, 2H), 7.51-7.42 (m, 1H), 4.80-4.14 (m, 1H), 4.13 (s, 1H), 3.85-3.37 (m, 1H), 3.29-2.81 (m, 2H), 2.08-1.87(m, 1H), 1.86-1.71 (m, 2H), 1.69-1.48 (m, 1H), 1.45-1.38 (m, 1H), 1.20-0.99 (m, 2H), 0.98-0.75 (m, 3H). LCMS (ES, m/z):446[M+H]+ |
| 266 | A | 2nd eluting isomer | | 446 | 1H-NMR (CD3OD, 400 MHz) δ (ppm): 8.05 (s, 1H), 7.85-7.80 (m, 1H), 7.79-7.73 (m, 1H), 7.73-7.68 (m, 2H), 7.58-7.51 (m, 2H), 7.51-7.42 (m, 1H), 4.67-4.15 (m, 1H), 4.13 (s, 3H), 3.69-3.38 (m, 1H), 3.30-2.82 (m, 2H), 2.08-1.87 (m, 1H), 1.86-1.71 (m, 2H), 1.69-1.48 (m, 1H), 1.45-1.38 (m, 1H), 1.20-0.99 (m, 2H), 0.97-0.74 (m, 3H). LCMS (ES, m/z):446[M+H]+ |
| 267 | D | 1st eluting isomer | 1-(4-(6-fluorobenzo[d]oxazol-2-yl)phenyl)-6-propionyl-6-azaspiro[2.5]octane-1-carboxylic acid | 423 | 1H-NMR (CD3OD, 400 MHz) δ (ppm): 8.18 (d, J = 8.0 Hz, 2H), 7.75-7.71 (m, 1H), 7.69-7.62(m, 2H), 7.52-7.48 (m, 1H), 7.25-7.13 (m, 1H), 4.37-4.14 (m,1H), 4.02-3.75(m, 1H), 3.40-3.32 (m, 1H), 3.24-3.02 (m, 1H), 2.53-3.32 (m, 2H), 1.98-1.81 (m, 3H), 1.60-1.43 (m, 2H), 1.20-1.02 (m, 3H), 0.82-0.63 (m, 1H). LCMS (ES, m/z): 423 [M+H]+ |

Figure 2-84

| | | | | | |
|---|---|---|---|---|---|
| 268 | B | 2nd eluting isomer | | 423 | 1H-NMR (CD3OD, 400 MHz) δ (ppm): 8.18 (d, J = 8.0 Hz, 2H), 7.77-7.72 (m, 1H), 7.67-7.61 (m, 2H), 7.55-7.48 (m, 1H), 7.25-7.13 (m, 1H), 4.41-4.16 (m,1H), 3.98-3.74 (m, 1H), 3.45-3.33 (m, 1H), 3.26-3.05 (m, 1H), 2.53-3.32 (m, 2H), 1.97-1.78 (m, 3H), 1.68-1.41 (m, 2H), 1.19-1.05 (m, 3H), 0.82-0.65 (m, 1H). LCMS (ES, m/z): 423 [M+H]+ |
| 269 | C | 1st eluting isomer | | 451 | 1H-NMR (CD3OD, 400 MHz) δ (ppm): 8.17 (d, J = 8.0 Hz, 2H), 7.76-7.70 (m, 1H), 7.65(d, J = 8.4 Hz, 2H), 7.55-7.48 (m, 1H), 7.38-7.23 (m, 1H), 4.43-4.22 (m, 2H), 3.64-3.42(m, 1H), 3.16-2.94 (m, 1H), 2.12-1.80 (m, 3H), 1.72-1.51 (m, 1H), 1.43-1.29 (m, 2H), 1.09-1.01 (m, 2H), 0.96-0.81(m, 2H), 0.79-0.68 (m, 1H). LCMS (ES, m/z): 451 [M+H]+ |
| 270 | A | 2nd eluting isomer | 1-(4-(6-fluorobenzo[d]oxazol-2-yl)phenyl)-6-((1-hydroxycyclopropane-1-carbonyl)-6-azaspiro[2.5]octane-1-carboxylic acid | 451 | 1H-NMR (CD3OD, 400 MHz) δ (ppm): 8.22-8.10 (m, 2H), 7.78-7.67 (m, 1H), 7.66-7.61 (m, 2H), 7.57-7.46 (m, 1H), 7.28-7.12 (m, 1H), 4.61-3.94 (m, 2H), 3.70-3.35 (m, 1H), 3.19-2.94 (m, 1H), 2.19-1.78 (m, 3H), 1.72-1.51 (m, 1H), 1.45-1.32 (m, 2H), 1.18-0.99 (m, 2H), 0.98-0.82 (m, 2H), 0.79-0.64 (m, 1H). LCMS (ES, m/z): 451 [M+H]+ |

Figure 2-85

| | | | | | |
|---|---|---|---|---|---|
| 271 | D | 1st eluting isomer | 1-(3-fluoro-2'-methyl-[1,1'-biphenyl]-4-yl)-6-propionyl-6-azaspiro[2.5]octane-1-carboxylic acid | 396 | 1H NMR (CD3OD, 400 MHz) δ (ppm): 7.42-7.15 (m, 5H), 7.11-7.02 (m, 2H), 4.53-4.31 (m, 1H), 4.07-3.86 (m, 1H), 3.34-3.15 (m, 1H), 2.94-2.80 (m, 1H), 2.49-2.39 (m, 2H), 2.28 (s, 3H), 2.09-2.03 (m, 1H), 1.93-1.82 (m, 3H), 1.41-1.40 (m, 1H), 1.17-1.11 (m, 3H), 0.90-0.70 (m, 1H).. LCMS (ES, m/z): 396 [M+H]+. |
| 272 | B | 2nd eluting isomer | 1-(3-fluoro-2'-methyl-[1,1'-biphenyl]-4-yl)-6-propionyl-6-azaspiro[2.5]octane-1-carboxylic acid | 396 | 1H NMR (CD3OD, 400 MHz) δ (ppm): 7.41-7.32 (m, 1H), 7.31-7.21 (m, 4H), 7.19-7.04 (m, 2H), 4.55-4.25 (m, 1H), 4.09-3.78 (m, 1H), 3.33-3.29 (m, 1H), 3.17-2.80 (m, 1H), 2.48-2.38 (m, 2H), 2.28 (s, 3H), 2.09-2.03 (m, 1H), 1.99-1.67 (m, 3H), 1.42-1.40 (m, 1H), 1.17-1.10 (m, 3H), 0.82-0.75 (m, 1H). LCMS (ES, m/z): 396 [M+H]+. |
| 273 | C | 1st eluting isomer | 1-(3-fluoro-2'-methyl-[1,1'-biphenyl]-4-yl)-6-(1-hydroxycyclopropane-1-carbonyl)-6-azaspiro[2.5]octane-1-carboxylic acid | 424 | 1H-NMR (400 MHz, CD3OD) δ (ppm): 7.38-7.34 (m, 1H), 7.28-7.20 (m, 4H), 7.12-7.04 (m, 2H), 4.75-4.20 (m, 2H), 3.30-2.76 (m, 2H), 2.28 (s, 3H), 2.11-1.78 (m, 4H), 1.43-1.40 (m, 1H), 1.08-1.02 (m, 2H), 0.92-0.78 (m, 3H). LCMS (ES, m/z): 424 [M+H]+. |

Figure 2-86

| | | | | |
|---|---|---|---|---|
| 274 | A | 2nd eluting isomer | | 424 | 1H-NMR (400 MHz, CD3OD) δ (ppm): 7.38-7.34 (m, 1H), 7.28-7.20 (m, 4H), 7.12-7.04 (m, 2H), 4.75-4.20 (m, 2H), 3.31-2.80 (m, 4H), 2.28 (s, 3H), 2.11-1.78 (m, 4H), 1.43-1.40 (m, 1H), 1.08-1.02 (m, 2H), 0.92-0.78 (m, 3H). LCMS (ES, m/z): 424 [M+H]+. |
| 275 | B | 1st eluting isomer | 6-(1-hydroxycyclopropane-1-carbonyl)-1-(2'-methyl-[1,1'-biphenyl]-4-yl)-6-azaspiro[2.5]octane-1-carboxylic acid | 406 | 1H-NMR (CD3OD, 400 MHz) δ (ppm): 7.49 (d, J=8.0 Hz, 2H), 7.32-7.15 (m, 6H), 4.71-3.82 (m, 2H), 3.78-3.35 (m, 1H), 3.28-2.92 (m, 1H), 2.27 (s, 3H), 2.12-1.87 (m, 1H), 1.86-1.75 (m, 2H), 1.74-1.52 (m, 1H), 1.41-1.35 (m, 1H), 1.15-0.99 (m, 2H), 0.95-0.75 (m, 3H). LCMS: (ES, m/z): 406 [M+H]+. |
| 276 | D | 2nd eluting isomer | | 406 | 1H-NMR (CD3OD, 400 MHz) δ (ppm): 7.50 (d, J=8.0 Hz, 2H), 7.31-7.15 (m, 6H), 4.71-3.82 (m, 2H), 3.72-3.35 (m, 1H), 3.38-2.58 (m, 1H), 2.27 (s, 3H), 2.08-1.85 (m, 1H), 1.85-1.72 (m, 2H), 1.70-1.50 (m, 1H), 1.48-1.38 (m, 1H), 1.18-0.98 (m, 2H), 0.98-0.72 (m, 3H). LCMS: (ES, m/z): 406 [M+H]+. |

Figure 2-87

| | | | | |
|---|---|---|---|---|
| 277 | B | 2nd eluting isomer | 2-{4-[(1R)-6-[(2R)-oxolane-2-carbonyl]-6-azaspiro[2.5]octan-1-yl]phenyl}-5-(2H-1,2,3,4-tetrazol-5-yl)-1,3-benzoxazole | 471 | 1H NMR (400 MHz, CD3OD-d4) δ(ppm): 8.41 (s, 1H), 8.22 (d, J = 8.0 Hz, 2H), 8.14 (d, J = 8.8 Hz, 1H), 7.87 (d, J = 8.4 Hz, 1H), 7.50 (d, J = 8.0 Hz, 2H), 4.85-4.67 (m, 1H), 3.95-3.93 (m, 1H), 3.88-3.80 (m, 2H), 3.80-3.65 (m, 1H), 3.55-3.40 (m, 2H), 2.30-1.85 (m, 5H), 1.80-1.58 (m, 2H),1.50-1.38 (m, 1H). 1.37-1.22 (m, 2H),1.07-1.04 (m, 1H). |
| 278 | A | 1st eluting isomer | 7-{4-[(1S)-6-[(2R)-oxolane-2-carbonyl]-6-azaspiro[2.5]octan-1-yl]phenyl}isoquinoline-4-carboxylic acid | 457 | 1H NMR (400 MHz, DMSO-d6) δ13.54 (br, 1H), 9.56 (s, 1H), 9.05 (s, 1H), 8.96 (d, J = 9.2 Hz, 1H), 8.55 (s, 1H), 8.34-8.26 (m, 1H), 7.81 (d, J = 8.0 Hz, 2H), 7.43 (d, J = 8.4 Hz, 2H), 4.72-4.53 (m, 1H), 3.81-3.53 (m, 4H), 3.25-3.16 (m, 1H), 2.16-2.09 (m, 1H), 2.10-1.88 (m, 2H), 1.87-1.72 (m, 2H), 1.69-1.47 (m, 2H), 1.37-1.08 (m, 4H), 0.94-0.91 (m, 1H). |
| 279 | C | 2nd eluting isomer | 7-{4-[(1R)-6-[(2R)-oxolane-2-carbonyl]-6-azaspiro[2.5]octan-1-yl]phenyl}isoquinoline-4-carboxylic acid | 457 | 1H NMR (400 MHz, DMSO-d6) δ13.54 (br, 1H), 9.56 (s, 1H), 9.06 (s, 1H), 8.96 (d, J = 8.8 Hz, 1H), 8.56 (d, J = 2.0 Hz, 1H), 8.33-8.26 (m, 1H), 7.81 (d, J = 8.0 Hz, 2H), 7.43 (d, J = 8.0 Hz, 2H), 4.74-4.56 (m, 1H), 3.81-3.57 (m, 4H), 3.41-3.37 (m, 1H), 3.28-3.09 (m, 1H), 2.18-2.11 (m, 1H), 2.07-1.89 (m, 2H), 1.88-1.69 (m, 2H), 1.67-1.44 (m, 2H), 1.28-1.05 (m, 3H), 0.95-0.88 (m, 1H). |

Figure 2-88

| | | | | |
|---|---|---|---|---|
| 280 | B | | 4-methoxy-3-(4-{7-[(2R)-oxolane-2-carbonyl]-7-azaspiro[3.5]nonan-2-yl}phenyl)benzoic acid | 450 | 1H-NMR (400 MHz, CD3OD) δ (ppm): 8.08-7.99 (m, 1H), 7.95 (s, 1H), 7.45 (d, J = 8.0 Hz, 2H), 7.30 (d, J = 8.4 Hz, 2H), 7.13 (d, J = 8.4 Hz, 1H), 4.84-4.61 (m, 1H), 4.12-3.95 (m, 1H), 3.95-3.78 (m, 4H), 3.74-3.38 (m, 5H), 2.44-2.34 (m, 2H), 2.31-2.18 (m, 1H), 2.08-1.92 (m, 5H), 1.92-1.78 (m, 2H), 1.78-1.57 (m, 2H). |
| 281 | B | | 3-{4-[7-(1-hydroxycyclopropanecarbonyl)-7-azaspiro[3.5]nonan-2-yl]phenyl}-4-methoxybenzoic acid | 436 | 1H-NMR (400 MHz, CD3OD) δ (ppm): 8.01-7.92 (m, 2H), 7.47 (d, J = 8.0 Hz, 2H), 7.28 (d, J = 8.4 Hz, 2H), 7.08-6.99 (m, 1H), 4.06-3.47 (m, 8H), 2.52-2.29 (m, 2H), 2.12-1.97 (m, 2H), 1.97-1.73 (m, 2H), 1.73-1.50 (m, 2H), 1.17-0.99 (m, 2H), 0.99-0.72 (m, 2H). |
| 282 | D | 1st eluting isomer | 4-methoxy-3-{4-[5-[(2R)-oxolane-2-carbonyl]-5-azaspiro[2.4]heptan-1-yl]phenyl}benzoic acid | 422 | 1H NMR (400 MHz, DMSO-d6) δ12.40 (br, 1H), 7.93 (d, J = 8.8, Hz, 1H), 7.82 (s, 1H), 7.43 (d, J = 8.0 Hz, 2H), 7.23-7.12 (m, 3H), 4.56-4.14 (m, 1H), 3.85 (s, 3H), 3.79-3.55 (m, 3H), 3.53-3.40 (m, 1H), 3.20-3.02 (m, 1H), 2.88-2.82 (m, 1H), 2.26-2.18 (m, 1H), 2.05-1.64 (m, 6H), 1.32-1.22 (m, 1H), 1.21-1.13 (m, 1H). |

Figure 2-89

| 283 | D | 2nd eluting isomer | | 422 | 1H NMR (400 MHz, DMSO-d6) δ 12.71 (br, 1H), 7.93 (d, J = 8.8, 1H), 7.884-7.78 (m, 1H), 7.45-7.41 (m, 2H), 7.24-7.16 (m, 3H), 4.54-4.04 (m, 1H), 3.85 (d, J = 3.2Hz, 3H), 3.80-3.58 (m, 3H), 3.50-3.33 (m, 2H), 2.91-2.78 (m, 1H), 2.26-2.15 (m, 1H), 2.04-1.90 (m, 2H), 1.87-1.52 (m, 3H), 1.46-1.13 (m, 3H). |
|---|---|---|---|---|---|
| 284 | D | 3rd eluting isomer | | 422 | 1H NMR (400 MHz, DMSO-d6) δ 12.72 (br, 1H), 7.93 (d, J = 8.4 Hz, 1H), 7.83 (s, 1H), 7.43 (d, J = 8.0 Hz, 2H), 7.28-7.17 (m, 3H), 4.58-4.46 (m, 1H), 3.85 (s, 3H), 3.84-3.70 (m, 1H), 3.68-3.35 (m, 4H), 3.33-3.25 (m, 1H), 2.28-2.21 (m, 1H), 2.08-1.94 (m, 2H), 1.92-1.41 (m, 4H), 1.31-1.12 (m, 2H). |
| 285 | A | 4th eluting isomer | | 422 | 1H NMR (400 MHz, DMSO-d6) δ12.71 (br, 1H), 7.96-7.91 (m, 1H), 7.82 (s, 1H), 7.42 (d, J = 8.0 Hz, 2H), 7.24-7.16 (m, 3H), 4.56-4.42 (m, 1H), 3.86 (s, 3H), 3.77-3.54 (m, 3H), 3.50-3.17(m, 3H), 2.28-2.21 (m, 1H), 2.07-1.98 (m, 2H), 1.87-1.52 (m, 3H), 1.45-1.30 (m, 1H), 1.35-1.32 (m, 1H), 1.31-1.12 (m, 1H). |

Figure 2-90

| 286 | C | 1st eluting isomer | 3-{4-[5-(1-hydroxycyclopropanecarbonyl)-5-azaspiro[2.4]heptan-1-yl]phenyl}-4-methoxybenzoic acid | 408 | 1H-NMR (CD3OD, 400 MHz) δ (ppm): 8.08-7.99 (m, 1H), 7.95 (s, 1H), 7.44 (d, J=8.0 Hz, 2H), 7.27-7.11 (m, 3H), 4.21-4.02 (m, 1H), 3.89 (s, 3H), 3.72-3.25 (m, 2H), 2.35-2.11 (m, 2H), 2.08-1.81 (m, 1H), 1.41-1.21 (m, 3H), 1.21-1.10 (m, 1H), 1.09-0.65 (m, 2H), 0.61-0.40 (m, 1H). |
|---|---|---|---|---|---|
| 287 | D | 2nd eluting isomer | | 408 | 1H-NMR (CD3OD, 400 MHz) δ (ppm): 8.08-8.01 (m, 1H), 7.95 (s, 1H), 7.51-7.41 (m, 2H), 7.31-7.09 (m, 3H), 4.08-3.78 (m, 5H), 3.74-3.37 (m, 2H), 2.41-2.09 (m, 1H), 1.92-1.49 (m, 2H), 1.38-1.05 (m, 4H), 1.01-0.85 (m, 2H). |
| 288 | C | 3rd eluting isomer | | 408 | 1H-NMR (CD3OD, 400 MHz) δ (ppm): 8.08-7.99 (m, 1H), 7.95 (s, 1H), 7.44 (d, J=8.0 Hz, 2H), 7.25-7.12 (m, 3H), 4.19-3.95 (m, 1H), 3.89 (s, 3H), 3.72-3.52 (m, 2H), 3.45-3.23 (m, 1H), 2.35-1.73 (m, 3H), 1.41-1.21 (m, 2H), 1.20-1.01 (m, 2H), 1.98-1.67 (m, 1H), 1.61-1.40 (m, 1H). |
| 289 | A | 4th eluting isomer | | 408 | 1H-NMR (CD3OD, 400 MHz) δ (ppm): 8.08-7.99 (m, 1H), 7.96 (s, 1H), 7.52-7.41 (m, 2H), 7.31-7.09 (m, 3H), 4.08-3.77 (m, 5H), 3.72-3.35 (m, 2H), 2.41-2.30 (m, 1H), 1.98-1.41 (m, 2H), 1.35-1.09 (m, 4H), 0.98-0.81 (m, 2H). |

Figure 2-91

| | | | | |
|---|---|---|---|---|
| 290 | A | 1st eluting isomer | 1-[1-[4-(quinolin-3-yl)phenyl]-1-(2H-1,2,3,4-tetrazol-5-yl)-6-azaspiro[2.5]octan-6-yl]propan-1-one | 439 | 1H NMR (DMSO-d6, 400 MHz) δ (ppm): 9.17 (s, 1H), 8.61 (s, 1H), 8.12-8.02 (m, 2H), 7.92-7.63 (m, 6H), 4.37-4.19 (m, 1H), 4.00-3.81 (m, 1H), 3.11-3.03 (m, 1H), 2.50-2.38 (m, 2H), 1.88-1.64 (m, 4H), 1.24-0.86 (m, 6H). |
| 291 | C | 2nd eluting isomer | 1-[1-[4-(quinolin-3-yl)phenyl]-1-(2H-1,2,3,4-tetrazol-5-yl)-6-azaspiro[2.5]octan-6-yl]propan-1-one | 439 | 1H NMR (DMSO-d6, 400 MHz) δ (ppm): 9.18 (s, 1H), 8.64 (s, 1H), 8.13-8.03 (m, 2H), 7.90-7.80 (m, 3H), 7.78-7.72 (m, 2H), 7.71-7.66 (m, 1H), 4.38-4.19 (m, 1H), 3.92-3.84 (m, 1H), 3.12-3.07 (m, 1H), 2.50-2.38 (m, 2H), 1.87-1.64 (m, 4H), 1.24-0.95 (m, 6H). |
| 292 | D | | 7-(1-hydroxycyclopropanecarbonyl)-2-(quinolin-7-yl)-7-azaspiro[3.5]nonane-2-carboxylic acid | 381 | 1H-NMR (CD3OD, 400 MHz) δ (ppm): 8.87-8.86 (m, 1H), 8.37 (d, J=8.0 Hz, 1H), 8.03 (s, 1H), 7.96 (d, J=8.8 Hz, 1H), 7.67-7.65 (m, 1H), 7.56-7.53 (m, 1H), 3.98-3.38 (m, 4H), 3.02-2.85 (m, 2H), 2.64-2.50 (m, 2H), 1.91-1.68 (m, 2H), 1.64-1.41 (m, 2H), 1.09-0.98 (m, 2H), 0.91-0.79 (m, 2H). |
| 293 | A | 1st eluting isomer | (1S)-6-[(2R)-oxolane-2-carbonyl]-1-{4-[5-(2H-1,2,3,4-tetrazol-5-yl)naphthalen-2-yl]phenyl}-6-azaspiro[2.5]octane | 480 | 1H NMR (400 MHz, DMSO-d6) δ (ppm): 8.68 (d, J=8.8 Hz, 1H), 8.40 (s, 1H), 8.27 (d, J=8.4 Hz, 1H), 8.04-7.98 (m, 2H), 7.81-7.71 (m, 3H), 7.41 (d, J=8.0 Hz, 2H), 4.73-4.57 (m, 1H), 3.78-3.60 (m, 5H), 3.32-3.21 (m, 1H), 2.18-2.12 (m, 1H), 2.11-1.99 (m, 2H), 1.97-1.80 (m, 2H), 1.76-1.45 (m, 2H), 1.28-1.08 (m, 3H), 0.95-0.86 (m,1H). |

Figure 2-92

| | | | | |
|---|---|---|---|---|
| 294 | B | 2nd eluting isomer | (1R)-6-[(2R)-oxolane-2-carbonyl]-1-{4-[5-(2H-1,2,3,4-tetrazol-5-yl)naphthalen-2-yl]phenyl}-6-azaspiro[2.5]octane | 480 | 1H NMR (400 MHz, DMSO-d6) δ (ppm): 8.66 (d, J = 8.8 Hz, 1H), 8.40 (s, 1H), 8.27 (d, J = 8.0 Hz, 1H), 8.05-7.96 (m, 2H), 7.80 (d, J = 8.0 Hz, 2H), 7.74 (t, J = 7.6 Hz, 1H), 7.41 (d, J = 8.0 Hz, 2H), 4.69-4.55 (m, 1H), 3.82-3.58 (m, 5H), 3.18-3.10 (m, 1H), 2.17-2.13 (m, 1H), 2.09-1.91 (m, 2H), 1.88-1.67 (m, 2H), 1.66-1.42 (m, 2H), 1.29-1.07 (m, 3H), 0.97-0.88 (m, 1H). |
| 295 | C | | 7-[(2R)-oxolane-2-carbonyl]-2-(quinolin-7-yl)-7-azaspiro[3.5]nonane-2-carboxylic acid | 395 | 1H-NMR (CD3OD, 400 MHz) δ (ppm): 8.87-8.86 (d, J = 3.2 Hz, 1H), 8.39-8.37 (d, J = 8.4 Hz, 1H), 8.03 (s, 1H), 7.96 (d, J=8.4 Hz, 1H), 7.66 (d, J = 8.4 Hz, 1H), 7.56-7.53 (m, 1H), 4.75-4.68 (m, 1H), 3.96-3.93 (m, 1H), 3.87-3.83 (m, 1H), 3.63-3.33 (m, 4H), 2.99-2.69 (m, 2H), 2.60-2.57 (m, 2H), 2.29-2.11 (m, 1H), 1.97-1.91 (m, 3H), 1.78-1.70 (m, 2H), 1.58-1.45 (m, 2H). |
| 296 | B | 1st eluting isomer | 6-methoxy-4'-[6-[(2R)-oxolane-2-carbonyl]-6-azaspiro[3.4]octan-2-yl]-[1,1'-biphenyl]-3-carboxylic acid | 436 | 1H-NMR (CD3OD, 400 MHz) δ (ppm): 8.08-7.99 (m, 1H), 7.95 (s, 1H), 7.545 (d, J=7.2 Hz, 2H), 7.31 (d, J=8.4 Hz, 2H), 7.15 (d, J=8.4 Hz, 1H), 4.68-4.55 (m, 1H), 4.05-3.92 (m, 1H), 3.90-3.82 (m, 4H), 3.80-3.40 (m, 5H), 2.49-2.38 (m, 2H), 2.31-2.19 (m, 4H), 2.19-2.11 (m, 1H), 2.08-1.89 (m, 3H). |

Figure 2-93

| | | | | |
|---|---|---|---|---|
| 297 | B | 2nd eluting isomer | 436 | 1H-NMR (CD3OD, 400 MHz) δ (ppm): 8.08-7.99 (m, 1H), 7.95 (s, 1H), 7.45 (d, J=8.0 Hz, 2H), 7.31 (d, J=7.6 Hz, 2H), 7.15 (d, J=8.8 Hz, 1H), 4.72-4.59 (m, 1H), 4.08-3.97 (m, 1H), 3.97-3.82 (m, 4H), 3.75-3.42 (m, 5H), 2.58-2.39 (m, 2H), 2.38-2.19 (m, 3H), 2.18-1.86 (m, 5H). |
| 298 | A | 7-(1-hydroxycyclopropanecarbonyl)-2-[4-(quinolin-7-yl)phenyl]-7-azaspiro[3.5]nonane-2-carboxylic acid | 457 | 1H-NMR (CD3OD, 400 MHz)δ(ppm): 8.94-8.86 (m, 1H), 8.47-8.37 (d, J = 8.4 Hz, 1H), 8.27 (s, 1H), 8.06 (d, J = 8.8 Hz, 1H), 8.02-7.92 (m, 1H), 7.82-7.78 (m, 2H), 7.62-7.51 (m, 3H), 3.93-3.36 (m, 4H), 2.92 (d, J = 12.8 Hz, 2H), 2.52 (d, J = 12.8 Hz, 2H), 1.78-1.71 (m, 2H), 1.57-1.46 (m, 2H), 1.09-0.97 (m, 2H), 0.92-0.73 (m, 2H). |
| 299 | A | 7-[(2R)-oxolane-2-carbonyl]-2-[4-(quinolin-7-yl)phenyl]-7-azaspiro[3.5]nonane-2-carboxylic acid | 471 | 1H-NMR (CD3OD, 400 MHz) δ(ppm): 8.90 (s, 1H), 8.41 (d, J = 8.4 Hz, 1H), 8.27 (s, 1H), 8.05 (d, J = 8.8 Hz, 1H), 7.97-7.92 (m, 1H), 7.81 (d, J = 8.4 Hz, 2H), 7.61-7.48 (m, 3H), 4.79-4.63 (m, 1H), 4.02-3.80 (m, 2H), 3.62 (s, 1H), 3.62-3.36 (m, 3H), 2.95-2.87 (m, 2H), 2.51 (d, J = 12.4 Hz, 2H), 2.29-2.07 (m, 1H), 2.05-1.87 (m, 3H), 1.75-1.66 (m, 2H), 1.57-1.42 (m, 2H). |

Figure 2-94

| | | | | 1H-NMR (CD3OD, 400 MHz) δ (ppm): |
|---|---|---|---|---|
| 300 | B | 1st eluting isomer | 422 | 1H-NMR (CD3OD, 400 MHz) δ (ppm): 8.08-7.99 (m, 1H), 7.96 (s, 1H), 7.45 (d, J=8.0 Hz, 2H), 7.31 (d, J=8.0 Hz, 2H), 7.13 (d, J=8.0 Hz, 1H), 4.00-3.90 (m, 1H), 3.89 (s, 3H), 3.80-3.41 (m, 4H), 2.58-2.41(m, 2H), 2.38-2.19 (m, 2H), 2.08-1.97 (m, 1H), 1.97-1.84 (m, 1H), 1.21-1.11 (m, 2H), 1.00-0.85 (m, 2H). |
| 301 | A | 2nd eluting isomer | 4-methoxy-3-{4-[6-(1-hydroxycyclopropanecarbonyl)-6-azaspiro[3.4]octan-2-yl]phenyl}benzoic acid | 422 | 1H-NMR (CD3OD, 400 MHz) δ (ppm): 8.08-7.99 (m, 1H), 7.96 (s, 1H), 7.45 (d, J=8.0 Hz, 2H), 7.31 (d, J=8.0 Hz, 2H), 7.13 (d, J=8.8 Hz, 1H), 4.05-3.98 (m, 1H), 3.88 (s, 3H), 3.85-3.80 (m, 1H), 3.75-3.60 (m, 1H), 3.62-3.55 (m, 1H), 3.53-3.42 (m, 1H), 2.58-2.35 (m, 2H), 2.35-2.15 (m, 3H), 2.15-1.95 (m, 1H), 1.24-1.09 (m, 2H), 0.94-0.87 (m, 2H). |
| 302 | A | | (1S)-6-[(2R)-oxolane-2-carbonyl]-1-(4-phenylphenyl)-6-azaspiro[2.5]octane | 362 | 1H-NMR (CD3OD, 400 MHz)δ(ppm): 7.60 (d, J = 8.0 Hz, 2H), 7.56 (d, J=7.6 Hz, 2H), 7.43 (t, J=7.6 Hz, 2H), 7.37-7.28 (m, 3H), 4.81-4.62 (m, 1H), 4.01-3.59 (m, 4H), 3.53-3.35 (m, 1H), 3.31-3.23 (m, 1H), 2.33-1.81 (m, 5H), 1.78-1.49 (m, 2H), 1.47-1.21 (m, 2H), 1.18-1.11 (m, 1H), 0.96-0.92 (m, 1H). |

Figure 2-95

| | | | | |
|---|---|---|---|---|
| 303 | A | | 1-[(1S)-1-(4-phenylphenyl)-6-azaspiro[2.5]octane-6-carbonyl]cyclopropan-1-ol | 348 | 1H-NMR (CD3OD, 400 MHz) δ (ppm): 7.61 (d, J = 7.6 Hz, 2H), 7.56 (d, J = 8.0 Hz, 2H), 7.43 (t, J = 8.0 Hz, 2H), 7.36-7.28 (m, 3H), 4.19-3.41 (m, 4H), 2.19-2.09 (m, 1H), 1.72-1.61 (m, 2H), 1.41-1.23 (m, 2H), 1.13 (t, J = 5.6 Hz, 1H), 1.07-1.01 (m, 2H), 0.99-0.92 (m, 1H), 0.89-0.83 (m, 2H). |
| 304 | B | | 2,6-difluoro-4-{4-[(1S)-6-[(2R)-oxolane-2-carbonyl]-6-azaspiro[2.5]octan-1-yl]phenyl}benzoic acid | 442 | 1H NMR (400 MHz, Methanol-d4) δ7.58 (d, J = 8.0 Hz, 2H), 7.38-7.31 (m, 2H), 7.21 (d, J = 8.0 Hz, 2H), 4.80-4.64 (m, 1H), 3.99-3.60 (m, 4H), 3.52-3.39 (m, 2H), 2.27-1.87 (m, 5H), 1.76-1.52 (m, 2H), 1.46-1.21 (m, 2H), 1.18-0.92 (m, 2H). |
| 305 | A | | 3,5-difluoro-4-{4-[(1S)-6-[(2R)-oxolane-2-carbonyl]-6-azaspiro[2.5]octan-1-yl]phenyl}benzoic acid | 442 | 1H-NMR (CD3OD, 400 MHz) δ (ppm): 7.65 (d, J =8.0 Hz, 2H), 7.45-7.36 (m, 4H), 4.81-4.65 (m, 1H), 3.99-3.91 (m, 1H), 3.89-3.61 (m, 3H), 3.52-3.40 (m, 2H), 2.29-2.11 (m, 2H), 2.07-1.90 (m, 3H), 1.81-15.1(m, 2H), 1.45-1.25 (m, 2H), 1.21-1.11 (m, 1H), 1.01-0.97 (m, 1H). |
| 306 | B | | 2-hydroxy-4-{4-[(1S)-6-[(2R)-oxolane-2-carbonyl]-6-azaspiro[2.5]octan-1-yl]phenyl}benzoic acid | 422 | 1H-NMR (CD3OD, 400 MHz) δ (ppm): 7.91 (d, J=8.8 Hz, 1H), 7.57 (d, J=8.0 Hz, 2H), 7.40-7.22(m, 2H), 7.15-6.97 (m, 2H), 4.85-4.65 (m, 1H), 4.03-3.60 (m, 4H), 3.55-3.25 (m, 2H), 2.32- 2.10 (m, 2H), 2.10-1.81 (m, 3H), 1.78-1.48 (m, 2H), 1.45-1.22 (m, 2H), 1.20-1.06 (m, 1H), 1.00-0.83 (m, 1H). |

Figure 2-96

| | | | | |
|---|---|---|---|---|
| 307 | A | 4-{4-[(1S)-6-[(2R)-oxolane-2-carbonyl]-6-azaspiro[2.5]octan-1-yl]phenyl}naphthalene-2-carboxylic acid | 456 | 1H NMR (400 MHz, Methanol-d4) δ 8.62 (s, 1H), 8.09 (d, J = 7.6 Hz, 1H), 7.98-7.88 (m, 2H), 7.64-7.54 (m, 2H), 7.48-7.35 (m, 4H), 4.85-4.68 (m, 1H), 4.01-3.92 (m, 1H), 3.91-3.63 (m, 3H), 3.56-3.37 (m, 2H), 2.29-1.86 (m, 5H), 1.82-1.57 (m, 2H), 1.55-1.28 (m, 2H), 1.22-1.16 (m, 1H), 1.04-0.96 (m, 1H). |
| 308 | A | 4-{4-[(1S)-6-[(2R)-oxolane-2-carbonyl]-6-azaspiro[2.5]octan-1-yl]phenyl}quinoline-2-carboxylic acid | 457 | 1H-NMR (CD3OD, 400 MHz) δ (ppm): 8.41-8.08 (m, 2H), 8.08-7.98 (m, 1H), 7.90-7.80 (m, 1H), 7.71-7.62 (m, 1H), 7.60-7.43 (m, 4H), 4.85-4.65 (m, 1H), 4.03-3.90 (m, 1H), 3.90-3.72 (m, 3H), 3.70-3.48 (m, 2H), 2.32- 2.11 (m, 2H), 2.11-1.85(m, 3H), 1.85-1.49 (m, 2H), 1.49-1.25 (m, 2H), 1.25-1.15 (m, 1H), 1.08-0.98 (m, 1H). |
| 309 | A | 2,6-difluoro-4-{4-[(1S)-6-(1-hydroxycyclopropanecarbonyl)-6-azaspiro[2.5]octan-1-yl]phenyl}benzoic acid | 428 | 1H-NMR (CD3OD, 400 MHz) δ (ppm): 7.69-7.51 (m, 1H), 7.41-7.23 (m, 1H), 4.25-3.48 (m, 4H), 2.21-2.04 (m, 1H), 1.77-1.58 (m, 2H), 1.39-1.21 (m, 2H), 1.18-1.12 (m,1H), 1.05-0.92 (m, 3H), 0.89-0.75 (m, 2H). |

Figure 2-97

| | | | | |
|---|---|---|---|---|
| 310 | A | 3,5-difluoro-4-{4-[(1S)-6-(1-hydroxycyclopropanecarbonyl)-6-azaspiro[2.5]octan-1-yl]phenyl}benzoic acid | 428 | 1H-NMR(400 MHz, CD3OD) δ (ppm): 7.68 (d, J=7.6 Hz, 2H), 7.79-7.30 (m, 4H), 4.21-3.33 (m, 4H), 2.33-2.03 (m, 1H), 1.89-1.53 (m, 2H), 1.42-1.21 (m, 2H), 1.21-1.09 (m, 1H), 1.09-0.93 (m, 3H), 0.93-0.67 (m, 2H). |
| 311 | B | 2-chloro-5-fluoro-4-{4-[(1S)-6-[(2R)-oxolane-2-carbonyl]-6-azaspiro[2.5]octan-1-yl]phenyl}benzoic acid | 458 | 1H-NMR (CD3OD, 400 MHz) δ (ppm): 7.58-7.42 (m, 4H), 7.39-7.32 (m, 2H), 4.87-4.66 (m, 2H), 3.99-3.61 (m, 4H), 3.50-3.40 (m, 1H), 3.28-3.13 (m, 1H), 2.23-2.10 (m, 2H), 1.99-1.88 (m, 2H), 1.81-1.51 (m, 2H), 1.47-1.21(m, 2H), 1.18-1.12 (m, 1H), 1.01-0.92 (m, 1H). |
| 312 | A | 2-chloro-5-fluoro-4-{4-[(1S)-6-(1-hydroxycyclopropanecarbonyl)-6-azaspiro[2.5]octan-1-yl]phenyl}benzoic acid | 444 | 1H NMR (400 MHz, Methanol-d4) δ7.71 (d, J = 10.8 Hz, 1H), 7.64 (d, J = 6.8 Hz, 1H), 7.55 (d, J = 7.2 Hz, 2H), 7.39 (d, J = 8.0 Hz, 2H), 3.78-3.74 (m, 4H), 2.22-2.14 (m, 1H), 1.69-1.65 (m, 2H), 1.35-1.30 (m, 2H), 1.20-1.13 (m, 1H), 1.04-0.95 (m, 3H), 0.89-0.85 (m, 2H). |
| 313 | B | 2-hydroxy-4-{4-[(1S)-6-(1-hydroxycyclopropanecarbonyl)-6-azaspiro[2.5]octan-1-yl]phenyl}benzoic acid | 408 | 1H-NMR (CD3OD, 400 MHz) δ (ppm): 7.93(d, J=8.8 Hz, 1H), 7.61(d, J=8.4 Hz, 2H), 7.35 (d, J=8.0 Hz,2H), 7.25-7.18 (m, 2H), 4.13-3.41 (m, 4H), 2.21-2.11 (m, 1H), 1.81-1.62 (m, 2H), 1.40-1.22 (m, 2H), 1.19-1.11(m, 1H), 1.05-0.95 (m, 3H), 0.91-0.84 (m, 2H). |

Figure 2-98

| | | | | |
|---|---|---|---|---|
| 314 | A | | 4-{4-[(1S)-6-(1-hydroxycyclopropanecarbonyl)-6-azaspiro[2.5]octan-1-yl]phenyl}quinoline-2-carboxylic acid | 443 | 1H-NMR (CD3OD, 400 MHz) δ (ppm): 9.18-8.04 (m, 2H), 8.00 (d, J=8.0 Hz, 1H), 7.84 (t, J=7.6 Hz, 1H), 7.64 (t, J=8.0 Hz, 1H), 7.59-7.33 (m, 4H), 4.24-3.41 (m, 4H), 2.29-2.18 (m, 1H), 1.82-1.59 (m, 2H), 1.48-1.28 (m, 2H), 1.28-1.19 (m, 1H), 1.12-0.98 (m, 3H), 0.95-0.83 (m, 2H). |
| 315 | A | | 8-{4-[(1S)-6-[(2R)-oxolane-2-carbonyl]-6-azaspiro[2.5]octan-1-yl]phenyl}quinoline-6-carboxylic acid | 457 | 1H NMR (400 MHz, Methanol-d4) δ 8.98-8.92 (m, 1H), 8.66 (s, 1H), 8.54 (d, J = 8.4 Hz, 1H), 8.29 (s, 1H), 7.67-7.58 (m, 3H), 7.44-7.37 (m, 2H), 4.83-4.66 (m, 1H), 4.02-3.65 (m, 4H), 3.56-3.46 (m, 1H), 3.38-3.33 (m, 1H), 2.30-1.87 (m, 5H), 1.77-1.52 (m, 2H), 1.53-1.28 (m, 2H), 1.23-1.14 (m, 1H), 1.03-0.95 (m, 1H). |
| 316 | C | 1st eluting isomer | 1-{4-[2-methoxy-5-(2H-1,2,3,4-tetrazol-5-yl)phenyl]phenyl}-5-[(2R)-oxolane-2-carbonyl]-5-azaspiro[2.4]heptane | 446 | 1H-NMR (CD3OD, 400 MHz) δ (ppm): 8.06-7.94 (m, 2H), 7.52 (t, J=8.0 Hz, 2H), 7.33-7.18 (m, 3H), 4.69-4.15 (m, 1H), 4.01-3.84 (m, 4H), 3.81-3.63 (m, 3H), 3.18-3.00 (m, 1H), 2.36-2.02 (m, 4H), 2.01-1.86 (m, 2H), 1.85-1.64 (m, 2H), 1.39-1.19 (m, 2H). |

Figure 2-99

| | | | | |
|---|---|---|---|---|
| 317 | C | 2nd eluting isomer | | 446 | 1H-NMR (CD3OD, 400 MHz) δ (ppm): 8.05-7.93 (m, 2H), 7.58-7.47 (m, 2H), 7.34-7.27 (m, 1H), 7.26-7.20 (m, 2H), 4.65-4.20 (m, 1H), 3.99-3.80 (m, 5H), 3.79-3.58 (m, 1H), 3.57-3.22 (m, 1H), 3.13-2.91 (m, 1H), 2.37-2.04 (m, 3H), 2.04-1.85 (m, 2H), 1.84-1.56 (m, 2H), 1.42-1.20 (m, 3H). |
| 318 | A | 3rd eluting isomer | | 446 | 1H-NMR (CD3OD, 400 MHz) δ (ppm): 8.06-7.94 (m, 2H), 7.53 (d, J=8.4 Hz, 2H), 7.33-7.18 (m, 3H), 4.69-4.56 (m, 1H), 4.23-4.14 (m, 1H), 3.98-3.84 (m, 4H), 3.81-3.61 (m, 3H), 3.18-3.00 (m, 1H), 2.36-2.18 (m, 2H), 2.11-1.92 (m, 3H), 1.91-1.52 (m, 2H), 1.37-1.19 (m, 2H). |
| 319 | B | 4th eluting isomer | | 446 | 1H-NMR (CD3OD, 400 MHz) δ (ppm): 8.05-7.93 (m, 2H), 7.53 (d, J=8.0 Hz, 2H), 7.34-7.27 (m, 3H), 4.67-4.55 (m, 1H), 4.08-3.98 (m, 1H), 3.97-3.80 (m, 4H), 3.76-3.37 (m, 4H), 2.38-2.17 (m, 2H), 2.10-1.91 (m, 3H), 1.90-1.52 (m, 2H), 1.36-1.21 (m, 2H). |
| 320 | C | 1st eluting isomer | 1-[1-{4-[2-methoxy-5-(2H-1,2,3,4-tetrazol-5-yl)phenyl]phenyl}-5-azaspiro[2.4]heptane-5-carbonyl]cyclopropan-1-ol | 432 | 1H-NMR (CD3OD, 400 MHz) δ (ppm): 8.09-7.86 (m, 2H), 7.51 (d, J = 7.6 Hz, 2H), 7.34-7.14 (m, 3H), 4.21-4.02 (m, 1H), 3.92 (s, 3H), 3.76-3.54 (m, 2H), 2.36-1.79 (m, 3H), 1.43-1.21 (m, 3H), 1.20-0.99 (m, 2H), 0.98-0.82 (m, 1H), 0.77-0.41 (m, 1H). |

Figure 2-100

| | | | | |
|---|---|---|---|---|
| 321 | A | 2nd eluting isomer | 432 | 1H-NMR (CD3OD, 400 MHz) δ (ppm): 8.05-7.93 (m, 2H), 7.53 (d, J = 7.6 Hz, 2H), 7.38-7.16 (m, 3H), 4.09-3.76 (m, 5H), 3.68-3.36 (m, 2H), 2.37-2.28 (m, 1H), 1.93-1.49 (m, 2H), 1.40-1.29 (m, 1H), 1.28-1.22 (m, 1H), 1.211-1.07 (m, 2H), 0.94-0.86 (m, 2H). |
| 322 | C | 3rd eluting isomer | 462 | 1H-NMR (CD3OD, 400 MHz) δ (ppm): 8.05-7.91 (m, 2H), 7.51 (d, J = 7.6 Hz, 2H), 7.34-7.14 (m, 3H), 4.20-3.99 (m, 1H), 3.91 (s, 3H), 3.76-3.54 (m, 2H), 3.42-3.05 (m, 1H), 2.38-1.77 (m, 3H), 1.39-1.21 (m, 2H), 1.20-0.99 (m, 2H), 0.98-0.79 (m, 1H), 0.76-0.42 (m, 1H). |
| 323 | C | 4th eluting isomer | 432 | 1H-NMR (CD3OD, 400 MHz) δ (ppm): 8.05-7.95 (m, 2H), 7.53 (d, J = 7.6 Hz, 2H), 7.34-7.23 (m, 3H), 4.08-3.76 (m, 5H), 3.65-3.38 (m, 2H), 2.38-2.27 (m, 1H), 1.89-1.52 (m, 2H), 1.35-1.31 (m, 1H), 1.27-1.22 (m, 1H), 1.21-1.05 (m, 2H), 0.97-0.86 (m, 2H). |

Figure 2-101

| | | | | |
|---|---|---|---|---|
| 324 | NT | | 4-{4-[(1S)-6-(1-hydroxycyclopropanecarbonyl)-6-azaspiro[2.5]octan-1-yl]phenyl}naphthalene-2-carboxylic acid | 442 | 1H-NMR-PH-FMA-PJ00224-430-0: (400 MHz, CD3OD) δ (ppm): 8.64 (s, 1H), 8.17-8.02 (m, 1H), 7.97 (s, 1H), 8.01-7.93 (m, 1H), 7.69-7.52 (m, 2H), 7.47-7.34 (m, 4H), 4.25-3.37 (m, 4H), 2.31-2.14 (m, 1H), 1.80-1.57 (m, 2H), 1.44-1.31 (m, 2H), 1.24-1.12 (m, 1H), 1.12-0.98 (m, 3H), 0.98-0.76 (m, 2H). |
| 325 | A | | 3-hydroxy-4-(4-methoxy-3-{4-[(1S)-6-[(2R)-oxolane-2-carbonyl]-6-azaspiro[2.5]octan-1-yl]phenyl}phenyl)cyclobut-3-ene-1,2-dione | 488 | 1H-NMR (CD3OD, 400 MHz) δ (ppm): 8.15-8.09(m, 2H), 7.49(d, J = 8.0 Hz, 2H), 7.29(d, J = 8.0 Hz, 2H), 7.18(d, J = 8.8 Hz, 1H), 4.82-4.65(m, 1H), 4.01-3.92(m, 1H), 3.90-3.86(m, 3H), 3.85-3.79(m, 1H), 3.78-3.59(m, 2H), 3.54-3.41(m, 2H), 2.30-2.10(m, 2H), 2.05-1.85(m, 3H), 1.79-1.51(m, 2H), 1.60-1.23(m, 2H), 1.20-1.08(m, 1H), 0.99-0.88(m, 1H). |
| 326 | A | | 3-hydroxy-4-(4-methyl-3-{4-[(1S)-6-[(2R)-oxolane-2-carbonyl]-6-azaspiro[2.5]octan-1-yl]phenyl}phenyl)cyclobut-3-ene-1,2-dione | 472 | 1H-NMR (CD3OD, 400 MHz) δ (ppm): 8.05 (s, 1H), 7.97 (d, J=8.0 Hz, 1H), 7.49-7.02 (m, 5H), 4.85-4.65 (m, 1H), 4.02-3.60 (m, 4H), 2.35-2.32 (m, 2H), 2.32 (s, 3H), 2.28-2.13 (m, 2H), 2.10-1.81 (m, 3H), 1.76-1.55 (m, 2H), 1.48-1.23 (m, 2H), 1.20-1.05 (m, 1H), 1.02-0.88 (m, 1H). |

Figure 2-102

| | | | | 1H-NMR (CD3OD, 400 MHz) δ (ppm) |
|---|---|---|---|---|
| 327 | B | N-(4-methoxy-3-{4-[(1S)-6-[(2R)-oxolane-2-carbonyl]-6-azaspiro[2.5]octan-1-yl]phenyl}benzenesulfonyl)acetamide | 513 | 1H-NMR (CD3OD, 400 MHz) δ (ppm): 8.02-7.86 (m, 2H), 7.53-7.40 (m, 2H), 7.36-7.19 (m, 3H), 4.85-4.61 (m, 1H), 4.02-3.81 (m, 4H), 3.87-3.60 (m, 3H), 3.55-3.40 (m, 2H), 2.32-2.10 (m, 2H), 2.09-1.90 (m, 6H), 1.79-1.50 (m, 2H), 1.46-1.20 (m, 2H), 1.19-1.05 (m, 1H), 1.04-0.86 (m, 1H). |
| 328 | B | (4-methoxy-3-{4-[(1S)-6-[(2R)-oxolane-2-carbonyl]-6-azaspiro[2.5]octan-1-yl]phenyl}phenyl)(methyl)phosphinic acid | 470 | 1H-NMR (CD3OD, 400 MHz) δ (ppm): 8.17-8.09 (m, 1H), 7.81-7.70 (m, 1H), 7.61-7.51 (m, 1H), 7.49-7.42 (m, 1H), 7.34-7.24 (m, 2H), 7.18-7.10 (m, 1H), 4.82-4.64 (m, 1H), 4.01-3.91(m, 2H), 3.89-3.79 (m, 3H), 3.78-3.39(m, 3H), 3.38-3.24 (m, 1H), 2.19-2.09 (m, 2H), 2.08-1.82(m, 3H), 1.72-1.52 (m, 4H), 1.51-1.34 (m, 2H), 1.34-1.22 (m, 1H), 1.16-1.08 (m, 1H), 0.99-0.91(m, 1H). |
| 329 | A | methyl(4-methyl-3-{4-[(1S)-6-[(2R)-oxolane-2-carbonyl]-6-azaspiro[2.5]octan-1-yl]phenyl}phenyl)phosphinic acid | 454 | 1H-NMR (CD3OD, 400 MHz) δ (ppm): 7.76-7.56 (m, 2H), 7.42-7.13 (m, 5H), 4.82-4.62 (m, 1H), 4.03-3.91 (m, 1H), 3.89-3.40 (m, 5H), 2.30 (s, 3H), 2.26-2.10 (m, 2H), 2.08-1.84 (m, 3H), 1.78-1.55 (m, 2H), 1.50 (d, J = 14.2 Hz, 3H), 1.43-1.21 (m 2H), 1.16-1.12 (m, 1H), 1.01-0.91 (m, 1H). |

Figure 2-103

| | | | |
|---|---|---|---|
| 330 | B | N-(3-{4-[(1S)-6-(1-hydroxycyclopropanecarbonyl)-6-azaspiro[2.5]octan-1-yl]phenyl}-4-methoxybenzenesulfonyl)acetamide | 499 | 1H-NMR (CD3OD, 400 MHz) δ (ppm): 8.01-7.85 (m, 2H), 7.47 (d, J = 8.0 Hz, 2H), 7.31 (d, J = 8.0 Hz, 2H), 7.22 (d, J = 8.8 Hz, 1H), 4.27-3.40 (m, 7H), 2.20-2.07 (m, 1H), 1.96 (s, 3H), 1.79-1.70 (m, 2H), 1.38-1.31 (m, 2H), 1.17-1.09 (m, 1H), 1.07-1.02 (m, 2H), 0.99-0.93 (m, 1H), 0.87-0.81 (m, 2H). |
| 331 | A | N-(3-{4-[(1S)-6-(1-hydroxycyclopropanecarbonyl)-6-azaspiro[2.5]octan-1-yl]phenyl}-4-methylbenzenesulfonyl)acetamide | 483 | 1H-NMR (CD3OD, 400 MHz) δ (ppm): 7.90-7.74 (m, 2H), 7.45 (d, J=8.0 Hz, 1H), 7.38-7.32 (m, 2H), 7.31-7.25 (m, 2H), 4.20-3.51 (m, 4H), 2.34 (s, 3H), 2.22-2.13 (m, 1H), 1.95 (s, 3H), 1.78-1.59 (m, 2H), 1.45-1.22 (m, 2H), 1.20-1.08 (m, 1H), 1.08-0.98 (m, 3H), 0.98-0.78 (m, 2H). |
| 332 | A | N-(4-methyl-3-{4-[(1S)-6-[(2R)-oxolane-2-carbonyl]-6-azaspiro[2.5]octan-1-yl]phenyl}benzenesulfonyl)acetamide | 497 | 1H-NMR (CD3OD, 400 MHz) δ (ppm): 7.95-7.74(m, 2H), 7.58-7.43(m, 1H), 7.41-7.20(m, 4H), 4.85-4.65(m, 1H), 4.02-3.55(m, 4H),3.55-3.39(m, 2H), 2.35(s, 3H), 2.28- 2.12 (m, 2H), 2.10- 1.90 (m, 6H), 1.80-1.60 (m, 2H), 1.48-1.23(m, 2H), 1.20-1.08 (m, 1H), 1.02-0.90 (m, 1H). |

Figure 2-104

| | | | | 1H-NMR (CD3OD, 400 MHz) δ (ppm) |
|---|---|---|---|---|
| 333 | B | 1st eluting isomer | 4-methoxy-3-{4-[7-[(2R)-oxolane-2-carbonyl]-7-azaspiro[3.5]nonan-1-yl]phenyl}benzoic acid | 450 | 1H-NMR (CD3OD, 400 MHz) δ (ppm): 8.08-7.89 (m, 2H), 7.52-7.38 (m, 2H), 7.31-7.20 (m, 2H), 7.20-7.06 (m, 1H), 4.76-4.59 (m, 1H), 4.08-3.75 (m, 6H), 3.62-3.50 (m, 1H), 3.44-3.29 (m, 1H), 3.25-3.15 (m, 1H), 3.00-2.79 (m, 1H), 2.54-2.39 (m, 1H), 2.30-1.71 (m, 9H), 1.61-1.48 (m, 1H), 1.19-1.00 (m, 1H). |
| 334 | D | 2nd eluting isomer | | 450 | 1H-NMR (CD3OD, 400 MHz) δ (ppm): 8.08-8.00 (m, 1H), 8.00-7.91 (m, 1H), 7.47 (d, J=8.0 Hz, 2H), 7.26 (d, J=7.2 Hz, 2H), 7.15 (d, J=8.8 Hz, 1H), 4.78-4.55 (m, 1H), 4.00-3.75 (m, 6H), 3.65-3.58 (m, 1H), 3.45-3.38 (m, 1H), 3.29-3.09 (m, 1H), 2.95-2.85 (m, 1H), 2.55-2.39 (m, 1H), 2.34-2.08 (m, 2H), 2.05-1.70 (m, 7H), 1.56-1.48 (m, 1H), 1.20-1.00 (m, 1H). |
| 335 | D | 1st eluting isomer | 3-{4-[7-(1-hydroxycyclopropanecarbonyl)-7-azaspiro[3.5]nonan-1-yl]phenyl}-4-methoxybenzoic acid | 436 | 1H-NMR (CD3OD, 400 MHz) δ (ppm): 8.02 (d, J=6.4 Hz, 1H), 8.01 (s, 1H), 7.46 (d, J=8.0 Hz, 2H), 7.27 (d, J=8.4 Hz, 2H), 7.16 (d, J=8.8 Hz, 1H), 4.51-3.82 (m, 6H), 3.45-3.40 (m, 1H), 3.11-2.80 (m, 1H), 2.60-2.40 (m, 1H), 2.35-2.15 (m, 1H), 2.12-1.91 (m, 2H), 1.91-1.72 (m, 2H), 1.62-1.45 (m, 1H), 1.21-1.08 (m, 1H), 1.02-0.89 (m, 2H), 0.88-0.78 (m, 2H). |

Figure 2-105

| | | | | |
|---|---|---|---|---|
| 336 | B | 2nd eluting isomer | 436 | 1H NMR (400 MHz, Methanol-d4) δ 8.02 (d, J=6.4 Hz, 1H), 7.95 (s, 1H), 7.46 (d, J=8.0 Hz, 2H), 7.27 (d, J=8.4 Hz, 2H), 7.16 (d, J = 8.8 Hz, 1H), 4.73-3.87 (m, 6H), 3.46-3.37 (m, 1H), 3.15-2.75 (m, 1 H), 2.56-2.42 (m, 1H), 2.31-2.19 (m, 1H), 2.07-1.89 (m, 2H), 1.86-1.81 (m, 2H), 1.58-1.50 (m, 1H), 1.22-1.05 (m, 1H), 0.99-0.94 (m, 2H), 0.86-0.82 (m, 2H). |
| 337 | B | (3-{4-[(1S)-6-(1-hydroxycyclopropanecarbonyl)-6-azaspiro[2.5]octan-1-yl]phenyl}-4-methylphenyl)(methyl)phos phinic acid | 440 | 1H-NMR (CD3OD, 400 MHz) δ (ppm): δ7.72-7.59 (m, 2H), 7.33-7.29 (m, 3H), 7.28-7.21 (m, 2H), 4.26-3.41 (m, 4H), 2.28 (s, 3H), 2.20-2.00 (m, 1H), 1.73-1.64 (m, 2H), 1.46-1.40 (m, 3H), 1.35-1.28 (m, 2H), 1.17-1.08 (m, 1H), 1.08-1.01 (m, 2H), 0.99-0.92 (m, 1H), 0.87-0.81 (m, 2H). |
| 338 | A | 3-hydroxy-4-(3-{4-[(1S)-6-(1-hydroxycyclopropanecarbonyl)-6-azaspiro[2.5]octan-1-yl]phenyl}-4-methoxyphenyl)cyclobut-3-ene-1,2-dione | 474 | 1H-NMR (CD3OD, 400 MHz) δ (ppm): 8.20-7.98(m, 2H), 7.52-7.42(m, 2H), 7.35-7.25(m, 2H), 7.22-7.13(m, 1H), 4.18-3.51(m, 7H), 2.24- 2.00(m, 1H), 1.72-1.57(m, 2H),1.48-1.24(m, 2H), 1.20-1.08(m, 1H), 1.08-0.99(m, 2H), 0.99-0.81(m, 1H), 0.99-0.72(m, 2H). |

Figure 2-106

| | | | | |
|---|---|---|---|---|
| 339 | A | 3-hydroxy-4-(3-{4-[(1S)-6-(1-hydroxycyclopropanecarbonyl)-6-azaspiro[2.5]octan-1-yl]phenyl}-4-methylphenyl)cyclobut-3-ene-1,2-dione | | 458 | 1H-NMR (CD3OD, 400 MHz) δ (ppm): 8.05 (s, 1H), 7.97 (d, J=8.0 Hz, 1H), 7.38-7.22 (m, 5H), 4.18-3.49 (m, 4H), 2.32(s, 3H), 2.20- 2.10 (m, 1H), 1.72-1.57 (m, 2H), 1.42-1.24 (m, 2H), 1.20-1.08(m, 1H), 1.08-0.99 (m, 2H), 0.99-0.91 (m, 1H), 0.91-0.80 (m, 2H). |
| 340 | A | 8-{4-[(1S)-6-(1-hydroxycyclopropanecarbonyl)-6-azaspiro[2.5]octan-1-yl]phenyl}quinoline-6-carboxylic acid | | 443 | 1H-NMR (CD3OD, 400 MHz) δ(ppm): 8.89-8.83 (m, 1H), 8.53 (s, 1H), 8.46 (d, J=8.0 Hz, 1H), 8.35 (s, 1H), 7.71-7.51 (m, 3H), 7.37 (d, J=7.6 Hz, 2H), 4.21-3.52 (m, 4H), 2.25-2.15 (m, 1H), 1.78-1.61 (m, 2H), 1.43-1.24 (m, 2H), 1.18-1.11 (m, 1H), 1.08-0.98 (m, 3H), 0.98-0.81 (m, 1H). |
| 341 | C | 3-{4-[(1S)-6-[(2R)-oxolane-2-carbonyl]-6-azaspiro[2.5]octan-1-yl]phenyl}cyclobutane-1-carboxylic acid | 1st eluting isomer | 384 | 1H-NMR (CD3OD, 400 MHz) δ (ppm): 7.28-7.12 (m, 4H), 4.80-4.60 (m, 1H), 4.02-3.89 (m, 1H), 3.89-3.58 (m, 3H), 3.48-3.39 (m, 2H), 3.30-3.18 (m, 1H), 3.17-3.00 (m, 1H), 2.62-2.50 (m, 2H), 2.40-2.25 (m, 2H), 2.25-2.10 (m, 1H), 2.10-1.78 (m, 4H), 1.78-1.48 (m, 2H), 1.41-1.25 (m, 1H), 1.25-1.13 (m, 1H), 1.10-1.00 (m, 1H), 0.97-0.80 (m, 1H). |

Figure 2-107

| | | | | 1H-NMR (CD3OD, 400 MHz) δ (ppm): |
|---|---|---|---|---|
| 342 | B | 2nd eluting isomer | 384 | 7.33-7.05 (m, 4H), 4.80-4.61 (m, 1H), 4.05-3.90 (m, 1H), 3.90-3.72 (m, 1H), 3.72-3.61 (m, 2H), 3.49-3.38 (m, 2H), 3.30-3.20 (m, 1H), 3.19-3.05 (m, 1H), 2.75-2.58 (m, 2H), 2.51-2.35 (m, 2H), 2.30-2.03 (m, 2H), 2.03-1.81 (m, 3H), 1.79-1.49 (m, 2H), 1.39-1.25 (m, 1H), 1.24-1.19 (m, 1H), 1.10-0.98 (m, 1H), 0.97-0.79 (m, 1H). |
| 343 | D | 3rd eluting isomer | 384 | 7.21-7.12 (m, 4H), 4.79-4.63 (m, 1H), 3.99-3.79 (m, 2H), 3.75-3.59 (m, 2H), 3.52-3.39 (m, 2H), 3.29-3.19 (m, 1H), 3.19-3.09 (m, 1H), 2.64-2.55 (m, 2H), 2.39-2.28 (m, 2H), 2.24-2.12 (m, 1H), 2.09-1.85 (m, 4H), 1.73-1.51 (m, 2H), 1.31-1.11 (m, 2H), 1.08-1.02 (m, 1H), 0.92-0.85 (m, 1H). |
| 344 | B | 4th eluting isomer | 384 | 7.23-7.11 (m, 4H), 4.79-4.61 (m, 1H), 4.00-3.61 (m, 4H), 3.50-3.38 (m, 2H), 3.30-3.20 (m, 1H), 3.18-3.09 (m, 1H), 2.65-2.55 (m, 2H), 2.40-2.29 (m, 2H), 2.25-1.85 (m, 5H), 1.71-1.49 (m, 2H), 1.39-1.17 (m, 2H), 1.09-1.01 (m, 1H), 0.92-0.85 (m, 1H). |

Figure 2-108

| | | | 1H-NMR (CD3OD, 400 MHz) δ (ppm): |
|---|---|---|---|
| 345 | NT | 1st eluting isomer | 1H-NMR (CD3OD, 400 MHz) δ (ppm): 8.03-7.99 (m, 1H), 7.96-7.92 (m, 1H), 7.49 (d, J=8.0 Hz, 2H), 7.30 (d, J=8.4 Hz, 2H), 7.15 (d, J=8.4 Hz, 1H), 4.18-4.12 (m, 1H), 3.90 (s, 3H), 3.85-3.77 (m, 1H), 3.73-3.68 (m, 1H), 3.62-3.55 (m, 1H), 3.52-3.43 (m, 2H), 3.27-3.12 (m, 2H), 2.48-2.36 (m, 1H), 2.32-2.21 (m, 2H), 2.20-1.99 (m, 3H), 1.96-1.82 (m, 1H), 1.79-1.65 (m, 2H), 1.36-1.21 (m, 1H). 436 |
| 346 | NT | 2nd eluting isomer | 4-methoxy-3-{4-[6-[(2R)-oxolane-2-carbonyl]-6-azaspiro[3.4]octan-1-yl]phenyl}benzoic acid — 1H NMR (400 MHz, Methanol-d4) δ 8.06-7.91 (m, 2H), 7.52-7.44 (m, 2H), 7.36-7.26 (m, 2H), 7.14 (d, J = 7.6 Hz, 1H), 4.48-3.97 (m, 1H), 3.91-3.86 (m, 3H), 3.85-3.65 (m, 2H), 3.63-3.36 (m, 4H), 3.22-3.14 (m, 1H), 2.50-2.30 (m, 1H), 2.29-2.08 (m, 3H), 2.08-1.91 (m, 2H), 1.88-1.71 (m, 2H), 1.70-1.59 (m, 1H), 1.41-1.34 (m, 1H). 436 |
| 347 | C | 3rd eluting isomer | 1H NMR (400 MHz, Methanol-d4) δ 8.06-7.99 (m, 1H), 7.96 (s, 1H), 7.49 (d, J = 7.6 Hz, 2H), 7.29 (d, J = 8.0 Hz, 2H), 7.15 (d, J = 8.4 Hz, 1H), 4.67-4.43 (m, 1H), 4.04-3.91 (m, 1H), 3.91-3.88 (m, 3H), 3.87-3.72 (m, 1H), 3.70-3.61 (m, 2H), 3.52-3.50 (m, 1H), 3.39-3.35 (m, 1H), 3.16-3.05 (m, 1H), 2.56-2.44 (m, 1H), 2.34-2.08 (m, 3H), 2.08-1.88 (m, 4H), 1.87-1.57 (m, 2H) 436 |

Figure 2-109

| | | | | |
|---|---|---|---|---|
| 348 | B | 4th eluting isomer | | 436 | 1H NMR (400 MHz, Methanol-d4) δ 8.02 (d, J = 8.4 Hz, 1H), 7.96 (s, 1H), 7.49 (d, J = 8.0 Hz, 2H), 7.29 (d, J = 8.0 Hz, 2H), 7.17-7.12 (m, 1H), 4.70-4.44 (m, 1H), 4.05-3.94 (m, 1H), 3.91 (s, 3H), 3.88-3.78 (m, 1H), 3.72-3.56 (m, 2H), 3.55-3.41 (m, 1H), 3.28-3.19 (m, 1H), 3.16-2.93 (m, 1H), 2.57-2.44 (m, 1H), 2.32-2.07 (m, 3H), 2.06-1.81 (m, 5H), 1.80-1.61 (m, 1H). |
| 349 | A | 1-[(1S)-1-{4-[2-(2H-1,2,3,4-tetrazol-5-yl)quinolin-4-yl]phenyl}-6-azaspiro[2.5]octane-6-carbonyl]cyclopropan-1-ol | 467 | 1H-NMR (CD3OD, 400 MHz) δ (ppm): 8.35-8.31(m, 2H), 8.06 (d, J=8.4 Hz, 1H), 7.91-7.83 (m, 1H), 7.72-7.63 (m, 1H), 7.63-7.55 (m, 2H), 7.55-7.47 (m, 2H), 4.18-3.52 (m, 4H), 2.31-2.24 (m, 1H), 1.79-1.61 (m, 2H), 1.48-1.31 (m, 2H), 1.29-1.19 (m, 1H), 1.11-0.95 (m, 3H), 0.95-0.80 (m, 2H). |
| 350 | A | 4-{4-[(1S)-6-[(2R)-oxolane-2-carbonyl]-6-azaspiro[2.5]octan-1-yl]phenyl}-2-(2H-1,2,3,4-tetrazol-5-yl)quinoline | 481 | 1H-NMR (CD3OD, 400 MHz) δ (ppm): 8.38-8.11 (m, 2H), 8.10-7.99 (m, 1H), 7.97-7.81 (m, 1H), 7.72-7.64 (m, 1H), 7.61-7.52 (m, 2H), 7.52-7.41 (m, 2H), 4.82-4.65 (m, 1H), 4.05-3.92 (m, 1H), 3.92-3.62 (m, 3H), 3.55-3.36 (m, 2H), 2.31-2.10 (m, 2H), 2.10-1.85 (m, 3H), 1.84-1.60 (m, 2H), 1.50-1.29 (m, 2H), 1.28-1.19 (m, 1H), 1.10-0.99 (m, 1H). |

Figure 2-110

| | | | |
|---|---|---|---|
| 351 | A | 1-[(1S)-1-{4-[6-(2H-1,2,3,4-tetrazol-5-yl]quinolin-8-yl]phenyl}-6-azaspiro[2.5]octane-6-carbonyl]cyclopropan-1-ol | 467 | 1H-NMR (CD3OD, 400 MHz) δ(ppm): 8.96-8.84 (m, 1H), 8.63 (s, 1H), 8.54 (d, J = 8.0 Hz, 1H), 8.42 (s, 1H), 7.73-7.58 (m, 3H), 7.43 (d, J = 7.6 Hz, 2H), 4.25-3.42 (m, 4H), 2.25-2.18 (m, 1H), 1.73-1.65 (m, 2H), 1.45-1.38 (m, 2H), 1.23-1.14 (m, 1H), 1.10-0.96 (m, 3H), 0.92-0.83 (m, 2H). |
| 352 | A | 8-{4-[(1S)-6-[(2R)-oxolane-2-carbonyl]-6-azaspiro[2.5]octan-1-yl]phenyl}-6-(2H-1,2,3,4-tetrazol-5-yl)quinoline | 481 | 1H-NMR (CD3OD, 400 MHz)δ(ppm): 8.97-8.89 (m, 1H), 8.63 (s, 1H), 8.54 (d, J=8.4 Hz, 1H), 8.40 (s, 1H), 7.72-7.59 (m, 3H), 7.42 (d, J=8.0 Hz, 2H), 4.79-4.66 (m, 1H), 4.04-3.92 (m, 1H), 3.92-3.81 (m, 2H), 3.79-3.68 (m, 2H), 3.55-3.48 (m, 1H), 2.28-2.13 (m, 2H), 2.09-1.85 (m, 3H), 1.78-1.56 (m, 2H), 1.41-1.28 (m, 2H), 1.23-1.15 (m, 1H), 1.05-0.94 (m, 1H). |

\* Absolute stereochemistry determined.

1. Unless otherwise indicated, the absolute stereochemistry of each stereocenter was not determined. The present disclosure provides methods of separating stereoisomers.
2. Where indicated, a racemate was tested.

Figure 2-111

| Comp. No. | Chemical Structure and Name | IC$_{50}$ |
|---|---|---|
| 363 | 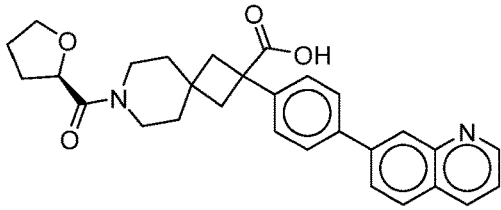<br>(R)-2-(4-(quinolin-7-yl)phenyl)-7-(tetrahydrofuran-2-carbonyl)-7-azaspiro[3.5]nonane-2-carboxylic acid | A |
| 364 | 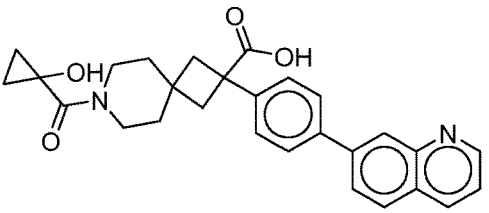<br>7-(1-hydroxycyclopropane-1-carbonyl)-2-(4-(quinolin-7-yl)phenyl)-7-azaspiro[3.5]nonane-2-carboxylic acid | A |
| 365 | 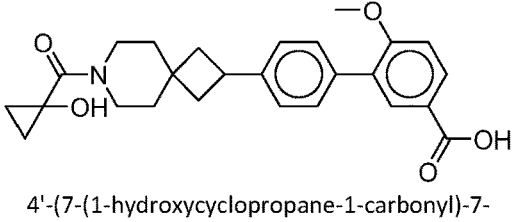<br>4'-(7-(1-hydroxycyclopropane-1-carbonyl)-7-azaspiro[3.5]nonan-2-yl)-6-methoxy-[1,1'-biphenyl]-3-carboxylic acid | B |
| 366 | 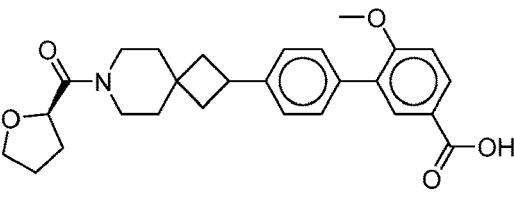<br>(R)-6-methoxy-4'-(7-(tetrahydrofuran-2-carbonyl)-7-azaspiro[3.5]nonan-2-yl)-[1,1'-biphenyl]-3-carboxylic acid | B |

Figure 3-1

| 367 | 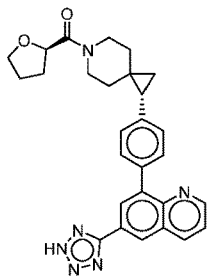<br>((S)-1-(4-(6-(2H-tetrazol-5-yl)quinolin-8-yl)phenyl)-6-azaspiro[2.5]octan-6-yl)((R)-tetrahydrofuran-2-yl)methanone | A |
|---|---|---|
| 368 | 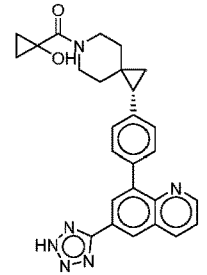<br>(S)-(1-(4-(6-(2H-tetrazol-5-yl)quinolin-8-yl)phenyl)-6-azaspiro[2.5]octan-6-yl)(1-hydroxycyclopropyl)methanone | A |
| 369 | 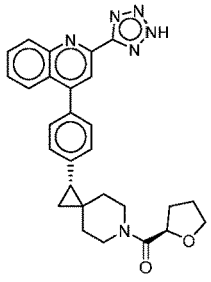<br>((S)-1-(4-(2-(2H-tetrazol-5-yl)quinolin-4-yl)phenyl)-6-azaspiro[2.5]octan-6-yl)((R)-tetrahydrofuran-2-yl)methanone | A |
| 370 | 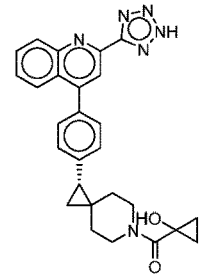<br>(S)-(1-(4-(2-(2H-tetrazol-5-yl)quinolin-4-yl)phenyl)-6-azaspiro[2.5]octan-6-yl)(1-hydroxycyclopropyl)methanone | A |
Figure 3-2

| | | |
|---|---|---|
| 371 | (1R,3r)-3-(4-((R)-6-((R)-tetrahydrofuran-2-carbonyl)-6-azaspiro[2.5]octan-1-yl)phenyl)cyclobutane-1-carboxylic acid | B |
| 372 | (1S,3s)-3-(4-((R)-6-((R)-tetrahydrofuran-2-carbonyl)-6-azaspiro[2.5]octan-1-yl)phenyl)cyclobutane-1-carboxylic acid | E |
| 373 | (S)-8-(4-(6-(1-hydroxycyclopropane-1-carbonyl)-6-azaspiro[2.5]octan-1-yl)phenyl)quinoline-6-carboxylic acid | A |
| 374 | (1S,3r)-3-(4-((S)-6-((R)-tetrahydrofuran-2-carbonyl)-6-azaspiro[2.5]octan-1-yl)phenyl)cyclobutane-1-carboxylic acid | B |

Figure 3-3

| | | |
|---|---|---|
| 375 | 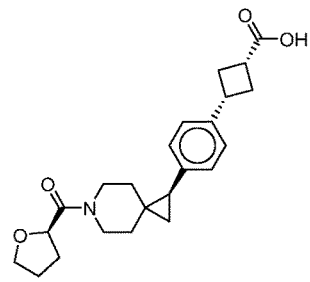<br>(1R,3s)-3-(4-((S)-6-((R)-tetrahydrofuran-2-carbonyl)-6-azaspiro[2.5]octan-1-yl)phenyl)cyclobutane-1-carboxylic acid | C |
| 376 | 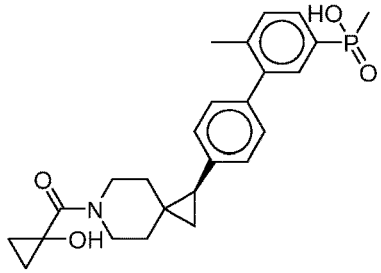<br>(4'-((S)-6-(1-hydroxycyclopropane-1-carbonyl)-6-azaspiro[2.5]octan-1-yl)-6-methyl-[1,1'-biphenyl]-3-yl)(methyl)phosphinic acid | B |
| 377 | 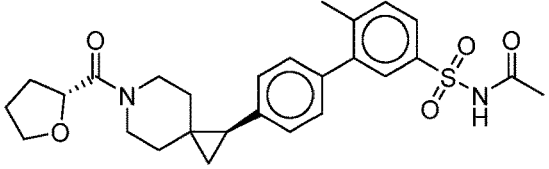<br>N-((6-methyl-4'-((S)-6-((R)-tetrahydrofuran-2-carbonyl)-6-azaspiro[2.5]octan-1-yl)-[1,1'-biphenyl]-3-yl)sulfonyl)acetamide | A |
| 378 | 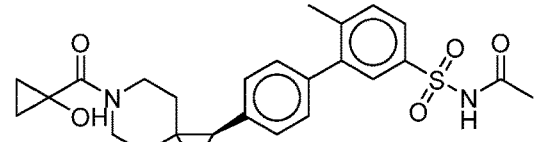<br>(S)-N-((4'-(6-(1-hydroxycyclopropane-1-carbonyl)-6-azaspiro[2.5]octan-1-yl)-6-methyl-[1,1'-biphenyl]-3-yl)sulfonyl)acetamide | A |

Figure 3-4

| | | |
|---|---|---|
| 379 | 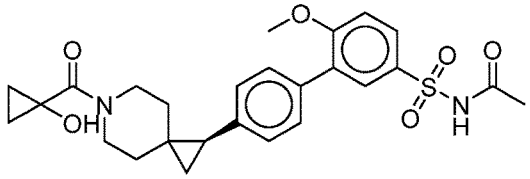<br>(S)-N-((4'-(6-(1-hydroxycyclopropane-1-carbonyl)-6-azaspiro[2.5]octan-1-yl)-6-methoxy-[1,1'-biphenyl]-3-yl)sulfonyl)acetamide | B |
| 380 | 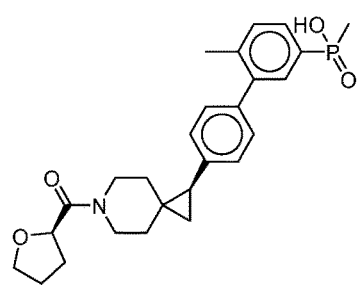<br>methyl(6-methyl-4'-((S)-6-((R)-tetrahydrofuran-2-carbonyl)-6-azaspiro[2.5]octan-1-yl)-[1,1'-biphenyl]-3-yl)phosphinic acid | A |
| 381 | 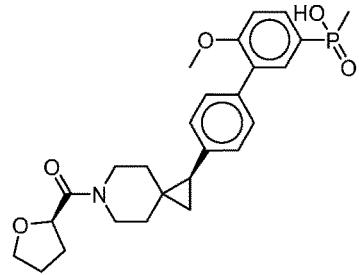<br>(6-methoxy-4'-((S)-6-((R)-tetrahydrofuran-2-carbonyl)-6-azaspiro[2.5]octan-1-yl)-[1,1'-biphenyl]-3-yl)(methyl)phosphinic acid | B |
| 382 | 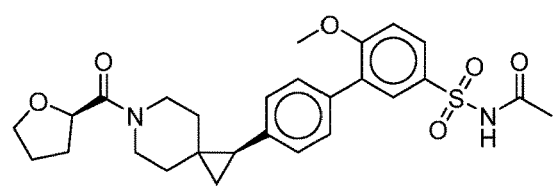<br>N-((6-methoxy-4'-((S)-6-((R)-tetrahydrofuran-2-carbonyl)-6-azaspiro[2.5]octan-1-yl)-[1,1'-biphenyl]-3-yl)sulfonyl)acetamide | B |

Figure 3-5

| 383 |  8-(4-((S)-6-((R)-tetrahydrofuran-2-carbonyl)-6-azaspiro[2.5]octan-1-yl)phenyl)quinoline-6-carboxylic acid | A |
|---|---|---|
| 384 |  4-[4-[(1S)-6-(1-hydroxycyclopropanecarbonyl)-6-azaspiro[2.5]octan-1-yl]phenyl]quinoline-2-carboxylic acid* | A |
| 385 |  (S)-3-hydroxy-4'-(6-(1-hydroxycyclopropane-1-carbonyl)-6-azaspiro[2.5]octan-1-yl)-[1,1'-biphenyl]-4-carboxylic acid | B |
| 386 |  (S)-5-chloro-2-fluoro-4'-(6-(1-hydroxycyclopropane-1-carbonyl)-6-azaspiro[2.5]octan-1-yl)-[1,1'-biphenyl]-4-carboxylic acid | A |

| | | |
|---|---|---|
| 387 | 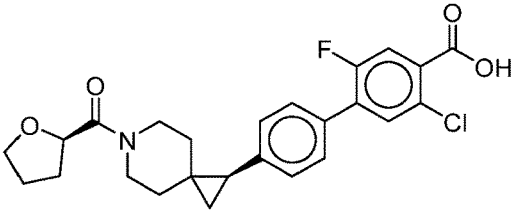<br>5-chloro-2-fluoro-4'-((S)-6-((R)-tetrahydrofuran-2-carbonyl)-6-azaspiro[2.5]octan-1-yl)-[1,1'-biphenyl]-4-carboxylic acid | B |
| 388 | 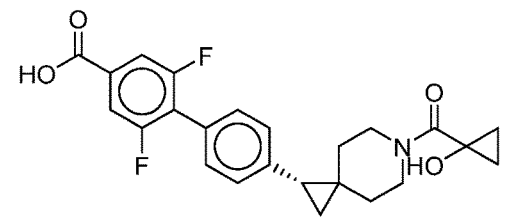<br>(S)-2,6-difluoro-4'-(6-(1-hydroxycyclopropane-1-carbonyl)-6-azaspiro[2.5]octan-1-yl)-[1,1'-biphenyl]-4-carboxylic acid | A |
| 389 | 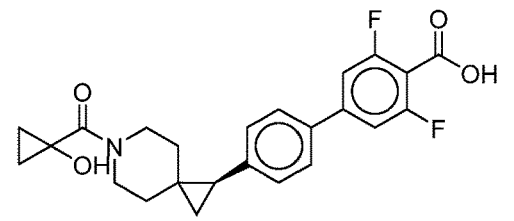<br>(S)-3,5-difluoro-4'-(6-(1-hydroxycyclopropane-1-carbonyl)-6-azaspiro[2.5]octan-1-yl)-[1,1'-biphenyl]-4-carboxylic acid | A |
| 390 | 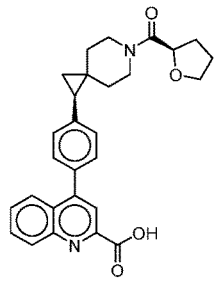<br>4-(4-((S)-6-((R)-tetrahydrofuran-2-carbonyl)-6-azaspiro[2.5]octan-1-yl)phenyl)quinoline-2-carboxylic acid | A |

Figure 3-7

| 391 | 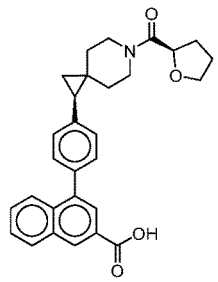
4-(4-((S)-6-((R)-tetrahydrofuran-2-carbonyl)-6-azaspiro[2.5]octan-1-yl)phenyl)-2-naphthoic acid | A |
|---|---|---|
| 392 | 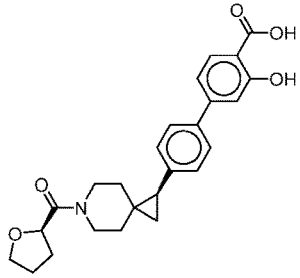
3-hydroxy-4'-((S)-6-((R)-tetrahydrofuran-2-carbonyl)-6-azaspiro[2.5]octan-1-yl)-[1,1'-biphenyl]-4-carboxylic acid | B |
| 393 | 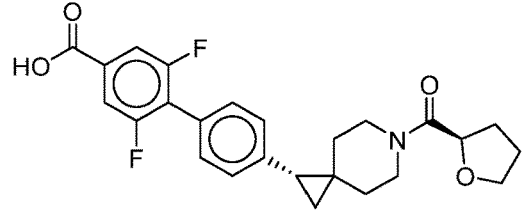
2,6-difluoro-4'-((S)-6-((R)-tetrahydrofuran-2-carbonyl)-6-azaspiro[2.5]octan-1-yl)-[1,1'-biphenyl]-4-carboxylic acid | A |
| 394 | 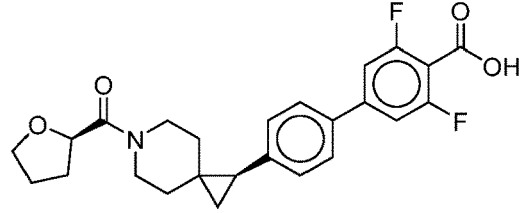
3,5-difluoro-4'-((S)-6-((R)-tetrahydrofuran-2-carbonyl)-6-azaspiro[2.5]octan-1-yl)-[1,1'-biphenyl]-4-carboxylic acid | B |
Figure 3-8

| 395 | 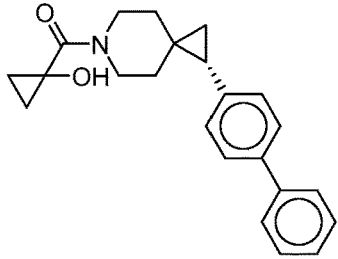<br>(S)-(1-([1,1'-biphenyl]-4-yl)-6-azaspiro[2.5]octan-6-yl)(1-hydroxycyclopropyl)methanone | A |
|---|---|---|
| 396 | 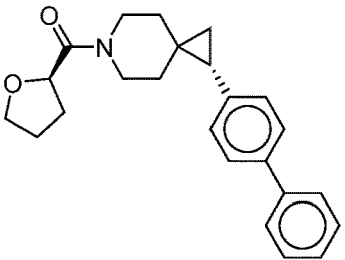<br>((S)-1-([1,1'-biphenyl]-4-yl)-6-azaspiro[2.5]octan-6-yl)((R)-tetrahydrofuran-2-yl)methanone | A |
| 397 | 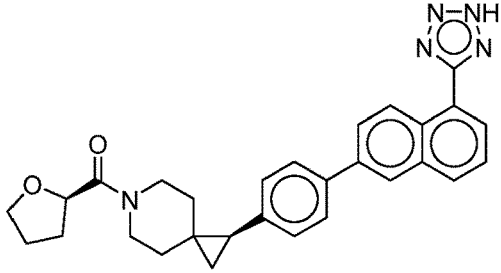<br>((S)-1-(4-(5-(2H-tetrazol-5-yl)naphthalen-2-yl)phenyl)-6-azaspiro[2.5]octan-6-yl)((R)-tetrahydrofuran-2-yl)methanone | A |
| 398 | 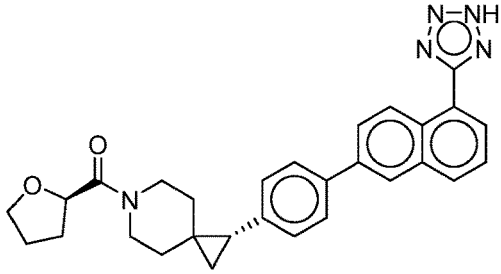<br>((R)-1-(4-(5-(2H-tetrazol-5-yl)naphthalen-2-yl)phenyl)-6-azaspiro[2.5]octan-6-yl)((R)-tetrahydrofuran-2-yl)methanone | B |
Figure 3-9

| | | |
|---|---|---|
| 399 | (S)-1-(1-(4-(quinolin-3-yl)phenyl)-1-(2H-tetrazol-5-yl)-6-azaspiro[2.5]octan-6-yl)propan-1-one | C |
| 400 | (R)-1-(1-(4-(quinolin-3-yl)phenyl)-1-(2H-tetrazol-5-yl)-6-azaspiro[2.5]octan-6-yl)propan-1-one | A |
| 401 | 7-(4-((R)-6-((R)-tetrahydrofuran-2-carbonyl)-6-azaspiro[2.5]octan-1-yl)phenyl)isoquinoline-4-carboxylic acid | C |
| 402 | 7-(4-((S)-6-((R)-tetrahydrofuran-2-carbonyl)-6-azaspiro[2.5]octan-1-yl)phenyl)isoquinoline-4-carboxylic acid | A |

Figure 3-10

| | | |
|---|---|---|
| 403 | 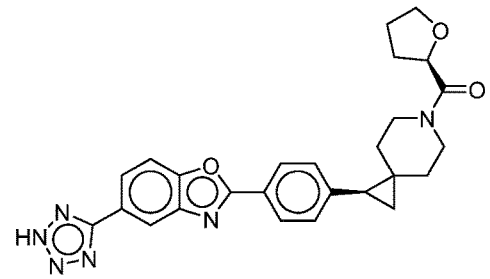<br>((R)-1-(4-(5-(2H-tetrazol-5-yl)benzo[d]oxazol-2-yl)phenyl)-6-azaspiro[2.5]octan-6-yl)((R)-tetrahydrofuran-2-yl)methanone | B |
| 404 | 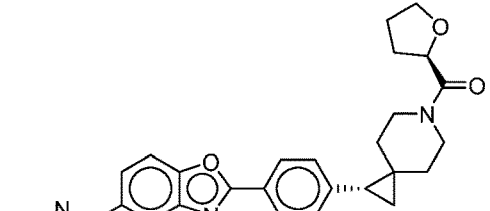<br>((S)-1-(4-(5-(2H-tetrazol-5-yl)benzo[d]oxazol-2-yl)phenyl)-6-azaspiro[2.5]octan-6-yl)((R)-tetrahydrofuran-2-yl)methanone | E |
| 405 | 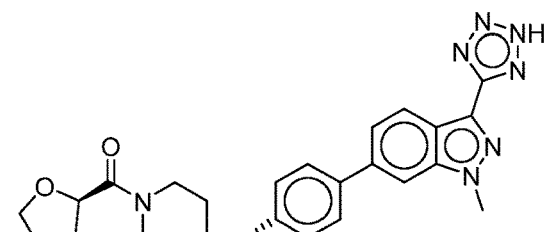<br>((R)-1-(4-(1-methyl-3-(2H-tetrazol-5-yl)-1H-indazol-6-yl)phenyl)-6-azaspiro[2.5]octan-6-yl)((R)-tetrahydrofuran-2-yl)methanone | D |
| 406 | 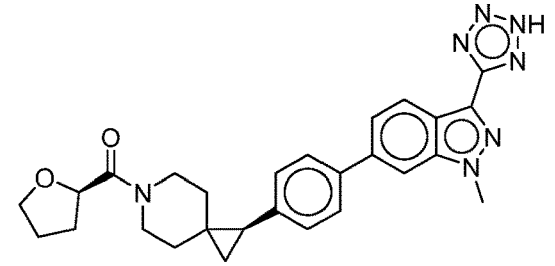<br>((S)-1-(4-(1-methyl-3-(2H-tetrazol-5-yl)-1H-indazol-6-yl)phenyl)-6-azaspiro[2.5]octan-6-yl)((R)-tetrahydrofuran-2-yl)methanone | A |

Figure 3-11

| 407 | 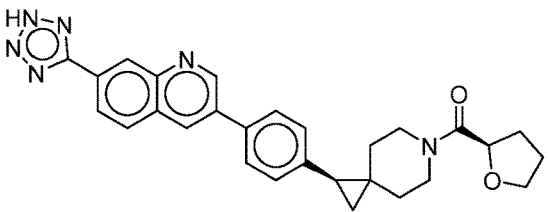<br>((R)-1-(4-(7-(2H-tetrazol-5-yl)quinolin-3-yl)phenyl)-6-azaspiro[2.5]octan-6-yl)((R)-tetrahydrofuran-2-yl)methanone | C |
|---|---|---|
| 408 | 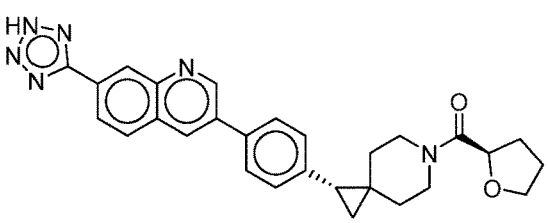<br>((S)-1-(4-(7-(2H-tetrazol-5-yl)quinolin-3-yl)phenyl)-6-azaspiro[2.5]octan-6-yl)((R)-tetrahydrofuran-2-yl)methanone | A |
| 409 | 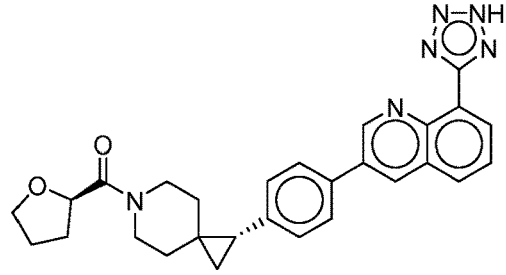<br>((R)-1-(4-(8-(2H-tetrazol-5-yl)quinolin-3-yl)phenyl)-6-azaspiro[2.5]octan-6-yl)((R)-tetrahydrofuran-2-yl)methanone | C |
| 410 | 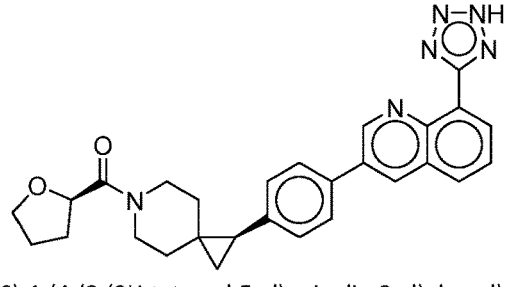<br>((S)-1-(4-(8-(2H-tetrazol-5-yl)quinolin-3-yl)phenyl)-6-azaspiro[2.5]octan-6-yl)((R)-tetrahydrofuran-2-yl)methanone | A |
Figure 3-12

| | | |
|---|---|---|
| 411 | 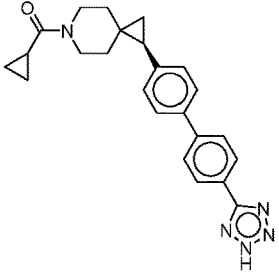<br>(R)-(1-(4'-(2H-tetrazol-5-yl)-[1,1'-biphenyl]-4-yl)-6-azaspiro[2.5]octan-6-yl)(cyclopropyl)methanone | C |
| 412 | 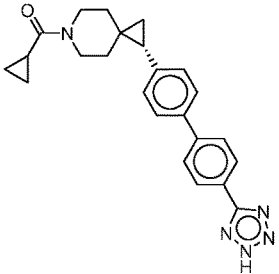<br>(S)-(1-(4'-(2H-tetrazol-5-yl)-[1,1'-biphenyl]-4-yl)-6-azaspiro[2.5]octan-6-yl)(cyclopropyl)methanone | A |
| 413 | 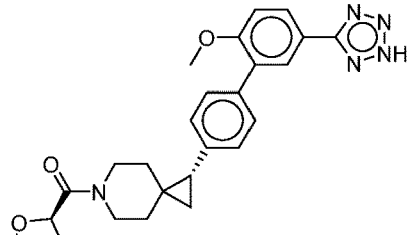<br>((R)-1-(2'-methoxy-5'-(2H-tetrazol-5-yl)-[1,1'-biphenyl]-4-yl)-6-azaspiro[2.5]octan-6-yl)((R)-tetrahydrofuran-2-yl)methanone | A |
| 414 | 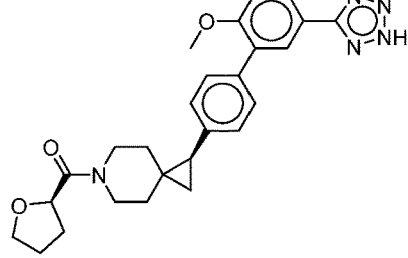<br>((S)-1-(2'-methoxy-5'-(2H-tetrazol-5-yl)-[1,1'-biphenyl]-4-yl)-6-azaspiro[2.5]octan-6-yl)((R)-tetrahydrofuran-2-yl)methanone | C |
Figure 3-13

| | | |
|---|---|---|
| 415 | 6-fluoro-5-methoxy-4'-((R)-6-((R)-tetrahydrofuran-2-carbonyl)-6-azaspiro[2.5]octan-1-yl)-[1,1'-biphenyl]-3-carboxylic acid | B |
| 416 | 6-fluoro-5-methoxy-4'-((S)-6-((R)-tetrahydrofuran-2-carbonyl)-6-azaspiro[2.5]octan-1-yl)-[1,1'-biphenyl]-3-carboxylic acid | E |
| 417 | 6-chloro-5-methoxy-4'-((R)-6-((R)-tetrahydrofuran-2-carbonyl)-6-azaspiro[2.5]octan-1-yl)-[1,1'-biphenyl]-3-carboxylic acid | A |
| 418 | 6-chloro-5-methoxy-4'-((S)-6-((R)-tetrahydrofuran-2-carbonyl)-6-azaspiro[2.5]octan-1-yl)-[1,1'-biphenyl]-3-carboxylic acid | C |

Figure 3-14

| 419 | 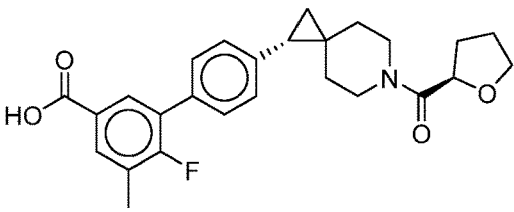 6-fluoro-5-methyl-4'-((R)-6-((R)-tetrahydrofuran-2-carbonyl)-6-azaspiro[2.5]octan-1-yl)-[1,1'-biphenyl]-3-carboxylic acid | C |
|---|---|---|
| 420 | 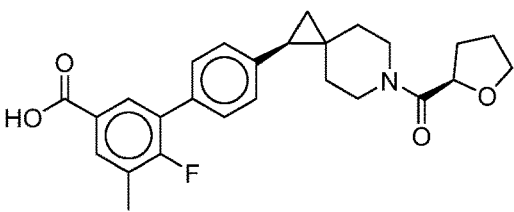 6-fluoro-5-methyl-4'-((S)-6-((R)-tetrahydrofuran-2-carbonyl)-6-azaspiro[2.5]octan-1-yl)-[1,1'-biphenyl]-3-carboxylic acid | A |
| 421 | 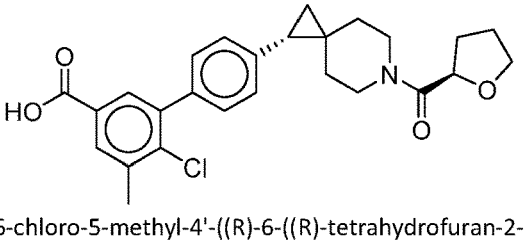 6-chloro-5-methyl-4'-((R)-6-((R)-tetrahydrofuran-2-carbonyl)-6-azaspiro[2.5]octan-1-yl)-[1,1'-biphenyl]-3-carboxylic acid | C |
| 422 | 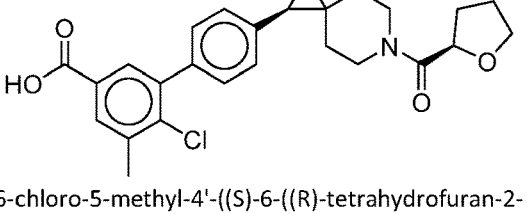 6-chloro-5-methyl-4'-((S)-6-((R)-tetrahydrofuran-2-carbonyl)-6-azaspiro[2.5]octan-1-yl)-[1,1'-biphenyl]-3-carboxylic acid | A |

Figure 3-15

| | | |
|---|---|---|
| 423 | 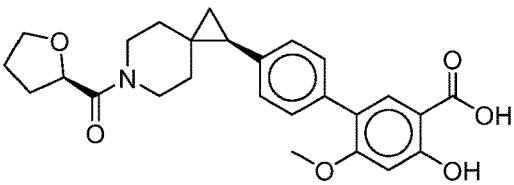<br>4-hydroxy-6-methoxy-4'-((R)-6-((R)-tetrahydrofuran-2-carbonyl)-6-azaspiro[2.5]octan-1-yl)-[1,1'-biphenyl]-3-carboxylic acid | B |
| 424 | 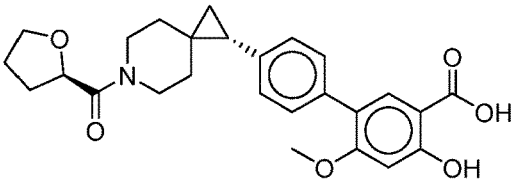<br>4-hydroxy-6-methoxy-4'-((S)-6-((R)-tetrahydrofuran-2-carbonyl)-6-azaspiro[2.5]octan-1-yl)-[1,1'-biphenyl]-3-carboxylic acid | A |
| 425 | 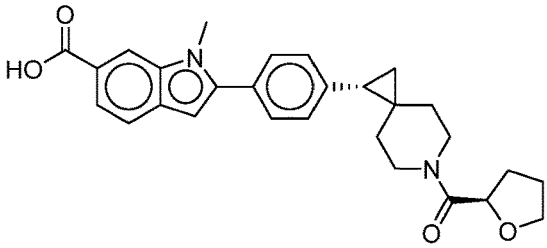<br>1-methyl-2-(4-((R)-6-((R)-tetrahydrofuran-2-carbonyl)-6-azaspiro[2.5]octan-1-yl)phenyl)-1H-indole-6-carboxylic acid | A |
| 426 | 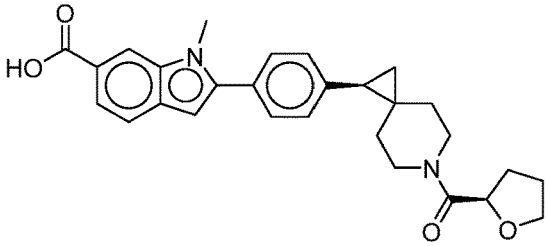<br>1-methyl-2-(4-((S)-6-((R)-tetrahydrofuran-2-carbonyl)-6-azaspiro[2.5]octan-1-yl)phenyl)-1H-indole-6-carboxylic acid | C |

Figure 3-16

| | | |
|---|---|---|
| 427 | 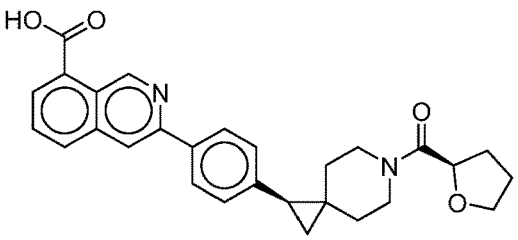<br>3-(4-((R)-6-((R)-tetrahydrofuran-2-carbonyl)-6-azaspiro[2.5]octan-1-yl)phenyl)isoquinoline-8-carboxylic acid | C |
| 428 | 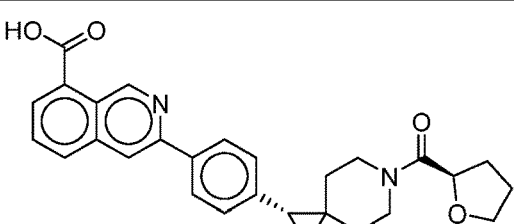<br>3-(4-((S)-6-((R)-tetrahydrofuran-2-carbonyl)-6-azaspiro[2.5]octan-1-yl)phenyl)isoquinoline-8-carboxylic acid | A |
| 429 | 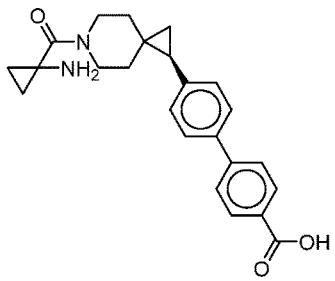<br>(R)-4'-(6-(1-aminocyclopropane-1-carbonyl)-6-azaspiro[2.5]octan-1-yl)-[1,1'-biphenyl]-4-carboxylic acid | B |
| 430 | 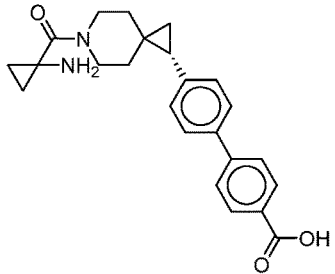<br>(S)-4'-(6-(1-aminocyclopropane-1-carbonyl)-6-azaspiro[2.5]octan-1-yl)-[1,1'-biphenyl]-4-carboxylic acid | E |
Figure 3-17

| | | |
|---|---|---|
| 431 | 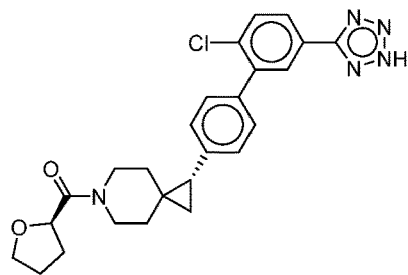<br>((R)-1-(2'-chloro-5'-(2H-tetrazol-5-yl)-[1,1'-biphenyl]-4-yl)-6-azaspiro[2.5]octan-6-yl)((R)-tetrahydrofuran-2-yl)methanone | B |
| 432 | 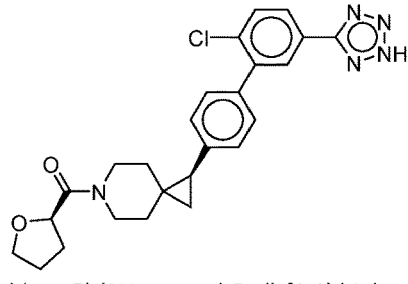<br>((S)-1-(2'-chloro-5'-(2H-tetrazol-5-yl)-[1,1'-biphenyl]-4-yl)-6-azaspiro[2.5]octan-6-yl)((R)-tetrahydrofuran-2-yl)methanone | A |
| 433 | 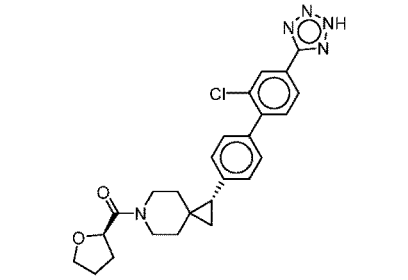<br>((R)-1-(2'-chloro-4'-(2H-tetrazol-5-yl)-[1,1'-biphenyl]-4-yl)-6-azaspiro[2.5]octan-6-yl)((R)-tetrahydrofuran-2-yl)methanone | C |
| 434 | 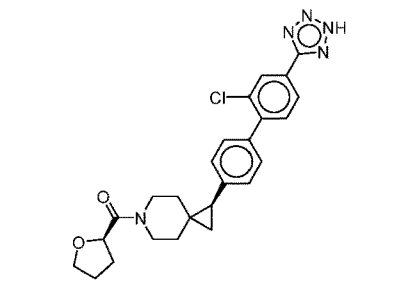<br>((S)-1-(2'-chloro-4'-(2H-tetrazol-5-yl)-[1,1'-biphenyl]-4-yl)-6-azaspiro[2.5]octan-6-yl)((R)-tetrahydrofuran-2-yl)methanone | A |

Figure 3-18

| 435 | 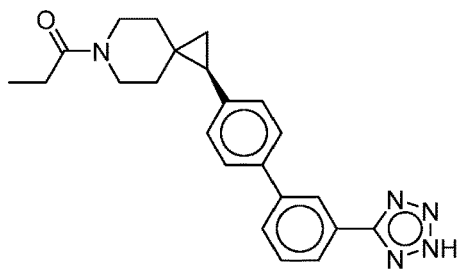<br>(R)-1-(1-(3'-(2H-tetrazol-5-yl)-[1,1'-biphenyl]-4-yl)-6-azaspiro[2.5]octan-6-yl)propan-1-one | B |
|---|---|---|
| 436 | 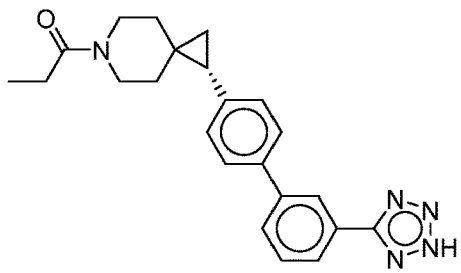<br>(S)-1-(1-(3'-(2H-tetrazol-5-yl)-[1,1'-biphenyl]-4-yl)-6-azaspiro[2.5]octan-6-yl)propan-1-one | A |
| 437 | 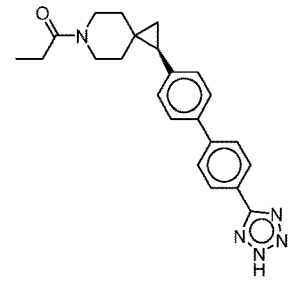<br>(R)-1-(1-(4'-(2H-tetrazol-5-yl)-[1,1'-biphenyl]-4-yl)-6-azaspiro[2.5]octan-6-yl)propan-1-one | C |
| 438 | 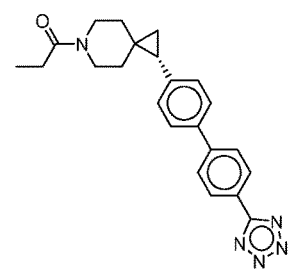<br>(S)-1-(1-(4'-(2H-tetrazol-5-yl)-[1,1'-biphenyl]-4-yl)-6-azaspiro[2.5]octan-6-yl)propan-1-one | A |
Figure 3-19

| | | |
|---|---|---|
| 439 | 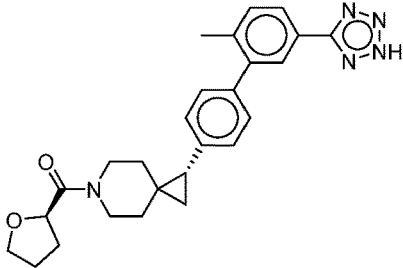<br>((R)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone | C |
| 440 | 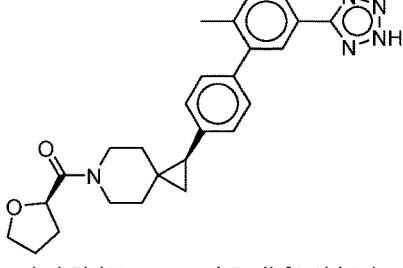<br>((S)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone | A |
| 441 | 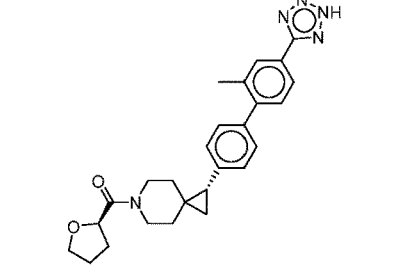<br>((R)-1-(2'-methyl-4'-(2H-tetrazol-5-yl)-[1,1'-biphenyl]-4-yl)-6-azaspiro[2.5]octan-6-yl)((R)-tetrahydrofuran-2-yl)methanone | C |
| 442 | 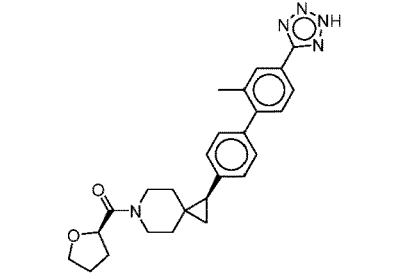<br>((S)-1-(2'-methyl-4'-(2H-tetrazol-5-yl)-[1,1'-biphenyl]-4-yl)-6-azaspiro[2.5]octan-6-yl)((R)-tetrahydrofuran-2-yl)methanone | A |

Figure 3-20

| | | |
|---|---|---|
| 443 | 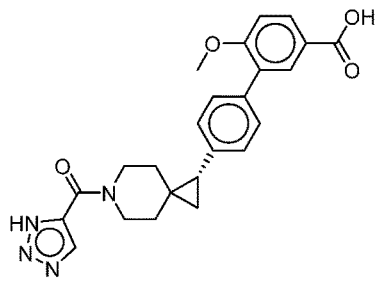<br>(R)-4'-(6-(1H-1,2,3-triazole-5-carbonyl)-6-azaspiro[2.5]octan-1-yl)-6-methoxy-[1,1'-biphenyl]-3-carboxylic acid | B |
| 444 | 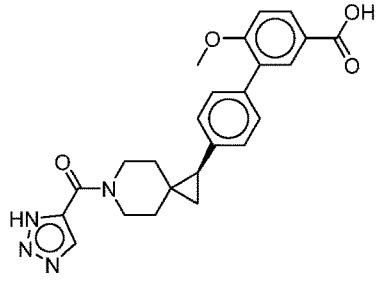<br>(S)-4'-(6-(1H-1,2,3-triazole-5-carbonyl)-6-azaspiro[2.5]octan-1-yl)-6-methoxy-[1,1'-biphenyl]-3-carboxylic acid | E |
| 445 | 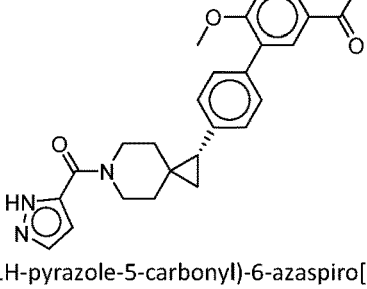<br>(R)-4'-(6-(1H-pyrazole-5-carbonyl)-6-azaspiro[2.5]octan-1-yl)-6-methoxy-[1,1'-biphenyl]-3-carboxylic acid | B |
| 446 | 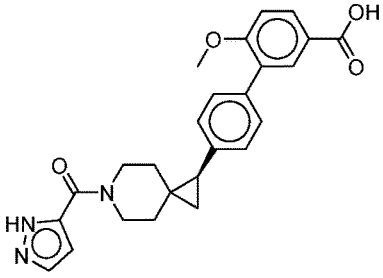<br>(S)-4'-(6-(1H-pyrazole-5-carbonyl)-6-azaspiro[2.5]octan-1-yl)-6-methoxy-[1,1'-biphenyl]-3-carboxylic acid | C |
Figure 3-21

| 447 | 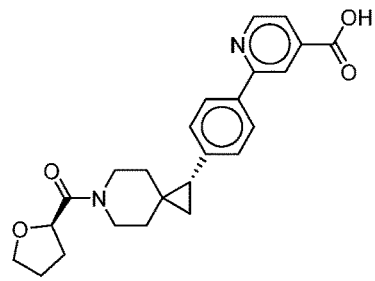 2-(4-((R)-6-((R)-tetrahydrofuran-2-carbonyl)-6-azaspiro[2.5]octan-1-yl)phenyl)isonicotinic acid | E |
| --- | --- | --- |
| 448 | 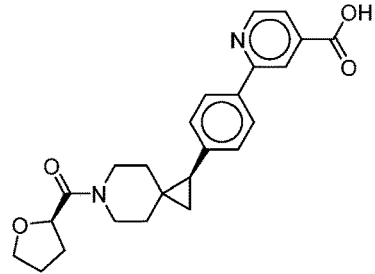 2-(4-((S)-6-((R)-tetrahydrofuran-2-carbonyl)-6-azaspiro[2.5]octan-1-yl)phenyl)isonicotinic acid | C |
| 449 | 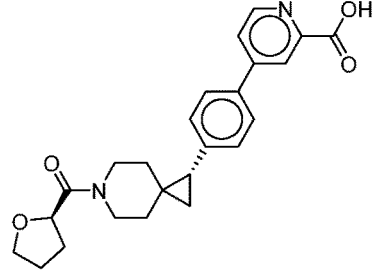 4-(4-((R)-6-((R)-tetrahydrofuran-2-carbonyl)-6-azaspiro[2.5]octan-1-yl)phenyl)picolinic acid | B |
| 450 | 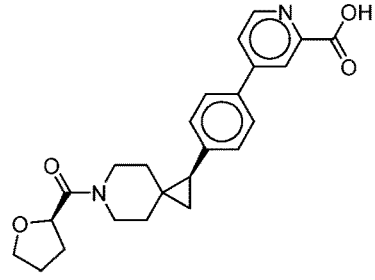 4-(4-((S)-6-((R)-tetrahydrofuran-2-carbonyl)-6-azaspiro[2.5]octan-1-yl)phenyl)picolinic acid | D |
Figure 3-22

| | | |
|---|---|---|
| 451 | 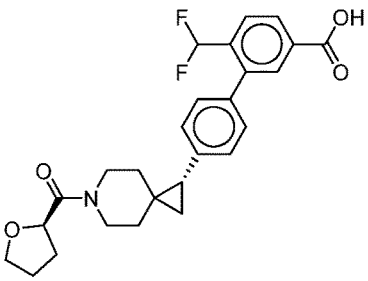<br>6-(difluoromethyl)-4'-((R)-6-((R)-tetrahydrofuran-2-carbonyl)-6-azaspiro[2.5]octan-1-yl)-[1,1'-biphenyl]-3-carboxylic acid | D |
| 452 | 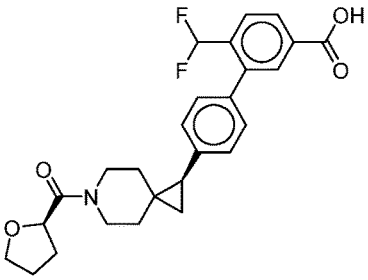<br>6-(difluoromethyl)-4'-((S)-6-((R)-tetrahydrofuran-2-carbonyl)-6-azaspiro[2.5]octan-1-yl)-[1,1'-biphenyl]-3-carboxylic acid | B |
| 453 | 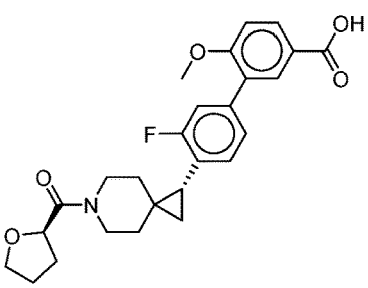<br>3'-fluoro-6-methoxy-4'-((R)-6-((R)-tetrahydrofuran-2-carbonyl)-6-azaspiro[2.5]octan-1-yl)-[1,1'-biphenyl]-3-carboxylic acid | D |
| 454 | 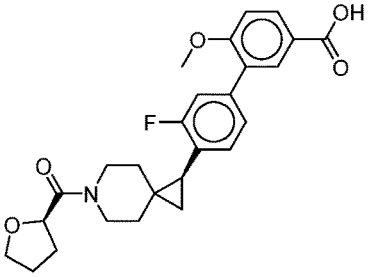<br>3'-fluoro-6-methoxy-4'-((S)-6-((R)-tetrahydrofuran-2-carbonyl)-6-azaspiro[2.5]octan-1-yl)-[1,1'-biphenyl]-3-carboxylic acid | A |

Figure 3-23

| | | | |
|---|---|---|---|
| 455 | 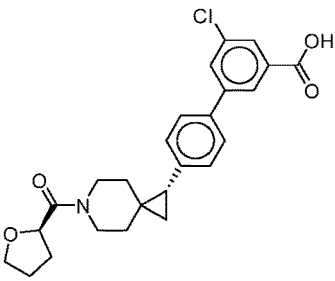<br>5-chloro-4'-((R)-6-((R)-tetrahydrofuran-2-carbonyl)-6-azaspiro[2.5]octan-1-yl)-[1,1'-biphenyl]-3-carboxylic acid | | B |
| 456 | 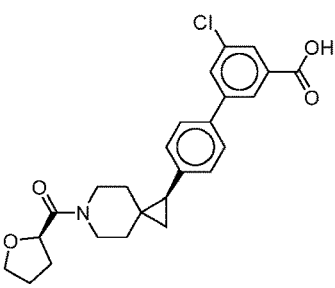<br>5-chloro-4'-((S)-6-((R)-tetrahydrofuran-2-carbonyl)-6-azaspiro[2.5]octan-1-yl)-[1,1'-biphenyl]-3-carboxylic acid | | A |
| 457 | 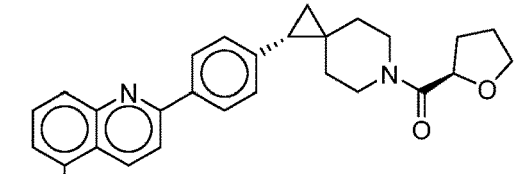<br>2-(4-((R)-6-((R)-tetrahydrofuran-2-carbonyl)-6-azaspiro[2.5]octan-1-yl)phenyl)quinoline-5-carboxylic acid | | C |
| 458 | 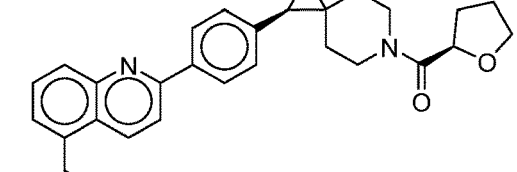<br>2-(4-((S)-6-((R)-tetrahydrofuran-2-carbonyl)-6-azaspiro[2.5]octan-1-yl)phenyl)quinoline-5-carboxylic acid | | B |
Figure 3-24

| | | |
|---|---|---|
| 459 | 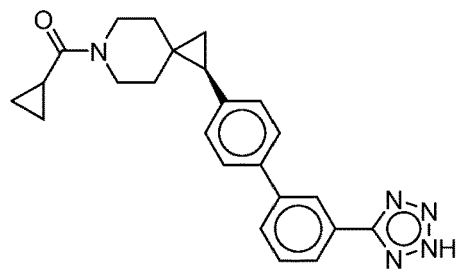<br>(R)-(1-(3'-(2H-tetrazol-5-yl)-[1,1'-biphenyl]-4-yl)-6-azaspiro[2.5]octan-6-yl)(cyclopropyl)methanone | C |
| 460 | 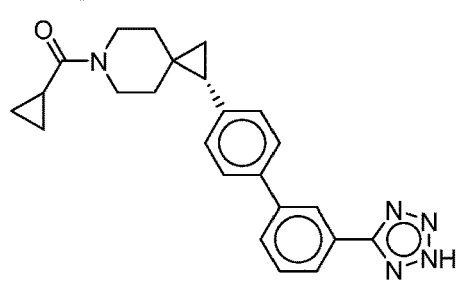<br>(S)-(1-(3'-(2H-tetrazol-5-yl)-[1,1'-biphenyl]-4-yl)-6-azaspiro[2.5]octan-6-yl)(cyclopropyl)methanone | A |
| 461 | 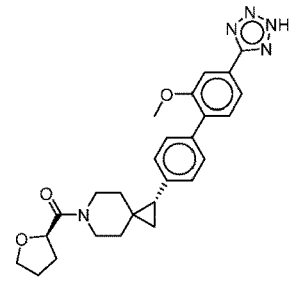<br>((R)-1-(2'-methoxy-4'-(2H-tetrazol-5-yl)-[1,1'-biphenyl]-4-yl)-6-azaspiro[2.5]octan-6-yl)((R)-tetrahydrofuran-2-yl)methanone | C |
| 462 | 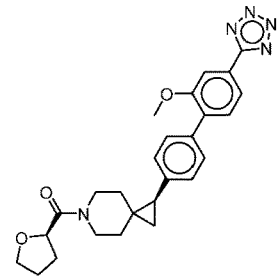<br>((S)-1-(2'-methoxy-4'-(2H-tetrazol-5-yl)-[1,1'-biphenyl]-4-yl)-6-azaspiro[2.5]octan-6-yl)((R)-tetrahydrofuran-2-yl)methanone | A |
Figure 3-25

| | | |
|---|---|---|
| 463 | 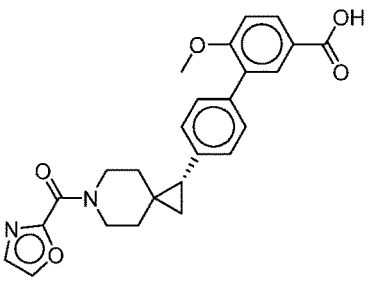<br>(R)-6-methoxy-4'-(6-(oxazole-2-carbonyl)-6-azaspiro[2.5]octan-1-yl)-[1,1'-biphenyl]-3-carboxylic acid | C |
| 464 | 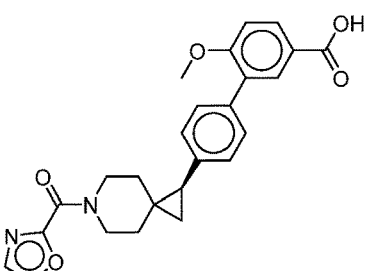<br>(S)-6-methoxy-4'-(6-(oxazole-2-carbonyl)-6-azaspiro[2.5]octan-1-yl)-[1,1'-biphenyl]-3-carboxylic acid | E |
| 465 | 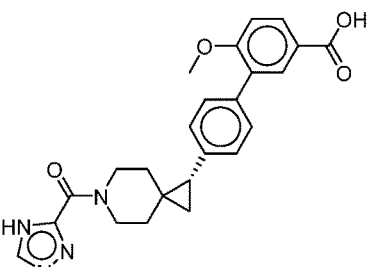<br>(R)-4'-(6-(4H-1,2,4-triazole-3-carbonyl)-6-azaspiro[2.5]octan-1-yl)-6-methoxy-[1,1'-biphenyl]-3-carboxylic acid | C |
| 466 | 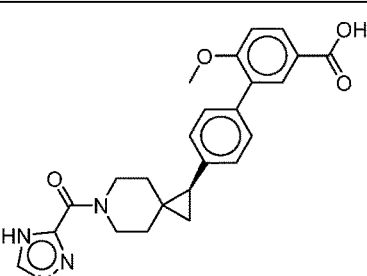<br>(S)-4'-(6-(4H-1,2,4-triazole-3-carbonyl)-6-azaspiro[2.5]octan-1-yl)-6-methoxy-[1,1'-biphenyl]-3-carboxylic acid | E |
Figure 3-26

| 467 | 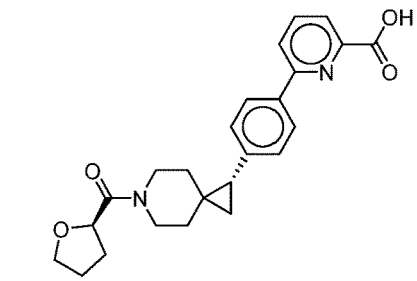<br>6-(4-((R)-6-((R)-tetrahydrofuran-2-carbonyl)-6-azaspiro[2.5]octan-1-yl)phenyl)picolinic acid | E |
|---|---|---|
| 468 | 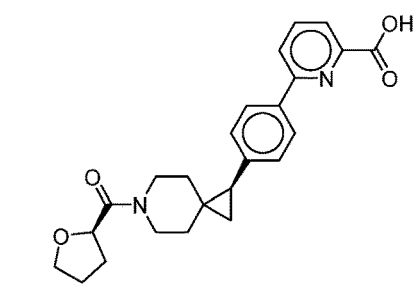<br>6-(4-((S)-6-((R)-tetrahydrofuran-2-carbonyl)-6-azaspiro[2.5]octan-1-yl)phenyl)picolinic acid | B |
| 469 | 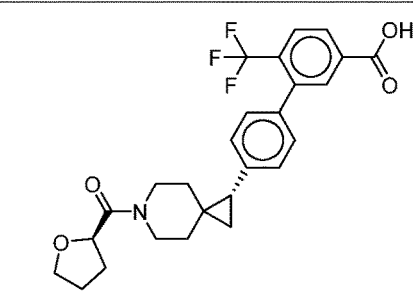<br>4'-((R)-6-((R)-tetrahydrofuran-2-carbonyl)-6-azaspiro[2.5]octan-1-yl)-6-(trifluoromethyl)-[1,1'-biphenyl]-3-carboxylic acid | C |
| 470 | 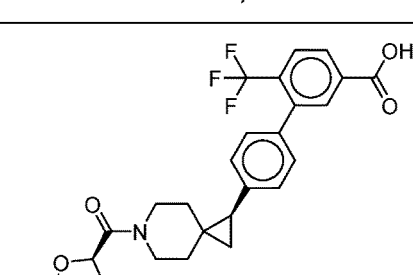<br>4'-((S)-6-((R)-tetrahydrofuran-2-carbonyl)-6-azaspiro[2.5]octan-1-yl)-6-(trifluoromethyl)-[1,1'-biphenyl]-3-carboxylic acid | A |
Figure 3-27

| | | | |
|---|---|---|---|
| 471 | 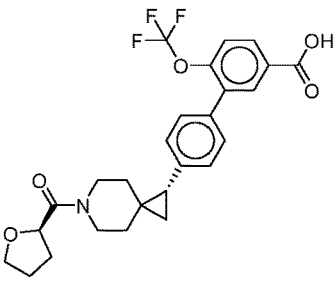<br>4'-((R)-6-((R)-tetrahydrofuran-2-carbonyl)-6-azaspiro[2.5]octan-1-yl)-6-(trifluoromethoxy)-[1,1'-biphenyl]-3-carboxylic acid | D |
| 472 | 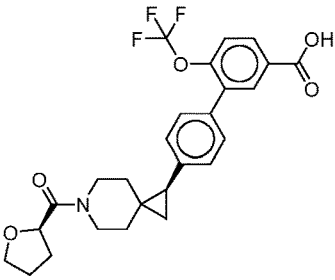<br>4'-((S)-6-((R)-tetrahydrofuran-2-carbonyl)-6-azaspiro[2.5]octan-1-yl)-6-(trifluoromethoxy)-[1,1'-biphenyl]-3-carboxylic acid | B |
| 473 | 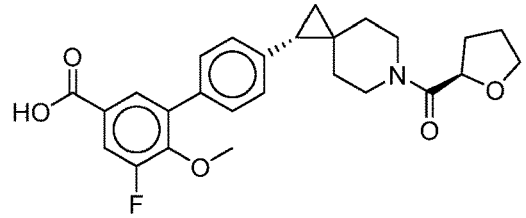<br>5-fluoro-6-methoxy-4'-((R)-6-((R)-tetrahydrofuran-2-carbonyl)-6-azaspiro[2.5]octan-1-yl)-[1,1'-biphenyl]-3-carboxylic acid | E |
| 474 | 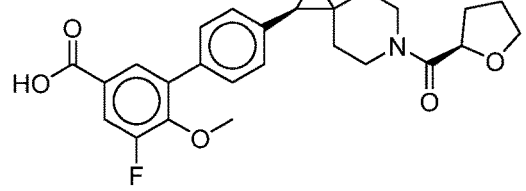<br>5-fluoro-6-methoxy-4'-((S)-6-((R)-tetrahydrofuran-2-carbonyl)-6-azaspiro[2.5]octan-1-yl)-[1,1'-biphenyl]-3-carboxylic acid | A |

Figure 3-28

| | | |
|---|---|---|
| 475 | 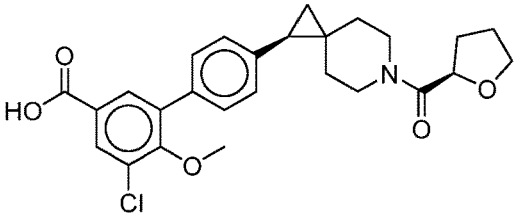<br>5-chloro-6-methoxy-4'-((S)-6-((R)-tetrahydrofuran-2-carbonyl)-6-azaspiro[2.5]octan-1-yl)-[1,1'-biphenyl]-3-carboxylic acid | A |
| 476 | 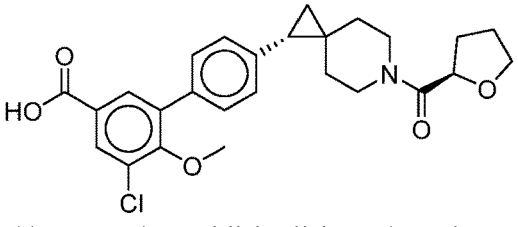<br>5-chloro-6-methoxy-4'-((R)-6-((R)-tetrahydrofuran-2-carbonyl)-6-azaspiro[2.5]octan-1-yl)-[1,1'-biphenyl]-3-carboxylic acid | D |
| 477 | 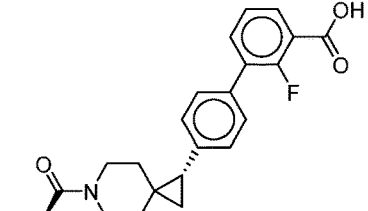<br>2-fluoro-4'-((R)-6-((R)-tetrahydrofuran-2-carbonyl)-6-azaspiro[2.5]octan-1-yl)-[1,1'-biphenyl]-3-carboxylic acid | D |
| 478 | 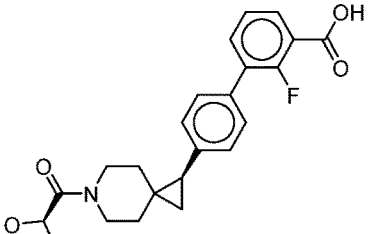<br>2-fluoro-4'-((S)-6-((R)-tetrahydrofuran-2-carbonyl)-6-azaspiro[2.5]octan-1-yl)-[1,1'-biphenyl]-3-carboxylic acid | B |

Figure 3-29

| | | |
|---|---|---|
| 479 | 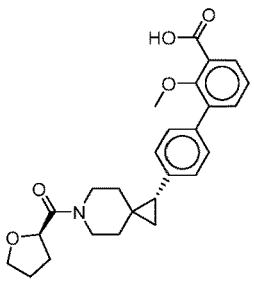<br>2-methoxy-4'-((R)-6-((R)-tetrahydrofuran-2-carbonyl)-6-azaspiro[2.5]octan-1-yl)-[1,1'-biphenyl]-3-carboxylic acid | E |
| 480 | 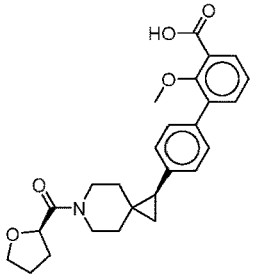<br>2-methoxy-4'-((S)-6-((R)-tetrahydrofuran-2-carbonyl)-6-azaspiro[2.5]octan-1-yl)-[1,1'-biphenyl]-3-carboxylic acid | B |
| 481 | 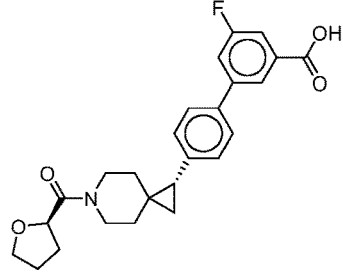<br>5-fluoro-4'-((R)-6-((R)-tetrahydrofuran-2-carbonyl)-6-azaspiro[2.5]octan-1-yl)-[1,1'-biphenyl]-3-carboxylic acid | E |
| 482 | 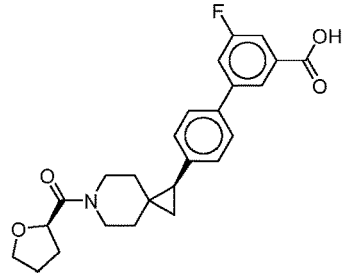<br>5-fluoro-4'-((S)-6-((R)-tetrahydrofuran-2-carbonyl)-6-azaspiro[2.5]octan-1-yl)-[1,1'-biphenyl]-3-carboxylic acid | A |
Figure 3-30

| 483 | 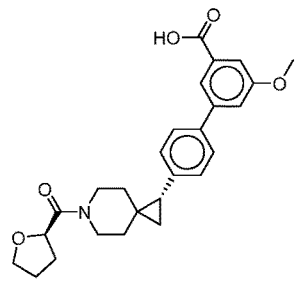<br>5-methoxy-4'-((R)-6-((R)-tetrahydrofuran-2-carbonyl)-6-azaspiro[2.5]octan-1-yl)-[1,1'-biphenyl]-3-carboxylic acid | C |
|---|---|---|
| 484 | 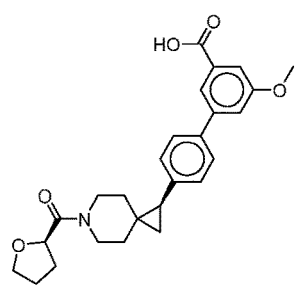<br>5-methoxy-4'-((S)-6-((R)-tetrahydrofuran-2-carbonyl)-6-azaspiro[2.5]octan-1-yl)-[1,1'-biphenyl]-3-carboxylic acid | A |
| 485 | 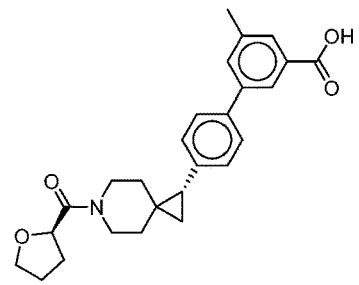<br>5-methyl-4'-((R)-6-((R)-tetrahydrofuran-2-carbonyl)-6-azaspiro[2.5]octan-1-yl)-[1,1'-biphenyl]-3-carboxylic acid | C |
| 486 | 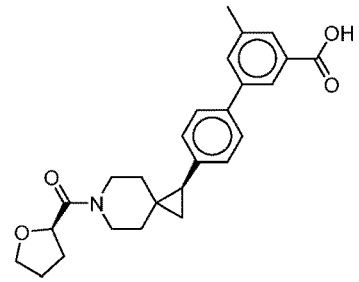<br>5-methyl-4'-((S)-6-((R)-tetrahydrofuran-2-carbonyl)-6-azaspiro[2.5]octan-1-yl)-[1,1'-biphenyl]-3-carboxylic acid | A |
Figure 3-31

| | | |
|---|---|---|
| 487 | 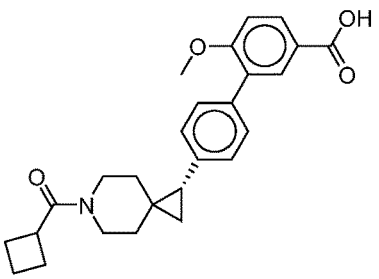<br>(R)-4'-(6-(cyclobutanecarbonyl)-6-azaspiro[2.5]octan-1-yl)-6-methoxy-[1,1'-biphenyl]-3-carboxylic acid | E |
| 488 | 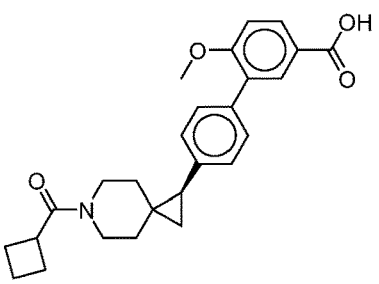<br>(S)-4'-(6-(cyclobutanecarbonyl)-6-azaspiro[2.5]octan-1-yl)-6-methoxy-[1,1'-biphenyl]-3-carboxylic acid | B |
| 489 | 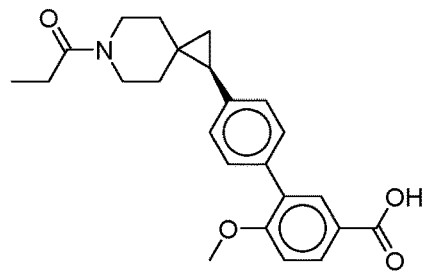<br>(R)-6-methoxy-4'-(6-propionyl-6-azaspiro[2.5]octan-1-yl)-[1,1'-biphenyl]-3-carboxylic acid | B |
| 490 | 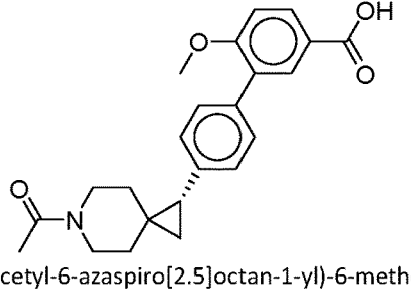<br>(R)-4'-(6-acetyl-6-azaspiro[2.5]octan-1-yl)-6-methoxy-[1,1'-biphenyl]-3-carboxylic acid | B |
Figure 3-32

| | | |
|---|---|---|
| 491 | 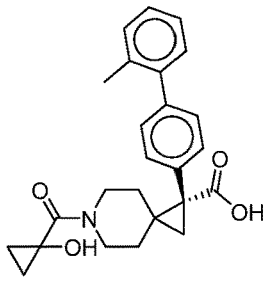<br>(R)-6-(1-hydroxycyclopropane-1-carbonyl)-1-(2'-methyl-[1,1'-biphenyl]-4-yl)-6-azaspiro[2.5]octane-1-carboxylic acid | D |
| 492 | 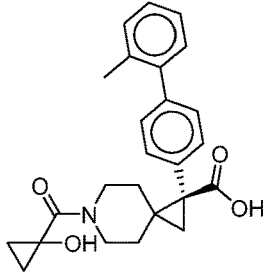<br>(S)-6-(1-hydroxycyclopropane-1-carbonyl)-1-(2'-methyl-[1,1'-biphenyl]-4-yl)-6-azaspiro[2.5]octane-1-carboxylic acid | B |
| 493 | 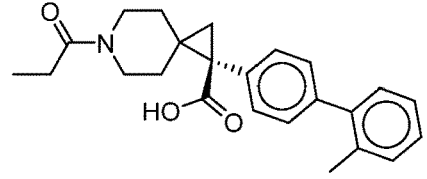<br>(R)-1-(2'-methyl-[1,1'-biphenyl]-4-yl)-6-propionyl-6-azaspiro[2.5]octane-1-carboxylic acid | C |
| 494 | 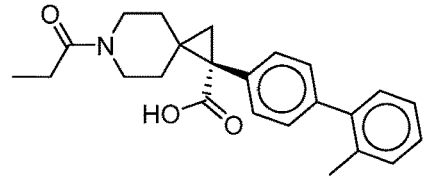<br>(S)-1-(2'-methyl-[1,1'-biphenyl]-4-yl)-6-propionyl-6-azaspiro[2.5]octane-1-carboxylic acid | E |
| 495 | 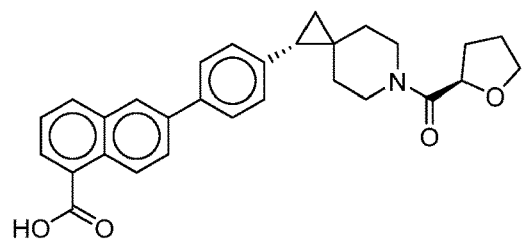<br>6-(4-((R)-6-((R)-tetrahydrofuran-2-carbonyl)-6-azaspiro[2.5]octan-1-yl)phenyl)-1-naphthoic acid | C |

Figure 3-33

| | | |
|---|---|---|
| 496 | 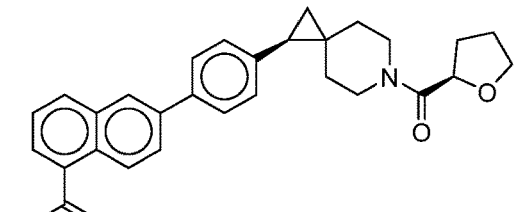6-(4-((S)-6-((R)-tetrahydrofuran-2-carbonyl)-6-azaspiro[2.5]octan-1-yl)phenyl)-1-naphthoic acid | A |
| 497 | 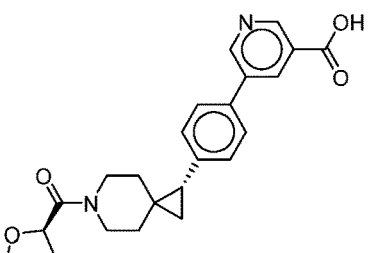5-(4-((R)-6-((R)-tetrahydrofuran-2-carbonyl)-6-azaspiro[2.5]octan-1-yl)phenyl)nicotinic acid | E |
| 498 | 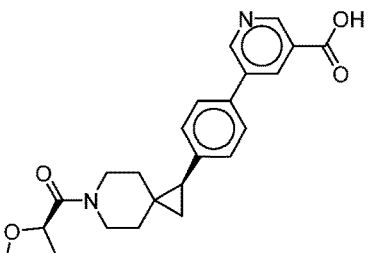5-(4-((S)-6-((R)-tetrahydrofuran-2-carbonyl)-6-azaspiro[2.5]octan-1-yl)phenyl)nicotinic acid | B |
| 499 | 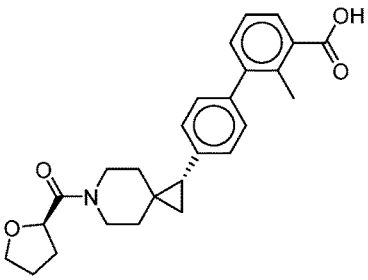2-methyl-4'-((R)-6-((R)-tetrahydrofuran-2-carbonyl)-6-azaspiro[2.5]octan-1-yl)-[1,1'-biphenyl]-3-carboxylic acid | E |
Figure 3-34

| | | |
|---|---|---|
| 500 | 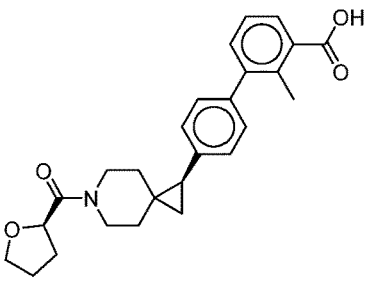<br>2-methyl-4'-((S)-6-((R)-tetrahydrofuran-2-carbonyl)-6-azaspiro[2.5]octan-1-yl)-[1,1'-biphenyl]-3-carboxylic acid | B |
| 501 | 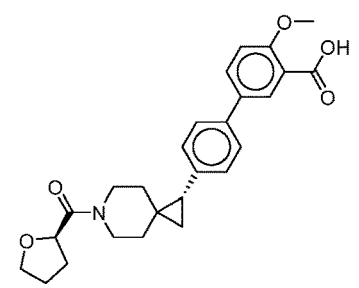<br>4-methoxy-4'-((R)-6-((R)-tetrahydrofuran-2-carbonyl)-6-azaspiro[2.5]octan-1-yl)-[1,1'-biphenyl]-3-carboxylic acid | C |
| 502 | 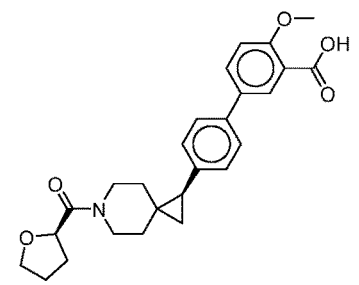<br>4-methoxy-4'-((S)-6-((R)-tetrahydrofuran-2-carbonyl)-6-azaspiro[2.5]octan-1-yl)-[1,1'-biphenyl]-3-carboxylic acid | B |
| 503 | 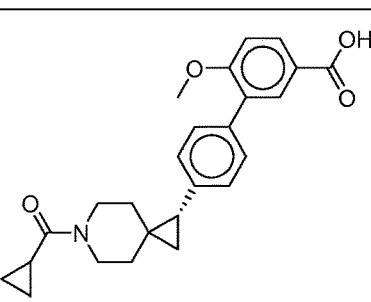<br>(R)-4'-(6-(cyclopropanecarbonyl)-6-azaspiro[2.5]octan-1-yl)-6-methoxy-[1,1'-biphenyl]-3-carboxylic acid | B |
Figure 3-35

| 504 | 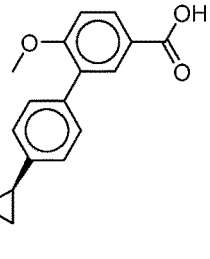<br>(S)-4'-(6-(cyclopropanecarbonyl)-6-azaspiro[2.5]octan-1-yl)-6-methoxy-[1,1'-biphenyl]-3-carboxylic acid | D |
|---|---|---|
| 505 | 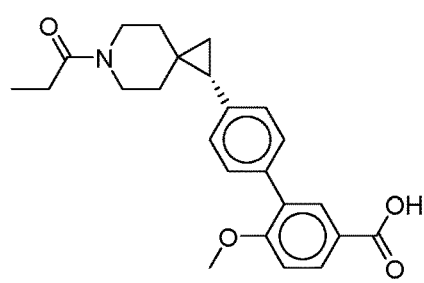<br>(S)-6-methoxy-4'-(6-propionyl-6-azaspiro[2.5]octan-1-yl)-[1,1'-biphenyl]-3-carboxylic acid | E |
| 506 | 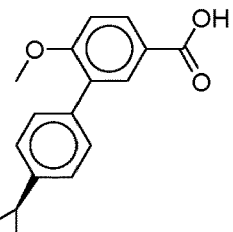<br>(S)-4'-(6-acetyl-6-azaspiro[2.5]octan-1-yl)-6-methoxy-[1,1'-biphenyl]-3-carboxylic acid | E |
| 507 | 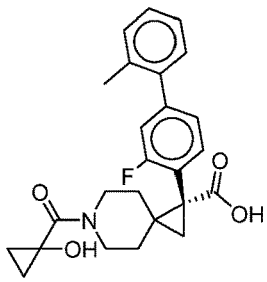<br>(R)-1-(3-fluoro-2'-methyl-[1,1'-biphenyl]-4-yl)-6-(1-hydroxycyclopropane-1-carbonyl)-6-azaspiro[2.5]octane-1-carboxylic acid | A |
Figure 3-36

| | | |
|---|---|---|
| 508 | (S)-1-(3-fluoro-2'-methyl-[1,1'-biphenyl]-4-yl)-6-(1-hydroxycyclopropane-1-carbonyl)-6-azaspiro[2.5]octane-1-carboxylic acid | C |
| 509 | (R)-1-(3-fluoro-2'-methyl-[1,1'-biphenyl]-4-yl)-6-propionyl-6-azaspiro[2.5]octane-1-carboxylic acid | B |
| 510 | (S)-1-(3-fluoro-2'-methyl-[1,1'-biphenyl]-4-yl)-6-propionyl-6-azaspiro[2.5]octane-1-carboxylic acid | E |
| 511 | (R)-4'-(6-(1H-1,2,3-triazole-5-carbonyl)-6-azaspiro[2.5]octan-1-yl)-2-methyl-[1,1'-biphenyl]-4-carboxylic acid | D |

Figure 3-37

| 512 | 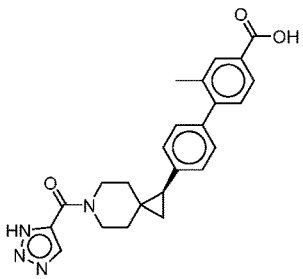<br>(S)-4'-(6-(1H-1,2,3-triazole-5-carbonyl)-6-azaspiro[2.5]octan-1-yl)-2-methyl-[1,1'-biphenyl]-4-carboxylic acid | B |
|---|---|---|
| 513 | 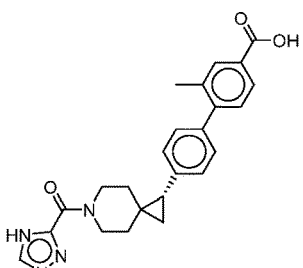<br>(R)-4'-(6-(4H-1,2,4-triazole-3-carbonyl)-6-azaspiro[2.5]octan-1-yl)-2-methyl-[1,1'-biphenyl]-4-carboxylic acid | C |
| 514 | 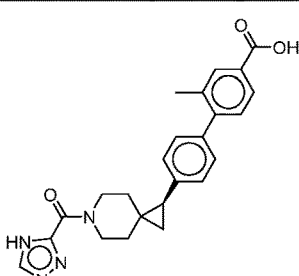<br>(S)-4'-(6-(4H-1,2,4-triazole-3-carbonyl)-6-azaspiro[2.5]octan-1-yl)-2-methyl-[1,1'-biphenyl]-4-carboxylic acid | E |
| 515 | 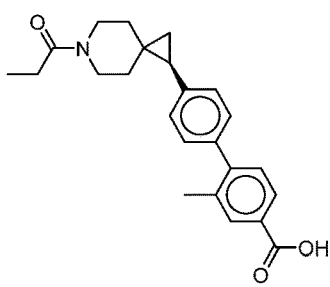<br>(R)-2-methyl-4'-(6-propionyl-6-azaspiro[2.5]octan-1-yl)-[1,1'-biphenyl]-4-carboxylic acid | D |
Figure 3-38

| 516 | 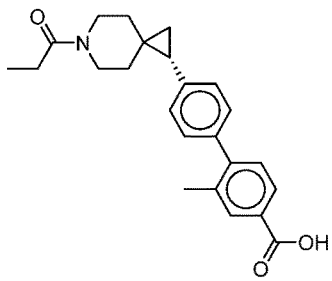<br>(S)-2-methyl-4'-(6-propionyl-6-azaspiro[2.5]octan-1-yl)-[1,1'-biphenyl]-4-carboxylic acid | A |
| 517 | 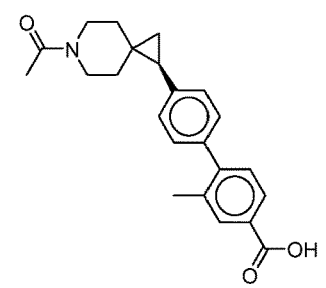<br>(R)-4'-(6-acetyl-6-azaspiro[2.5]octan-1-yl)-2-methyl-[1,1'-biphenyl]-4-carboxylic acid | E |
| 518 | 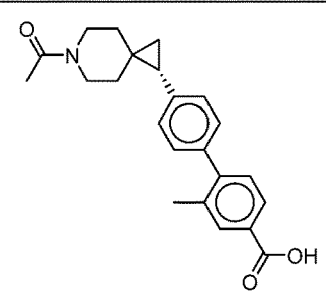<br>(S)-4'-(6-acetyl-6-azaspiro[2.5]octan-1-yl)-2-methyl-[1,1'-biphenyl]-4-carboxylic acid | B |
| 519 | 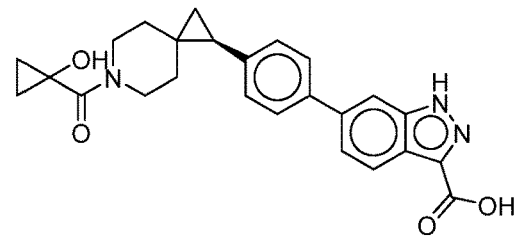<br>(R)-6-(4-(6-(1-hydroxycyclopropane-1-carbonyl)-6-azaspiro[2.5]octan-1-yl)phenyl)-1H-indazole-3-carboxylic acid | C |
Figure 3-39

| | | |
|---|---|---|
| 520 | 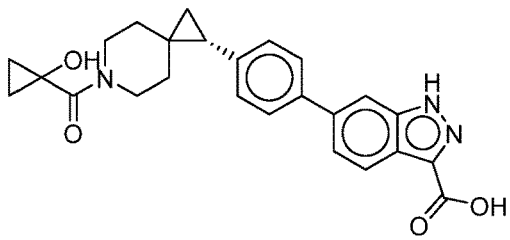<br>(S)-6-(4-(6-(1-hydroxycyclopropane-1-carbonyl)-6-azaspiro[2.5]octan-1-yl)phenyl)-1H-indazole-3-carboxylic acid | A |
| 521 | 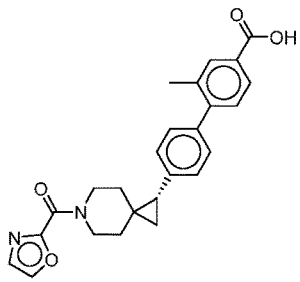<br>(R)-2-methyl-4'-(6-(oxazole-2-carbonyl)-6-azaspiro[2.5]octan-1-yl)-[1,1'-biphenyl]-4-carboxylic acid | D |
| 522 | 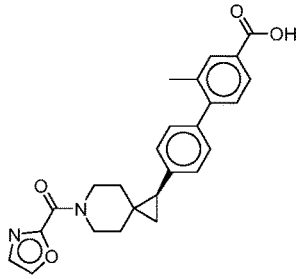<br>(S)-2-methyl-4'-(6-(oxazole-2-carbonyl)-6-azaspiro[2.5]octan-1-yl)-[1,1'-biphenyl]-4-carboxylic acid | B |
| 523 | 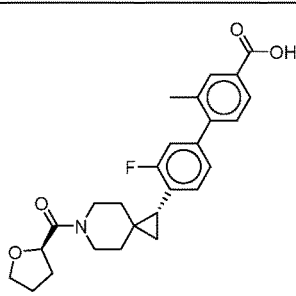<br>3'-fluoro-2-methyl-4'-((R)-6-((R)-tetrahydrofuran-2-carbonyl)-6-azaspiro[2.5]octan-1-yl)-[1,1'-biphenyl]-4-carboxylic acid | C |
Figure 3-40

| | | |
|---|---|---|
| 524 | 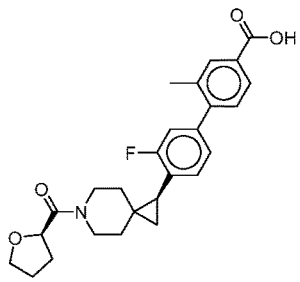<br>3'-fluoro-2-methyl-4'-((S)-6-((R)-tetrahydrofuran-2-carbonyl)-6-azaspiro[2.5]octan-1-yl)-[1,1'-biphenyl]-4-carboxylic acid | A |
| 525 | 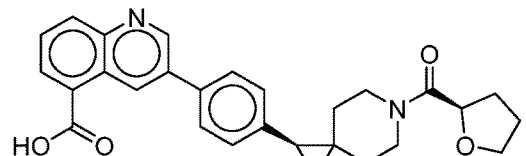<br>3-(4-((R)-6-((R)-tetrahydrofuran-2-carbonyl)-6-azaspiro[2.5]octan-1-yl)phenyl)quinoline-5-carboxylic acid | C |
| 526 | 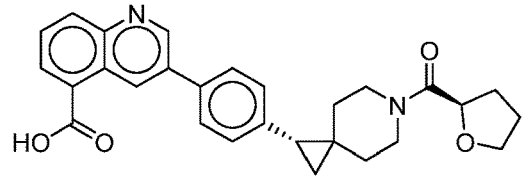<br>3-(4-((S)-6-((R)-tetrahydrofuran-2-carbonyl)-6-azaspiro[2.5]octan-1-yl)phenyl)quinoline-5-carboxylic acid | C |
| 527 | 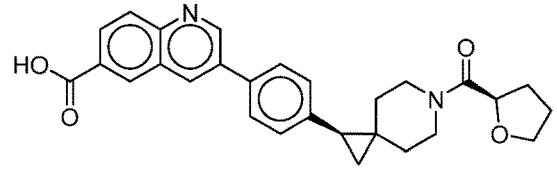<br>3-(4-((R)-6-((R)-tetrahydrofuran-2-carbonyl)-6-azaspiro[2.5]octan-1-yl)phenyl)quinoline-6-carboxylic acid | A |
| 528 | 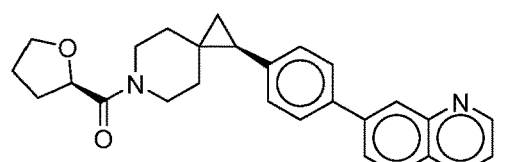<br>7-(4-((R)-6-((R)-tetrahydrofuran-2-carbonyl)-6-azaspiro[2.5]octan-1-yl)phenyl)quinoline-4-carboxylic acid | B |

Figure 3-41

| | | |
|---|---|---|
| 529 | 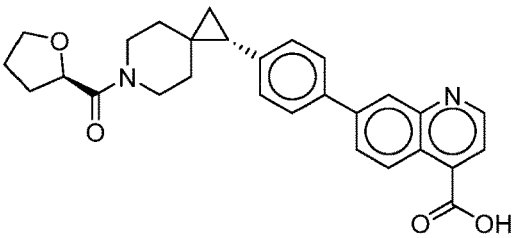<br>7-(4-((S)-6-((R)-tetrahydrofuran-2-carbonyl)-6-azaspiro[2.5]octan-1-yl)phenyl)quinoline-4-carboxylic acid | E |
| 530 | 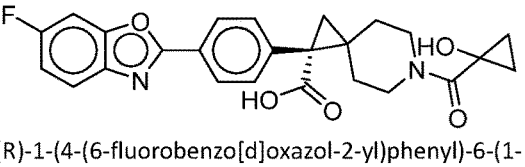<br>(R)-1-(4-(6-fluorobenzo[d]oxazol-2-yl)phenyl)-6-(1-hydroxycyclopropane-1-carbonyl)-6-azaspiro[2.5]octane-1-carboxylic acid | A |
| 531 | 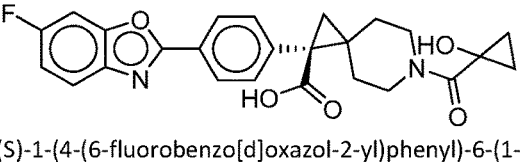<br>(S)-1-(4-(6-fluorobenzo[d]oxazol-2-yl)phenyl)-6-(1-hydroxycyclopropane-1-carbonyl)-6-azaspiro[2.5]octane-1-carboxylic acid | C |
| 532 | 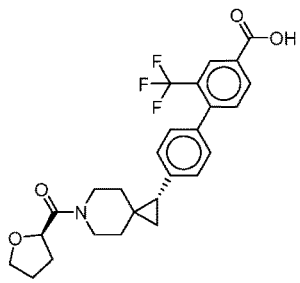<br>4'-((R)-6-((R)-tetrahydrofuran-2-carbonyl)-6-azaspiro[2.5]octan-1-yl)-2-(trifluoromethyl)-[1,1'-biphenyl]-4-carboxylic acid | D |

Figure 3-42

| | | |
|---|---|---|
| 533 | 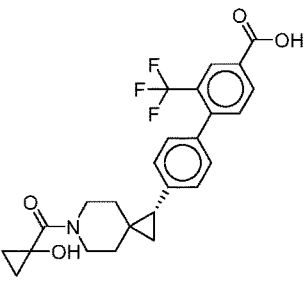<br>(R)-4'-(6-(1-hydroxycyclopropane-1-carbonyl)-6-azaspiro[2.5]octan-1-yl)-2-(trifluoromethyl)-[1,1'-biphenyl]-4-carboxylic acid | E |
| 534 | 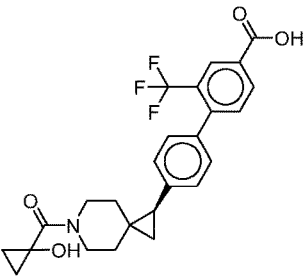<br>(S)-4'-(6-(1-hydroxycyclopropane-1-carbonyl)-6-azaspiro[2.5]octan-1-yl)-2-(trifluoromethyl)-[1,1'-biphenyl]-4-carboxylic acid | A |
| 535 | 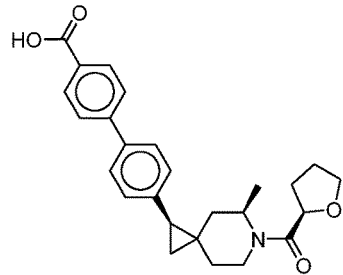<br>4'-((1R,5R)-5-methyl-6-((R)-tetrahydrofuran-2-carbonyl)-6-azaspiro[2.5]octan-1-yl)-[1,1'-biphenyl]-4-carboxylic acid | B |
| 536 | 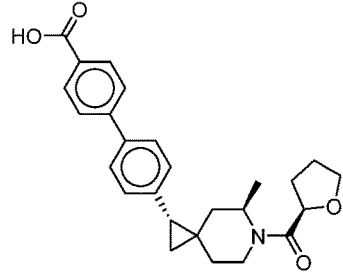<br>4'-((1S,5R)-5-methyl-6-((R)-tetrahydrofuran-2-carbonyl)-6-azaspiro[2.5]octan-1-yl)-[1,1'-biphenyl]-4-carboxylic acid | D |

Figure 3-43

| | | |
|---|---|---|
| 537 | 4'-((1R,5R)-6-(1-hydroxycyclopropane-1-carbonyl)-5-methyl-6-azaspiro[2.5]octan-1-yl)-[1,1'-biphenyl]-4-carboxylic acid | B |
| 538 | 4'-((1S,5R)-6-(1-hydroxycyclopropane-1-carbonyl)-5-methyl-6-azaspiro[2.5]octan-1-yl)-[1,1'-biphenyl]-4-carboxylic acid | E |
| 539 | (R)-5-(4-(6-(1-hydroxycyclopropane-1-carbonyl)-6-azaspiro[2.5]octan-1-yl)phenyl)thiophene-2-carboxylic acid | C |
| 540 | (S)-5-(4-(6-(1-hydroxycyclopropane-1-carbonyl)-6-azaspiro[2.5]octan-1-yl)phenyl)thiophene-2-carboxylic acid | A |

Figure 3-44

| | | |
|---|---|---|
| 541 | 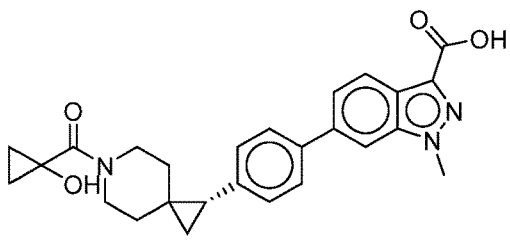<br>(R)-6-(4-(6-(1-hydroxycyclopropane-1-carbonyl)-6-azaspiro[2.5]octan-1-yl)phenyl)-1-methyl-1H-indazole-3-carboxylic acid | A |
| 542 | 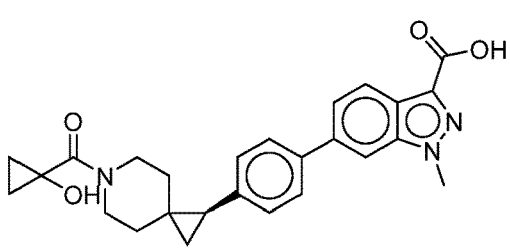<br>(S)-6-(4-(6-(1-hydroxycyclopropane-1-carbonyl)-6-azaspiro[2.5]octan-1-yl)phenyl)-1-methyl-1H-indazole-3-carboxylic acid | B |
| 543 | 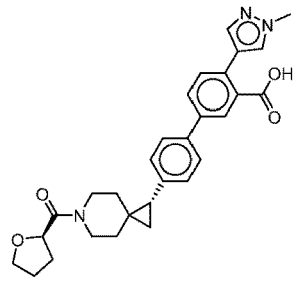<br>4-(1-methyl-1H-pyrazol-4-yl)-4'-((R)-6-((R)-tetrahydrofuran-2-carbonyl)-6-azaspiro[2.5]octan-1-yl)-[1,1'-biphenyl]-3-carboxylic acid | E |
| 544 | 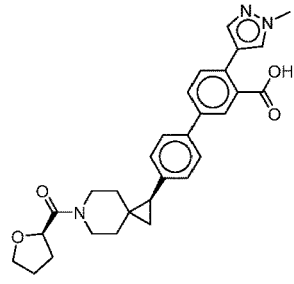<br>4-(1-methyl-1H-pyrazol-4-yl)-4'-((S)-6-((R)-tetrahydrofuran-2-carbonyl)-6-azaspiro[2.5]octan-1-yl)-[1,1'-biphenyl]-3-carboxylic acid | B |

Figure 3-45

| | | |
|---|---|---|
| 545 | 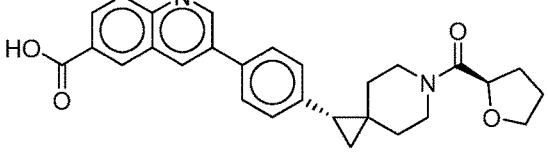<br>3-(4-((S)-6-((R)-tetrahydrofuran-2-carbonyl)-6-azaspiro[2.5]octan-1-yl)phenyl)quinoline-6-carboxylic acid | C |
| 546 | 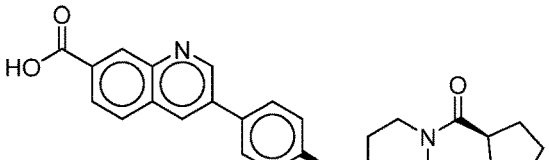<br>3-(4-((R)-6-((R)-tetrahydrofuran-2-carbonyl)-6-azaspiro[2.5]octan-1-yl)phenyl)quinoline-7-carboxylic acid | A |
| 547 | 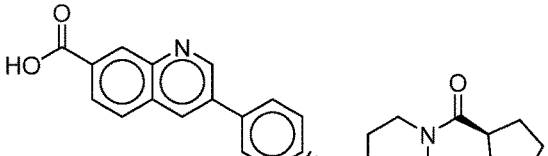<br>3-(4-((S)-6-((R)-tetrahydrofuran-2-carbonyl)-6-azaspiro[2.5]octan-1-yl)phenyl)quinoline-7-carboxylic acid | C |
| 548 | 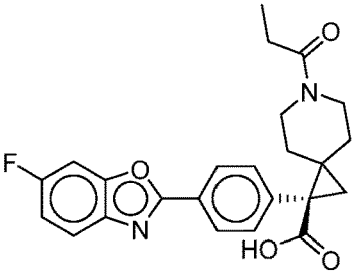<br>(R)-1-(4-(6-fluorobenzo[d]oxazol-2-yl)phenyl)-6-propionyl-6-azaspiro[2.5]octane-1-carboxylic acid | B |
| 549 | 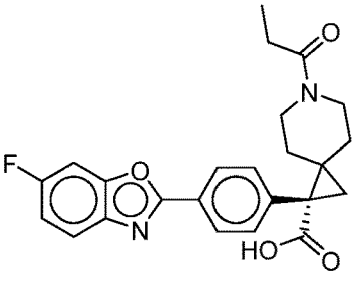<br>(S)-1-(4-(6-fluorobenzo[d]oxazol-2-yl)phenyl)-6-propionyl-6-azaspiro[2.5]octane-1-carboxylic acid | E |

Figure 3-46

| | | |
|---|---|---|
| 550 | (R)-6-(1-hydroxycyclopropane-1-carbonyl)-1-(4-(1-methyl-1H-indazol-6-yl)phenyl)-6-azaspiro[2.5]octane-1-carboxylic acid | A |
| 551 | (S)-6-(1-hydroxycyclopropane-1-carbonyl)-1-(4-(1-methyl-1H-indazol-6-yl)phenyl)-6-azaspiro[2.5]octane-1-carboxylic acid | C |
| 552 | (R)-1-(4-(1-methyl-1H-indazol-6-yl)phenyl)-6-propionyl-6-azaspiro[2.5]octane-1-carboxylic acid | B |
| 553 | (S)-1-(4-(1-methyl-1H-indazol-6-yl)phenyl)-6-propionyl-6-azaspiro[2.5]octane-1-carboxylic acid | E |

Figure 3-47

| | | |
|---|---|---|
| 554 | 4'-((S)-6-((R)-tetrahydrofuran-2-carbonyl)-6-azaspiro[2.5]octan-1-yl)-2-(trifluoromethyl)-[1,1'-biphenyl]-4-carboxylic acid | B |
| 555 | 4'-((1R,5S)-5-methyl-6-((R)-tetrahydrofuran-2-carbonyl)-6-azaspiro[2.5]octan-1-yl)-[1,1'-biphenyl]-4-carboxylic acid | B |
| 556 | 4'-((1S,5S)-5-methyl-6-((R)-tetrahydrofuran-2-carbonyl)-6-azaspiro[2.5]octan-1-yl)-[1,1'-biphenyl]-4-carboxylic acid | E |
| 557 | 4'-((1R,5S)-6-(1-hydroxycyclopropane-1-carbonyl)-5-methyl-6-azaspiro[2.5]octan-1-yl)-[1,1'-biphenyl]-4-carboxylic acid | B |

Figure 3-48

| | | |
|---|---|---|
| 558 | 4'-((1S,5S)-6-(1-hydroxycyclopropane-1-carbonyl)-5-methyl-6-azaspiro[2.5]octan-1-yl)-[1,1'-biphenyl]-4-carboxylic acid | C |
| 559 | (R)-5-(4-(6-(1-hydroxycyclopropane-1-carbonyl)-6-azaspiro[2.5]octan-1-yl)phenyl)thiophene-3-carboxylic acid | A |
| 560 | (S)-5-(4-(6-(1-hydroxycyclopropane-1-carbonyl)-6-azaspiro[2.5]octan-1-yl)phenyl)thiophene-3-carboxylic acid | C |
| 561 | 7-((R)-6-((R)-tetrahydrofuran-2-carbonyl)-6-azaspiro[2.5]octan-1-yl)-2-naphthoic acid | D |
| 562 | 7-((S)-6-((R)-tetrahydrofuran-2-carbonyl)-6-azaspiro[2.5]octan-1-yl)-2-naphthoic acid | E |

Figure 3-49

| | | |
|---|---|---|
| 563 | (S)-7-(4-(6-(1-hydroxycyclopropane-1-carbonyl)-6-azaspiro[2.5]octan-1-yl)phenyl)quinoline-3-carboxylic acid | A |
| 564 | (R)-7-(4-(6-(1-hydroxycyclopropane-1-carbonyl)-6-azaspiro[2.5]octan-1-yl)phenyl)quinoline-3-carboxylic acid | B |
| 565 | (R)-2-(4-(6-(1-hydroxycyclopropane-1-carbonyl)-6-azaspiro[2.5]octan-1-yl)phenyl)benzo[d]oxazole-6-carboxylic acid | B |
| 566 | (S)-2-(4-(6-(1-hydroxycyclopropane-1-carbonyl)-6-azaspiro[2.5]octan-1-yl)phenyl)benzo[d]oxazole-6-carboxylic acid | E |

Figure 3-50

| | | |
|---|---|---|
| 567 | 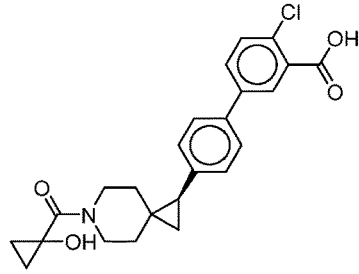<br>(S)-4-chloro-4'-(6-(1-hydroxycyclopropane-1-carbonyl)-6-azaspiro[2.5]octan-1-yl)-[1,1'-biphenyl]-3-carboxylic acid | D |
| 568 | 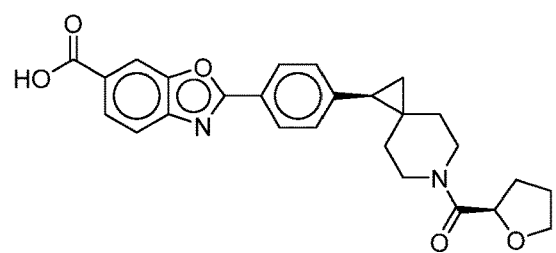<br>2-(4-((S)-6-((R)-tetrahydrofuran-2-carbonyl)-6-azaspiro[2.5]octan-1-yl)phenyl)benzo[d]oxazole-6-carboxylic acid | B |
| 569 | 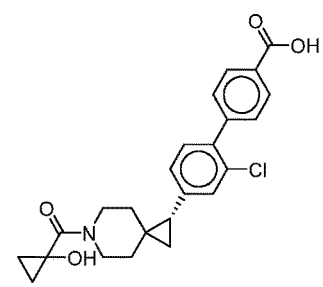<br>(R)-2'-chloro-4'-(6-(1-hydroxycyclopropane-1-carbonyl)-6-azaspiro[2.5]octan-1-yl)-[1,1'-biphenyl]-4-carboxylic acid | A |
| 570 | 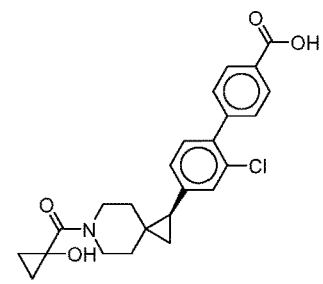<br>(S)-2'-chloro-4'-(6-(1-hydroxycyclopropane-1-carbonyl)-6-azaspiro[2.5]octan-1-yl)-[1,1'-biphenyl]-4-carboxylic acid | D |

Figure 3-51

| | | |
|---|---|---|
| 571 | (R)-1-(2-fluoro-4-(1-methyl-1H-benzo[d]imidazol-5-yl)phenyl)-6-propionyl-6-azaspiro[2.5]octane-1-carboxylic acid | C |
| 572 | (S)-1-(2-fluoro-4-(1-methyl-1H-benzo[d]imidazol-5-yl)phenyl)-6-propionyl-6-azaspiro[2.5]octane-1-carboxylic acid | A |
| 573 | 6-((R)-6-((R)-tetrahydrofuran-2-carbonyl)-6-azaspiro[2.5]octan-1-yl)-2-naphthoic acid | B |
| 574 | 6-((S)-6-((R)-tetrahydrofuran-2-carbonyl)-6-azaspiro[2.5]octan-1-yl)-2-naphthoic acid | E |
| 575 | (R)-7-(3-fluoro-4-(6-(1-hydroxycyclopropane-1-carbonyl)-6-azaspiro[2.5]octan-1-yl)phenyl)quinoline-3-carboxylic acid | A |

Figure 3-52

| | | |
|---|---|---|
| 576 | 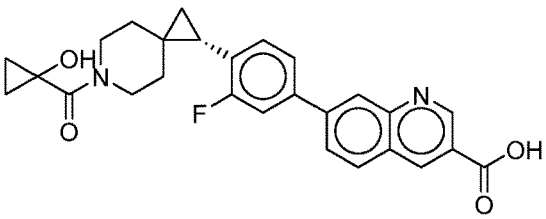<br>(S)-7-(3-fluoro-4-(6-(1-hydroxycyclopropane-1-carbonyl)-6-azaspiro[2.5]octan-1-yl)phenyl)quinoline-3-carboxylic acid | C |
| 577 | 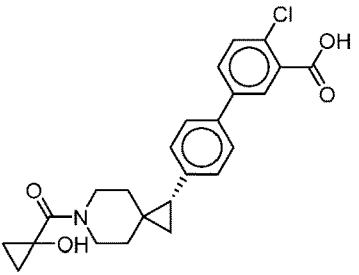<br>(R)-4-chloro-4'-(6-(1-hydroxycyclopropane-1-carbonyl)-6-azaspiro[2.5]octan-1-yl)-[1,1'-biphenyl]-3-carboxylic acid | B |
| 578 | 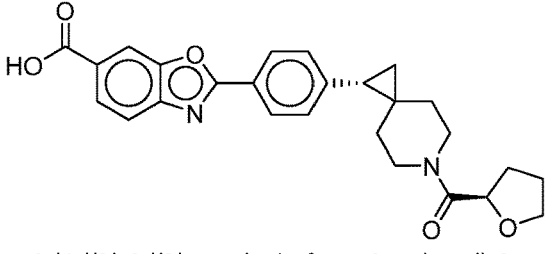<br>2-(4-((R)-6-((R)-tetrahydrofuran-2-carbonyl)-6-azaspiro[2.5]octan-1-yl)phenyl)benzo[d]oxazole-6-carboxylic acid | C |
| 579 | 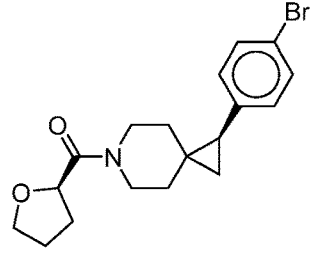<br>((S)-1-(4-bromophenyl)-6-azaspiro[2.5]octan-6-yl)((R)-tetrahydrofuran-2-yl)methanone | A |
Figure 3-53

| | | |
|---|---|---|
| 580 | 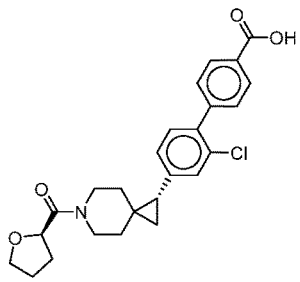<br>2'-chloro-4'-((R)-6-((R)-tetrahydrofuran-2-carbonyl)-6-azaspiro[2.5]octan-1-yl)-[1,1'-biphenyl]-4-carboxylic acid | C |
| 581 | 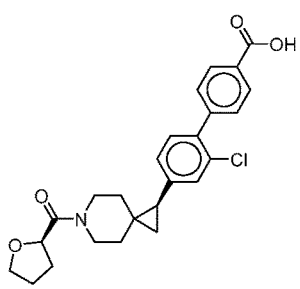<br>2'-chloro-4'-((S)-6-((R)-tetrahydrofuran-2-carbonyl)-6-azaspiro[2.5]octan-1-yl)-[1,1'-biphenyl]-4-carboxylic acid | A |
| 582 | 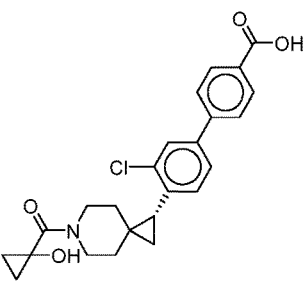<br>(R)-3'-chloro-4'-(6-(1-hydroxycyclopropane-1-carbonyl)-6-azaspiro[2.5]octan-1-yl)-[1,1'-biphenyl]-4-carboxylic acid | B |
| 583 | 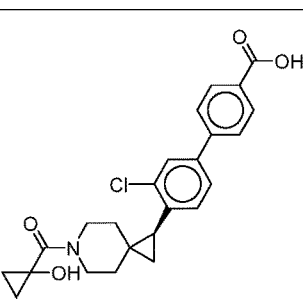<br>(S)-3'-chloro-4'-(6-(1-hydroxycyclopropane-1-carbonyl)-6-azaspiro[2.5]octan-1-yl)-[1,1'-biphenyl]-4-carboxylic acid | E |

Figure 3-54

| 584 | 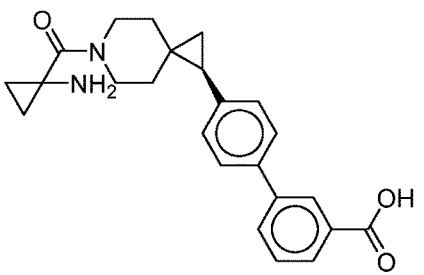<br>(R)-4'-(6-(1-aminocyclopropane-1-carbonyl)-6-azaspiro[2.5]octan-1-yl)-[1,1'-biphenyl]-3-carboxylic acid | B |
|---|---|---|
| 585 | 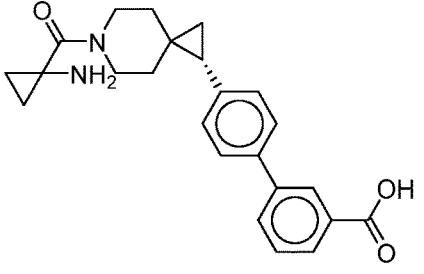<br>(S)-4'-(6-(1-aminocyclopropane-1-carbonyl)-6-azaspiro[2.5]octan-1-yl)-[1,1'-biphenyl]-3-carboxylic acid | E |
| 586 | 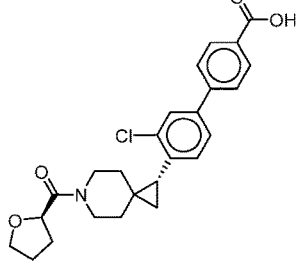<br>3'-chloro-4'-((R)-6-((R)-tetrahydrofuran-2-carbonyl)-6-azaspiro[2.5]octan-1-yl)-[1,1'-biphenyl]-4-carboxylic acid | B |
| 587 | 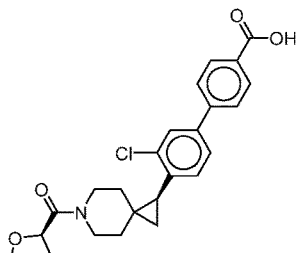<br>3'-chloro-4'-((S)-6-((R)-tetrahydrofuran-2-carbonyl)-6-azaspiro[2.5]octan-1-yl)-[1,1'-biphenyl]-4-carboxylic acid | E |
Figure 3-55

| | | |
|---|---|---|
| 588 | 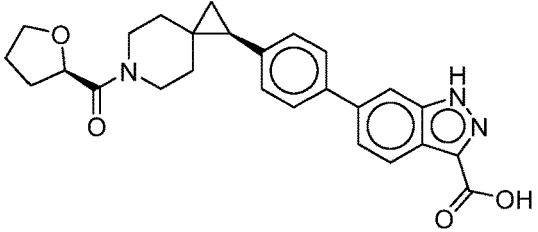<br>6-(4-((R)-6-((R)-tetrahydrofuran-2-carbonyl)-6-azaspiro[2.5]octan-1-yl)phenyl)-1H-indazole-3-carboxylic acid | D |
| 589 | 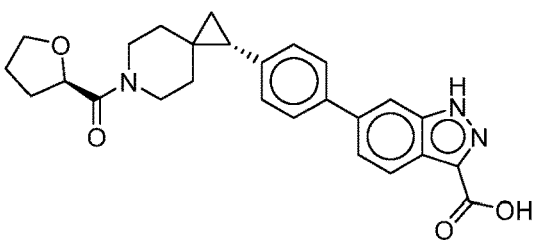<br>6-(4-((S)-6-((R)-tetrahydrofuran-2-carbonyl)-6-azaspiro[2.5]octan-1-yl)phenyl)-1H-indazole-3-carboxylic acid | B |
| 590 | 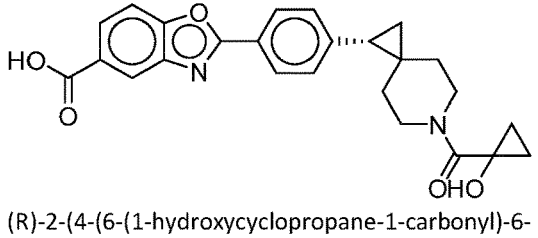<br>(R)-2-(4-(6-(1-hydroxycyclopropane-1-carbonyl)-6-azaspiro[2.5]octan-1-yl)phenyl)benzo[d]oxazole-5-carboxylic acid | A |
| 591 | 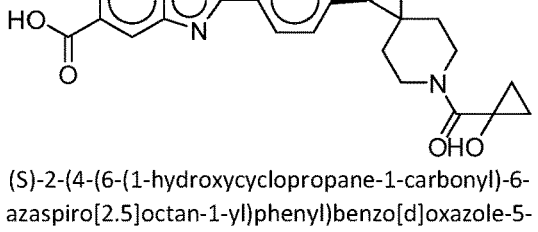<br>(S)-2-(4-(6-(1-hydroxycyclopropane-1-carbonyl)-6-azaspiro[2.5]octan-1-yl)phenyl)benzo[d]oxazole-5-carboxylic acid | C |

Figure 3-56

| | | |
|---|---|---|
| 592 | 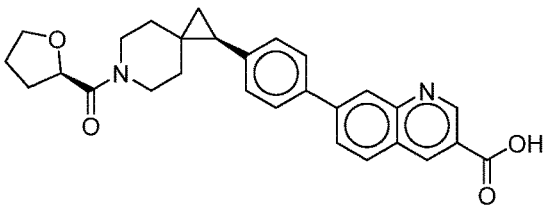  7-(4-((R)-6-((R)-tetrahydrofuran-2-carbonyl)-6-azaspiro[2.5]octan-1-yl)phenyl)quinoline-3-carboxylic acid | B |
| 593 | 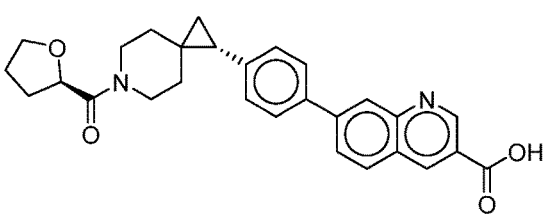  7-(4-((S)-6-((R)-tetrahydrofuran-2-carbonyl)-6-azaspiro[2.5]octan-1-yl)phenyl)quinoline-3-carboxylic acid | B |
| 594 | 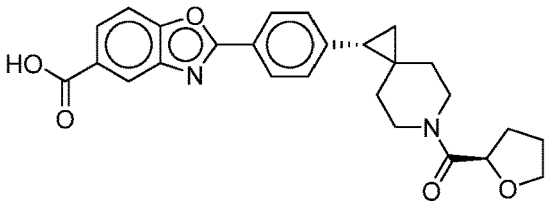  2-(4-((R)-6-((R)-tetrahydrofuran-2-carbonyl)-6-azaspiro[2.5]octan-1-yl)phenyl)benzo[d]oxazole-5-carboxylic acid | B |
| 595 | 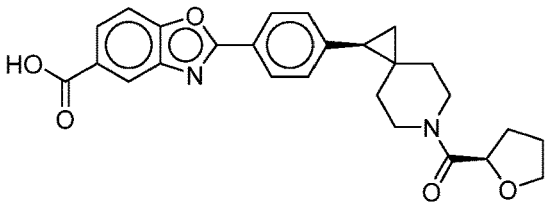  2-(4-((S)-6-((R)-tetrahydrofuran-2-carbonyl)-6-azaspiro[2.5]octan-1-yl)phenyl)benzo[d]oxazole-5-carboxylic acid | D |
| 596 | 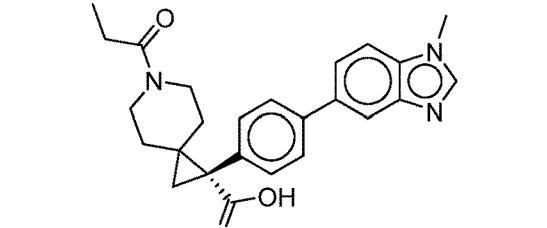  (R)-1-(4-(1-methyl-1H-benzo[d]imidazol-5-yl)phenyl)-6-propionyl-6-azaspiro[2.5]octane-1-carboxylic acid | E |

Figure 3-57

| | | |
|---|---|---|
| 597 | 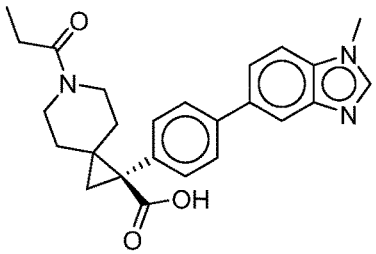<br>(S)-1-(4-(1-methyl-1H-benzo[d]imidazol-5-yl)phenyl)-6-propionyl-6-azaspiro[2.5]octane-1-carboxylic acid | B |
| 598 | 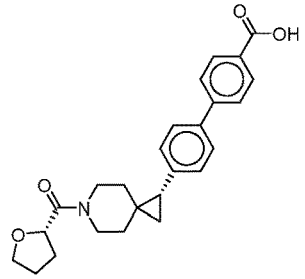<br>4'-((R)-6-((S)-tetrahydrofuran-2-carbonyl)-6-azaspiro[2.5]octan-1-yl)-[1,1'-biphenyl]-4-carboxylic acid | B |
| 599 | 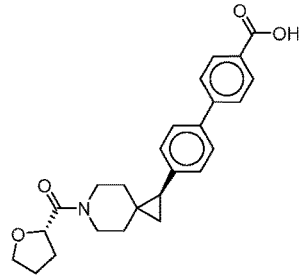<br>4'-((S)-6-((S)-tetrahydrofuran-2-carbonyl)-6-azaspiro[2.5]octan-1-yl)-[1,1'-biphenyl]-4-carboxylic acid | D |
| 600 | 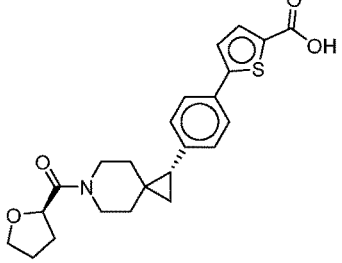<br>5-(4-((R)-6-((R)-tetrahydrofuran-2-carbonyl)-6-azaspiro[2.5]octan-1-yl)phenyl)thiophene-2-carboxylic acid | A |
Figure 3-58

| 601 | 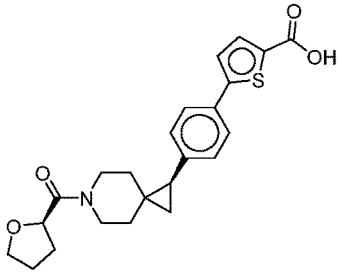<br>5-(4-((S)-6-((R)-tetrahydrofuran-2-carbonyl)-6-azaspiro[2.5]octan-1-yl)phenyl)thiophene-2-carboxylic acid | D |
|---|---|---|
| 602 | 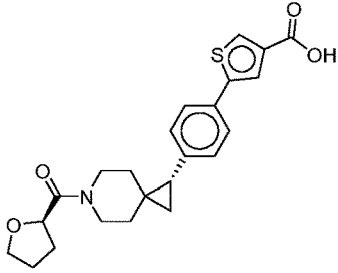<br>5-(4-((R)-6-((R)-tetrahydrofuran-2-carbonyl)-6-azaspiro[2.5]octan-1-yl)phenyl)thiophene-3-carboxylic acid | C |
| 603 | 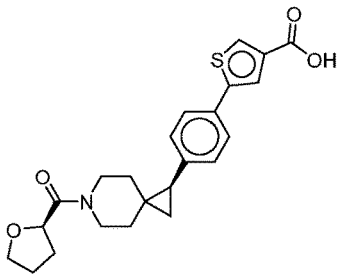<br>5-(4-((S)-6-((R)-tetrahydrofuran-2-carbonyl)-6-azaspiro[2.5]octan-1-yl)phenyl)thiophene-3-carboxylic acid | A |
| 604 | 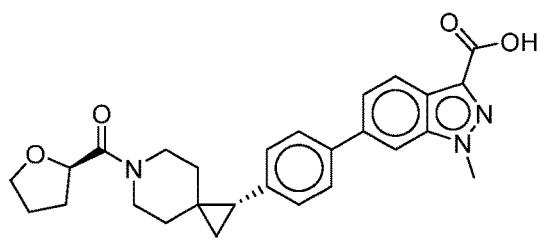<br>1-methyl-6-(4-((R)-6-((R)-tetrahydrofuran-2-carbonyl)-6-azaspiro[2.5]octan-1-yl)phenyl)-1H-indazole-3-carboxylic acid | A |
Figure 3-59

| | | |
|---|---|---|
| 605 | 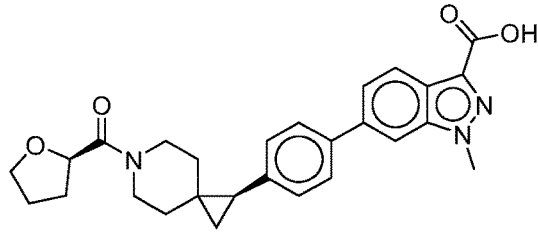<br>1-methyl-6-(4-((S)-6-((R)-tetrahydrofuran-2-carbonyl)-6-azaspiro[2.5]octan-1-yl)phenyl)-1H-indazole-3-carboxylic acid | B |
| 606 | 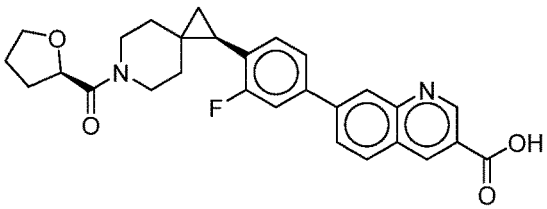<br>7-(3-fluoro-4-((R)-6-((R)-tetrahydrofuran-2-carbonyl)-6-azaspiro[2.5]octan-1-yl)phenyl)quinoline-3-carboxylic acid | B |
| 607 | 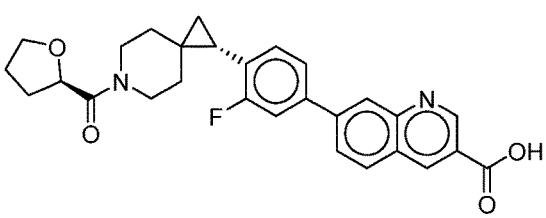<br>7-(3-fluoro-4-((S)-6-((R)-tetrahydrofuran-2-carbonyl)-6-azaspiro[2.5]octan-1-yl)phenyl)quinoline-3-carboxylic acid | A |
| 608 | 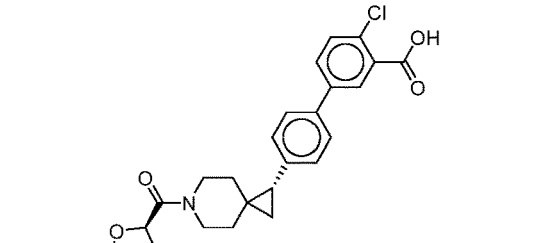<br>4-chloro-4'-((R)-6-((R)-tetrahydrofuran-2-carbonyl)-6-azaspiro[2.5]octan-1-yl)-[1,1'-biphenyl]-3-carboxylic acid | C |

Figure 3-60

| | | |
|---|---|---|
| 609 | 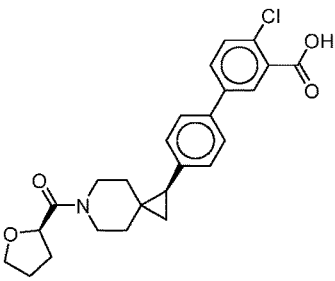<br>4-chloro-4'-((S)-6-((R)-tetrahydrofuran-2-carbonyl)-6-azaspiro[2.5]octan-1-yl)-[1,1'-biphenyl]-3-carboxylic acid | B |
| 610 | 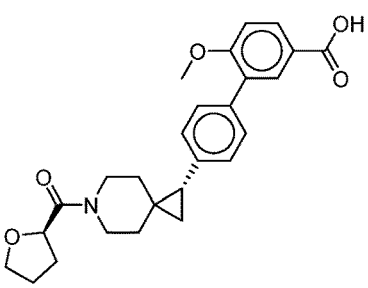<br>6-methoxy-4'-((R)-6-((R)-tetrahydrofuran-2-carbonyl)-6-azaspiro[2.5]octan-1-yl)-[1,1'-biphenyl]-3-carboxylic acid | D |
| 611 | 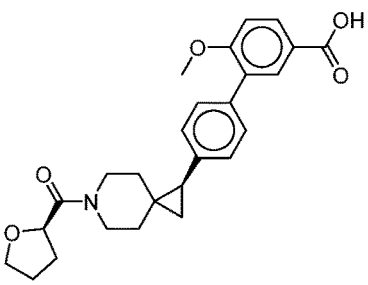<br>6-methoxy-4'-((S)-6-((R)-tetrahydrofuran-2-carbonyl)-6-azaspiro[2.5]octan-1-yl)-[1,1'-biphenyl]-3-carboxylic acid | A |
| 612 | 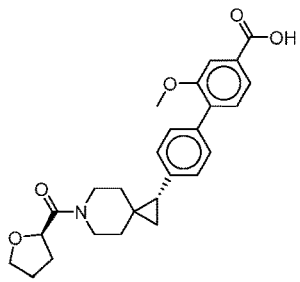<br>2-methoxy-4'-((R)-6-((R)-tetrahydrofuran-2-carbonyl)-6-azaspiro[2.5]octan-1-yl)-[1,1'-biphenyl]-4-carboxylic acid | C |
Figure 3-61

| | | |
|---|---|---|
| 613 | 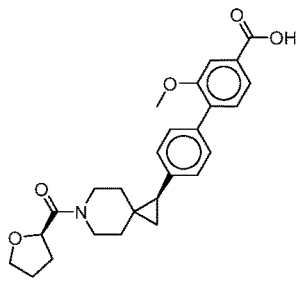<br>2-methoxy-4'-((S)-6-((R)-tetrahydrofuran-2-carbonyl)-6-azaspiro[2.5]octan-1-yl)-[1,1'-biphenyl]-4-carboxylic acid | A |
| 614 | 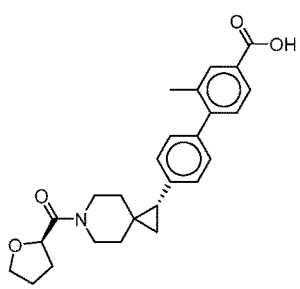<br>2-methyl-4'-((R)-6-((R)-tetrahydrofuran-2-carbonyl)-6-azaspiro[2.5]octan-1-yl)-[1,1'-biphenyl]-4-carboxylic acid | C |
| 615 | 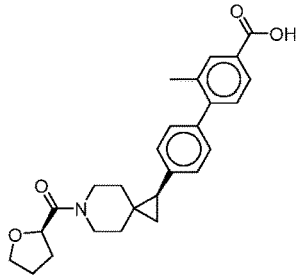<br>2-methyl-4'-((S)-6-((R)-tetrahydrofuran-2-carbonyl)-6-azaspiro[2.5]octan-1-yl)-[1,1'-biphenyl]-4-carboxylic acid | A |
| 616 | 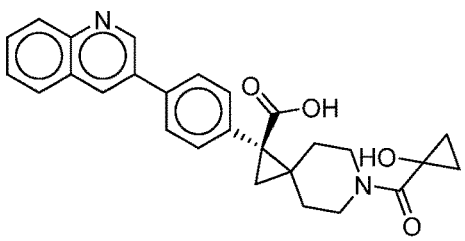<br>(R)-6-(1-hydroxycyclopropane-1-carbonyl)-1-(4-(quinolin-3-yl)phenyl)-6-azaspiro[2.5]octane-1-carboxylic acid | C |
Figure 3-62

| 617 | 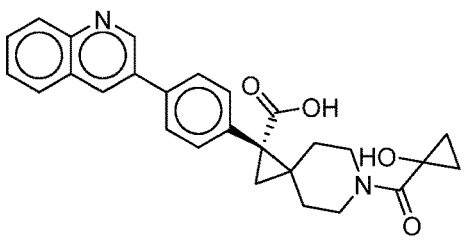 (S)-6-(1-hydroxycyclopropane-1-carbonyl)-1-(4-(quinolin-3-yl)phenyl)-6-azaspiro[2.5]octane-1-carboxylic acid | A |
|---|---|---|
| 618 | 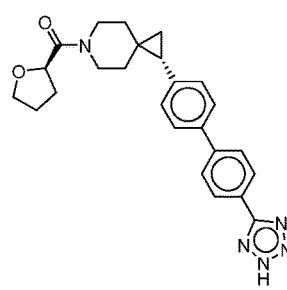 ((S)-1-(4'-(2H-tetrazol-5-yl)-[1,1'-biphenyl]-4-yl)-6-azaspiro[2.5]octan-6-yl)((R)-tetrahydrofuran-2-yl)methanone | A |
| 619 | 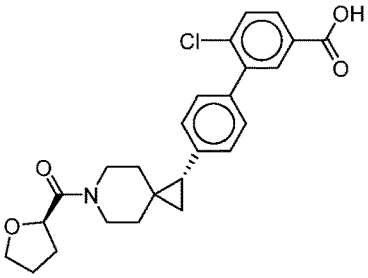 6-chloro-4'-((R)-6-((R)-tetrahydrofuran-2-carbonyl)-6-azaspiro[2.5]octan-1-yl)-[1,1'-biphenyl]-3-carboxylic acid | C |
| 620 | 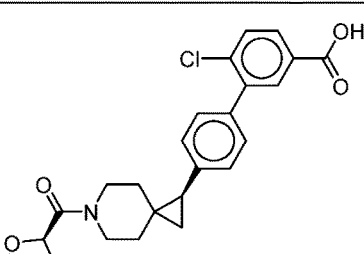 6-chloro-4'-((S)-6-((R)-tetrahydrofuran-2-carbonyl)-6-azaspiro[2.5]octan-1-yl)-[1,1'-biphenyl]-3-carboxylic acid | A |
Figure 3-63

| | | |
|---|---|---|
| 621 | 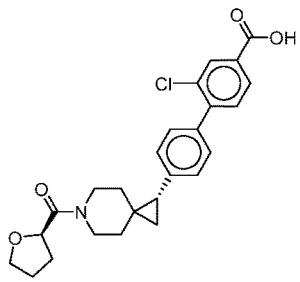<br>2-chloro-4'-((R)-6-((R)-tetrahydrofuran-2-carbonyl)-6-azaspiro[2.5]octan-1-yl)-[1,1'-biphenyl]-4-carboxylic acid | C |
| 622 | 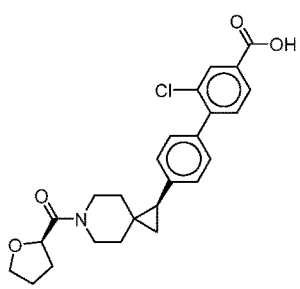<br>2-chloro-4'-((S)-6-((R)-tetrahydrofuran-2-carbonyl)-6-azaspiro[2.5]octan-1-yl)-[1,1'-biphenyl]-4-carboxylic acid | A |
| 623 | 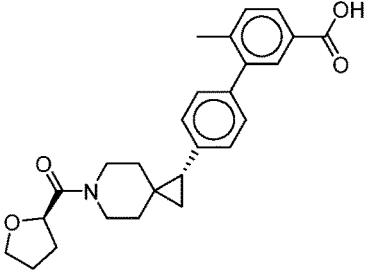<br>6-methyl-4'-((R)-6-((R)-tetrahydrofuran-2-carbonyl)-6-azaspiro[2.5]octan-1-yl)-[1,1'-biphenyl]-3-carboxylic acid | C |
| 624 | 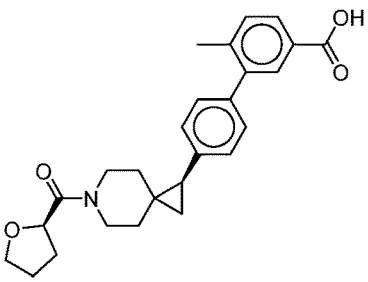<br>6-methyl-4'-((S)-6-((R)-tetrahydrofuran-2-carbonyl)-6-azaspiro[2.5]octan-1-yl)-[1,1'-biphenyl]-3-carboxylic acid | A |
Figure 3-64

| | | |
|---|---|---|
| 625 | (R)-4'-(6-(1-hydroxycyclopropane-1-carbonyl)-6-azaspiro[2.5]octan-1-yl)-2-methoxy-[1,1'-biphenyl]-4-carboxylic acid | C |
| 626 | 3-(4-((S)-6-((R)-tetrahydrofuran-2-carbonyl)-6-azaspiro[2.5]octan-1-yl)phenyl)quinoline-8-carboxylic acid | A |
| 627 | 3-(4-((R)-6-((R)-tetrahydrofuran-2-carbonyl)-6-azaspiro[2.5]octan-1-yl)phenyl)quinoline-8-carboxylic acid | C |
| 628 | 1-methyl-6-(4-((R)-6-((R)-tetrahydrofuran-2-carbonyl)-6-azaspiro[2.5]octan-1-yl)phenyl)-1H-indole-2-carboxylic acid | C |
| 629 | 1-methyl-6-(4-((S)-6-((R)-tetrahydrofuran-2-carbonyl)-6-azaspiro[2.5]octan-1-yl)phenyl)-1H-indole-2-carboxylic acid | A |

Figure 3-65

| | | |
|---|---|---|
| 630 | 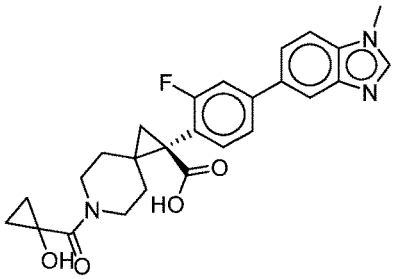<br>(R)-1-(2-fluoro-4-(1-methyl-1H-benzo[d]imidazol-5-yl)phenyl)-6-(1-hydroxycyclopropane-1-carbonyl)-6-azaspiro[2.5]octane-1-carboxylic acid | A |
| 631 | 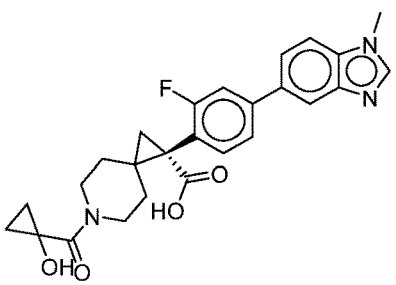<br>(S)-1-(2-fluoro-4-(1-methyl-1H-benzo[d]imidazol-5-yl)phenyl)-6-(1-hydroxycyclopropane-1-carbonyl)-6-azaspiro[2.5]octane-1-carboxylic acid | B |
| 632 | 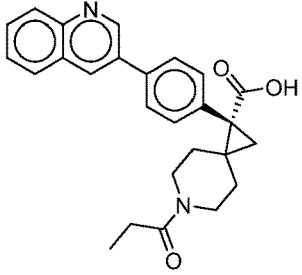<br>(R)-6-propionyl-1-(4-(quinolin-3-yl)phenyl)-6-azaspiro[2.5]octane-1-carboxylic acid | D |
| 633 | 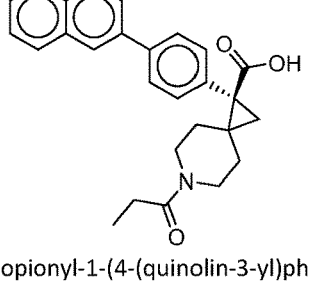<br>(S)-6-propionyl-1-(4-(quinolin-3-yl)phenyl)-6-azaspiro[2.5]octane-1-carboxylic acid | A |

Figure 3-66

| | | |
|---|---|---|
| 634 | 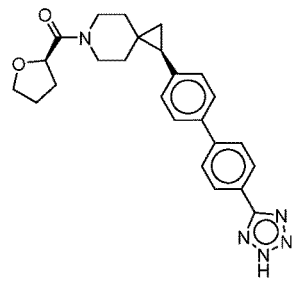<br>((R)-1-(4'-(2H-tetrazol-5-yl)-[1,1'-biphenyl]-4-yl)-6-azaspiro[2.5]octan-6-yl)((R)-tetrahydrofuran-2-yl)methanone | C |
| 635 | 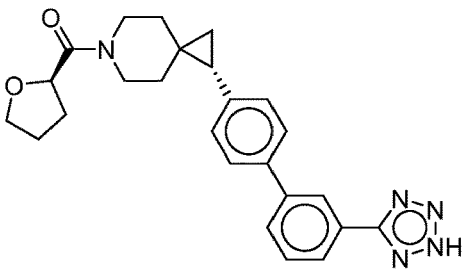<br>((S)-1-(3'-(2H-tetrazol-5-yl)-[1,1'-biphenyl]-4-yl)-6-azaspiro[2.5]octan-6-yl)((R)-tetrahydrofuran-2-yl)methanone | A |
| 636 | 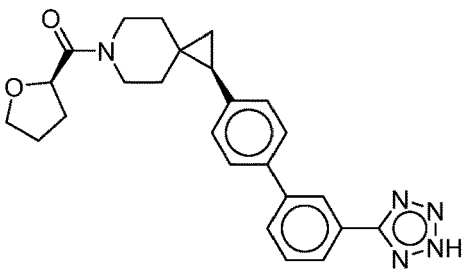<br>((R)-1-(3'-(2H-tetrazol-5-yl)-[1,1'-biphenyl]-4-yl)-6-azaspiro[2.5]octan-6-yl)((R)-tetrahydrofuran-2-yl)methanone | C |
| 637 | 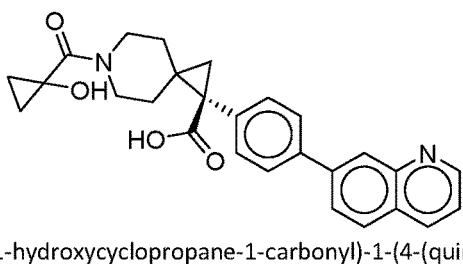<br>(R)-6-(1-hydroxycyclopropane-1-carbonyl)-1-(4-(quinolin-7-yl)phenyl)-6-azaspiro[2.5]octane-1-carboxylic acid | B |
Figure 3-67

| 638 | 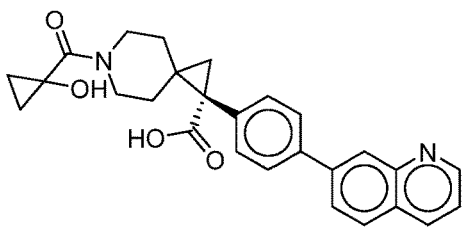<br>(S)-6-(1-hydroxycyclopropane-1-carbonyl)-1-(4-(quinolin-7-yl)phenyl)-6-azaspiro[2.5]octane-1-carboxylic acid | A |
|---|---|---|
| 639 | 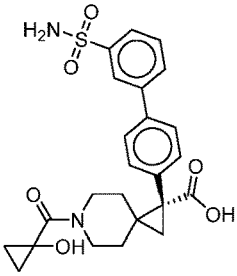<br>(R)-6-(1-hydroxycyclopropane-1-carbonyl)-1-(3'-sulfamoyl-[1,1'-biphenyl]-4-yl)-6-azaspiro[2.5]octane-1-carboxylic acid | E |
| 640 | 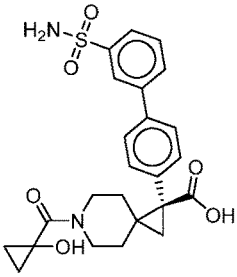<br>(S)-6-(1-hydroxycyclopropane-1-carbonyl)-1-(3'-sulfamoyl-[1,1'-biphenyl]-4-yl)-6-azaspiro[2.5]octane-1-carboxylic acid | B |
| 641 | 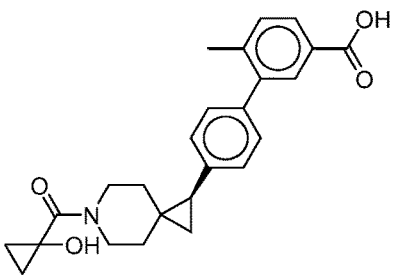<br>(S)-4'-(6-(1-hydroxycyclopropane-1-carbonyl)-6-azaspiro[2.5]octan-1-yl)-6-methyl-[1,1'-biphenyl]-3-carboxylic acid | B |

Figure 3-68

| | | |
|---|---|---|
| 642 | 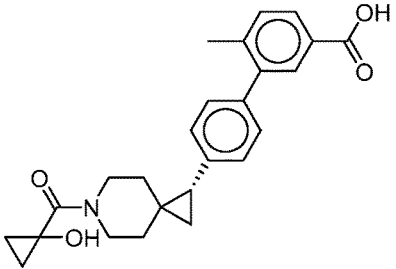<br>(R)-4'-(6-(1-hydroxycyclopropane-1-carbonyl)-6-azaspiro[2.5]octan-1-yl)-6-methyl-[1,1'-biphenyl]-3-carboxylic acid | C |
| 643 | 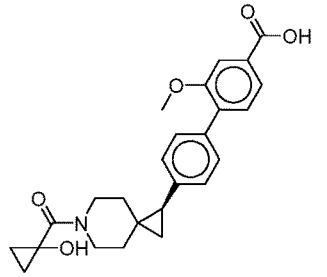<br>(S)-4'-(6-(1-hydroxycyclopropane-1-carbonyl)-6-azaspiro[2.5]octan-1-yl)-2-methoxy-[1,1'-biphenyl]-4-carboxylic acid | A |
| 644 | 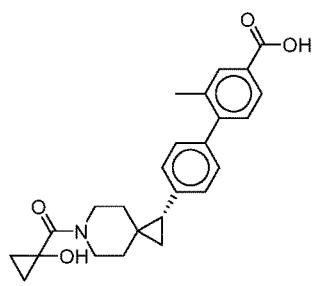<br>(R)-4'-(6-(1-hydroxycyclopropane-1-carbonyl)-6-azaspiro[2.5]octan-1-yl)-2-methyl-[1,1'-biphenyl]-4-carboxylic acid | C |
| 645 | 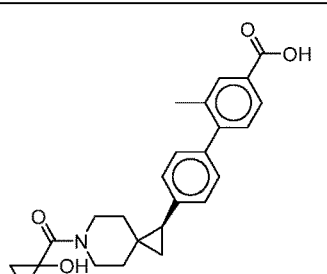<br>(S)-4'-(6-(1-hydroxycyclopropane-1-carbonyl)-6-azaspiro[2.5]octan-1-yl)-2-methyl-[1,1'-biphenyl]-4-carboxylic acid | A |

Figure 3-69

| | | |
|---|---|---|
| 646 | (R)-6-(1-hydroxycyclopropane-1-carbonyl)-1-(4-(1-methyl-1H-benzo[d]imidazol-5-yl)phenyl)-6-azaspiro[2.5]octane-1-carboxylic acid | B |
| 647 | (S)-6-(1-hydroxycyclopropane-1-carbonyl)-1-(4-(1-methyl-1H-benzo[d]imidazol-5-yl)phenyl)-6-azaspiro[2.5]octane-1-carboxylic acid | C |
| 648 | ((S)-2-(3'-(2H-tetrazol-5-yl)-[1,1'-biphenyl]-4-yl)-1,1-difluoro-6-azaspiro[2.5]octan-6-yl)((R)-tetrahydrofuran-2-yl)methanone | B |
| 649 | ((R)-2-(3'-(2H-tetrazol-5-yl)-[1,1'-biphenyl]-4-yl)-1,1-difluoro-6-azaspiro[2.5]octan-6-yl)((R)-tetrahydrofuran-2-yl)methanone | E |

Figure 3-70

| | | |
|---|---|---|
| 650 | (R)-4'-(6-(1-hydroxycyclopropane-1-carbonyl)-6-azaspiro[2.5]octan-1-yl)-6-methoxy-[1,1'-biphenyl]-3-carboxylic acid | B |
| 651 | (S)-4'-(6-(1-hydroxycyclopropane-1-carbonyl)-6-azaspiro[2.5]octan-1-yl)-6-methoxy-[1,1'-biphenyl]-3-carboxylic acid | D |
| 652 | ((S)-2-(4'-(2H-tetrazol-5-yl)-[1,1'-biphenyl]-4-yl)-1,1-difluoro-6-azaspiro[2.5]octan-6-yl)((R)-tetrahydrofuran-2-yl)methanone | B |
| 653 | ((R)-2-(4'-(2H-tetrazol-5-yl)-[1,1'-biphenyl]-4-yl)-1,1-difluoro-6-azaspiro[2.5]octan-6-yl)((R)-tetrahydrofuran-2-yl)methanone | D |

Figure 3-71

| | | |
|---|---|---|
| 654 | 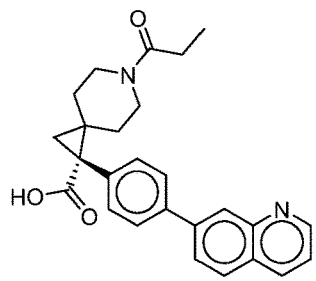<br>(R)-6-propionyl-1-(4-(quinolin-7-yl)phenyl)-6-azaspiro[2.5]octane-1-carboxylic acid | C |
| 655 | 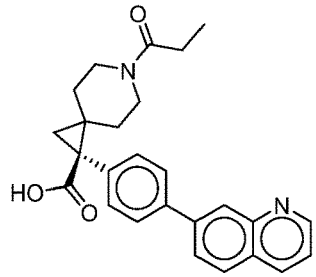<br>(S)-6-propionyl-1-(4-(quinolin-7-yl)phenyl)-6-azaspiro[2.5]octane-1-carboxylic acid | B |
| 656 | 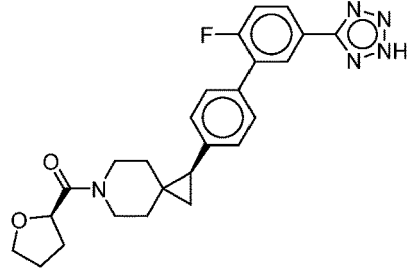<br>((S)-1-(2'-fluoro-5'-(2H-tetrazol-5-yl)-[1,1'-biphenyl]-4-yl)-6-azaspiro[2.5]octan-6-yl)((R)-tetrahydrofuran-2-yl)methanone | A |
| 657 | 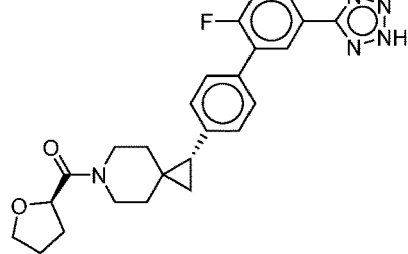<br>((R)-1-(2'-fluoro-5'-(2H-tetrazol-5-yl)-[1,1'-biphenyl]-4-yl)-6-azaspiro[2.5]octan-6-yl)((R)-tetrahydrofuran-2-yl)methanone | B |
Figure 3-72

| | | |
|---|---|---|
| 658 | 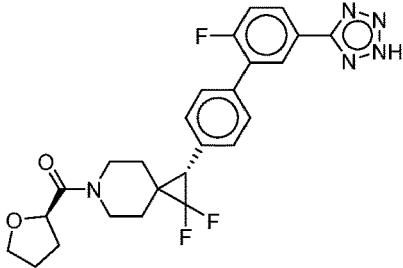<br>((S)-1,1-difluoro-2-(2'-fluoro-5'-(2H-tetrazol-5-yl)-[1,1'-biphenyl]-4-yl)-6-azaspiro[2.5]octan-6-yl)((R)-tetrahydrofuran-2-yl)methanone | B |
| 659 | 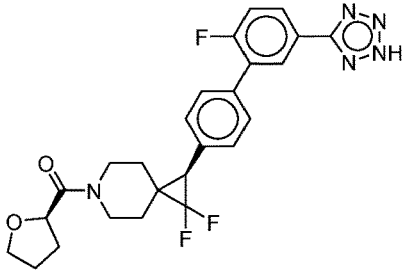<br>((R)-1,1-difluoro-2-(2'-fluoro-5'-(2H-tetrazol-5-yl)-[1,1'-biphenyl]-4-yl)-6-azaspiro[2.5]octan-6-yl)((R)-tetrahydrofuran-2-yl)methanone | E |
| 660 | 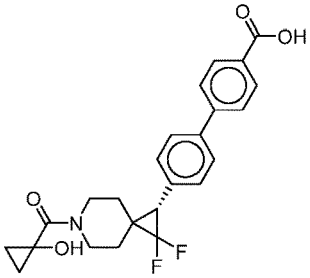<br>(S)-4'-(2,2-difluoro-6-(1-hydroxycyclopropane-1-carbonyl)-6-azaspiro[2.5]octan-1-yl)-[1,1'-biphenyl]-4-carboxylic acid | A |
| 661 | 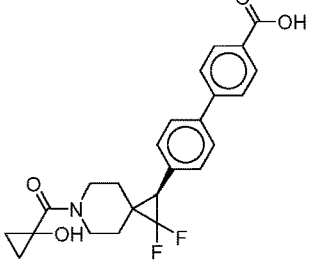<br>(R)-4'-(2,2-difluoro-6-(1-hydroxycyclopropane-1-carbonyl)-6-azaspiro[2.5]octan-1-yl)-[1,1'-biphenyl]-4-carboxylic acid | E |

Figure 3-73

| | | |
|---|---|---|
| 662 | 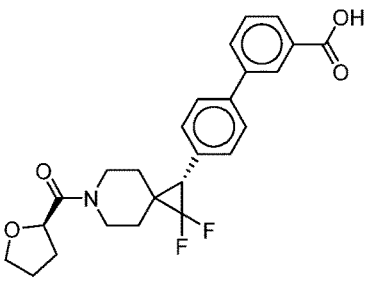<br>4'-((S)-2,2-difluoro-6-((R)-tetrahydrofuran-2-carbonyl)-6-azaspiro[2.5]octan-1-yl)-[1,1'-biphenyl]-3-carboxylic acid | B |
| 663 | 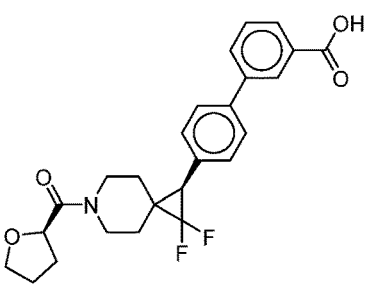<br>4'-((R)-2,2-difluoro-6-((R)-tetrahydrofuran-2-carbonyl)-6-azaspiro[2.5]octan-1-yl)-[1,1'-biphenyl]-3-carboxylic acid | E |
| 664 | 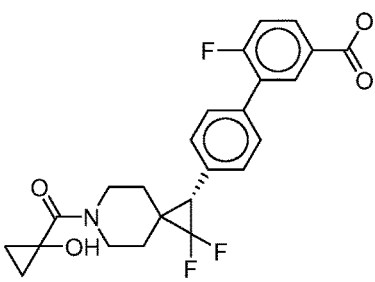<br>(S)-4'-(2,2-difluoro-6-(1-hydroxycyclopropane-1-carbonyl)-6-azaspiro[2.5]octan-1-yl)-6-fluoro-[1,1'-biphenyl]-3-carboxylic acid | A |
| 665 | 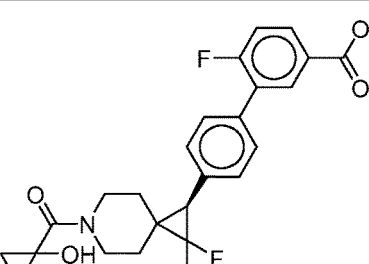<br>(R)-4'-(2,2-difluoro-6-(1-hydroxycyclopropane-1-carbonyl)-6-azaspiro[2.5]octan-1-yl)-6-fluoro-[1,1'-biphenyl]-3-carboxylic acid | E |

Figure 3-74

| | | |
|---|---|---|
| 666 | 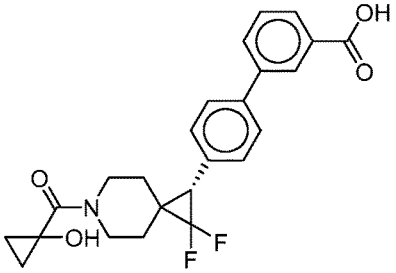<br>(S)-4'-(2,2-difluoro-6-(1-hydroxycyclopropane-1-carbonyl)-6-azaspiro[2.5]octan-1-yl)-[1,1'-biphenyl]-3-carboxylic acid | B |
| 667 | 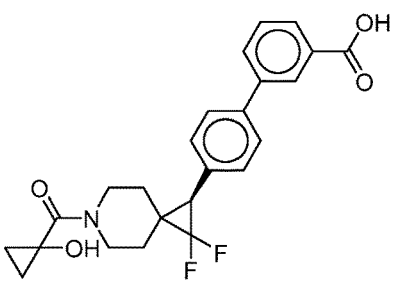<br>(R)-4'-(2,2-difluoro-6-(1-hydroxycyclopropane-1-carbonyl)-6-azaspiro[2.5]octan-1-yl)-[1,1'-biphenyl]-3-carboxylic acid | E |
| 668 | 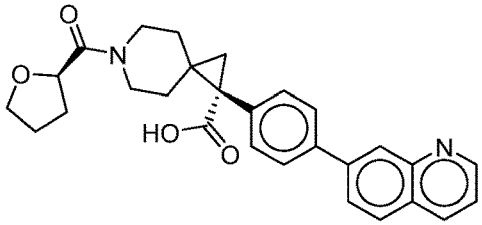<br>(S)-1-(4-(quinolin-7-yl)phenyl)-6-((R)-tetrahydrofuran-2-carbonyl)-6-azaspiro[2.5]octane-1-carboxylic acid | C |
| 669 | 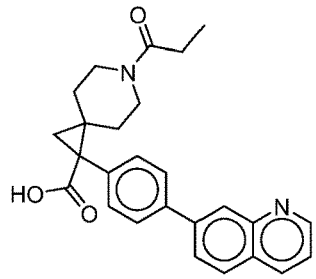<br>6-propionyl-1-(4-(quinolin-7-yl)phenyl)-6-azaspiro[2.5]octane-1-carboxylic acid | B |
Figure 3-75

| | | |
|---|---|---|
| 670 | 6-fluoro-4'-((R)-6-((R)-tetrahydrofuran-2-carbonyl)-6-azaspiro[2.5]octan-1-yl)-[1,1'-biphenyl]-3-carboxylic acid | E |
| 671 | 6-fluoro-4'-((S)-6-((R)-tetrahydrofuran-2-carbonyl)-6-azaspiro[2.5]octan-1-yl)-[1,1'-biphenyl]-3-carboxylic acid | B |
| 672 | (R)-6-fluoro-4'-(6-(1-hydroxycyclopropane-1-carbonyl)-6-azaspiro[2.5]octan-1-yl)-[1,1'-biphenyl]-3-carboxylic acid | B |
| 673 | (S)-6-fluoro-4'-(6-(1-hydroxycyclopropane-1-carbonyl)-6-azaspiro[2.5]octan-1-yl)-[1,1'-biphenyl]-3-carboxylic acid | C |

Figure 3-76

| | | |
|---|---|---|
| 674 | 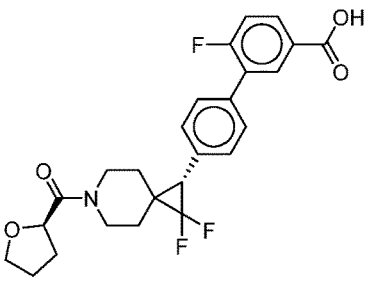<br>4'-((S)-2,2-difluoro-6-((R)-tetrahydrofuran-2-carbonyl)-6-azaspiro[2.5]octan-1-yl)-6-fluoro-[1,1'-biphenyl]-3-carboxylic acid | B |
| 675 | 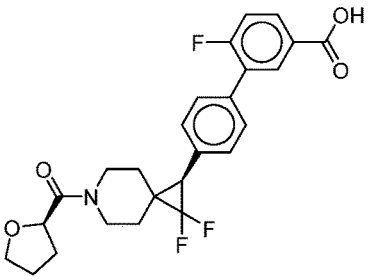<br>4'-((R)-2,2-difluoro-6-((R)-tetrahydrofuran-2-carbonyl)-6-azaspiro[2.5]octan-1-yl)-6-fluoro-[1,1'-biphenyl]-3-carboxylic acid | E |
| 676 | 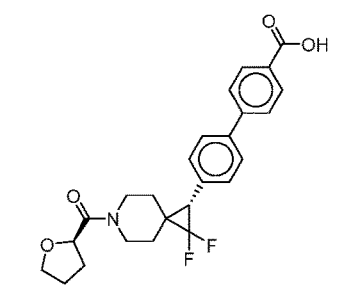<br>4'-((S)-2,2-difluoro-6-((R)-tetrahydrofuran-2-carbonyl)-6-azaspiro[2.5]octan-1-yl)-[1,1'-biphenyl]-4-carboxylic acid | E |
| 677 | 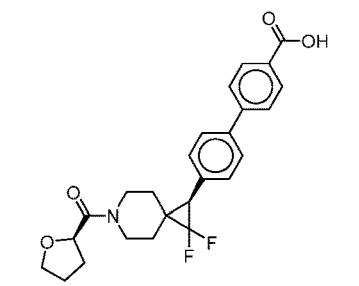<br>4'-((R)-2,2-difluoro-6-((R)-tetrahydrofuran-2-carbonyl)-6-azaspiro[2.5]octan-1-yl)-[1,1'-biphenyl]-4-carboxylic acid | B |

Figure 3-77

| | | |
|---|---|---|
| 678 | 4'-((R)-6-((R)-tetrahydrofuran-2-carbonyl)-6-azaspiro[2.5]octan-1-yl)-[1,1'-biphenyl]-4-carboxylic acid | C |
| 679 | 4'-((S)-6-((R)-tetrahydrofuran-2-carbonyl)-6-azaspiro[2.5]octan-1-yl)-[1,1'-biphenyl]-4-carboxylic acid | A |
| 680 | (R)-4'-(6-(1-hydroxycyclopropane-1-carbonyl)-6-azaspiro[2.5]octan-1-yl)-[1,1'-biphenyl]-4-carboxylic acid | A |
| 681 | (S)-4'-(6-(1-hydroxycyclopropane-1-carbonyl)-6-azaspiro[2.5]octan-1-yl)-[1,1'-biphenyl]-4-carboxylic acid | D |

Figure 3-78

| | | |
|---|---|---|
| 682 | 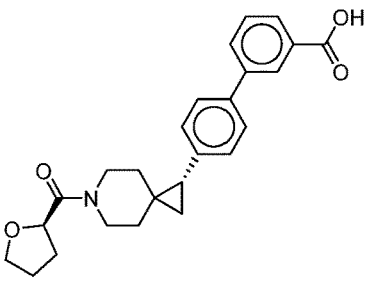<br>4'-((R)-6-((R)-tetrahydrofuran-2-carbonyl)-6-azaspiro[2.5]octan-1-yl)-[1,1'-biphenyl]-3-carboxylic acid | E |
| 683 | 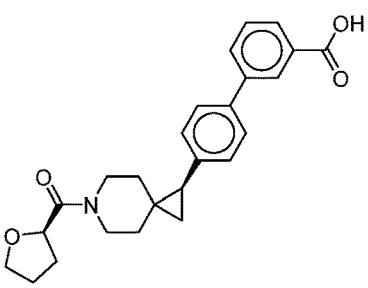<br>4'-((S)-6-((R)-tetrahydrofuran-2-carbonyl)-6-azaspiro[2.5]octan-1-yl)-[1,1'-biphenyl]-3-carboxylic acid | B |
| 684 | 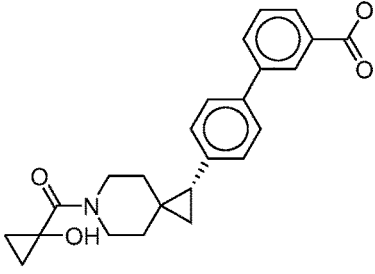<br>(R)-4'-(6-(1-hydroxycyclopropane-1-carbonyl)-6-azaspiro[2.5]octan-1-yl)-[1,1'-biphenyl]-3-carboxylic acid | B |
| 685 | 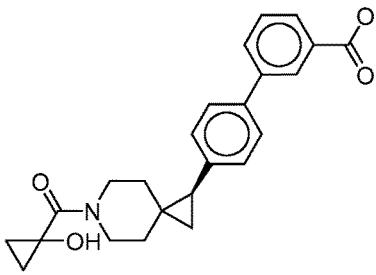<br>(S)-4'-(6-(1-hydroxycyclopropane-1-carbonyl)-6-azaspiro[2.5]octan-1-yl)-[1,1'-biphenyl]-3-carboxylic acid | D |
Figure 3-79

| | | |
|---|---|---|
| 686 | 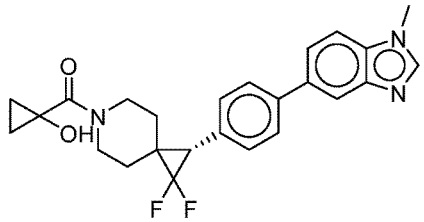<br>(S)-(1,1-difluoro-2-(4-(1-methyl-1H-benzo[d]imidazol-5-yl)phenyl)-6-azaspiro[2.5]octan-6-yl)(1-hydroxycyclopropyl)methanone | A |
| 687 | 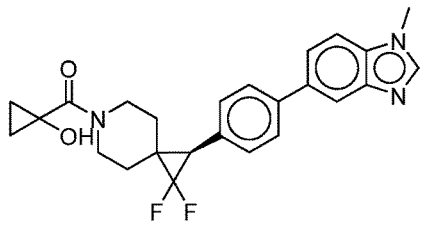<br>(R)-(1,1-difluoro-2-(4-(1-methyl-1H-benzo[d]imidazol-5-yl)phenyl)-6-azaspiro[2.5]octan-6-yl)(1-hydroxycyclopropyl)methanone | C |
| 688 | 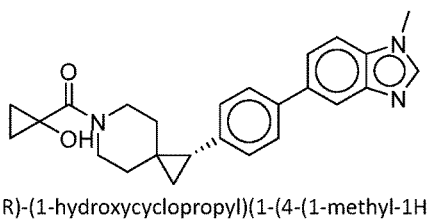<br>(R)-(1-hydroxycyclopropyl)(1-(4-(1-methyl-1H-benzo[d]imidazol-5-yl)phenyl)-6-azaspiro[2.5]octan-6-yl)methanone | B |
| 689 | 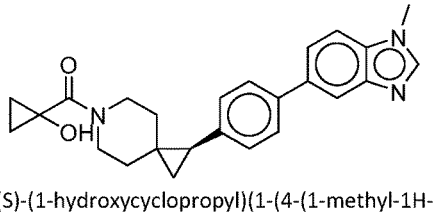<br>(S)-(1-hydroxycyclopropyl)(1-(4-(1-methyl-1H-benzo[d]imidazol-5-yl)phenyl)-6-azaspiro[2.5]octan-6-yl)methanone | A |

Figure 3-80

| 690 | 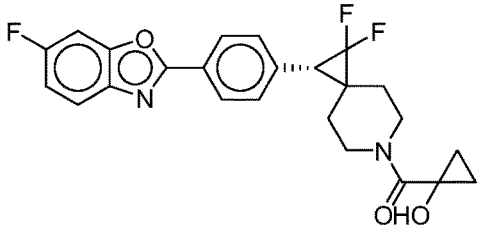<br>(S)-(1,1-difluoro-2-(4-(6-fluorobenzo[d]oxazol-2-yl)phenyl)-6-azaspiro[2.5]octan-6-yl)(1-hydroxycyclopropyl)methanone | A |
|---|---|---|
| 691 | 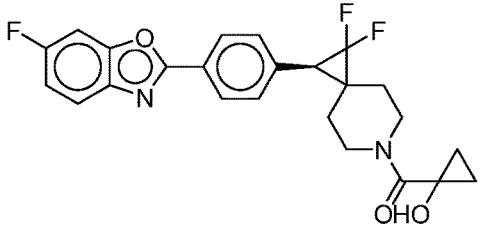<br>(R)-(1,1-difluoro-2-(4-(6-fluorobenzo[d]oxazol-2-yl)phenyl)-6-azaspiro[2.5]octan-6-yl)(1-hydroxycyclopropyl)methanone | C |
| 692 | 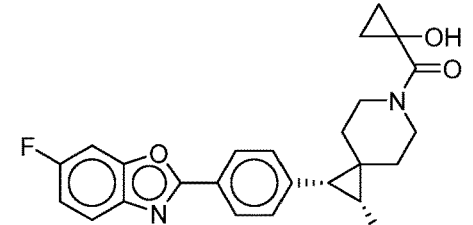<br>((1R,2R)-1-chloro-2-(4-(6-fluorobenzo[d]oxazol-2-yl)phenyl)-6-azaspiro[2.5]octan-6-yl)(1-hydroxycyclopropyl)methanone | B |
| 693 | 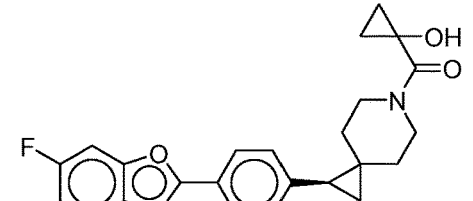<br>(R)-(1-(4-(6-fluorobenzo[d]oxazol-2-yl)phenyl)-6-azaspiro[2.5]octan-6-yl)(1-hydroxycyclopropyl)methanone | A |

Figure 3-81

| | | |
|---|---|---|
| 694 | 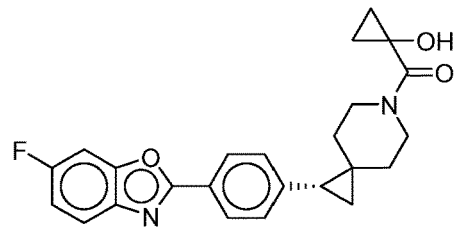<br>(S)-(1-(4-(6-fluorobenzo[d]oxazol-2-yl)phenyl)-6-azaspiro[2.5]octan-6-yl)(1-hydroxycyclopropyl)methanone | B |
| 695 | 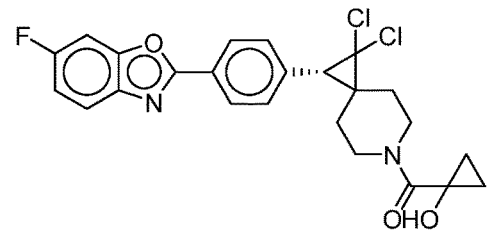<br>(S)-(1,1-dichloro-2-(4-(6-fluorobenzo[d]oxazol-2-yl)phenyl)-6-azaspiro[2.5]octan-6-yl)(1-hydroxycyclopropyl)methanone | D |
| 696 | 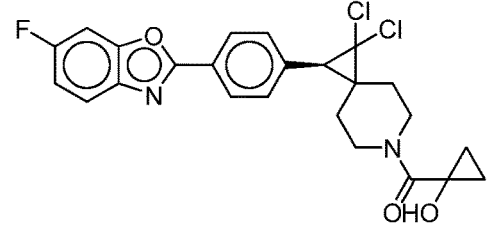<br>(R)-(1,1-dichloro-2-(4-(6-fluorobenzo[d]oxazol-2-yl)phenyl)-6-azaspiro[2.5]octan-6-yl)(1-hydroxycyclopropyl)methanone | D |
| 697 | 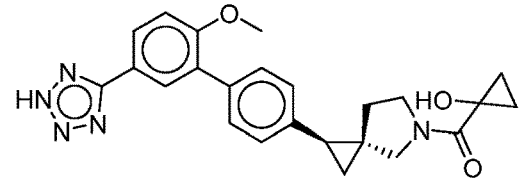<br>(1-hydroxycyclopropyl)((1S,3S)-1-(2'-methoxy-5'-(2H-tetrazol-5-yl)-[1,1'-biphenyl]-4-yl)-5-azaspiro[2.4]heptan-5-yl)methanone | C |
| 698 | 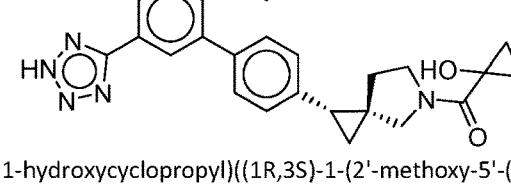<br>(1-hydroxycyclopropyl)((1R,3S)-1-(2'-methoxy-5'-(2H-tetrazol-5-yl)-[1,1'-biphenyl]-4-yl)-5-azaspiro[2.4]heptan-5-yl)methanone | C |

Figure 3-82

| | | |
|---|---|---|
| 699 | 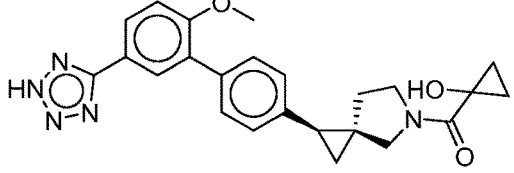<br>(1-hydroxycyclopropyl)((1S,3R)-1-(2'-methoxy-5'-(2H-tetrazol-5-yl)-[1,1'-biphenyl]-4-yl)-5-azaspiro[2.4]heptan-5-yl)methanone | A |
| 700 | 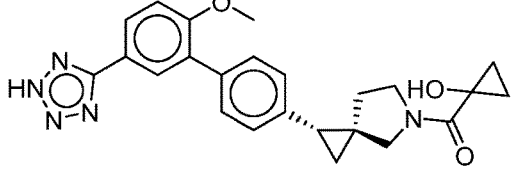<br>(1-hydroxycyclopropyl)((1R,3R)-1-(2'-methoxy-5'-(2H-tetrazol-5-yl)-[1,1'-biphenyl]-4-yl)-5-azaspiro[2.4]heptan-5-yl)methanone | C |
| 701 | 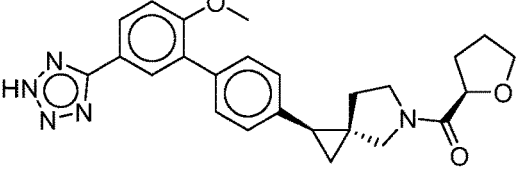<br>((1S,3S)-1-(2'-methoxy-5'-(2H-tetrazol-5-yl)-[1,1'-biphenyl]-4-yl)-5-azaspiro[2.4]heptan-5-yl)((R)-tetrahydrofuran-2-yl)methanone | B |
| 702 | 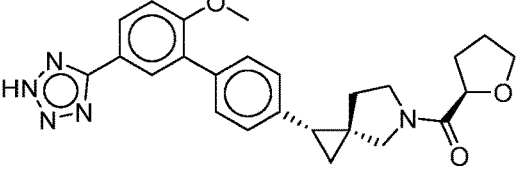<br>((1R,3S)-1-(2'-methoxy-5'-(2H-tetrazol-5-yl)-[1,1'-biphenyl]-4-yl)-5-azaspiro[2.4]heptan-5-yl)((R)-tetrahydrofuran-2-yl)methanone | A |
| 703 | 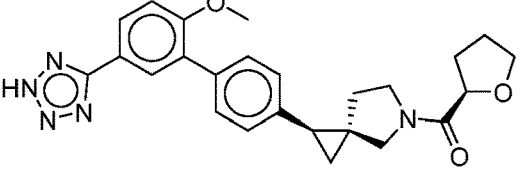<br>((1S,3R)-1-(2'-methoxy-5'-(2H-tetrazol-5-yl)-[1,1'-biphenyl]-4-yl)-5-azaspiro[2.4]heptan-5-yl)((R)-tetrahydrofuran-2-yl)methanone | C |

Figure 3-83

| | | |
|---|---|---|
| 704 | 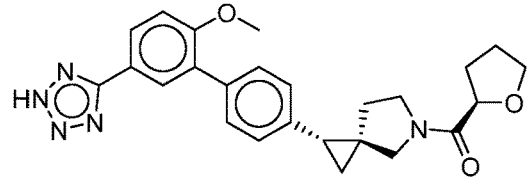<br>((1R,3R)-1-(2'-methoxy-5'-(2H-tetrazol-5-yl)-[1,1'-biphenyl]-4-yl)-5-azaspiro[2.4]heptan-5-yl)((R)-tetrahydrofuran-2-yl)methanone | C |
| 705 | 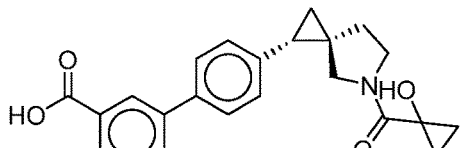<br>4'-((1S,3S)-5-(1-hydroxycyclopropane-1-carbonyl)-5-azaspiro[2.4]heptan-1-yl)-6-methoxy-[1,1'-biphenyl]-3-carboxylic acid | A |
| 706 | 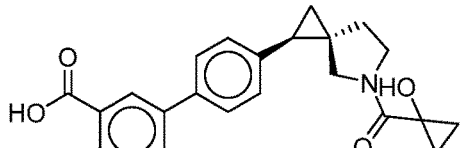<br>4'-((1R,3S)-5-(1-hydroxycyclopropane-1-carbonyl)-5-azaspiro[2.4]heptan-1-yl)-6-methoxy-[1,1'-biphenyl]-3-carboxylic acid | C |
| 707 | 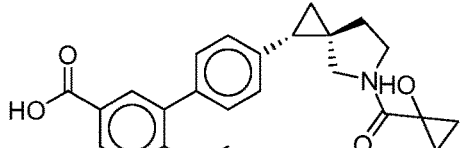<br>4'-((1S,3R)-5-(1-hydroxycyclopropane-1-carbonyl)-5-azaspiro[2.4]heptan-1-yl)-6-methoxy-[1,1'-biphenyl]-3-carboxylic acid | D |
| 708 | 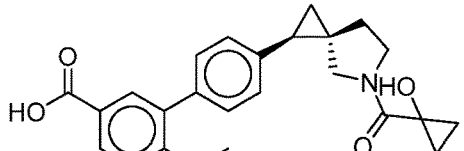<br>4'-((1R,3R)-5-(1-hydroxycyclopropane-1-carbonyl)-5-azaspiro[2.4]heptan-1-yl)-6-methoxy-[1,1'-biphenyl]-3-carboxylic acid | C |

Figure 3-84

| | | |
|---|---|---|
| 709 | 6-methoxy-4'-((1S,3S)-5-((R)-tetrahydrofuran-2-carbonyl)-5-azaspiro[2.4]heptan-1-yl)-[1,1'-biphenyl]-3-carboxylic acid | A |
| 710 | 6-methoxy-4'-((1R,3S)-5-((R)-tetrahydrofuran-2-carbonyl)-5-azaspiro[2.4]heptan-1-yl)-[1,1'-biphenyl]-3-carboxylic acid | D |
| 711 | 6-methoxy-4'-((1S,3R)-5-((R)-tetrahydrofuran-2-carbonyl)-5-azaspiro[2.4]heptan-1-yl)-[1,1'-biphenyl]-3-carboxylic acid | E |
| 712 | 6-methoxy-4'-((1R,3R)-5-((R)-tetrahydrofuran-2-carbonyl)-5-azaspiro[2.4]heptan-1-yl)-[1,1'-biphenyl]-3-carboxylic acid | D |
| 713 | 4'-((2r,4r)-6-(1-hydroxycyclopropane-1-carbonyl)-6-azaspiro[3.4]octan-2-yl)-6-methoxy-[1,1'-biphenyl]-3-carboxylic acid | A |

Figure 3-85

| 714 | 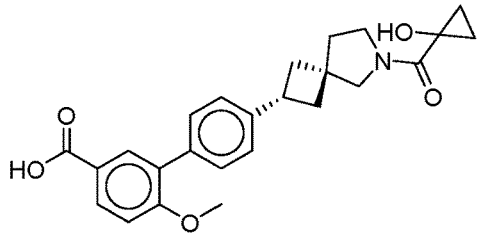 4'-((2s,4s)-6-(1-hydroxycyclopropane-1-carbonyl)-6-azaspiro[3.4]octan-2-yl)-6-methoxy-[1,1'-biphenyl]-3-carboxylic acid | B |
|---|---|---|
| 715 | 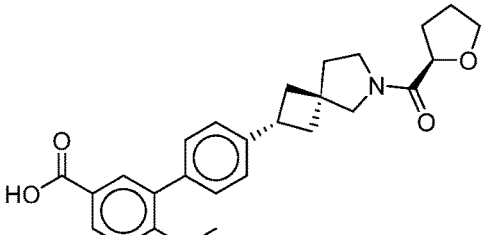 6-methoxy-4'-((2R,4r)-6-((R)-tetrahydrofuran-2-carbonyl)-6-azaspiro[3.4]octan-2-yl)-[1,1'-biphenyl]-3-carboxylic acid | B |
| 716 | 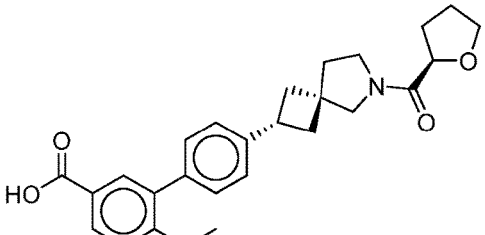 6-methoxy-4'-((2S,4s)-6-((R)-tetrahydrofuran-2-carbonyl)-6-azaspiro[3.4]octan-2-yl)-[1,1'-biphenyl]-3-carboxylic acid | B |

\* Absolute stereochemistry determined.

Unless otherwise indicated, the absolute stereochemistry of each stereocenter was not determined. The present disclosure provides methods of separating stereoisomers.

Figure 3-86

INHIBITING FATTY ACID SYNTHASE (FASN)

CROSS-REFERENCE TO RELATED APPLICATIONS

This application is a continuation of U.S. patent application Ser. No. 16/598,481, filed Oct. 10, 2019, which claims the benefit of U.S. Provisional Application No. 62/744,071, filed on Oct. 10, 2018, both of which are incorporated by reference in their entirety.

TECHNICAL FIELD

The present disclosure relates to novel chemical compositions for inhibiting fatty acid synthase (FASN).

BACKGROUND

Non-alcoholic steatohepatitis (NASH) is a chronic liver disease with varying degrees of inflammation and fibrosis that can progress to cirrhosis and end-stage liver complications. The disease affects greater than 16 million people in the US and is the second leading cause of liver transplants in the US. Moreover, NASH is a strong predictor for type 2 diabetes, cardiovascular disease and end-stage kidney disease. There are no pharmacological agents currently approved for the treatment of NASH, which represents a substantial healthcare burden. The pathogenesis of NASH has been associated with obesity or aberrant metabolic syndrome. Consistent with a proposed role for increased de novo lipogenesis (DNL) as a mediator of steatosis and liver injury, FASN expression is significantly elevated in the liver from NASH patients with FASN mRNA expression exceeding 17-fold greater levels as compared to normal controls. Thus, FASN is an attractive therapeutic target for treating NASH by modulating the DNL pathway and reducing steatosis.

SUMMARY

Novel compounds useful for inhibiting FASN, including FASN Inhibitor Compounds, are disclosed herein. A first aspect of the present disclosure relates to compounds of Formula (I):

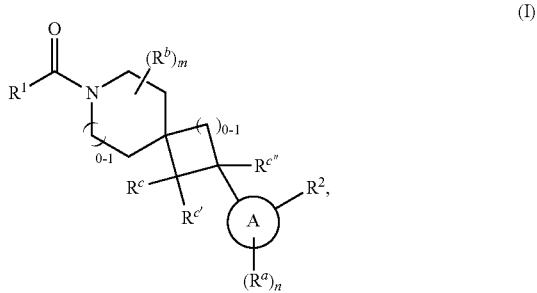

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N, and S, or 5-10 membered heteroaryl containing 1-3 heteroatoms independently selected from the group consisting of O, N, and S,
wherein $R^1$ is optionally substituted with halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or $C_{1-3}$ alkyl optionally substituted with halogen or —CO$_2$R$^3$;
$R^2$ is halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl, and 5-10 membered heteroaryl containing 1-4 heteroatoms independently selected from the group consisting of O, N, and S,
wherein an optionally substituted group of $R^2$ is optionally substituted with 1-6 $R^d$;
each $R^a$ is independently halogen, —CN, —NO$_2$, —OR$^3$, —CO$_2$R$^3$, —SR$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), —P(O)R$^4$OR$^3$, tetrazolyl, or $C_{1-3}$ aliphatic optionally substituted with halogen;
each $R^b$ is independently halogen, oxo, —CN, —NO$_2$, —OR, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or $C_{1-6}$ aliphatic optionally substituted with halogen;
$R^c$ is hydrogen, halogen, —OH, —NH$_2$, —CN, —CO$_2$R$^3$, —C(O)N(R$^4$)$_2$, or tetrazole;
$R^{c'}$ is hydrogen, halogen, —OH, —NH$_2$, —CN, —CO$_2$R$^3$, —C(O)N(R$^4$)$_2$, or tetrazole;
$R^{c''}$ is hydrogen, halogen, —OH, —NH$_2$, —CN, —CO$_2$R$^3$, —C(O)N(R$^4$)$_2$, or tetrazole;
each $R^d$ is independently halogen, oxo, —CN, —NO$_2$, —OR, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —P(O)R$^4$OR$^3$, —CH$_2$CO$_2$R$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^4$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;
wherein an optionally substituted group of $R^d$ is optionally substituted with halogen, —OH, —NH$_2$, —CN, oxo, or $C_{1-3}$ aliphatic;
each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of $R^3$ is optionally substituted with halogen, —OH, —NH$_2$, —CN, or oxo;

each $R^4$ is independently hydrogen, —OH, —CN, or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of $R^4$ is optionally substituted with halogen, —OH, —NH$_2$, —CN, or oxo;

each $R^{4'}$ is independently hydrogen, or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of $R^{4'}$ is optionally substituted with halogen, —OH, —NH$_2$, —CN, or oxo;

each $R^5$ is an optionally substituted group independently selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of $R^5$ is optionally substituted with halogen, —OH, —NH$_2$, —CN or oxo;

m is 0-4; and n is 0-6.

Another aspect of the present disclosure relates to a pharmaceutical composition comprising a compound of Formula (I), or a pharmaceutically acceptable salt. The pharmaceutically acceptable carrier can further include an excipient, diluent, or surfactant. The pharmaceutical composition can be effective for treating a disease or disorder associated with FASN modulation in a subject in need thereof. The pharmaceutical compositions can comprise the compounds of the present disclosure for use in treating diseases described herein. The compositions can contain at least one compound of the disclosure and a pharmaceutically acceptable carrier.

Another aspect of the present disclosure relates to a method of inhibiting FASN. The method can comprise administering to a patient in need thereof a therapeutically effective amount of a compound of Formula (I), or a pharmaceutically acceptable salt thereof.

DETAILED DESCRIPTION

Figure 1:
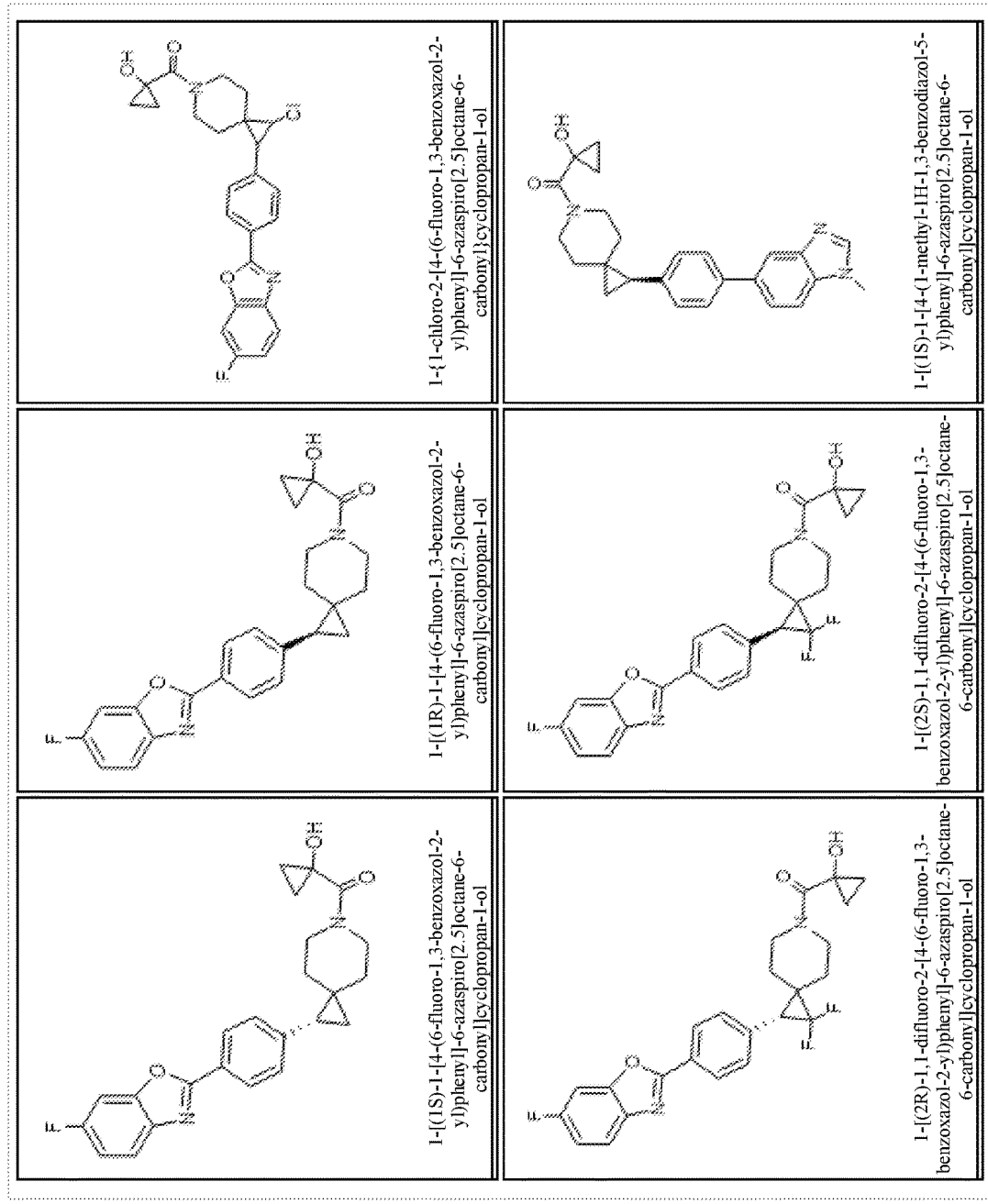
FIG. 1 is a table of compounds in accordance with an embodiment of the present disclosure.

The present disclosure relates to compounds and compositions that are capable of modulating the activity of FASN. The disclosure features methods of treating, preventing or ameliorating a disease or disorder in which FASN plays a role by administering to a patient in need thereof a therapeutically effective amount of a compound of Formula (I), or a pharmaceutically acceptable salt thereof. The methods of the present disclosure can be used in the treatment of a variety of FASN dependent diseases and disorders by inhibiting the activity of FASN. Inhibition of FASN provides a novel approach to the treatment of diseases including, but not limited to, NASH.

In certain embodiments, novel FASN Inhibitor Compounds are provided. Unless otherwise indicated, "FASN Inhibitor Compound" as used herein refers to a compound having one or more of the following characteristic when tested according to the biochemical Assay Protocol of Example 3 below: (1) a FASN IC$_{50}$ value of less than or equal to 10 μM; and (2) a FASN IC$_{50}$ value of greater than or equal to 0.001 μM and less than or equal to 10 μM; and (3) a FASN IC$_{50}$ value greater than or equal to 0.001 μM and less than or equal to 1 μM.

Compounds of Formula (I), unless otherwise indicated may exist in their tautomeric form (for example, as an amide or imino ether). All such tautomeric forms are contemplated herein as part of the present disclosure.

The compounds of Formula (I), unless otherwise indicated, may contain asymmetric or chiral centers, and, therefore, exist in different stereoisomeric forms. It is intended that unless otherwise indicated all stereoisomeric forms of the compounds of Formula (I) as well as mixtures thereof, including racemic mixtures, form part of the present disclosure. In addition, the present disclosure embraces all geometric and positional isomers. For example, if a compound of Formula (I), incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this disclosure. Enantiomers can also be separated by use of a chiral HPLC column.

The compounds of Formula (I) may form salts which are also within the scope of this disclosure. Reference to a compound of Formula (I) herein is understood to include reference to salts thereof, unless otherwise indicated.

The disclosure is directed to compounds as described herein and pharmaceutically acceptable salts thereof. The disclosure also includes pharmaceutical compositions comprising one or more compounds as described herein, or a pharmaceutically acceptable salt thereof, and a pharmaceutically acceptable excipient. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of Formula (I) can be a capsule. In some embodiments, an oral dosage form of a compound of Formula (I) is a tablet. In some embodiments, an oral dosage form comprises one or more fillers, disintigrants, lubricants, glidants, anti-adherents, and/or anti-statics. In some embodiments, an oral dosage form is prepared via dry blending. In some embodiments, an oral dosage form is a tablet and is prepared via dry granulation.

In some embodiments, a compound of the present disclosure can be dosed at 1 mg to 1 g at a therapeutically effective frequency (e.g., once a day to once a week).

Compounds of the Disclosure

The present disclosure relates to compounds, or pharmaceutically acceptable salts thereof, capable of modulating FASN which are useful for the treatment of diseases and disorders associated with modulation of FASN. The disclosure further relates to compounds, or pharmaceutically acceptable salts thereof, which are useful for inhibiting FASN.

In some embodiments, compounds of the disclosure have the Formula (I):

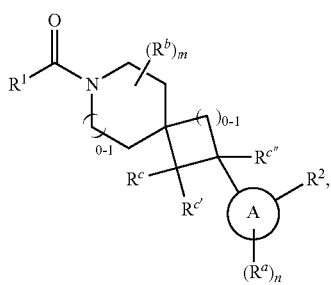

(I)

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S,
wherein $R^1$ is optionally substituted with halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or $C_{1-3}$ alkyl optionally substituted with halogen or —CO$_2$R$^3$;
$R^2$ is halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl, and 5-10 membered heteroaryl containing 1-4 heteroatoms independently selected from the group consisting of O, N, and S,
wherein an optionally substituted group of $R^2$ is optionally substituted with 1-6 $R^d$;
each $R^a$ is independently halogen, —CN, —NO$_2$, —OR, —CO$_2$R$^3$, —SR$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), —P(O)R$^4$OR$^3$, tetrazolyl, or $C_{1-3}$ aliphatic optionally substituted with halogen;
each $R^b$ is independently halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), $C_{1-6}$ aliphatic optionally substituted with halogen;
$R^c$ is hydrogen, halogen, —OH, —NH$_2$, —CN, —C$_2$R$^3$, —C(O)N(R$^4$)$_2$, or tetrazole;
$R^{c'}$ is hydrogen, halogen, —OH, —NH$_2$, —CN, —C$_2$R$^3$, —C(O)N(R$^4$)$_2$, or tetrazole;
$R^{c''}$ is hydrogen, halogen, —OH, —NH$_2$, —CN, —C$_2$R$^3$, —C(O)N(R$^4$)$_2$, or tetrazole;
each $R^d$ is independently halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —P(O)R$^4$OR$^3$, —CH$_2$CO$_2$R$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^4$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;
wherein an optionally substituted group of $R^d$ is optionally substituted with halogen, —OH, —NH$_2$, —CN, oxo, or $C_{1-3}$ aliphatic;
each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S,
wherein an optionally substituted group of $R^3$ is optionally substituted with halogen, —OH, —NH$_2$, —CN, or oxo;
each $R^4$ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S,
wherein an optionally substituted group of $R^4$ is optionally substituted with halogen, —OH, —NH$_2$, —CN, or oxo;

each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S,
  wherein an optionally substituted group of $R^{4'}$ is optionally substituted with halogen, —OH, —NH$_2$, —CN, or oxo;
each $R^5$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S,
  wherein an optionally substituted group of $R^5$ is optionally substituted with halogen, —OH, —NH$_2$, —CN or oxo;
m is 0-4; and
n is 0-6.

In some embodiments, compounds of the disclosure have the Formula (I), or a pharmaceutically acceptable salt thereof, wherein Formula (I) has the formula

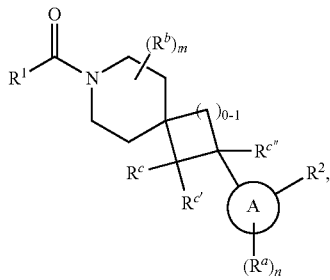

wherein:
$R^2$ is halogen, oxo, —CN, —NO$_2$, —OR, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl, and 5-10 membered heteroaryl containing 1-4 heteroatoms independently selected from the group consisting of O, N, and S,
  wherein an optionally substituted group of $R^2$ is optionally substituted with 1-6 $R^d$;
each $R^a$ is independently halogen, —CN, —NO$_2$, —OR, —CO$_2$R$^3$, —SR$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or $C_{1-3}$ aliphatic optionally substituted with halogen;
each $R^d$ is independently halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;
  wherein an optionally substituted group of $R^d$ is optionally substituted with halogen, —OH, —NH$_2$, —CN, oxo, or $C_{1-3}$ aliphatic; and
Ring A, $R^1$, $R^b$, $R^c$, $R^{c'}$, $R^{c''}$, $R^3$, $R^4$, $R^{4'}$, $R^5$, m, and n are defined as provided above.

In some embodiments, compounds of the disclosure have the Formula (I-a):

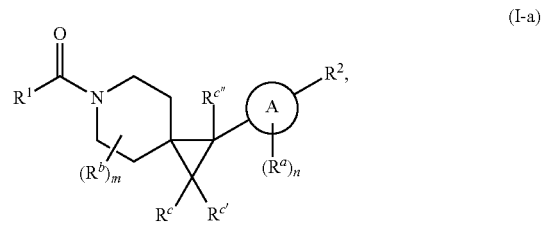

or a pharmaceutically acceptable salt thereof,
Ring A is 6-10 membered aryl or 5-10 membered heteroaryl containing 1-4 heteroatoms independently selected from the group consisting of O, N, and S;
$R^1$ is $C_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S,
  wherein $R^1$ is optionally substituted with —OH, —NH$_2$, or $C_{1-3}$ alkyl optionally substituted with halogen or —CO$_2$R$^3$;
$R^2$ is —CO$_2$R$^3$, —SO$_2$NHCOR$^3$, or an optionally substituted group selected from the group consisting of 3-7 membered cycloalkyl, phenyl, and 5-10 membered heteroaryl containing 1-2 heteroatoms independently selected from the group consisting of O, N, and S,
  wherein an optionally substituted group of $R^2$ is optionally substituted with 1-6 $R^d$;
each $R^a$ is independently halogen;
each $R^b$ is independently $C_{1-3}$ aliphatic;
$R^c$ is hydrogen or halogen;
$R^{c'}$ is hydrogen or halogen;
$R^{c''}$ is hydrogen, halogen, or —CO$_2$H;
each $R^d$ is independently halogen, —CO$_2$R$^3$, —OR$^3$, —S(O)$_2$NH$_2$, —SO$_2$NHCOR$^3$, —P(O)R$^4$OR$^3$, or an optionally substituted group selected from the group consisting of $C_{1-3}$ aliphatic, or 5-7 membered heteroaryl containing 1-4 heteroatoms independently selected from the group consisting of O, N, and S;
  wherein an optionally substituted group of $R^d$ is optionally substituted with halogen or $C_{1-3}$ aliphatic;
each $R^3$ is independently hydrogen or $C_{1-3}$ alkyl optionally substituted with fluoro;
$R^4$ is $C_{1-6}$ aliphatic;
m is 0-4; and
n is 0-6.

In some embodiments, compounds of Formula (I-a) are provided, wherein $R^2$ is —CO$_2$R$^3$ or an optionally substituted group selected from the group consisting of 3-7 membered cycloalkyl, phenyl, and 5-10 membered heteroaryl containing 1-2 heteroatoms independently selected from the group consisting of O, N, and S, wherein an optionally substituted group of $R^2$ is optionally substituted with 1-6 $R^d$; and each $R^d$ is independently halogen, —$CO_2R^3$, —$OR^3$, —$S(O)_2NH_2$, or an optionally substituted group selected from the group consisting of $C_{1-3}$ aliphatic, or 5-7 membered heteroaryl containing 1-4 heteroatoms independently selected from the group consisting of O, N, and S, wherein an optionally substituted group of $R^d$ is optionally substituted with halogen or $C_{1-3}$ aliphatic.

In some embodiments, compounds of Formula (I) are provided wherein:
Ring A is phenyl or naphthyl;
$R^1$ is methyl, ethyl, tetrohydrofuranyl, oxazolyl, triazolyl, cyclobutyl, or cyclopropyl optionally substituted with —$CH_2CO_2H$, —OH, or —$NH_2$;
$R^2$ is —$CO_2H$, cyclobutyl, benzoxazolyl, indolyl, indazolyl, benzimidazolyl, quinolinyl, phenyl, naphthyl, pyridyl, or isoquinolinyl;
each $R^a$ is independently fluoro or chloro;
each $R^b$ is independently methyl;
$R^c$ is hydrogen or fluoro;
$R^{c'}$ is hydrogen or fluoro;
$R^{c''}$ is hydrogen or —$CO_2H$;
each $R^d$ is fluoro, methyl, —$CO_2H$, tetrazolyl, methoxy, chloro, —$CF_3$, —$OCF_3$, or N-methyl pyrazolyl;
m is 0-1; and
n is 0-3.

In some embodiments, compounds of the disclosure have the Formula (II):

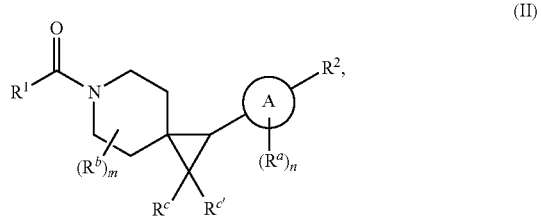

(II)

or a pharmaceutically acceptable salt thereof,
wherein Ring A, $R^1$, $R^2$, $R^a$, $R^b$, $R^c$, $R^{c'}$, m, and n are as defined above and described in classes and subclasses herein, both singly and in combination.

In some embodiments, compounds of Formula (II) are provided wherein:
Ring A is 6-10 membered aryl or 5-10 membered heteroaryl containing 1-2 heteroatoms independently selected from the group consisting of O, N, and S;
$R^1$ is $C_{1-6}$ aliphatic, 3-6 membered cycloalkyl, 4-6-membered heterocyclyl containing 1-3 heteroatoms independently selected from the group consisting of O, N, and S, or 5-6 membered heteroaryl containing 1-3 heteroatoms independently selected from the group consisting of O, N, and S,
wherein $R^1$ is optionally substituted with halogen, oxo, —CN, —$NO_2$, —$OR^3$, —$SR^3$, —$CO_2R^3$, —$N(R^4)(R^{4'})$, —$C(O)N(R^4)(R^{4'})$, —$S(O)_2N(R^4)(R^{4'})$, tetrazolyl, or $C_{1-3}$ alkyl optionally substituted with halogen or —$CO_2R^3$;
$R^2$ is —CN, —$NO_2$, —$OR^3$, —$SR^3$, —$C_2R^3$, —$N(R^4)(R^{4'})$, —$C(O)N(R^4)(R^{4'})$, —$S(O)_2N(R^4)(R^{4'})$, or an optionally substituted group selected from the group consisting of 3-7 membered cycloalkyl, 6-10 membered aryl, and 5-10 membered heteroaryl containing 1-4 heteroatoms independently selected from the group consisting of O, N, and S,
wherein an optionally substituted group of $R^2$ is optionally substituted with 1-6 $R^d$;
each $R^a$ is independently halogen, —CN, —$NO_2$, —$OR^3$, —$CO_2R^3$, —$N(R^4)(R^{4'})$, —$SR^3$, —$C(O)N(R^4)(R^{4'})$, —$S(O)_2N(R^4)(R^{4'})$, tetrazolyl, or $C_{1-3}$ aliphatic optionally substituted with halogen;
each $R^b$ is independently $C_{1-6}$ aliphatic optionally substituted with halogen;
$R^c$ is hydrogen or halogen;
$R^{c'}$ is hydrogen or halogen;
each $R^d$ is independently halogen, oxo, —CN, —$NO_2$, —$OR^3$, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, or an optionally substituted group selected from the group consisting of $C_{1-6}$ aliphatic and 5-10 membered heteroaryl containing 1-4 heteroatoms independently selected from the group consisting of O, N, and S;
wherein an optionally substituted group of $R^d$ is optionally substituted with halogen, —OH, —$NH_2$, —CN, oxo, or $C_{1-3}$ alkyl;
each $R^3$ is independently hydrogen or $C_{1-6}$ aliphatic optionally substituted with halogen, —OH, —$NH_2$, —CN or oxo;
each $R^4$ is independently hydrogen, —OH, —CN, or $C_{1-6}$ aliphatic optionally substituted with halogen, —OH, —$NH_2$, —CN or oxo;
each $R^{4'}$ is independently hydrogen, or $C_{1-6}$ aliphatic optionally substituted with halogen, —OH, —$NH_2$, —CN or oxo;
each $R^5$ is independently hydrogen or $C_{1-6}$ aliphatic optionally substituted with halogen, —OH, —$NH_2$, —CN or oxo;
m is 0-4; and
n is 0-6.

In some embodiments, compounds of Formula (II) are provided wherein:
Ring A is 6-10 membered aryl;
$R^1$ is $C_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S,
wherein $R^1$ is optionally substituted with —OH or —$NH_2$;
$R^2$ is —$CO_2R^3$ or an optionally substituted group selected from the group consisting of 6-membered aryl and 5-10 membered heteroaryl containing 1-2 heteroatoms independently selected from the group consisting of O, N, and S,
wherein an optionally substituted group of $R^2$ is optionally substituted with 1-6 $R^d$;
each $R^a$ is independently halogen;
each $R^b$ is independently $C_{1-3}$ aliphatic;
$R^c$ is hydrogen or halogen;
$R^{c'}$ is hydrogen or halogen;
each $R^d$ is independently halogen, —$CO_2R^3$, —$OR^3$, or an optionally substituted group selected from the group consisting of $C_{1-3}$ aliphatic, and 5-7 membered heteroaryl containing 1-4 heteroatoms independently selected from the group consisting of O, N, and S;
wherein an optionally substituted group of $R^d$ is optionally substituted with halogen or $C_{1-3}$ aliphatic;
each $R^3$ is independently hydrogen or $C_{1-3}$ alkyl optionally substituted with fluoro;

m is 0-4; and n is 0-6.

In some embodiments, compounds of Formula (II) are provided wherein:

Ring A is phenyl or naphthyl;

$R^1$ is methyl, ethyl, tetrohydrofuranyl (e.g., 2-tetrohydrofuranyl), oxazolyl, triazolyl (e.g., 4-triazolyl), cyclobutyl, or cyclopropyl optionally substituted with —$CH_2CO_2H$, —OH, or —$NH_2$;

$R^2$ is —$CO_2H$, cyclobutyl, benzoxazolyl, indolyl, indazolyl, benzimidazolyl, quinolinyl, phenyl, naphthyl, pyridyl, or isoquinolinyl;

each $R^a$ is independently fluoro or chloro;

$R^b$ is methyl;

$R^c$ is hydrogen or fluoro;

$R^{c'}$ is hydrogen or fluoro;

each $R^d$ is independently fluoro, methyl, —$CO_2H$, tetrazolyl, methoxy, chloro, —$CF_3$, —$OCF_3$, or N-methyl pyrazolyl;

m is 0-1; and n is 0-3.

In some embodiments, compounds of the disclosure have the Formula (III):

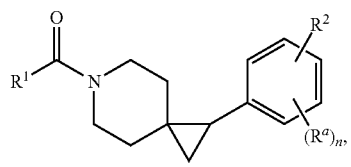

(III)

or a pharmaceutically acceptable salt thereof, wherein:

$R^1$ is $C_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S;

wherein $R^1$ is optionally substituted with —OH or $NH_2$;

$R^2$ is —$CO_2H$ or an optionally substituted group selected from the group consisting of phenyl and 5-10 membered heteroaryl containing 1-2 heteroatoms independently selected from the group consisting of O, N, and S, wherein an optionally substituted group of $R^2$ is optionally substituted with 1-6 $R^d$;

each $R^a$ is independently halogen;

each $R^d$ is independently halogen, —$OR^3$, —$CO_2R^3$, —$S(O)_2NH_2$, or an optionally substituted group selected from the group consisting of $C_{1-3}$ aliphatic, and 5-7 membered heteroaryl containing 1-4 heteroatoms independently selected from the group consisting of O, N, and S;

wherein an optionally substituted group of $R^d$ is optionally substituted with halogen or $C_{1-3}$ aliphatic;

each $R^3$ is independently hydrogen or $C_{1-3}$ alkyl; and n is 0-4.

In some embodiments, compounds of the disclosure have the Formula (IV):

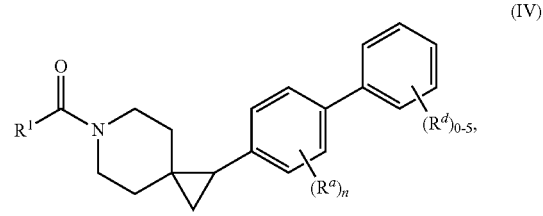

(IV)

or a pharmaceutically acceptable salt thereof, wherein:

$R^1$ is $C_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S, wherein $R^1$ is optionally substituted with —OH or —$NH_2$;

each $R^a$ is independently halogen;

each $R^d$ is independently halogen, —$CO_2R^3$, —$OR^3$, —$S(O)_2NH_2$, or an optionally substituted group selected from the group consisting of $C_{1-3}$ aliphatic and 5-membered heteroaryl containing 1-4 heteroatoms independently selected from the group consisting of O, N, and S, wherein an optionally substituted group of $R^d$ is optionally substituted with halogen or $C_{1-3}$ aliphatic;

each $R^3$ is independently hydrogen or $C_{1-3}$ alkyl; and n is 0-4.

In some embodiments, compounds of the disclosure have the Formula (V):

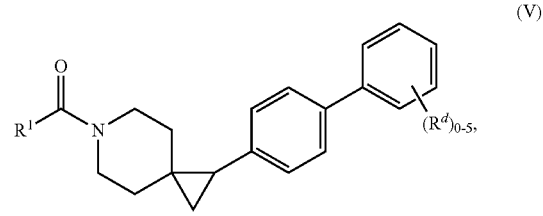

(V)

or a pharmaceutically acceptable salt thereof, wherein:

$R^1$ is 3-membered cycloalkyl optionally substituted with —OH, or 5-membered heterocyclyl containing 1-3 heteroatoms independently selected from the group consisting of O, N, and S;

each $R^d$ is independently halogen, —$CO_2H$, —$OR^3$, $C_{1-3}$ aliphatic, or 5-membered heteroaryl containing 1-4 heteroatoms independently selected from the group consisting of O, N, and S; and each $R^3$ is independently hydrogen or $C_{1-3}$ alkyl.

In some embodiments, compounds of the disclosure have the Formula (VI-A):

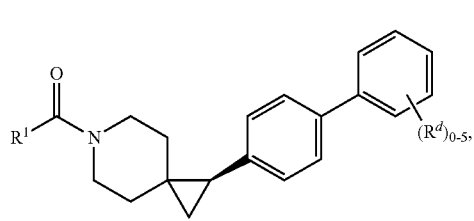

(VI-A)

or a pharmaceutically acceptable salt thereof,
wherein:
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, —$SO_2NHCOR^3$, $C_{1-3}$ aliphatic, or 5-membered heteroaryl containing 1-4 heteroatoms independently selected from the group consisting of O, N, and S; and
each $R^3$ is independently hydrogen or $C_{1-3}$ alkyl.

In some embodiments, compounds of the disclosure have the Formula (VI-B):

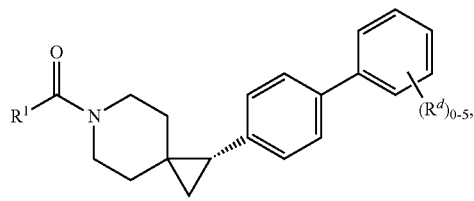

(VI-B)

or a pharmaceutically acceptable salt thereof,
wherein:
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, —$SO_2NHCOR^3$, $C_{1-3}$ aliphatic, or 5-membered heteroaryl containing 1-4 heteroatoms independently selected from the group consisting of O, N, and S; and
each $R^3$ is independently hydrogen or $C_{1-3}$ alkyl.

In some embodiments, compounds of the disclosure have the Formula (VII-A):

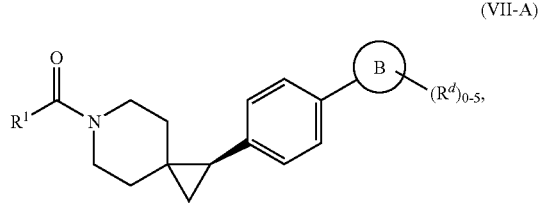

(VII-A)

or a pharmaceutically acceptable salt thereof,
wherein:
Ring B is phenyl, fused bicyclic 8-10 membered aryl, or fused bicyclic 8-10 membered heteroaryl containing 1-2 heteroatoms independently selected from the group consisting of O, N, and S;
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, $SO_2NHCOR^3$, $C_{1-3}$ aliphatic, or 5-membered heteroaryl containing 1-4 heteroatoms independently selected from the group consisting of O, N, and S; and
each $R^3$ is independently hydrogen or $C_{1-3}$ alkyl. In some embodiments, Ring A is fused bicyclic 8-10 membered aryl or heteroaryl containing 1-2 heteroatoms independently selected from the group consisting of O, N, and S.

In some embodiments, compounds of the disclosure have the Formula (VII-B):

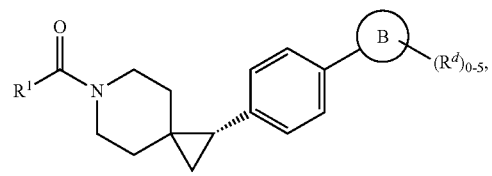

(VII-B)

or a pharmaceutically acceptable salt thereof,
wherein:
Ring B is phenyl, fused bicyclic 8-10 membered aryl, or fused bicyclic 8-10 membered heteroaryl containing 1-2 heteroatoms independently selected from the group consisting of O, N, and S;
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, $SO_2NHCOR^3$, $C_{1-3}$ aliphatic, or 5-membered heteroaryl containing 1-4 heteroatoms independently selected from the group consisting of O, N, and S; and
each $R^3$ is independently hydrogen or $C_{1-3}$ alkyl. In some embodiments, Ring A is fused bicyclic 8-10 membered aryl or heteroaryl containing 1-2 heteroatoms independently selected from the group consisting of O, N, and S.

It will be appreciated that throughout the present disclosure, unless otherwise indicated, reference to a compound of Formula (I) is intended to also include formulae (I), (I-a), (II), (III), (IV), and (V) and compound species 1-276 of such formulae disclosed herein. Further, it will be appreciated that throughout the present disclosure, unless otherwise indicated, reference to a compound of Formula (I) is intended to also include a compound of any of the subformulae describe herein, including formulae (I), (I-a), (II), (III), (IV), (V), (VI-A), (VI-B), (VII-A), and (VII-B), and and the species disclosed herein.

In some embodiments of compounds of formula (I), at least one of $R^2$, $R^a$, $R^b$, $R^c$, $R^{c'}$, $R^{c''}$, or $R^d$ is —$CO_2H$. In some embodiments of compounds of formula (I-a), at least one of $R^2$, $R^a$, $R^b$, $R^c$, $R^{c'}$, $R^{c''}$, or $R^d$ is —$CO_2H$. In some embodiments of compounds of formula (II), at least one of $R^2$, $R^a$, $R^b$, $R^c$, $R^{c'}$, or $R^d$ is —$CO_2H$. In some embodiments of compounds of formula (III), at least one of $R^2$, $R^a$, or $R^d$ is —$CO_2H$. In some embodiments of compounds of formula (IV), at least one of $R^a$, or $R^d$ is —$CO_2H$. In some embodiments of compounds of formula (V), $R^d$ is —$CO_2H$. In some embodiments of compounds of formula (VI-A), (VI-B), (VII-A), and (VII-B), $R^d$ is —$CO_2H$.

In some embodiments, compounds of the present disclosure are compounds wherein $R^c$ is hydrogen. In some embodiments, compounds of the present disclosure are compounds wherein $R^{c'}$ is hydrogen. In some embodiments, compounds of the present disclosure are compounds wherein $R^c$ and $R^{c'}$ are hydrogen.

In some embodiments, Ring A is 6-10 membered aryl. In some embodiments, $R^1$ is 3-7 membered heterocyclyl containing 1-4 heteroatoms independently selected from the group consisting of O, N, and S. In some embodiments, $R^2$ is 6-10 membered aryl substituted with 1-5 $R^d$. In some embodiments, each $R^d$ is independently —$CO_2R^3$, —$OR^3$, or 5-10 membered heteroaryl containing 1-4 heteroatoms independently selected from the group consisting of O, N, and S. In some embodiments, each $R^3$ is independently hydrogen or $C_{1-6}$ aliphatic. In some embodiments, m is 0. In some embodiments, n is 0. In some embodiments, compounds of the present disclosure are compounds wherein Ring A is 6-10 membered aryl; $R^1$ is 3-7 membered heterocyclyl containing 1-4 heteroatoms independently selected from the group consisting of O, N, and S; $R^2$ is 6-10 membered aryl substituted with 1-5 $R^d$; each $R^d$ is independently —$CO_2R^3$, —$OR^3$, or 5-10 membered heteroaryl containing 1-4 heteroatoms independently selected from the group consisting of O, N, and S; each $R^3$ is independently hydrogen or $C_{1-6}$ aliphatic; m is 0; and n is 0.

In some embodiments, $R^1$ is 3-7 membered cycloalkyl substituted with —$OR^3$. In some embodiments, each $R^d$ is independently —$CO_2R^3$ or $C_{1-6}$ aliphatic. In some embodiments, compounds of the present disclosure are compounds wherein Ring A is 6-10 membered aryl; $R^1$ is 3-7 membered cycloalkyl substituted with —$OR^3$; $R^2$ is 6-10 membered aryl substituted with 1-5 $R^d$; each $R^d$ is independently —$CO_2R^3$ or $C_{1-6}$ aliphatic; each $R^3$ is independently hydrogen or $C_{1-6}$ aliphatic; m is 0; and n is 0.

In some embodiments, Ring A is phenyl. In some embodiments, $R^1$ is 5-membered heterocyclyl containing 1-4 heteroatoms independently selected from the group consisting of O, N, and S. In some embodiments, $R^2$ is phenyl substituted with 1-5 $R^d$. In some embodiments, each $R^d$ is independently —$CO_2R^3$, —$OR^3$, or 5-membered heteroaryl containing 1-4 heteroatoms independently selected from the group consisting of O, N, and S. In some embodiments, compounds of the present disclosure are compounds wherein Ring A is phenyl; $R^1$ is 5-membered heterocyclyl containing 1-4 heteroatoms independently selected from the group consisting of O, N, and S; $R^2$ is phenyl substituted with 1-5 $R^d$; each $R^d$ is independently —$CO_2R^3$, —$OR^3$, or 5-membered heteroaryl containing 1-4 heteroatoms independently selected from the group consisting of O, N, and S; each $R^3$ is independently hydrogen or $C_{1-6}$ aliphatic; m is 0; and n is 0.

In some embodiments, $R^1$ is 3-membered cycloalkyl substituted with —$OR^3$. In some embodiments, each $R^d$ is independently —$CO_2R^3$ or $C_{1-6}$ aliphatic. In some embodiments, compounds of the present disclosure are compounds wherein, Ring A is phenyl; $R^1$ is 3-membered cycloalkyl substituted with —$OR^3$; $R^2$ is phenyl substituted with 1-5 $R^d$; each $R^d$ is independently —$CO_2R^3$ or $C_{1-6}$ aliphatic; each $R^3$ is independently hydrogen or $C_{1-6}$ aliphatic; m is 0; and n is 0.

In some embodiments of compounds of Formulae (I), (II), (III), (IV) and (V), $R^1$ is methyl, ethyl,

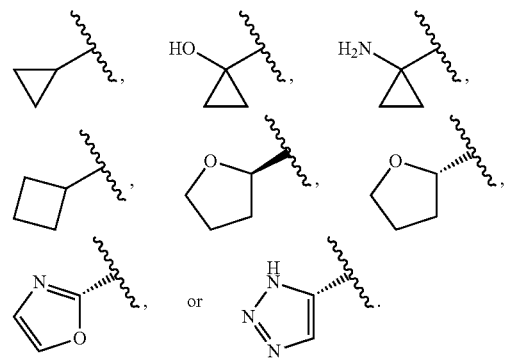

In some embodiments of compounds of Formulae (I), (II), (III), (IV), (V), (VI-A), (VI-B), (VII-A), and (VII-B), $R^1$ is methyl, ethyl,

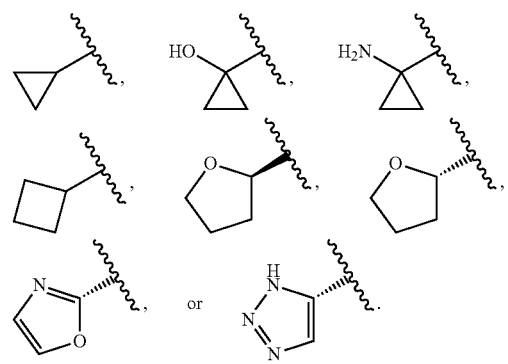

In some embodiments, $R^1$ is cyclopropyl,

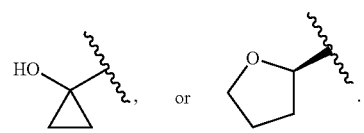 [SMILES: *C1(O)CC1 ; *[C@H]1CCCO1]

In some embodiments, $R^1$ is

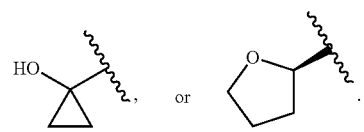 [SMILES: *C1(O)CC1 ; *[C@H]1CCCO1]

In some embodiments, $R^1$ is

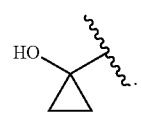

In some embodiments, R¹ is
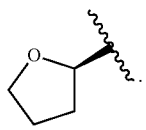
In some embodiments, R² is —CO₂R³ or an optionally substituted group selected from the group consisting of phenyl,
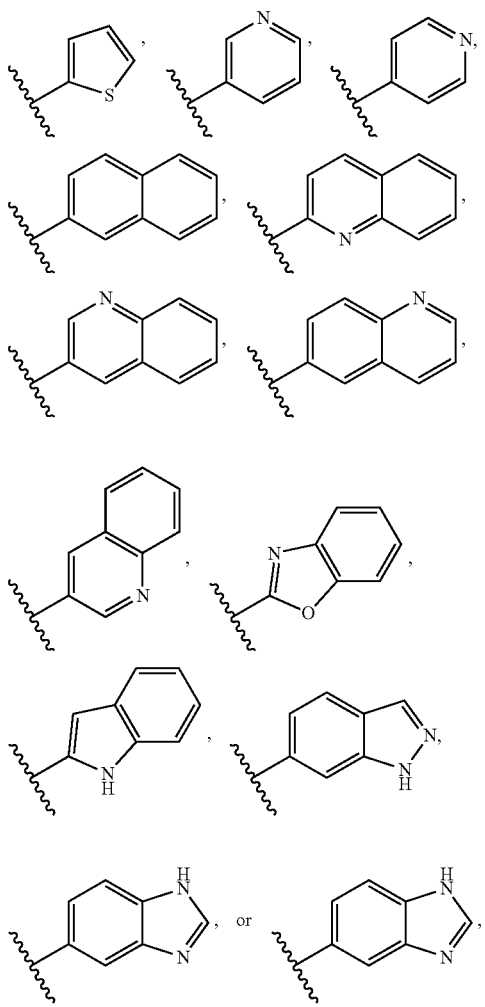
wherein an R² is optionally substituted with 1-6 R$^d$.
In some embodiments, R² is
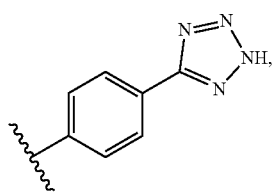
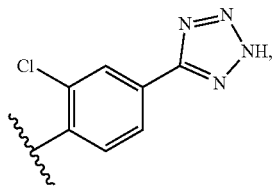
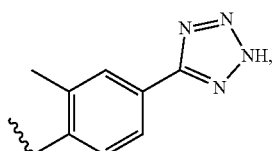
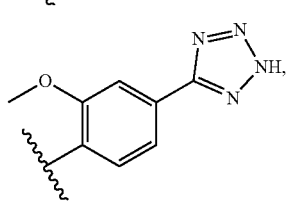
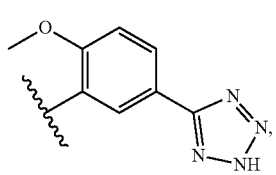
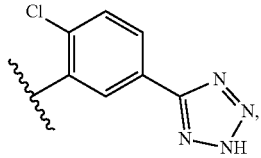
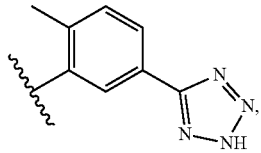
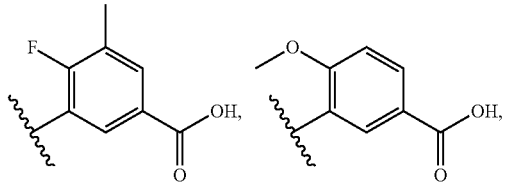
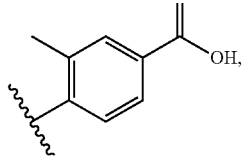
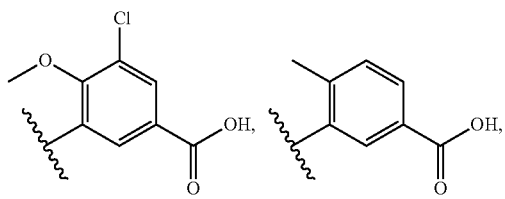

-continued
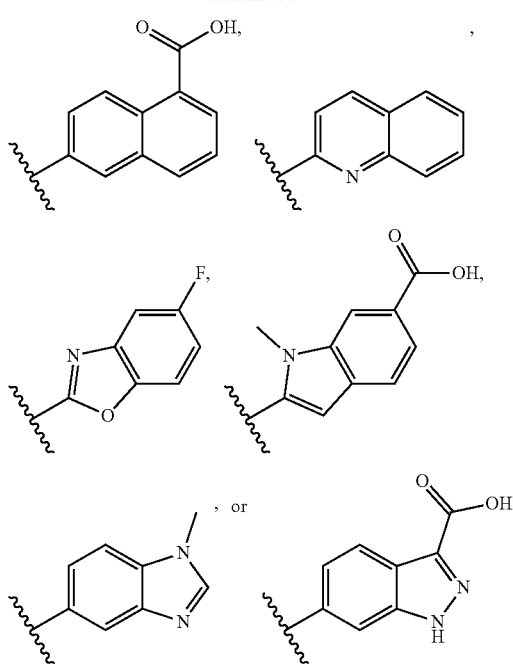
In some embodiments, $R^2$ is
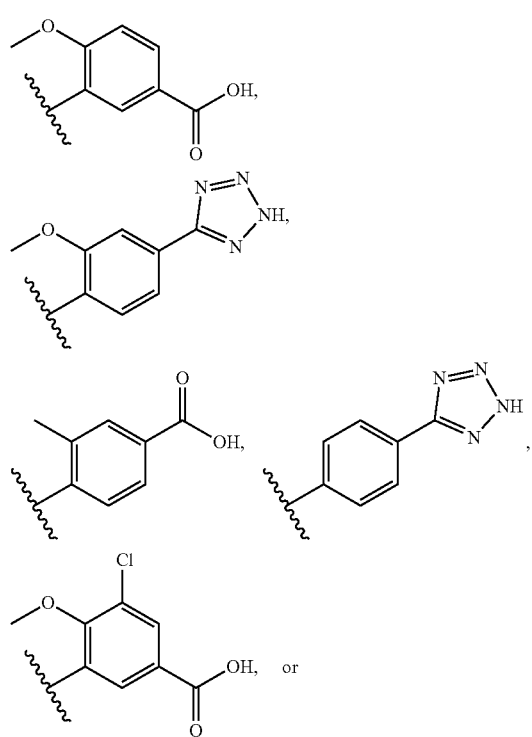
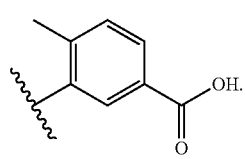 [SMILES: *c1cc(C(=O)O)ccc1C]
In some embodiments, $R^2$ is
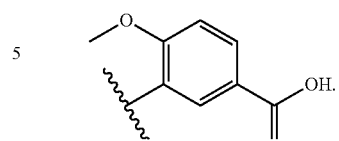
In some embodiments, $R^2$ is
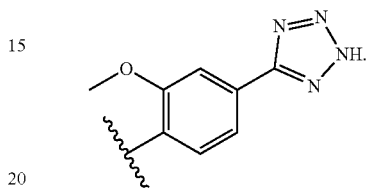
In some embodiments, $R^2$ is
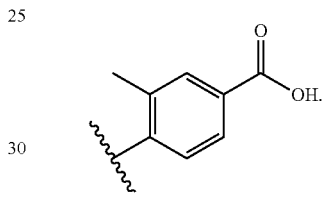
In some embodiments, $R^2$ is
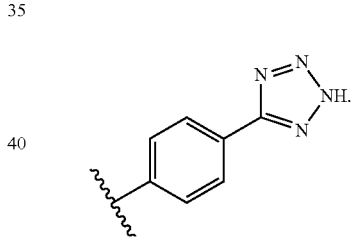
In some embodiments, $R^2$ is
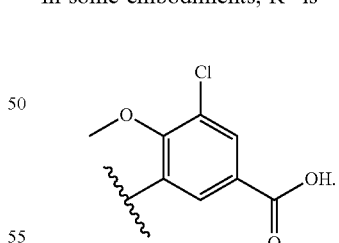
In some embodiments, $R^2$ is
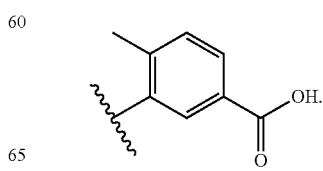

In some embodiments, a provided compound is selected from a group consisting of those described in FIG. 1, or a pharmaceutically acceptable salt thereof.

Figures 1, 2:
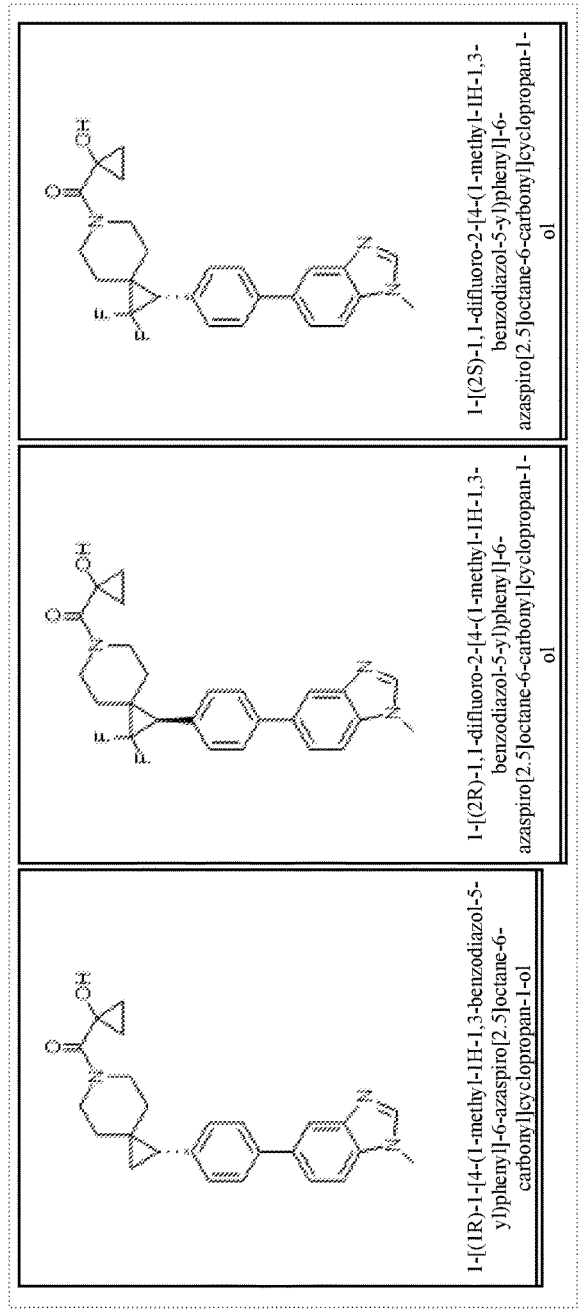
FIG. 2 is a table of compounds in accordance with an embodiment of the present disclosure, along with IC$_{50}$, MS, and NMR data for such compounds.

In some embodiments, the disclosure relates to a compound selected from FIG. 2, or a pharmaceutically acceptable salt thereof. In some embodiments, the compound is the first eluting isomer under the conditions specified in the corresponding example. In some embodiments, the compound is the second eluting isomer under the conditions specified in the corresponding example. In some embodiments, the compound is the third eluting isomer under the conditions specified in the corresponding example. In some embodiments, the compound is the fourth eluting isomer under the conditions specified in the corresponding example.

Figures 1, 2, 3:
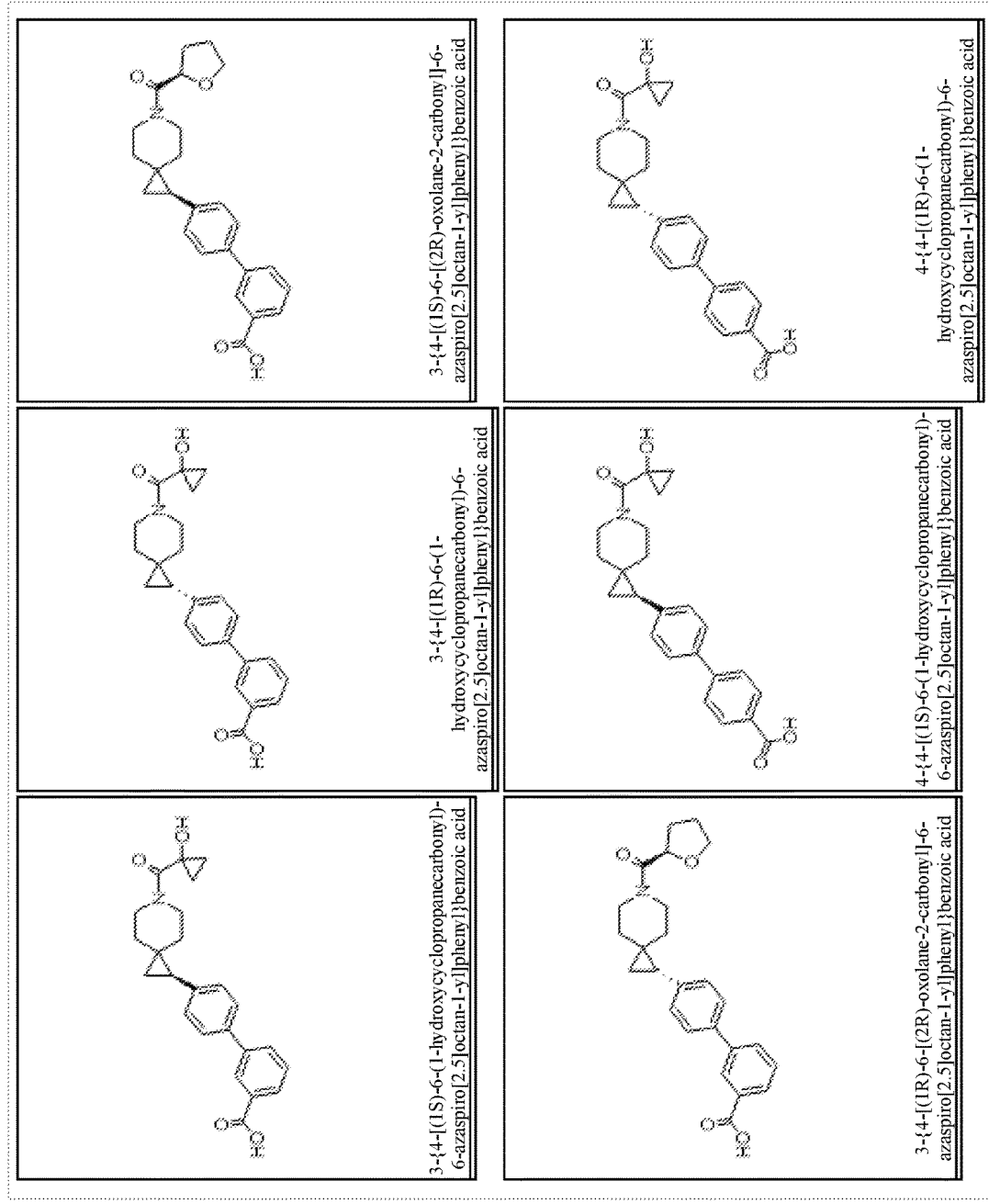
FIG. 3 is a table of compounds in accordance with an embodiment of the present disclosure, along with IC$_{50}$ data for such compounds.
Figures 1, 2, 3, 4:
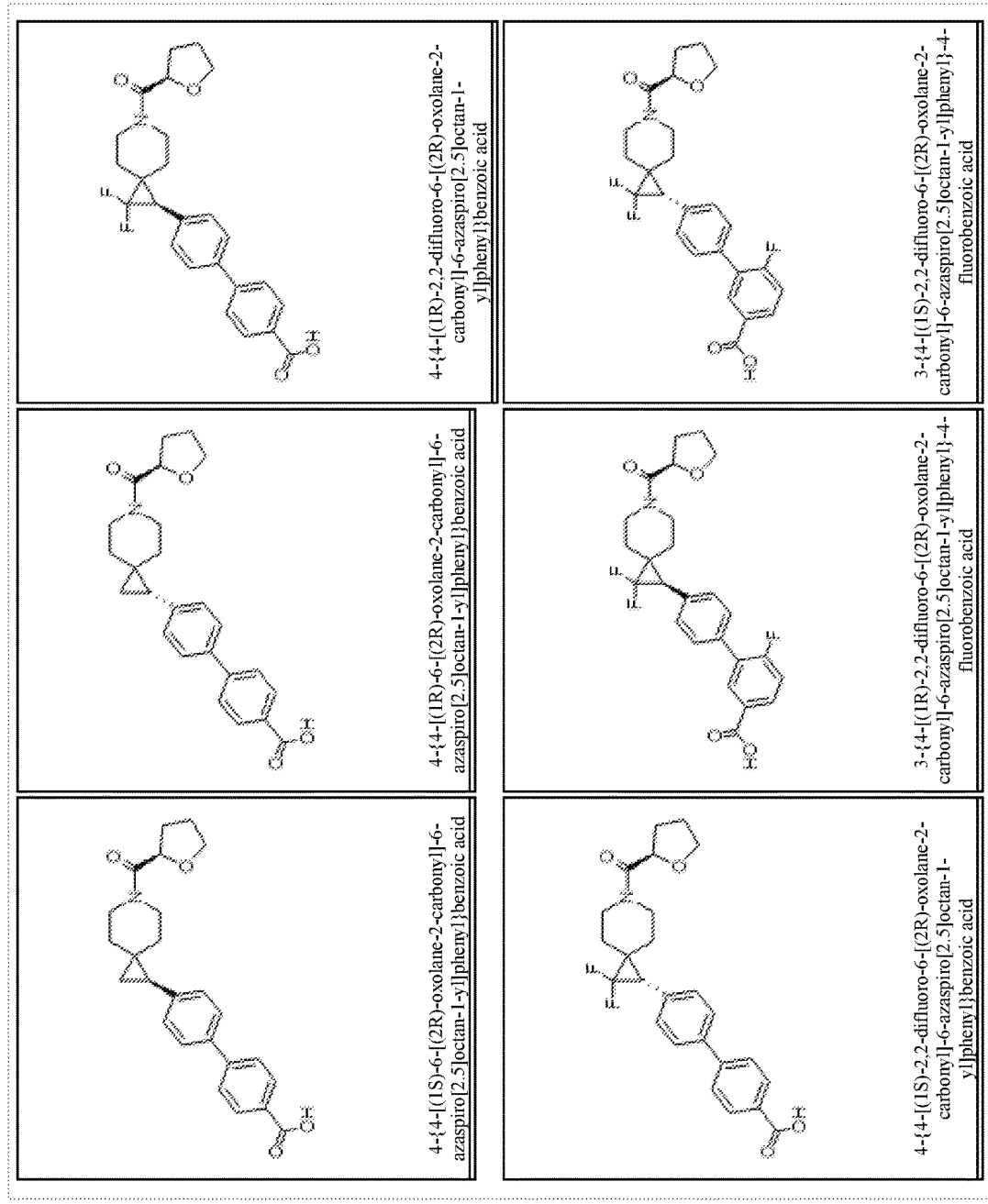
Figures 1, 2, 3, 4, 5:
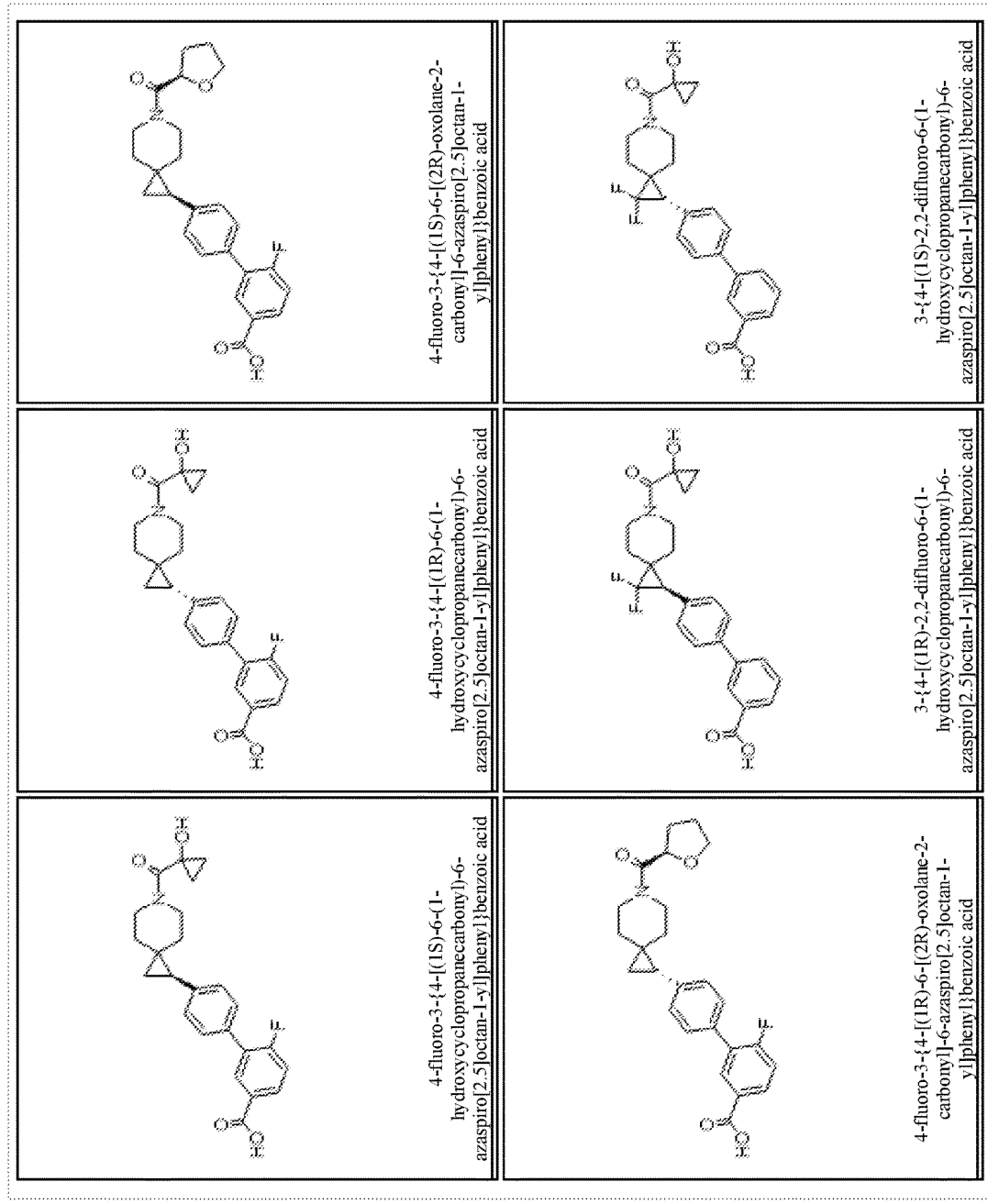
Figures 1, 2, 3, 4, 5, 6:
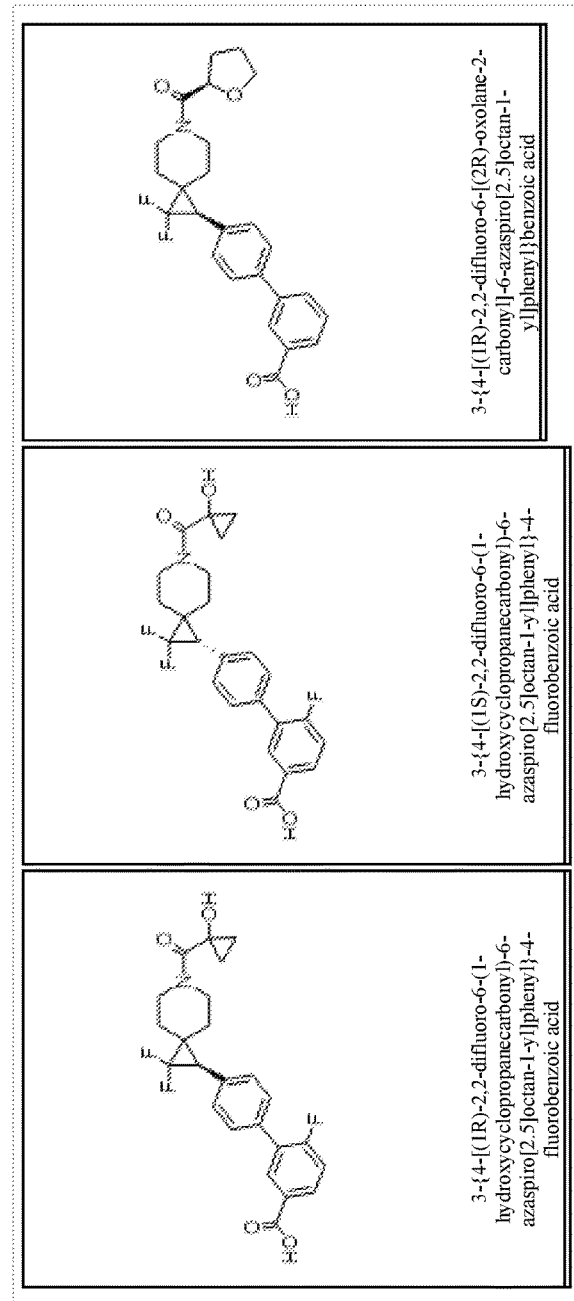
Figures 1, 2, 3, 4, 5, 6, 7:
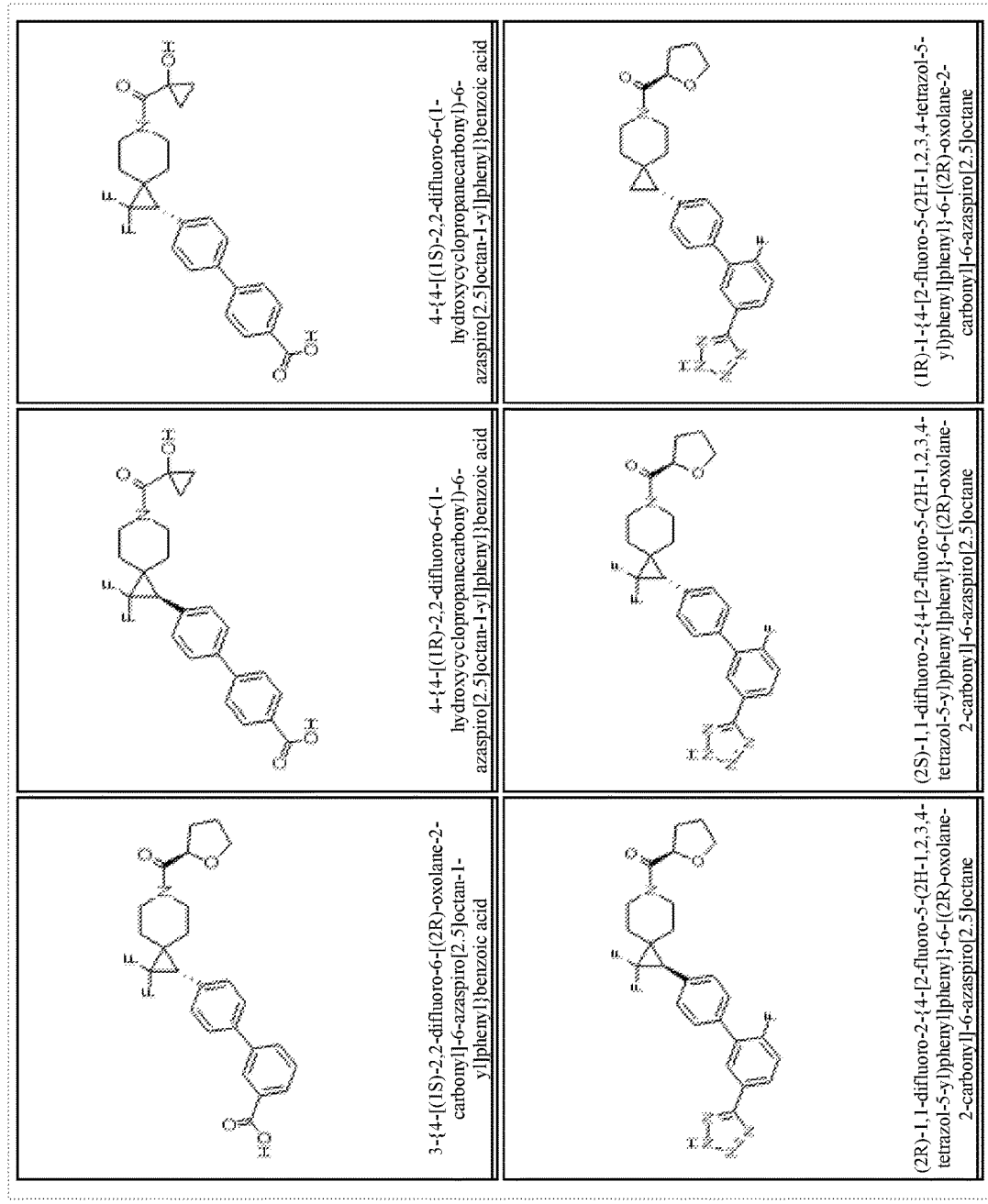
Figures 1, 2, 3, 4, 5, 6, 7, 8:
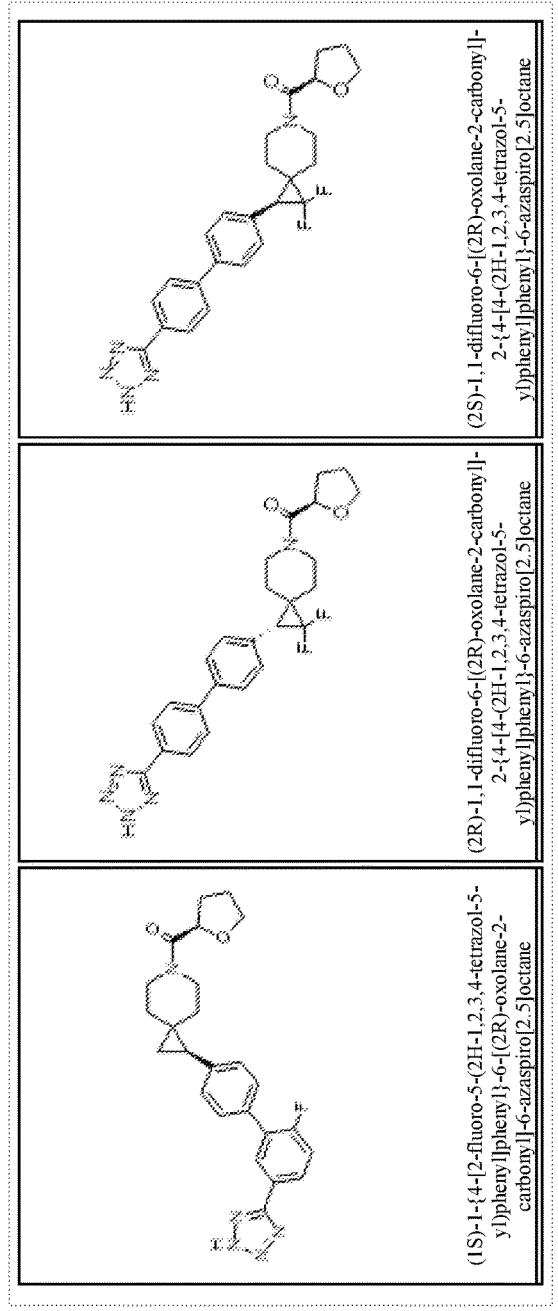
Figures 1, 2, 3, 4, 5, 6, 7, 8, 9:
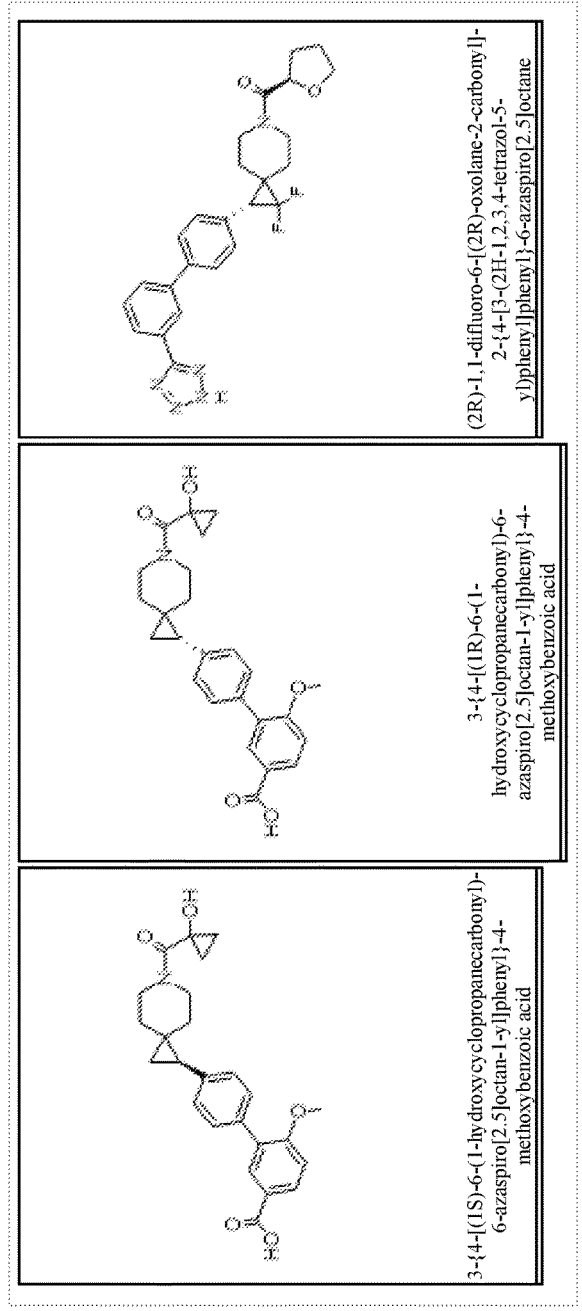
Figures 1, 2, 3, 4, 5, 6, 7, 8, 9, 10:
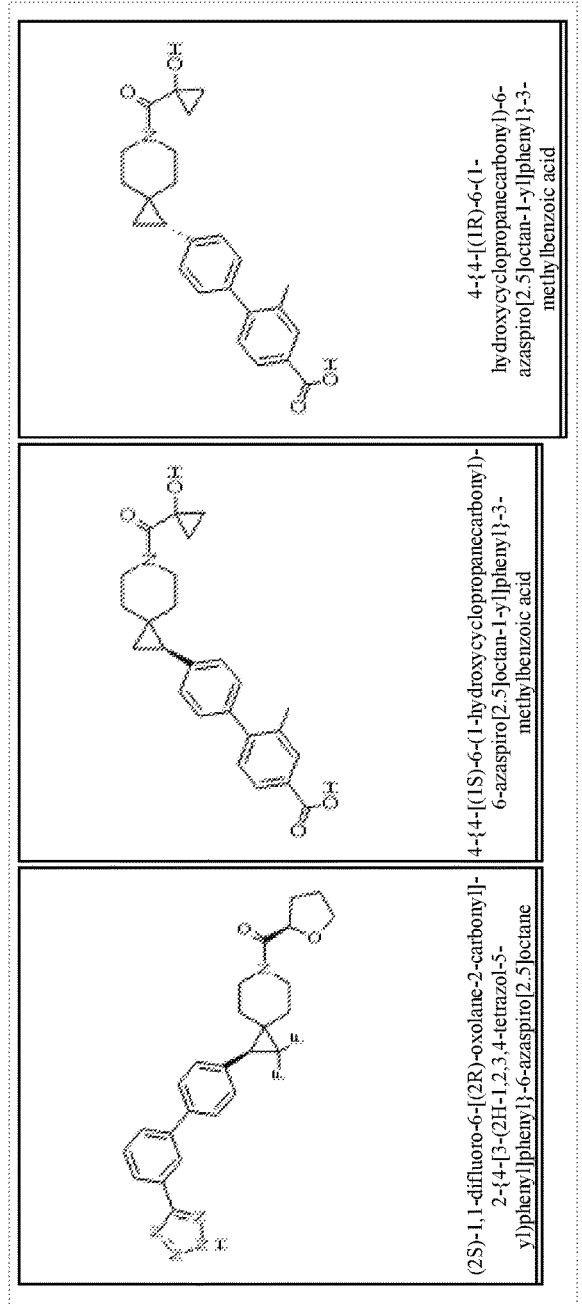
Figures 1, 2, 3, 4, 5, 6, 7, 8, 9, 10, 11:
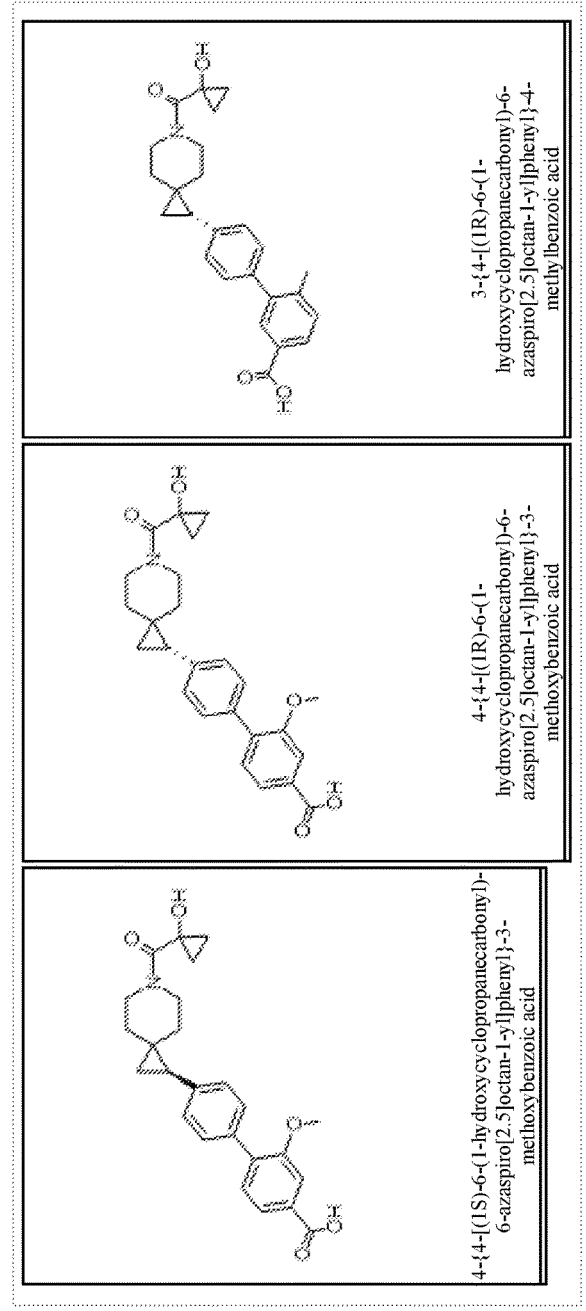
Figures 1, 2, 3, 4, 5, 6, 7, 8, 9, 10, 11, 12:
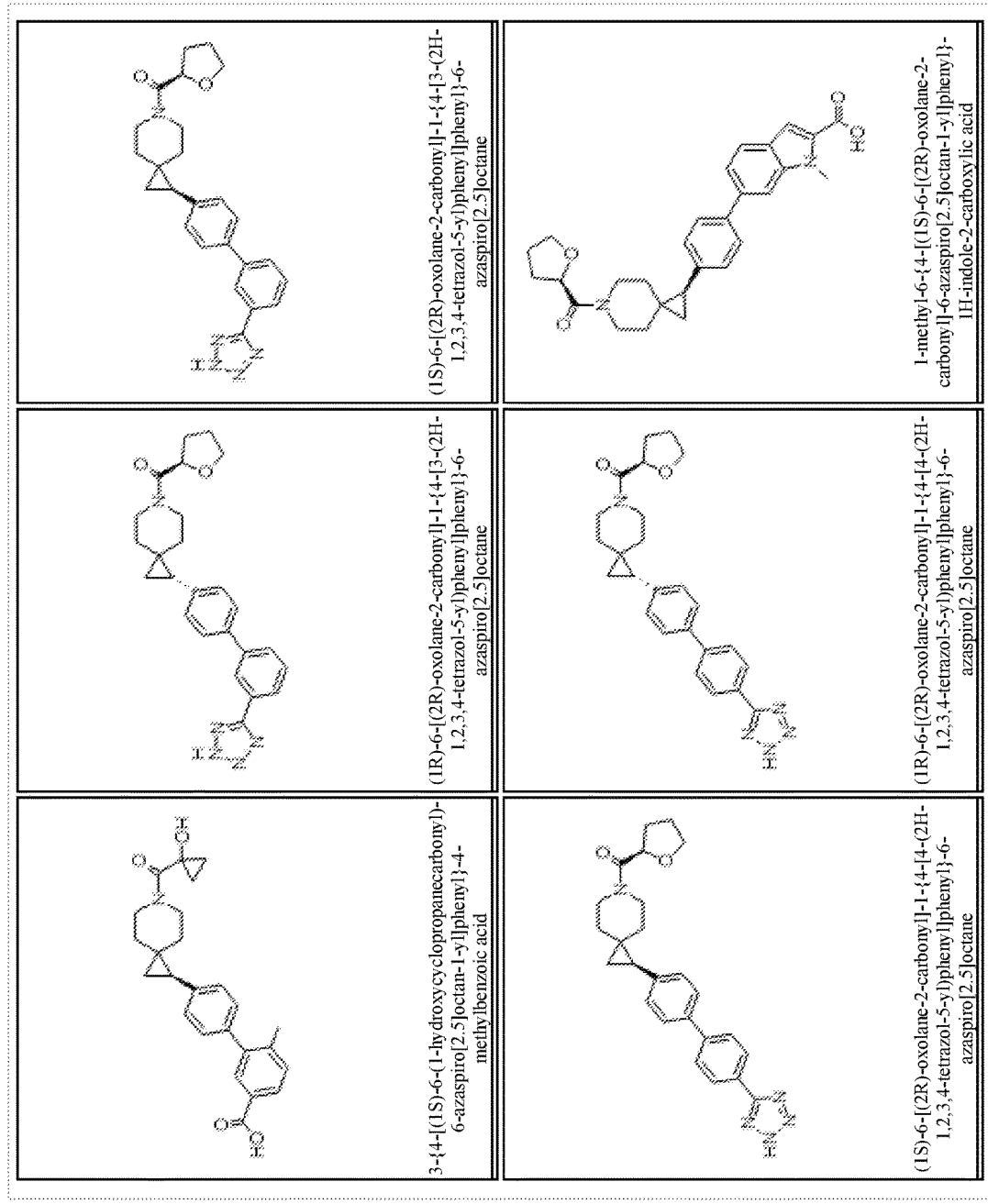
Figures 1, 2, 3, 4, 5, 6, 7, 8, 9, 10, 11, 12, 13:
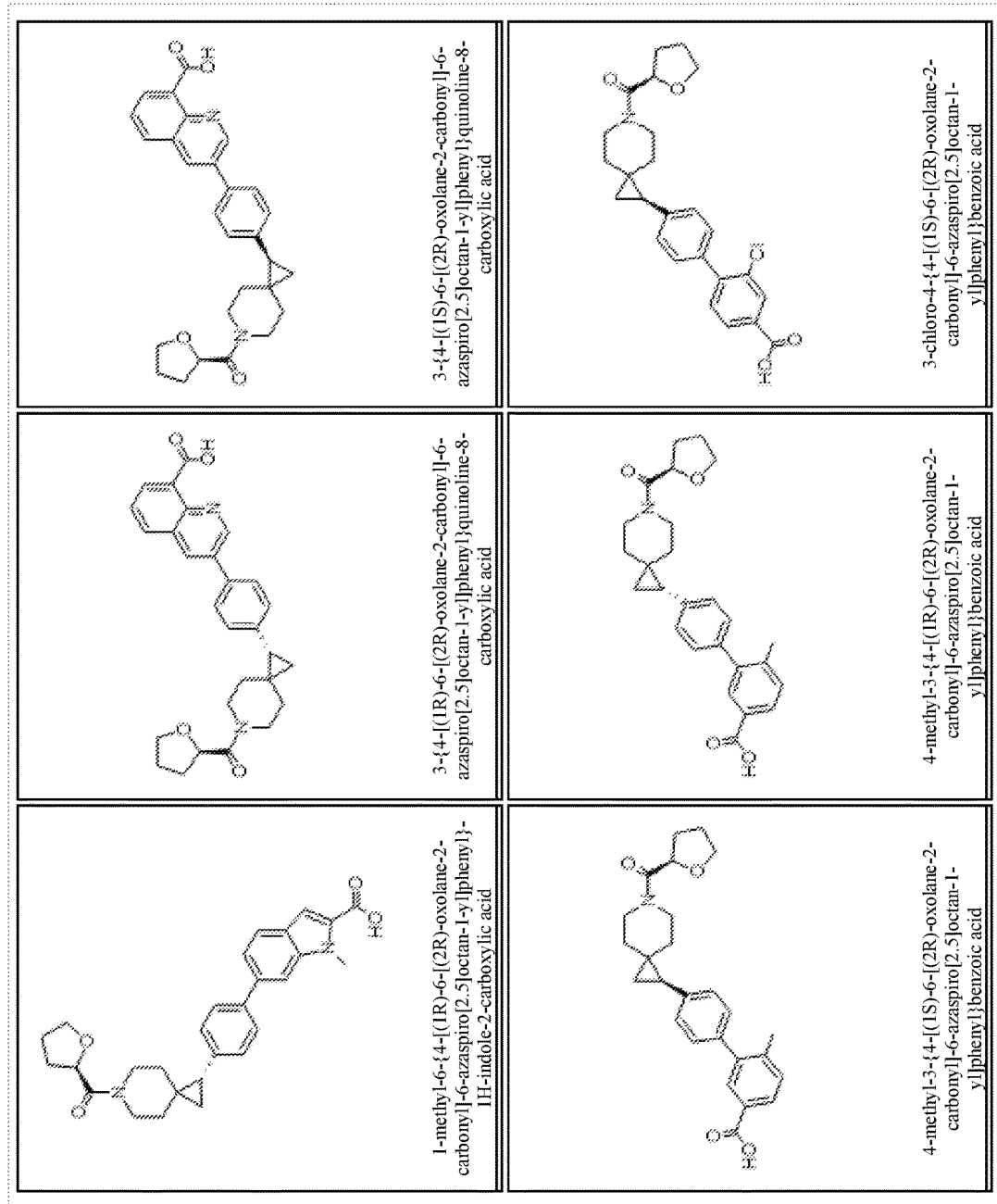
Figures 1, 2, 3, 4, 5, 6, 7, 8, 9, 10, 11, 12, 13, 14:
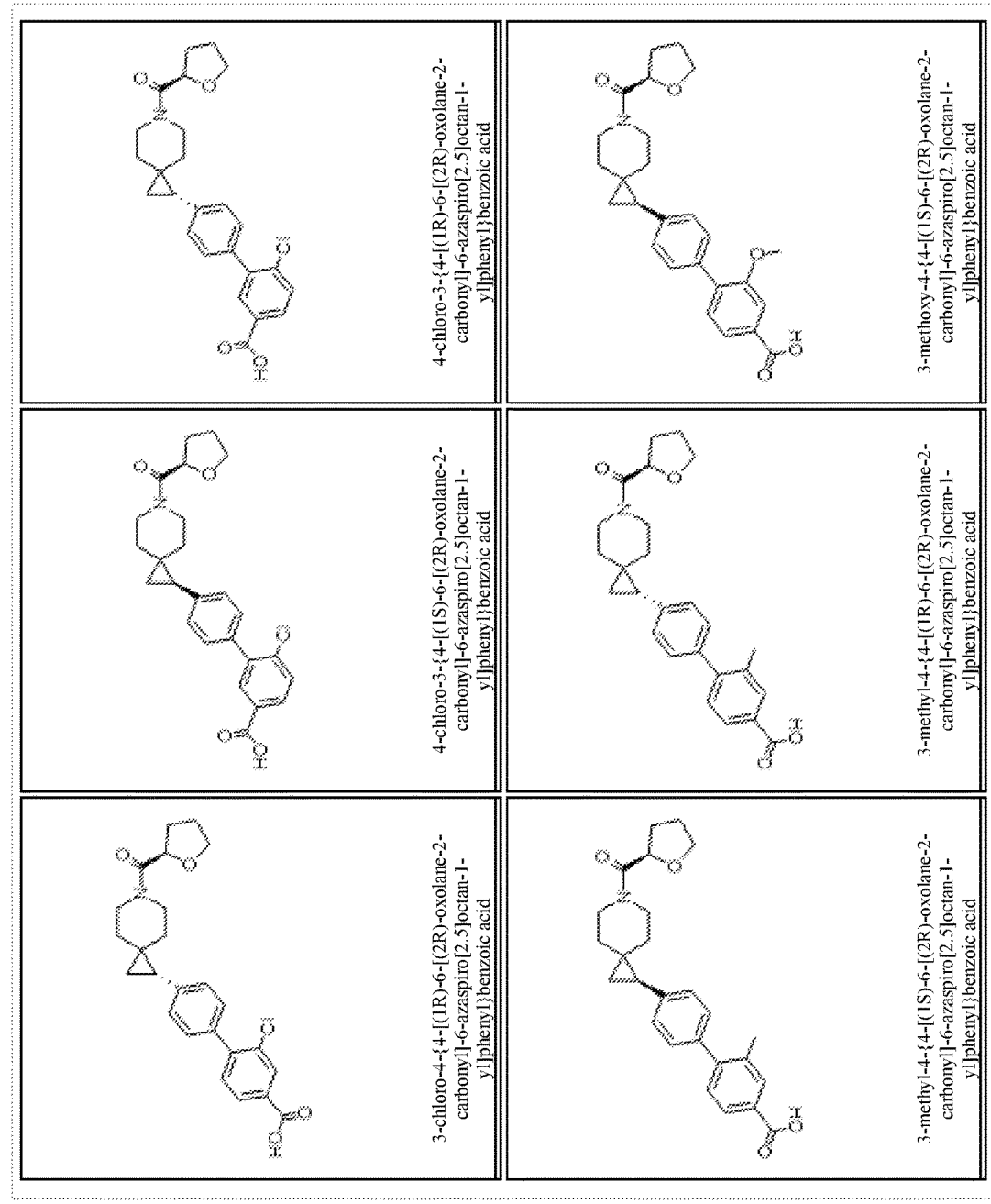
Figures 1, 2, 3, 4, 5, 6, 7, 8, 9, 10, 11, 12, 13, 14, 15:
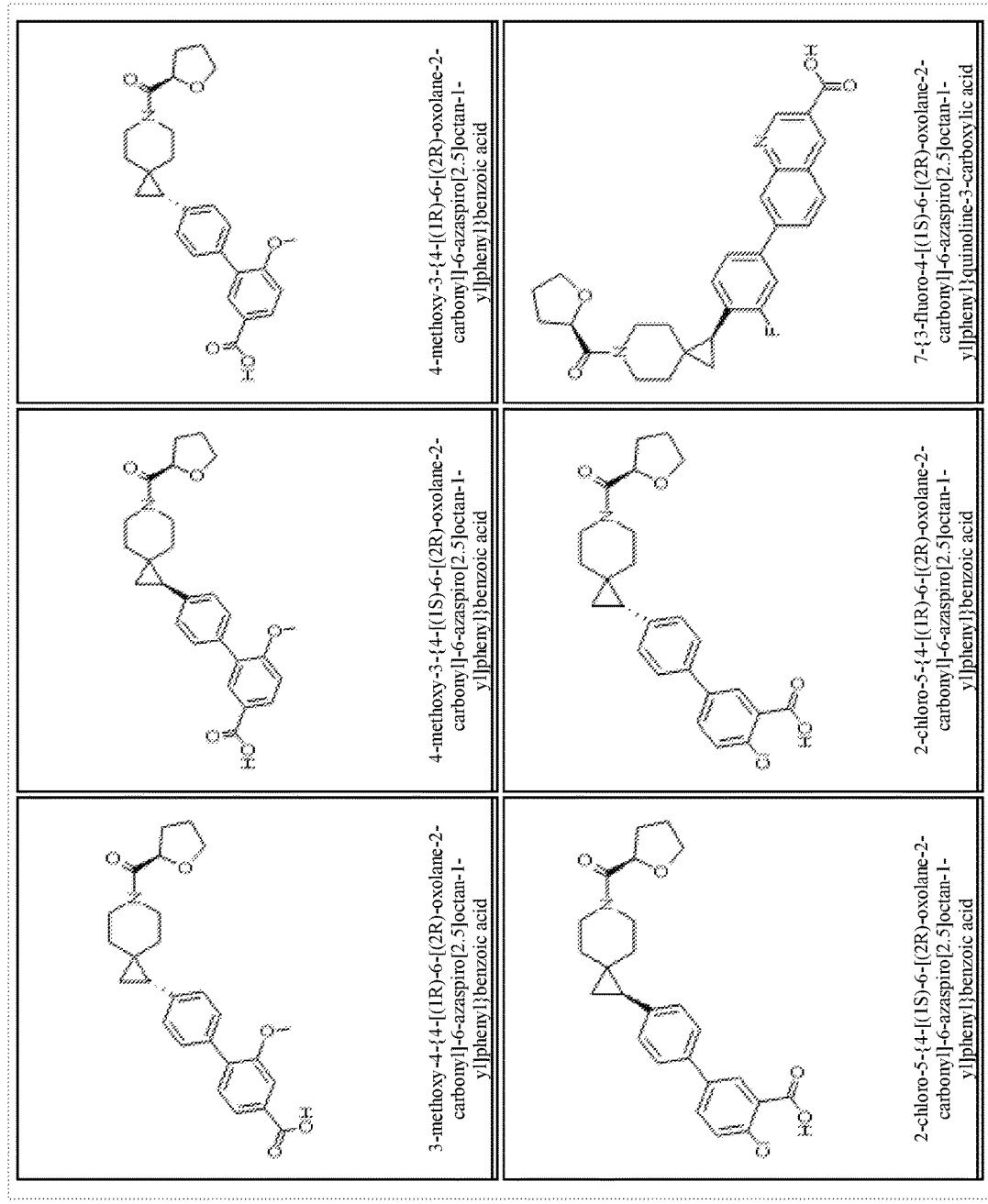
Figures 1, 2, 3, 4, 5, 6, 7, 8, 9, 10, 11, 12, 13, 14, 15, 16:
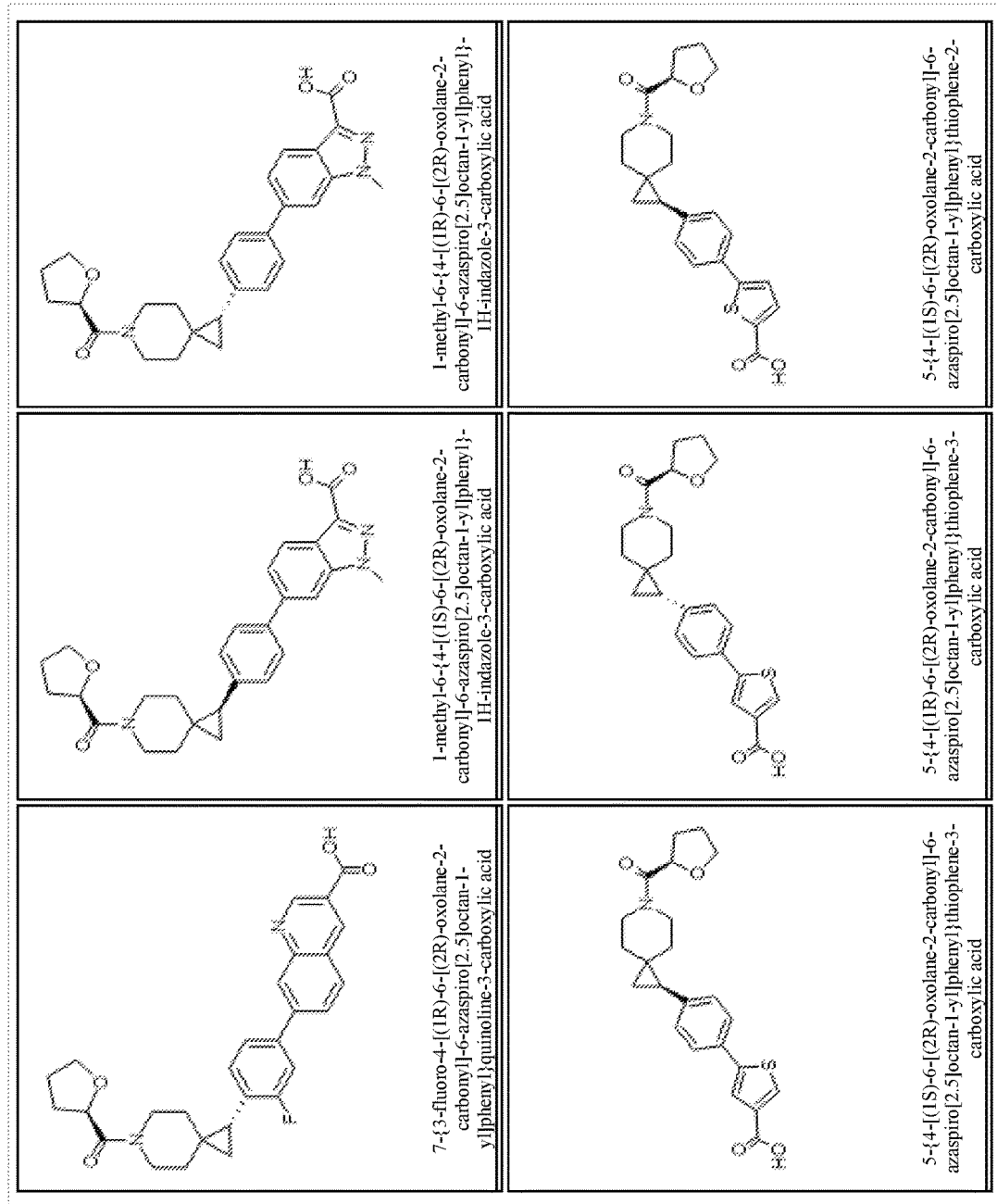
Figures 1, 2, 3, 4, 5, 6, 7, 8, 9, 10, 11, 12, 13, 14, 15, 16, 17:
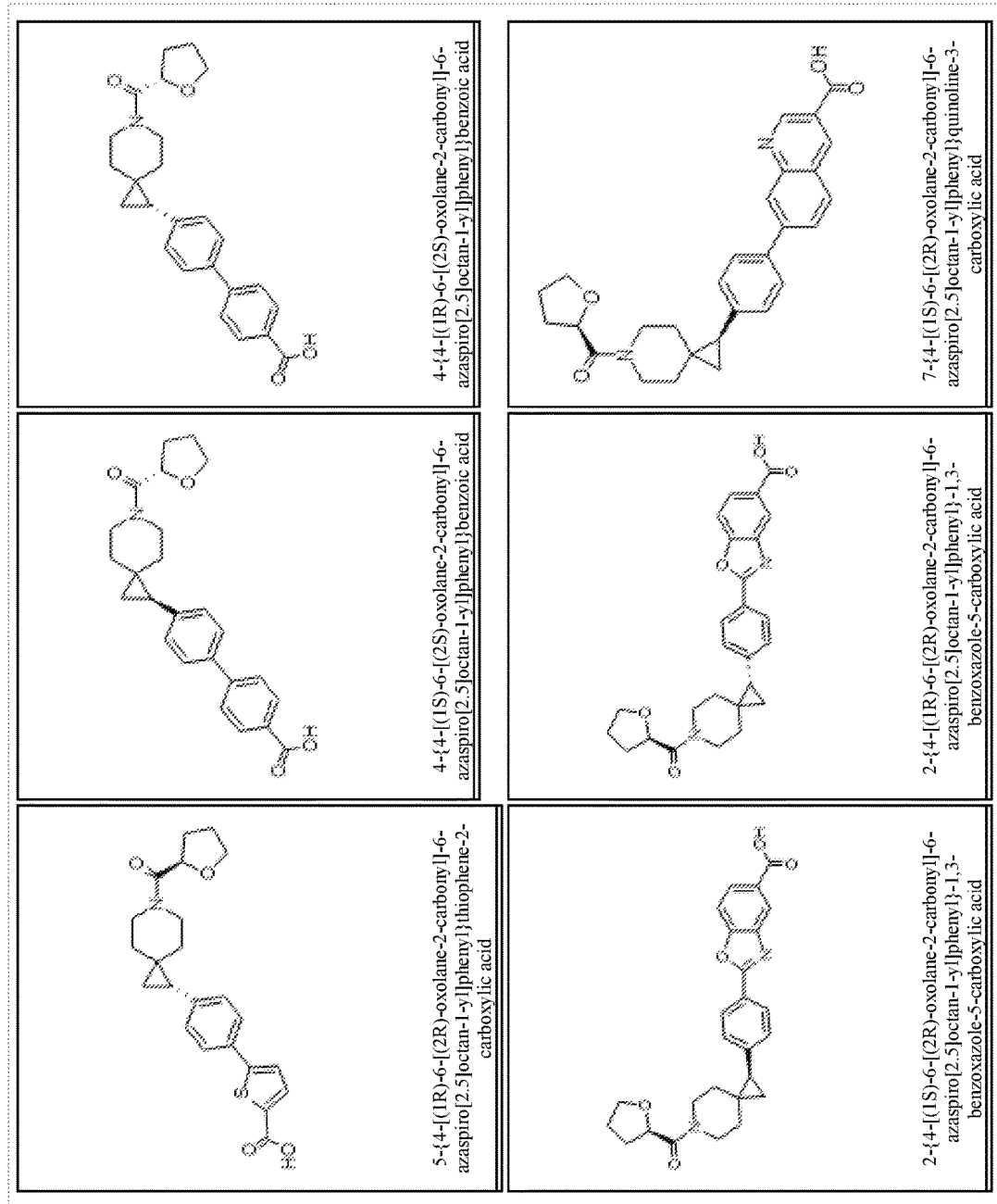
Figures 1, 2, 3, 4, 5, 6, 7, 8, 9, 10, 11, 12, 13, 14, 15, 16, 17, 18:
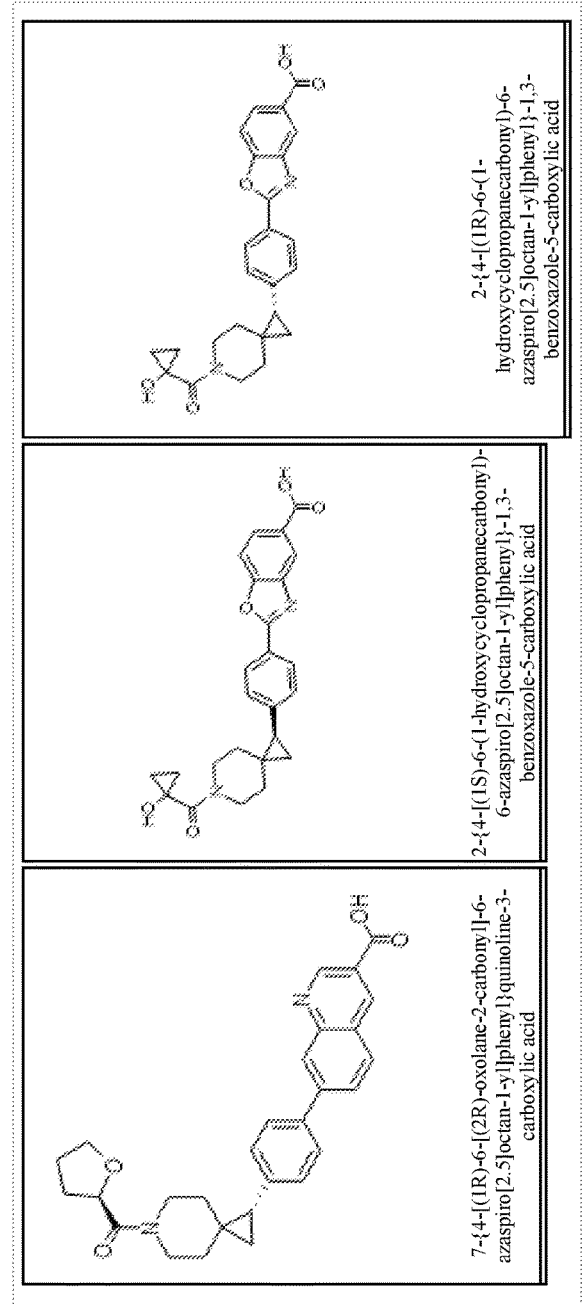
Figures 1, 2, 3, 4, 5, 6, 7, 8, 9, 10, 11, 12, 13, 14, 15, 16, 17, 18, 19:
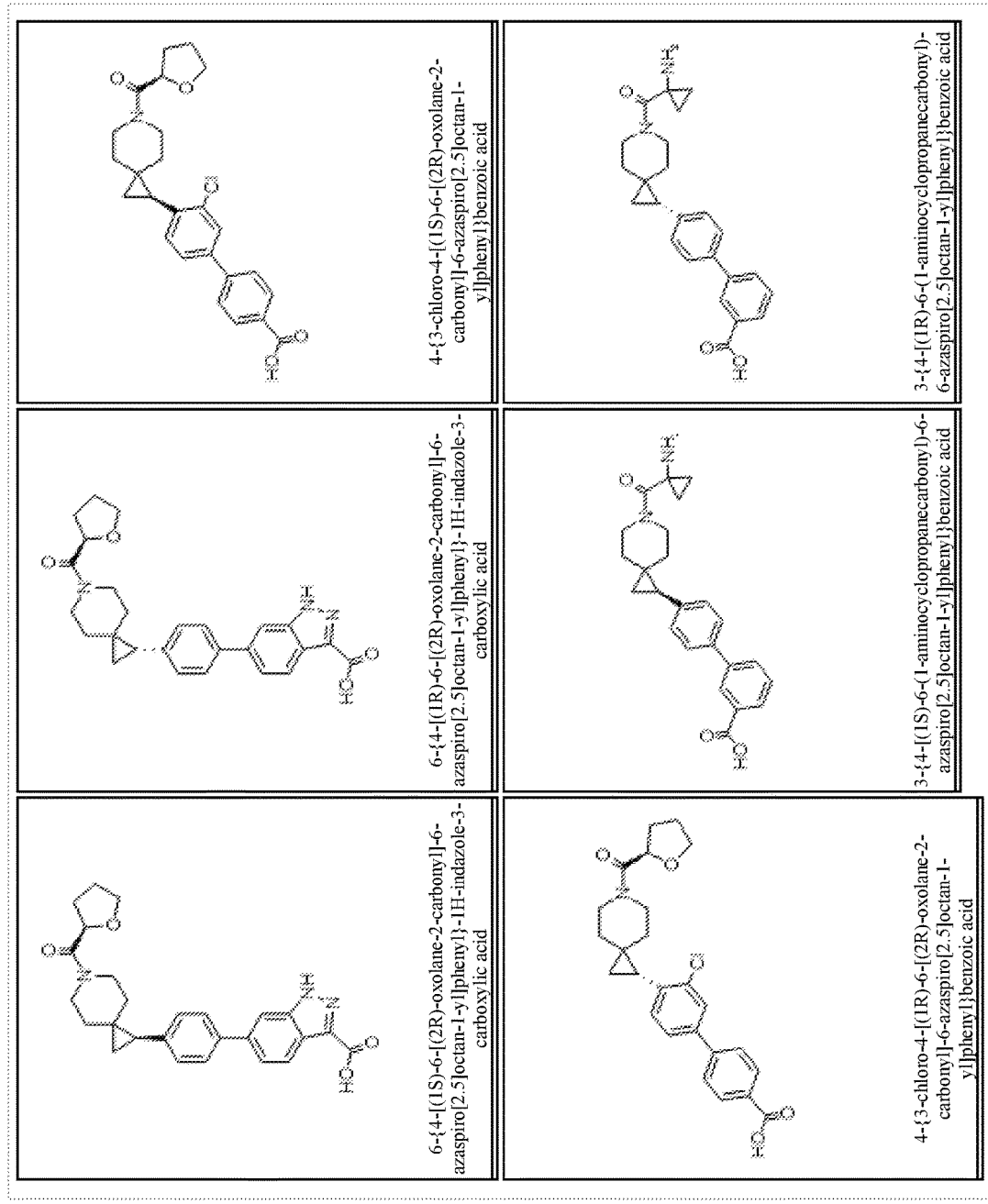
Figures 1, 2, 3, 4, 5, 6, 7, 8, 9, 10, 11, 12, 13, 14, 15, 16, 17, 18, 19, 20:
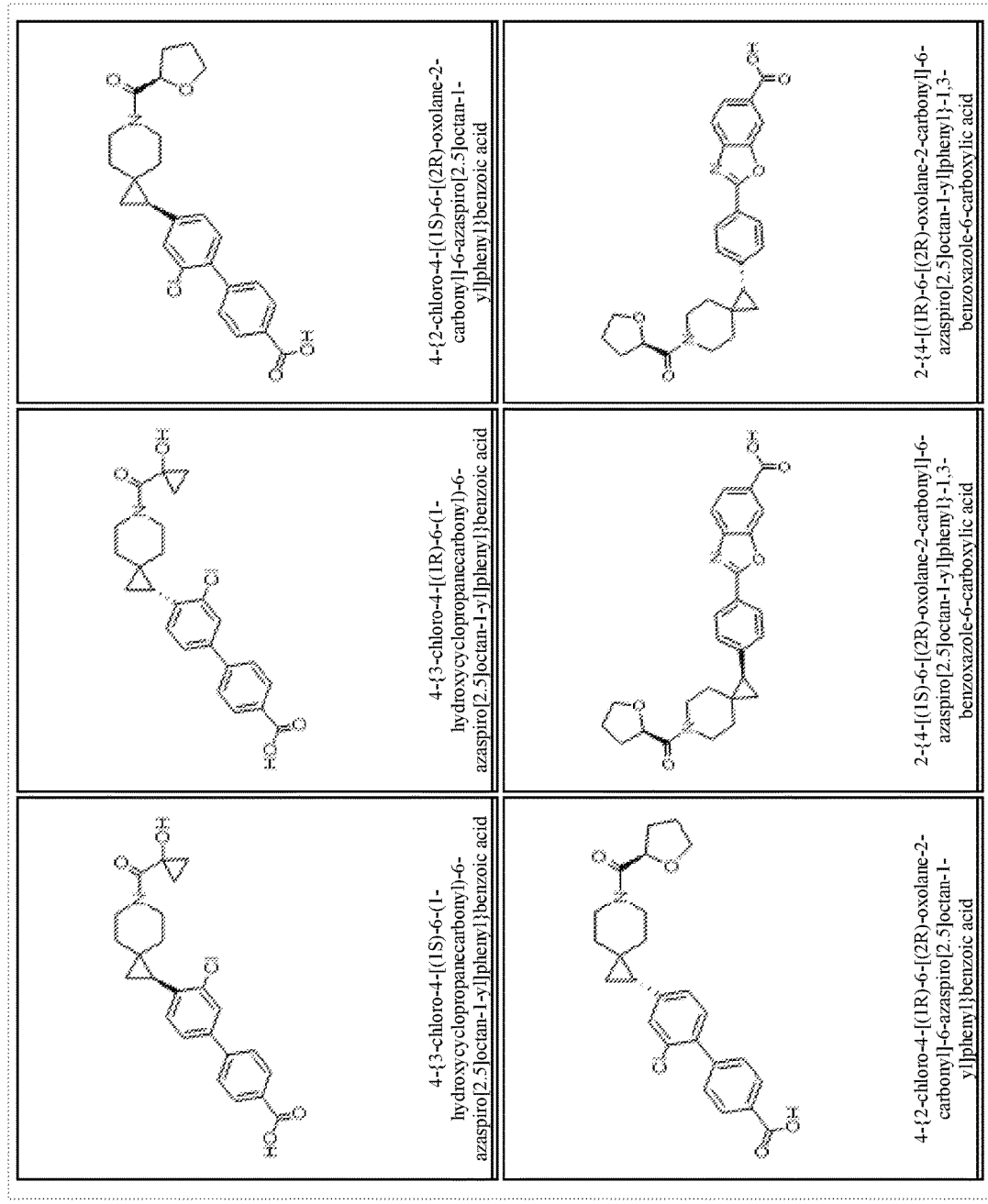
Figures 1, 2, 3, 4, 5, 6, 7, 8, 9, 10, 11, 12, 13, 14, 15, 16, 17, 18, 19, 20, 21:
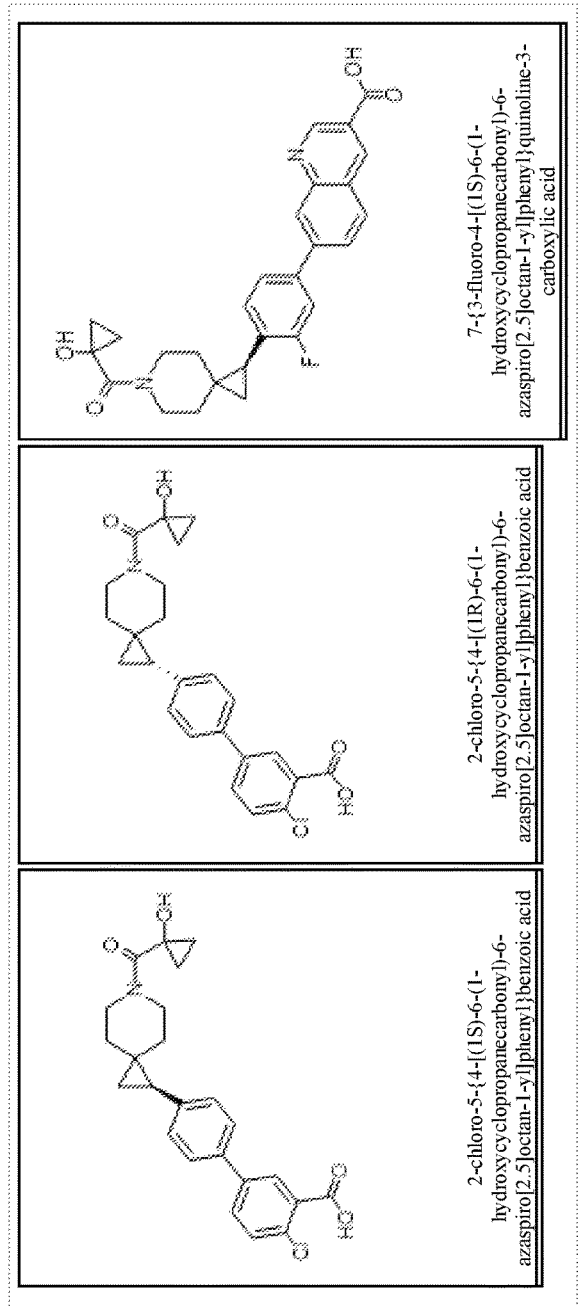
Figures 1, 2, 3, 4, 5, 6, 7, 8, 9, 10, 11, 12, 13, 14, 15, 16, 17, 18, 19, 20, 21, 22:
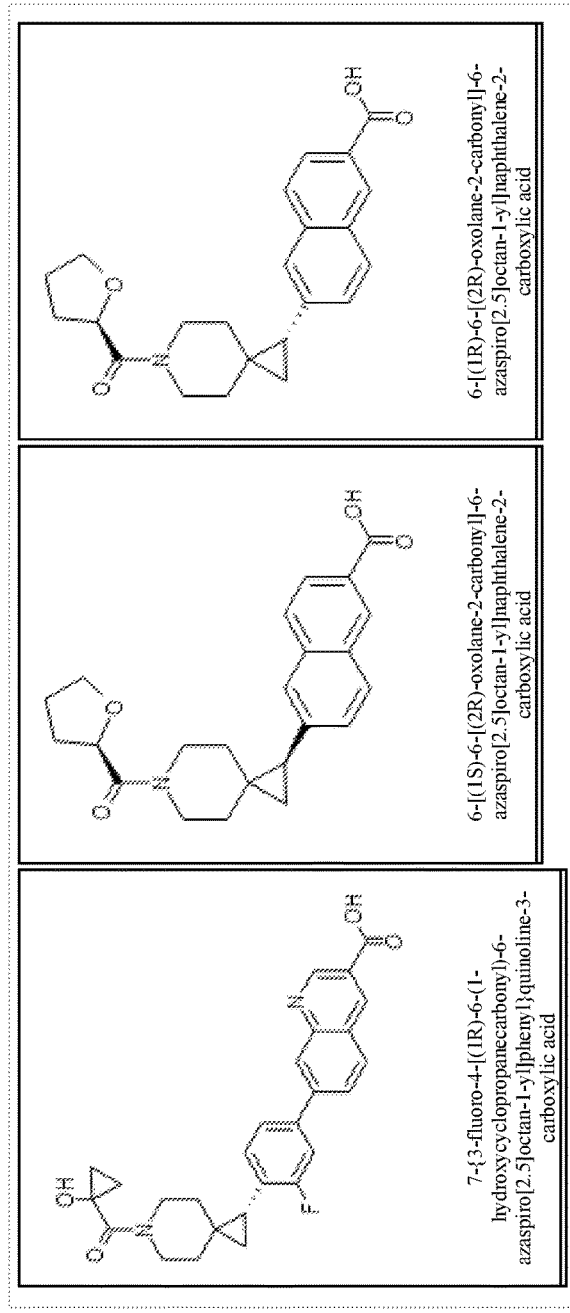
Figures 1, 2, 3, 4, 5, 6, 7, 8, 9, 10, 11, 12, 13, 14, 15, 16, 17, 18, 19, 20, 21, 22, 23:
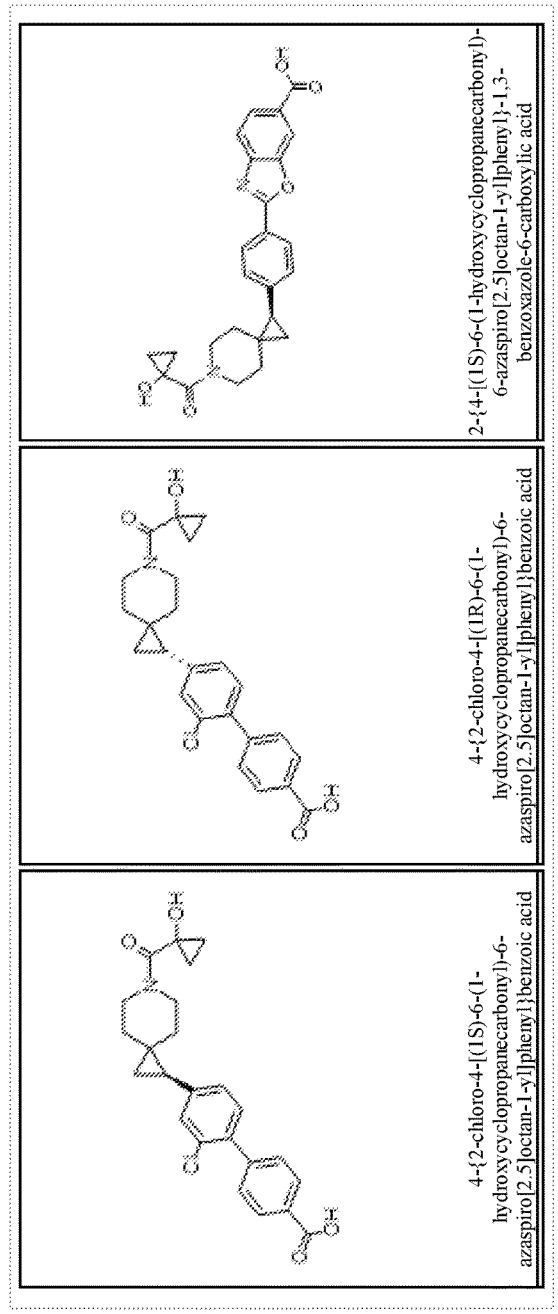
Figures 1, 2, 3, 4, 5, 6, 7, 8, 9, 10, 11, 12, 13, 14, 15, 16, 17, 18, 19, 20, 21, 22, 23, 24:
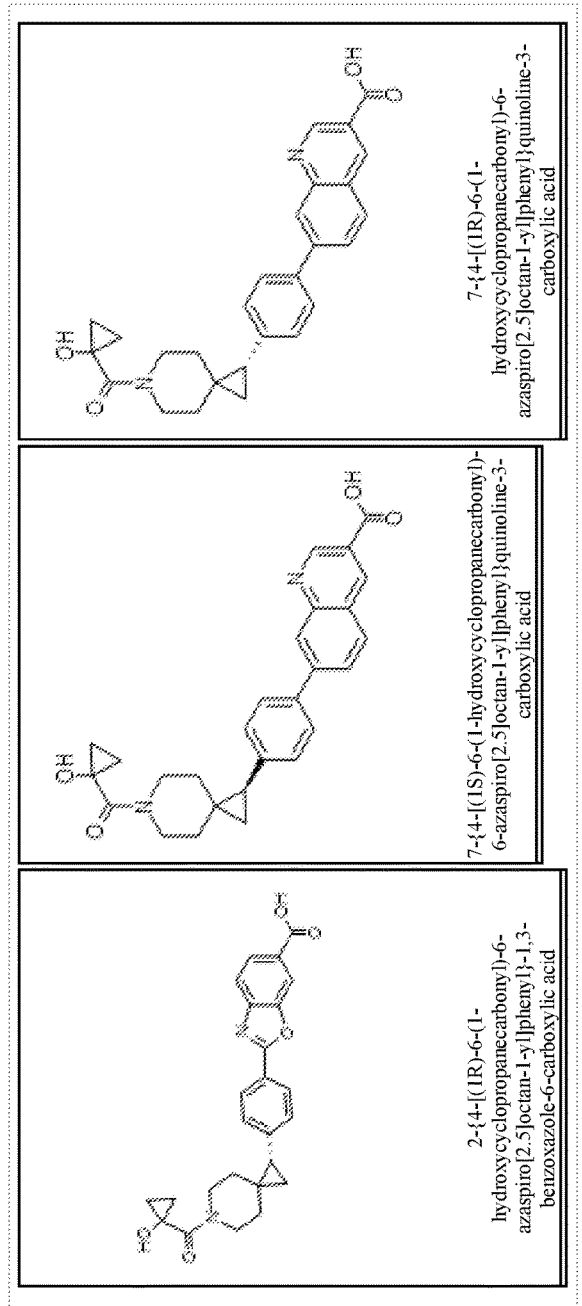
Figures 1, 2, 3, 4, 5, 6, 7, 8, 9, 10, 11, 12, 13, 14, 15, 16, 17, 18, 19, 20, 21, 22, 23, 24, 25:
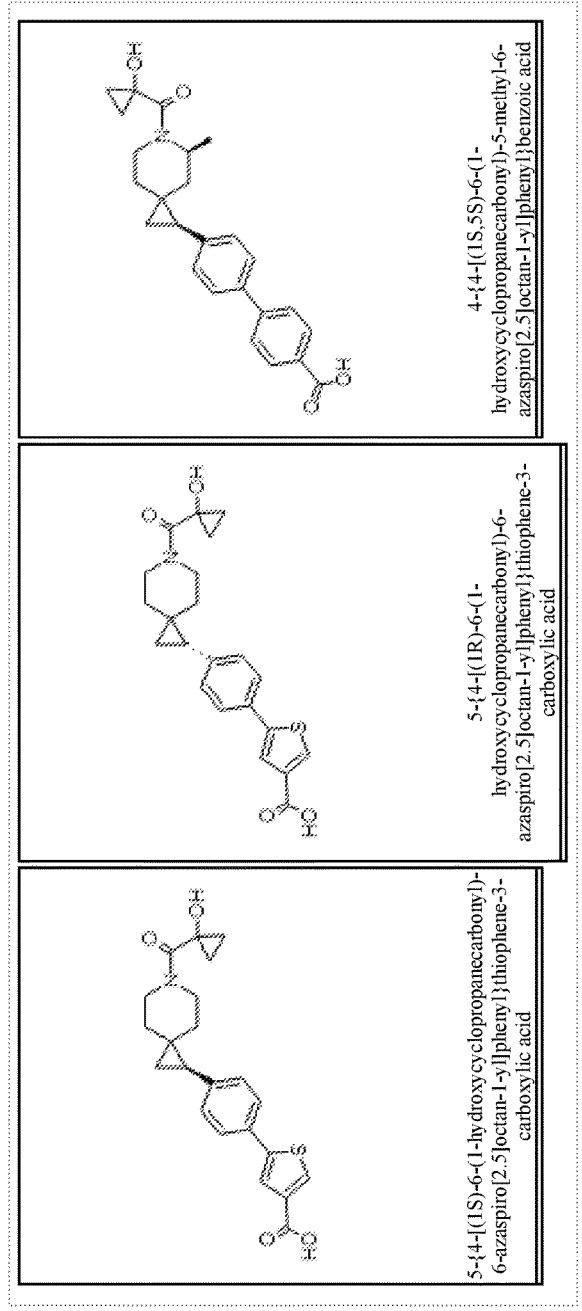
Figures 1, 2, 3, 4, 5, 6, 7, 8, 9, 10, 11, 12, 13, 14, 15, 16, 17, 18, 19, 20, 21, 22, 23, 24, 25, 26:
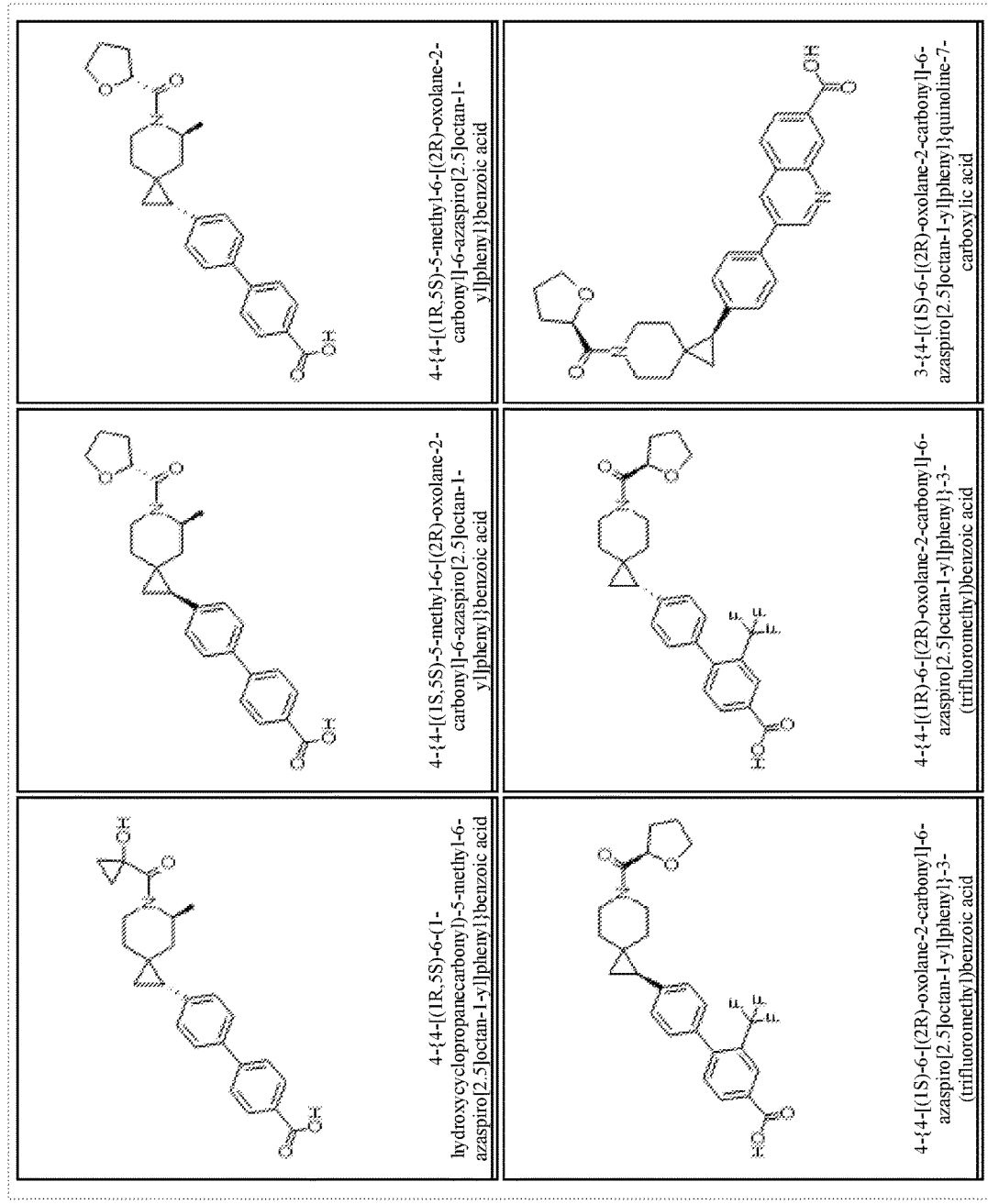
Figures 1, 2, 3, 4, 5, 6, 7, 8, 9, 10, 11, 12, 13, 14, 15, 16, 17, 18, 19, 20, 21, 22, 23, 24, 25, 26, 27:
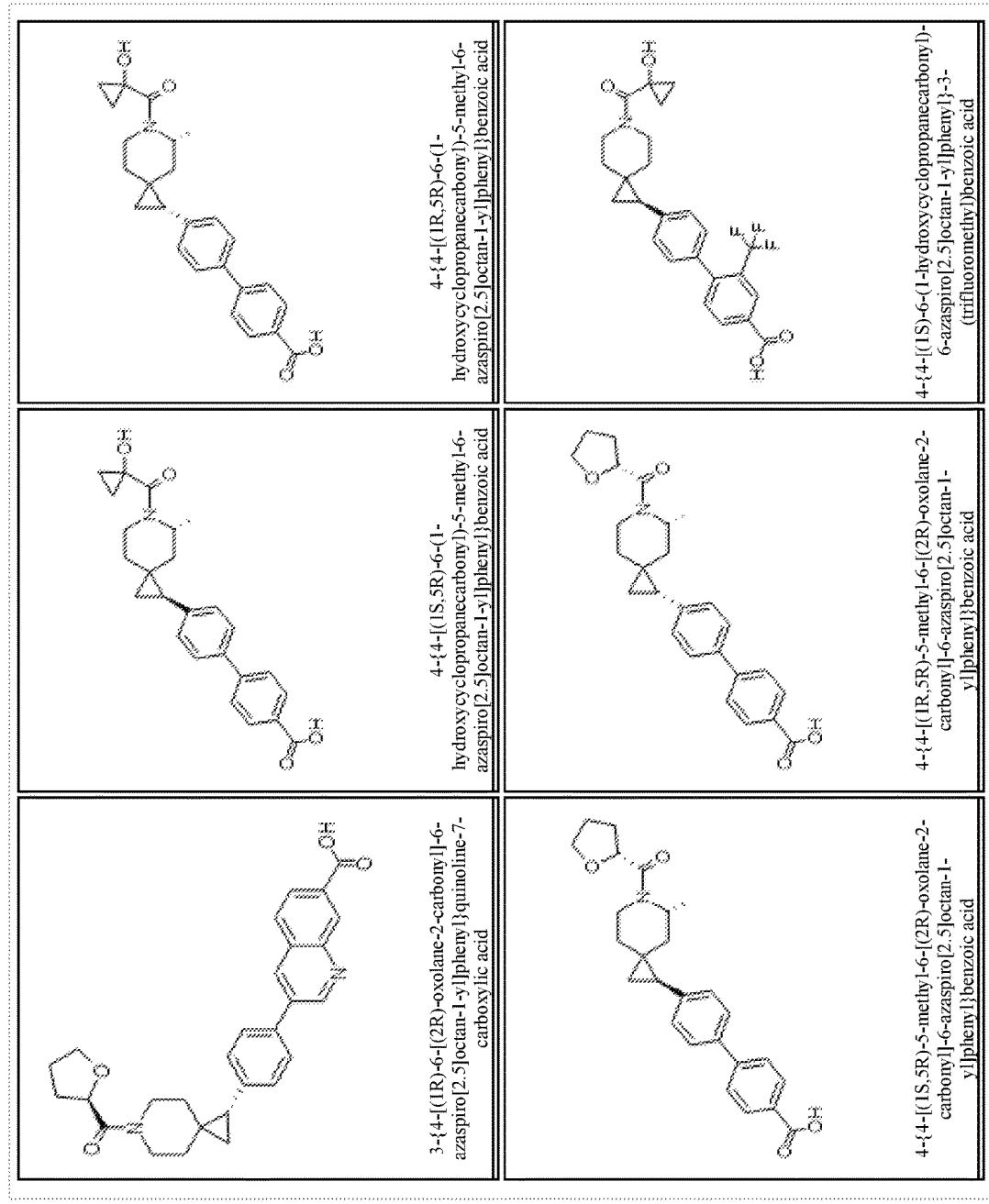
Figures 1, 2, 3, 4, 5, 6, 7, 8, 9, 10, 11, 12, 13, 14, 15, 16, 17, 18, 19, 20, 21, 22, 23, 24, 25, 26, 27, 28:
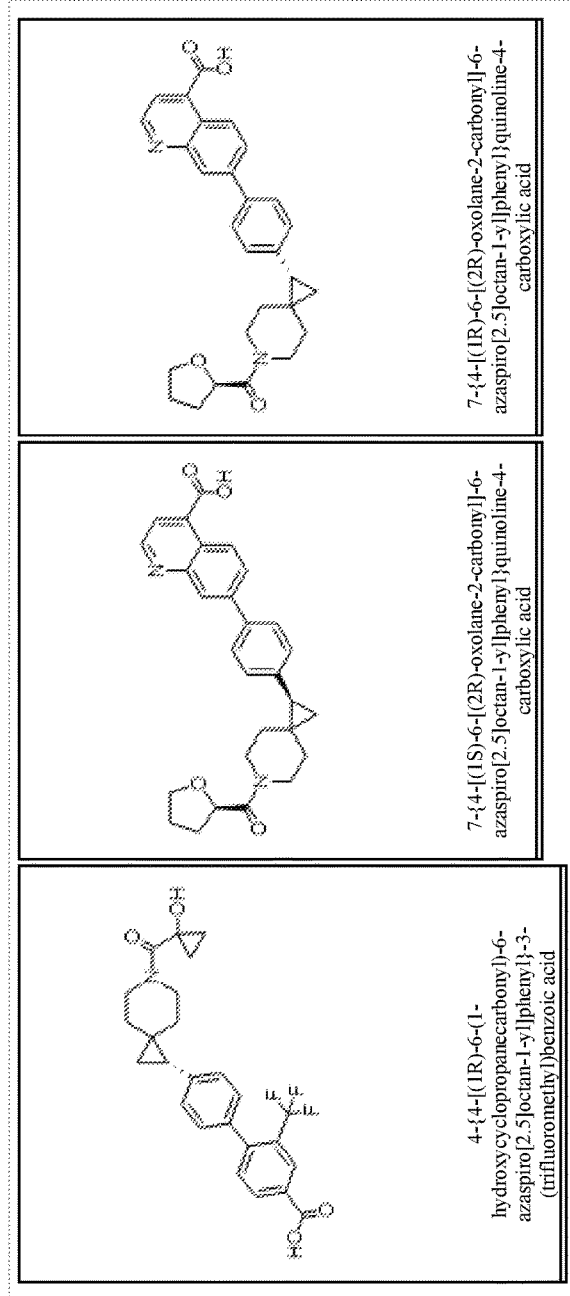
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
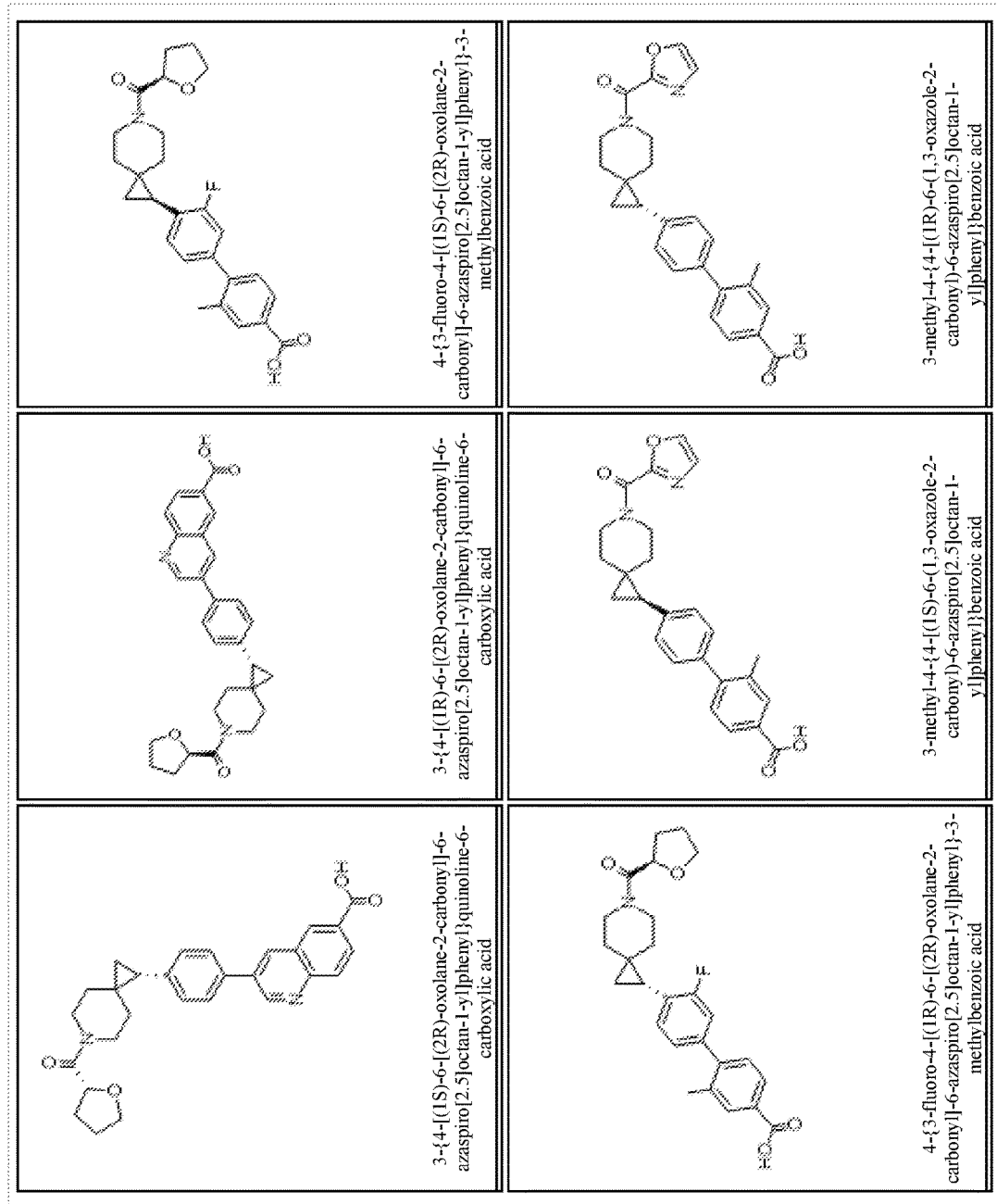
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30:
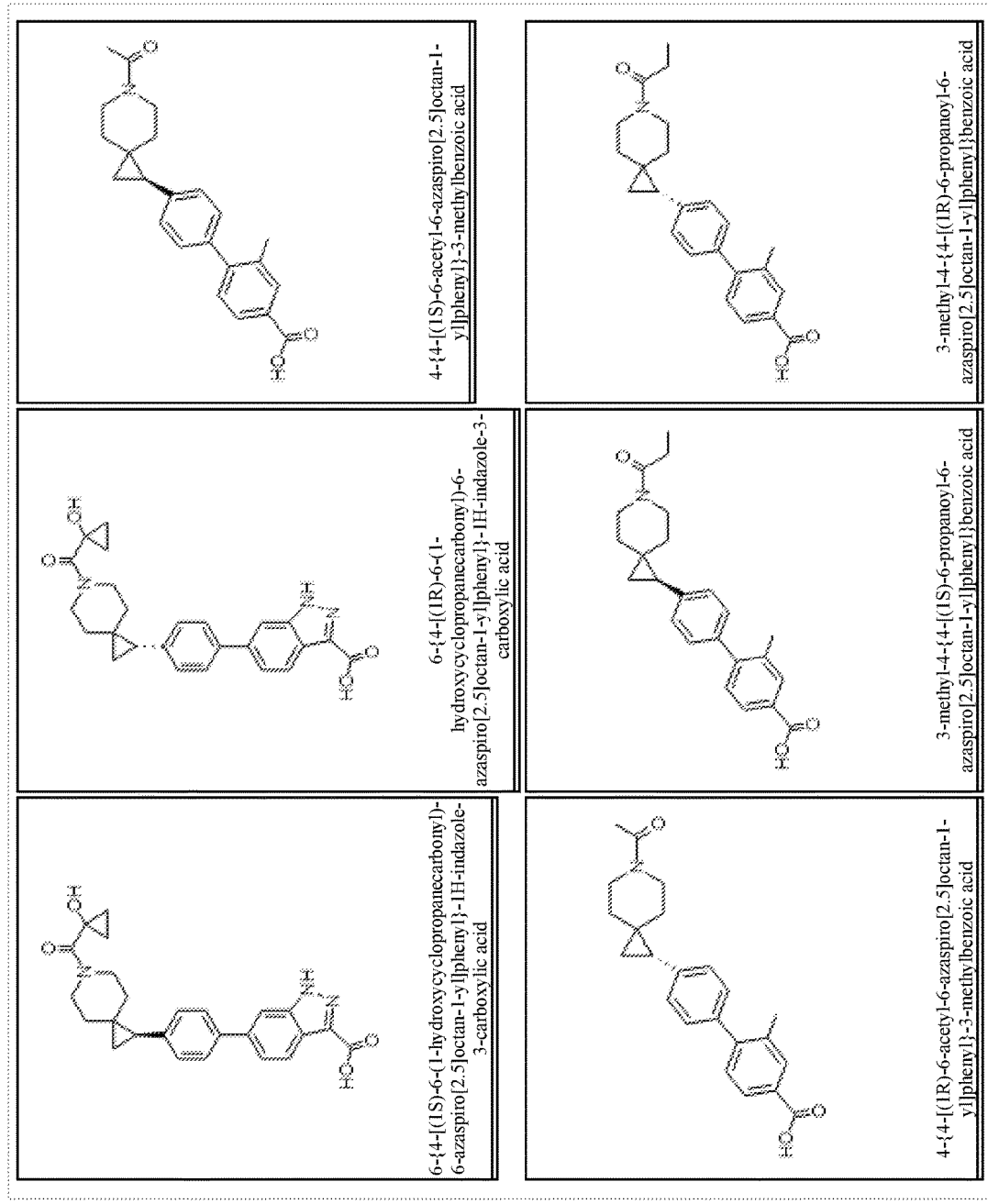
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
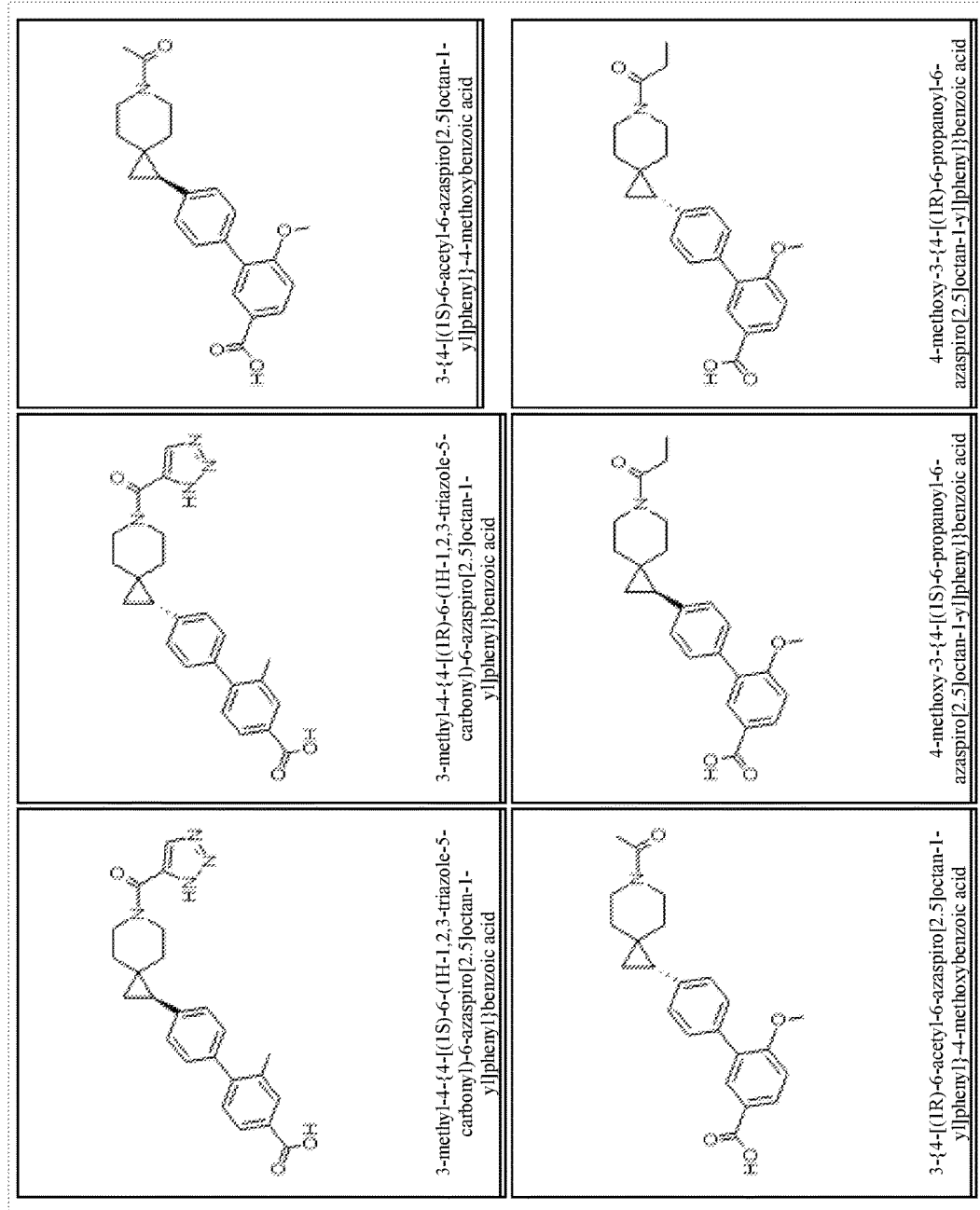
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
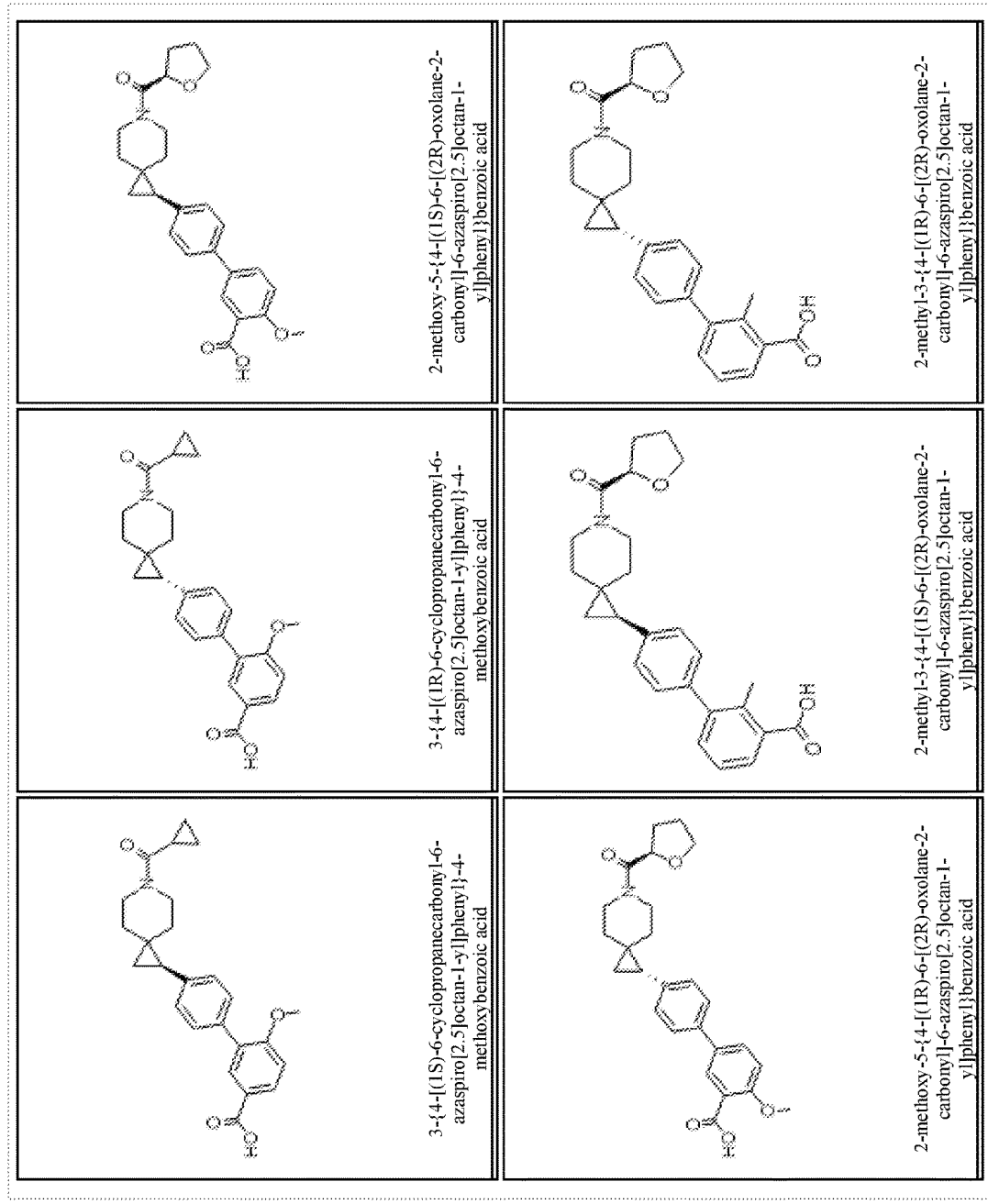
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
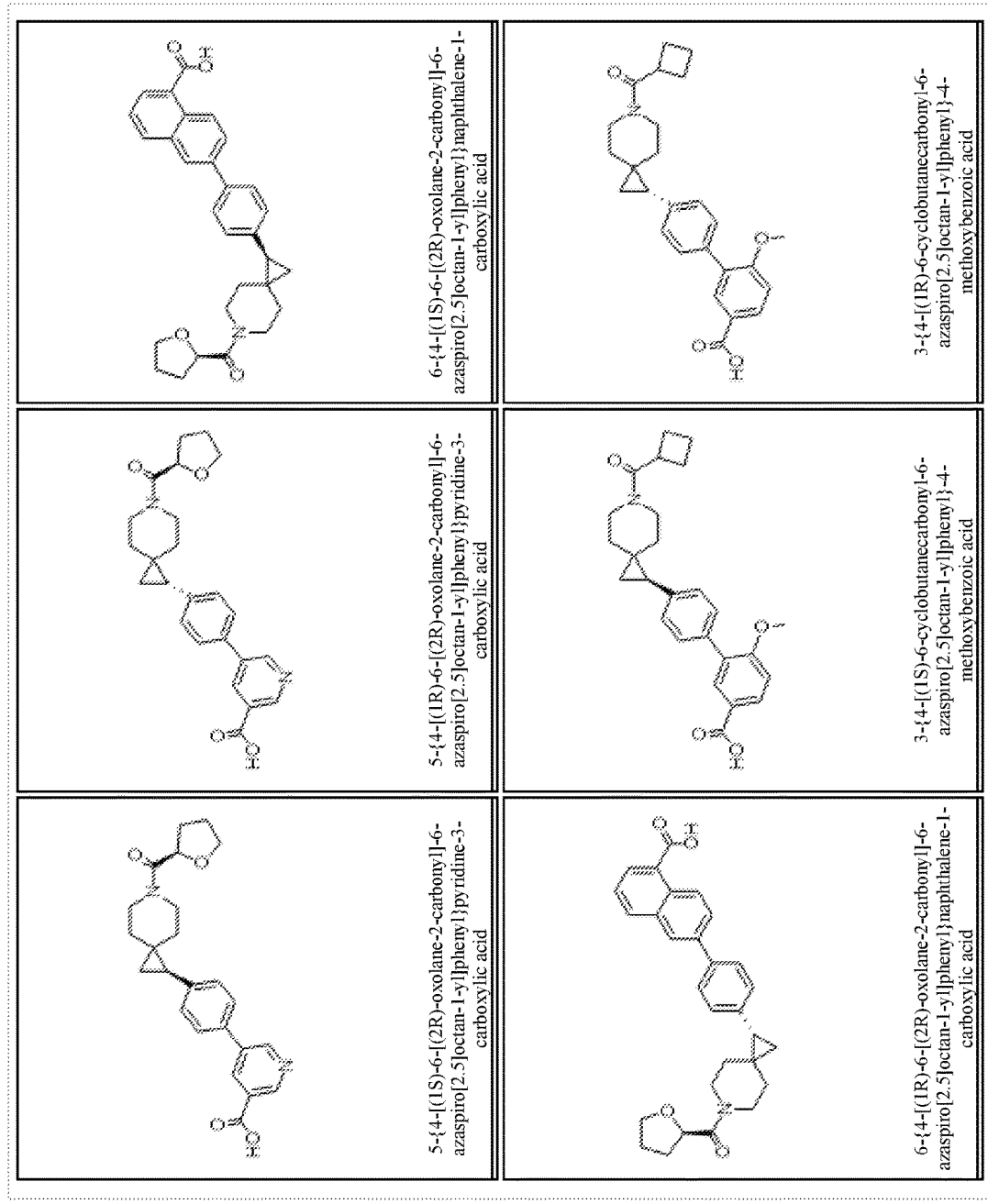
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
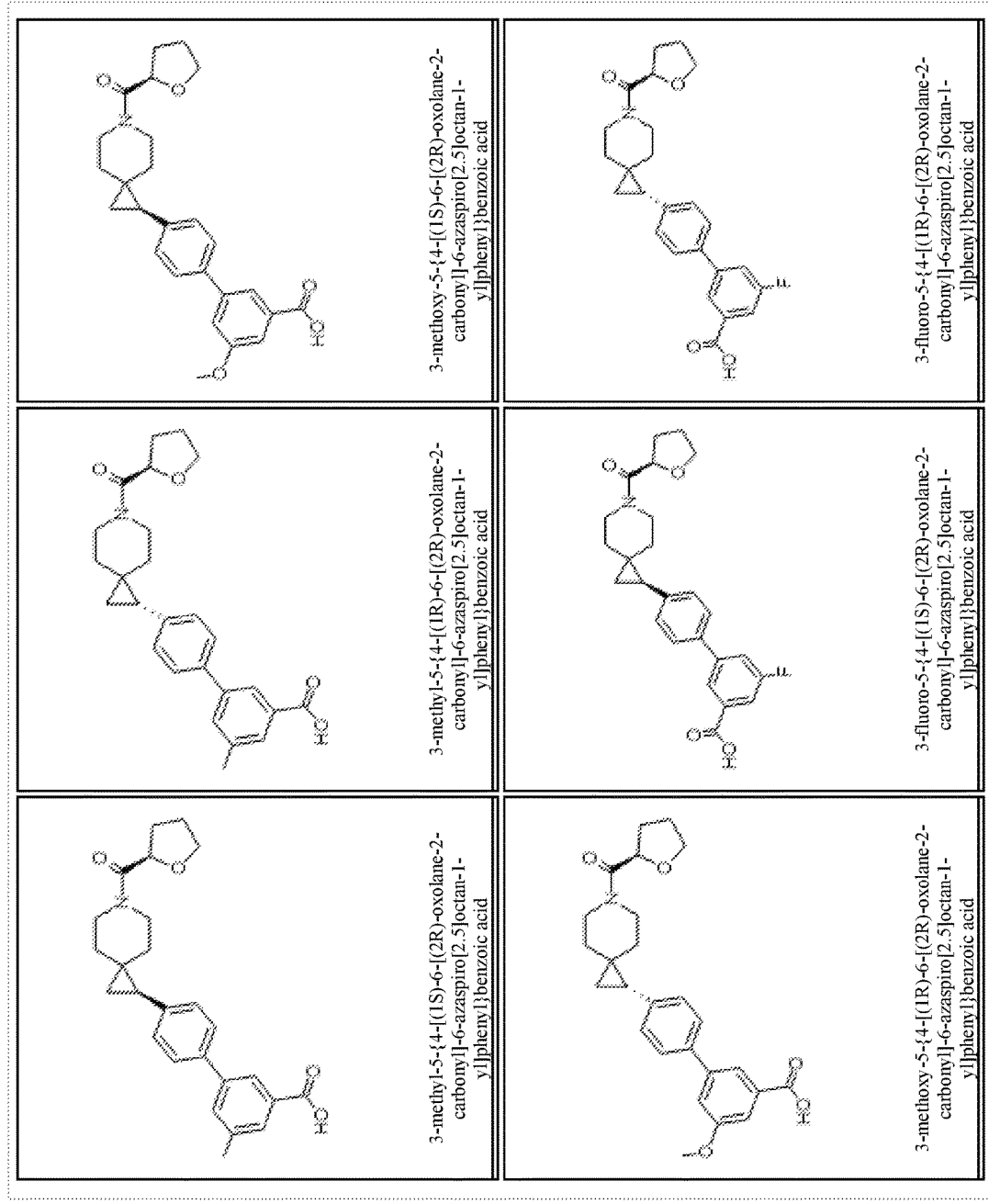
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
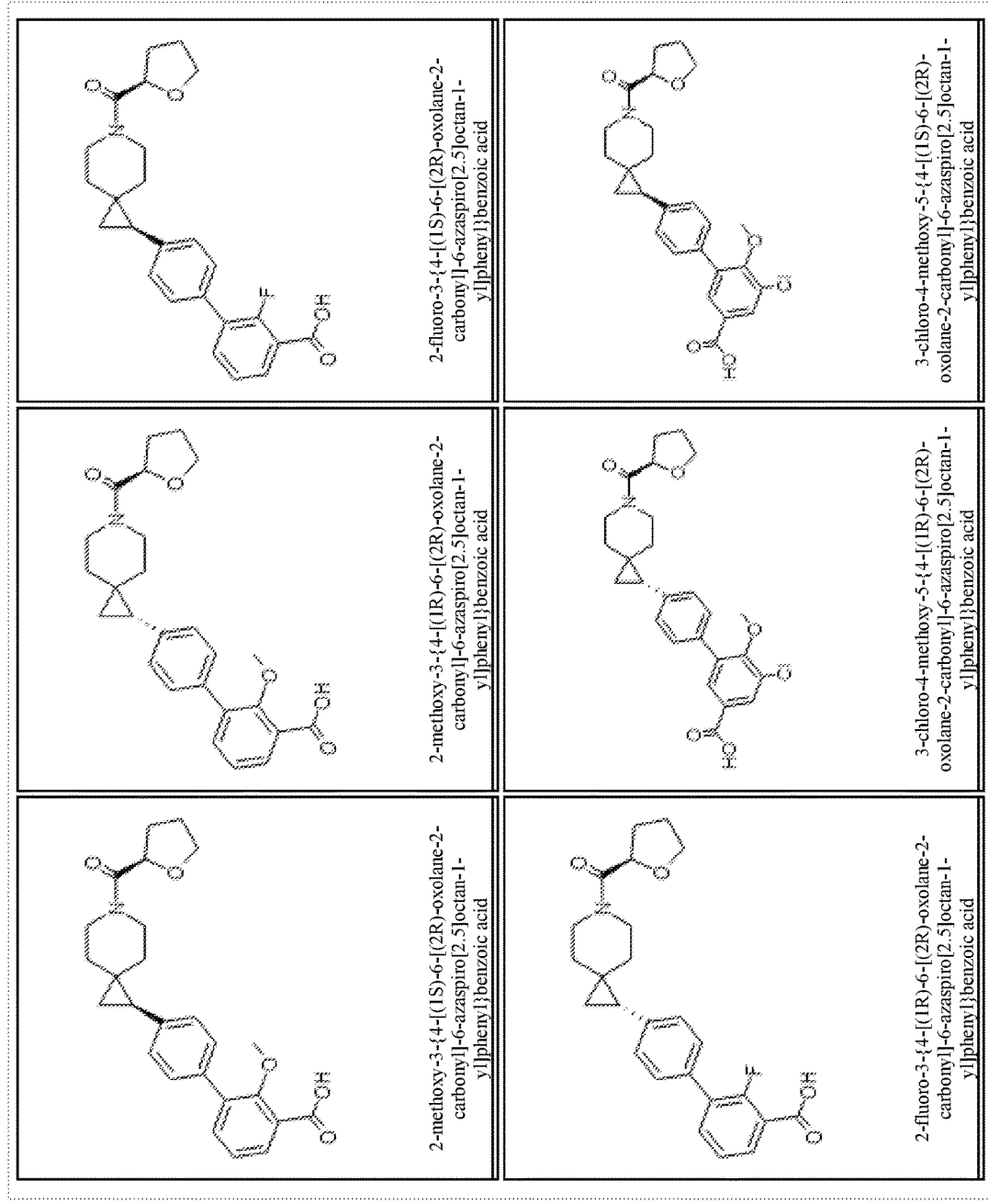
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
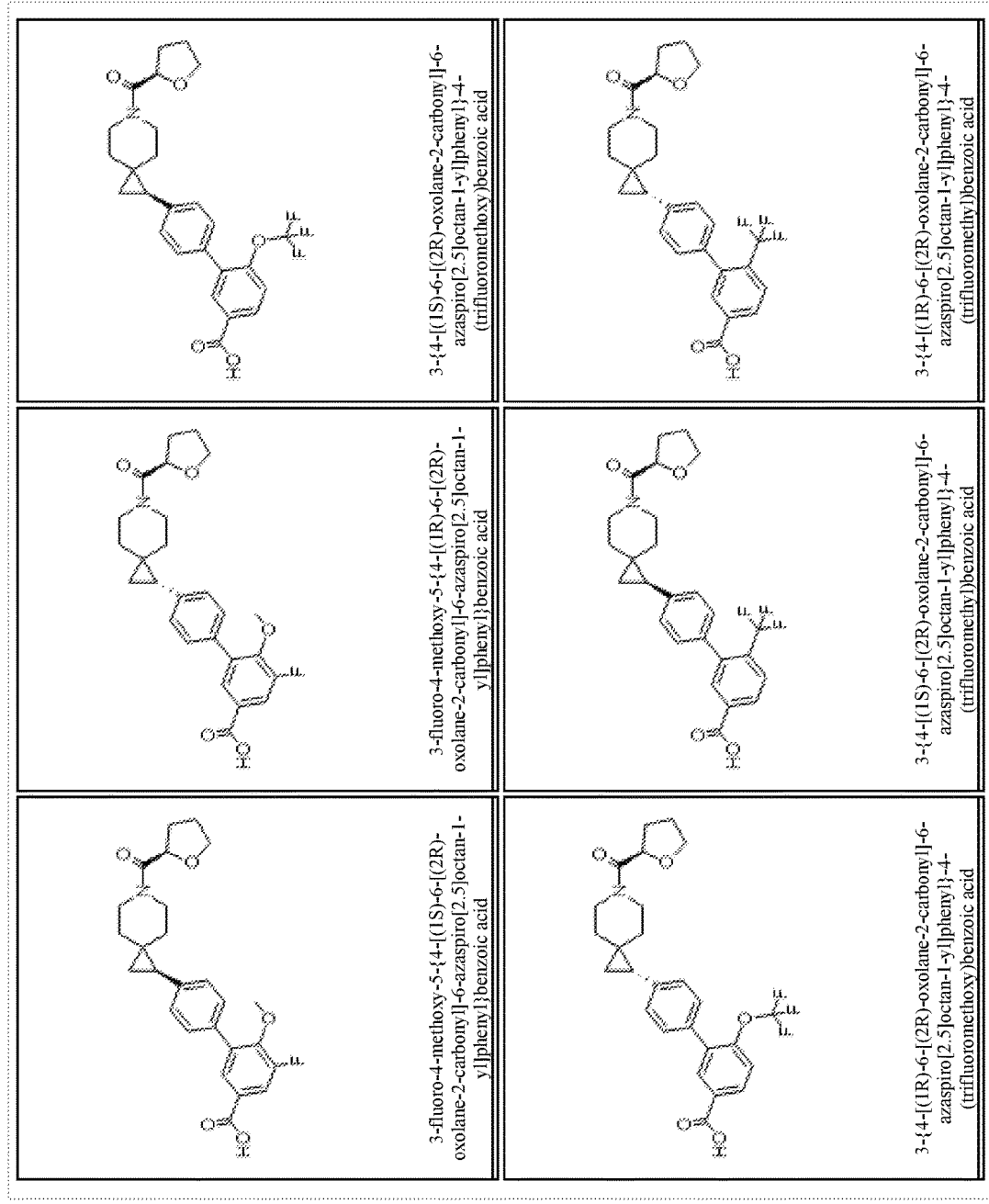
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
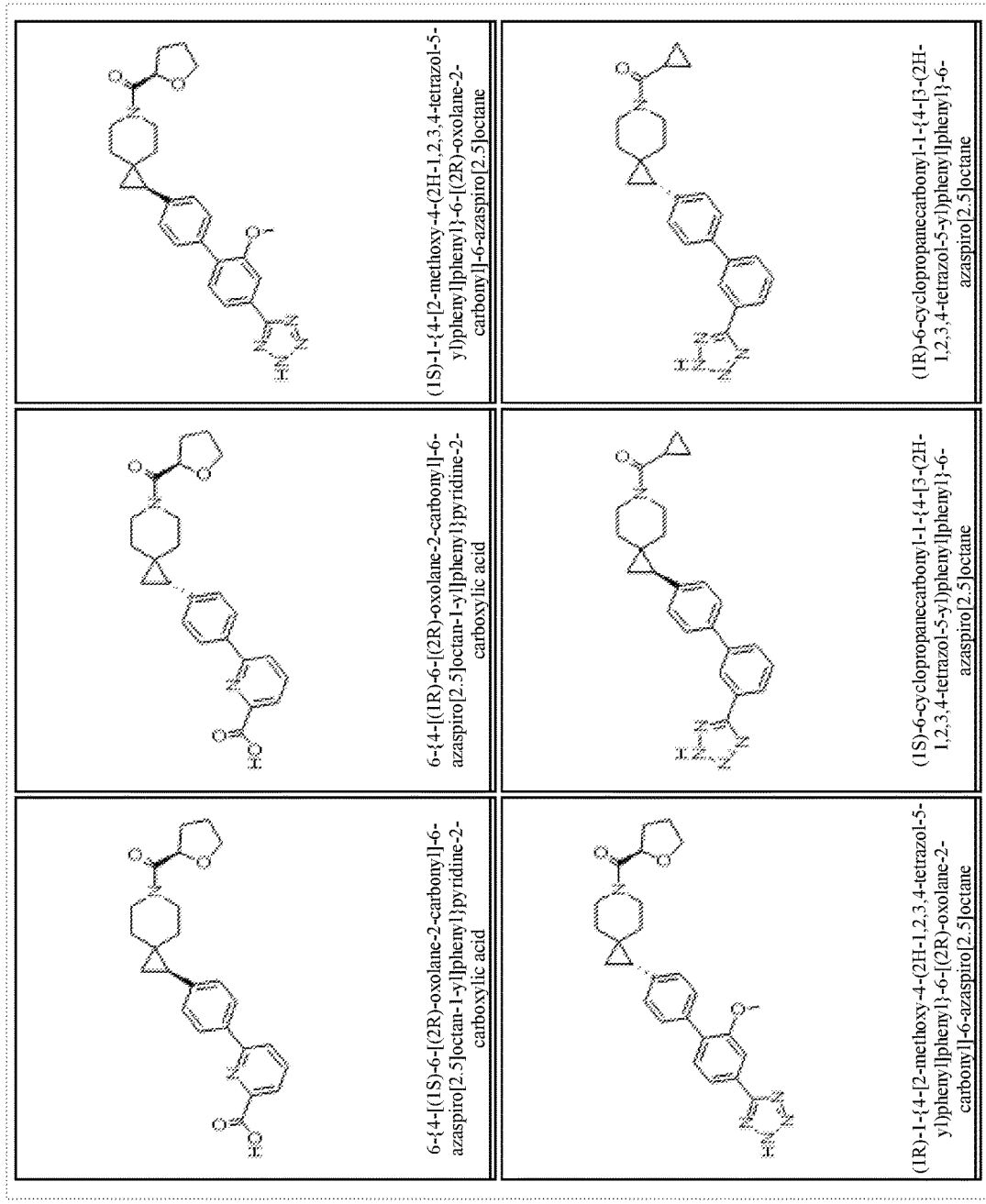
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
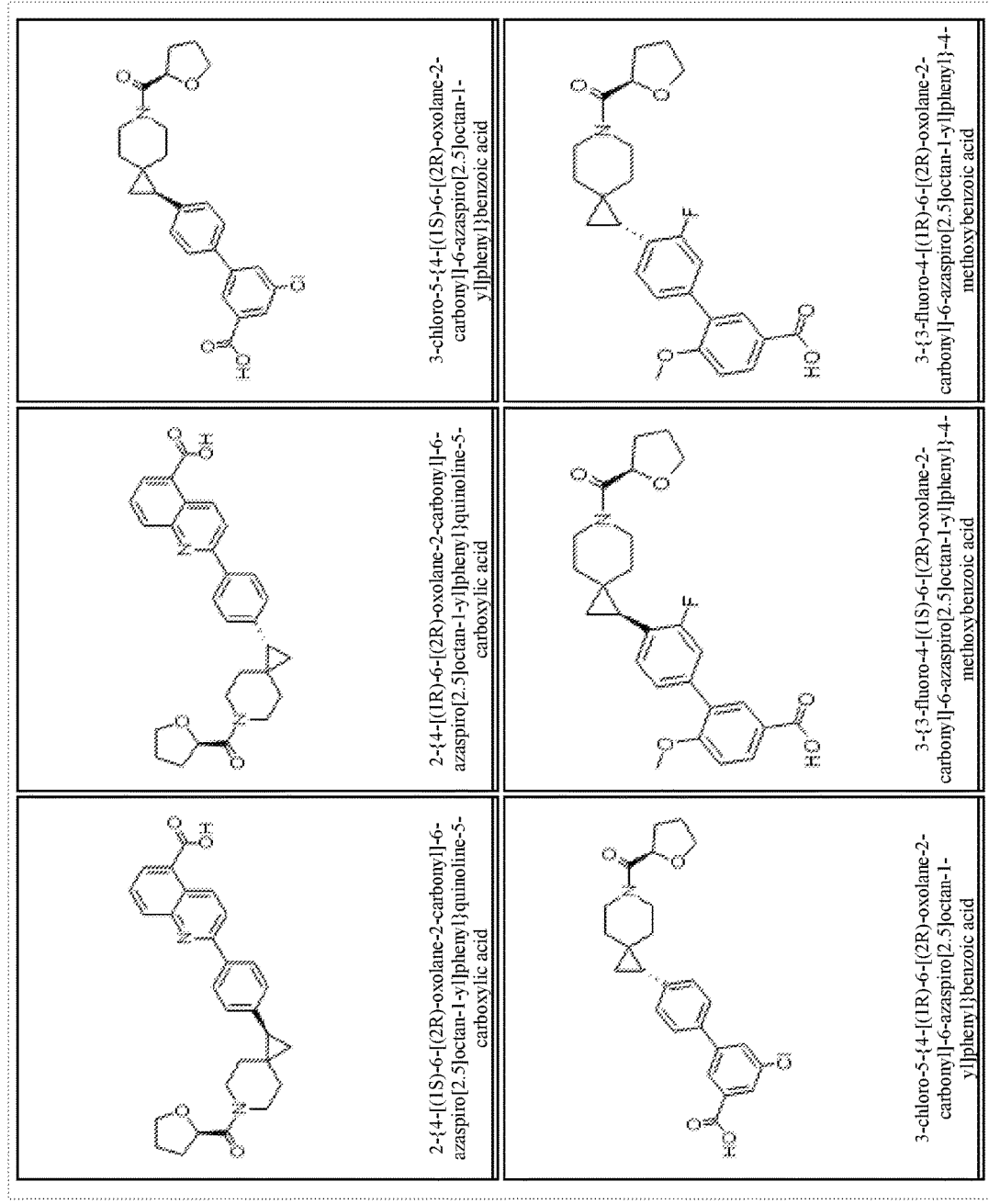
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
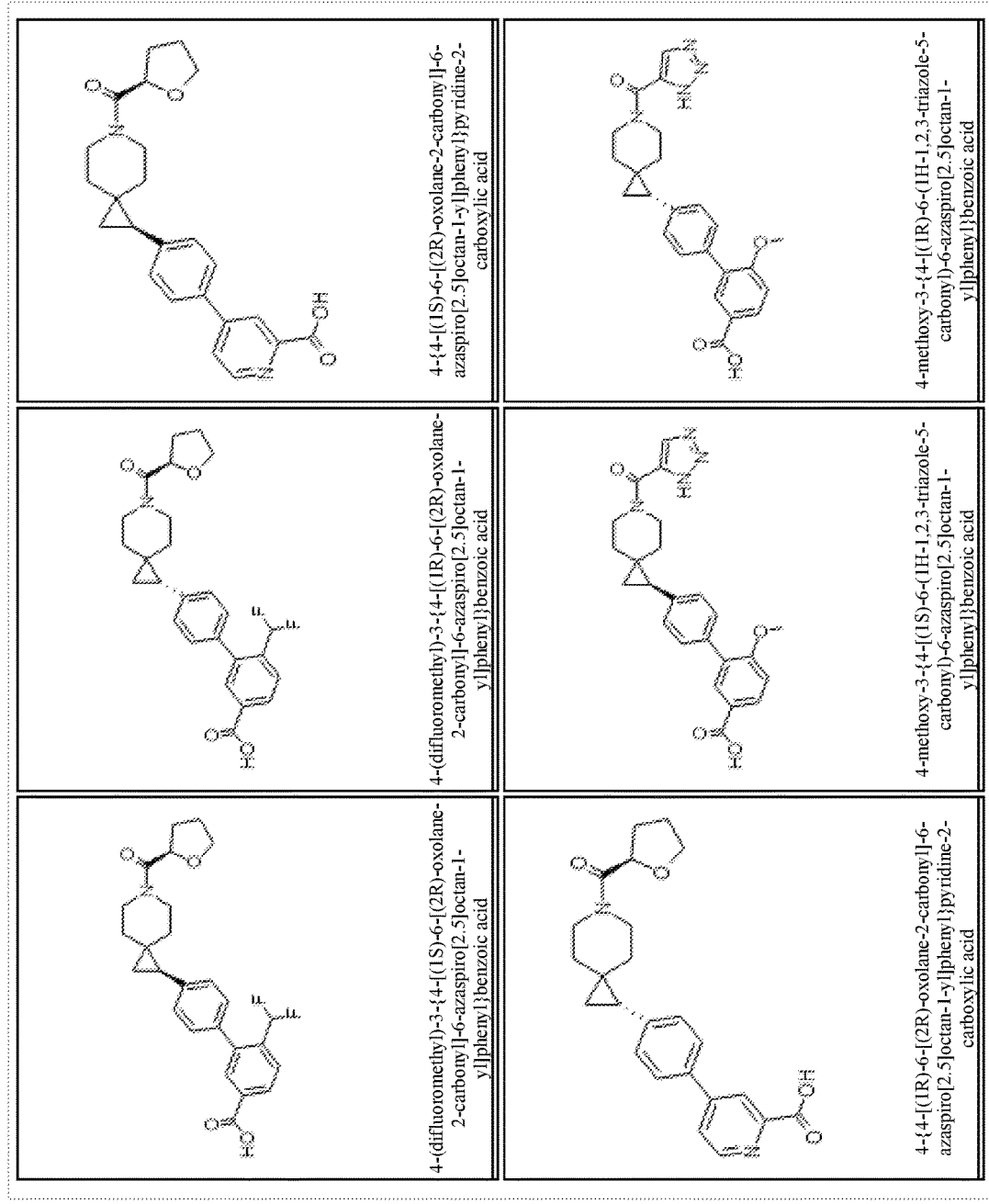
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
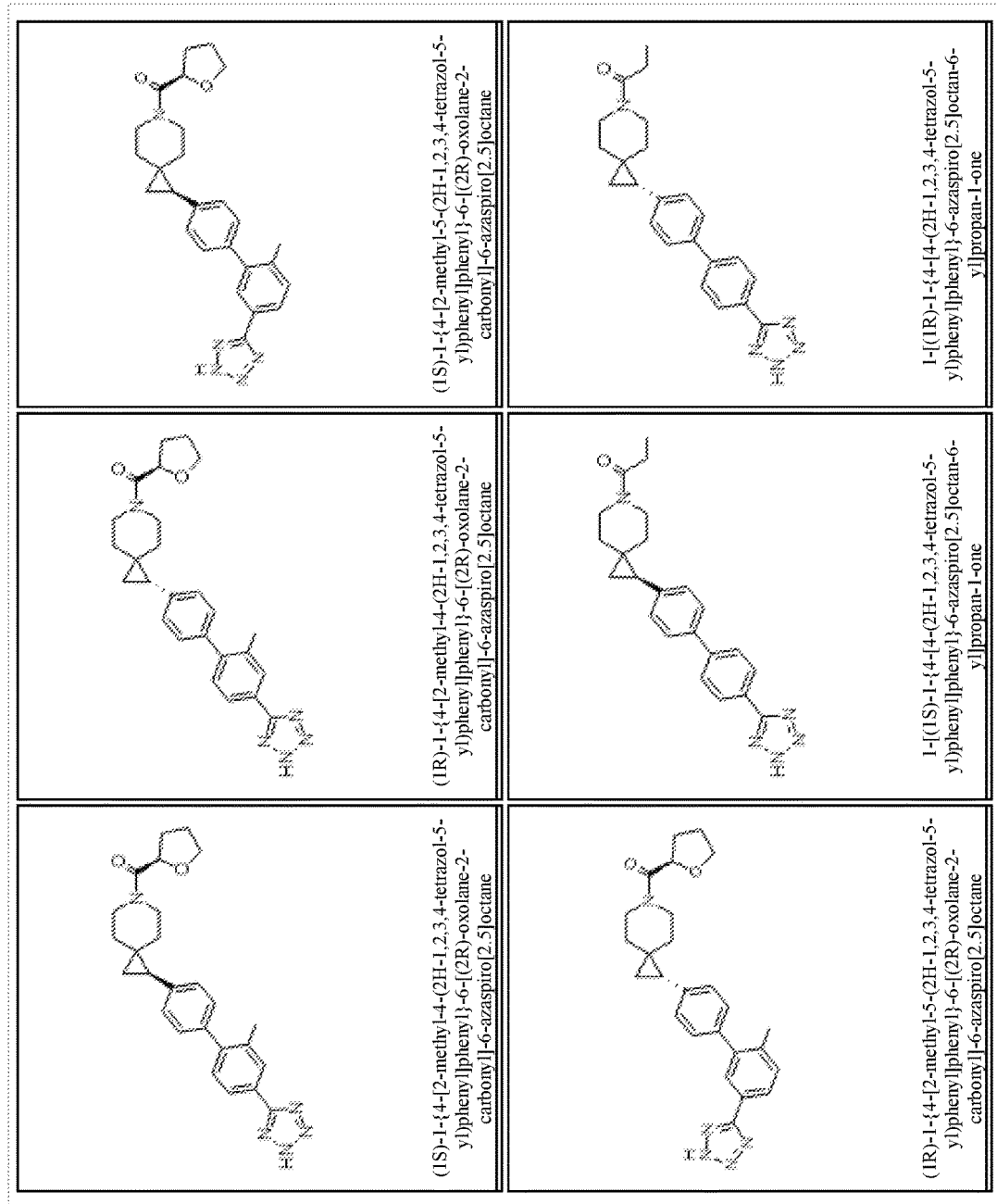
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
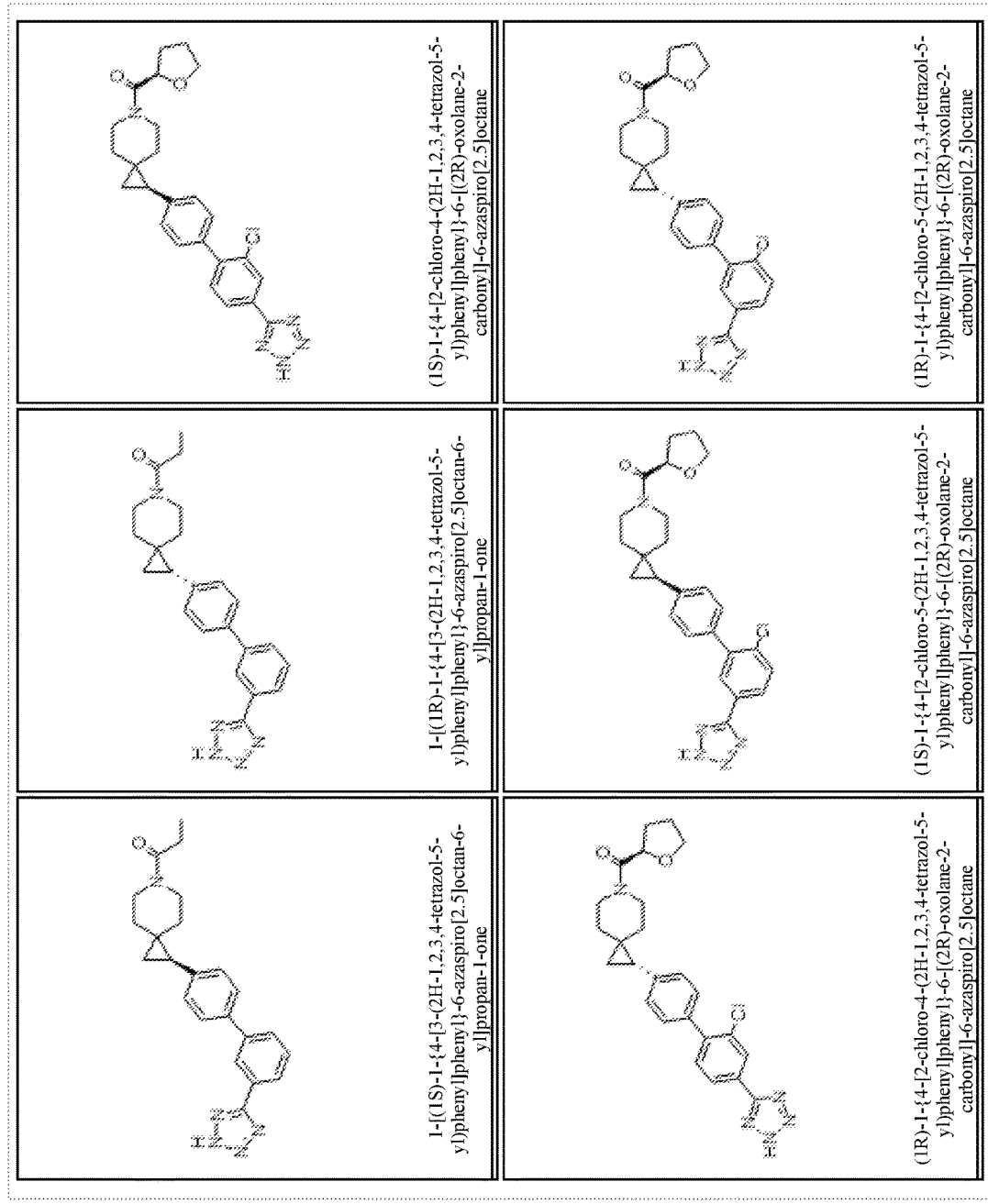
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
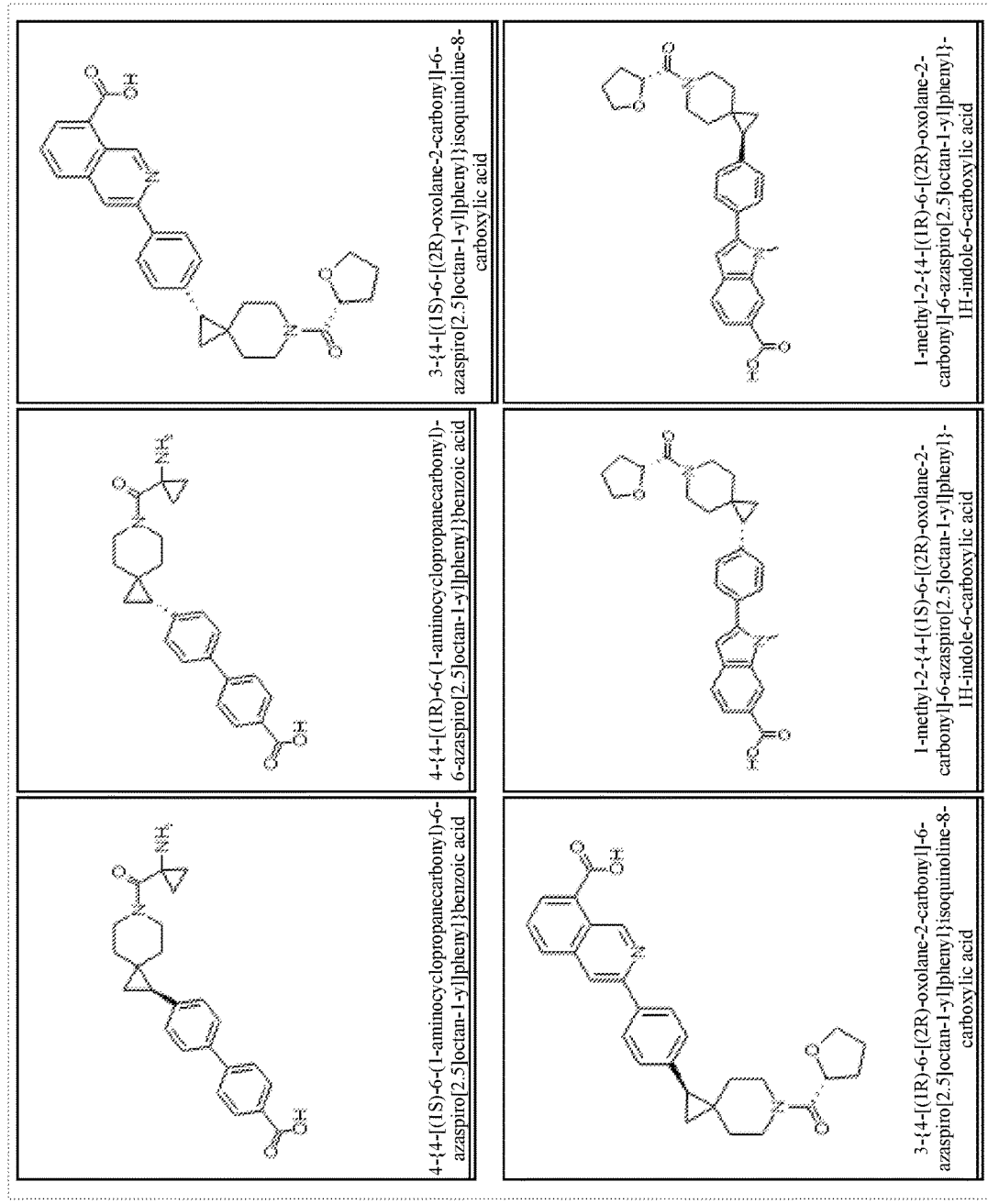
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
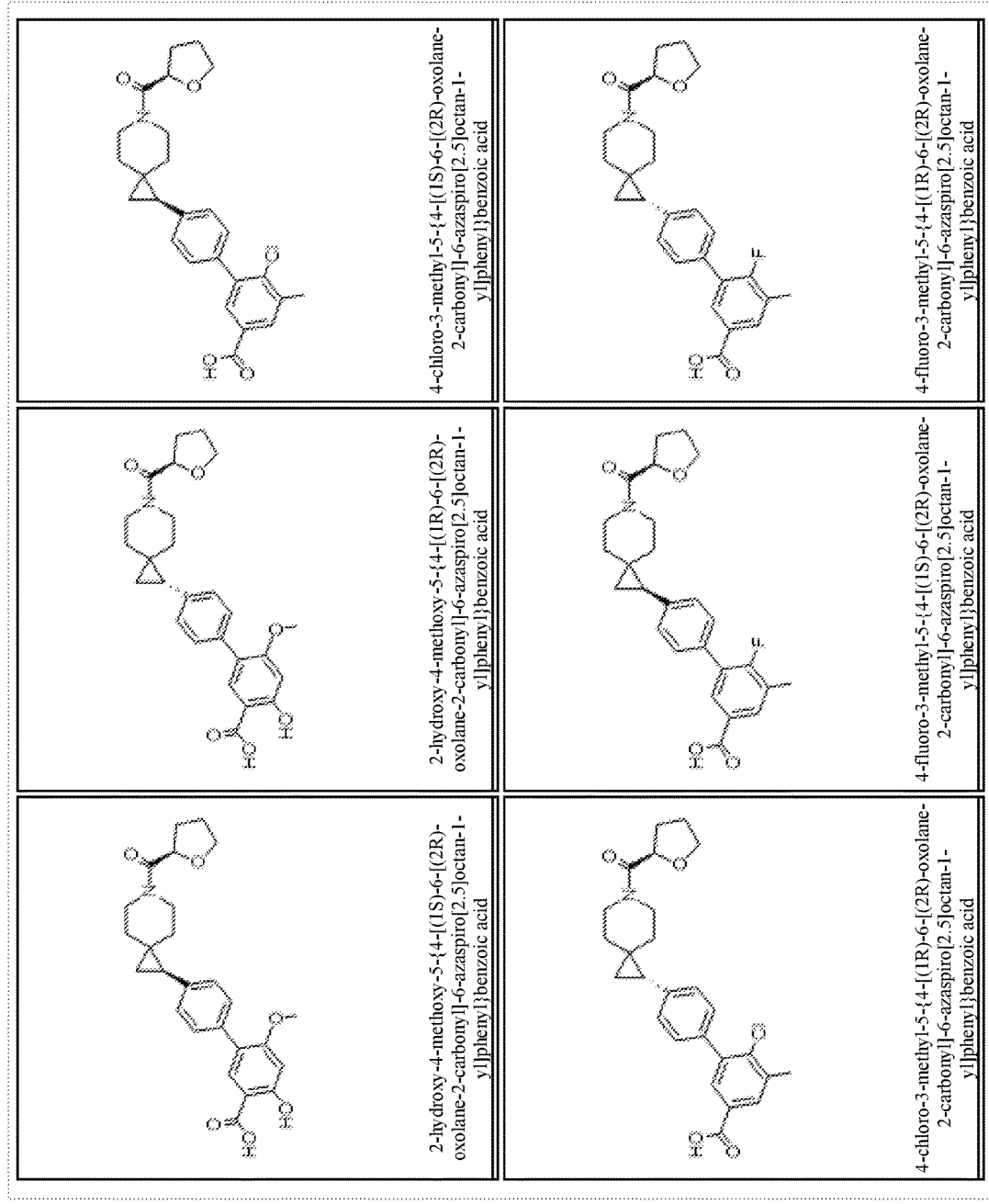
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
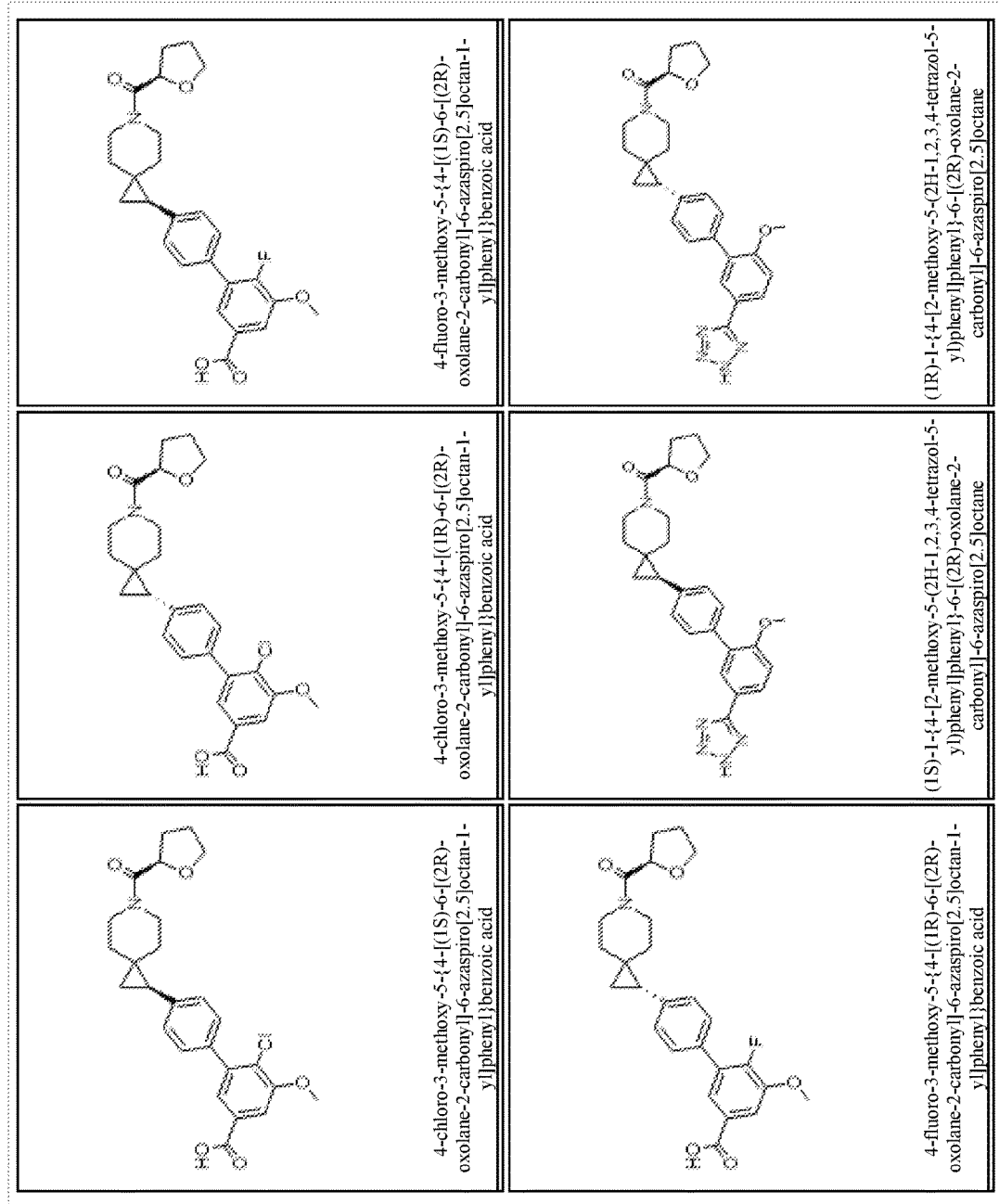
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
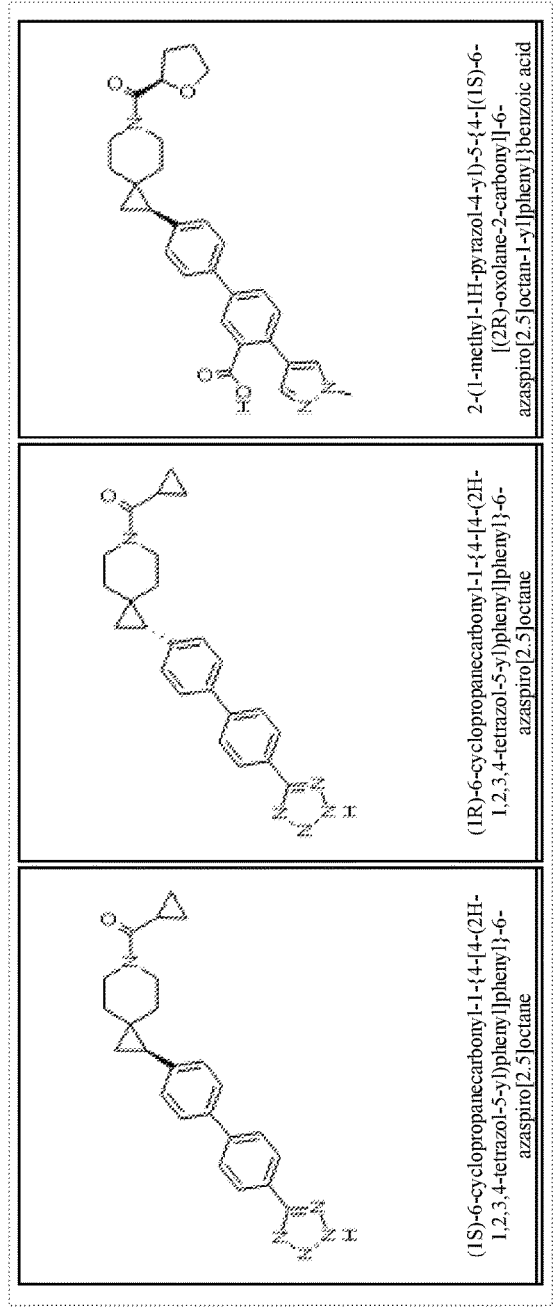
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
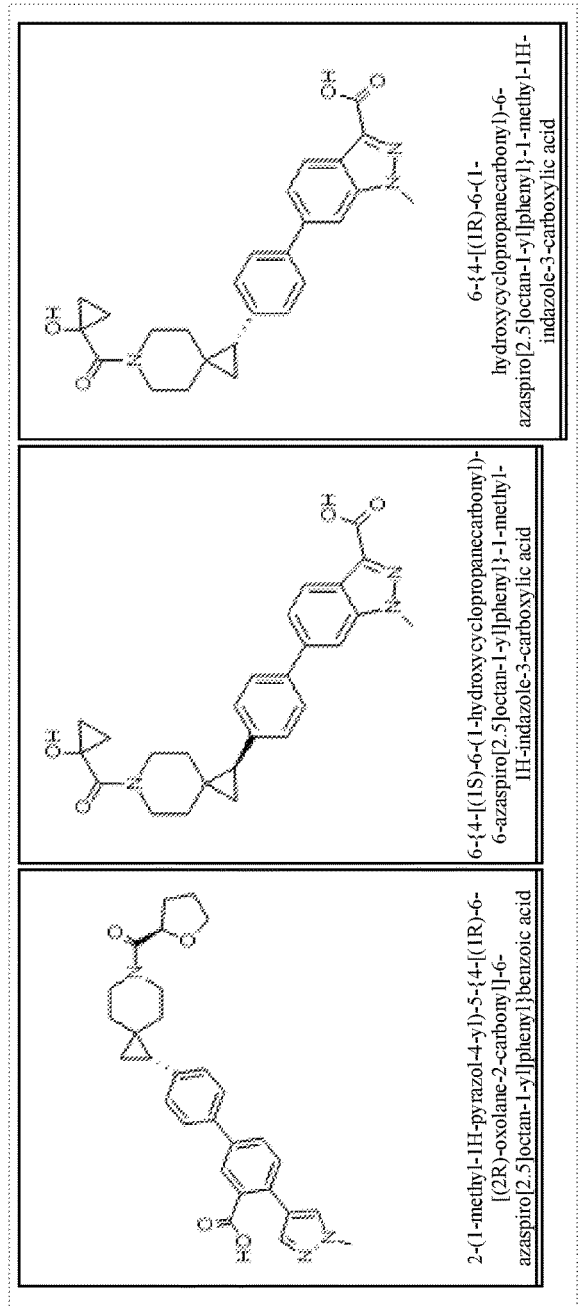
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
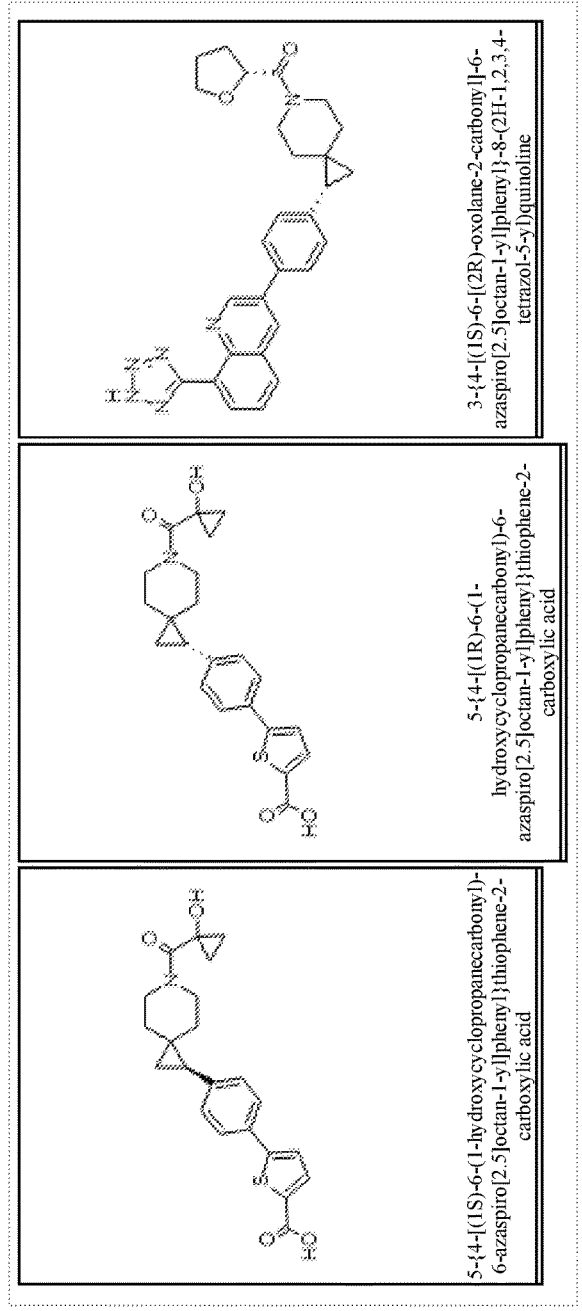
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
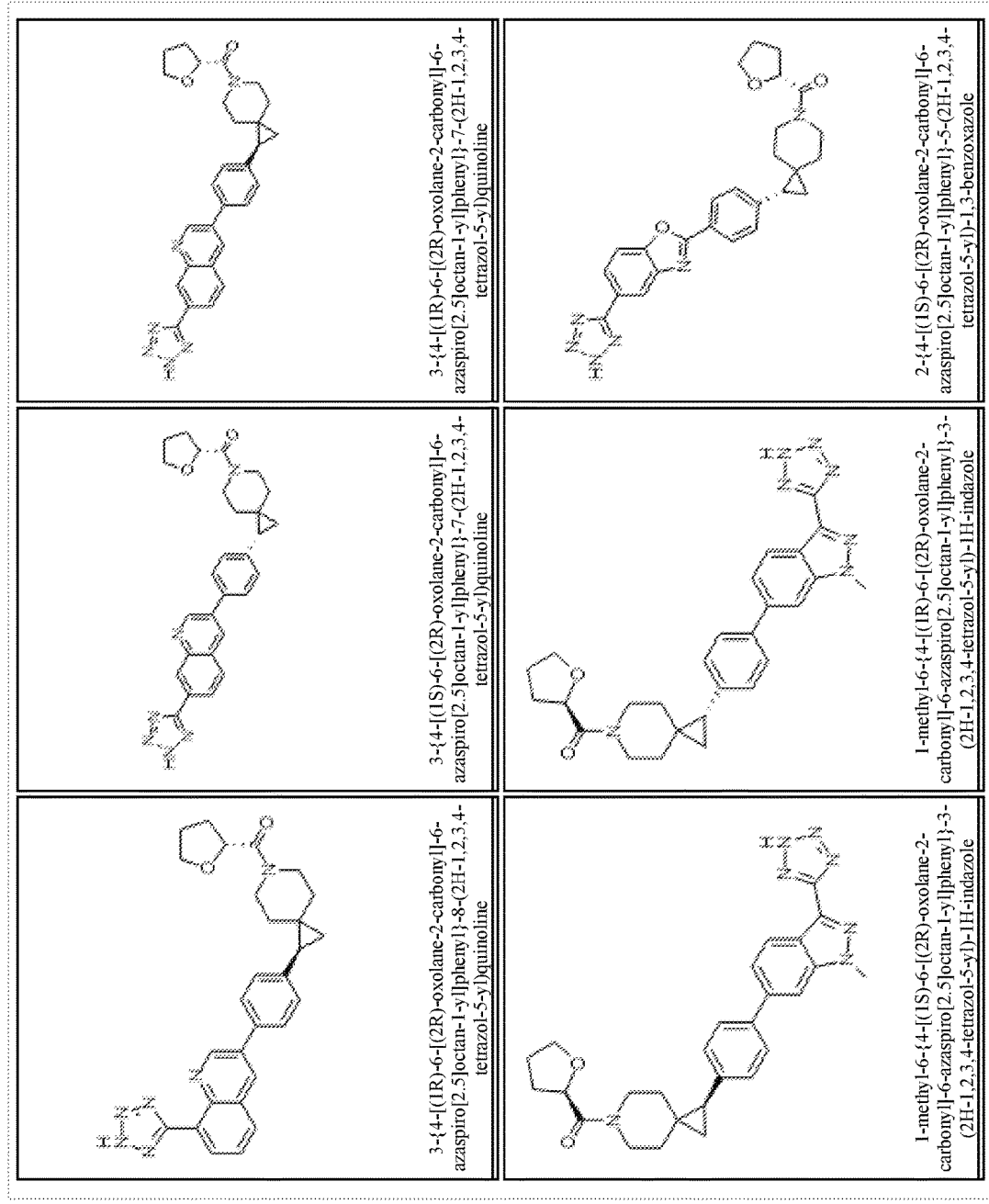
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
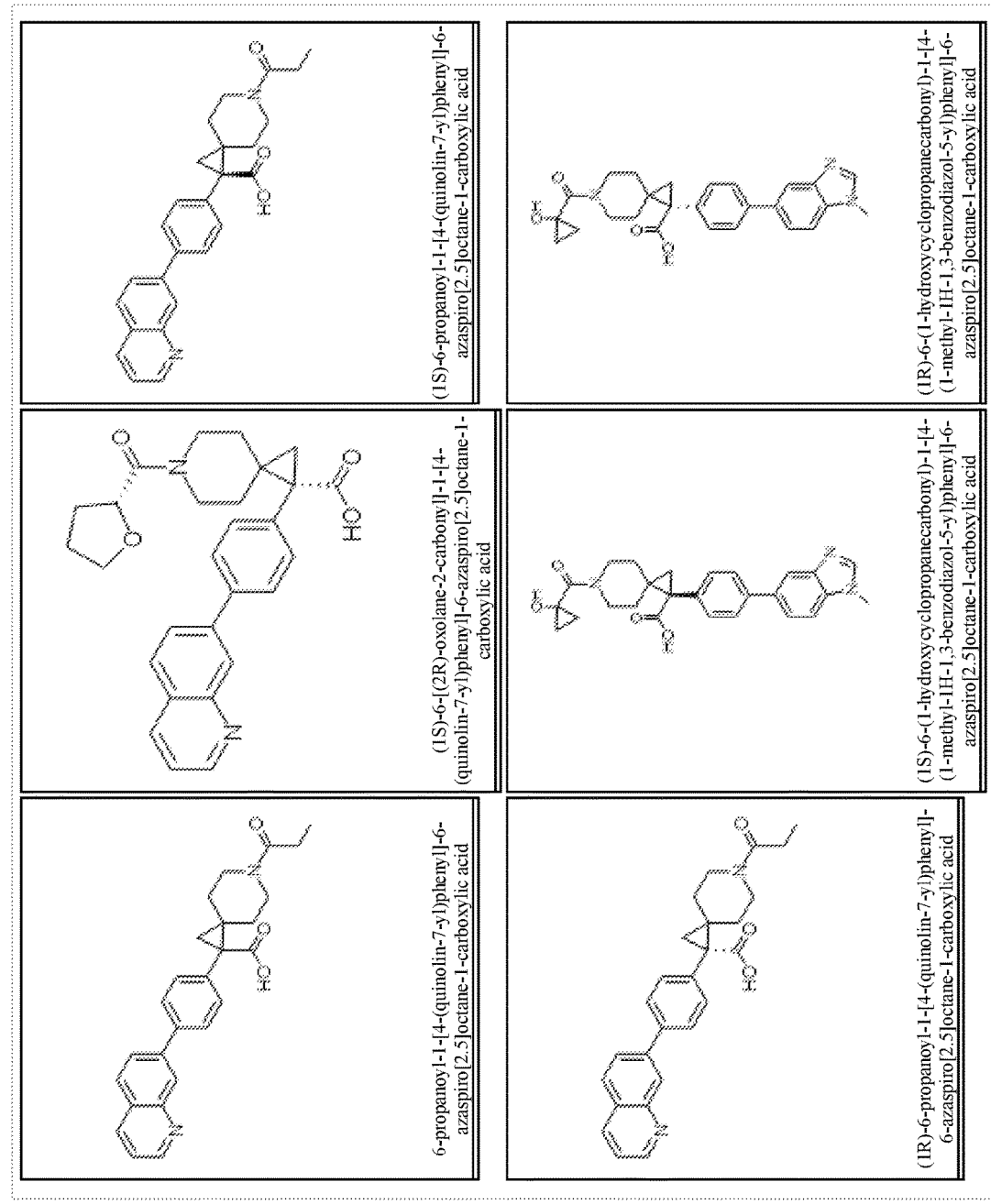
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
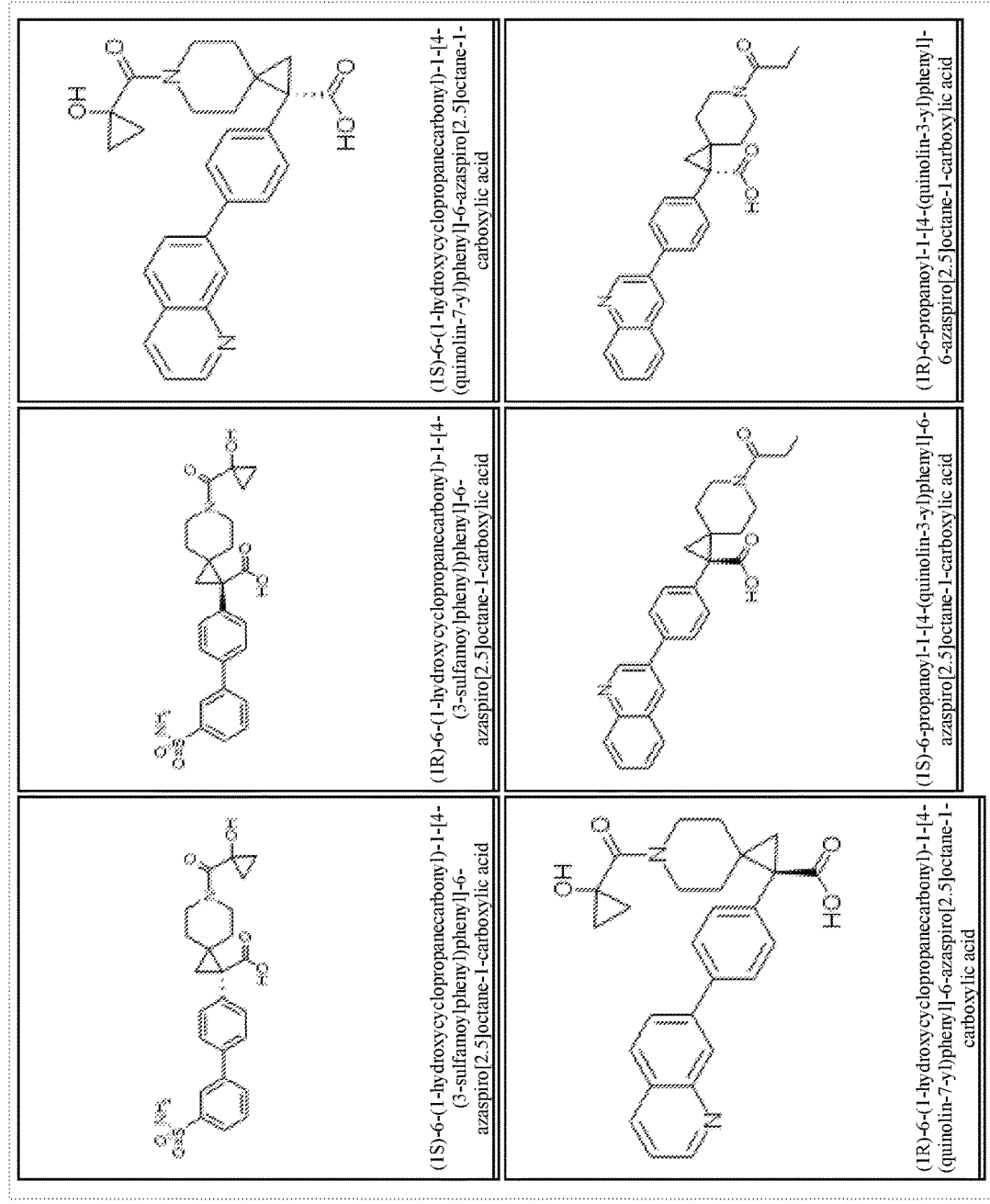
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
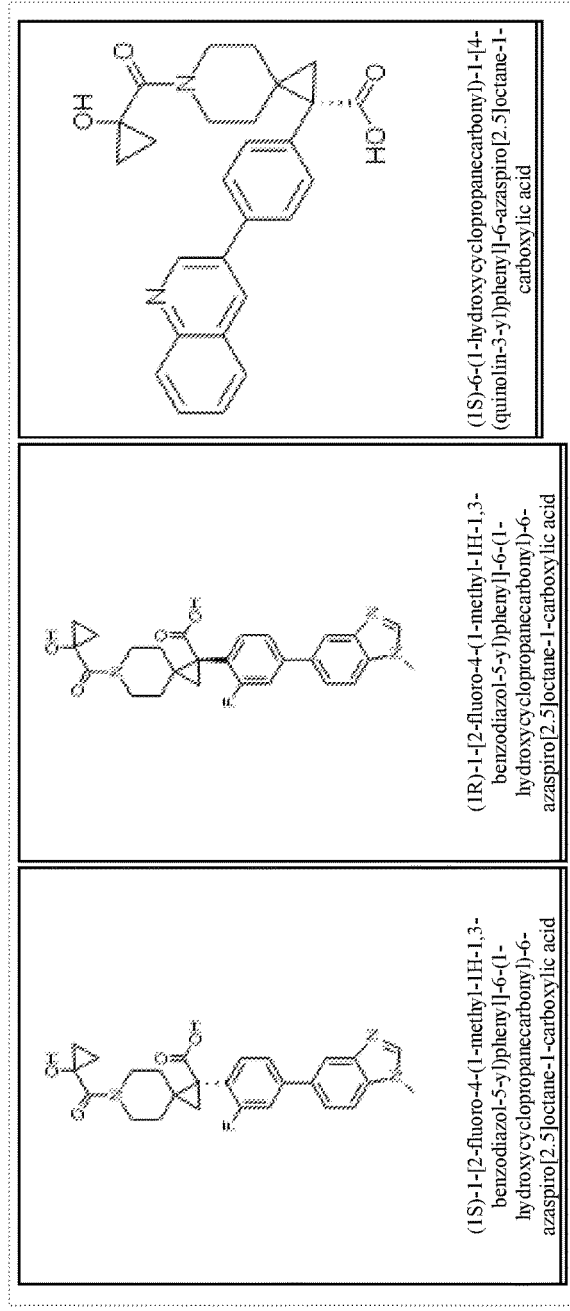
Figures 1, 52:
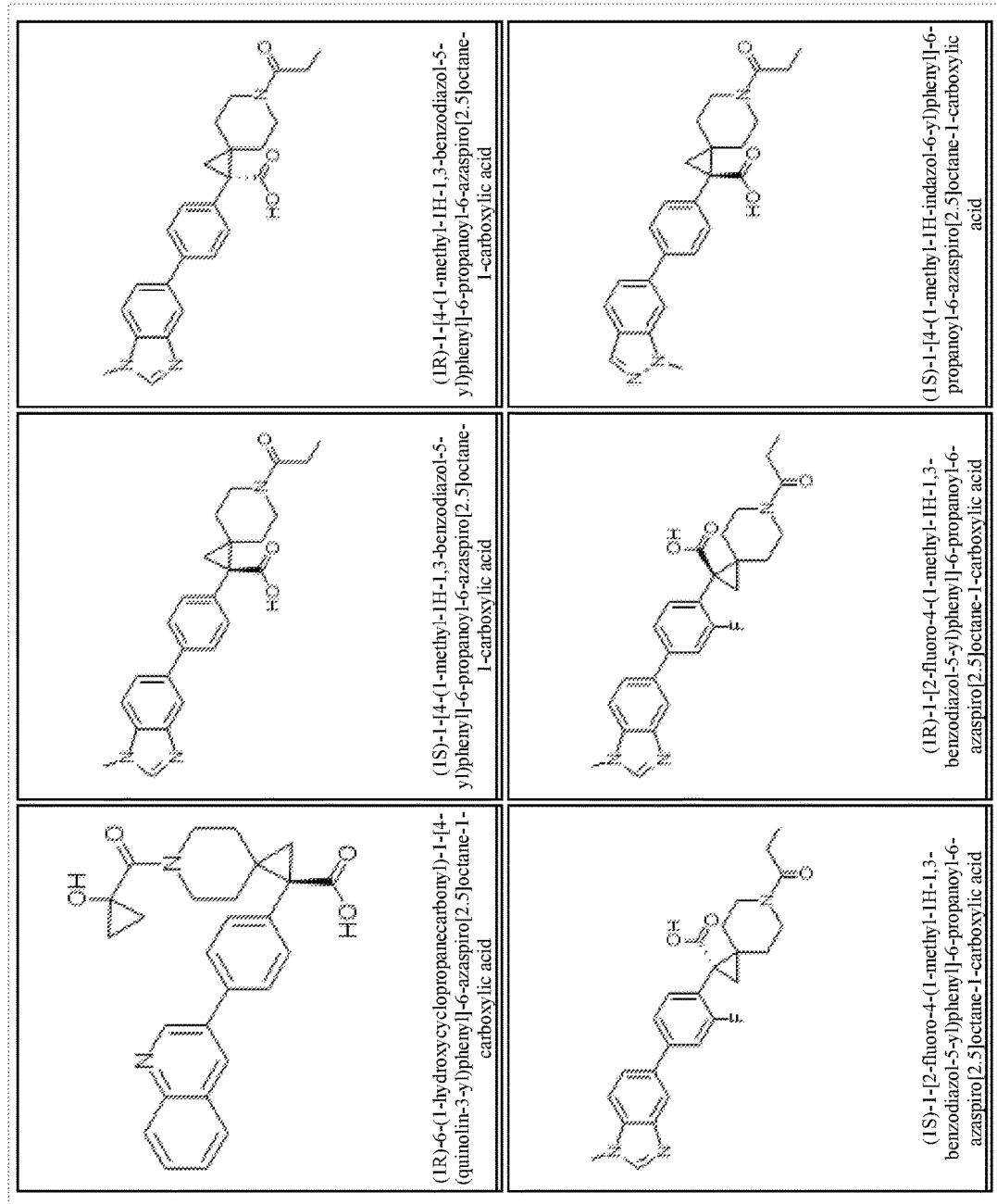
Figures 1, 53:
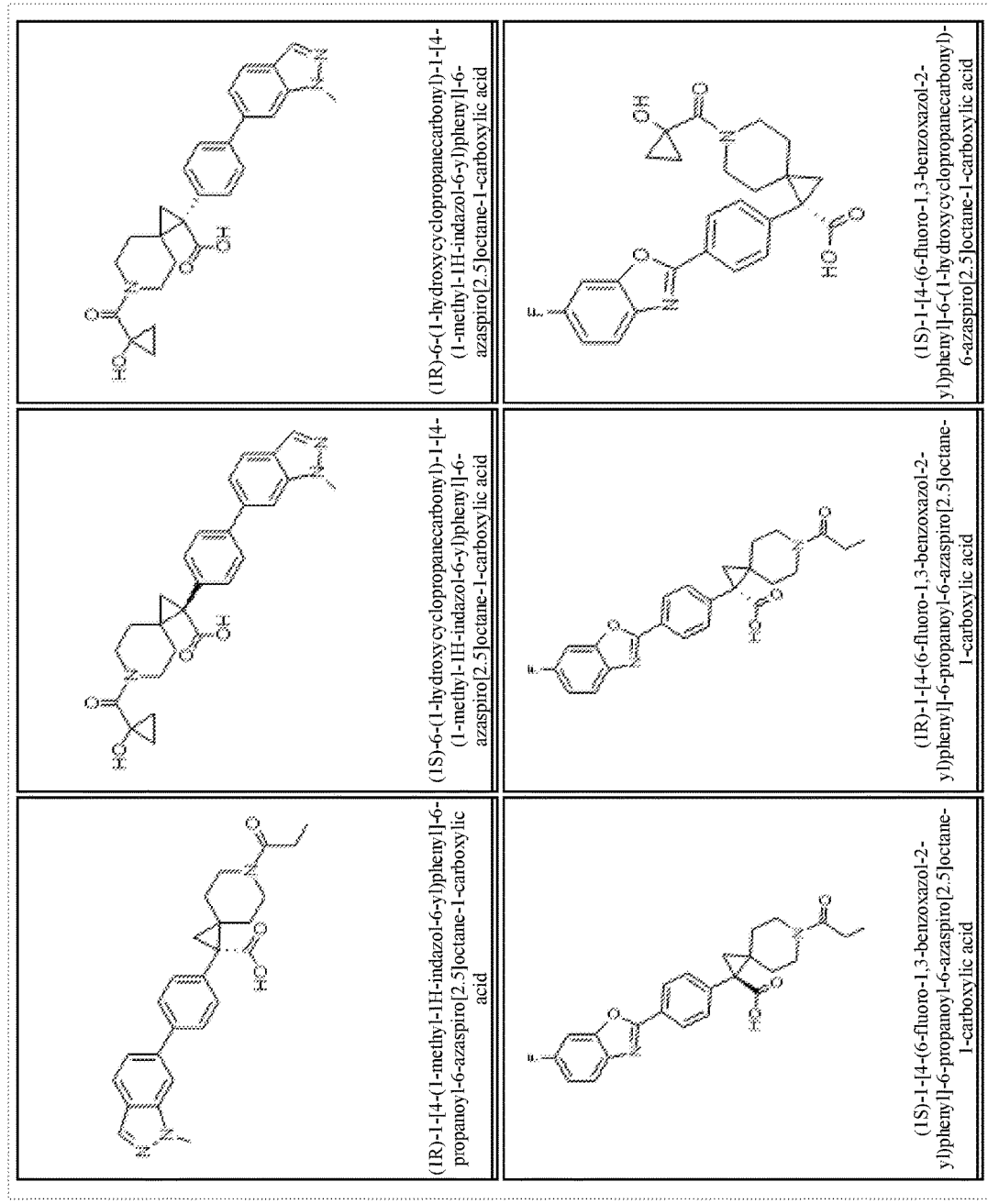
Figures 1, 54:
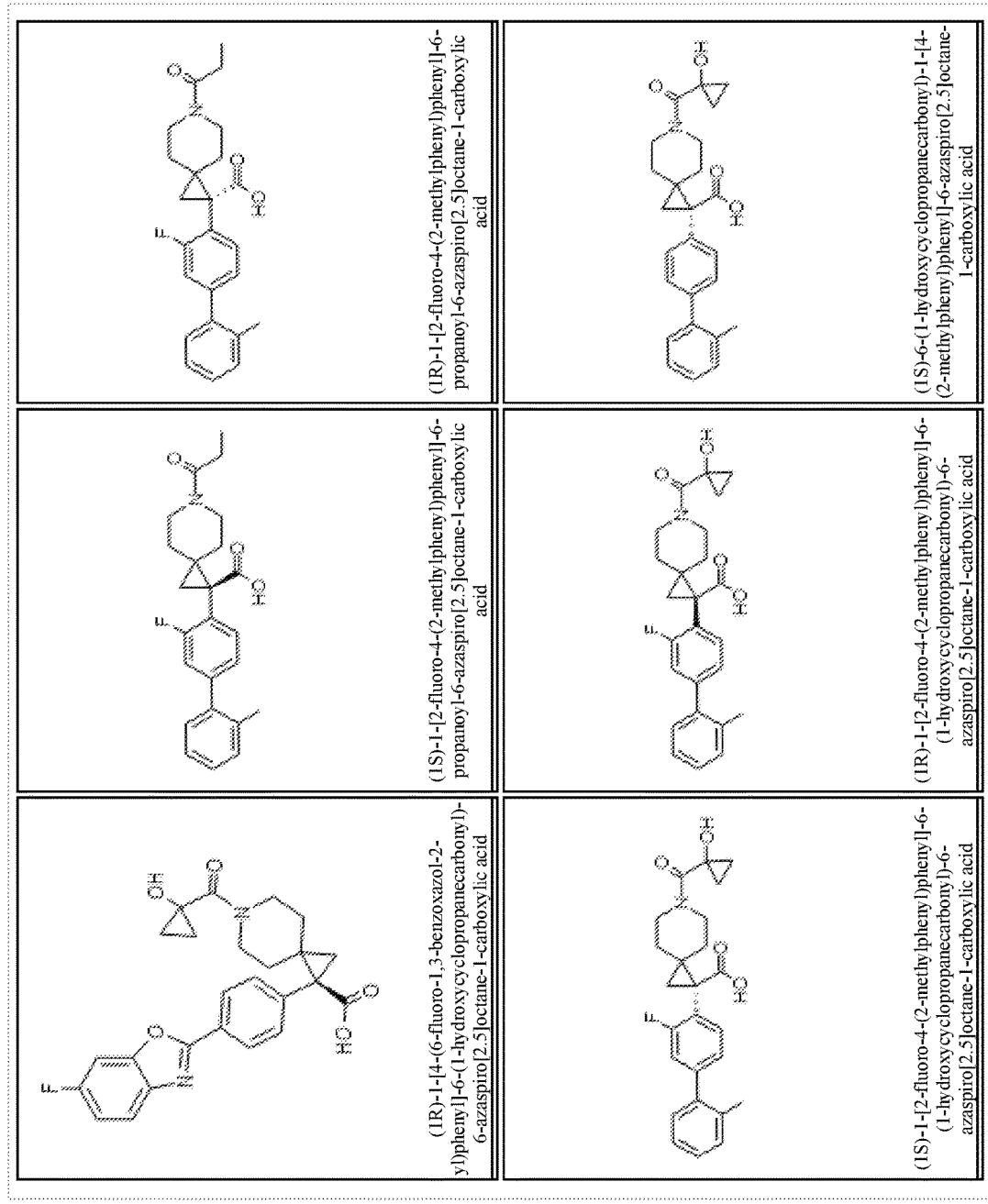
Figures 1, 55:
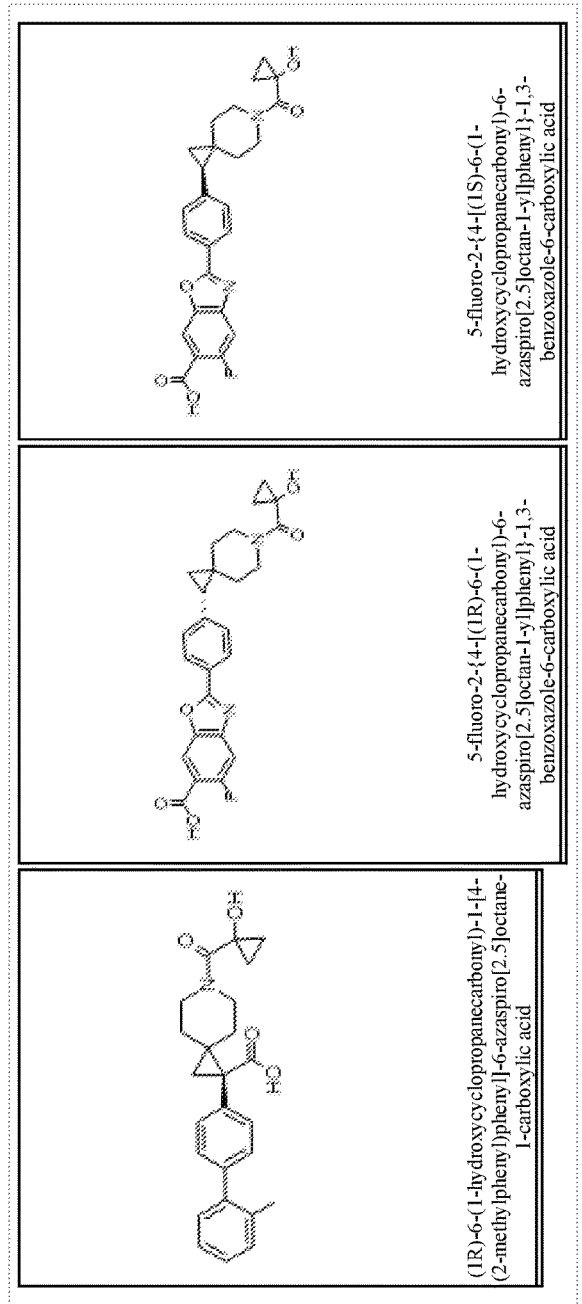
Figures 1, 56:
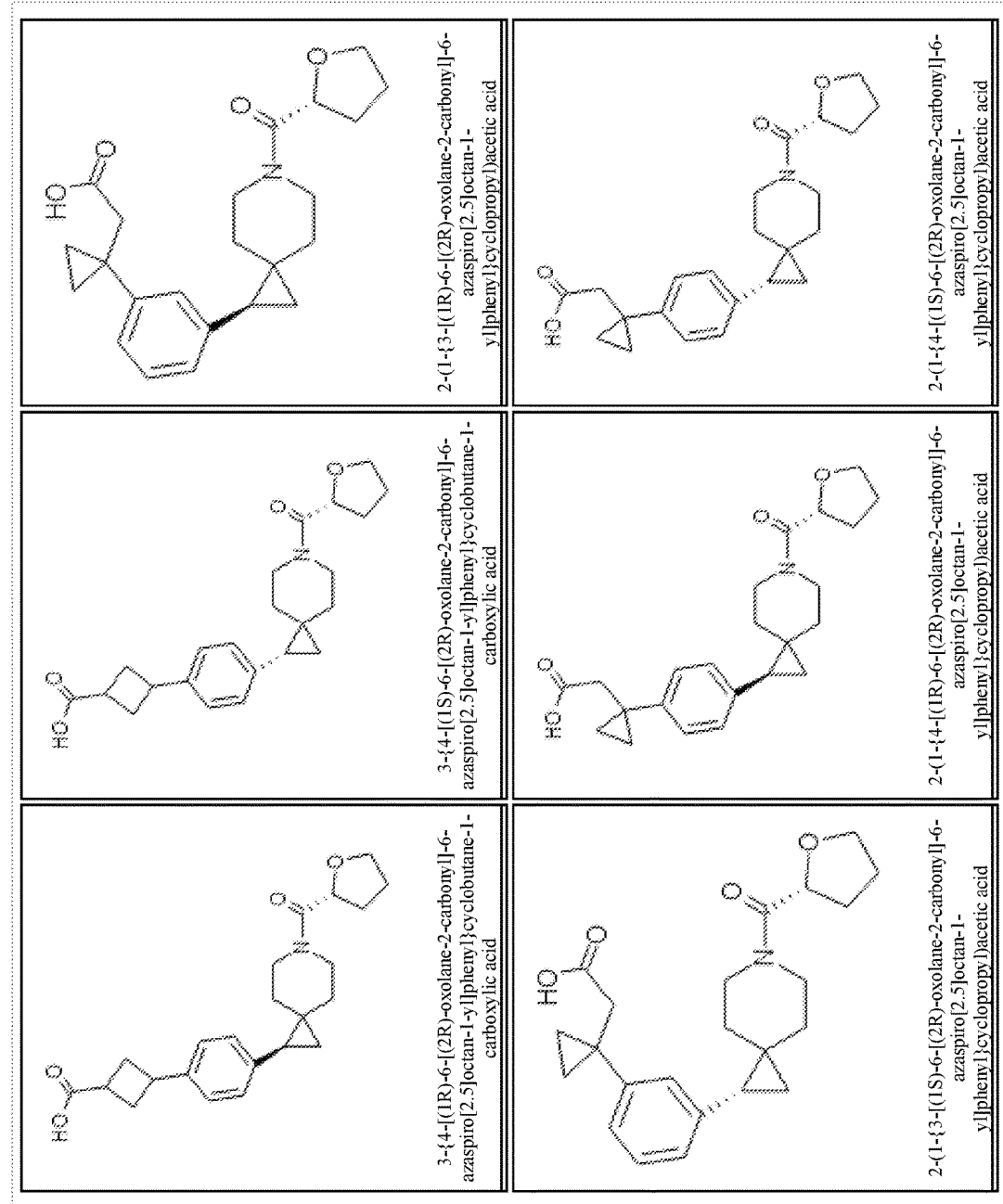
Figures 1, 57:
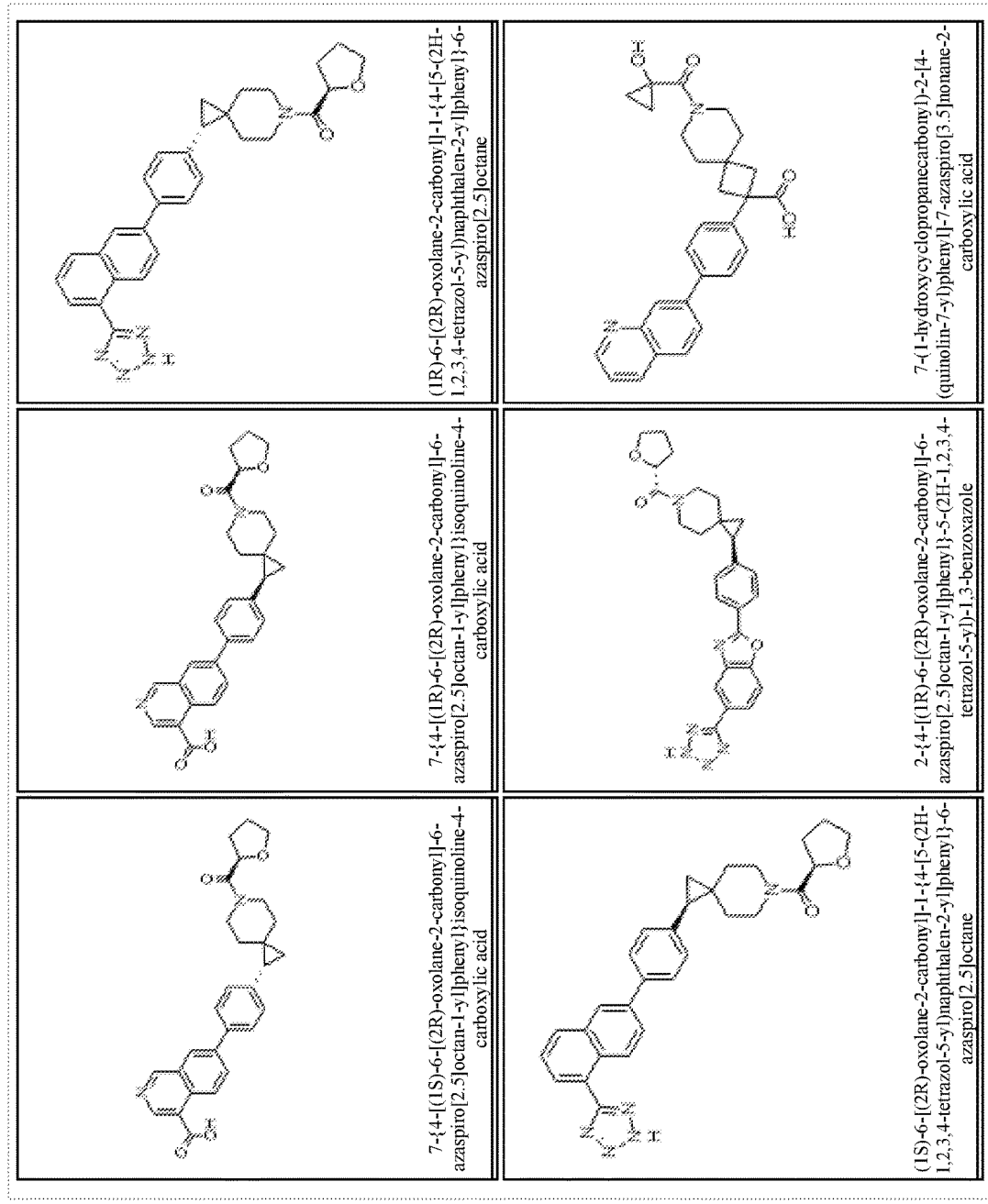
Figures 1, 58:
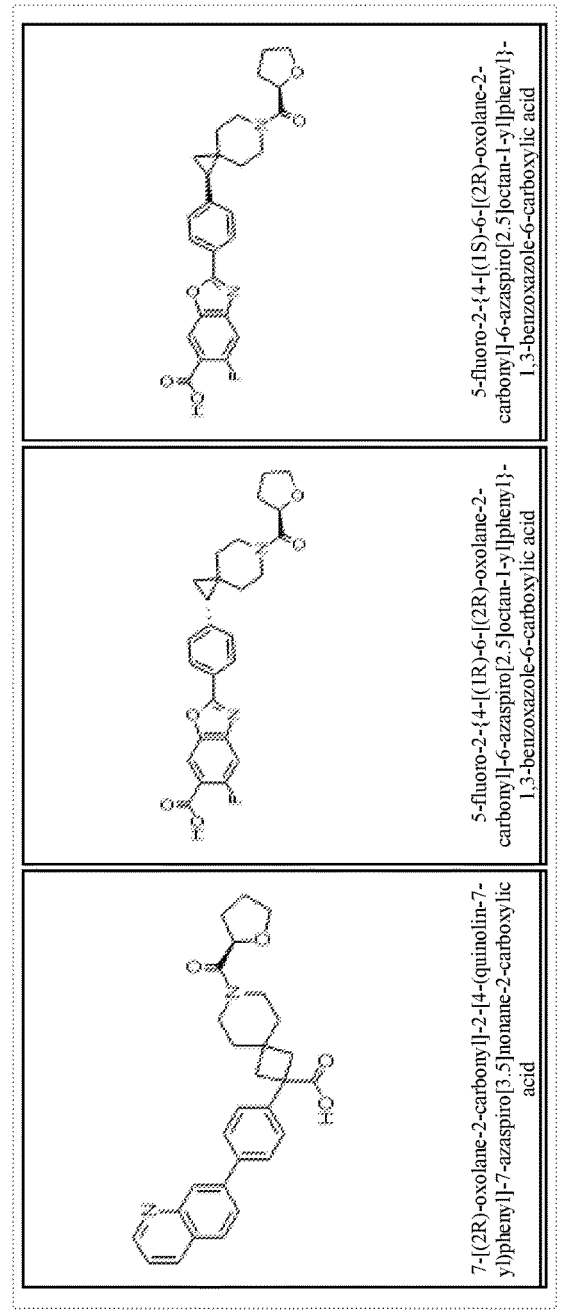
Figures 1, 59:
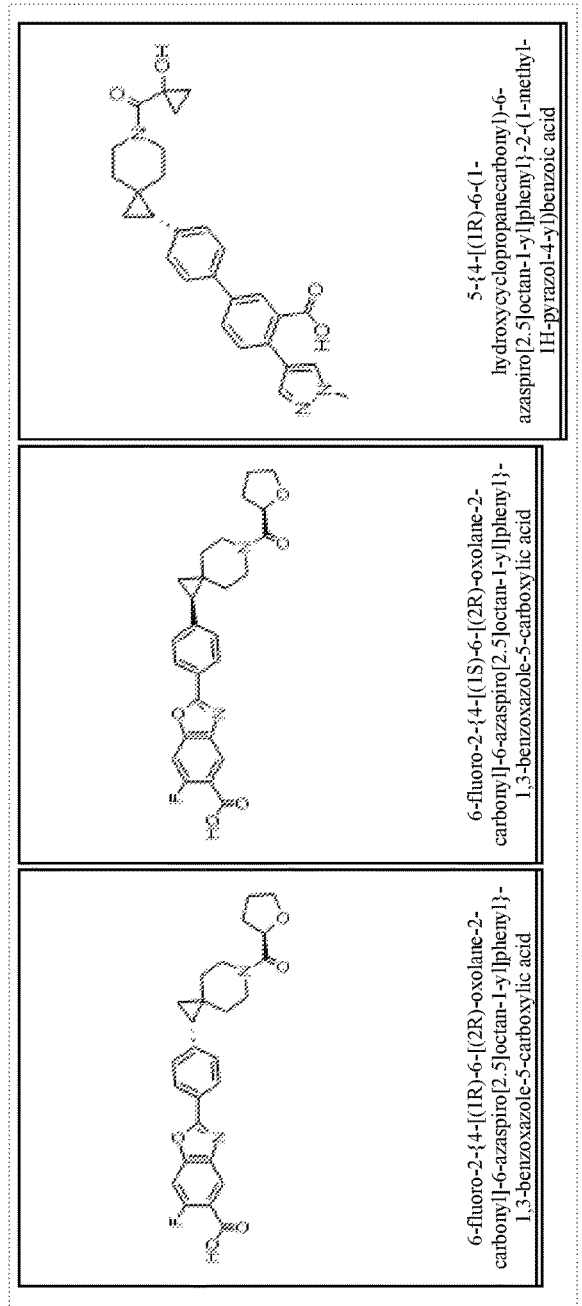
Figures 1, 60:
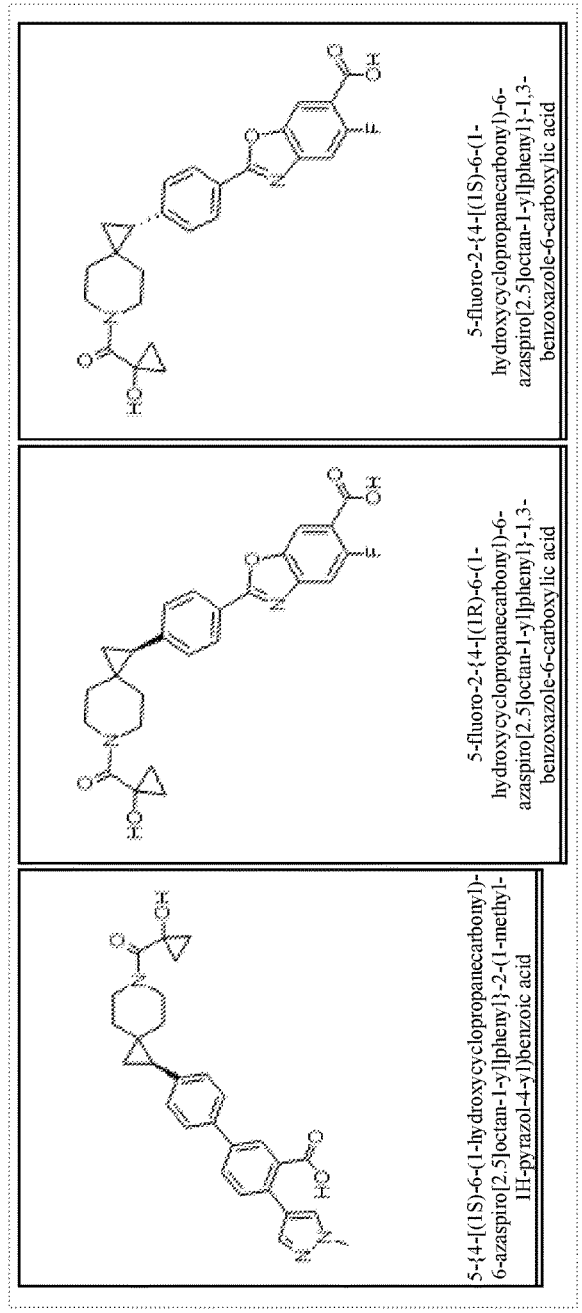
Figures 1, 61:
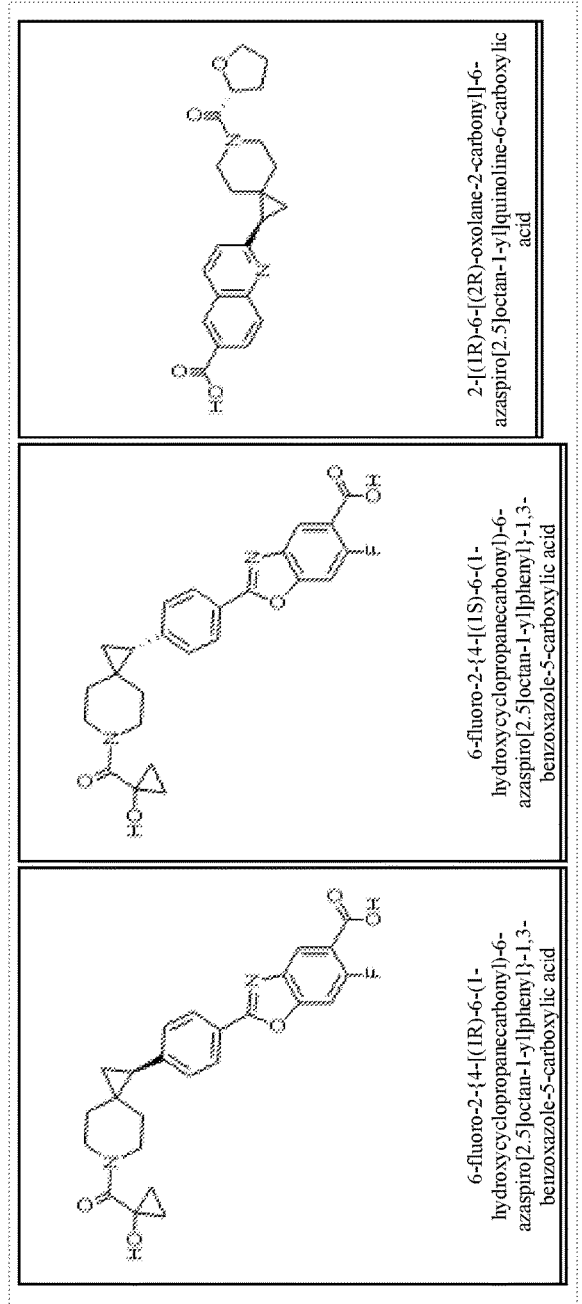
Figures 1, 62:
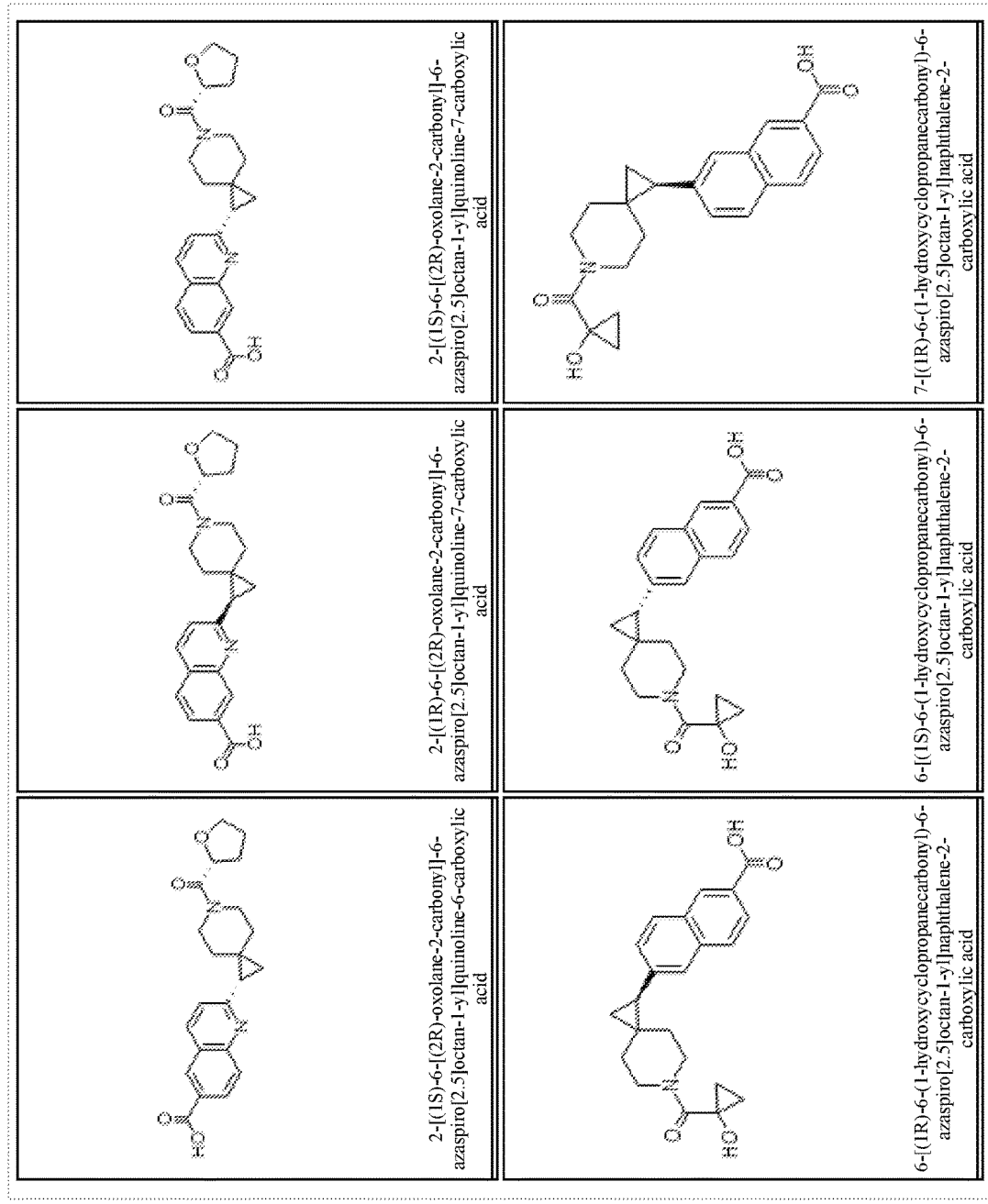
Figures 1, 63:
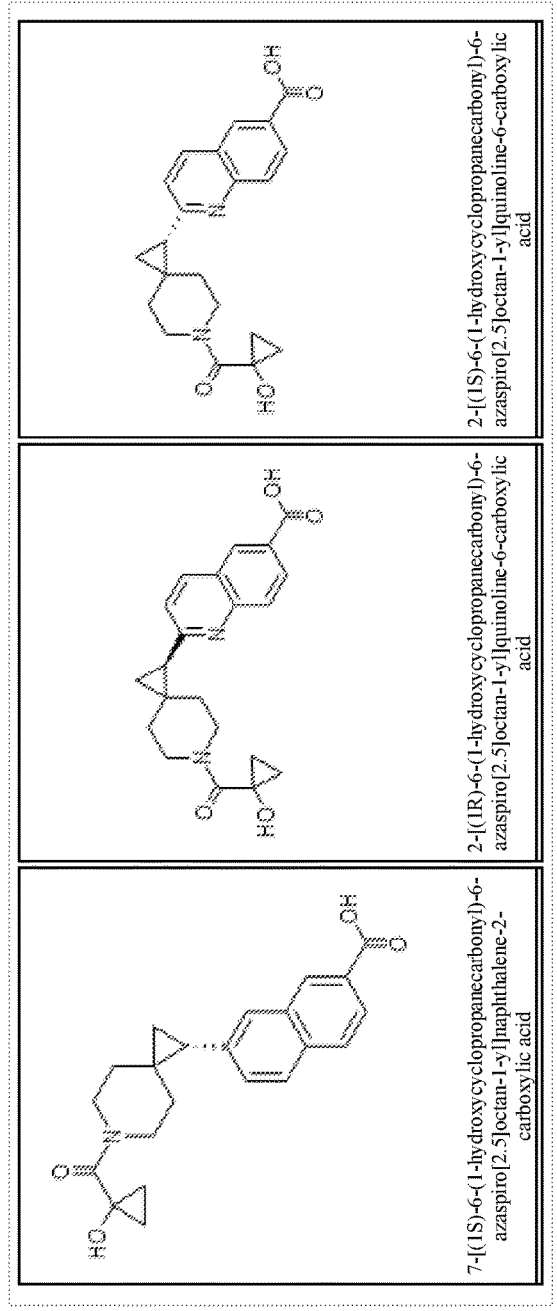
Figures 1, 64:
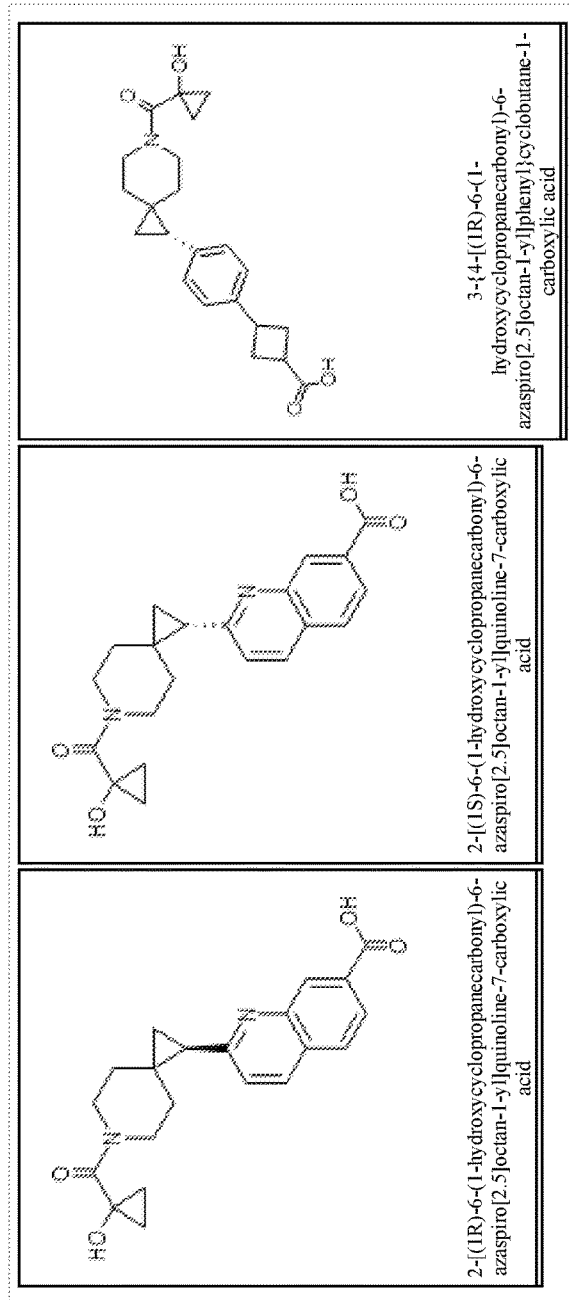
Figures 1, 65:
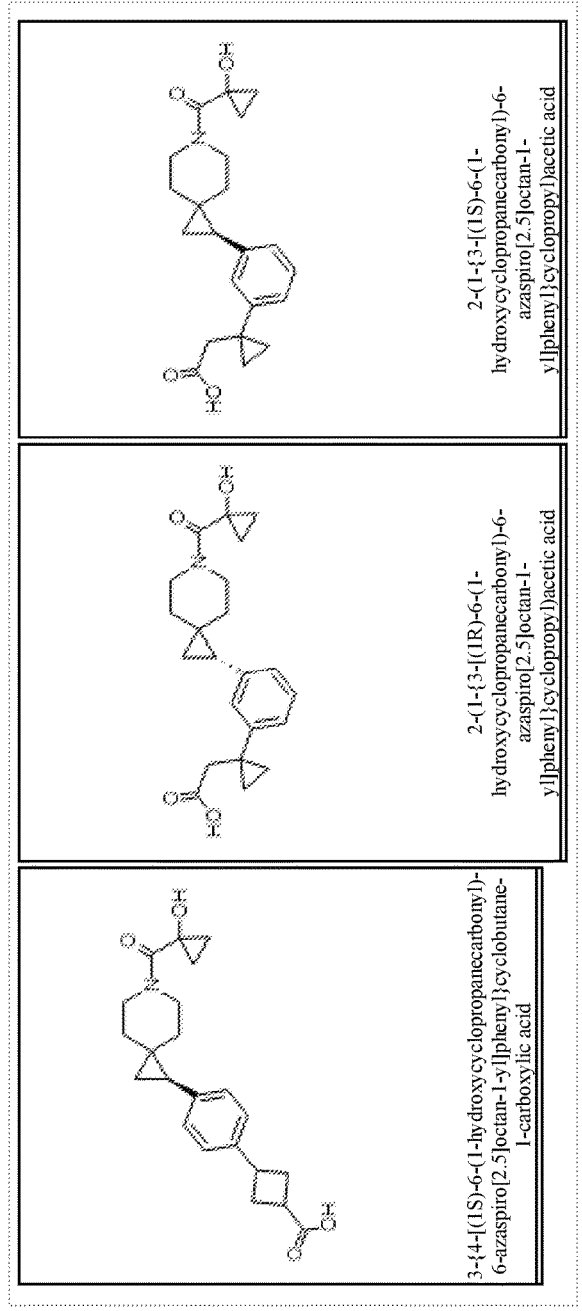
Figures 1, 66:
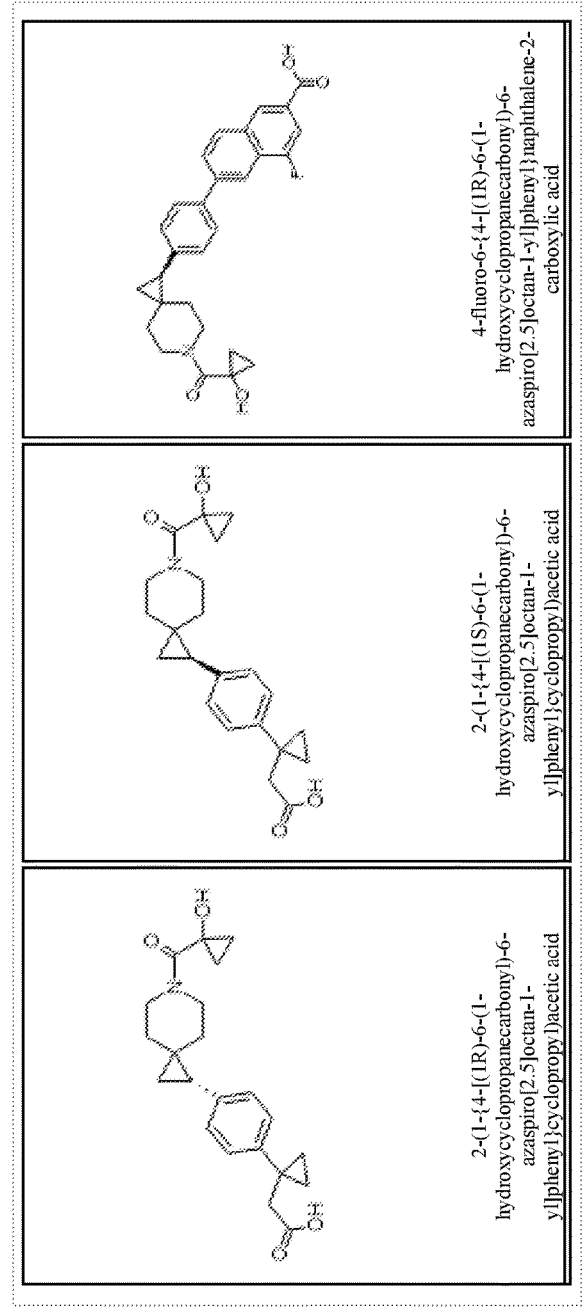
Figures 1, 67:
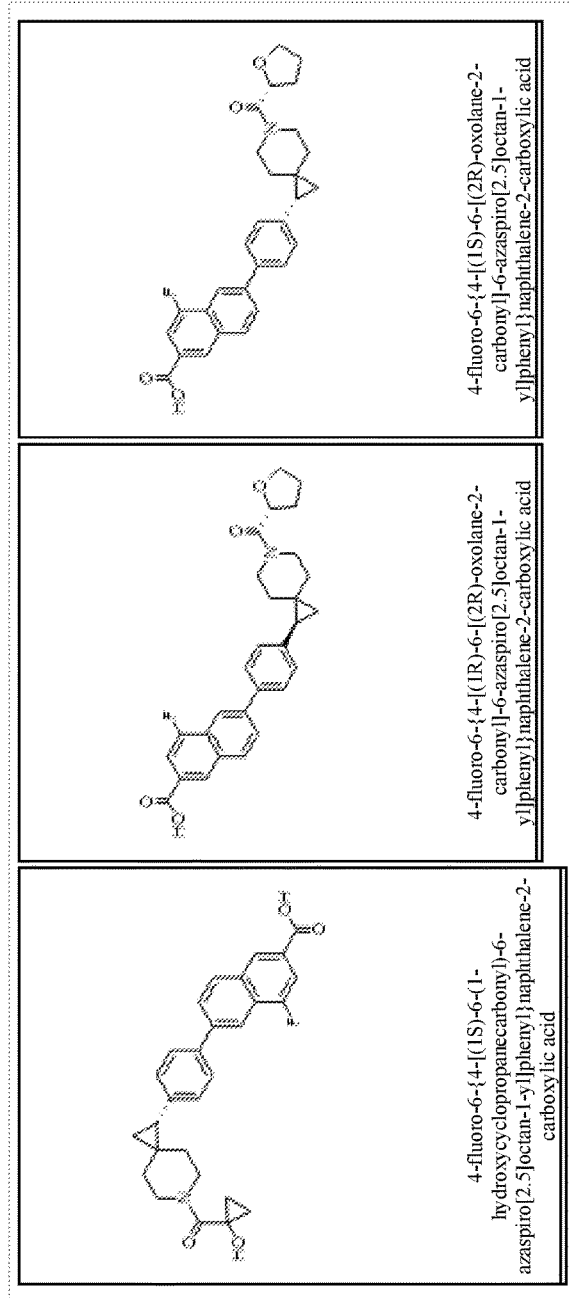
Figures 1, 68:
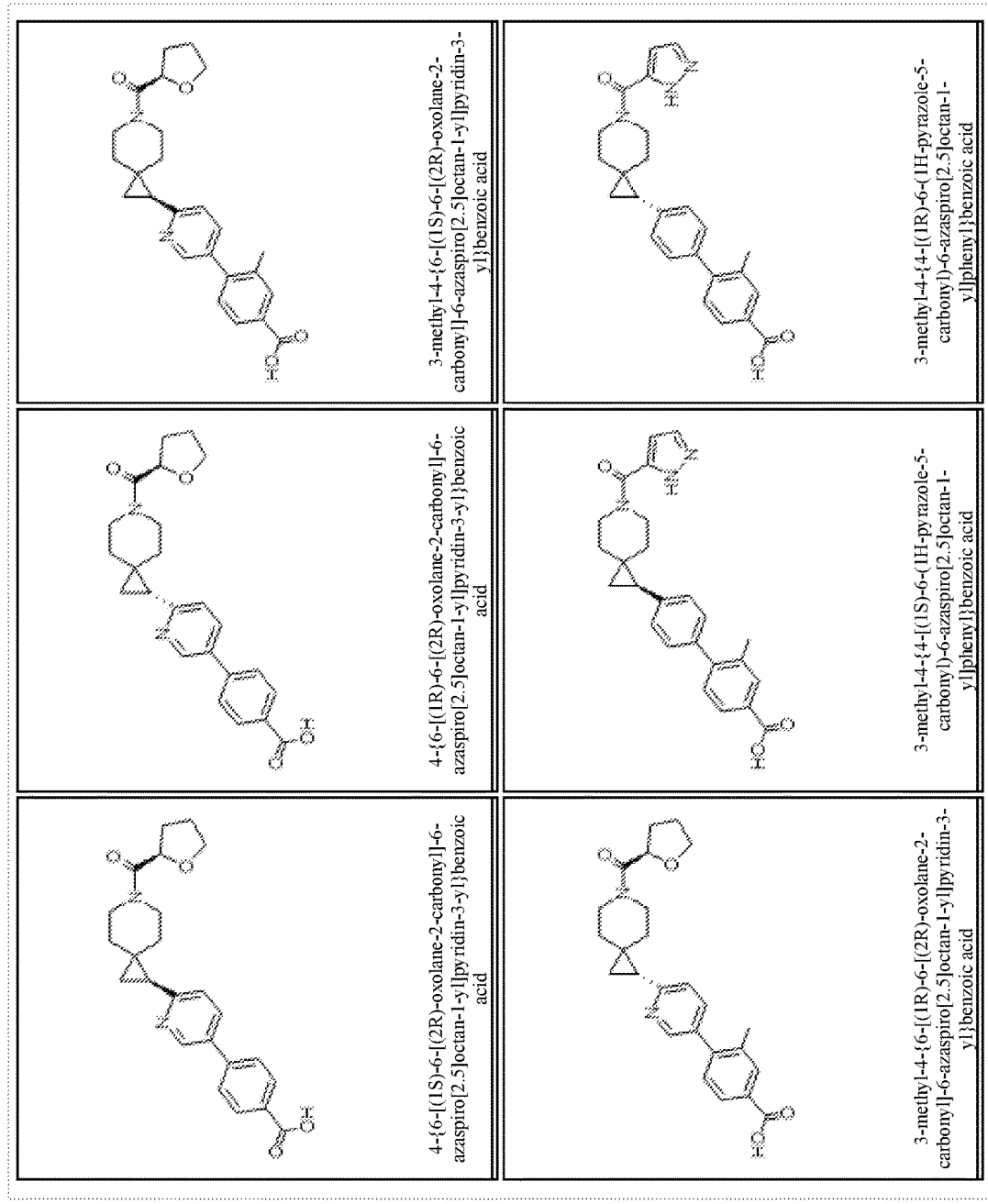
Figures 1, 69:
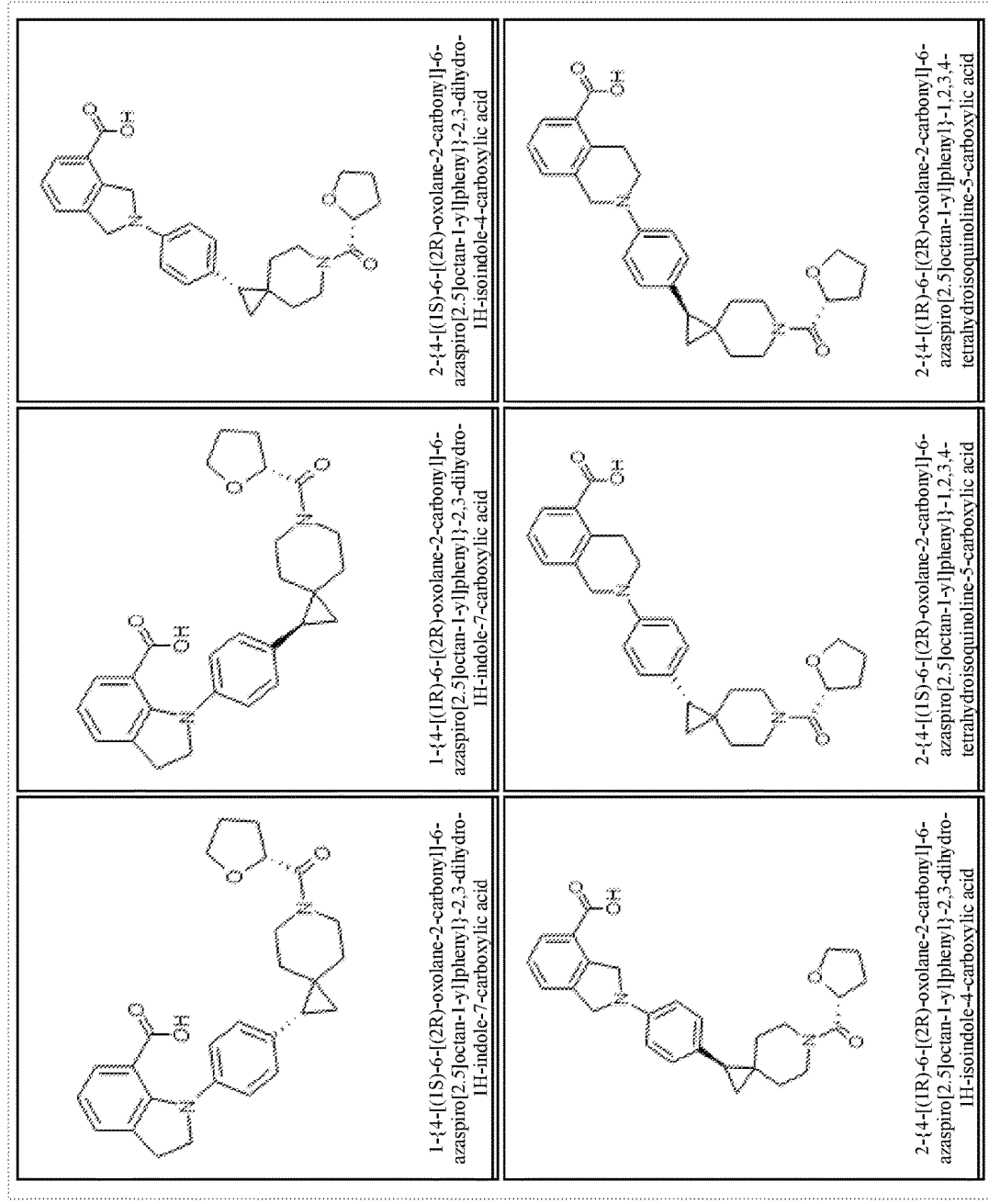
Figures 1, 70:
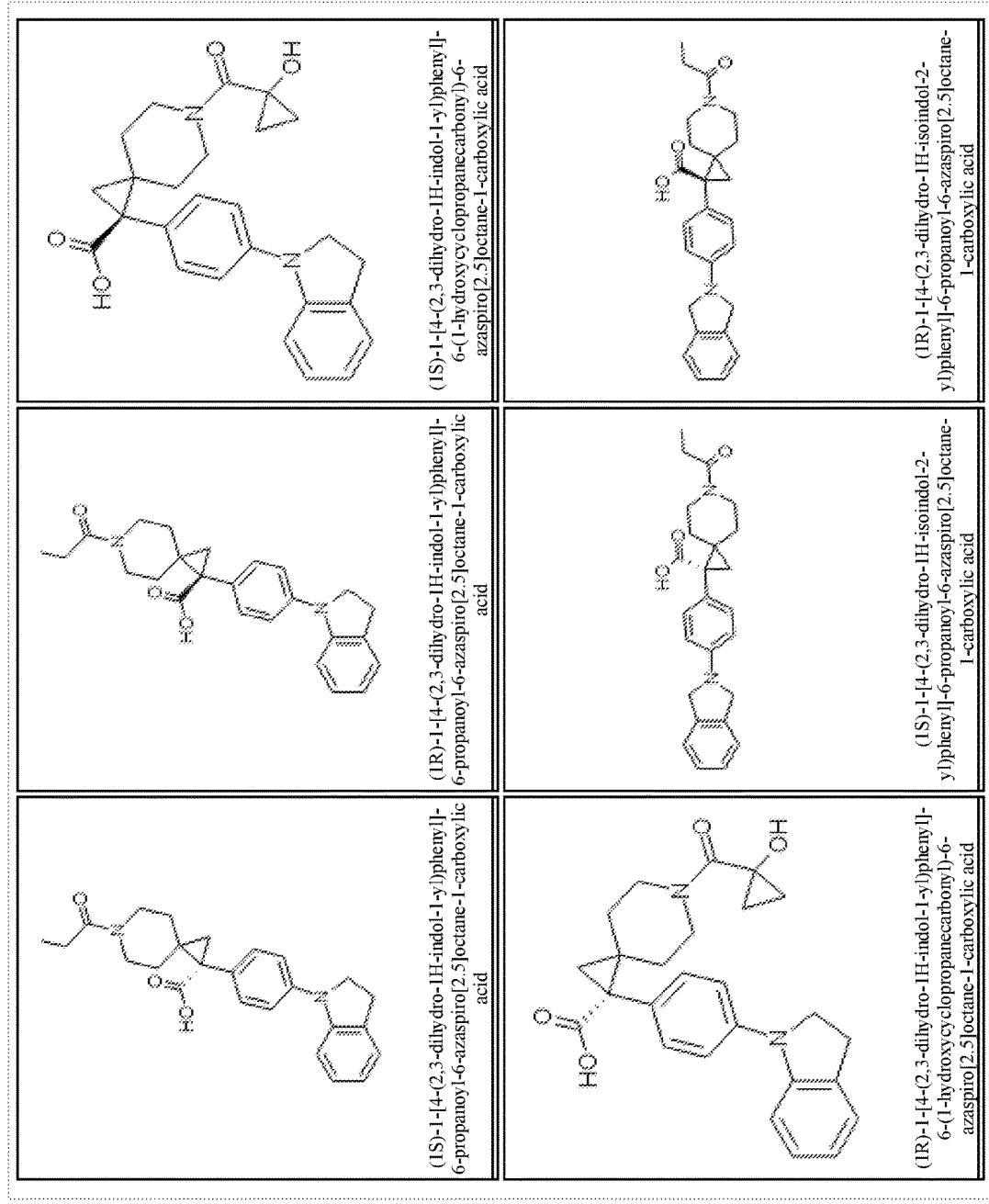
Figures 1, 71:
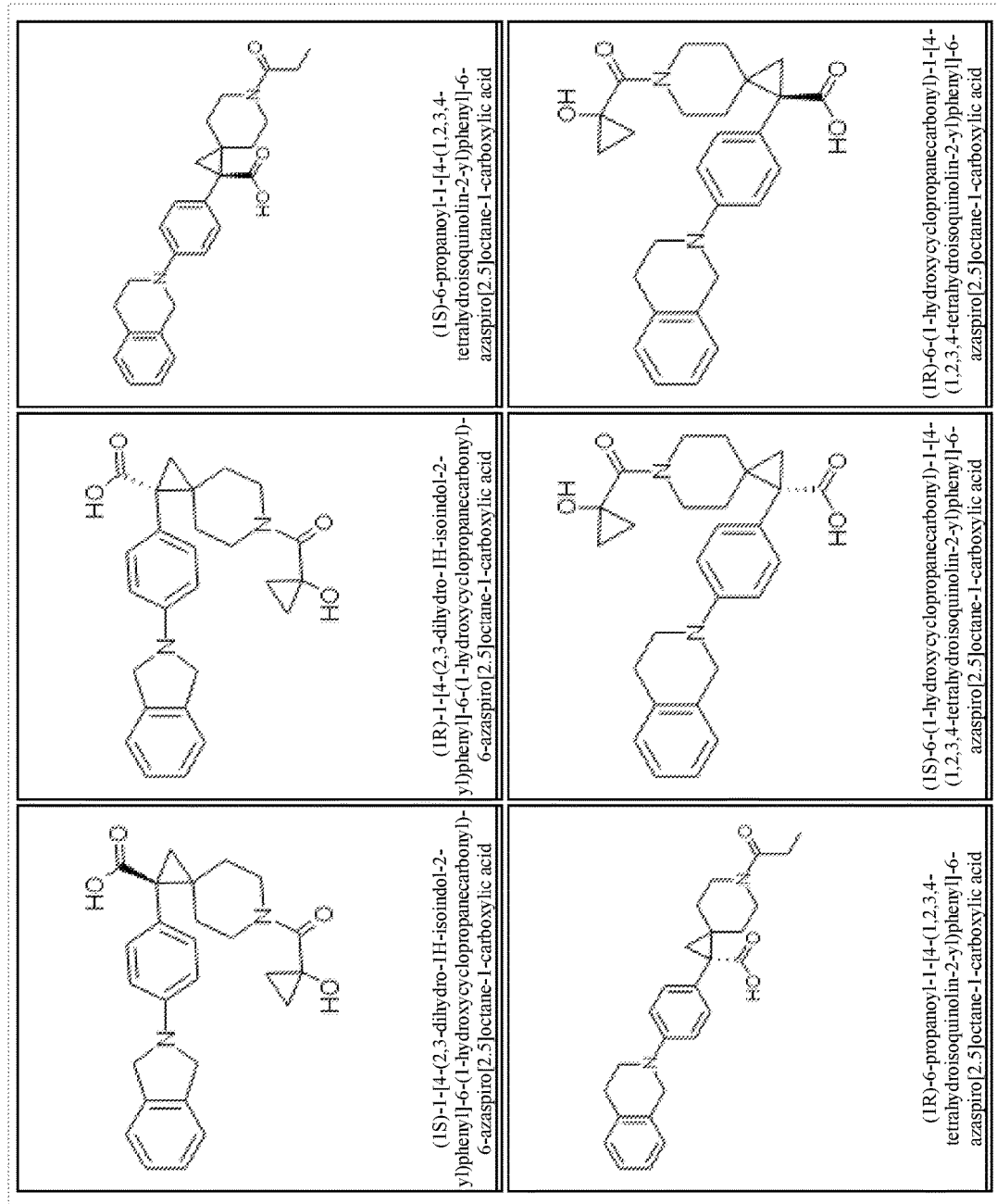
Figures 1, 72:
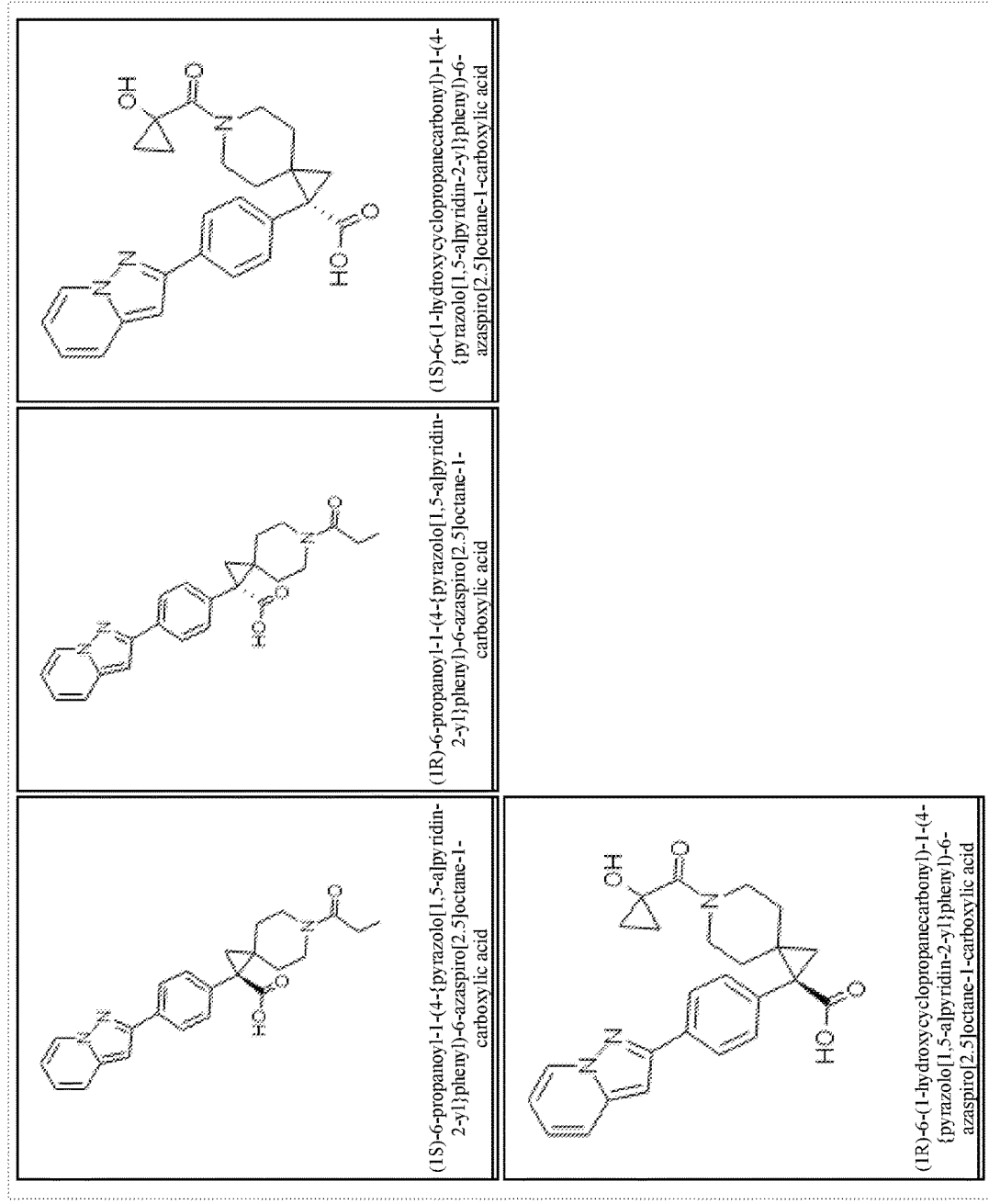
Figure 3:
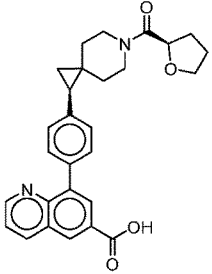
Figure 4:
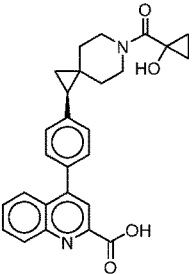
Figure 5:
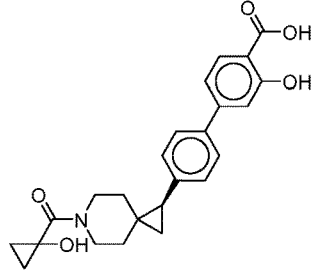
Figure 6:
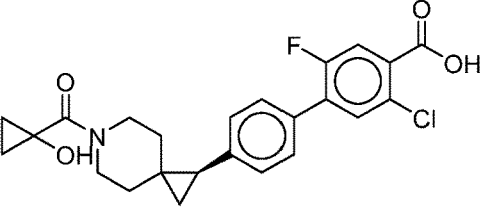

In some embodiments, the disclosure relates to a compound selected from FIG. 3, or a pharmaceutically acceptable salt thereof.

In some embodiments, the disclosure relates to a compound of formula

44

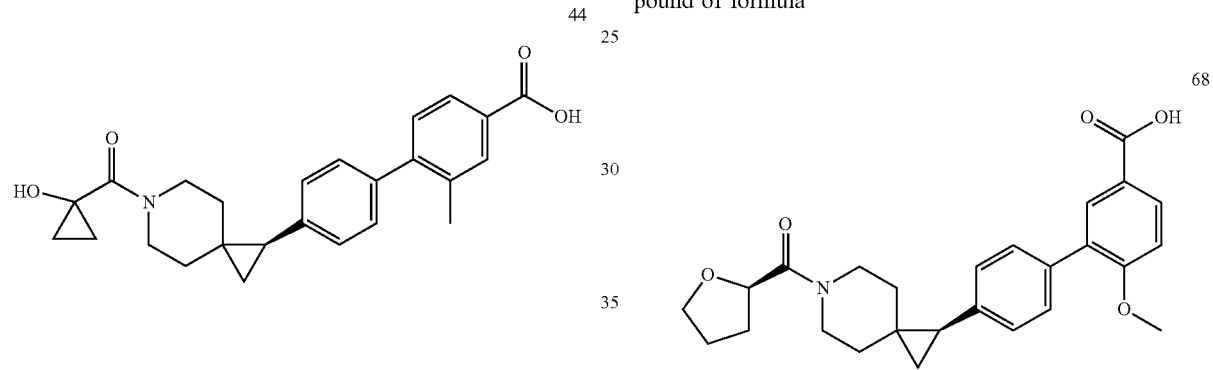

or a pharmaceutically acceptable salt thereof.

In some embodiments, the disclosure relates to a compound 4-{4-[(1S)-6-(1-hydroxycyclopropanecarbonyl)-6-azaspiro[2.5]octan-1-yl]phenyl}-3-methylbenzoic acid, or a pharmaceutically acceptable salt thereof.

In some embodiments, the disclosure relates to a compound of formula

49

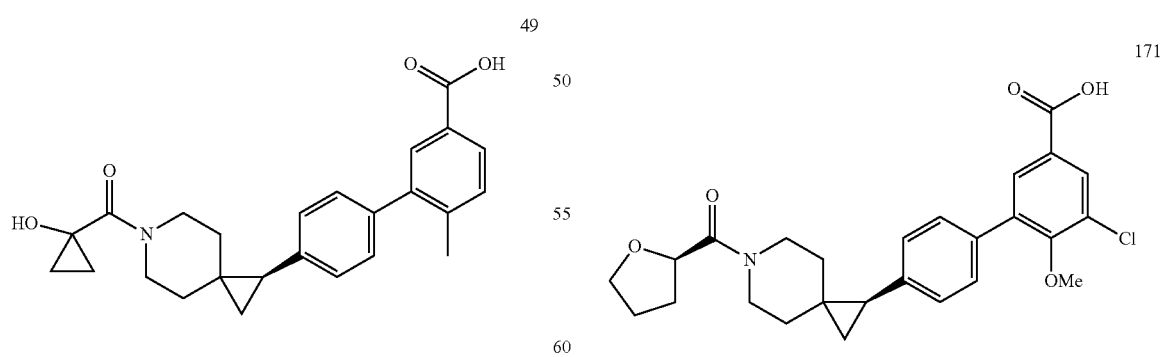

or a pharmaceutically acceptable salt thereof.

In some embodiments, the disclosure relates to a compound (S)-4'-(6-(1-hydroxycyclopropane-1-carbonyl)-6-azaspiro[2.5]octan-1-yl)-6-methyl-[1,1'-biphenyl]-3-carboxylic acid, or a pharmaceutically acceptable salt thereof.

In some embodiments, the disclosure relates to a compound of formula

52

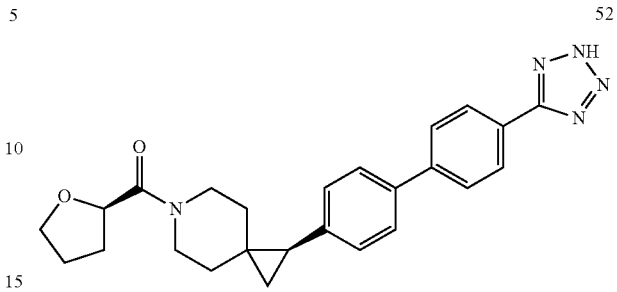

or a pharmaceutically acceptable salt thereof.

In some embodiments, the disclosure relates to a compound ((S)-1-(4'-(2H-tetrazol-5-yl)-[1,1'-biphenyl]-4-yl)-6-azaspiro[2.5]octan-6-yl)((R)-tetrahydrofuran-2-yl)methanone, or a pharmaceutically acceptable salt thereof.

In some embodiments, the disclosure relates to a compound of formula

68 or a pharmaceutically acceptable salt thereof.

In some embodiments, the disclosure relates to a compound 6-methoxy-4'-((S)-6-((R)-tetrahydrofuran-2-carbonyl)-6-azaspiro[2.5]octan-1-yl)-[1,1'-biphenyl]-3-carboxylic acid, or a pharmaceutically acceptable salt thereof.

In some embodiments, the disclosure relates to a compound of formula

171 or a pharmaceutically acceptable salt thereof.

In some embodiments, the disclosure relates to a compound 5-chloro-6-methoxy-4'-((S)-6-((R)-tetrahydrofuran-2-carbonyl)-6-azaspiro[2.5]octan-1-yl)-[1,1'-biphenyl]-3-carboxylic acid, or a pharmaceutically acceptable salt thereof.

In some embodiments, the disclosure relates to a compound of formula

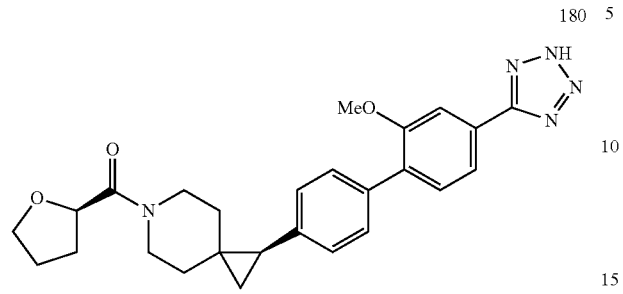

or a pharmaceutically acceptable salt thereof.

In some embodiments, the disclosure relates to a compound ((S)-1-(2'-methoxy-4'-(2H-tetrazol-5-yl)-1',2',3',4',5', 6'-hexahydro-[1,1'-biphenyl]-4-yl)-6-azaspiro[2.5]octan-6-yl)((R)-tetrahydrofuran-2-yl)methanone, or a pharmaceutically acceptable salt thereof.

In some embodiments, the disclosure relates to a compound of formula

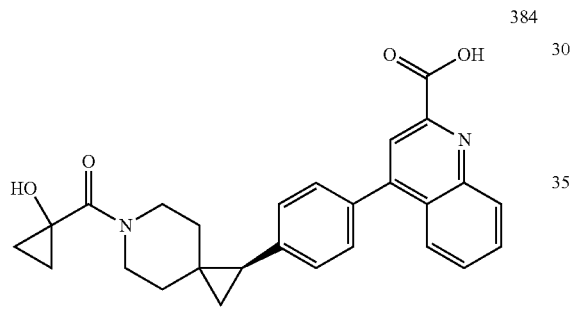

or a pharmaceutically acceptable salt thereof.

In some embodiments, the disclosure relates to a compound 4-[4-[(1S)-6-(1-hydroxycyclopropanecarbonyl)-6-azaspiro[2.5]octan-1-yl]phenyl]quinoline-2-carboxylic acid, or a pharmaceutically acceptable salt thereof.

In some embodiments, the disclosure relates to a compound selected from the group consisting of 4-{4-[(1S)-6-(1-hydroxycyclopropanecarbonyl)-6-azaspiro[2.5]octan-1-yl]phenyl}-3-methylbenzoic acid; (S)-4'-(6-(1-hydroxycyclopropane-1-carbonyl)-6-azaspiro[2.5]octan-1-yl)-6-methyl-[1,1'-biphenyl]-3-carboxylic acid; ((S)-1-(4'-(2H-tetrazol-5-yl)-[1,1'-biphenyl]-4-yl)-6-azaspiro[2.5] octan-6-yl)((R)-tetrahydrofuran-2-yl)methanone; 6-methoxy-4'-((S)-6-((R)-tetrahydrofuran-2-carbonyl)-6-azaspiro[2.5]octan-1-yl)-[1,1'-biphenyl]-3-carboxylic acid; 5-chloro-6-methoxy-4'-((S)-6-((R)-tetrahydrofuran-2-carbonyl)-6-azaspiro[2.5]octan-1-yl)-[1,1'-biphenyl]-3-carboxylic acid; ((S)-1-(2'-methoxy-4'-(2H-tetrazol-5-yl)-1',2',3',4', 5',6'-hexahydro-[1,1'-biphenyl]-4-yl)-6-azaspiro[2.5]octan-6-yl)((R)-tetrahydrofuran-2-yl)methanone; and 4-[4-[(1S)-6-(1-hydroxycyclopropanecarbonyl)-6-azaspiro[2.5]octan-1-yl]phenyl]quinoline-2-carboxylic acid; or a pharmaceutically acceptable salt thereof.

In some embodiments, the disclosure relates to:
1. A compound of Formula (I):

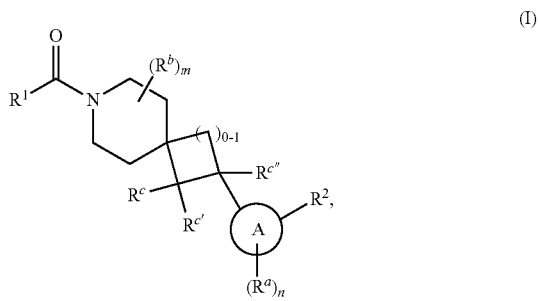

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S,
wherein $R^1$ is optionally substituted with halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or $C_{1-3}$ alkyl optionally substituted with halogen or —CO$_2$R$^3$;
$R^2$ is halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of $R^2$ is optionally substituted with 1-6 $R^d$;
each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), —COR$^5$, —N(R$^4$)COR$^5$, —N(R$^4$) SOR$^5$, —N(R$^4$)SO$_2$R$^5$, —SOR$^5$, —SO$_2$R$^5$, —N(R$^4$) CO$_2$R$^3$, —N(R$^4$)C(O)N(R$^4$)(R$^{4'}$), tetrazolyl, or $C_{1-3}$ aliphatic optionally substituted with halogen;
each $R^b$ is independently halogen, oxo, —CN, —NO$_2$, —OR, —SR$^3$, —CO$_2$R$^3$, —N(R$^4$)(R$^{4'}$), —C(O)N(R$^4$) (R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), $C_{1-6}$ aliphatic optionally substituted with halogen;
$R^c$ is hydrogen, halogen, —OH, —NH$_2$, —CN, —CO$_2$R$^3$, —C(O)N(R$^4$)$_2$, or tetrazole;
$R^{c'}$ is hydrogen, halogen, —OH, —NH$_2$, —CN, —CO$_2$R$^3$, —C(O)N(R$^4$)$_2$, or tetrazole;
$R^{c''}$ is hydrogen, halogen, —OH, —NH$_2$, —CN, —CO$_2$R$^3$, —C(O)N(R$^4$)$_2$, or tetrazole;
each $R^d$ is independently halogen, oxo, —CN, —NO$_2$, —OR, —SR$^3$, —CO$_2$R$^3$, —N(R$^4$)(R$^{4'}$), —C(O)N(R$^4$) (R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;
  wherein an optionally substituted group of $R^d$ is optionally substituted with halogen, —OH, —NH$_2$, —CN, oxo, or $C_{1-3}$ aliphatic;
each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
  wherein an optionally substituted group of $R^3$ is optionally substituted with halogen, —OH, —NH$_2$, —CN or oxo;
each $R^4$ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
  wherein an optionally substituted group of $R^4$ is optionally substituted with halogen, —OH, —NH$_2$, —CN or oxo;
each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S,
  wherein an optionally substituted group of $R^{4'}$ is optionally substituted with halogen, —OH, —NH$_2$, —CN, or oxo;
each $R^5$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
  wherein an optionally substituted group of $R^5$ is optionally substituted with halogen, —OH, —NH$_2$, —CN or oxo;
m is 0-4; and
n is 0-6.

2. The compound of embodiment 1, wherein the compound is of Formula (I-a):

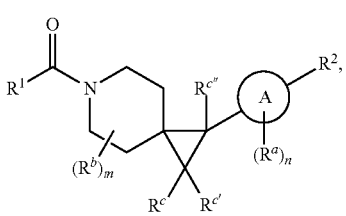

(I-a)

or a pharmaceutically acceptable salt thereof,

Ring A is 6-10 membered aryl or 5-10 membered heteroaryl containing 1-4 heteroatoms independently selected from the group consisting of O, N, and S;

$R^1$ is $C_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S,
  wherein $R^1$ is optionally substituted with —OH, —NH$_2$, or $C_{1-3}$ alkyl optionally substituted with halogen or —CO$_2$R$^3$;

$R^2$ is —CO$_2$R$^3$ or an optionally substituted group selected from the group consisting of 3-7 membered cycloalkyl, phenyl, and 5-10 membered heteroaryl containing 1-2 heteroatoms independently selected from the group consisting of O, N, and S,
  wherein an optionally substituted group of $R^2$ is optionally substituted with 1-6 $R^d$;

each $R^a$ is independently halogen;

each $R^b$ is independently $C_{1-3}$ aliphatic;

$R^c$ is hydrogen or halogen;

$R^{c'}$ is hydrogen or halogen;

$R^{c''}$ is hydrogen, halogen, or —CO$_2$H;

each $R^d$ is independently halogen, —CO$_2$R$^3$, —OR$^3$, —S(O)$_2$NH$_2$ or an optionally substituted group selected from the group consisting of $C_{1-3}$ aliphatic, and 5-7 membered heteroaryl containing 1-4 heteroatoms independently selected from the group consisting of O, N, and S;
  wherein an optionally substituted group of $R^d$ is optionally substituted with halogen or $C_{1-3}$ aliphatic;

each $R^3$ is independently hydrogen or $C_{1-3}$ alkyl optionally substituted with fluoro;

m is 0-4; and n is 0-6.

3. The compound of embodiment 2, wherein Ring A is 6-10 membered aryl.

4. The compound of embodiment 3, wherein $R^1$ is —CO$_2$H, cyclobutyl, benzoxazolyl, indolyl, indazolyl, benzimidazolyl, quinolinyl, phenyl, naphthyl, pyridyl, or isoquinolinyl 5. The compound of embodiment 4, wherein each $R^a$ is independently fluoro or chloro.

6. The compound of embodiment 5, wherein each $R^b$ is methyl.

7. The compound of embodiment 6, wherein
  $R^c$ is hydrogen or fluoro;
  $R^{c'}$ is hydrogen or fluoro; and
  $R^{c''}$ is hydrogen or —CO$_2$H.

8. The compound of embodiment 7, wherein each $R^d$ is independently fluoro, methyl, —CO$_2$H, tetrazolyl, methoxy, chloro, —CF$_3$, —OCF$_3$, or N-methyl pyrazolyl.

9. The compound of embodiment 8, wherein
  m is 0-1; and
  n is 0-3.

10. The compound of embodiment 1, wherein the compound is of Formula (II):

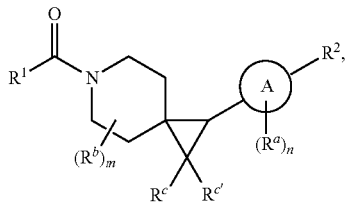

(II)

or a pharmaceutically acceptable salt thereof,

Ring A is 6-10 membered aryl or 5-10 membered heteroaryl containing 1-2 heteroatoms independently selected from the group consisting of O, N, and S;

$R^1$ is $C_{1-6}$ aliphatic, 3-6 membered cycloalkyl, 4-6-membered heterocyclyl containing 1-3 heteroatoms independently selected from the group consisting of O, N, and S, or 5-6 membered heteroaryl containing 1-3 heteroatoms independently selected from the group consisting of O, N, and S, wherein $R^1$ is optionally substituted with halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), tetrazolyl, or $C_{1-3}$ alkyl optionally substituted with halogen or —CO$_2$R$^3$;

$R^2$ is —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of $R^2$ is optionally substituted with 1-6 $R^d$;

each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), tetrazolyl, or $C_{1-3}$ aliphatic optionally substituted with halogen;

each $R^b$ is independently $C_{1-6}$ aliphatic optionally substituted with halogen;

$R^c$ is hydrogen or halogen;

$R^{c'}$ is hydrogen or halogen;

each $R^d$ is independently halogen, oxo, —CN, —NO$_2$, —OR$^3$, —SR$^3$, —CO$_2$R$^3$, —N(R$^4$)(R$^{4'}$)N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic and 5-10 membered heteroaryl containing 1-4 heteroatoms independently selected from the group consisting of O, N, and S;

wherein an optionally substituted group of $R^d$ is optionally substituted with halogen, —OH, —NH$_2$, —CN, oxo, or $C_{1-3}$ alkyl;

each $R^3$ is independently hydrogen or $C_{1-6}$ aliphatic optionally substituted with halogen, —OH, —NH$_2$, —CN, or oxo;

each $R^4$ is independently hydrogen, —OH, —CN, or $C_{1-6}$ aliphatic optionally substituted with halogen, —OH, —NH$_2$, —CN, or oxo;

each $R^{4'}$ is independently hydrogen, or $C_{1-6}$ aliphatic optionally substituted with halogen, —OH, —NH$_2$, —CN, or oxo;

each $R^5$ is independently hydrogen or $C_{1-6}$ aliphatic optionally substituted with halogen, —OH, —NH$_2$, —CN, or oxo;

m is 0-4; and n is 0-6.

11. The compound of embodiment 1, wherein the compound is of Formula (III):

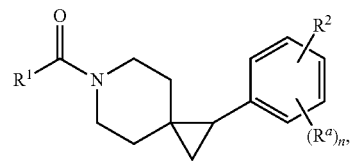

(III)

or a pharmaceutically acceptable salt thereof, wherein:

$R^1$ is $C_{1-3}$ aliphatic, 3-4 membered cycloalkyl, 5-membered heterocyclyl containing 1-3 heteroatoms independently selected from the group consisting of O, N and S, or 5-membered heteroaryl containing 1-3 heteroatoms independently selected from the group consisting of O, N, and S;

wherein $R^1$ is optionally substituted with —OH or NH$_2$;

$R^2$ is —CO$_2$H or an optionally substituted group selected from the group consisting of phenyl and 5-10 membered heteroaryl containing 1-2 heteroatoms independently selected from the group consisting of O, N, and S, wherein an optionally substituted group of $R^2$ is optionally substituted with 1-6 $R^d$;

each $R^a$ is independently halogen;

each $R^d$ is independently halogen, —OR$^3$, —CO$_2$R$^3$, —S(O)$_2$NH$_2$, or an optionally substituted group selected from the group consisting of $C_{1-3}$ aliphatic, 5-7 membered heteroaryl containing 1-4 heteroatoms independently selected from the group consisting of O, N, and S;

wherein an optionally substituted group of $R^d$ is optionally substituted with halogen or $C_{1-3}$ aliphatic;

each $R^3$ is independently hydrogen or $C_{1-3}$ alkyl; and n is 0-4.

12. The compound of embodiment 1, wherein the compound is of Formula (IV):

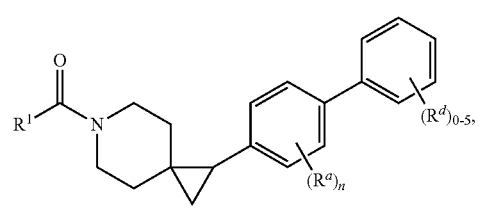

(IV)

or a pharmaceutically acceptable salt thereof, wherein:

$R^1$ is $C_{1-3}$ aliphatic, 3-4 membered cycloalkyl, 5-membered heterocyclyl containing 1-3 heteroatoms independently selected from the group consisting of O, N, and S, and 5-membered heteroaryl containing 1-3 heteroatoms independently selected from the group consisting of O, N, and S, wherein $R^1$ is optionally substituted with —OH or —NH$_2$;

each $R^a$ is independently halogen;

each $R^d$ is independently halogen, —$CO_2R^3$, —$OR^3$, —$S(O)_2NH_2$, or an optionally substituted group selected from the group consisting of $C_{1-3}$ aliphatic and 5-membered heteroaryl containing 1-4 heteroatoms independently selected from the group consisting of O, N, and S, wherein an optionally substituted group of $R^d$ is optionally substituted with halogen or $C_{1-3}$ aliphatic;

each $R^3$ is independently hydrogen or $C_{1-3}$ alkyl; and n is 0-4.

13. The compound of embodiment 1, wherein the compound is of Formula (V):

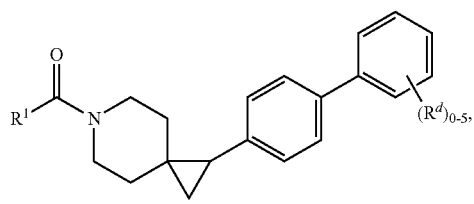

(V)

or a pharmaceutically acceptable salt thereof, wherein:

$R^1$ is 3-membered cycloalkyl optionally substituted with —OH, or 5-membered heterocyclyl containing 1-3 heteroatoms independently selected from the group consisting of O, N, and S;

each $R^d$ is independently halogen, —$CO_2H$, —$OR^3$, $C_{1-3}$ aliphatic, or 5-membered heteroaryl containing 1-4 heteroatoms independently selected from the group consisting of O, N and S; and each $R^3$ is independently hydrogen or $C_{1-3}$ alkyl.

14. The compound of embodiment 1, wherein the compound is selected from Table 1.

15. The compound of embodiment 1, wherein the compound is selected from the group consisting of:

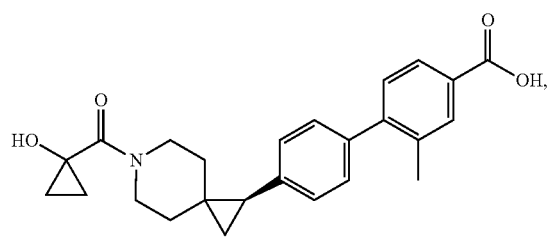

44

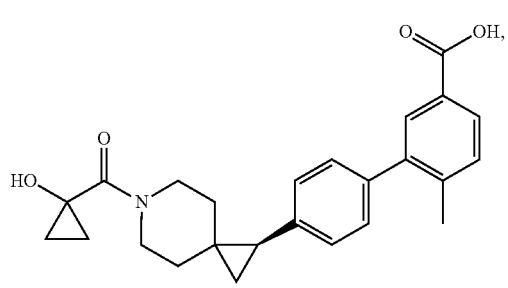

49

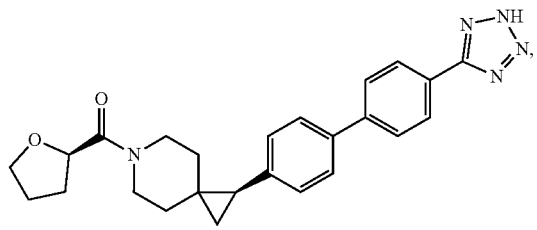

52

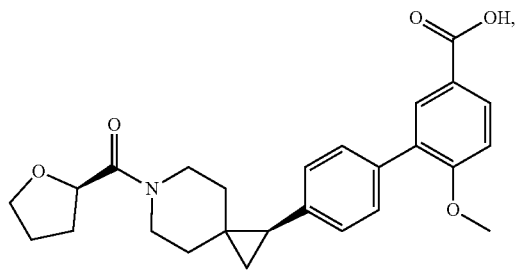

68

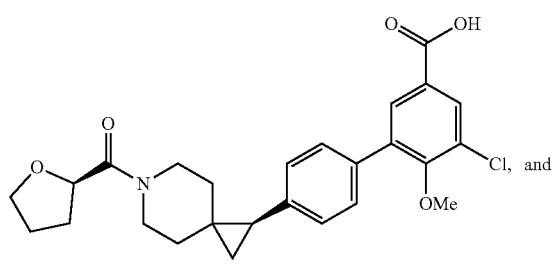

171

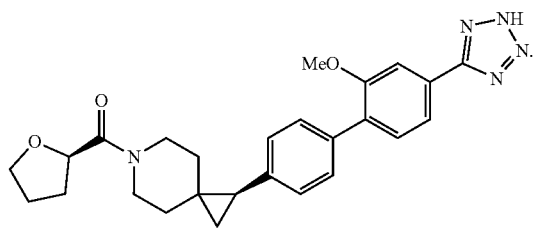

180

16. A pharmaceutical composition comprising the compound of any of embodiments 1-15.

17. A FASN inhibitor of Formula (I):

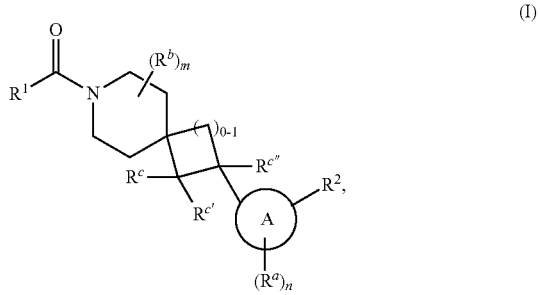

(I)

or a pharmaceutically acceptable salt thereof, wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S,
wherein $R^1$ is optionally substituted with halogen, oxo, —CN, —NO$_2$, —OR$^3$, —SR$^3$, —CO$_2$R$^3$, —N(R$^4$)(R$^{4'}$) N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$) SO$_2$R$^5$, —SOR$^5$, —SO$_2$R$^5$, —N(R$^4$)CO$_2$R$^3$, —N(R$^4$) C(O)N(R$^4$)(R$^{4'}$), tetrazolyl, or $C_{1-3}$ alkyl optionally substituted with halogen or —CO$_2$R$^3$;
$R^2$ is halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$) (R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S,
wherein an optionally substituted group of $R^2$ is optionally substituted with 1-6 $R^d$;
each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), —COR$^5$, —N(R$^4$)COR$^5$, —N(R$^4$) SOR$^5$, —N(R$^4$)SO$_2$R$^5$, —SOR$^5$, —SO$_2$R$^5$, —N(R$^4$) CO$_2$R$^3$, —N(R$^4$)C(O)N(R$^4$)(R$^{4'}$), tetrazolyl, or $C_{1-3}$ aliphatic optionally substituted with halogen;
each $R^b$ is independently halogen, oxo, —CN, —NO$_2$, —OR$^3$, —SR$^3$, —CO$_2$R$^3$, —N(R$^4$)(R$^{4'}$), —C(O)N(R$^4$) (R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), $C_{1-6}$ aliphatic optionally substituted with halogen;
$R^c$ is hydrogen, halogen, —OH, —NH$_2$, —CN, —CO$_2$R$^3$, —C(O)N(R$^4$)$_2$, or tetrazole;
$R^{c'}$ is hydrogen, halogen, —OH, —NH$_2$, —CN, —CO$_2$R$^3$, —C(O)N(R$^4$)$_2$, or tetrazole;
$R^{c''}$ is hydrogen, halogen, —OH, —NH$_2$, —CN, —C$_2$R$^3$, —C(O)N(R$^4$)$_2$, or tetrazole;
each $R^d$ is independently halogen, oxo, —CN, —NO$_2$, —OR$^3$, —SR$^3$, —CO$_2$R$^3$, —N(R$^4$)(R$^{4'}$), —C(O)N(R$^4$) (R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;
wherein an optionally substituted group of $R^d$ is optionally substituted with halogen, —OH, —NH$_2$, —CN, oxo, or $C_{1-3}$ aliphatic;
each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^3$ is optionally substituted with halogen, —OH, —NH$_2$, —CN or oxo;
each $R^4$ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^4$ is optionally substituted with halogen, —OH, —NH$_2$, —CN or oxo;
each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^{4'}$ is optionally substituted with halogen, —OH, —NH$_2$, —CN or oxo;
each $R^5$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^5$ is optionally substituted with halogen, —OH, —NH$_2$, —CN or oxo;
m is 0-4; and
n is 0-6.
18. A compound of Formula (I) obtained by a process disclosed herein:

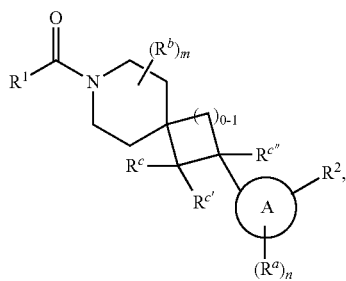

(I)

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S,
wherein $R^1$ is optionally substituted with halogen, oxo, —CN, —$NO_2$, —$OR^3$, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, tetrazolyl, or $C_{1-3}$ alkyl optionally substituted with halogen or —$CO_2R^3$;

$R^2$ is halogen, oxo, —CN, —$NO_2$, —$OR^3$, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of $R^2$ is optionally substituted with 1-6 $R^d$;

each $R^a$ is independently halogen, —CN, —$NO_2$, —$OR^3$, —$CO_2R^3$, —$N(R^4)(R^{4'})$, —$SR^3$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, tetrazolyl, or $C_{1-3}$ aliphatic optionally substituted with halogen;

each $R^b$ is independently halogen, oxo, —CN, —$NO_2$, —OR, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, $C_{1-6}$ aliphatic optionally substituted with halogen;

$R^c$ is hydrogen, halogen, —OH, —$NH_2$, —CN, —$CO_2R^3$, —$C(O)N(R^4)_2$, or tetrazolyl;

$R^{c'}$ is hydrogen, halogen, —OH, —$NH_2$, —CN, —$CO_2R^3$, —$C(O)N(R^4)_2$, or tetrazolyl;

$R^{c''}$ is hydrogen, halogen, —OH, —$NH_2$, —CN, —$CO_2R^3$, —$C(O)N(R^4)_2$, or tetrazolyl;

each $R^d$ is independently halogen, oxo, —CN, —$NO_2$, —OR, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —$SOR^5$, —$SO_2R^5$, —$N(R^4)CO_2R^3$, —$N(R^4)C(O)N(R^4)(R^{4'})$, or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;
wherein an optionally substituted group of $R^d$ is optionally substituted with halogen, —OH, —$NH_2$, —CN, oxo, or $C_{1-3}$ aliphatic;

each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^3$ is optionally substituted with halogen, —OH, —$NH_2$, —CN or oxo;

each $R^4$ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^4$ is optionally substituted with halogen, —OH, —$NH_2$, —CN or oxo;

each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^{4'}$ is optionally substituted with halogen, —OH, —$NH_2$, —CN or oxo;

each $R^5$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^5$ is optionally substituted with halogen, —OH, —$NH_2$, —CN or oxo;

m is 0-4; and
n is 0-6.

In some embodiments, the disclosure relates to:
1. A compound of Formula (I):

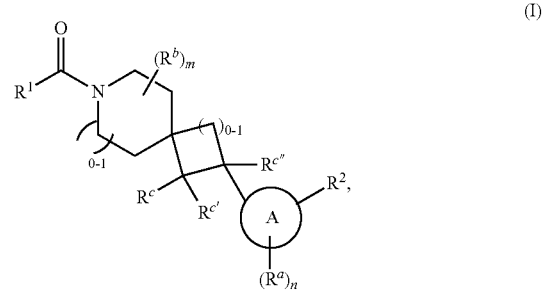

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S,
wherein $R^1$ is optionally substituted with halogen, oxo, —CN, —$NO_2$, —$OR^3$, —$SR^3$, —$CO_2R^3$, —$N(R^4)(R^{4'})$, —$C(O)N(R^4)(R^{4'})$, —$S(O)_2N(R^4)(R^{4'})$, —$COR^5$, —$N(R^4)COR^5$, —$N(R^4)SOR^5$, —$N(R^4)SO_2R^5$, —SOR⁵, —SO₂R⁵, —N(R⁴)CO₂R³, —N(R⁴)C(O)N(R⁴)(R⁴'), tetrazolyl, or $C_{1-3}$ alkyl optionally substituted with halogen or —CO₂R³;

R² is halogen, oxo, —CN, —NO₂, —OR³, —SR³, —CO₂R³, —N(R⁴)(R⁴'), —C(O)N(R⁴)(R⁴'), —S(O)₂N(R⁴)(R⁴'), —SO₂NHCOR³, —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of R² is optionally substituted with 1-6 $R^d$;

each $R^a$ is independently halogen, —CN, —NO₂, —OR³, —CO₂R³, —N(R⁴)(R⁴'), —SR³, —C(O)N(R⁴)(R⁴'), —S(O)₂N(R⁴)(R⁴'), —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), —P(O)R⁴OR³, tetrazolyl, or $C_{1-3}$ aliphatic optionally substituted with halogen;

each $R^b$ is independently halogen, oxo, —CN, —NO₂, —OR³, —SR³, —CO₂R³, —N(R⁴)(R⁴'), —C(O)N(R⁴)(R⁴'), —S(O)₂N(R⁴)(R⁴'), —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), $C_{1-6}$ aliphatic optionally substituted with halogen;

$R^c$ is hydrogen, halogen, —OH, —NH₂, —CN, —CO₂R³, —C(O)N(R⁴)₂, or tetrazole;

$R^{c'}$ is hydrogen, halogen, —OH, —NH₂, —CN, —C₂R³, —C(O)N(R⁴)₂, or tetrazole;

$R^{c''}$ is hydrogen, halogen, —OH, —NH₂, —CN, —C₂R³, —C(O)N(R⁴)₂, or tetrazole;

each $R^d$ is independently halogen, oxo, —CN, —NO₂, —OR³, —SR³, —CO₂R³, —N(R⁴)(R⁴'), —C(O)N(R⁴)(R⁴'), —S(O)₂N(R⁴)(R⁴'), —SO₂NHCOR³, —P(O)R⁴OR³, —CH₂CO₂R³, —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;

wherein an optionally substituted group of $R^d$ is optionally substituted with halogen, —OH, —NH₂, —CN, oxo, or $C_{1-3}$ aliphatic;

each R³ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of R³ is optionally substituted with halogen, —OH, —NH₂, —CN or oxo;

each R⁴ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of R⁴ is optionally substituted with halogen, —OH, —NH₂, —CN or oxo;

each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S, wherein an optionally substituted group of $R^{4'}$ is optionally substituted with halogen, —OH, —NH₂, —CN, or oxo;

each R⁵ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of R⁵ is optionally substituted with halogen, —OH, —NH₂, —CN or oxo;

m is 0-4; and n is 0-6.

2. The compound of embodiment 1, wherein the compound is of formula:

or a pharmaceutically acceptable salt thereof, wherein:

R² is halogen, oxo, —CN, —NO₂, —OR, —SR³, —CO₂R³, —N(R⁴)(R⁴'), —C(O)N(R⁴)(R⁴'), —S(O)₂N(R⁴)(R⁴'), —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), or an optionally substituted group selected from the group consisting of 3-7 membered cycloalkyl, 6-10 membered aryl, and 5-10 membered heteroaryl containing 1-4 heteroatoms independently selected from the group consisting of O, N, and S, wherein an optionally substituted group of R² is optionally substituted with 1-6 $R^d$;

each $R^a$ is independently halogen, —CN, —NO₂, —OR, —CO₂R³, —SR³, —N(R⁴)(R⁴'), —C(O)N(R⁴)(R⁴'), —S(O)₂N(R⁴)(R⁴'), —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), tetrazolyl, or $C_{1-3}$ aliphatic optionally substituted with halogen;

each $R^d$ is independently halogen, oxo, —CN, —NO₂, —OR³, —SR³, —C₂R³, —N(R⁴)(R⁴'), —C(O)N(R⁴)(R⁴'), —S(O)₂N(R⁴)(R⁴'), —COR⁵, —N(R⁴)COR⁵, —N(R⁴)SOR⁵, —N(R⁴)SO₂R⁵, —SOR⁵, —SO₂R⁵, —N(R⁴)CO₂R³, —N(R⁴)C(O)N(R⁴)(R⁴'), or an optionally substituted group selected from the group consisting of C$_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;
   wherein an optionally substituted group of R$^d$ is optionally substituted with halogen, —OH, —NH₂, —CN, oxo, or C$_{1-3}$ aliphatic.
3. The compound of embodiment 1, wherein the compound is of Formula (I-a):

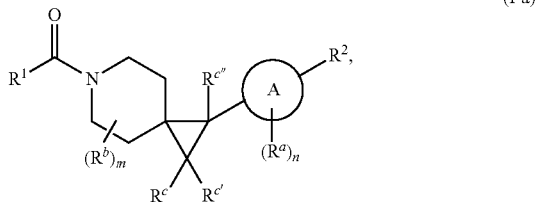

or a pharmaceutically acceptable salt thereof,
Ring A is 6-10 membered aryl or 5-10 membered heteroaryl containing 1-4 heteroatoms independently selected from the group consisting of O, N, and S;
R¹ is C$_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S,
   wherein R¹ is optionally substituted with —OH, —NH₂, or C$_{1-3}$ alkyl optionally substituted with halogen or —CO₂R³;
R² is —CO₂R³, —SO₂NHCOR³, or an optionally substituted group selected from the group consisting of 3-7 membered cycloalkyl, phenyl, and 5-10 membered heteroaryl containing 1-2 heteroatoms independently selected from the group consisting of O, N, and S,
   wherein an optionally substituted group of R² is optionally substituted with 1-6 R$^d$;
each R$^a$ is independently halogen;
each R$^b$ is independently C$_{1-3}$ aliphatic;
R$^c$ is hydrogen or halogen;
R$^{c'}$ is hydrogen or halogen;
R$^{c''}$ is hydrogen, halogen, or —CO₂H;
each R$^d$ is independently halogen, —CO₂R³, —OR, —S(O)₂NH₂, —SO₂NHCOR³, —P(O)R⁴OR³, or an optionally substituted group selected from the group consisting of C$_{1-3}$ aliphatic, and 5-7 membered heteroaryl containing 1-4 heteroatoms independently selected from the group consisting of O, N, and S;
   wherein an optionally substituted group of R$^d$ is optionally substituted with halogen or C$_{1-3}$ aliphatic;
each R³ is independently hydrogen or C$_{1-3}$ alkyl optionally substituted with fluoro;
R⁴ is C$_{1-6}$ aliphatic;
m is 0-4; and
n is 0-6.
4. The compound of embodiment 3, or a pharmaceutically acceptable salt thereof, wherein R² is —CO₂R³ or an optionally substituted group selected from the group consisting of 3-7 membered cycloalkyl, phenyl, and 5-10 membered heteroaryl containing 1-2 heteroatoms independently selected from the group consisting of O, N, and S, wherein an optionally substituted group of R² is optionally substituted with 1-6 R$^d$.
5. The compound of embodiment 4, wherein Ring A is 6-10 membered aryl.
6. The compound of embodiment 5, wherein R¹ is —CO₂H, cyclobutyl, benzoxazolyl, indolyl, indazolyl, benzimidazolyl, quinolinyl, phenyl, naphthyl, pyridyl, or isoquinolinyl
7. The compound of embodiment 6, wherein each R$^a$ is independently fluoro or chloro.
8. The compound of embodiment 7, wherein each R$^b$ is methyl.
9. The compound of embodiment 8, wherein
   R$^c$ is hydrogen or fluoro;
   R$^{c'}$ is hydrogen or fluoro; and
   R$^{c''}$ is hydrogen or —CO₂H.
10. The compound of embodiment 9, wherein each R$^d$ is independently fluoro, methyl, —CO₂H, tetrazolyl, methoxy, chloro, —CF₃, —OCF₃, or N-methyl pyrazolyl.
11. The compound of embodiment 10, wherein
   m is 0-1; and
   n is 0-3.
12. The compound of embodiment 1, wherein the compound is of Formula (II):

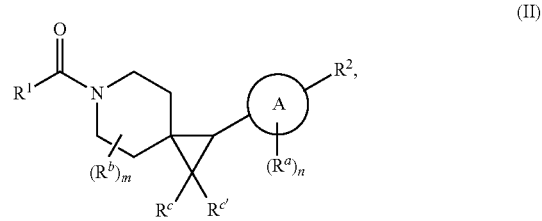

or a pharmaceutically acceptable salt thereof,
Ring A is 6-10 membered aryl or 5-10 membered heteroaryl containing 1-2 heteroatoms independently selected from the group consisting of O, N, and S;
R¹ is C$_{1-6}$ aliphatic, 3-6 membered cycloalkyl, 4-6-membered heterocyclyl containing 1-3 heteroatoms independently selected from the group consisting of O, N, and S, or 5-6 membered heteroaryl containing 1-3 heteroatoms independently selected from the group consisting of O, N, and S,
   wherein R¹ is optionally substituted with halogen, oxo, —CN, —NO₂, —OR³, —SR³, —CO₂R³, —N(R⁴)(R⁴'), —C(O)N(R⁴)(R⁴'), —S(O)₂N(R⁴)(R⁴'), tetrazolyl, or C$_{1-3}$ alkyl optionally substituted with halogen or —CO₂R³;
R² is —CN, —NO₂, —OR³, —SR³, —C₂R³, —N(R⁴)(R⁴'), —C(O)N(R⁴)(R⁴'), —S(O)₂N(R⁴)(R⁴'), or an optionally substituted group selected from the group consisting of 3-7 membered cycloalkyl, 6-10 membered aryl and 5-10 membered heteroaryl containing 1-4 heteroatoms independently selected from the group consisting of O, N, and S,
   wherein an optionally substituted group of R² is optionally substituted with 1-6 R$^d$;
each R$^a$ is independently halogen, —CN, —NO₂, —OR³, —CO₂R³, —N(R⁴)(R⁴'), —SR³, —C(O)N(R⁴)(R⁴'), —S(O)₂N(R⁴)(R⁴'), tetrazolyl, or C$_{1-3}$ aliphatic optionally substituted with halogen;
each R$^b$ is independently C$_{1-6}$ aliphatic optionally substituted with halogen;

$R^c$ is hydrogen or halogen;

$R^{c'}$ is hydrogen or halogen;

each $R^d$ is independently halogen, oxo, —CN, —NO$_2$, —OR$^3$, —SR$^3$, —CO$_2$R$^3$, —N(R$^4$)(R$^{4'}$)N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of C$_{1-6}$ aliphatic and 5-10 membered heteroaryl containing 1-4 heteroatoms independently selected from the group consisting of O, N, and S;

wherein an optionally substituted group of $R^d$ is optionally substituted with halogen, —OH, —NH$_2$, —CN, oxo, or C$_{1-3}$ alkyl;

each $R^3$ is independently hydrogen or C$_{1-6}$ aliphatic optionally substituted with halogen, —OH, —NH$_2$, —CN, or oxo;

each $R^4$ is independently hydrogen, —OH, —CN, or C$_{1-6}$ aliphatic optionally substituted with halogen, —OH, —NH$_2$, —CN, or oxo;

each $R^{4'}$ is independently hydrogen, or C$_{1-6}$ aliphatic optionally substituted with halogen, —OH, —NH$_2$, —CN, or oxo;

each $R^5$ is independently hydrogen or C$_{1-6}$ aliphatic optionally substituted with halogen, —OH, —NH$_2$, —CN, or oxo;

m is 0-4; and n is 0-6.

13. The compound of embodiment 1, wherein the compound is of Formula (III):

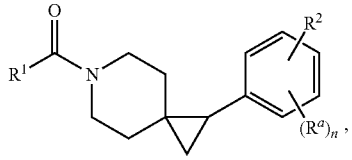

(III)

or a pharmaceutically acceptable salt thereof, wherein:

$R^1$ is C$_{1-3}$ aliphatic, 3-4 membered cycloalkyl, 5-membered heterocyclyl containing 1-3 heteroatoms independently selected from the group consisting of O, N and S, or 5-membered heteroaryl containing 1-3 heteroatoms independently selected from the group consisting of O, N, and S;

wherein $R^1$ is optionally substituted with —OH or NH$_2$;

$R^2$ is —CO$_2$H or an optionally substituted group selected from the group consisting of phenyl and 5-10 membered heteroaryl containing 1-2 heteroatoms independently selected from the group consisting of O, N, and S, wherein an optionally substituted group of $R^2$ is optionally substituted with 1-6 $R^d$;

each $R^a$ is independently halogen;

each $R^d$ is independently halogen, —OR$^3$, —CO$_2$R$^3$, —S(O)$_2$NH$_2$, or an optionally substituted group selected from the group consisting of C$_{1-3}$ aliphatic, 5-7 membered heteroaryl containing 1-4 heteroatoms independently selected from the group consisting of O, N, and S;

wherein an optionally substituted group of $R^d$ is optionally substituted with halogen or C$_{1-3}$ aliphatic;

each $R^3$ is independently hydrogen or C$_{1-3}$ alkyl; and n is 0-4.

14. The compound of embodiment 1, wherein the compound is of Formula (IV):

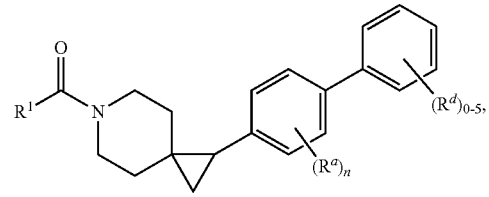

(IV)

or a pharmaceutically acceptable salt thereof, wherein:

$R^1$ is C$_{1-3}$ aliphatic, 3-4 membered cycloalkyl, 5-membered heterocyclyl containing 1-3 heteroatoms independently selected from the group consisting of O, N, and S, and 5-membered heteroaryl containing 1-3 heteroatoms independently selected from the group consisting of O, N, and S, wherein $R^1$ is optionally substituted with —OH or —NH$_2$;

each $R^a$ is independently halogen;

each $R^d$ is independently halogen, —CO$_2$R$^3$, —OR$^3$, —S(O)$_2$NH$_2$, or an optionally substituted group selected from the group consisting of C$_{1-3}$ aliphatic and 5-membered heteroaryl containing 1-4 heteroatoms independently selected from the group consisting of O, N, and S, wherein an optionally substituted group of $R^d$ is optionally substituted with halogen or C$_{1-3}$ aliphatic;

each $R^3$ is independently hydrogen or C$_{1-3}$ alkyl; and n is 0-4.

15. The compound of embodiment 1, wherein the compound is of Formula (V):

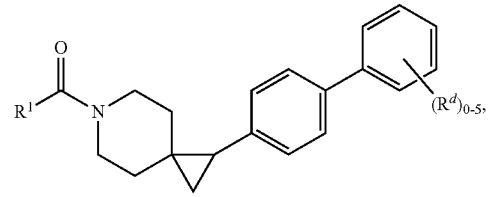

(V)

or a pharmaceutically acceptable salt thereof, wherein:

$R^1$ is 3-membered cycloalkyl optionally substituted with —OH, or 5-membered heterocyclyl containing 1-3 heteroatoms independently selected from the group consisting of O, N, and S;

each $R^d$ is independently halogen, —CO$_2$H, —OR$^3$, C$_{1-3}$ aliphatic, or 5-membered heteroaryl containing 1-4 heteroatoms independently selected from the group consisting of O, N and S; and each $R^3$ is independently hydrogen or C$_{1-3}$ alkyl.

16. The compound of embodiment 1, wherein the compound is of Formula (VI-A):

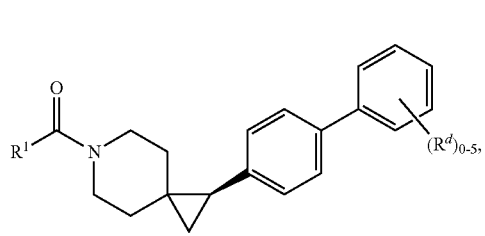

(VI-A)

or a pharmaceutically acceptable salt thereof,
wherein:
R¹ is 3-membered cycloalkyl optionally substituted with —OH, or 5-membered heterocyclyl containing 1-3 heteroatoms independently selected from the group consisting of O, N, and S;
each $R^d$ is independently halogen, —CO₂H, —OR³, —SO₂NHCOR³, C₁₋₃ aliphatic, or 5-membered heteroaryl containing 1-4 heteroatoms independently selected from the group consisting of O, N, and S; and
each R³ is independently hydrogen or C₁₋₃ alkyl.

17. The compound of embodiment 1, wherein the compound is of Formula (VI-B):

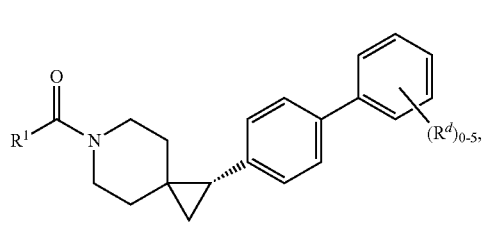

(VI-B)

or a pharmaceutically acceptable salt thereof,
wherein:
R¹ is 3-membered cycloalkyl optionally substituted with —OH, or 5-membered heterocyclyl containing 1-3 heteroatoms independently selected from the group consisting of O, N, and S;
each $R^d$ is independently halogen, —CO₂H, —OR³, —SO₂NHCOR³, C₁₋₃ aliphatic, or 5-membered heteroaryl containing 1-4 heteroatoms independently selected from the group consisting of O, N, and S; and
each R³ is independently hydrogen or C₁₋₃ alkyl.

18. The compound of embodiment 1, wherein the compound is of Formula (VII-A):

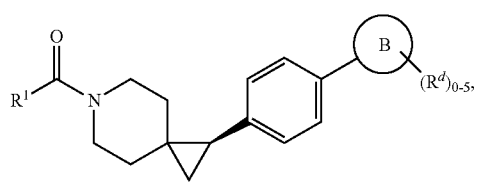

(VII-A)

or a pharmaceutically acceptable salt thereof, wherein:
Ring B is phenyl, fused bicyclic 8-10 membered aryl, or fused bicyclic 8-10 membered heteroaryl containing 1-2 heteroatoms independently selected from the group consisting of O, N, and S; or Ring A is fused bicyclic 8-10 membered aryl or heteroaryl containing 1-2 heteroatoms independently selected from the group consisting of O, N, and S;
R¹ is 3-membered cycloalkyl optionally substituted with —OH, or 5-membered heterocyclyl containing 1-3 heteroatoms independently selected from the group consisting of O, N, and S;
each $R^d$ is independently halogen, —CO₂H, —OR³, SO₂NHCOR³, C₁₋₃ aliphatic, or 5-membered heteroaryl containing 1-4 heteroatoms independently selected from the group consisting of O, N, and S; and
each R³ is independently hydrogen or C₁₋₃ alkyl.

19. The compound of embodiment 1, wherein the compound is of Formula (VII-B):

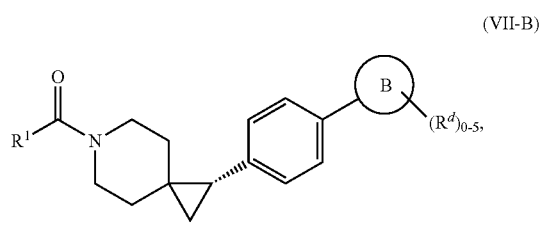

(VII-B)

or a pharmaceutically acceptable salt thereof,
wherein:
Ring B is phenyl, fused bicyclic 8-10 membered aryl, or fused bicyclic 8-10 membered heteroaryl containing 1-2 heteroatoms independently selected from the group consisting of O, N, and S; or Ring A is fused bicyclic 8-10 membered aryl or heteroaryl containing 1-2 heteroatoms independently selected from the group consisting of O, N, and S;
R¹ is 3-membered cycloalkyl optionally substituted with —OH, or 5-membered heterocyclyl containing 1-3 heteroatoms independently selected from the group consisting of O, N, and S;
each $R^d$ is independently halogen, —CO₂H, —OR³, SO₂NHCOR³, C₁₋₃ aliphatic, or 5-membered heteroaryl containing 1-4 heteroatoms independently selected from the group consisting of O, N, and S; and
each R³ is independently hydrogen or C₁₋₃ alkyl.

20. The compound of any one of embodiments 14-19, or a pharmaceutically acceptable salt thereof, wherein R¹ is methyl, ethyl,

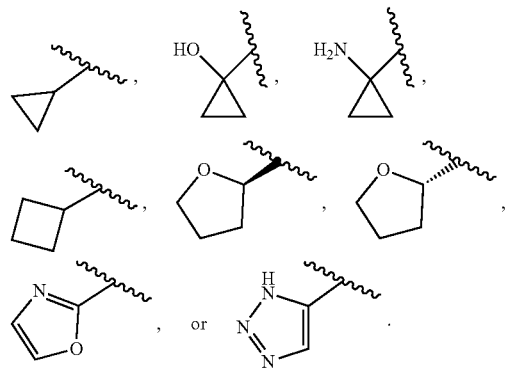

21. The compound of any one of embodiments 14-20, or a pharmaceutically acceptable salt thereof, wherein $R^d$ is $CO_2H$.

22. The compound of embodiment 1, or a pharmaceutically acceptable salt thereof, wherein the compound is selected from FIG. 1.

23. The compound of embodiment 1, or a pharmaceutically acceptable salt thereof, wherein the compound is selected from FIG. 2.

24. The compound of embodiment 1, or a pharmaceutically acceptable salt thereof, wherein the compound is selected from FIG. 3.

25. The compound of embodiment 1, or a pharmaceutically acceptable salt thereof, wherein the compound is selected from the group consisting of:

44

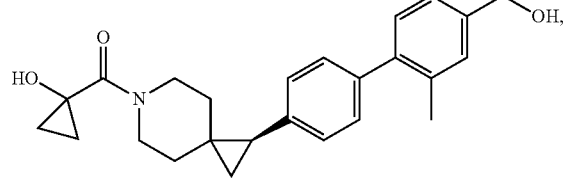

49

52

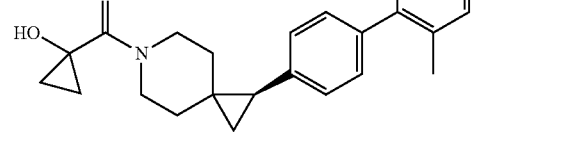

68

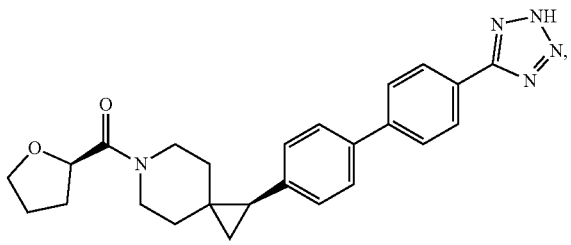

171

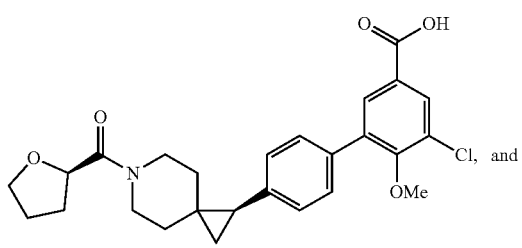

and

180

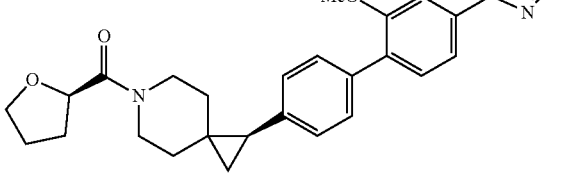

26. The compound of embodiment 1, or a pharmaceutically acceptable salt thereof, wherein the compound is selected from the group consisting of:

45

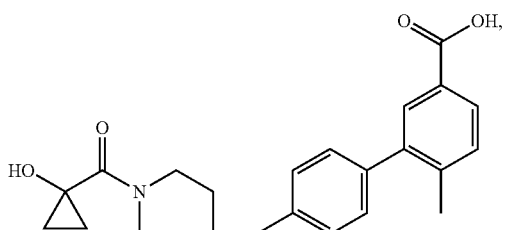

48

52

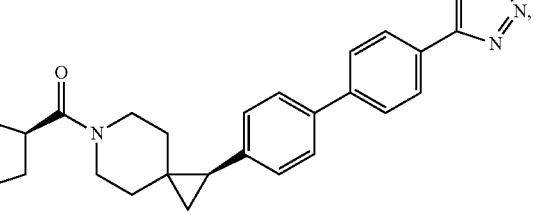

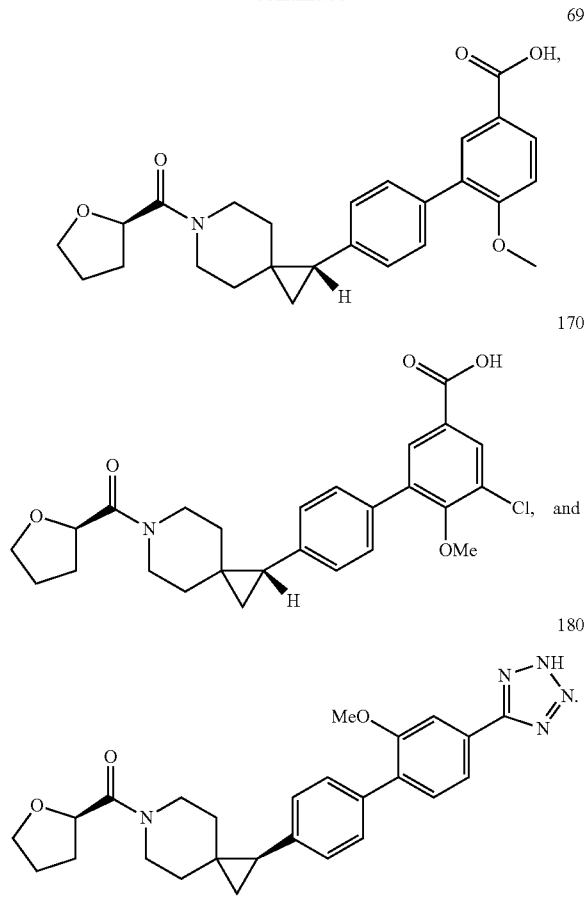

27. A pharmaceutical composition comprising the compound of any of embodiments 1-26, or a pharmaceutically acceptable salt thereof, and a pharmaceutically acceptable excipient.

28. A FASN Inhibitor Compound of Formula (I):

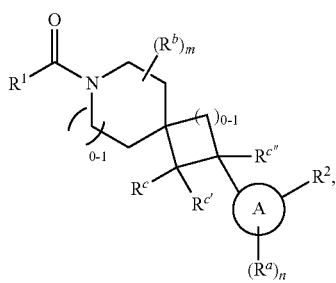

or a pharmaceutically acceptable salt thereof,
wherein:
Ring A is 6-10 membered aryl or 5-10 membered heteroaryl containing 1-4 heteroatoms independently selected from the group consisting of O, N, and S;
$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S, wherein $R^1$ is optionally substituted with halogen, oxo, —CN, —NO$_2$, —OR$^3$, —SR$^3$, —CO$_2$R$^3$, —N(R$^4$)(R$^{4'}$) N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$) SO$_2$R$^5$, —SOR$^5$, —SO$_2$R$^5$, —N(R$^4$)CO$_2$R$^3$, —N(R$^4$) C(O)N(R$^4$)(R$^{4'}$), tetrazolyl, or $C_{1-3}$ alkyl optionally substituted with halogen or —CO$_2$R$^3$;

$R^2$ is halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —COR$^5$, —N(R$^4$)COR$^5$, —N(R$^4$) SOR$^5$, —N(R$^4$)SO$_2$R$^5$, —SOR$^5$, —SO$_2$R$^5$, —N(R$^4$) CO$_2$R$^3$, —N(R$^4$)C(O)N(R$^4$)(R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of $R^2$ is optionally substituted with 1-6 $R^d$;

each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), —COR$^5$, —N(R$^4$)COR$^5$, —N(R$^4$) SOR$^5$, —N(R$^4$)SO$_2$R$^5$, —SOR$^5$, —SO$_2$R$^5$, —N(R$^4$) CO$_2$R$^3$, —N(R$^4$)C(O)N(R$^4$)(R$^{4'}$), —P(O)R$^4$OR$^3$, tetrazolyl, or $C_{1-3}$ aliphatic optionally substituted with halogen;

each $R^b$ is independently halogen, oxo, —CN, —NO$_2$, —OR$^3$, —SR$^3$, —C$_2$R$^3$, —N(R$^4$)(R$^{4'}$), —C(O)N(R$^4$) (R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), $C_{1-6}$ aliphatic optionally substituted with halogen;

$R^c$ is hydrogen, halogen, —OH, —NH$_2$, —CN, —CO$_2$R$^3$, —C(O)N(R$^4$)$_2$, or tetrazole;

$R^{c'}$ is hydrogen, halogen, —OH, —NH$_2$, —CN, —CO$_2$R$^3$, —C(O)N(R$^4$)$_2$, or tetrazole;

$R^{c''}$ is hydrogen, halogen, —OH, —NH$_2$, —CN, —CO$_2$R$^3$, —C(O)N(R$^4$)$_2$, or tetrazole;

each $R^d$ is independently halogen, oxo, —CN, —NO$_2$, —OR$^3$, —SR$^3$, —C$_2$R$^3$, —N(R$^4$)(R$^{4'}$), —C(O)N(R$^4$) (R$^{4'}$), —S(O)$_2$N(R$^4$)(R$^{4'}$), —SO$_2$NHCOR$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;

wherein an optionally substituted group of $R^d$ is optionally substituted with halogen, —OH, —NH$_2$, —CN, oxo, or $C_{1-3}$ aliphatic;

each $R^3$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of $R^3$ is optionally substituted with halogen, —OH, —NH$_2$, —CN or oxo;

each $R^4$ is independently hydrogen, —OH, —CN, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of $R^4$ is optionally substituted with halogen, —OH, —NH$_2$, —CN or oxo;

each $R^{4'}$ is independently hydrogen, or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of $R^{4'}$ is optionally substituted with halogen, —OH, —NH$_2$, —CN or oxo;

each $R^5$ is independently hydrogen or an optionally substituted group selected from the group consisting of $C_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S, wherein an optionally substituted group of $R^5$ is optionally substituted with halogen, —OH, —NH$_2$, —CN or oxo;

m is 0-4; and n is 0-6.

29. The FASN Inhibitor Compound of embodiment 28, wherein the compound is of formula:

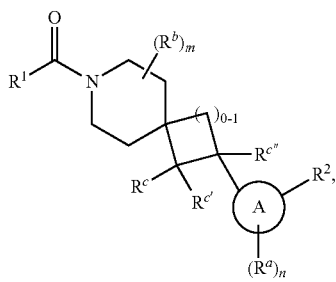

or a pharmaceutically acceptable salt thereof, wherein:

$R^2$ is halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl, and 5-10 membered heteroaryl containing 1-4 heteroatoms independently selected from the group consisting of O, N, and S, wherein an optionally substituted group of $R^2$ is optionally substituted with 1-6 $R^d$;

each $R^a$ is independently halogen, —CN, —NO$_2$, —OR, —CO$_2$R$^3$, —SR$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)

CO$_2$R$^3$, —N(R$^4$)C(O)N(R$^4$)(R$^{4'}$), tetrazolyl, or $C_{1-3}$ aliphatic optionally substituted with halogen;

each $R^d$ is independently halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of $C_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;

wherein an optionally substituted group of $R^d$ is optionally substituted with halogen, —OH, —NH$_2$, —CN, oxo, or $C_{1-3}$ aliphatic.

30. A compound of Formula (I) obtained by a process disclosed herein:

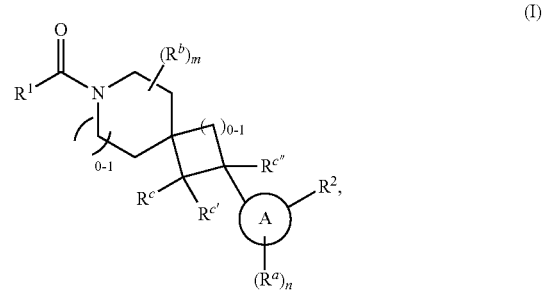

or a pharmaceutically acceptable salt thereof, wherein:

Ring A is 6-10 membered aryl or 5-10 membered heteroaryl containing 1-4 heteroatoms independently selected from the group consisting of O, N, and S;

$R^1$ is $C_{1-6}$ aliphatic, 3-7 membered cycloalkyl, 3-7 membered heterocyclyl containing 1-4 heteroatoms independently selected from the group consisting of O, N and S, or 5-10 membered heteroaryl containing 1-3 heteroatoms independently selected from the group consisting of O, N, and S, wherein $R^1$ is optionally substituted with halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or $C_{1-3}$ alkyl optionally substituted with halogen or —CO$_2$R$^3$;

$R^2$ is halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S, wherein an optionally substituted group of $R^2$ is optionally substituted with 1-6 $R^d$;

each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), —P(O)R$^4$OR$^3$, tetrazolyl, or C$_{1-3}$ aliphatic optionally substituted with halogen;

each $R^b$ is independently halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), C$_{1-6}$ aliphatic optionally substituted with halogen;

$R^c$ is hydrogen, halogen, —OH, —NH$_2$, —CN, —CO$_2$R$^3$, —C(O)N(R$^4$)$_2$, or tetrazolyl;

$R^{c'}$ is hydrogen, halogen, —OH, —NH$_2$, —CN, —C$_2$R$^3$, —C(O)N(R$^4$)$_2$, or tetrazolyl;

$R^{c''}$ is hydrogen, halogen, —OH, —NH$_2$, —CN, —C$_2$R$^3$, —C(O)N(R$^4$)$_2$, or tetrazolyl;

each $R^d$ is independently halogen, oxo, —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —SO$_2$NHCOR$^3$, —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of C$_{1-6}$ aliphatic, 3-7 membered cycloalkyl, 3-7 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S;
wherein an optionally substituted group of $R^d$ is optionally substituted with halogen, —OH, —NH$_2$, —CN, oxo, or C$_{1-3}$ aliphatic;

each $R^3$ is independently hydrogen or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^3$ is optionally substituted with halogen, —OH, —NH$_2$, —CN or oxo;

each $R^4$ is independently hydrogen, —OH, —CN, or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^4$ is optionally substituted with halogen, —OH, —NH$_2$, —CN or oxo;

each $R^{4'}$ is independently hydrogen, or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^{4'}$ is optionally substituted with halogen, —OH, —NH$_2$, —CN or oxo;

each $R^5$ is independently hydrogen or an optionally substituted group selected from the group consisting of C$_{1-6}$ aliphatic, 3-7 membered cycloalkyl, 3-12 membered heterocyclyl containing 1-3 heteroatoms independently selected from the group consisting of O, N, and S, 6-10 membered aryl and 5-10 membered heteroaryl containing 1-4 heteroatoms independently selected from the group consisting of O, N, and S,
wherein an optionally substituted group of $R^5$ is optionally substituted with halogen, —OH, —NH$_2$, —CN or oxo;

m is 0-4; and
n is 0-6.

31. The compound of embodiment 30, wherein the compound is of formula:

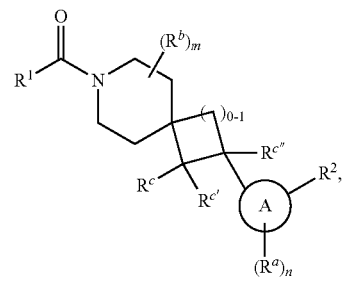

or a pharmaceutically acceptable salt thereof, wherein:
$R^2$ is halogen, oxo, —CN, —NO$_2$, —OR, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of 3-7 membered cycloalkyl, 6-10 membered aryl, and 5-10 membered heteroaryl containing 1-4 heteroatoms independently selected from the group consisting of O, N, and S,
wherein an optionally substituted group of $R^2$ is optionally substituted with 1-6 $R^d$;

each $R^a$ is independently halogen, —CN, —NO$_2$, —OR, —CO$_2$R$^3$, —SR$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), tetrazolyl, or C$_{1-3}$ aliphatic optionally substituted with halogen;

each $R^d$ is independently halogen, oxo, —CN, —NO$_2$, —OR$^3$, —SR$^3$, —C$_2$R$^3$, —N(R$^4$)(R$^{4'}$), —C(O)N(R$^4$)(R$^{4'}$), —S(O)$_2$N(R$^4$)(R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$)CO$_2$R$^3$, —N(R$^4$)C(O)N(R$^4$)(R$^{4'}$), or an optionally substituted group selected from the group consisting of C$_{1-6}$ aliphatic, 3-7 membered cycloalkyl, 3-7 membered heterocyclyl containing 1-3 heteroatoms independently selected from the group consisting of O, N, and S, 6-10 membered aryl, and 5-10 membered heteroaryl containing 1-4 heteroatoms independently selected from the group consisting of O, N, and S;

wherein an optionally substituted group of $R^d$ is optionally substituted with halogen, —OH, —NH$_2$, —CN, oxo, or $C_{1-3}$ aliphatic.

32. A method of inhibiting FASN in a patient, comprising administering to the patient a therapeutically effective amount of the compound of any one of embodiments 1-26 and 28-31, or a pharmaceutically acceptable salt thereof, or the pharmaceutical composition of embodiment 27.

33. A method of treating a FASN dependent disease or disorder in a patient, comprising administering to the patient a therapeutically effective amount of the compound of any one of embodiments 1-26 and 28-31, or a pharmaceutically acceptable salt thereof, or the pharmaceutical composition of embodiment 27.

34. A compound of formula

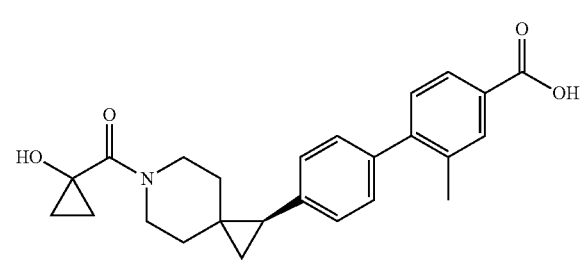

or a pharmaceutically acceptable salt thereof.

35. A compound 4-{4-[(1S)-6-(1-hydroxycyclopropanecarbonyl)-6-azaspiro[2.5]octan-1-yl]phenyl}-3-methylbenzoic acid, or a pharmaceutically acceptable salt thereof.

36. A compound of formula

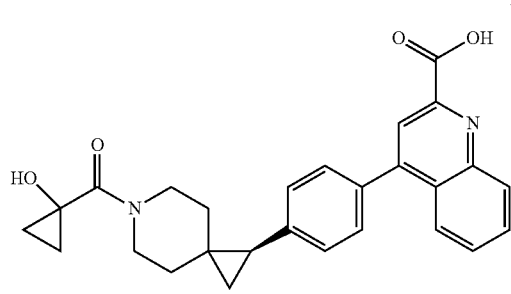

or a pharmaceutically acceptable salt thereof.

37. A compound 4-[4-[(1S)-6-(1-hydroxycyclopropanecarbonyl)-6-azaspiro[2.5]octan-1-yl]phenyl]quinoline-2-carboxylic acid, or a pharmaceutically acceptable salt thereof.

38. A pharmaceutical composition comprising the compound of any one of embodiments 34 to 37, or a pharmaceutically acceptable salt thereof, and a pharmaceutically acceptable excipient.

39. A method of inhibiting FASN in a patient, comprising administering to the patient a therapeutically effective amount of the compound of any one of embodiments 34 to 37, or a pharmaceutically acceptable salt thereof, or the pharmaceutical composition of embodiment 38.

40. A method of treating a FASN dependent disease or disorder in a patient, comprising administering to the patient a therapeutically effective amount of the compound of any one of embodiments 34 to 37, or a pharmaceutically acceptable salt thereof, or the pharmaceutical composition of embodiment 38.

Method of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), or a pharmaceutically acceptable salt thereof, may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

An illustrative method for the synthesis of the compounds of Formula (VII-A), is outlined in Scheme 1. Treatment of commercially available 4-bromobenzaldehyde (1-1) with tosylhydrazine affords the corresponding hydrazone 1-2. Cyclopropanation of olefin 1-3 affords the 6-azaspiro[2.5] octane compound 1-4. Supercritical fluid chromatography (SFC) separation affords S-isomer 1-5. Treatment of 1-5 with bis-(pinacolato)diboron yields boronic ester 1-6, which is subsequently utilized in a palladium-catalyzed Suzuki coupling with bromide 1-7 to provide the biaryl intermediate 1-8. Removal of the N-Boc-protecting group affords amine intermediate 1-9, which is coupled with carboxylic acid 1-10 to afford the compound of Formula VII-A. It will be understood that suitable protecting groups can be employed in the synthesis outlined in Scheme 1. Compounds of Formula VII-B can be obtained by an analogous method by employing the R-enantiomer obtained in the SFC separation. Other compounds of the present disclosure, i.e., compounds of Formula (I), can be prepared by similar methods.

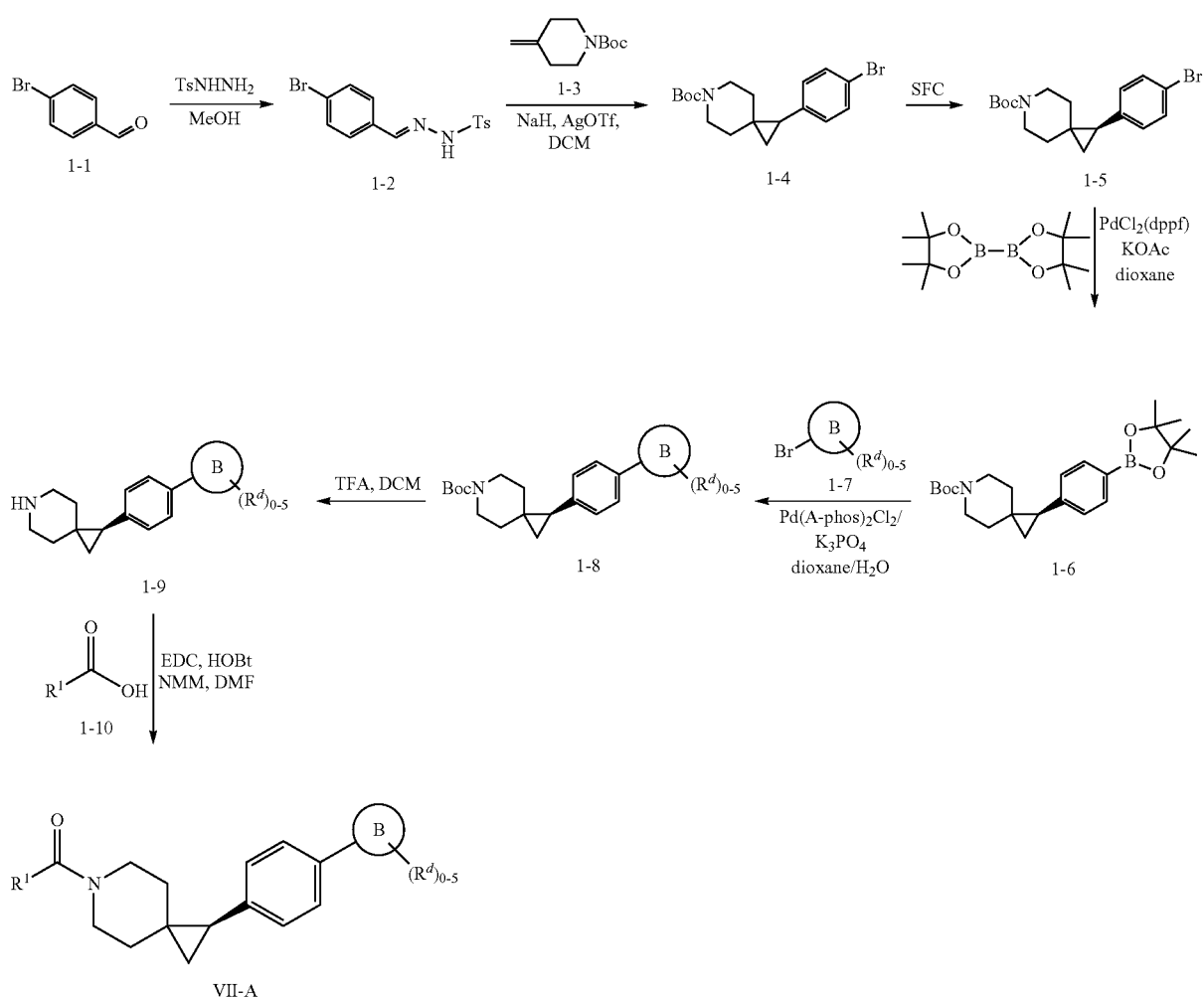
In some embodiments, the disclosure relates to a compound useful as an intermediate in the synthesis of the compounds of the present disclosure, i.e., compounds of Formula (I).
In some embodiments, the compound is:
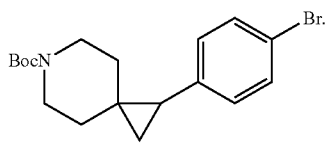 [SMILES: CC(C)(C)OC(=O)N1CCC2(CC1)CC2c1ccc(Br)cc1]
In some embodiments, the compound is:
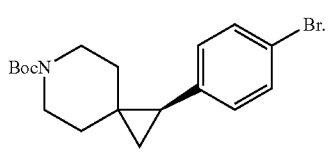
In some embodiments, the compound is:
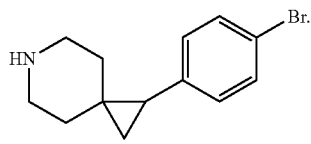 [SMILES: Brc1ccc(C2CC23CCNCC3)cc1]
In some embodiments, the compound is:
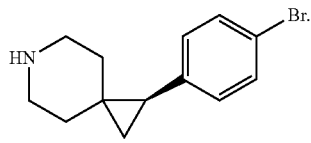 [SMILES: Brc1ccc([C@H]2CC23CCNCC3)cc1]

In some embodiments, the compound is a compound of formula

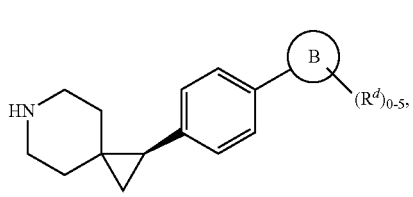

wherein Ring B and $R^d$ are defined as set forth in any embodiment herein.

In some embodiments, the compound is:

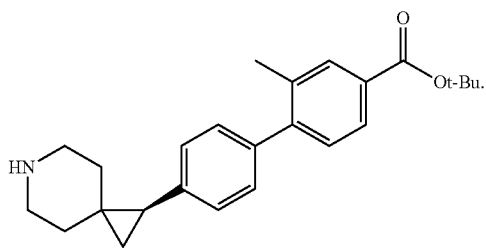 [SMILES: Cc1cc(C(=O)OC(C)(C)C)ccc1-c1ccc([C@H]2CC23CCNCC3)cc1]

In some embodiments, the compound is:

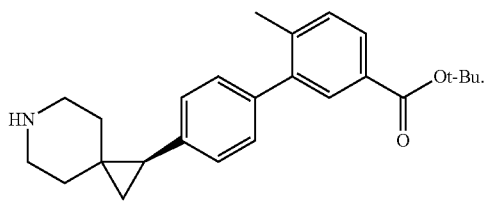 [SMILES: Cc1ccc(C(=O)OC(C)(C)C)cc1-c1ccc([C@H]2CC23CCNCC3)cc1]

In some embodiments, the compound is:

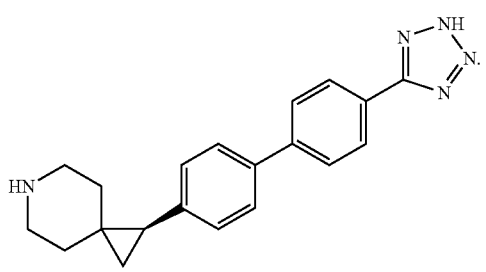 [SMILES: c1cc(-c2nn[nH]n2)ccc1-c1ccc([C@H]2CC23CCNCC3)cc1]

In some embodiments, the compound is:

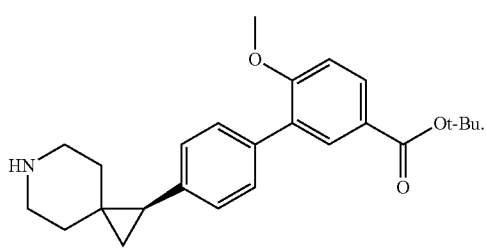 [SMILES: COc1ccc(C(=O)OC(C)(C)C)cc1-c1ccc([C@H]2CC23CCNCC3)cc1]

In some embodiments, the compound is:

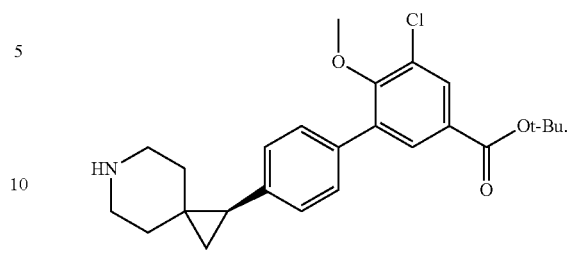

In some embodiments, the compound is:

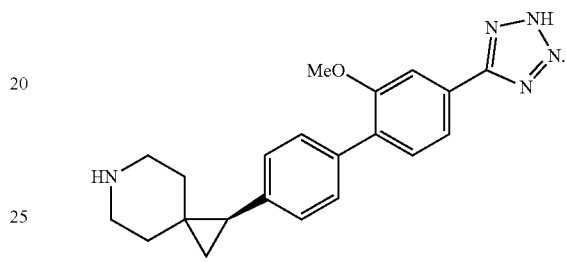

In some embodiments, the compound is a compound of formula

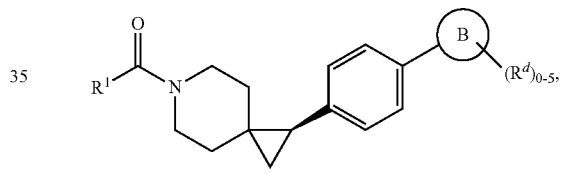

wherein Ring B and $R^d$ are defined as set forth in any embodiment herein.

In some embodiments, the compound is:

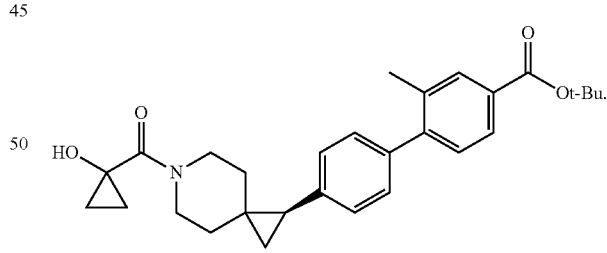

In some embodiments, the compound is:

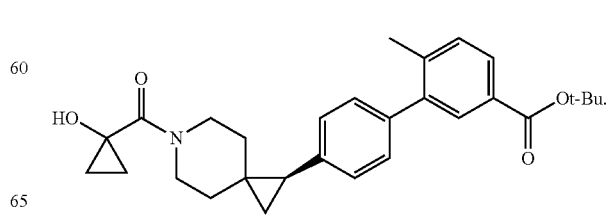

In some embodiments, the compound is:

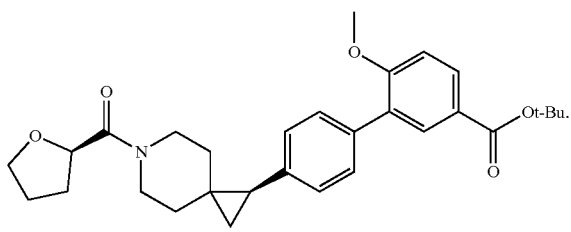 [SMILES: COc1ccc(C(=O)OC(C)(C)C)cc1-c1ccc([C@H]2CC23CCN(C(=O)[C@H]2CCCO2)CC3)cc1]

In some embodiments, the compound is:

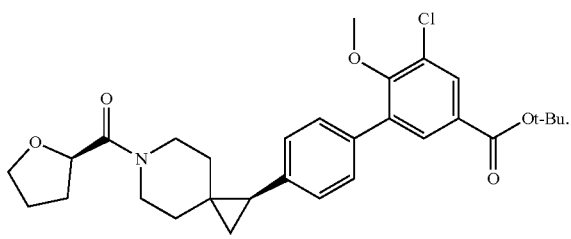 [SMILES: COc1c(Cl)cc(C(=O)OC(C)(C)C)cc1-c1ccc([C@H]2CC23CCN(C(=O)[C@H]2CCCO2)CC3)cc1]

Methods of Using the Disclosed Compounds

One aspect of the present disclosure relates to a compound of Formula (I) for use in medicine. Another aspect of the present disclosure relates to a method of modulating FASN, comprising administering to a patient in need thereof a therapeutically effective amount of a compound of Formula (I). Another aspect of the present disclosure relates to a method of modulating FASN, comprising administering to a patient in need thereof a therapeutically effective amount of a compound of Formula (I) or a pharmaceutically acceptable salt thereof. Another aspect of the present disclosure relates to a method of inhibiting FASN, comprising administering to a patient in need thereof a therapeutically effective amount of a compound of Formula (I). Another aspect of the present disclosure relates to a method of inhibiting FASN, comprising administering to a patient in need thereof a therapeutically effective amount of a compound of Formula (I) or a pharmaceutically acceptable salt thereof. In another aspect, the present disclosure relates to a method of inhibiting FASN, comprising administering to a patient in need thereof a therapeutically effective amount of a pharmaceutical composition comprising a compound of Formula (I). In another aspect, the present disclosure relates to a method of inhibiting FASN, comprising administering to a patient in need thereof a therapeutically effective amount of a pharmaceutical composition comprising a compound of Formula (I) or a pharmaceutically acceptable salt thereof. Another aspect of the present disclosure relates to a method of treating a disease or disorder associated with FASN modulation, comprising administering to a patient in need thereof a therapeutically effective amount of a compound of Formula (I), or a pharmaceutically acceptable salt thereof.

Accordingly, preferred embodiments include pharmaceutical compositions comprising a FASN Inhibitor having a chemical structure disclosed and/or otherwise described herein. The pharmaceutical composition can be a capsule, tablet or other suitable dosage form comprising a FASN inhibitor, which can be a compound of Formula (I), Formula (I-a), Formula (II), Formula (III), Formula (IV) and/or Formula (V) or a pharmaceutically acceptable salt thereof. The pharmaceutical composition can be a capsule, tablet or other suitable dosage form comprising a FASN inhibitor, which can be a compound of Formula (I), Formula (I-a), Formula (II), Formula (III), Formula (IV), Formula (V), Formula (VI), or Formula (VII) or a pharmaceutically acceptable salt thereof. The pharmaceutical composition comprising a FASN inhibitor can be administered to a patient in need thereof (e.g., a patient diagnosed with a form of cancer believed to be responsive to a FASN inhibitor) in a therapeutically effective amount throughout a course of treatment to provide a desired therapeutic effect to the patient.

The invention also relates to compounds and compositions disclosed herein for use in the methods of treatment and prevention disclosed herein.

Pharmaceutical Formulations

Compounds of Formula (I) can be formulated in various pharmaceutically acceptable formulations (e.g., for oral delivery as a capsule or for parenteral administration as a solution). For use in therapy, a compound of Formula (I), as well as salts, solvates and physiological functional derivatives thereof, may be administered as the active pharmaceutical ingredient (API) as a pharmaceutical composition. Accordingly, a pharmaceutical composition can comprise a compound of Formula (I) or salts, solvates and physiological functional derivatives thereof, and one or more pharmaceutically acceptable carriers, diluents, and/or excipients. The carrier(s), diluent(s) or excipient(s) can be selected to be compatible with the other ingredients of the formulation and appropriately safe and effective for an intended therapy.

Pharmaceutical compositions can be provided in unit dose forms containing a predetermined amount of API comprising a compound of Formula (I) per unit dose. Such a unit may contain, a desired amount of a compound of the Formula (I) or pharmaceutically acceptable salt thereof, depending on the condition being treated, the route of administration and the age, weight and condition of the patient. Such unit doses may therefore be administered at a desired dose interval.

A pharmaceutically acceptable composition can comprise a desired weight concentration of the compound of formula (I) as the active pharmaceutical ingredient (API) in combination with other ingredients to form a drug substance (DS) in a formulation batch. The DS formulation batch can be divided into unit dosage forms. Pharmaceutically acceptable compositions can be formulated for administration by an appropriate route, for example by the oral delivery (including as a capsule or tablet) in unit dosage forms. Such compositions may be prepared by bringing into association the active pharmaceutical ingredient (API) comprising a compound of Formula (I) with the carrier(s) or excipient(s). Pharmaceutical compositions comprising a compound of Formula (I) formulated for oral delivery can be prepared in a unit dosage form, such as a capsule at a desired dosage strength of the compound of Formula (I). For oral administration in liquid form, the oral drug components can be combined with any oral, non-toxic, pharmaceutically acceptable inert carrier such as ethanol, glycerol, water and the like.

Pharmaceutically acceptable compositions comprising the compound of Formula (I) can be prepared by various procedures. For example, the compounds of Formula (I) can be formulated with suitable excipients, diluents, or carriers, and formed into tablets, or capsules, and other suitable dosage forms. For oral administration in the form of a tablet or capsule, the compound of Formula (I) can be combined with an oral, non-toxic, pharmaceutically acceptable, inert carrier.

Other examples of excipients, diluents, and carriers that are suitable for such formulations include the following:

fillers and extenders such as starch, and sugars; and binding agents such as cellulose derivatives. Moreover, when desired or necessary, suitable binders, lubricants, disintegrating agents and coloring agents can also be incorporated into the mixture. Suitable binders include starch, natural sugars, natural and synthetic gums, and the like. Lubricants and/or glidants can be used in these dosage forms.

The compounds also can be formulated as solutions appropriate for parenteral administration, for example, by intramuscular, subcutaneous or intravenous routes. For example, a compound of Formula (I) can be dissolved at pH 8 in a suitable buffer (e.g., 50 mM phosphate buffer solution or a solution with EtOH/PEG400). A pharmaceutical composition comprising a desired concentration of a compound of Formula (I) can be formulated as an injectable drug solution (useful, e.g., in preclinical animal studies).

Embodiments

In other embodiments, the disclosure relates to:
1. A compound of Formula (I)

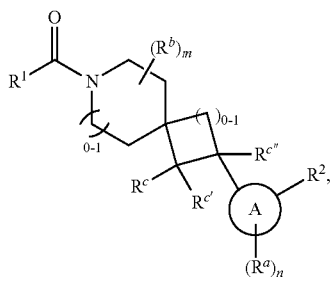

(I)

or a pharmaceutically acceptable salt thereof, wherein:
Ring A is 6-10 membered aryl or 6-10 membered heteroaryl containing 1-2 N atoms;
$R^1$ is $C_{1-3}$ aliphatic, 3-4 membered cycloalkyl, 5-membered heterocyclyl containing 10 atom, or 5-membered heteroaryl containing 1-3 heteroatoms independently selected from the group consisting of O and N,
wherein $R^1$ is optionally substituted with —OH or —NH$_2$;
$R^2$ is —CO$_2$R$^3$, —SO$_2$NHCOR$^3$, or an optionally substituted group selected from the group consisting of 3-4 membered cycloalkyl, 6-10 membered aryl, and 5-10 membered heteroaryl containing 1-2 heteroatoms independently selected from the group consisting of O, N, and S, wherein an optionally substituted group of $R^2$ is optionally substituted with 1-6 $R^d$;
each $R^a$ is independently halogen;
each $R^b$ is independently $C_{1-3}$ aliphatic;
$R^c$ is hydrogen or halogen;
$R^{c'}$ is hydrogen or halogen;
$R^{c''}$ is hydrogen, halogen, —CO$_2$H, or tetrazole;
each $R^d$ is independently halogen, —CO$_2$R$^3$, —OR$^3$, —S(O)$_2$NH$_2$, —SO$_2$NHCOR$^3$, —P(O)R$^4$OR$^3$, —CH$_2$CO$_2$R$^3$, or an optionally substituted group selected from the group consisting of $C_{1-3}$ aliphatic, 4-membered cycloalkyl, and 5-membered heteroaryl containing 1-4 N atoms;
wherein an optionally substituted group of $R^d$ is optionally substituted with halogen, oxo, OH, or $C_{1-3}$ aliphatic;

each $R^3$ is independently hydrogen or $C_{1-3}$ alkyl optionally substituted with fluoro;
$R^4$ is $C_{1-6}$ aliphatic;
m is 0-4; and
n is 0-6.
2. The compound of embodiment 1, wherein:
$R^2$ is an optionally substituted group selected from the group consisting of 3-4 membered cycloalkyl, phenyl, and 5-10 membered heteroaryl containing 1-2 heteroatoms independently selected from the group consisting of O, N, and S; and wherein an optionally substituted group of $R^2$ is optionally substituted with 1-6 $R^d$; and
each $R^d$ is independently halogen, —C$_2$R$^3$, —OR$^3$, —S(O)$_2$NH$_2$, —SO$_2$NHCOR$^3$, —P(O)R$^4$OR$^3$, or an optionally substituted group selected from the group consisting of $C_{1-3}$ aliphatic, or 5-7 membered heteroaryl containing 1-4 heteroatoms independently selected from the group consisting of O, N, and S; wherein an optionally substituted group of $R^d$ is optionally substituted with halogen or $C_{1-3}$ aliphatic.
3. A compound of Formula (II)

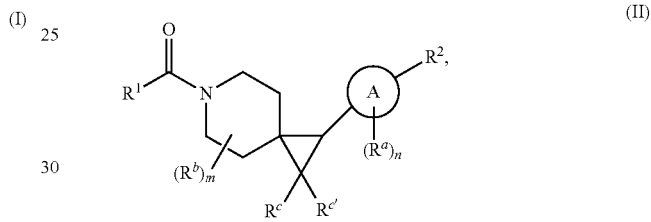

(II)

or a pharmaceutically acceptable salt thereof, wherein:
Ring A is 6-10 membered aryl or 5-10 membered heteroaryl containing 1-2 heteroatoms independently selected from the group consisting of O, N, and S;
$R^1$ is $C_{1-6}$ aliphatic, 3-6 membered cycloalkyl, 4-6-membered heterocyclyl containing 1-3 heteroatoms independently selected from the group consisting of O, N, and S, or 5-6 membered heteroaryl containing 1-3 heteroatoms independently selected from the group consisting of O, N, and S; wherein $R^1$ is optionally substituted with halogen, oxo, —CN, —NO$_2$, —OR, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), tetrazolyl, or $C_{1-3}$ alkyl optionally substituted with halogen or —CO$_2$R$^3$;
$R^2$ is —CN, —NO$_2$, —OR$^3$, —SR$^3$, —CO$_2$R$^3$, —N(R$^4$)(R$^{4'}$), —C(O)N(R$^4$)(R$^{4'}$), —S(O)$_2$N(R$^4$)(R$^{4'}$), or an optionally substituted group selected from the group consisting of 3-7 membered cycloalkyl, 6-10 membered aryl and 5-10 membered heteroaryl containing 1-4 heteroatoms independently selected from the group consisting of O, N, and S;
wherein an optionally substituted group of $R^2$ is optionally substituted with 1-6 $R^d$;
each $R^a$ is independently halogen, —CN, —NO$_2$, —OR$^3$, —CO$_2$R$^3$, —N(R$^4$)(R$^{4'}$), —SR$^3$, —C(O)N(R$^4$)(R$^{4'}$), —S(O)$_2$N(R$^4$)(R$^{4'}$), tetrazolyl, or $C_{1-3}$ aliphatic optionally substituted with halogen;
each $R^b$ is independently $C_{1-6}$ aliphatic optionally substituted with halogen;
$R^c$ is hydrogen or halogen;
$R^{c'}$ is hydrogen or halogen;

each $R^d$ is independently halogen, oxo, —CN, —NO$_2$, —OR$^3$, —SR$^3$, —CO$_2$R$^3$, —N(R$^4$)(R$^{4'}$) N(R$^4$)(R$^{4'}$), —C(O)N(R$^4$)(R$^{4'}$), —S(O)$_2$N(R$^4$) (R$^{4'}$), —COR$^5$, —N(R$^4$)COR$^5$, —N(R$^4$)SOR$^5$, —N(R$^4$)SO$_2$R$^5$, —SOR$^5$, —SO$_2$R$^5$, —N(R$^4$) CO$_2$R$^3$, —N(R$^4$)C(O)N(R$^4$)(R$^{4'}$), or an optionally substituted group selected from the group consisting of C$_{1-6}$ aliphatic and 5-10 membered heteroaryl containing 1-4 heteroatoms independently selected from the group consisting of O, N, and S; wherein an optionally substituted group of R$^d$ is optionally substituted with halogen, —OH, —NH$_2$, —CN, oxo, or C$_{1-3}$ alkyl;

each $R^3$ is independently hydrogen or C$_{1-6}$ aliphatic optionally substituted with halogen, —OH, —NH$_2$, —CN, or oxo;

each $R^4$ is independently hydrogen, —OH, —CN, or C$_{1-6}$ aliphatic optionally substituted with halogen, —OH, —NH$_2$, —CN, or oxo;

each $R^{4'}$ is independently hydrogen, or C$_{1-6}$ aliphatic optionally substituted with halogen, —OH, —NH$_2$, —CN, or oxo;

each $R^5$ is independently hydrogen or C$_{1-6}$ aliphatic optionally substituted with halogen, —OH, —NH$_2$, —CN, or oxo;

m is 0-4; and n is 0-6.

4. A compound of embodiment 3, wherein the compound is a compound of Formula (III):

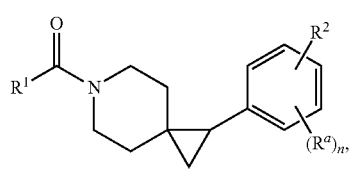

(III)

or a pharmaceutically acceptable salt thereof, wherein:
R$^1$ is C$_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S;
wherein R$^1$ is optionally substituted with —OH or NH$_2$;
R$^2$ is —CO$_2$H or an optionally substituted group selected from the group consisting of phenyl and 5-10 membered heteroaryl containing 1-2 heteroatoms independently selected from the group consisting of O, N, and S,
wherein an optionally substituted group of R$^2$ is optionally substituted with 1-6 R$^d$;
each R$^a$ is independently halogen;
each R$^d$ is independently halogen, —OR$^3$, —CO$_2$R$^3$, —S(O)$_2$NH$_2$, or an optionally substituted group selected from the group consisting of C$_{1-3}$ aliphatic, and 5-7 membered heteroaryl containing 1-4 heteroatoms independently selected from the group consisting of O, N, and S;
wherein an optionally substituted group of R$^d$ is optionally substituted with halogen or C$_{1-3}$ aliphatic;

each R$^3$ is independently hydrogen or C$_{1-3}$ alkyl; and
n is 0-4.

5. The compound of embodiment 4, or a pharmaceutically acceptable salt thereof, wherein
R$^1$ is 3-4 membered cycloalkyl or 5-membered heterocyclyl containing 1-3 heteroatoms independently selected from the group consisting of O, N and S; wherein R$^1$ is optionally substituted with —OH or NH$_2$; and
R$^2$ is an optionally substituted group selected from the group consisting of phenyl and 5-10 membered heteroaryl containing 1-2 heteroatoms independently selected from the group consisting of O, N, and S, wherein an optionally substituted group of R$^2$ is optionally substituted with 1-6 R$^d$.

6. The compound of embodiment 3, wherein the compound is a compound of formula (IV)

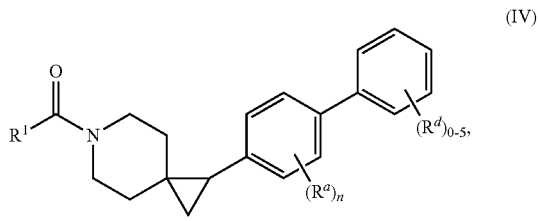

(IV)

or a pharmaceutically acceptable salt thereof, wherein:
R$^1$ is C$_{1-3}$ aliphatic, 3-4 membered cycloalkyl, 5-membered heterocyclyl containing 1-3 heteroatoms independently selected from the group consisting of O, N, and S, or 5-membered heteroaryl containing 1-3 heteroatoms independently selected from the group consisting of O, N, and S; and wherein R$^1$ is optionally substituted with —OH or —NH$_2$;
each R$^a$ is independently halogen;
each R$^d$ is independently halogen, —CO$_2$R$^3$, —OR$^3$, —S(O)$_2$NH$_2$, or an optionally substituted group selected from the group consisting of C$_{1-3}$ aliphatic and 5-membered heteroaryl containing 1-4 heteroatoms independently selected from the group consisting of O, N, and S,
wherein an optionally substituted group of R$^d$ is optionally substituted with halogen or C$_{1-3}$ aliphatic;
each R$^3$ is independently hydrogen or C$_{1-3}$ alkyl; and
n is 0-4.

7. The compound of embodiment 3, wherein the compound is a compound of formula (VI-A)

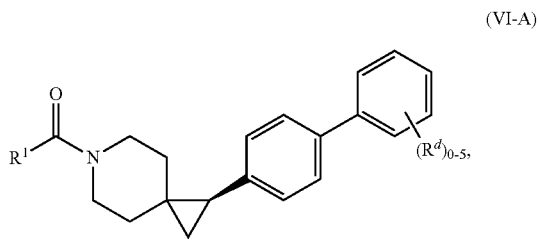

(VI-A)

or a pharmaceutically acceptable salt thereof, wherein:
R$^1$ is 3-membered cycloalkyl optionally substituted with —OH, or 5-membered heterocyclyl containing 1-3 heteroatoms independently selected from the group consisting of O, N, and S;
each R$^d$ is independently halogen, —CO$_2$H, —OR$^3$, C$_{1-3}$ aliphatic, or 5-membered heteroaryl containing 1-4 heteroatoms independently selected from the group consisting of O, N, and S; and
each $R^3$ is independently hydrogen or $C_{1-3}$ alkyl.

8. The compound of embodiment 3, wherein the compound is a compound of formula (V)

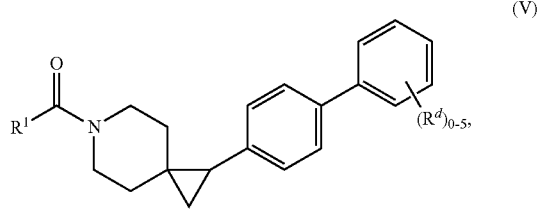

(V)

or a pharmaceutically acceptable salt thereof, wherein:
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, $C_{1-3}$ aliphatic, or 5-membered heteroaryl containing 1-4 heteroatoms independently selected from the group consisting of 0, N and S; and
each $R^3$ is independently hydrogen or $C_{1-3}$ alkyl.

9. The compound of embodiment 3, wherein m is 0 and n is 0.

10. The compound of embodiment 9, wherein:
Ring A is 6-10 membered aryl;
$R^2$ is 6-10 membered aryl substituted with 1-5 $R^d$; and
each $R^3$ is independently hydrogen or $C_{1-6}$ aliphatic.

11. The compound of embodiment 3, wherein:
$R^1$ is 4-6 membered heterocyclyl containing 1-3 heteroatoms independently selected from the group consisting of O, N, and S; and
each $R^d$ is independently —$CO_2R^3$, —$OR^3$, or 5-10 membered heteroaryl containing 1-4 heteroatoms independently selected from the group consisting of O, N, and S.

12. The compound of embodiment 10, wherein
$R^1$ is 3-6 membered cycloalkyl substituted with —$OR^3$; and
each $R^d$ is independently —$CO_2R^3$ or $C_{1-6}$ aliphatic.

13. The compound of embodiment 10, wherein
Ring A is phenyl;
$R^1$ is 5-membered heterocyclyl containing 1-3 heteroatoms independently selected from the group consisting of O, N, and S;
$R^2$ is phenyl substituted with 1-5 $R^d$; and
each $R^d$ is independently —$CO_2R^3$, —$OR^3$, or 5-membered heteroaryl containing 1-4 heteroatoms independently selected from the group consisting of O, N, and S.

14. The compound of embodiment 3, wherein $R^1$ is selected from the group consisting of methyl, ethyl,

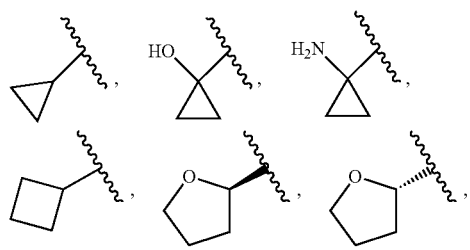

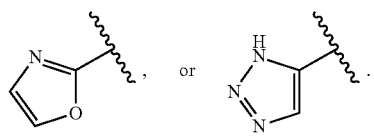

15. The compound of embodiment 3, wherein $R^2$ is —$CO_2R^3$ or an optionally substituted group selected from the group consisting of phenyl,

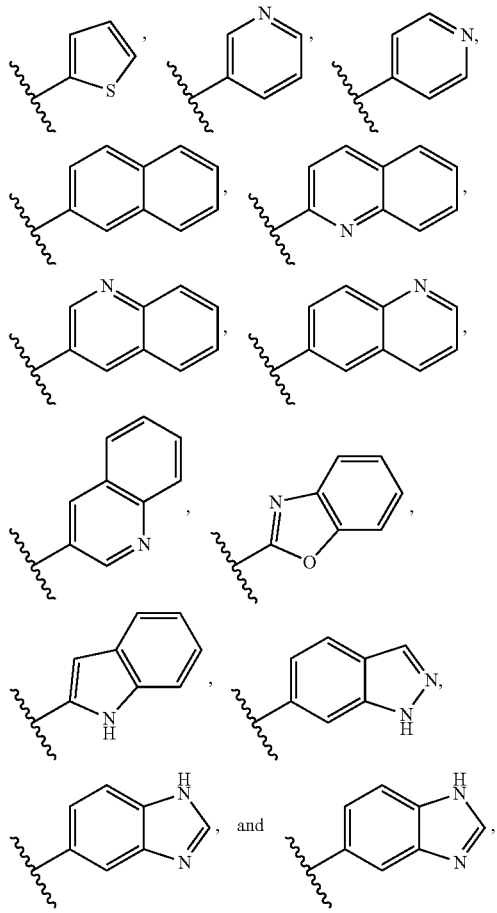

wherein $R^2$ is optionally substituted with 1-6 $R^d$.

16. A compound of formula (I):

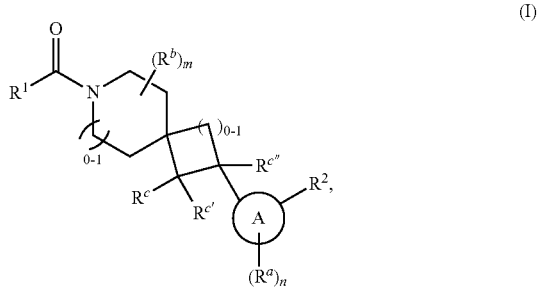

(I)

or a pharmaceutically acceptable salt thereof, wherein:

Ring A is phenyl or naphthyl;

$R^1$ is methyl, ethyl, tetrohydrofuranyl, oxazolyl, triazolyl, cyclobutyl, or cyclopropyl optionally substituted with —$CH_2CO_2H$, —OH, or —$NH_2$;

$R^2$ is —$CO_2H$, cyclobutyl, benzoxazolyl, indolyl, indazolyl, benzimidazolyl, quinolinyl, phenyl, naphthyl, pyridyl, or isoquinolinyl;

each $R^a$ is independently fluoro or chloro;

each $R^b$ is independently methyl;

$R^c$ is hydrogen or fluoro;

$R^{c'}$ is hydrogen or fluoro;

$R^{c''}$ is hydrogen or —$CO_2H$;

each $R^d$ is fluoro, methyl, —$CO_2H$, tetrazolyl, methoxy, chloro, —$CF_3$, —$OCF_3$, or N-methyl pyrazolyl;

m is 0-1; and n is 0-3.

17. The compound of embodiment 16, wherein the compound is a compound of formula (V)

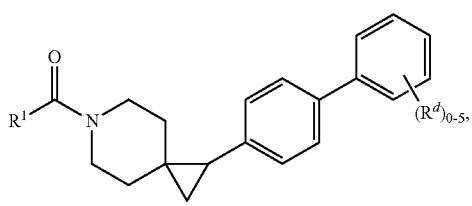

(V)

or a pharmaceutically acceptable salt thereof.

18. The compound of embodiment 17, wherein $R^1$ is selected from the group consisting of cyclopropyl,

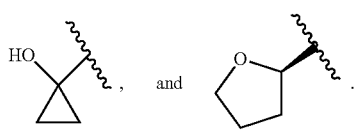

19. The compound of embodiment 18, wherein the compound is a compound of formula (VI-A)

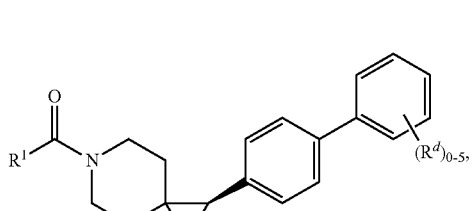

(VI-A)

or a pharmaceutically acceptable salt thereof.

20. The compound of embodiment 1, or a pharmaceutically acceptable salt thereof, wherein the compound is:

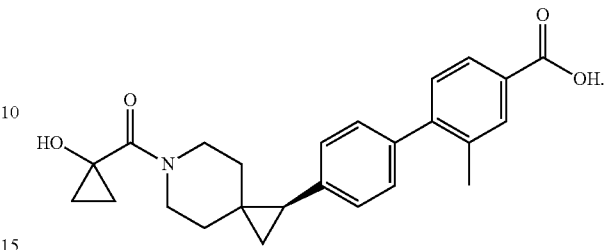

44

21. The compound of embodiment 1, or a pharmaceutically acceptable salt thereof, wherein the compound is:

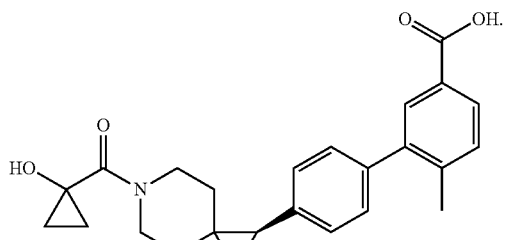

49

22. The compound of embodiment 1, or a pharmaceutically acceptable salt thereof, wherein the compound is:

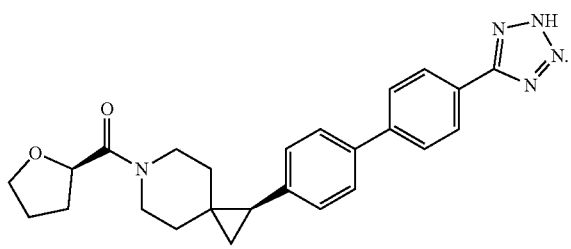

52

23. The compound of embodiment 1, or a pharmaceutically acceptable salt thereof, wherein the compound is:

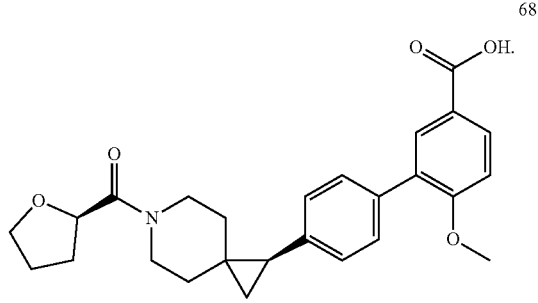 [SMILES: COc1ccc(C(=O)O)cc1-c1ccc([C@H]2CC23CCN(C(=O)[C@H]2CCCO2)CC3)cc1]

68

24. The compound of embodiment 1, or a pharmaceutically acceptable salt thereof, wherein the compound is:

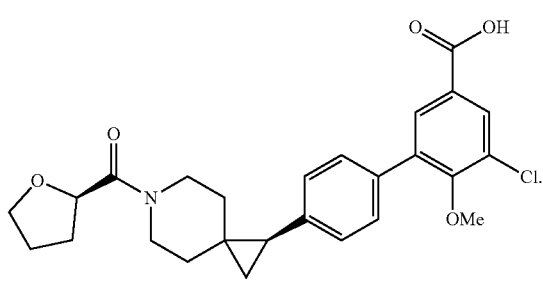
171

25. The compound of embodiment 1, or a pharmaceutically acceptable salt thereof, wherein the compound is:

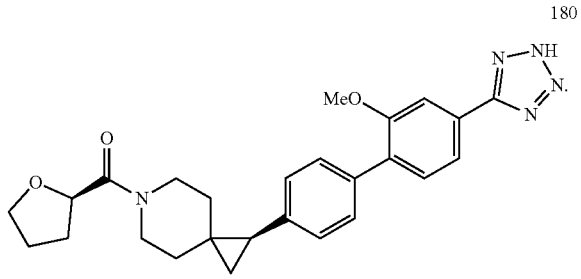 [SMILES: COc1cc(-c2nn[nH]n2)ccc1-c1ccc([C@H]2CC23CCN(C(=O)[C@H]2CCCO2)CC3)cc1]
180

26. The compound of embodiment 1, or a pharmaceutically acceptable salt thereof, wherein the compound is:

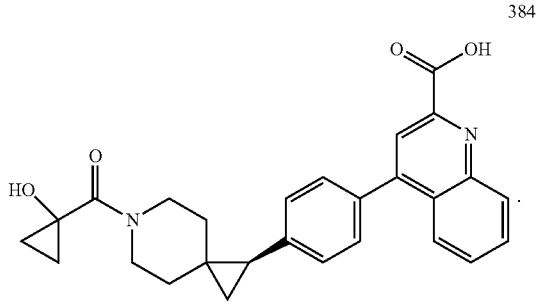 [SMILES: O=C(O)c1cc(-c2ccc([C@H]3CC34CCN(C(=O)C3(O)CC3)CC4)cc2)c2ccccc2n1]
384

27. The compound of embodiment 1, wherein the compound is selected from the group consisting of 4-{4-[(1S)-6-(1-hydroxycyclopropanecarbonyl)-6-azaspiro[2.5]octan-1-yl]phenyl}-3-methylbenzoic acid; (S)-4'-(6-(1-hydroxycyclopropane-1-carbonyl)-6-azaspiro[2.5]octan-1-yl)-6-methyl-[1,1'-biphenyl]-3-carboxylic acid; ((S)-1-(4'-(2H-tetrazol-5-yl)-[1,1'-biphenyl]-4-yl)-6-azaspiro[2.5]octan-6-yl)((R)-tetrahydrofuran-2-yl)methanone; 6-methoxy-4'-((S)-6-((R)-tetrahydrofuran-2-carbonyl)-6-azaspiro[2.5]octan-1-yl)-[1,1'-biphenyl]-3-carboxylic acid; 5-chloro-6-methoxy-4'-((S)-6-((R)-tetrahydrofuran-2-carbonyl)-6-azaspiro[2.5]octan-1-yl)-[1,1'-biphenyl]-3-carboxylic acid; ((S)-1-(2'-methoxy-4'-(2H-tetrazol-5-yl)-1',2',3',4',5',6'-hexahydro-[1,1'-biphenyl]-4-yl)-6-azaspiro[2.5]octan-6-yl)((R)-tetrahydrofuran-2-yl)methanone; and 4-[4-[(1S)-6-(1-hydroxycyclopropanecarbonyl)-6-azaspiro[2.5]octan-1-yl]phenyl]quinoline-2-carboxylic acid; or a pharmaceutically acceptable salt thereof.

EXAMPLES

Definitions Used in the Following Schemes and Elsewhere Herein are

Abbreviations

ACN Acetonitrile
AcOH Acetic Acid
$CH_2Cl_2$ methylene chloride, dichloromethane
$CH_3CN$ Acetonitrile
CO Carbon monoxide
$CO_2$ Carbon dioxide
$Cs_2CO_3$ Cesium carbonate
CuI Copper (I) Iodide
DCM methylene chloride, dichloromethane
DCE 1,2-dichloroethane
DIEA diisopropylethylamine
DMF N,N-dimethylformamide
DMSO Dimethylsulfoxide
DBU 1,8-Diazabicyclo[5.4.0]undec-7-ene
Et3N Triethylamine
$Et_2O$ Diethyl ether
EtOAc Ethyl acetate
EtOH Ethanol
FA Formic acid
$H_2$ Hydrogen (gas)
$H_2O$ Water
HCl Hydrochloric acid
IPA Isopropyl Alcohol
$K_2CO_3$ Potassium carbonate
$K_3PO_4$ Potassium phosphate tribasic
MeOH Methanol
$MgSO_4$ Magnesium sulfate
MTBE Methyl tert-butyl ether
$Na_2SO_4$ Sodium sulfate
$NH_4Cl$ Ammonium chloride
$NH_4HCO_3$ Ammonium bicarbonate
NaH Sodium hydride
$NaHCO_3$ Sodium bicarbonate
$NH_3$ Ammonia
NaI Sodium Iodide
NaOH Sodium hydroxide
$Pd(dppf)Cl_2$ [1,1'-bis(diphenylphosphino)ferrocene]dichloropalladium(II)
$Pd(dppf)Cl_2.CH_2Cl_2$ [1,1'-bis(diphenylphosphino)ferrocene]dichloropalladium(II)-dichloromethane adduct
$Pd(OAc)_2$ palladium(II) acetate
$Pd_2(dba)_3$ tris(dibenzylideneacetone)dipalladium(0)
PE Petroleum ether
t-BuOK Potassium tert-butoxide
TFA Trifluoroacetic acid
XantPhos 4,5-bis(diphenylphosphino)-9,9-dimethylxanthene Materials Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI).

Example 1—Preparation of Common Intermediates

Preparation for the Common Intermediate tert-butyl-1-(4-bromophenyl)-6-azaspiro[2.5]octane-6-carboxylate and Chiral Separation to the Single Enantiomers

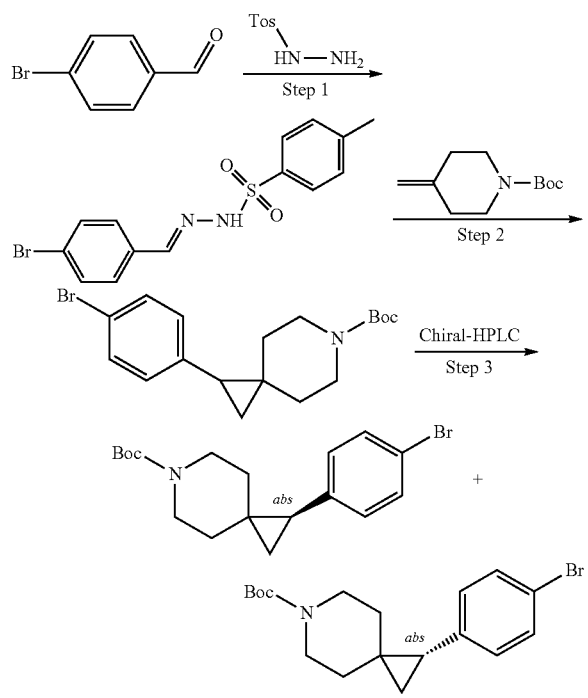

Step 1. (E)-N'-(4-bromobenzylidene)-4-methylbenzenesulfonohydrazide

A solution of 4-bromobenzaldehyde (21.00 g, 0.10 mol) and 4-methylbenzene-1-sulfonohydrazide (21.22 g, 0.11 mol) in methanol (100 mL) was stirred for 1 h at room temperature. The resulting mixture was filtered, and the filter cake was washed with methanol (3×50 mL). The solid was dried under reduced pressure to afford (E)-N'-(4-bromobenzylidene)-4-methylbenzenesulfonohydrazide (38.05 g, 94%) as a white solid. $^1$H-NMR (CD$_3$OD, 400 MHz) δ (ppm): 7.83 (d, J=8.0 Hz, 2H), 7.79 (s, 1H), 7.57-7.45 (m, 4H), 7.40 (d, J=8.0 Hz, 2H), 2.42 (s, 3H). LCMS (ES, m/z): 353, 355 [M+H]$^+$.

Step 2. tert-butyl 1-(4-bromophenyl)-6-azaspiro[2.5] octane-6-carboxylate

To a solution of (E)-N'-(4-bromobenzylidene)-4-methylbenzenesulfonohydrazide (30.00 g, 84.93 mmol) in dichloromethane (500 mL) was added sodium hydride (8.49 g, 0.21 mol, 60%) at 0° C. The mixture was stirred for 1 h. Then tert-butyl 4-methylenepiperidine-1-carboxylate (20.11 g, 0.10 mol) was added slowly and stirred for 15 min, followed by silver trifluoromethanesulfonate (5.46 g, 21.233 mmol). The resulting mixture was stirred overnight at 40° C. under nitrogen atmosphere. The reaction was quenched by saturated ammonium chloride (200 mL) at 0° C. The organic layer was washed with brine (200 mL×3), dried over sodium sulfate, filtered and concentrated under reduced pressure. The crude product was purified by silica gel column, eluted with petroleum ether/ethyl acetate (10:1) to afford tert-butyl 1-(4-bromophenyl)-6-azaspiro[2.5]octane-6-carboxylate (14 g, 43%) as a white solid. $^1$H-NMR (CD$_3$OD, 400 MHz) δ (ppm): 7.42 (d, J=8.4 Hz, 2H), 7.16 (d, J=8.4 Hz, 2H), 3.62-3.45 (m, 2H), 3.33-3.12 (m, 2H), 2.08-1.95 (m, 1H), 1.55-1.51 (m, 2H), 1.46 (s, 9H), 1.17 (t, J=5.6 Hz, 2H), 1.03 (t, J=5.6 Hz, 1H), 0.93-0.88 (m, 1H). LCMS (ES, m/z): 366, 368 [M+H]$^+$.

Step 3. tert-butyl (S)-1-(4-bromophenyl)-6-azaspiro [2.5]octane-6-carboxylate and tert-butyl (R)-1-(4-bromophenyl)-6-azaspiro[2.5]octane-6-carboxylate tert-Butyl 1-(4-bromophenyl)-6-azaspiro[2.5]octane-6-carboxylate (10 g, 27.25 mmol) was purified by Prep-SFC with the following conditions: Column: CHIRALPAK AD-3 3×100 mm, 3 μm; mobile phase: EtOH (20 mM NH$_3$) (5%-20% in 2 mins and hold 1 min at 20%); Detector: UV220 nm to afford the first eluting peak tert-butyl (S)-1-(4-bromophenyl)-6-azaspiro[2.5]octane-6-carboxylate (4 g, 40%) as a white oil and the second eluting peak tert-butyl (R)-1-(4-bromophenyl)-6-azaspiro[2.5]octane-6-carboxylate (4 g, 40%) as a white oil.

tert-butyl (S)-1-(4-bromophenyl)-6-azaspiro[2.5] octane-6-carboxylate $^1$H-NMR (d6-DMSO, 400 MHz) δ (ppm): 7.45 (d, J=8.4 Hz, 2H), 7.19 (d, J=8.4 Hz, 2H), 3.43-3.37 (m, 2H), 3.25-3.12 (m, 1H), 3.04-2.90 (m, 1H), 2.03-1.92 (m, 1H), 1.51-1.40 (m, 2H), 1.37 (s, 9H), 1.19-1.10 (m, 1H), 1.08-0.92 (m, 2H), 0.86-0.78 (m, 1H). LCMS (ES, m/z): 366,368 [M+H]$^+$.

tert-butyl (R)-1-(4-bromophenyl)-6-azaspiro[2.5] octane-6-carboxylate $^1$H-NMR (d6-DMSO, 400 MHz) δ (ppm): 7.45 (d, J=8.4 Hz, 2H), 7.20 (d, J=8.4 Hz, 2H), 3.43-3.37 (m, 2H), 3.27-3.12 (m, 1H), 3.03-2.91 (m, 1H), 2.03-1.92 (m, 1H), 1.50-1.41 (m, 2H), 1.38 (s, 9H), 1.19-1.10 (m, 1H), 1.08-0.92 (m, 2H), 0.86-0.78 (m, 1H). LCMS (ES, m/z): 366,368 [M+H]$^+$.

Preparation for the Common Intermediate (1-(4-bromophenyl)-6-azaspiro[2.5]octan-6-yl)((R)-tetrahydrofuran-2-yl)methanone and Chiral Separation to the Single Enantiomers

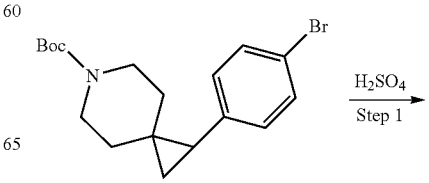

-continued

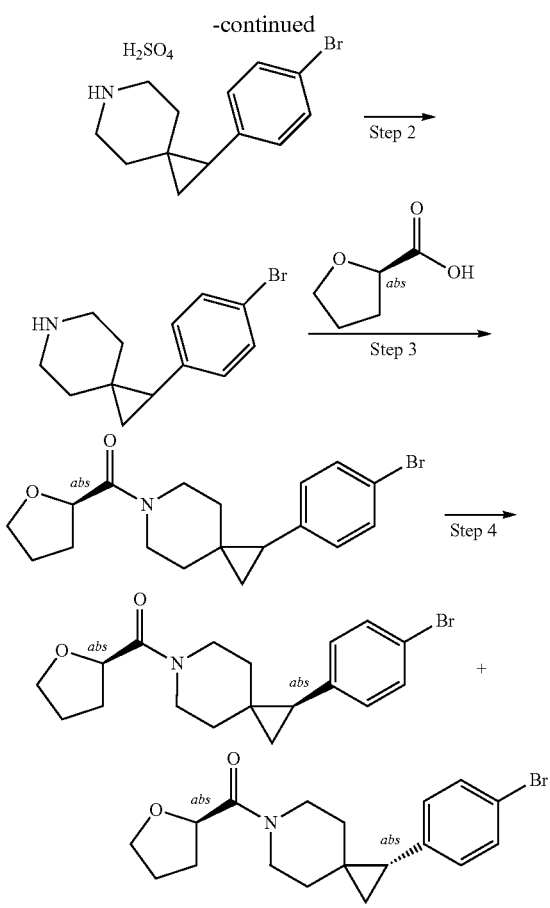

Step 1. 1-(4-bromophenyl)-6-azaspiro[2.5]octane sulfuric salt

A solution of tert-butyl 1-(4-bromophenyl)-6-azaspiro[2.5]octane-6-carboxylate (30.00 g, 81.90 mmol) and sulfuric acid (12 mL) in tetrahydrofuran (120 mL) was stirred for 1 h at 50° C. The mixture was cooled to room temperature and stirred for 2 h. The precipitated solids were collected by filtration and washed with tetrahydrofuran (3×20 mL), dried under reduced pressure to afford 1-(4-bromophenyl)-6-azaspiro[2.5]octane sulfuric salt (29.1 g, 97%) as a white solid. LCMS (ES, m/z): 266, 268 [M+H]+.

Step 2. 1-(4-bromophenyl)-6-azaspiro[2.5]octane

To a solution of 1-(4-bromophenyl)-6-azaspiro[2.5]octane sulfuric salt (29.1 g, 79.95 mol) in tert-butyl methyl ether (300 mL) was added sodium hydroxide (128 mL, 0.32 mol, 2.5 M) at room temperature. The mixture was stirred for 2 h at room temperature. The organic layer was dried over magnesium sulfate, filtered and concentrated to afford 1-(4-bromophenyl)-6-azaspiro[2.5]octane (21.1 g, 99%) as a colorless oil. LCMS (ES, m/z): 266, 268 [M+H]+.

Step 3. (1-(4-bromophenyl)-6-azaspiro[2.5]octan-6-yl)((R)-tetrahydrofuran-2-yl)methanone A mixture of (R)-tetrahydrofuran-2-carboxylic acid (13.85 g, 119.43 mmol), 1-hydroxybenzotriazole (12.90 g, 95.54 mmol), 1-ethyl-3-(3-dimethylaminopropyl) carbodiimide hydrochloride (18.34 g, 95.54 mmol) and 1-(4-bromophenyl)-6-azaspiro[2.5]octane (21.1 g, 79.62 mmol) in N,N-dimethylformamide (150 mL) was stirred for 2 h at room temperature. The reaction was quenched by the addition of ice water (300 mL). The resulting mixture was extracted with ethyl acetate (3×300 mL). The organic layers were combined, dried over sodium sulfate, filtered and concentrated under vacuum. The residue was purified by silica gel column chromatography, eluted with petroleum ether/ethyl acetate (1:2) to afford (1-(4-bromophenyl)-6-azaspiro[2.5]octan-6-yl)((R)-tetrahydrofuran-2-yl)methanone (28 g, 95%) as a yellow oil. 1H-NMR (CD3OD, 400 MHz) δ (ppm): 7.43 (d, J=8.4 Hz, 2H), 7.17 (d, J=8.4 Hz, 2H), 4.71-4.65 (m, 1H), 4.01-3.55 (m, 4H), 3.52-3.35 (m, 1H), 3.33-3.21 (m, 1H), 2.26-1.88 (m, 5H), 1.78-1.52 (m, 2H), 1.34-1.11 (m, 2H), 1.09-1.02 (m, 1H), 0.99-0.91 (m, 1H). LCMS (ES, m/z): 364, 366 [M+H]+.

Step 4. ((S)-1-(4-bromophenyl)-6-azaspiro[2.5]octan-6-yl)((R)-tetrahydrofuran-2-yl)methanone and ((R)-1-(4-bromophenyl)-6-azaspiro[2.5]octan-6-yl)((R)-tetrahydrofuran-2-yl)methanone (1-(4-bromophenyl)-6-azaspiro[2.5]octan-6-yl)((R)-tetrahydrofuran-2-yl)methanone (200 mg, 0.55 mmol) was purified by Chiral HPLC with the following conditions (Agela High-pressure Flash): Column: CHIRALPAK IG, 20×250 mm, 5 μm; mobile phase: n-hexane and isopropanol (hold 40% isopropanol in 20 min); Detector: UV 254 nm to afford the first eluting peak ((S)-1-(4-bromophenyl)-6-azaspiro[2.5]octan-6-yl)((R)-tetrahydrofuran-2-yl)methanone (64.9 mg, 32.13%) and the second eluting peak ((R)-1-(4-bromophenyl)-6-azaspiro[2.5]octan-6-yl)((R)-tetrahydrofuran-2-yl)methanone (73.5 mg, 36%) as a yellow oil.

((S)-1-(4-bromophenyl)-6-azaspiro[2.5]octan-6-yl)((R)-tetrahydrofuran-2-yl)methanone 1H-NMR (CD3OD, 400 MHz) δ (ppm): 7.43 (d, J=8.0 Hz, 2H), 7.18 (d, J=8.0 Hz, 2H), 4.71-4.63 (m, 1H), 4.01-3.58 (m, 4H), 3.50-3.21 (m, 2H), 2.26-1.88 (m, 5H), 1.78-1.52 (m, 2H), 1.34-1.11 (m, 2H), 1.09-1.02 (m, 1H), 0.99-0.91 (m, 1H). LCMS (ES, m/z): 364,366 [M+H]+.

((R)-1-(4-bromophenyl)-6-azaspiro[2.5]octan-6-yl)((R)-tetrahydrofuran-2-yl)methanone 1H-NMR (CD3OD, 400 MHz) δ (ppm): 7.43 (d, J=8.4 Hz, 2H), 7.18 (d, J=8.4 Hz, 2H), 4.81-4.65 (m, 1H), 4.01-3.57 (m, 4H), 3.52-3.22 (m, 2H), 2.26-1.88 (m, 5H), 1.78-1.52 (m, 2H), 1.34-1.11 (m, 2H), 1.09-1.02 (m, 1H), 0.99-0.91 (m, 1H). LCMS (ES, m/z): 364,366 [M+H]+.

Preparation for the Common Intermediate ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone

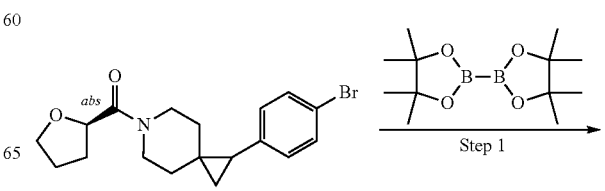

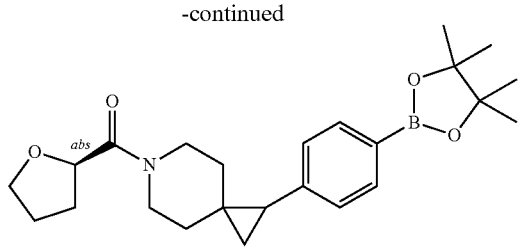

A mixture of (1-(4-bromophenyl)-6-azaspiro[2.5]octan-6-yl)((R)-tetrahydrofuran-2-yl)methanone (12.00 g, 32.94 mmol), 4,4,5,5-tetramethyl-2-(4,4,5,5-tetramethyl-1,3,2-dioxaborolan-2-yl)-1,3,2-dioxaborolane (15.06 g, 59.30 mmol), potassium acetate (9.70 g, 98.84 mmol) and 1,1'-Bis(diphenylphosphino)ferrocene-palladium(II)dichloride dichloromethane complex (2.69 g, 3.29 mmol) in dioxane (60 mL) was stirred for 2 h at 90° C. under nitrogen atmosphere. The mixture was cooled to room temperature. The resulting mixture was concentrated under vacuum. The residue was purified by silica gel column chromatography, eluted with petroleum ether/ethyl acetate (1:1) to afford ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (120 g, 84%) as a white solid. LCMS (ES, m/z): 412 [M+H]$^+$.

Preparation for the Common Intermediate 6-benzyl 1-tert-butyl 1-(4-bromophenyl)-6-azaspiro[2.5]octane-1,6-dicarboxylate

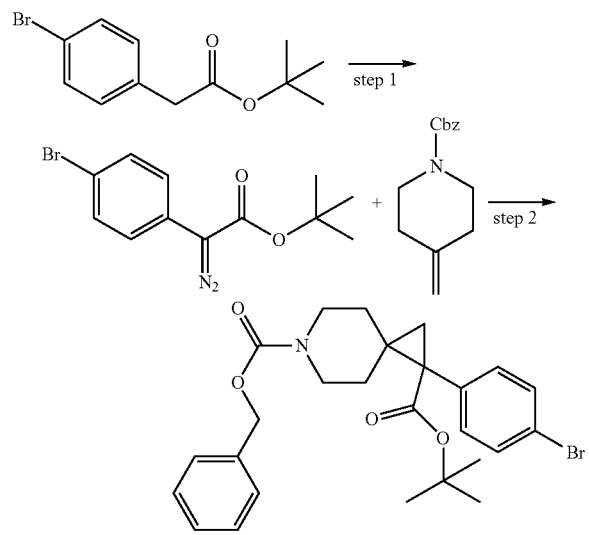

Molecular Weight: 500.43

Step 1 tert-butyl 2-(4-bromophenyl)-2-diazoacetate

DBU (0.903 ml, 5.99 mmol) was added dropwise to a solution of 4-methylbenzenesulfonyl azide (8.59 g, 4.79 mmol, 11% in toluene) and tert-butyl 2-(4-bromophenyl) acetate (0.971 g, 3.99 mmol) in acetonitrile (20 mL). The mixture stirred at room temperature for 2 days. The reaction was concentrated under vacuum, and the residue was purified by normal phase column chromatography using Biotage (Column: 50 g KP-SIL, elution 0 to 10% hexanes/ethyl acetate) to afford ethyl 2-(4-bromophenyl)-2-diazoacetate (1.02 g, 92%) as a yellow solid.

Step 2. 6-benzyl 1-ethyl 1-(4-bromophenyl)-6-azaspiro[2.5]octane-1,6-dicarboxylate tert-Butyl 2-(4-bromophenyl)-2-diazoacetate (0.538 g, 2 mmol) was added via a syringe pump (rate of addition 0.1 mL/min) to a refluxing solution of rhodium(II) acetate dimer (0.027 g, 0.060 mmol) and benzyl 4-methylenepiperidine-1-carboxylate (0.555 g, 2.400 mmol) in dichloromethane (10 mL). The reaction mixture stirred at reflux overnight. The reaction was cooled to room temperature and concentrated under vacuum. The residue was purified directly by normal phase column chromatography using Biotage (Column: 25 g KP-SIL, elution with 5 to 40% Hexanes/ethyl acetate) to afford 6-benzyl 1-tert-butyl 1-(4-bromophenyl)-6-azaspiro[2.5]octane-1,6-dicarboxylate (0.584 g, 62%) as a yellow oil 62. $^1$H NMR (CD3)2CO, 400 MHz) δ (ppm): 7.74-7.49 (d, 2H), 7.35-7.31 (m, 7H), 5.06 (s, 2H), 3.88-3.73 (dd, 2H), 2.50-2.49 (br d, 2H), 1.71-1.65 (m, 1H), 1.51-1.49 (m, 2H), 1.32 (s, 9H), 1.28-1.21 (m, 1H), 0.55-0.52 (d, 1H). LCMS (ES, m/z): 522 [M+Na+H]$^+$.

Preparation for the Common Intermediate (1S)-1-[4-(4,4,5,5-tetramethyl-1,3,2-dioxaborolan-2-yl)phenyl]-6-azaspiro[2.5]octane

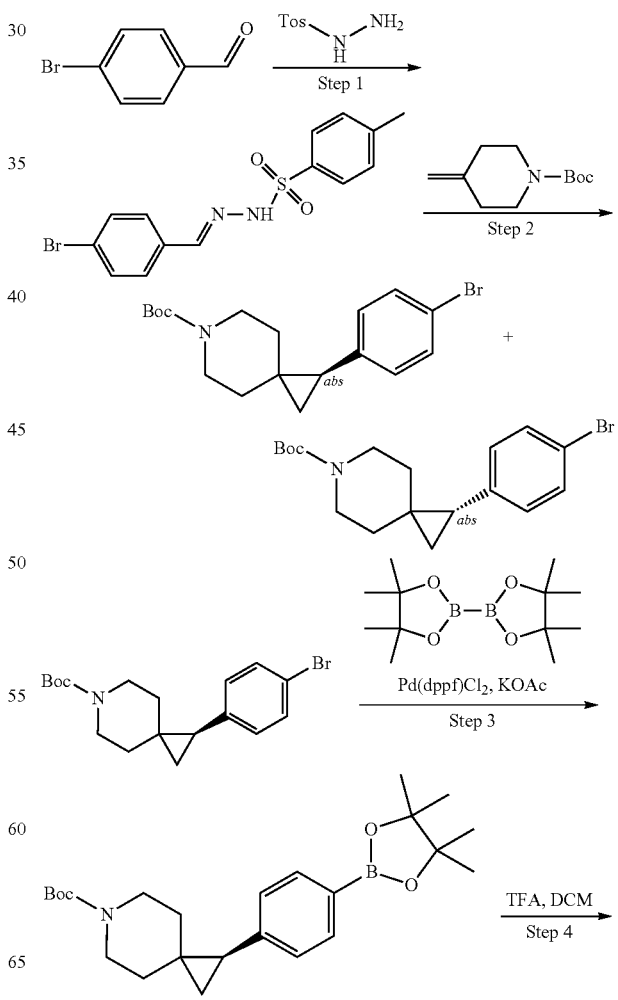

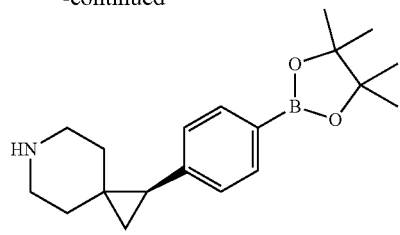

Step 1. (E)-N'-(4-bromobenzylidene)-4-methylbenzenesulfonohydrazide

A solution of 4-bromobenzaldehyde (50.00 g, 0.27 mol) and 4-methylbenzene-1-sulfonohydrazide (50.5 g, 0.27 mol) in methanol (200 mL) was stirred for 1 hour at room temperature. The solids were collected by filtration, washed with methanol (100 mL×3) and dried under reduced pressure to afford (E)-N'-(4-bromobenzylidene)-4-methylbenzenesulfonohydrazide (90 g, 94%) as a white solid. LCMS (ES, m/z): 353, 355 [M+H]$^+$. (The reaction was repeated to generate 6 batches, totaling 500 g of the desired product).

Step 2. Tert-butyl (S)-1-(4-bromophenyl)-6-azaspiro[2.5]octane-6-carboxylate and tert-butyl (R)-1-(4-bromophenyl)-6-azaspiro[2.5]octane-6-carboxylate To a solution of (E)-N'-(4-bromobenzylidene)-4-methyl-benzenesulfonohydrazide (30.0 g, 84.9 mmol) in dichloromethane (500 mL) was added sodium hydride (8.49 g, 0.21 mol, 60%) in portions at 0° C. The mixture was stirred for 1 hour. Then tert-butyl 4-methylidenepiperidine-1-carboxylate (20.11 g, 0.10 mol) was added slowly and the mixture was stirred for 15 minutes. Silver trifluoromethanesulfonate (5.46 g, 21.2 mmol) was then added, and the resulting mixture was stirred overnight at 40° C. under a nitrogen atmosphere. The reaction was quenched by the addition of saturated aqueous ammonium chloride (200 mL) at 0° C. The organic layer was separated and washed with brine (200 mL×3), dried over sodium sulfate, filtered and concentrated under reduced pressure. The crude product was purified by silica gel column chromatography, eluted with petroleum ether/ethyl acetate (10:1) to afford tert-butyl 1-(4-bromophenyl)-6-azaspiro[2.5]octane-6-carboxylate (racemate, 14 g, 43%) as a white solid. (The reaction was repeated to generate 16 batches, totaling 200 g desired product). The racemic product (200 g) was separated by Anal-SFC (Column, CHIRALPAK AD-3 3×100 mm, 3 μm; mobile phase, EtOH (20 mM NH$_3$) (5%-20% in 2 minutes and hold 1 minute at 20%); Detector: UV-220 nm) to afford tert-butyl (S)-1-(4-bromophenyl)-6-azaspiro[2.5]octane-6-carboxylate (20 g, 40%) as a white oil and tert-butyl (R)-1-(4-bromophenyl)-6-azaspiro[2.5]octane-6-carboxylate (80 g, 40%) as a white oil.

tert-butyl (S)-1-(4-bromophenyl)-6-azaspiro[2.5]octane-6-carboxylate $^1$H-NMR (d6-DMSO, 400 MHz) δ (ppm): 7.45 (d, J=8.4 Hz, 2H), 7.19 (d, J=8.4 Hz, 2H), 3.43-3.40 (m, 2H), 3.25-3.12 (m, 1H), 3.04-2.90 (m, 1H), 2.03-1.92 (m, 1H), 1.51-1.40 (m, 2H), 1.37 (s, 9H), 1.19-1.10 (m, 1H), 1.08-0.92 (m, 2H), 0.86-0.78 (m, 1H). LCMS (ES, m/z): 366,368 [M+H]$^+$.

tert-butyl (R)-1-(4-bromophenyl)-6-azaspiro[2.5]octane-6-carboxylate $^1$H-NMR (d6-DMSO, 400 MHz) δ (ppm): 7.45 (d, J=8.4 Hz, 2H), 7.20 (d, J=8.4 Hz, 2H), 3.43-3.40 (m, 2H), 3.27-3.12 (m, 1H), 3.03-2.91 (m, 1H), 2.03-1.92 (m, 1H), 1.50-1.41 (m, 2H), 1.38 (s, 9H), 1.19-1.10 (m, 1H), 1.08-0.92 (m, 2H), 0.86-0.78 (m, 1H). LCMS (ES, m/z): 366,368 [M+H]$^+$.

Step 3. tert-butyl (1S)-1-[4-(4,4,5,5-tetramethyl-1,3,2-dioxaborolan-2-yl)phenyl]-6-azaspiro[2.5]octane-6-carboxylate To a solution of tert-butyl (1S)-1-(4-bromophenyl)-6-azaspiro[2.5]octane-6-carboxylate (41.3 g, 113 mmol) and 4,4,5,5-tetramethyl-2-(4,4,5,5-tetramethyl-1,3,2-dioxaborolan-2-yl)-1,3,2-dioxaborolane (34.4 g, 135 mmol) in 1,4-dioxane (300 mL) were added potassium acetate (22.0 g, 224 mmol) and Pd(dppf)Cl$_2$ (5.77 g, 7.89 mmol). After stirring for 2 hours at 90° C. under a nitrogen atmosphere, the mixture was cooled to room temperature and filtered. The filter cake was washed with ethyl acetate (3×30 mL). The filtrate was concentrated under reduced pressure, and the residue was purified by silica gel column chromatography, eluted with petroleum ether/ethyl acetate (4:1) to afford tert-butyl (1S)-1-[4-(4,4,5,5-tetramethyl-1,3,2-dioxaborolan-2-yl)phenyl]-6-azaspiro[2.5]octane-6-carboxylate (47.0 g, 87%) as a yellow oil. LCMS (ES, m/z): 414 [M+H]$^+$.

Step 4. (1S)-1-[4-(4,4,5,5-tetramethyl-1,3,2-dioxaborolan-2-yl)phenyl]-6-azaspiro[2.5]octane To a stirred solution of tert-butyl (1S)-1-[4-(4,4,5,5-tetramethyl-1,3,2-dioxaborolan-2-yl)phenyl]-6-azaspiro[2.5]octane-6-carboxylate (10.0 g, 21.8 mmol) in dichloromethane (40 mL) was added trifluoroacetic acid (5 mL) dropwise at 0° C. The resulting mixture was stirred for 1 hour at room temperature. The mixture was brought to pH 8 with saturated sodium bicarbonate solution at 0° C. The resulting mixture was extracted with dichloromethane (2×50 mL) and the combined organic layers were dried over anhydrous sodium sulfate. After filtration, the filtrate was concentrated under reduced pressure to afford (1S)-1-[4-(4,4,5,5-tetramethyl-1,3,2-dioxaborolan-2-yl)phenyl]-6-azaspiro[2.5]octane (7.57 g, 99%) as a light yellow solid. LCMS (ES, m/z): 314 [M+H]$^+$.

Example 2—Preparation of Compounds 1-716

Method 1: Preparation of Compounds 60 and 61: 2-chloro-4'-((S)-6-((R)-tetrahydrofuran-2-carbonyl)-6-azaspiro[2.5]octan-1-yl)-[1,1'-biphenyl]-4-carboxylic Acid and 2-chloro-4'-((R)-6-((R)-tetrahydrofuran-2-carbonyl)-6-azaspiro[2.5]octan-1-yl)-[1,1'-biphenyl]-4-carboxylic Acid

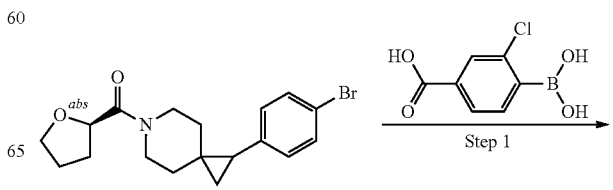

-continued

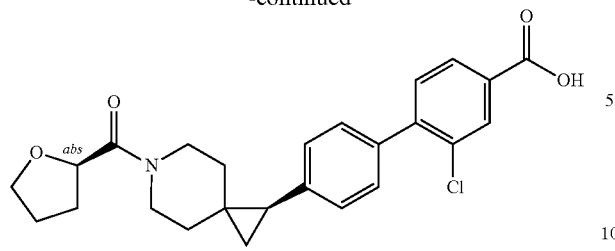

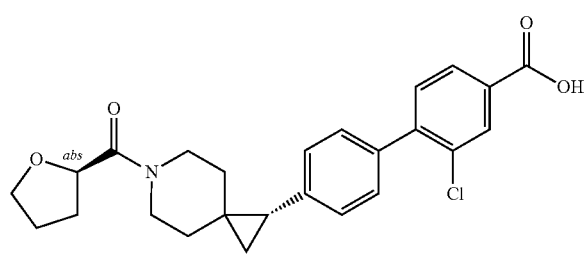

To a mixture of (1-(4-bromophenyl)-6-azaspiro[2.5]octan-6-yl)((R)-tetrahydrofuran-2-yl)methanone (450 mg, 1.17 mmol), 4-(dihydroxyboranyl)-3-methylbenzoic acid (237.06 mg, 1.29 mmol) and water (2 mL) in dioxane (10 mL) were added bis(di-tert-butyl(4-dimethylaminophenyl)phosphine)dichloropalladium (86.80 mg, 0.12 mmol) and potassium phosphate (770.42 mg, 3.52 mmol). The resulting mixture was stirred for 1 h at 70° C. under nitrogen atmosphere. After cooling to room temperature, the resulting mixture was filtered and concentrated under reduced pressure. The crude product was purified by reverse phase column chromatography with water (0.1% FA)/ACN (5% to 50% over 35 min). The product was separated by Chiral HPLC with the following conditions: Column: (R,R)Whelk-01, 21.1×250 mm, 5 μm; mobile phase: Hexanes (0.1% FA) and IPA (hold 50% IPA in 30 min); Detector: UV 254 nm to afford the first eluting peak as Compound 60 (82.8 mg, 31%) and the second eluting peak as Compound 61 (82.4 mg, 30%).

Compound 60

$^1$H-NMR (CD$_3$OD, 400 MHz) δ (ppm): 8.11 (s, 1H), 7.98 (d, J=8.0 Hz, 1H), 7.49-7.31 (m, 5H), 4.82-4.65 (m, 1H), 4.03-3.91 (m, 1H), 3.90-3.63 (m, 3H), 3.54-3.41 (m, 2H), 2.30-2.11 (m, 2H), 2.10-1.89 (m, 3H), 1.78-1.56 (m, 2H), 1.47-1.22 (m, 2H), 1.19-1.12 (m, 1H), 1.01-0.94 (m, 1H). LCMS (ES, m/z): 440, 442 [M+H]$^+$.

Compound 61

$^1$H-NMR (CD$_3$OD, 400 MHz) δ (ppm): 8.11 (s, 1H), 7.99 (d, J=8.0 Hz, 1H), 7.51-7.31 (m, 5H), 4.84-4.61 (m, 1H), 4.02-3.91 (m, 1H), 3.90-3.65 (m, 3H), 3.58-3.39 (m, 2H), 2.32-2.11 (m, 2H), 2.10-1.89 (m, 3H), 1.78-1.53 (m, 2H), 1.42-1.21 (m, 2H), 1.19-1.13 (m, 1H), 1.01-0.95 (m, 1H). LCMS (ES, m/z): 440, 442 [M+H]$^+$.

Method 2: Preparation of Compounds 62 and 63: 6-chloro-4'-((S)-6-((R)-tetrahydrofuran-2-carbonyl)-6-azaspiro[2.5]octan-1-yl)-[1,1'-biphenyl]-3-carboxylic Acid and 6-chloro-4'-((R)-6-((R)-tetrahydrofuran-2-carbonyl)-6-azaspiro[2.5]octan-1-yl)-[1,1'-biphenyl]-3-carboxylic Acid

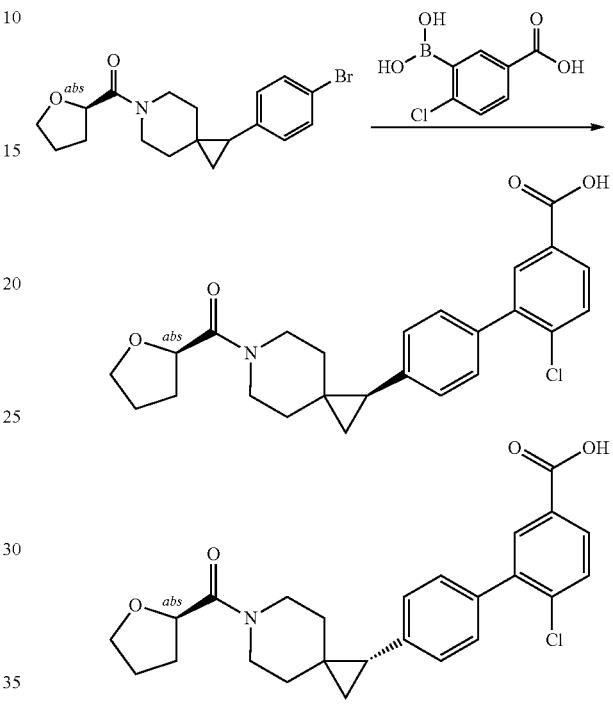

6-chloro-4'-((S)-6-((R)-tetrahydrofuran-2-carbonyl)-6-azaspiro[2.5]octan-1-yl)-[1,1'-biphenyl]-3-carboxylic Acid and 6-chloro-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (300 mg, 0.74 mmol), 5-carboxy-2-chlorophenylboronic acid (200 mg, 1.1 mmol), bis(di-tert-butyl(4-dimethylaminophenyl)phosphine)dichloropalladium (59 mg, 0.082 mmol) and potassium phosphate (472 mg, 2.22 mmol) in dioxane (10 mL) and water (3 mL) was stirred for 1 h at 90° C. under nitrogen atmosphere. The mixture was cooled to room temperature and concentrated under vacuum. The crude product was purified by reverse phase chromatography with water (containing 10 mmol/L NH$_4$HCO$_3$) and ACN (5% to 40% over 60 min). The product was separated by Chiral HPLC (Column: CHIRALPAK IC, 2×25 cm, 5 μm; mobile phase: A: Hexanes (0.1% FA) and B: EtOH; Detector: UV 254 nm to afford the first eluting peak as Compound 62 (69.2 mg, 38.23%) as a white solid and the second eluting peak as Compound 63 (57.2 mg, 32%) as a white solid Compound 62

$^1$H-NMR (CD$_3$OD, 400 MHz) δ (ppm): 8.04-7.87 (m, 2H), 7.71-7.56 (m, 1H), 7.44-7.30 (m, 4H), 4.84-4.62 (m, 1H), 4.07-3.91 (m, 1H), 3.91-3.55 (m, 3H), 3.53-3.39 (m, 2H), 2.34-2.09 (m, 2H), 2.09-1.82 (m, 3H), 1.82-1.55 (m, 2H), 1.51-1.22 (m, 2H), 1.22-1.08 (m, 1H), 1.03-0.93 (m, 1H). LCMS (ES, m/z): 440 [M+H]+.

Compound 63

1H-NMR (CD3OD, 400 MHz) δ (ppm): 8.09-7.88 (m, 2H), 7.71-7.54 (m, 1H), 7.47-7.27 (m, 4H), 4.83-4.58 (m, 1H), 4.04-3.49 (m, 5H), 3.47-3.37 (m, 1H), 2.33-2.12 (m, 2H), 2.12-1.82 (m, 3H), 1.79-1.53 (m, 2H), 1.42-1.20 (m, 2H), 1.20-1.03 (m, 1H), 1.03-0.87 (m, 1H). LCMS (ES, m/z): 440 [M+H]+.

Method 3: Preparation of Compounds 82 and 83:
2-(4-((S)-6-((R)-tetrahydrofuran-2-carbonyl)-6-azaspiro[2.5]octan-1-yl)phenyl)benzo[d]oxazole-5-carboxylic Acid and 2-(4-((R)-6-((R)-tetrahydrofuran-2-carbonyl)-6-azaspiro[2.5]octan-1-yl)phenyl)benzo[d]oxazole-5-carboxylic Acid

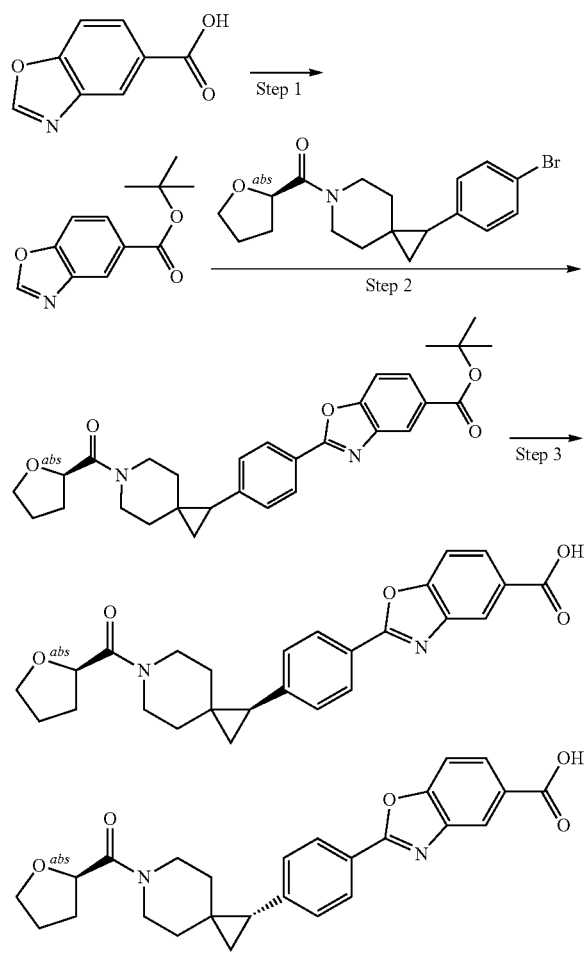

Step 1. tert-butyl benzo[d]oxazole-5-carboxylate

A mixture of benzo[d]oxazole-5-carboxylic acid (4.0 g, 22.1 mmol), 4-dimethylaminopyridine (1.5 g, 12.0 mmol) and di-tert-butyl dicarbonate (8.0 g, 34.8 mmol) in tert-butanol (100 mL) was stirred overnight at 50° C. The mixture was cooled to room temperature. The resulting mixture was diluted with water (80 mL) and extracted with hexane (3×100 mL). The combined organic layers were washed with brine (2×100 mL), dried over anhydrous sodium sulfate, filtrated and concentrated under reduced pressure. The residue was purified by silica gel column chromatography eluted with petroleum ether/ethyl acetate (3:1) to afford tert-butyl benzo[d]oxazole-5-carboxylate (900 mg, 17%) as a yellow oil. LCMS (ES, m/z): 220[M+H]+.

Step 2. tert-butyl 2-(4-(6-((R)-tetrahydrofuran-2-carbonyl)-6-azaspiro[2.5]octan-1-yl)phenyl) benzo[d]oxazole-5-carboxylate A mixture of (1-(4-bromophenyl)-6-azaspiro[2.5]octan-6-yl)((R)-tetrahydrofuran-2-yl)methanone (400 mg, 0.99 mmol), tert-butyl benzo[d]oxazole-5-carboxylate (290 mg, 1.19 mmol), cesium carbonate (898 mg, 2.70 mmol), Xant-Phos (128 mg, 0.22 mmol), copper iodide (42 mg, 0.22 mmol) and palladium acetate (26 mg, 0.054 mmol) in toluene (20 mL) was stirred overnight at 110° C. under nitrogen atmosphere. The mixture was cooled to room temperature. The resulting mixture was filtered. The filter cake was washed with ethyl acetate (3×10 mL). The filtrate was concentrated under reduced pressure. The residue was purified by silica gel column chromatography, eluted with petroleum ether/ethyl acetate (2:1) to afford tert-butyl 2-(4-(6-((R)-tetrahydrofuran-2-carbonyl)-6-azaspiro[2.5]octan-1-yl)phenyl)benzo[d]oxazole-5-carboxylate (260 mg, 47%) as a yellow solid. LCMS (ES, m/z): 503[M+H]+.

Step 3. 2-(4-((S)-6-((R)-tetrahydrofuran-2-carbonyl)-6-azaspiro[2.5]octan-1-yl)phenyl)benzo[d]oxazole-5-carboxylic Acid and 2-(4-((R)-6-((R)-tetrahydrofuran-2-carbonyl)-6-azaspiro[2.5]octan-1-yl)phenyl)benzo[d]oxazole-5-carboxylic Acid A solution of tert-butyl 2-(4-(6-((R)-tetrahydrofuran-2-carbonyl)-6-azaspiro[2.5]octan-1-yl)phenyl)benzo[d]oxazole-5-carboxylate (260 mg, 0.47 mmol) and trifluoroacetic acid (2 mL) in dichloromethane (6 mL) was stirred for 1 h at room temperature. The resulting mixture was concentrated under vacuum. The residue was applied onto a reverse phase column chromatography with water (0.1% FA)/ACN (5% to 50% over 30 min). The product was separated by Chiral HPLC (Column: CHIRALPAK IA, 2.12×15 cm, 5 μm; Mobile phase: A: MTBE (0.1% FA) and B: EtOH (hold 50% EtOH in 18 min); Detector: UV 254 nm to afford the first eluting peak as Compound 82 (66.9 mg, 64%) as a white solid and the second eluting peak as Compound 83 (64.2 mg, 61%) as a white solid.

Compound 82

1H-NMR (CD3OD, 400 MHz) δ (ppm): 8.21 (s, 1H), 8.31-8.04 (m, 3H), 7.84-7.63 (m, 1H), 7.57-7.28 (m, 2H), 4.83-4.49 (m, 1H), 4.07-3.61 (m, 4H), 3.61-3.15 (m, 2H), 2.37-2.09 (m, 2H), 2.09-1.80 (m, 3H), 1.80-1.47 (m, 2H), 1.39-1.13 (m, 4H). LCMS (ES, m/z): 447 [M+H]+.

Compound 83

1H-NMR (CD3OD, 400 MHz) δ (ppm): 8.39 (s, 1H), 8.29-8.04 (m, 3H), 7.86-7.68 (m, 1H), 7.57-7.38 (m, 2H), 4.86-4.55 (m, 1H), 4.07-3.57 (m, 4H), 3.52-3.32 (m, 2H), 2.28-1.84 (m, 5H), 1.82-1.52 (m, 2H), 1.51-1.20 (m, 4H). LCMS (ES, m/z): 447 [M+H]⁺.

Method 4: Preparation of Compounds 58 and 59 6-methyl-4'-((S)-6-((R)-tetrahydrofuran-2-carbonyl)-6-azaspiro[2.5]octan-1-yl)-[1,1'-biphenyl]-3-carboxylic Acid and 6-methyl-4'-((R)-6-((R)-tetrahydrofuran-2-carbonyl)-6-azaspiro[2.5]octan-1-yl)-[1,1'-biphenyl]-3-carboxylic Acid

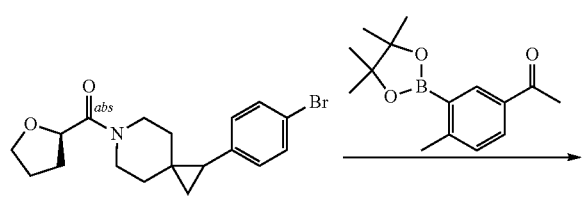

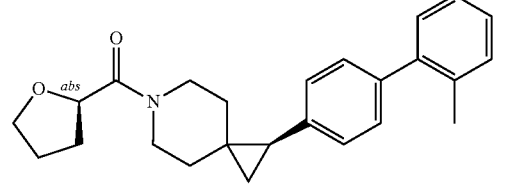

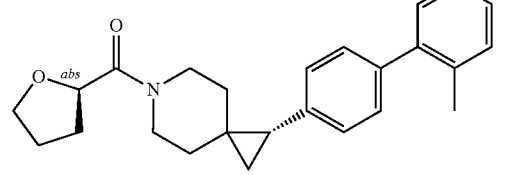

6-methyl-4'-((S)-6-((R)-tetrahydrofuran-2-carbonyl)-6-azaspiro[2.5]octan-1-yl)-[1,1'-biphenyl]-3-carboxylic Acid and 6-methyl-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (450 mg, 1.24 mmol), 1-(4-methyl-3-(4,4,5,5-tetramethyl-1,3,2-dioxaborolan-2-yl)phenyl)ethan-1-one (386 mg, 1.48 mmol), bis(di-tert-butyl(4-dimethylaminophenyl)phosphine)dichloropalladium (87 mg, 0.124 mmol), potassium phosphate (524 mg, 2.47 mmol) in dioxane (10 mL) and water (2 mL) was stirred for 2 h at 90° C. under nitrogen atmosphere. The resulting mixture was cooled to room temperature and concentrated under vacuum. The crude product was purified by reverse phase column chromatography with water (containing 10 mmol/L NH₄HCO₃) and ACN (5% to 45% over 30 min). The product was separated by Chiral HPLC with the following conditions: Column: CHIRALPAK IA, 2×25 cm, 5 μm; mobile phase: Hexanes (0.1% FA) and EtOH (hold 15% EtOH in 30 min); Detector: UV254 nm to afford the first eluting peak as Compound 58 (117.4 mg, 22%) and the second eluting peak as Compound 59 (97.3 mg, 18%) as a white solid.

Compound 58

¹H-NMR (CD₃OD, 400 MHz) δ (ppm): 7.98-7.89 (m, 1H), 7.89-7.80 (m, 1H), 7.50-7.31 (m, 3H), 7.31-7.23 (m, 2H), 4.81-4.62 (m, 1H), 4.04-3.92 (m, 1H), 3.92-3.59 (m, 3H), 3.56-3.40 (m, 2H), 2.33 (s, 3H), 2.30-2.12 (m, 2H), 2.12-1.84 (m, 3H), 1.83-1.25 (m, 4H), 1.21-1.09 (m, 1H), 1.03-0.92 (m, 1H). LCMS (ES, m/z): 420 [M+H]⁺.

Compound 59

¹H-NMR (CD₃OD, 400 MHz) δ (ppm): 7.99-7.79 (m, 2H), 7.48-7.18 (m, 5H), 4.85-4.61 (m, 1H), 4.06-3.61 (m, 4H), 3.61-3.40 (m, 2H), 2.33 (s, 3H), 2.29-2.12 (m, 2H), 2.12-1.81 (m, 3H), 1.71-1.50 (m, 2H) 1.44-1.22 (m, 2H), 1.20-1.09 (m, 1H), 1.08-0.82 (m, 1H). LCMS (ES, m/z): 420 [M+H]⁺.

Method 5: Preparation of Compounds 78 and 79: 5-(4-((S)-6-((R)-tetrahydrofuran-2-carbonyl)-6-azaspiro[2.5]octan-1-yl)phenyl)thiophene-2-carboxylic Acid and 5-(4-((R)-6-((R)-tetrahydrofuran-2-carbonyl)-6-azaspiro[2.5]octan-1-yl)phenyl)thiophene-2-carboxylic Acid

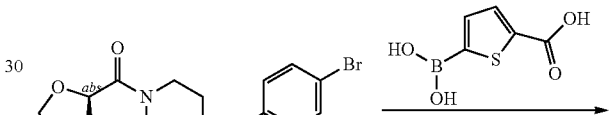

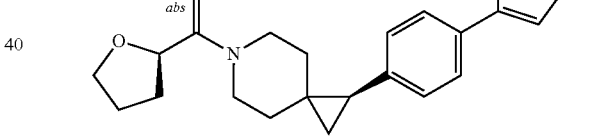

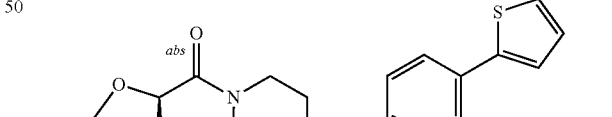

A mixture of (1-(4-bromophenyl)-6-azaspiro[2.5]octan-6-yl)((R)-tetrahydrofuran-2-yl)methanone (400 mg, 1.10 mmol), 5-boronothiophene-2-carboxylic acid (227 mg, 1.32 mmol), bis(di-tert-butyl(4-dimethylaminophenyl)phosphine)dichloropalladium (77.8 mg, 0.11 mmol), potassium phosphate (466 mg, 2.20 mmol) in dioxane (10 mL) and water (2 mL) was stirred for 2 h at 90° C. under nitrogen atmosphere. The resulting mixture was cooled to room temperature and was concentrated under vacuum. The crude product was purified by reverse phase column chromatography with water (containing 10 mmol/L $NH_4HCO_3$) and ACN (5% to 55% over 30 min). The product was separated by Chiral HPLC with the following conditions: Column: CHIRALPAK IC, 2×25 cm, 5 μm; mobile phase: Hexanes (0.1% FA) and EtOH (hold 50% EtOH in 24 min); Detector: UV254 nm to afford the first eluting peak as Compound 78 (50.4 mg, 11%) as a white solid and the second eluting peak as Compound 79 (51.4 mg, 11%) as a white solid.

Compound 78

1H-NMR (d6-DMSO, 400 MHz) δ (ppm): 13.14 (br, 1H), 7.69 (d, J=4.0 Hz, 1H), 7.65 (d, J=4.0 Hz, 2H), 7.54 (d, J=8.0 Hz, 1H), 7.33 (d, J=7.6 Hz, 2H), 4.80-4.45 (m, 1H), 3.88-3.62 (m, 2H), 3.62-3.48 (m, 2H), 3.48-3.38 (m, 1H), 3.22-3.00 (m, 1H), 2.19-2.08 (m, 1H), 2.08-1.91 (m, 2H), 1.89-1.67 (m, 2H), 1.66-1.30 (m, 2H), 1.29-0.97 (m, 3H), 0.96-0.80 (m, 1H). LCMS (ES, m/z): 412 [M+H]+.

Compound 79

1H-NMR (d6-DMSO, 400 MHz) δ (ppm): 13.12 (br, 1H), 7.69 (d, J=3.6 Hz, 1H), 7.65 (d, J=8.0 Hz, 2H), 7.55 (d, J=3.6 Hz, 1H), 7.35 (d, J=8.0 Hz, 2H), 4.76-4.46 (m, 1H), 3.89-3.67 (m, 2H), 3.65-3.45 (m, 2H), 3.44-3.35 (m, 1H), 3.20-3.00 (m, 1H), 2.18-2.09 (m, 1H), 2.08-1.89 (m, 2H), 1.88-1.68 (m, 2H), 1.62-1.35 (m, 2H), 1.34-1.02 (m, 3H), 1.00-0.75 (m, 1H). LCMS (ES, m/z): 412 [M+H]+.

Method 6: Preparation of Compounds 214 and 215: 1-methyl-2-(4-((S)-6-((R)-tetrahydrofuran-2-carbonyl)-6-azaspiro[2.5]octan-1-yl)phenyl)-1H-indole-6-carboxylic Acid and 1-methyl-2-(4-((R)-6-((R)-tetrahydrofuran-2-carbonyl)-6-azaspiro[2.5]octan-1-yl)phenyl)-1H-indole-6-carboxylic Acid

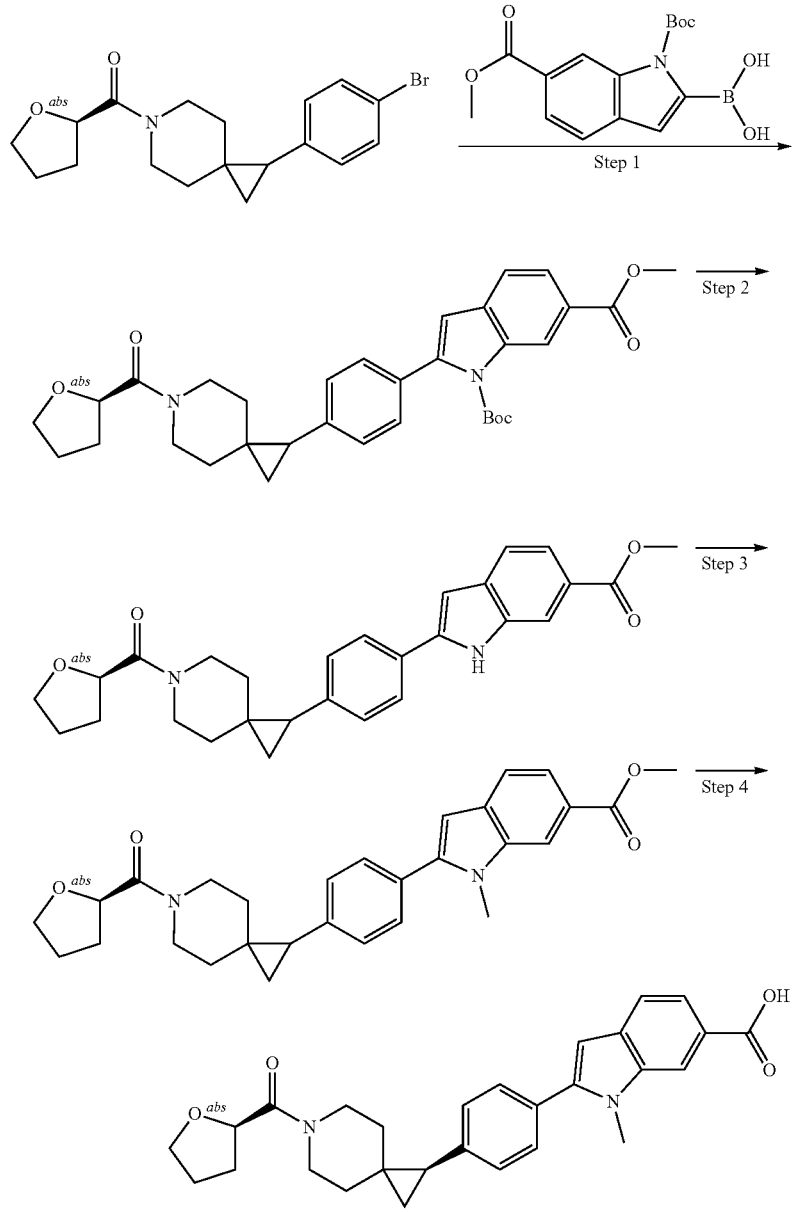

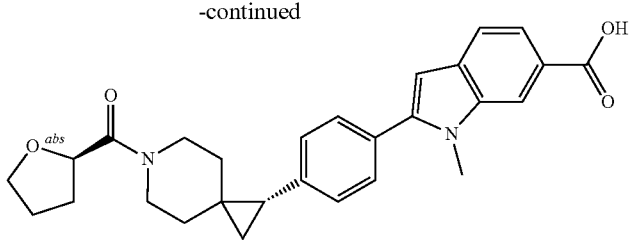

Step 1. 1-(tert-butyl) 6-methyl 2-(4-(6-((R)-tetrahydrofuran-2-carbonyl)-6-azaspiro[2.5]octan-1-yl)phenyl)-1H-indole-1,6-dicarboxylate A mixture of (1-(4-bromophenyl)-6-azaspiro[2.5]octan-6-yl)((R)-tetrahydrofuran-2-yl)methanone (1.0 g, 2.75 mmol), (1-(tert-butoxycarbonyl)-6-(methoxycarbonyl)-1H-indol-2-yl)boronic acid (876 mg, 2.75 mmol), bis(di-tert-butyl(4-dimethylaminophenyl)phosphine)dichloropalladium (194 mg, 0.28 mmol) and potassium phosphate (1.17 g, 5.49 mmol) in dioxane (20 mL) and water (4 mL) was stirred for 2 h at 90° C. under nitrogen atmosphere. The mixture was cooled to room temperature and concentrated under reduced pressure. The residue was purified by reverse flash chromatography with water (containing 10 mmol/L $NH_4HCO_3$) and ACN (35% to 65% over 30 min) to yield 1-(tert-butyl) 6-methyl 2-(4-(6-((R)-tetrahydrofuran-2-carbonyl)-6-azaspiro[2.5]octan-1-yl)phenyl)-1H-indole-1,6-dicarboxylate (550 mg, 34%) as a yellow oil. LCMS (ES, m/z): 559 $[M+H]^+$.

Step 2. methyl 2-(4-(6-((R)-tetrahydrofuran-2-carbonyl)-6-azaspiro[2.5]octan-1-yl)phenyl)-1H-indole-6-carboxylate A solution of 1-(tert-butyl) 6-methyl 2-(4-(6-((R)-tetrahydrofuran-2-carbonyl)-6-azaspiro[2.5]octan-1-yl)phenyl)-1H-indole-1,6-dicarboxylate (550 mg, 0.98 mmol) in trifluoroacetic acid (3 mL) and DCM (10 mL) was stirred for 40 min at room temperature. The resulting mixture was concentrated under reduced pressure to afford methyl 2-(4-(6-((R)-tetrahydrofuran-2-carbonyl)-6-azaspiro[2.5]octan-1-yl)phenyl)-1H-indole-6-carboxylate (400 mg, crude) as a yellow oil. LCMS (ES, m/z): 459 $[M+H]^+$.

Step 3. methyl 1-methyl-2-(4-(6-((R)-tetrahydrofuran-2-carbonyl)-6-azaspiro[2.5]octan-1-yl)phenyl)-1H-indole-6-carboxylate A mixture of methyl 2-(4-[6-[(2R)-oxolane-2-carbonyl]-6-azaspiro[2.5]octan-1-yl]phenyl)-1H-indole-6-carboxylate (500 mg, 1.09 mmol) and sodium hydride (131 mg, 3.27 mmol, 60%) in dimethyl formamide (15 mL) was stirred for 30 min at 0° C. Then iodomethane (170 mg, 1.20 mmol) was added. The mixture was stirred overnight at room temperature. The reaction mixture was quenched by water (50 mL) and extracted with ethyl acetate (3×50 mL). The organic layers were combined, dried over anhydrous sodium sulfate, filtered and concentrated under reduced pressure. The residue was purified by silica gel column chromatography, eluted with petroleum ether/ethyl acetate (3:1) to afford methyl 1-methyl-2-(4-(6-((R)-tetrahydrofuran-2-carbonyl)-6-azaspiro[2.5]octan-1-yl)phenyl)-1H-indole-6-carboxylate (400 mg, 74%) as a yellow oil. LCMS (ES, m/z): 473 $[M+H]^+$.

Step 4. 1-methyl-2-(4-((S)-6-((R)-tetrahydrofuran-2-carbonyl)-6-azaspiro[2.5]octan-1-yl)phenyl)-1H-indole-6-carboxylic Acid and 1-methyl-2-(4-((R)-6-((R)-tetrahydrofuran-2-carbonyl)-6-azaspiro[2.5]octan-1-yl)phenyl)-1H-indole-6-carboxylic Acid A solution of methyl 1-methyl-2-(4-(6-((R)-tetrahydrofuran-2-carbonyl)-6-azaspiro[2.5]octan-1-yl)phenyl)-1H-indole-6-carboxylate (350 mg, 0.74 mmol) and lithium hydroxide (53 mg, 2.22 mmol) in methanol (15 mL) was stirred for 2 h at 40° C. The mixture was cooled to room temperature. The mixture was acidified to pH 5 with hydrochloric acid (1M). The resulting mixture was extracted with ethyl acetate (3×50 mL). The organic layers were combined, dried over anhydrous sodium sulfate, filtered and concentrated under reduced pressure. The residue was purified by silica gel column chromatography, eluted with dichloromethane/methanol (10:1). The product was separated by Chiral HPLC with the following conditions: Column: CHIRALPAK IG, 2×25 cm, 5 μm; mobile phase: MTBE (0.1% FA) and EtOH (hold 30% EtOH in 15 min); Detector: UV254 to afford the first eluting peak as Compound 214 (92.5 mg, 27%) as an off-white solid and the second eluting peak as Compound 215 (100.6 mg, 29%) as an off-white solid.

Compound 214

$^1$H NMR ($CD_3OD$, 400 MHz) δ (ppm): 8.18 (s, 1H), 7.78 (d, J=8.4 Hz, 1H), 7.62 (d, J=8.4 Hz, 1H), 7.53 (d, J=8.0 Hz, 2H), 7.41 (d, J=8.0 Hz, 2H), 6.60 (s, 1H), 4.80-4.66 (m, 1H), 4.02-3.93 (m, 1H), 3.88-3.82 (m, 4H), 3.73-3.70 (m, 2H), 3.57-3.49 (m, 1H), 3.43-3.40 (m, 1H), 2.28-2.13 (m, 2H), 2.09-1.85 (m, 3H), 1.75-1.57 (m, 2H), 1.36-1.31 (m, 2H), 1.19-1.62 (m, 1H), 1.02-0.98 (m, 1H). LCMS (ES, m/z): 459 $[M+H]^+$.

Compound 215

$^1$H NMR ($CD_3OD$, 400 MHz) δ (ppm): 8.18 (s, 1H), 7.79 (d, J=8.4 Hz, 1H), 7.61 (d, J=8.4 Hz, 1H), 7.53 (d, J=8.0 Hz, 2H), 7.42-7.39 (m, 2H), 6.60 (s, 1H), 4.78-4.67 (m, 1H), 3.97-3.81 (m, 5H), 3.79-3.73 (m, 2H), 3.46-3.44 (m, 1H), 3.33-3.32 (m, 1H), 2.21-2.19 (m, 2H), 2.09-1.85 (m, 3H), 1.80-1.55 (m, 2H), 1.44-1.28 (m, 2H) 1.18-1.17 (m, 1H), 1.02-0.98 (m, 1H). LCMS (ES, m/z): 459 $[M+H]^+$.

Method 7: Preparation of Compounds 166 and 167: 2-methoxy-4'-((S)-6-((R)-tetrahydrofuran-2-carbonyl)-6-azaspiro[2.5]octan-1-yl)-[1,1'-biphenyl]-3-carboxylic Acid and 2-methoxy-4'-((R)-6-((R)-tetrahydrofuran-2-carbonyl)-6-azaspiro[2.5]octan-1-yl)-[1,1'-biphenyl]-3-carboxylic Acid

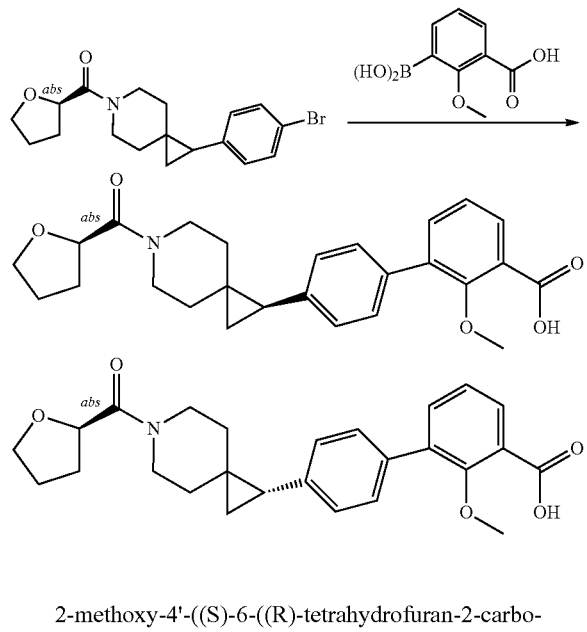

2-methoxy-4'-((S)-6-((R)-tetrahydrofuran-2-carbonyl)-6-azaspiro[2.5]octan-1-yl)-[1,1'-biphenyl]-3-carboxylic Acid and 2-methoxy-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (600 mg, 1.657 mmol), 3-(dihydroxyboranyl)-2-methoxybenzoic acid (323 mg, 1.65 mmol), bis(di-tert-butyl(4-dimethylaminophenyl)phosphine)dichloropalladium (117 mg, 0.17 mmol) and potassium phosphate (699 mg, 3.29 mmol) in dioxane (20 mL) and water (4 mL) was stirred for 2 h at 90° C. under nitrogen atmosphere. The mixture was cooled to room temperature and concentrated under reduced pressure. The residue was purified by reverse flash chromatography with water (containing 0.1% FA) and ACN (10% to 50% over 25 min). The product was separated by Prep-SFC with the following conditions: Column: CHIRALPAK AS-H, 2.0 cm×25 cm L (5 μm); mobile phase: CO$_2$ and MeOH (0.1% FA) (10% to 50% in 4.0 min, hold 2.0 min at 50%); Detector: UV254 nm to afford the first eluting peak as Compound 166 (149 mg, 21%) as a white solid and the second eluting peak as Compound 167 (156 mg, 22%) as a white solid.

Compound 166

$^1$H-NMR (CD$_3$OD, 400 MHz) δ (ppm): 7.68-7.62 (m, 1H), 7.50 (d, J=8.0 Hz, 2H), 7.49-7.41 (m, 1H), 7.33 (d, J=8.0 Hz, 2H), 7.22 (t, J=7.6 Hz, 1H), 4.85-4.63 (m, 1H), 4.03-3.59 (m, 4H), 3.49 (s, 3H), 3.48-3.26 (m, 2H), 2.30-1.81 (m, 5H), 1.76-1.50 (m, 2H), 1.44-1.20 (m, 2H), 1.18-1.11 (m, 1H), 1.02-0.92 (m, 1H). LCMS (ES, m/z): 436 [M+H]$^+$.

Compound 167

$^1$H-NMR (CD$_3$OD, 400 MHz) δ (ppm): 7.75 (d, J=8.0 Hz, 1H), 7.56-7.47 (m, 3H), 7.34 (d, J=8.4 Hz, 2H), 7.26 (t, J=7.6 Hz, 1H), 4.82-4.63 (m, 1H), 4.02-3.63 (m, 4H), 3.47 (s, 3H), 3.43-3.25 (m, 2H), 2.30-1.83 (m, 5H), 1.79-1.52 (m, 2H), 1.42-1.20 (m, 2H), 1.18-1.12 (m, 1H), 1.01-0.93 (m, 1H). LCMS (ES, m/z): 436 [M+H]$^+$.

Method 8: Preparation of Compounds 70 and 71: 4-chloro-4'-((S)-6-((R)-tetrahydrofuran-2-carbonyl)-6-azaspiro[2.5]octan-1-yl)-[1,1'-biphenyl]-3-carboxylic Acid and 4-chloro-4'-((R)-6-((R)-tetrahydrofuran-2-carbonyl)-6-azaspiro[2.5]octan-1-yl)-[1,1'-biphenyl]-3-carboxylic Acid

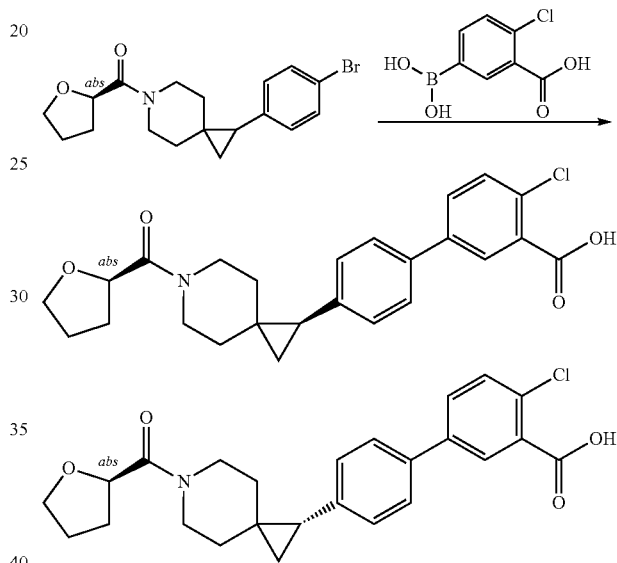

4-chloro-4'-((S)-6-((R)-tetrahydrofuran-2-carbonyl)-6-azaspiro[2.5]octan-1-yl)-[1,1'-biphenyl]-3-carboxylic Acid and 4-chloro-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (450 mg, 1.17 mmol), 5-borono-2-chlorobenzoic acid (237 mg, 1.29 mmol), bis(di-tert-butyl(4-dimethylaminophenyl)phosphine)dichloropalladium (87 mg, 0.12 mmol) and potassium phosphate (770 mg, 3.52 mmol) in dioxane (20 mL) and water (4 mL) was stirred for 2 h at 90° C. under nitrogen atmosphere. The mixture was cooled to room temperature and concentrated under reduced pressure. The residue was purified by reverse flash chromatography with water (containing 0.1% FA) and ACN (10% to 55% over 30 min). The product was separated by Chiral HPLC with the following conditions: Column: (R, R)Whelk-01, 21.1×250 mm, 5 μm; mobile phase: Hexanes (0.1% FA) and IPA (hold 50% IPA in 30 min); Detector: UV254 nm to afford the first eluting peak as Compound 70 (62.6 mg, 26%) as a white solid and the second eluting peak as Compound 71 (64 mg, 27%) as a white solid.

Compound 70

¹H-NMR (CD₃OD, 400 MHz) δ (ppm): 8.06-8.02 (m, 1H), 7.78-7.73 (m, 1H), 7.63-7.54 (m, 3H), 7.38-7.33 (m, 2H), 4.84-4.66 (m, 1H), 4.02-3.92 (m, 1H), 3.91-3.60 (m, 3H), 3.50-3.21 (m, 2H), 2.30-2.15 (m, 2H), 2.10-1.85 (m, 3H), 1.80-1.61 (m, 2H), 1.41-1.23 (m, 2H), 1.18-1.11 (m, 1H), 1.00-0.91 (m, 1H). LCMS (ES, m/z): 440 [M+H]⁺.

Compound 71

¹H-NMR (CD₃OD, 400 MHz) δ (ppm): 8.06-8.02 (m, 1H), 7.78-7.73 (m, 1H), 7.63-7.54 (m, 3H), 7.36 (d, J=8.0 Hz, 2H), 4.84-4.65 (m, 1H), 4.01-3.92 (m, 1H), 3.92-3.60 (m, 3H), 3.50-3.25 (m, 2H), 2.29-2.12 (m, 2H), 2.10-1.87 (m, 3H), 1.82-1.56 (m, 2H), 1.39-1.18 (m, 2H), 1.15-1.05 (m, 1H), 1.00-0.92 (m, 1H). LCMS (ES, m/z): 440 [M+H]⁺.

Method 9: Preparation of Compounds 98 and 99: 2-(4-((S)-6-((R)-tetrahydrofuran-2-carbonyl)-6-azaspiro[2.5]octan-1-yl)cyclohexan-1-yl)-3H-1l3-benzo[d]oxazole-6-carboxylic Acid and 2-{4-[(1R)-6-[(2R)-oxolane-2-carbonyl]-6-azaspiro[2.5]octan-1-yl]phenyl}-1,3-benzoxazole-6-carboxylic Acid

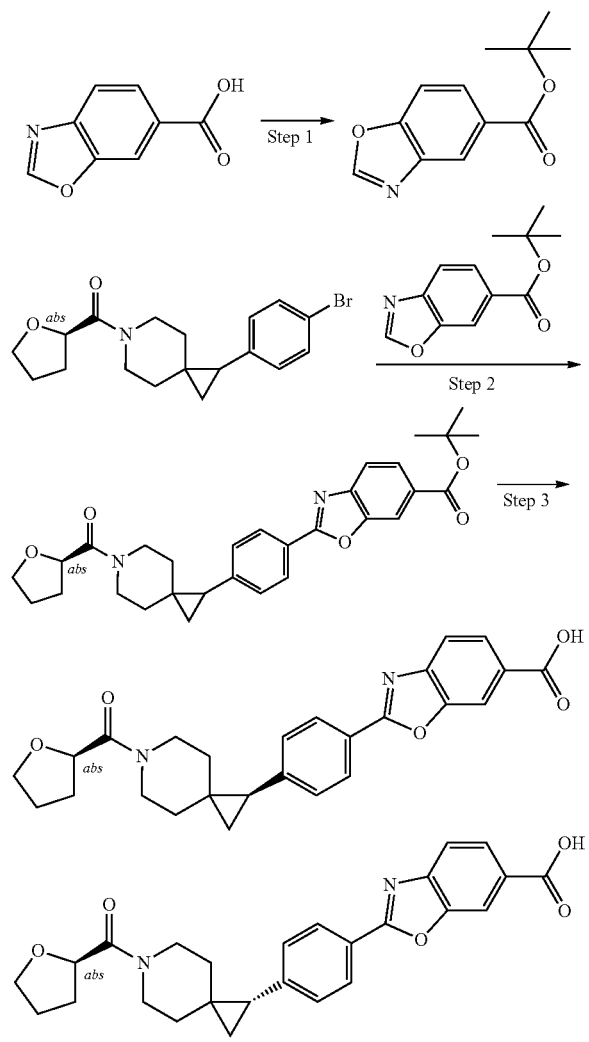

Step 1. tert-butyl benzo[d]oxazole-6-carboxylate

To a mixture of 1,3-benzoxazole-6-carboxylic acid (5 g, 30.0 mmol) and 4-dimethylaminopyridine (1.83 g, 15.02 mmol) in tert-butanol (50 mL) was added di-tert-butyl dicarbonate (13.1 g, 60.07 mmol) at room temperature under nitrogen atmosphere. The resulting mixture was stirred overnight at 50° C. under nitrogen atmosphere. The resulting mixture was diluted with water (100 mL). The mixture was extracted with ethyl acetate (3×100 mL). The organic layers were combined, dried over sodium sulfate, filtered and concentrated under reduced pressure. The residue was purified by silica gel column chromatography, eluted with petroleum ether/ethyl acetate (10:1) to afford tert-butyl benzo[d]oxazole-6-carboxylate (3.8 g, 55%) as a yellow solid. LCMS (ES, m/z): 220 [M+H]⁺.

Step 2. tert-butyl 2-(4-[6-[(2R)-oxolane-2-carbonyl]-6-azaspiro[2.5]octan-1-yl]phenyl)-1,3-benzoxazole-6-carboxylate A mixture of tert-butyl benzo[d]oxazole-6-carboxylate (250 mg, 1.08 mmol), (1-(4-bromophenyl)-6-azaspiro[2.5]octan-6-yl)((R)-tetrahydrofuran-2-yl)methanone (483 mg, 1.30 mmol), copper iodide (42 mg, 0.22 mmol), XantPhos (126 mg, 0.22 mmol), cesium carbonate (891 mg, 2.70 mmol) and palladium acetate (12 mg, 0.054 mmol) in toluene (10 mL) was stirred overnight at 110° C. under nitrogen atmosphere. The resulting mixture was concentrated under reduced pressure. The residue was purified by silica gel column chromatography, eluted with petroleum ether/ethyl acetate (1:1) to afford tert-butyl 2-(4-(6-((R)-tetrahydrofuran-2-carbonyl)-6-azaspiro[2.5]octan-1-yl)phenyl)benzo[d]oxazole-6-carboxylate (170 mg, 30%) as a yellow solid. LCMS (ES, m/z): 503 [M+H]⁺.

Step 3. 2-(4-((S)-6-((R)-tetrahydrofuran-2-carbonyl)-6-azaspiro[2.5]octan-1-yl)cyclohexan-1-yl)-3H-1l3-benzo[d]oxazole-6-carboxylic Acid and 2-{4-[(1R)-6-[(2R)-oxolane-2-carbonyl]-6-azaspiro[2.5]octan-1-yl]phenyl}-1,3-benzoxazole-6-carboxylic Acid A mixture of tert-butyl 2-(4-(6-((R)-tetrahydrofuran-2-carbonyl)-6-azaspiro[2.5]octan-1-yl)phenyl)benzo[d]oxazole-6-carboxylate (170 mg, 0.29 mmol) and trifluoroacetic acid (3 mL) in dichloromethane (10 mL) was stirred for 1 h at room temperature. The mixture was under reduced pressure. The residue was purified by reverse flash chromatography with water (containing 0.1% FA) and ACN (10% to 45% over 35 min). The product was separated by Chiral HPLC (Column: (R,R) Whelk-01, 21.1×250 mm, 5 μm; mobile phase: Hexanes (0.1% FA) and IPA (hold 50% IPA in 30 min); Detector: UV 254 nm to afford the first eluting peak as Compound 98 (53 mg, 44%) as a white solid and the second eluting peak as Compound 99 (58.7 mg, 48%) as a white solid.

Compound 98

¹H-NMR (CD₃OD, 400 MHz) δ (ppm): 8.31 (s, 1H), 8.21 (d, J=8.0 Hz, 2H), 8.11 (d, J=8.0 Hz, 2H), 7.76 (d, J=7.6 Hz, 2H), 7.50 (d, J=7.6 Hz, 2H), 4.82-4.63 (m, 1H), 4.02-3.62 (m, 4H), 3.49-3.36 (m, 2H), 2.28-1.82 (m, 5H), 1.80-1.61 (m, 2H), 1.45-1.22 (m, 3H), 1.09-1.02 (m, 1H). LCMS (ES, m/z): 447 [M+H]⁺.

Compound 99

¹H-NMR (CD₃OD, 400 MHz) δ (ppm): 8.31 (s, 1H), 8.21 (d, J=7.6 Hz, 2H), 8.12 (d, J=8.8 Hz, 2H), 7.76 (d, J=8.4 Hz, 2H), 7.52-7.45 (m, 2H), 4.85-4.62 (m, 1H), 4.02-3.62 (m, 4H), 3.49-3.36 (m, 2H), 2.32-1.87 (m, 5H), 1.80-1.59 (m, 2H), 1.52-1.21 (m, 3H), 1.09-1.01 (m, 1H). LCMS (ES, m/z): 447 [M+H]⁺.

Method 10: Preparation of Compounds 68 and 69: 6-methoxy-4'-((S)-6-((R)-tetrahydrofuran-2-carbonyl)-6-azaspiro[2.5]octan-1-yl)-[1,1'-biphenyl]-3-carboxylic Acid and 6-methoxy-4'-((R)-6-((R)-tetrahydrofuran-2-carbonyl)-6-azaspiro[2.5]octan-1-yl)-[1,1'-biphenyl]-3-carboxylic Acid

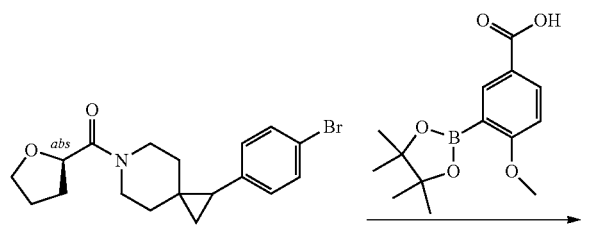

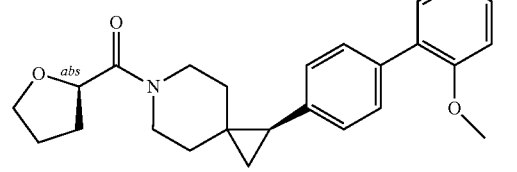

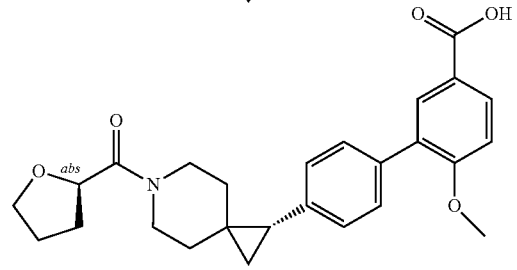

Step 1. 6-methoxy-4'-((S)-6-((R)-tetrahydrofuran-2-carbonyl)-6-azaspiro[2.5]octan-1-yl)-[1,1'-biphenyl]-3-carboxylic Acid and 6-methoxy-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (450 mg, 1.24 mmol), 4-methoxy-3-(4,4,5,5-tetramethyl-1,3,2-dioxaborolan-2-yl)benzoic acid (409 mg, 1.48 mmol), bis(di-tert-butyl (4-dimethylaminophenyl)phosphine)dichloropalladium (87 mg, 0.12 mmol) and potassium phosphate (770 mg, 3.52 mmol) in dioxane (15 mL) and water (3 mL) was stirred for 2 h at 90° C. under nitrogen atmosphere. The resulting mixture was cooled to room temperature and concentrated under reduced pressure. The residue was purified by reverse flash chromatography with water (containing 0.1% FA) and ACN (10% to 55% over 30 min). The product separated by Chiral HPLC with the following conditions: Column: CHIRALPAK IC, 2×25 cm, 5 μm; mobile phase: (Hexanes: DCM=3:1) (0.1% FA) and IPA (hold 50% IPA in 25 min); Detector: UV254 nm to afford the first eluting peak as Compound 68 (68.9 mg, 13%) and the second eluting peak as Compound 69 (95.7 mg, 17%) as a white solid.

Compound 68

¹H-NMR (CD₃OD, 400 MHz) (ppm): 8.09-7.99 (m, 1H), 7.99-7.89 (m, 1H), 7.45 (d, J=8.0 Hz, 2H), 7.35-7.22 (m, 2H), 7.16 (7.45 (d, J=8.8 Hz, 1H), 4.81-4.61 (m, 1H), 4.05-3.91 (m, 1H), 3.89 (s, 3H), 3.88-3.55 (m, 3H), 3.52-3.35 (m, 2H), 2.40-2.12 (m, 2H), 2.10-1.81 (m, 3H), 1.78-1.51 (m, 2H), 1.48-1.21 (m, 2H), 1.19-1.03 (m, 1H), 1.02-0.84 (m, 1H). LCMS (ES, m/z): 436 [M+H]⁺.

Compound 69

¹H-NMR (CD₃OD, 400 MHz) (ppm): 8.01-7.91 (m, 1H), 7.90-7.65 (m, 1H), 7.42 (d, J=8.0 Hz, 2H), 7.29 (d, J=8.0 Hz, 2H), 7.20 (d, J=8.8 Hz, 1H), 4.78-4.51 (m, 1H), 3.85 (s, 3H), 3.84-3.67 (m, 2H), 3.65-3.51 (m, 2H), 3.28-3.09 (m, 2H), 2.19-2.05 (m, 1H), 2.04-1.88 (m, 2H), 1.87-1.68 (m, 2H), 1.61-1.40 (m, 2H), 1.30-1.00 (m, 3H), 0.99-0.79 (m, 1H). LCMS (ES, m/z): 436 [M+H]⁺.

Method 11: Preparation of Compounds 164 and 165: 5-fluoro-4'-((S)-6-((R)-tetrahydrofuran-2-carbonyl)-6-azaspiro[2.5]octan-1-yl)-[1,1'-biphenyl]-3-carboxylic Acid and 5-fluoro-4'-((R)-6-((R)-tetrahydrofuran-2-carbonyl)-6-azaspiro[2.5]octan-1-yl)-[1,1'-biphenyl]-3-carboxylic Acid

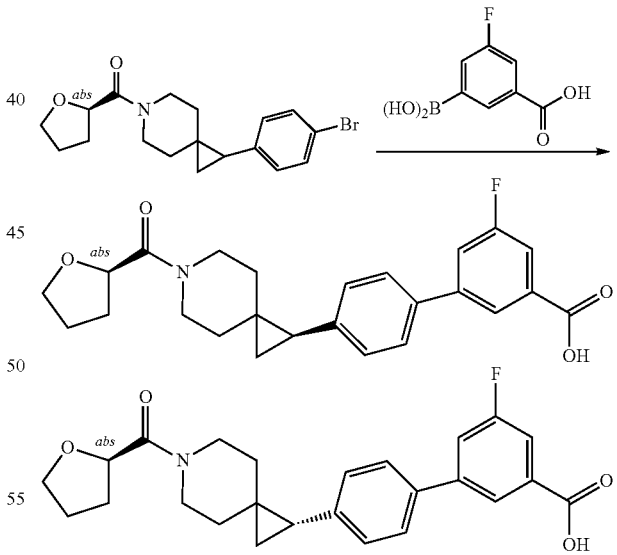

5-fluoro-4'-((S)-6-((R)-tetrahydrofuran-2-carbonyl)-6-azaspiro[2.5]octan-1-yl)-[1,1'-biphenyl]-3-carboxylic Acid and 5-fluoro-4'-((R)-6-((R)-tetrahydrofuran-2-carbonyl)-6-azaspiro[2.5]octan-1-yl)-[1,1'-biphenyl]-3-carboxylic Acid A mixture of (1-(4-bromophenyl)-6-azaspiro[2.5]octan-6-yl)((R)-tetrahydrofuran-2-yl)methanone (500 mg, 1.37 mmol), 3-(dihydroxyboranyl)-5-fluorobenzoic acid (379 mg, 2.06 mmol), potassium phosphate (583 mg, 2.75 mmol) and bis(di-tert-butyl(4-dimethylaminophenyl)phosphine)dichloropalladium (97.2 mg, 0.14 mmol) in 1,4-dioxane (15.00 mL) and water (3.00 mL) was stirred for 2 h at 80° C. under nitrogen atmosphere. The mixture was cooled to room temperature and was concentrated under reduced pressure. The crude product was purified by Prep-HPLC with water (containing 0.1% FA) and ACN (35% to 65% over 7 min). The product was separated by Chiral HPLC with the following conditions: Column: CHIRALPAK IC, 2×25 cm, 5 μm; mobile phase: Hexanes (containing 0.1% Formic acid) and 2-Propanol (hold 50% 2-Propanol in 16 min); Detector: uv 254 nm to afford the first eluting peak as Compound 164 (129 mg, 33%) as a white solid and the second eluting peak as Compound 165 (116.7 mg, 31%) as a white solid.

Compound 164

1H NMR (400 MHz, DMSO-d6) δ (ppm): 13.42 (br, 1H), 8.03 (s, 1H), 7.86-7.79 (m, 1H), 7.72-7.59 (m, 3H), 7.37 (d, J=8.0 Hz, 2H), 4.76-4.51 (m, 1H), 3.81-3.52 (m, 4H), 3.25-3.14 (m, 2H), 2.15-1.88 (m, 3H), 1.87-1.67 (m, 2H), 1.59-1.47 (m, 2H), 1.28-1.03 (m, 3H), 0.94-0.88 (m, 1H). LCMS (ES, m/z): 424[M+H]$^+$.

Compound 165

1H NMR (400 MHz, DMSO-d6) δ (ppm): 13.40 (br, 1H), 8.03 (s, 1H), 7.86-7.78 (m, 1H), 7.73-7.58 (m, 3H), 7.37 (d, J=8.0 Hz, 2H), 4.75-4.51 (m, 1H), 3.80-3.55 (m, 4H), 3.27-3.10 (m, 2H), 2.14-1.90 (m, 3H), 1.87-1.69 (m, 2H), 1.63-1.47 (m, 2H), 1.25-1.06 (m, 3H), 0.93-0.88 (m, 1H). LCMS (ES, m/z): 424 [M+H]$^+$.

Method 12: Preparation of Compounds 150 and 151: 4-methoxy-4'-((R)-6-((R)-tetrahydrofuran-2-carbonyl)-6-azaspiro[2.5]octan-1-yl)-[1,1'-biphenyl]-3-carboxylic Acid and 4-methoxy-4'-((S)-6-((R)-tetrahydrofuran-2-carbonyl)-6-azaspiro[2.5]octan-1-yl)-[1,1'-biphenyl]-3-carboxylic Acid 4-methoxy-4'-((S)-6-((R)-tetrahydrofuran-2-carbonyl)-6-azaspiro[2.5]octan-1-yl)-[1,1'-biphenyl]-3-carboxylic Acid and 4-methoxy-4'-((R)-6-((R)-tetrahydrofuran-2-carbonyl)-6-azaspiro[2.5]octan-1-yl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (800 mg, 1.95 mmol), 5-bromo-2-methoxybenzoic acid (447.7 mg, 1.95 mmol), bis(di-tert-butyl(4-dimethylaminophenyl)phosphine) dichloropalladium (137.81 mg, 0.195 mmol), potassium phosphate (825 mg, 3.90 mmol) and water (2 mL) in dioxane (10 mL) was stirred for 2 h at 70° C. under nitrogen atmosphere. The mixture was cooled to room temperature and concentrated under vacuum. The residue was purified by reverse phase column chromatography with water (0.1% FA)/ACN (5% to 55% over 30 min). The product was separated by Chiral HPLC with the following conditions: Column: CHIRALPAK IE, 2×25 cm, 5 μm; mobile phase: (Hexanes and DCM 3:1)(0.1% FA) and EtOH (hold 3% EtOH in 9 Min) to afford the first eluting peak as Compound 150 (150 mg, 15%) as a white solid and the second eluting peak as Compound 151 (150.2 mg, 13%) as a white solid.

Compound 150

$^1$H-NMR (CD$_3$OD, 400 MHz) δ (ppm): 8.08 (s, 1H), 7.82 (d, J=8.4 Hz, 1H), 7.54 (d, J=8.0 Hz, 2H), 7.37-7.32 (m, 2H), 7.23 (d, J=8.8 Hz, 1H), 4.81-4.62 (m, 1H), 3.97 (s, 3H), 3.95-3.60 (m, 4H), 3.52-3.35 (m, 1H), 3.33-3.19 (m, 1H), 2.30-2.11 (m, 2H), 2.10-1.82 (m, 3H), 1.78-1.52 (m, 2H), 1.46-1.22 (m, 2H), 1.18-1.14 (m, 1H), 1.00-0.95 (m, 1H). LCMS (ES, m/z): 436 [M+H]$^+$.

Compound 151

$^1$H-NMR (CD$_3$OD, 400 MHz) δ (ppm): 8.08 (s, 1H), 7.82 (d, J=8.4 Hz, 1H), 7.54 (d, J=8.4 Hz, 2H), 7.33 (d, J=8.4 Hz, 2H), 7.23 (d, J=8.8 Hz, 1H), 4.82-4.61 (m, 1H), 3.97 (s, 3H), 3.95-3.61 (m, 4H), 3.59-3.35 (m, 1H), 3.33-3.21 (m, 1H), 2.30-2.11 (m, 2H), 2.10-1.85 (m, 3H), 1.79-1.52 (m, 2H), 1.47-1.25 (m, 2H), 1.15-1.08 (m, 1H), 0.98-0.92 (m, 1H). LCMS (ES, m/z): 436 [M+H]$^+$.

Method 13: Preparation of Compounds 152 and 153: 2-methyl-4'-((S)-6-((R)-tetrahydrofuran-2-carbonyl)-6-azaspiro[2.5]octan-1-yl)-[1,1'-biphenyl]-3-carboxylic Acid and 2-methyl-4'-((R)-6-((R)-tetrahydrofuran-2-carbonyl)-6-azaspiro[2.5]octan-1-yl)-[1,1'-biphenyl]-3-carboxylic Acid

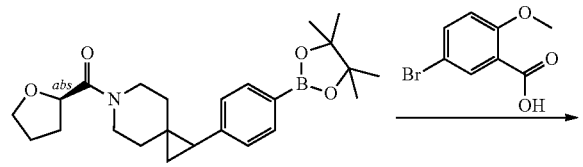

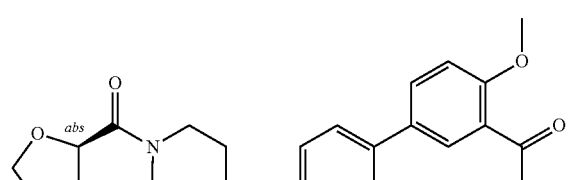

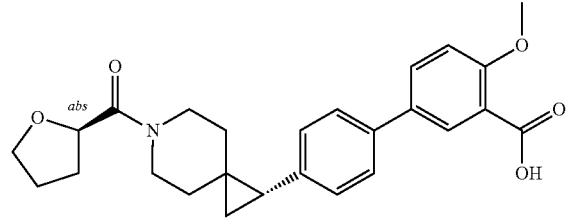

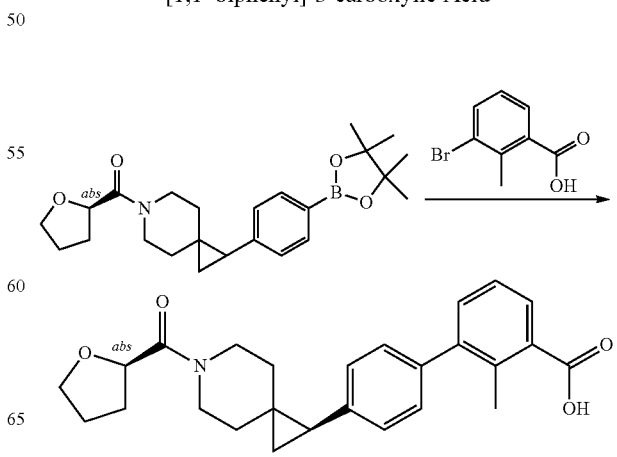

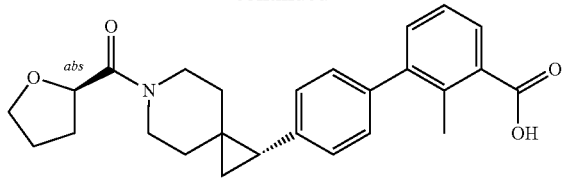

2-methyl-4'-((S)-6-((R)-tetrahydrofuran-2-carbonyl)-6-azaspiro[2.5]octan-1-yl)-[1,1'-biphenyl]-3-carboxylic Acid and 2-methyl-4'-((R)-6-((R)-tetrahydrofuran-2-carbonyl)-6-azaspiro[2.5]octan-1-yl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (800 mg, 1.95 mmol), 3-bromo-2-methylbenzoic acid (408.22 mg, 1.95 mmol), bis(di-tert-butyl(4-dimethylaminophenyl)phosphine) dichloropalladium (137.71 mg, 0.20 mmol), potassium phosphate (825.64 mg, 3.90 mmol) and water (2 mL) in dioxane (10 mL) was stirred for 2 h at 70° C. under nitrogen atmosphere. The mixture was cooled to room temperature and concentrated under vacuum. The residue was purified by reverse phase column chromatography with water (0.1% FA)/ACN (5% to 55% over 35 min). The product was separated by Chiral HPLC with the following conditions: Column: CHIRALPAK IE, 2×25 cm, 5 μm; mobile phase: Hexanes (0.1% FA) and EtOH (hold 50% EtOH in 23 min) to afford the first eluting peak as Compound 152 (141.9 mg, 18%) as a white solid and the second eluting peak as Compound 153 (141.5 mg, 18%) as a white solid.

Compound 152

$^1$H-NMR (CD$_3$OD, 400 MHz) δ (ppm): 7.81 (d, J=7.6 Hz, 1H), 7.35-7.31 (m, 4H), 7.31-7.21 (m, 2H), 4.91-4.68 (m, 1H), 3.97-3.73 (m, 4H), 3.46-3.32 (m, 2H), 2.40 (s, 3H), 2.18-2.09 (m, 2H), 2.07-1.83 (m, 3H), 1.78-1.54 (m, 2H), 1.45-1.25 (m, 2H), 1.18-1.11 (m, 1H), 0.10-0.95 (m, 1H). LCMS (ES, m/z): 420 [M+H]$^+$.

Compound 153

$^1$H-NMR (CD$_3$OD, 400 MHz) δ (ppm): 7.81 (d, J=7.2 Hz, 1H), 7.35-7.32 (m, 4H), 7.30-7.22 (m, 2H), 4.91-4.68 (m, 1H), 3.96-3.70 (m, 4H), 3.46-3.34 (m, 2H), 2.39 (s, 3H), 2.32-2.11 (m, 2H), 2.15-1.94 (m, 3H), 1.92-1.63 (m, 2H), 1.35-1.28 (m, 2H), 1.45-1.20 (m, 1H), 0.98-0.92 (m, 1H). LCMS (ES, m/z): 420 [M+H]$^+$.

Method 14: Preparation of Compounds 128 and 129: 7-(4-((S)-6-((R)-tetrahydrofuran-2-carbonyl)-6-azaspiro[2.5]octan-1-yl)phenyl)quinoline-4-carboxylic acid and (R)-7-(4-(6-(cyclopentanecarbonyl)-6-azaspiro[2.5]octan-1-yl)phenyl)quinoline-4-carboxylic Acid

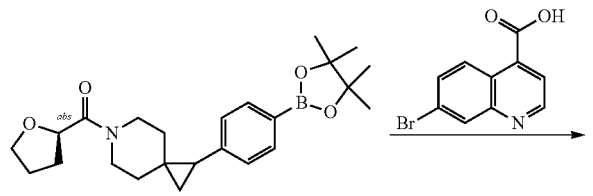

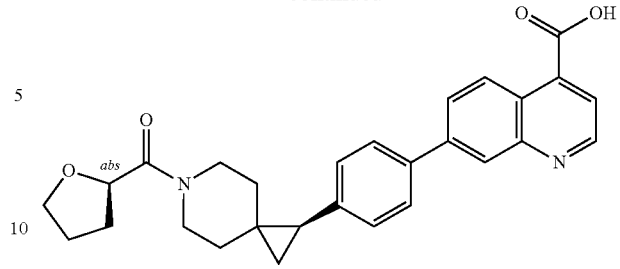

7-(4-((S)-6-((R)-tetrahydrofuran-2-carbonyl)-6-azaspiro[2.5]octan-1-yl)phenyl)quinoline-4-carboxylic acid and (R)-7-(4-(6-(cyclopentanecarbonyl)-6-azaspiro[2.5]octan-1-yl)phenyl)quinoline-4-carboxylic Acid A mixture of 7-bromoquinoline-4-carboxylic acid (300 mg, 1.14 mmol), ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (982 mg, 2.15 mmol), sodium carbonate (390 mg, 3.61 mmol), [1,1'-Bis(diphenylphosphino)ferrocene] dichloropalladium (180 mg, 0.24 mmol) in dioxane (15 mL) and water (3 mL) was stirred for 2 h at 100° C. under nitrogen atmosphere. The mixture was cooled to room temperature and concentrated under vacuum. The crude product was purified by reverse phase column chromatography with the following conditions: water (containing 10M NH$_4$HCO$_3$)/ACN (15% to 50% over 30 min). The product was purified by Chiral-Prep-HPLC with the following conditions: Column: CHIRAL ART Cellulose-SB, 2×25 cm, 5 μm; mobile phase: Hexanes (0.1% FA) and EtOH (hold 30% EtOH in 22 min); Detector: UV to afford the first eluting peak as Compound 128 as a white solid (72.7 mg, 26%) and the second eluting peak as Compound 129 as a white solid (90 mg, 33%)

Compound 128

$^1$H-NMR (CD$_3$OD, 400 MHz) δ (ppm): 9.00 (d, J=4.8 Hz, 1H), 8.90 (d, J=8.8 Hz, 1H), 8.32 (s, 1H), 8.07-8.03 (m, 1H), 7.99 (d, J=4.8 Hz, 1H), 7.78 (d, J=8.4 Hz, 2H), 7.42 (d, J=8.0 Hz, 2H), 4.85-4.67 (m, 1H), 4.01-3.66 (m, 4H), 3.64-3.25 (m, 2H), 2.31-2.18 (m, 2H), 2.16-1.81 (m, 3H), 1.64-1.61 (m, 2H), 1.35-1.30 (m, 2H), 1.18-1.16 (m, 1H), 1.10-0.97 (m, 1H). LCMS (ES, m/z): 457 [M+H]$^+$.

Compound 129

$^1$H-NMR (CD$_3$OD 400 MHz) δ (ppm): 8.95 (d, J=4.8 Hz, 1H), 8.79 (d, J=8.4 Hz, 1H), 8.29 (s, 1H), 7.99 (d, J=4.8 Hz, 1H), 7.87 (d, J=4.4 Hz, 1H), 7.76 (d, J=7.2 Hz, 2H), 7.42-7.39 (m, 2H), 4.83-4.64 (m, 1H), 4.08-3.61 (m, 4H), 3.67-3.20 (m, 2H), 2.28-2.11 (m, 2H), 2.10-1.82 (m, 3H), 1.80-1.53 (m, 2H), 1.48-1.25 (m, 2H), 1.21-1.13 (m, 1H), 1.02-0.94 (m, 1H). LCMS (ES, m/z): 457 [M+H]$^+$.
Method 15: Preparation of Compounds 156 and 157 6-(4-((S)-6-((R)-tetrahydrofuran-2-carbonyl)-6-azaspiro[2.5]octan-1-yl)phenyl)-1-naphthoic Acid and 6-(4-((R)-6-((R)-tetrahydrofuran-2-carbonyl)-6-azaspiro[2.5]octan-1-yl)phenyl)-1-naphthoic Acid
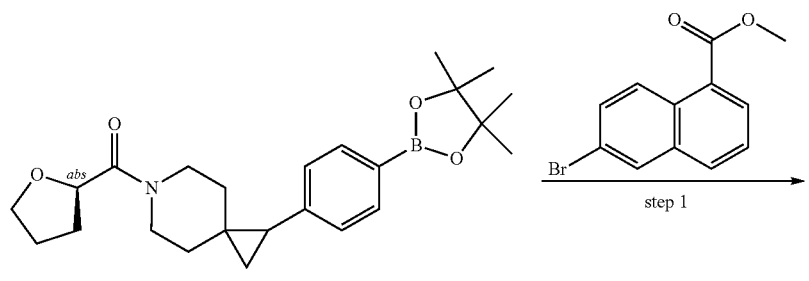
step 1
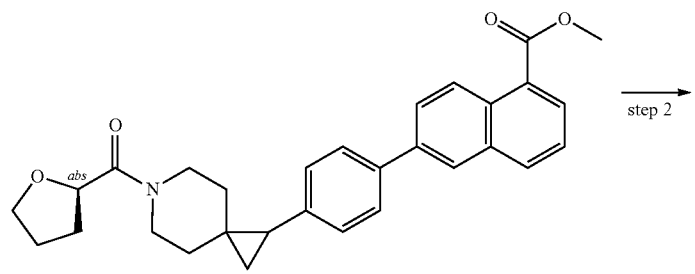
step 2
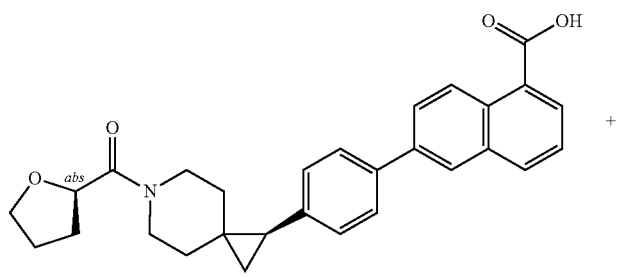
+
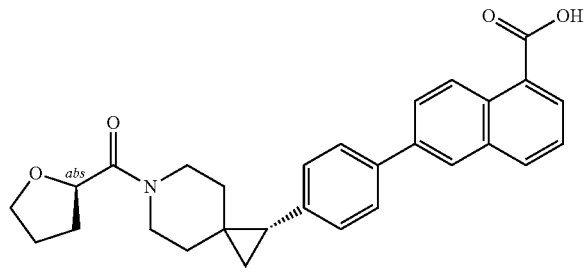

Step 1. methyl 6-(4-(6-((R)-tetrahydrofuran-2-carbonyl)-6-azaspiro[2.5]octan-1-yl)phenyl)-1-naphthoate A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (332 mg, 0.81 mmol), methyl 6-bromonaphthalene-1-carboxylate (1.06 g, 4.00 mmol), potassium phosphate (0.80 g, 3.75 mmol), bis(di-tert-butyl (4-dimethylaminophenyl)phosphine)dichloropalladium (172.1 mg, 0.25 mmol) in dioxane (20 mL) and water (4 mL) was stirred for 2 h at 70° C. under nitrogen atmosphere. The mixture was cooled to room temperature and concentrated under vacuum. The residue was purified by silica gel chromatography (eluting with 1:1 ethyl acetate/petroleum ether) to afford methyl 6-(4-(6-((R)-tetrahydrofuran-2-carbonyl)-6-azaspiro[2.5]octan-1-yl)phenyl)-1-naphthoate (194 mg, 49%) as a white solid. LCMS: (ES, m/z): 470 [M+H]$^+$.

Step 2 6-(4-((S)-6-((R)-tetrahydrofuran-2-carbonyl)-6-azaspiro[2.5]octan-1-yl)phenyl)-1-naphthoic Acid and 6-(4-((R)-6-((R)-tetrahydrofuran-2-carbonyl)-6-azaspiro[2.5]octan-1-yl)phenyl)-1-naphthoic Acid A mixture of methyl 6-(4-(6-((R)-tetrahydrofuran-2-carbonyl)-6-azaspiro[2.5]octan-1-yl)phenyl)-1-naphthoate (194.0 mg, 0.38 mmol) and lithium hydroxide (49.8 mg, 2.00 mmol) in tetrahydrofuran (10 mL) and water (5 mL) was stirred for 16 h at 25° C. The resulting mixture was concentrated under vacuum. The crude product was purified by reverse phase column chromatography with the following conditions: water (containing 10M NH$_4$HCO$_3$)/ACN (20% to 50% over 25 min). The product was separated by Chiral HPLC (Column: (R,R)Whelk-01, 21.1×250 mm, 5 μm; mobile phase: Hexanes (0.1% FA) and IPA (hold 50% IPA in 30 min); Detector: UV 254 nm to afford the first eluting peak as Compound 156 as a white solid (39.0 mg, 53%) and the second eluting peak as Compound 157 as a white solid (59.7 mg, 80%).

Compound 156

$^1$H-NMR (CD$_3$OD, 400 MHz) δ (ppm): 9.00 (d, J=8.0 Hz, 1H), 8.22-8.15 (m, 3H), 7.92 (d, J=9.2 Hz, 1H), 7.74 (d, J=8.0 Hz, 1H), 7.58 (t, J=7.6 Hz, 1H), 7.49-7.37 (m, 2H), 4.89-4.78 (m, 1H), 3.97-3.67 (m, 4H), 3.62-3.32 (m, 2H), 2.17-1.92 (m, 5H), 1.81-1.29 (m, 4H), 1.28-0.96 (m, 2H). LCMS (ES, m/z): 456 [M+H]$^+$.

Compound 157

$^1$H-NMR (CD$_3$OD, 400 MHz) δ (ppm): 9.00 (d, J=8.0 Hz, 1H), 8.22-8.15 (m, 3H), 7.92 (d, J=8.8 Hz, 1H), 7.74 (d, J=8.0 Hz, 1H), 7.58 (d, J=8.0 Hz, 1H), 7.55-7.38 (m, 2H), 4.85-4.68 (m, 1H), 3.97-3.74 (m, 4H), 3.69-3.32 (m, 2H), 2.23-1.92 (m, 5H), 1.92-1.29 (m, 4H), 1.28-0.98 (m, 2H). LCMS (ES, m/z): 456 [M+H]$^+$.

Method 16: Preparation of Compounds 74 and 75: 1-methyl-6-(4-((S)-6-((R)-tetrahydrofuran-2-carbonyl)-6-azaspiro[2.5]octan-1-yl)phenyl)-1H-indazole-3-carboxylic Acid and 1-methyl-6-(4-((R)-6-((R)-tetrahydrofuran-2-carbonyl)-6-azaspiro[2.5]octan-1-yl)phenyl)-1H-indazole-3-carboxylic Acid

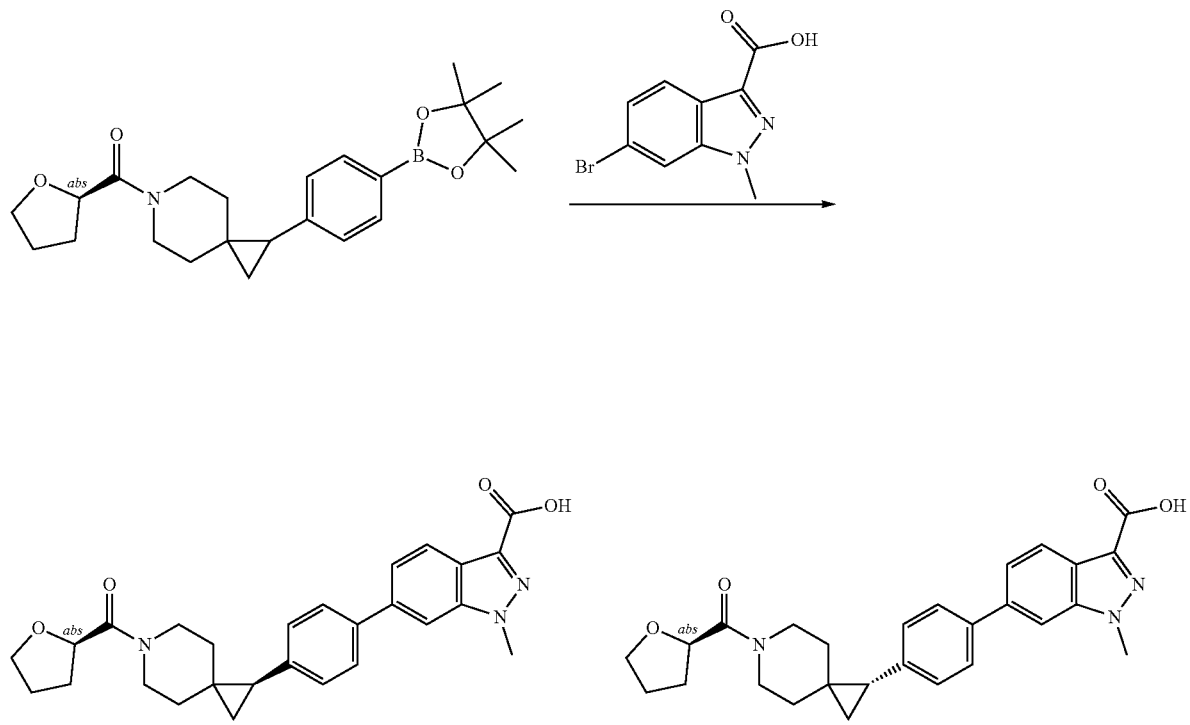

1-methyl-6-(4-((S)-6-((R)-tetrahydrofuran-2-carbonyl)-6-azaspiro[2.5]octan-1-yl)phenyl)-1H-indazole-3-carboxylic Acid and 1-methyl-6-(4-((R)-6-((R)-tetrahydrofuran-2-carbonyl)-6-azaspiro[2.5]octan-1-yl)phenyl)-1H-indazole-3-carboxylic Acid A solution of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (280 mg, 0.65 mmol), 6-bromo-1-methyl-1H-indazole-3-carboxylic acid (260 mg, 0.97 mmol), bis(di-tert-butyl(4-dimethylaminophenyl) phosphine)dichloropalladium (46 mg, 0.065 mmol) and potassium phosphate (411.3 mg, 1.94 mmol) in dioxane (12 mL) and water (3 mL) was stirred for 1 h at 70° C. under nitrogen atmosphere. The mixture was cooled to room temperature and concentrated under vacuum. The residue was purified by silica gel column chromatography, eluted with petroleum ether/ethyl acetate (1:1). The product was separated by Chiral HPLC with the following conditions (Column: CHIRALPAK IG, 2×25 cm, 5 μm; Mobile Phase A: MTBE (0.1% FA), Mobile Phase B: EtOH (hold 20% EtOH in 5.5 min); Detector: UV 254 nm to afford the first eluting peak as Compound 74 (74.5 mg, 24%) as a white solid and the second eluting peak as Compound 75 (74.8 mg, 24%) as a white solid.

Compound 74

$^1$H-NMR (CD$_3$OD, 400 MHz) δ (ppm): 8.33 (s, 1H), 7.78-7.75 (m, 1H), 7.71-7.69 (m, 1H), 7.61 (d, J=8.0 Hz, 2H), 7.33 (d, J=8.0 Hz, 2H), 4.94-4.63 (m, 1H), 4.19 (s, 3H), 3.95-3.92 (m, 1H), 3.88-3.80 (m, 1H), 3.74-3.65 (m, 2H), 3.41-3.34 (m, 1H), 3.33-3.25 (m, 1H), 2.15-2.11 (m, 2H), 1.99-1.87 (m, 3H), 1.60-1.51 (m, 2H), 1.35-1.28 (m, 2H), 1.21-1.11 (m, 1H), 0.96-0.91 (m, 1H). LCMS (ES, m/z): 460 [M+H]$^+$

Compound 75

$^1$H-NMR (CD$_3$OD, 400 MHz) δ (ppm): 8.33 (s, 1H), 7.79-7.72 (m, 2H), 7.64-7.62 (m, 2H), 7.50-7.25 (m, 2H), 4.89-4.66 (m, 1H), 4.21 (s, 3H), 3.99-3.61 (m, 4H), 3.53-3.35 (m, 2H), 2.24-1.80 (m, 5H), 1.79-1.51 (m, 2H), 1.48-1.17 (m, 2H), 1.15-0.85 (m, 2H). LCMS (ES, m/z): 460 [M+H]$^+$

Method 17: Preparation of Compounds 160 and 161: 5-methyl-4'-((S)-6-((R)-tetrahydrofuran-2-carbonyl)-6-azaspiro[2.5]octan-1-yl)-[1,1'-biphenyl]-3-carboxylic Acid and 5-methyl-4'-((R)-6-((R)-tetrahydrofuran-2-carbonyl)-6-azaspiro[2.5]octan-1-yl)-[1,1'-biphenyl]-3-carboxylic Acid

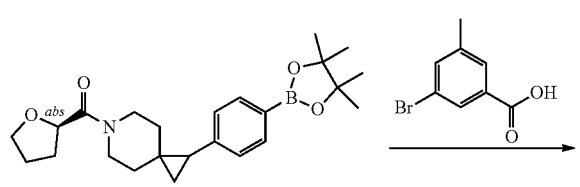

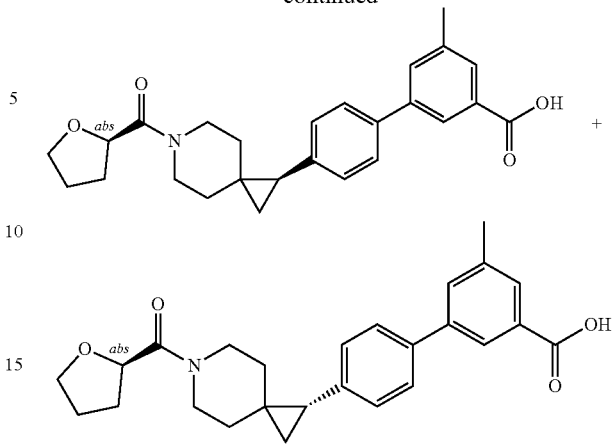

5-methyl-4'-((S)-6-((R)-tetrahydrofuran-2-carbonyl)-6-azaspiro[2.5]octan-1-yl)-[1,1'-biphenyl]-3-carboxylic Acid and 5-methyl-4'-((R)-6-((R)-tetrahydrofuran-2-carbonyl)-6-azaspiro[2.5]octan-1-yl)-[1,1'-biphenyl]-3-carboxylic Acid A solution of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (800 mg, 2.31 mmol), 3-bromo-5-methylbenzoic acid (360 mg, 1.59 mmol), bis(di-tert-butyl (4-dimethylaminophenyl) phosphine)dichloropalladium (113 mg, 0.16 mmol) and potassium phosphate (844 mg, 3.98 mmol) in dioxane (15 mL) and water (5 mL) was stirred for 1 h at 70° C. under nitrogen atmosphere. The mixture was cooled to room temperature and concentrated under vacuum. The residue was purified by reverse phase column chromatography with the following conditions: water (containing 0.1% FA)/ACN (0% to 40% over 20 min). The product was separated by Chiral HPLC with the following conditions: (Column: CHIRALPAK AS-H(03), 2×25 cm (5 μm); Mobile Phase A: CO$_2$, Mobile Phase B: MeOH (2 mM NH$_3$/MeOH) (10% to 50% in 2.0 min, hold 1.0 min at 50%) to afford the first eluting peak as Compound 160 (100 mg, 14%) as a white solid and the second eluting peak as Compound 161 (100 mg, 14%) as a white solid.

Compound 160

$^1$H-NMR (CD$_3$OD, 400 MHz) δ (ppm): 8.07 (s, 1H), 7.82 (s, 1H), 7.71-7.65 (m, 1H), 7.59 (d, J=8.0 Hz, 2H), 7.38-7.32 (m, 2H), 4.82-4.66 (m, 1H), 4.03-3.61 (m, 4H), 3.49-3.25 (m, 2H), 2.48 (s, 3H), 2.28-2.10 (m, 2H), 2.08-1.82 (m, 3H), 1.80-1.52 (m, 2H), 1.49-1.27 (m, 2H), 1.25-1.11 (m, 2H), 1.01-0.92 (m, 1H). LCMS (ES, m/z): 420 [M+H]$^+$

Compound 161

$^1$H-NMR (CD$_3$OD, 400 MHz) δ (ppm): 8.07 (s, 1H), 7.82 (s, 1H), 7.69-7.64 (m, 1H), 7.59 (d, J=8.0 Hz, 2H), 7.38-7.31 (m, 2H), 4.81-4.62 (m, 1H), 4.05-3.79 (m, 2H), 3.77-3.61 (m, 2H), 3.58-3.25 (m, 2H), 2.48 (s, 3H), 2.27-2.12 (m, 2H), 2.10-1.86 (m, 3H), 1.84-1.55 (m, 2H), 1.48-1.22 (m, 2H), 1.21-1.13 (m, 1H), 0.97-0.91 (m, 1H). LCMS (ES, m/z): 420 [M+H]$^+$ Method 18: Preparation of Compounds 88 and 89: 6-(4-((S)-6-((R)-tetrahydrofuran-2-carbonyl)-6-azaspiro[2.5]octan-1-yl)phenyl)-1H-indazole-3-carboxylic Acid and 6-(4-((R)-6-((R)-tetrahydrofuran-2-carbonyl)-6-azaspiro[2.5]octan-1-yl)phenyl)-1H-indazole-3-carboxylic Acid

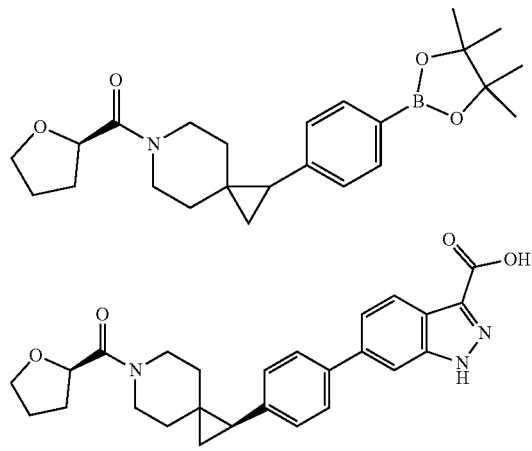
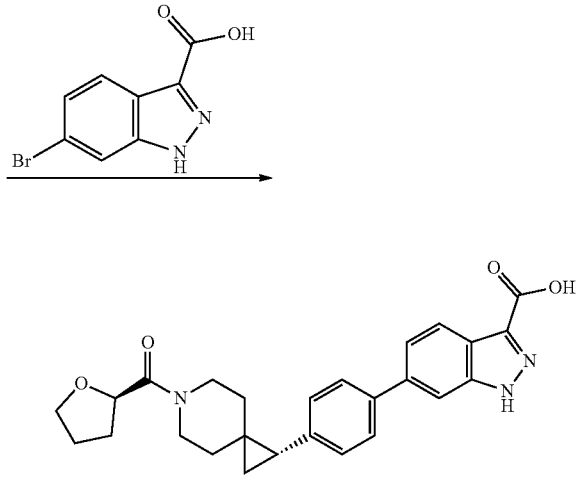

6-(4-((S)-6-((R)-tetrahydrofuran-2-carbonyl)-6-azaspiro[2.5]octan-1-yl)phenyl)-1H-indazole-3-carboxylic Acid and 6-(4-((R)-6-((R)-tetrahydrofuran-2-carbonyl)-6-azaspiro[2.5]octan-1-yl)phenyl)-1H-indazole-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (400 mg, 0.88 mmol), 6-bromo-1H-indazole-3-carboxylic acid (258 mg, 1.05 mmol), bis(di-tert-butyl(4-dimethylaminophenyl) phosphine) dichloropalladium (62 mg, 0.088 mmol), potassium phosphate (558 mg, 2.63 mmol) in dioxane (10 mL) and water (3 mL) was stirred overnight at 90° C. under nitrogen atmosphere. The resulting mixture was cooled to room temperature and concentrated under reduced pressure. The residue was purified by reverse phase chromatography with the following conditions: water (containing 0.05% TFA)/ACN (0% to 40% over 25 min). The product was purified by Chiral HPLC with the following conditions: Column: CHIRALPAK IG, 2×25 cm, 5 µm; mobile phase: Hex (0.1% FA) and EtOH (hold 50% EtOH in 10 min); Detector: UV254 nm to afford the first eluting peak as Compound 88 (11.4 mg, 3%) as an off-white solid and the second eluting peak as Compound 89 (20 mg, 5%) as an off-white solid.

Compound 88

$^1$H-NMR (CD$_3$OD, 400 MHz) δ (ppm): 8.22 (d, J=8.0 Hz, 1H), 7.80 (s, 1H), 7.66 (d, J=7.6 Hz, 2H), 7.61 (d, J=8.0 Hz, 1H), 7.42-7.34 (m, 2H), 4.81-4.62 (m, 1H), 4.01-3.91 (m, 1H), 3.90-3.74 (m, 2H), 3.72-3.61 (m, 1H), 3.53-3.39 (m, 2H), 2.30-2.10 (m, 2H), 2.09-1.81 (m, 3H), 1.80-1.52 (m, 2H), 1.49-1.24 (m, 2H), 1.23-1.09 (m, 1H), 1.02-0.91 (m, 1H). LCMS (ES, m/z): 446 [M+H]$^+$.

Compound 89

$^1$H-NMR (CD$_3$OD, 400 MHz) δ (ppm): 8.22 (d, J=8.0 Hz, 1H), 7.79 (s, 1H), 7.66 (d, J=8.0 Hz, 2H), 7.61 (d, J=8.8 Hz, 1H), 7.37 (d, J=8.0 Hz, 2H), 4.81-4.63 (m, 1H), 4.10-3.80 (m, 2H), 3.79-3.62 (m, 2H), 3.61-3.49 (m, 1H), 3.47-3.39 (m, 1H), 2.41-2.11 (m, 2H), 2.10-1.84 (m, 3H), 1.80-1.54 (m, 2H), 1.48-1.19 (m, 2H), 1.21-1.08 (m, 1H), 1.01-0.91 (m, 1H). LCMS (ES, m/z): 446 [M+H]$^+$.

Method 19: Preparation of Compounds 220 and 221: 6-fluoro-5-methyl-4'-((S)-6-((R)-tetrahydrofuran-2-carbonyl)-6-azaspiro[2.5]octan-1-yl)-[1,1'-biphenyl]-3-carboxylic Acid and 6-fluoro-5-methyl-4'-((R)-6-((R)-tetrahydrofuran-2-carbonyl)-6-azaspiro[2.5]octan-1-yl)-[1,1'-biphenyl]-3-carboxylic Acid

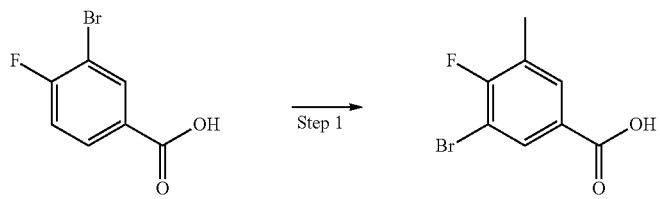

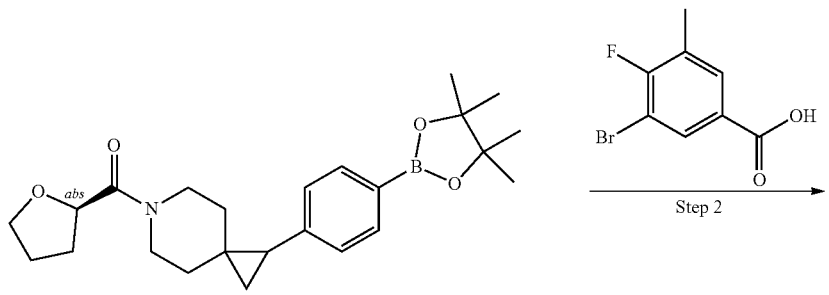

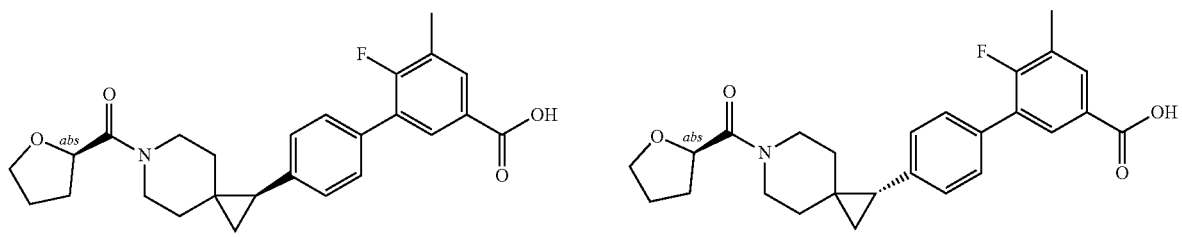

Step 1. 3-bromo-4-fluoro-5-methylbenzoic Acid

To a stirred solution of 2,2,6,6-tetramethylpiperidine (4.65 g, 32.9 mmol) in tetrahydrofuran (15 mL) were added n-butyllithium (2.11 g, 32.9 mmol) dropwise at −78° C. under nitrogen atmosphere. The mixture was stirred at −60° C. for 30 min. Then 3-bromo-4-fluorobenzoic acid (3.28 g, 14.98 mmol) and iodomethane (3.75 mL, 60.2 mmol) were added dropwise at −78° C. The resulting mixture was stirred overnight at room temperature. The reaction was quenched with saturated ammonium chloride (50 mL). The resulting mixture was extracted with ethyl acetate (2×50 mL). The combined organic layers were washed with brine (2×50 mL), dried over anhydrous sodium sulfate, filtered and concentrated under reduced pressure. The crude product was purified by Prep-HPLC with the following conditions: water (containing 0.1% FA) and ACN (5% to 50% over 30 min) to afford 3-bromo-4-fluoro-5-methylbenzoic acid (1.3 g, 34%) as a white solid. LCMS (ES, m/z): 232,234 [M+H]$^+$.

Step 2. 6-fluoro-5-methyl-4'-((S)-6-((R)-tetrahydrofuran-2-carbonyl)-6-azaspiro[2.5]octan-1-yl)-[1,1'-biphenyl]-3-carboxylic Acid and 6-fluoro-5-methyl-4'-((R)-6-((R)-tetrahydrofuran-2-carbonyl)-6-azaspiro[2.5]octan-1-yl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (514 mg, 1.25 mmol), 3-bromo-4-fluoro-5-methylbenzoic acid (349 mg, 1.50 mmol), bis(di-tert-butyl(4-dimethylaminophenyl) phosphine) dichloropalladium (88.5 mg, 0.125 mmol), potassium phosphate (530 mg, 2.50 mmol) in dioxane (10 mL) and water (3 mL) was stirred overnight at 90° C. under nitrogen atmosphere. The resulting mixture was cooled to room temperature and concentrated under reduced pressure. The residue was purified by reverse phase chromatography with the following conditions: water (containing 0.05% TFA) and ACN (0% to 45% over 35 min). The product was purified by Chiral HPLC with the following conditions: Column: CHIRALPAK IC, 2×25 cm, 5 μm; mobile phase: Hexanes (0.1% FA) and EtOH (hold 50% EtOH in 16 min); Detector: UV254 nm to afford the first eluting peak as Compound 220 (141.2 mg, 25%) and the second eluting peak as Compound 221 (150.5 mg, 27%) as a white solid.

Compound 220

$^1$H-NMR (CD$_3$OD, 400 MHz) δ (ppm): 8.10-7.69 (m, 2H), 7.65-7.15 (m, 4H), 4.85-4.55 (m, 1H), 4.00-3.55 (m, 4H), 3.54-3.34 (m, 2H), 2.39 (s, 3H), 2.38-1.80 (m, 5H), 1.78-1.47 (m, 2H), 1.46-1.19 (m, 2H), 1.18-0.80 (m, 2H). LCMS (ES, m/z): 438[M+H]$^+$

Compound 221

$^1$H-NMR (CD$_3$OD, 400 MHz) δ (ppm): 8.05-7.80 (m, 2H), 7.60-7.42 (m, 2H), 7.41-7.21 (m, 2H), 4.81-4.52 (m, 1H), 4.05-3.82 (m, 2H), 3.80-3.58 (m, 2H), 3.57-3.35 (m, 2H), 2.39 (s, 3H), 2.38-1.80 (m, 5H), 1.79-1.41 (m, 2H), 1.40-1.20 (m, 2H), 1.19-0.80 (m, 2H). LCMS (ES, m/z): 438 [M+H]$^+$.

Method 20: Preparation of Compounds 192 and 193: 4-(4-((S)-6-((R)-tetrahydrofuran-2-carbonyl)-6-azaspiro[2.5]octan-1-yl)phenyl)picolinic Acid and 4-(4-((R)-6-((R)-tetrahydrofuran-2-carbonyl)-6-azaspiro[2.5]octan-1-yl)phenyl)picolinic Acid

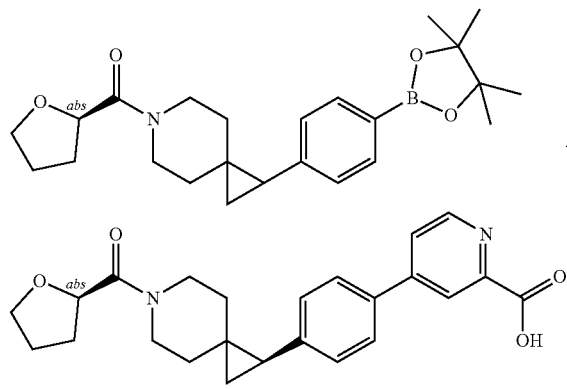
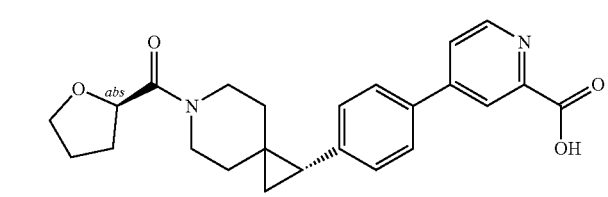

4-(4-((S)-6-((R)-tetrahydrofuran-2-carbonyl)-6-azaspiro[2.5]octan-1-yl)phenyl)picolinic Acid and 4-(4-((R)-6-((R)-tetrahydrofuran-2-carbonyl)-6-azaspiro[2.5]octan-1-yl)phenyl)picolinic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (700 mg, 1.70 mmol), 4-bromopyridine-2-carboxylic acid (344 mg, 1.70 mmol), bis(di-tert-butyl(4-dimethylaminophenyl) phosphine) dichloropalladium (120 mg, 0.17 mmol), potassium phosphate (722 mg, 3.70 mmol) and water (2 mL) in dioxane (10 mL) was stirred for 2 h at 90° C. under nitrogen atmosphere. The mixture was cooled to room temperature and concentrated under reduced pressure. The residue was purified by reverse flash chromatography with the following conditions: water (0.1% FA)/ACN (30% to 70% in 15 min). The product was purified by Chiral HPLC with the following conditions: Column: CHIRALPAK IG-3, 0.46×5 cm, 3 μm; mobile phase: MTBE (0.1% FA) and EtOH (hold 30% EtOH in 21 min); Detector: UV254 nm to afford the first eluting peak as Compound 192 (101.0 mg, 15%) as a white solid and the second eluting peak as Compound 193 (100.5 mg, 15%) as a white solid.

Compound 192

$^1$H-NMR (CD$_3$OD, 400 MHz) δ (ppm): 8.70 (d, J=5.2 Hz, 1H), 8.49 (s, 1H), 8.02-8.01 (m, 1H), 7.81 (d, J=8.0 Hz, 2H), 7.46 (d, J=8.4 Hz, 2H), 4.90-4.67 (m, 1H), 3.95-3.72 (m, 4H), 3.57-3.39 (m, 1H), 3.33-3.32 (m, 1H), 2.21-2.18 (m, 2H), 1.99-1.91 (m, 3H), 1.65-1.30 (m, 2H), 1.26-1.19 (m, 3H), 1.03-1.00 (m, 1H). LCMS (ES, m/z): 407 [M+H]$^+$.

Compound 193

$^1$H-NMR (CD$_3$OD, 400 MHz) δ (ppm): 8.70 (d, J=5.2 Hz, 1H), 8.50 (s, 1H), 8.02 (d, J=5.2 Hz, 1H), 7.81 (d, J=7.6 Hz, 2H), 7.48-7.45 (m, 2H), 4.90-4.78 (m, 1H), 3.97-3.93 (m, 1H), 3.88-3.81 (m, 2H), 3.71-3.57 (m, 1H), 3.45-3.42 (m, 1H), 3.30 (s, 1H), 2.22-2.17 (m, 2H), 2.14-1.85 (m, 3H), 1.81-1.35 (m, 3H), 1.30-1.26 (m, 1H), 1.25-1.19 (m, 1H), 1.03-0.98 (m, 1H). LCMS (ES, m/z): 407 [M+H]$^+$.

Method 21: Preparation of Compounds 198 and 199: ((S)-1-(2'-methyl-4'-(1H-tetrazol-5-yl)-[1,1'-biphenyl]-4-yl)-6-azaspiro[2.5]octan-6-yl)((R)-tetrahydrofuran-2-yl)methanone and ((R)-1-(2'-methyl-4'-(1H-tetrazol-5-yl)-[1,1'-biphenyl]-4-yl)-6-azaspiro[2.5]octan-6-yl)((R)-tetrahydrofuran-2-yl)methanone

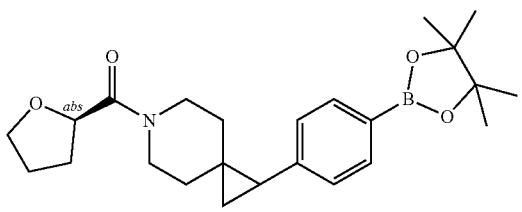
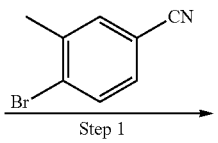

Step 1

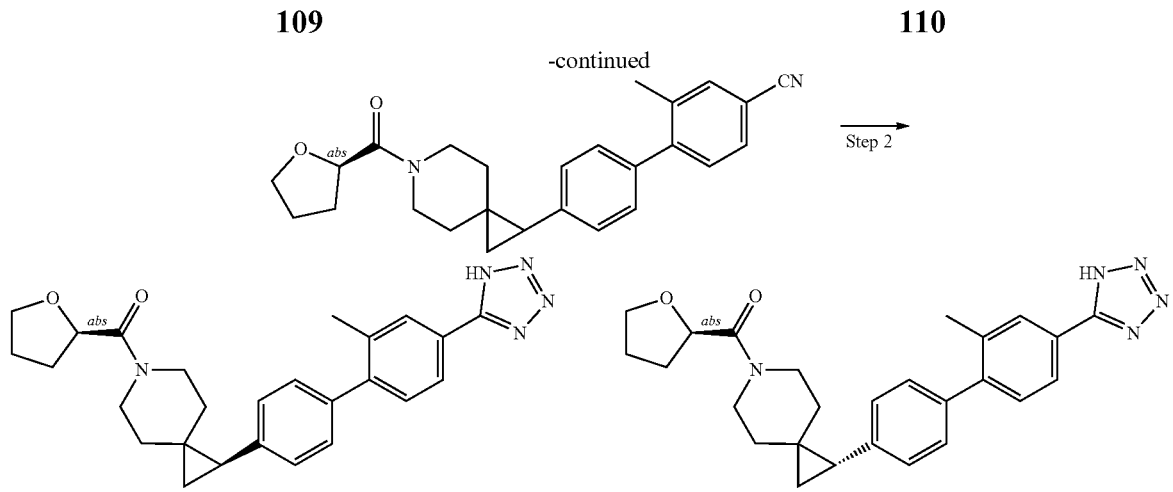

Step 1. 2-methyl-4'-(6-((R)-tetrahydrofuran-2-carbonyl)-6-azaspiro[2.5]octan-1-yl)-[1,1'-biphenyl]-4-carbonitrile A solution of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (826 mg, 2.01 mmol), 4-bromo-3-methylbenzonitrile (394 mg, 2.01 mmol), bis(di-tert-butyl(4-dimethylaminophenyl)phosphine)dichloropalladium (142 mg, 0.20 mmol), potassium phosphate (852 mg, 4.02 mmol) and water (2 mL) in dioxane (10 mL) was stirred for 2 h at 90° C. under nitrogen atmosphere. The mixture was cooled to room temperature and concentrated under vacuum. The residue was purified by silica gel column chromatography, eluted with petroleum ether/ethyl acetate (1:1) to afford 2-methyl-4'-(6-((R)-tetrahydrofuran-2-carbonyl)-6-azaspiro[2.5]octan-1-yl)-[1,1'-biphenyl]-4-carbonitrile (600 mg, 75%) as a yellow solid. LCMS (ES, m/z): 401 [M+H]⁺.

Step 2. ((S)-1-(2'-methyl-4'-(1H-tetrazol-5-yl)-[1,1'-biphenyl]-4-yl)-6-azaspiro[2.5]octan-6-yl)((R)-tetrahydrofuran-2-yl)methanone and ((R)-1-(2'-methyl-4'-(1H-tetrazol-5-yl)-[1,1'-biphenyl]-4-yl)-6-azaspiro[2.5]octan-6-yl)((R)-tetrahydrofuran-2-yl)methanone A mixture of 2-methyl-4'-(6-((R)-tetrahydrofuran-2-carbonyl)-6-azaspiro[2.5]octan-1-yl)-[1,1'-biphenyl]-4-carbonitrile (600 mg, 1.50 mmol), sodium azide (292 mg, 4.50 mmol), water (4 mL) and zinc iodide (717.30 mg, 2.25 mmol) in tert-butanol (8 mL) was stirred for 20 h at 90° C. under nitrogen atmosphere. The mixture was cooled to room temperature. The reaction was quenched with saturated sodium bicarbonate (30 mL). The solid was collected by filtration. The crude was purified by silica gel column chromatography, eluted with dichloromethane/methanol (10:1). The product was purified by Chiral HPLC with the following conditions: Column: CHIRALPAK IG, 20×250 mm, 5 μm; mobile phase: hexanes (0.1% FA) and EtOH (hold 30% EtOH in 22 min); Detector: UV254 nm to afford the first eluting peak as Compound 198 (57.7 mg, 8%) as a white solid and the second eluting peak as Compound 199 (85.2 mg, 12%) as a white solid.

Compound 198

¹H-NMR (CD₃OD, 400 MHz) δ (ppm): 7.97 (s, 1H), 7.90 (d, J=8.0 Hz, 1H), 7.42 (d, J=8.0 Hz, 1H), 7.42-7.35 (m, 4H), 4.84-4.65 (m, 1H), 4.10-3.98 (m, 1H), 3.92-3.80 (m, 1H), 3.80-3.60 (m, 2H), 3.55-3.45 (m, 2H), 2.38 (s, 3H), 2.31-2.10 (m, 2H), 2.10-1.88 (m, 3H), 1.85-1.57 (m, 2H), 1.45-1.21 (m, 2H), 1.19-1.11 (m, 1H), 0.99-0.90 (m, 1H). LCMS (ES, m/z): 444 [M+H]⁺.

Compound 199

¹H-NMR (CD₃OD, 400 MHz) δ (ppm): 7.97 (s, 1H), 7.90 (d, J=8.0 Hz, 1H), 7.42 (d, J=7.6 Hz, 1H), 7.39-7.24 (m, 4H), 4.85-4.61 (m, 1H), 4.08-3.60 (m, 4H), 3.55-3.33 (m, 2H), 2.38 (s, 3H), 2.30-2.10 (m, 2H), 2.10-1.85 (m, 3H), 1.80-1.53 (m, 2H), 1.45-1.22 (m, 2H), 1.19-1.12 (m, 1H), 1.01-0.92 (m, 1H). LCMS (ES, m/z): 444 [M+H]⁺.

Method 22: Preparation of Compounds 200 and 201 ((S)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone and ((R)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone

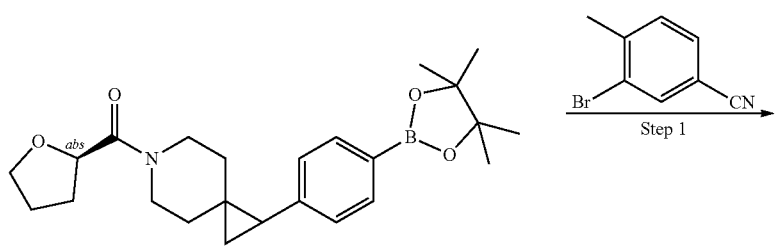

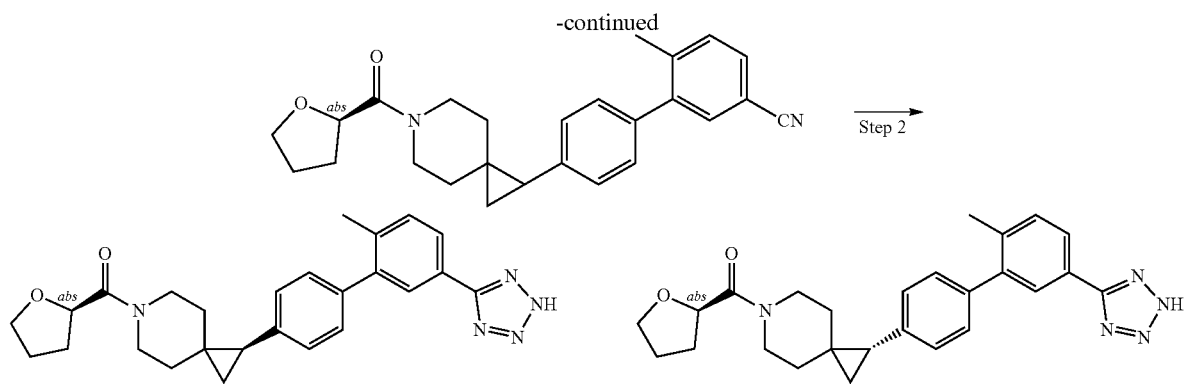

Step 1. 6-methyl-4'-(6-((R)-tetrahydrofuran-2-carbonyl)-6-azaspiro[2.5]octan-1-yl)-[1,1'-biphenyl]-3-carbonitrile A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (826 mg, 2.01 mmol), 3-bromo-4-methylbenzonitrile (394 mg, 2.09 mmol), bis (di-tert-butyl (4-dimethylaminophenyl) phosphine)dichloropalladium (142 mg, 0.20 mmol), potassium phosphate (852 mg, 4.02 mmol) and water (2 mL) in dioxane (10 mL) was stirred for 2 h at 90° C. under nitrogen atmosphere. The mixture was cooled to room temperature and concentrated under vacuum. The residue was purified by silica gel column chromatography, eluted with petroleum ether/ethyl acetate (1:1) to afford 6-methyl-4'-(6-((R)-tetrahydrofuran-2-carbonyl)-6-azaspiro[2.5]octan-1-yl)-[1,1'-biphenyl]-3-carbonitrile (636 mg, 80%) as a yellow solid. LCMS (ES, m/z): 401 [M+H]⁺.

Step 2. ((S)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone and ((R)-1-(2'-methyl-5'-(2H-tetrazol-5-yl)-[1,1'-biphenyl]-4-yl)-6-azaspiro[2.5]octan-6-yl)((R)-tetrahydrofuran-2-yl)methanone A mixture of 6-methyl-4'-(6-((R)-tetrahydrofuran-2-carbonyl)-6-azaspiro[2.5]octan-1-yl)-[1,1'-biphenyl]-3-carbonitrile (636 mg, 1.59 mmol), sodium azide (309 mg, 4.76 mmol), water (4 mL) and zinc iodide (760 mg, 2.38 mmol) in tert-butanol (8 mL) was stirred for 20 h at 90° C. under nitrogen atmosphere. The mixture was cooled to room temperature. The reaction was quenched with saturated sodium bicarbonate (30 mL). The solid was collected by filtration. The crude was purified by silica gel column chromatography, eluted with dichloromethane/methanol (10:1). The product was purified by Chiral HPLC with the following conditions: Column: CHIRALPAK AS-3, 3×100 mm, 3 um; mobile phase: MeOH (20 mM NH3) (10% to 50% in 4.0 min, hold 2.0 min at 50%); Detector: UV254 nm to afford the first eluting peak as Compound 200 (101.0 mg, 14%) as a white solid and the second eluting peak as Compound 201 (95.5 mg, 14%) as a white solid.

Compound 200

$^1$H-NMR (CD$_3$OD, 400 MHz) δ (ppm): 7.98-7.81 (m, 2H), 7.50 (d, J=7.6 Hz, 1H), 7.43-7.19 (m, 4H), 4.90-4.74 (m, 1H), 3.98-3.74 (s, 4H), 3.46 (s, 2H), 2.35 (s, 3H), 2.24-1.83 (m, 5H), 1.78-1.52 (m, 2H), 1.47-1.21 (m, 2H), 1.18-1.12 (m, 1H), 1.02-0.95 (m, 1H). LCMS (ES, n/z): 444 [M+H]⁺.

Compound 201

$^1$H-NMR (CD$_3$OD, 400 MHz) δ (ppm): 7.85-7.83 (m, 2H), 7.50 (d, J=8.0 Hz, 1H), 7.38-7.27 (m, 4H), 4.90-4.69 (m, 1H), 4.03-3.64 (m, 4H), 3.43-3.32 (m, 2H), 2.35 (s, 3H), 2.18-2.00 (m, 2H), 1.99-1.93 (m, 3H), 1.80-1.47 (m, 2H), 1.47-1.21 (m, 2H), 1.17-1.14 (m, 1H), 1.01-0.94 (m, 1H). LCMS (ES, m/z): 444 [M+H]⁺.

Method 23: Preparation of Compounds 84 and 85: 7-(4-((S)-6-((R)-tetrahydrofuran-2-carbonyl)-6-azaspiro[2.5]octan-1-yl)phenyl)quinoline-3-carboxylic Acid and 7-(4-((R)-6-((R)-tetrahydrofuran-2-carbonyl)-6-azaspiro[2.5]octan-1-yl)phenyl)quinoline-3-carboxylic Acid

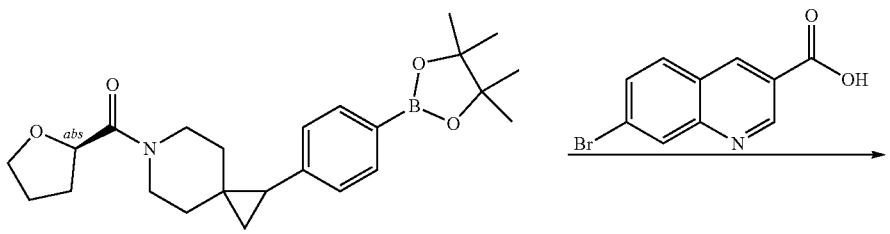

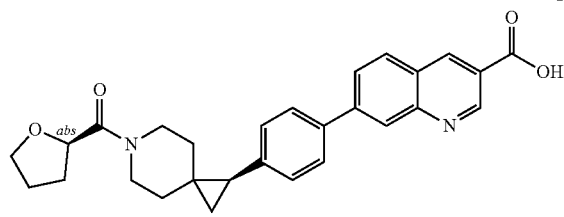
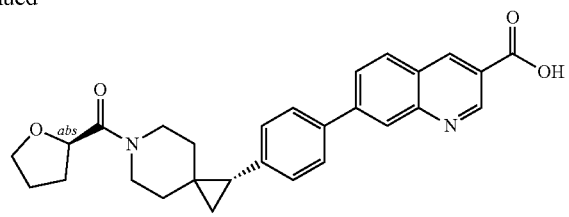

7-(4-((S)-6-((R)-tetrahydrofuran-2-carbonyl)-6-azaspiro[2.5]octan-1-yl)phenyl)quinoline-3-carboxylic Acid and 7-(4-((R)-6-((R)-tetrahydrofuran-2-carbonyl)-6-azaspiro[2.5]octan-1-yl)phenyl)quinoline-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (500 mg, 1.22 mmol) and 7-bromoquinoline-3-carboxylic acid (306 mg, 1.22 mmol), bis(di-tert-butyl(4-dimethylaminophenyl) phosphine) dichloropalladium (86 mg, 0.12 mmol), potassium phosphate (516 mg, 2.43 mmol) and water (3 mL) in dioxane (15 mL) was stirred for 2 h at 90° C. under nitrogen atmosphere. The mixture was cooled to room temperature and concentrated under reduced pressure. The residue was purified by reverse flash chromatography with the following conditions: water (0.1% FA)/ACN (30% to 60% in 25 min). The product was purified by Chiral HPLC with the following conditions: Column: CHIRALPAK IG, 2×25 cm, 5 μm; mobile phase: MTBE (0.1% FA), IPA and DCM (hold 30% DCM in 20 min); Detector: UV254 nm to afford the first eluting peak as Compound 84 (125.7 mg, 22%) as a yellow solid and the second eluting peak as Compound 85 (144.4 mg, 26%) as a yellow solid.

Compound 84

$^1$H-NMR (DMSO-$d_6$, 400 MHz) δ (ppm): 9.35 (s, 1H), 8.93 (s, 1H), 8.32 (s, 1H), 8.24 (d, J=8.4 Hz, 1H), 8.04 (d, J=8.4 Hz, 1H), 7.82 (d, J=8.0 Hz, 2H), 7.41 (d, J=8.0 Hz, 2H), 4.74-4.52 (m, 1H), 3.83-3.52 (m, 2H), 3.47-3.05 (m, 3H), 2.17-2.08 (m, 1H), 2.08-1.87 (m, 2H), 1.85-1.72 (m, 2H), 1.64-1.46 (m, 2H), 1.32-1.21 (m, 1H), 1.20-1.05 (m, 2H), 1.04 (d, J=6.0 Hz, 1H), 0.96-0.87 (m, 1H). LCMS (ES, m/z): 457 [M+H]$^+$.

Compound 85

$^1$H-NMR (DMSO-$d_6$, 400 MHz) δ (ppm): 9.34 (s, 1H), 8.73 (s, 1H), 8.26 (s, 1H), 8.13 (d, J=8.4 Hz, 1H), 7.95 (d, J=8.8 Hz, 1H), 7.80 (d, J=8.0 Hz, 2H), 7.40 (d, J=8.4 Hz, 2H), 4.73-4.55 (m, 1H), 3.82-3.62 (m, 3H), 3.62-3.56 (m, 2H), 3.26-3.13 (m, 1H), 2.16-2.11 (m, 1H), 2.09-1.92 (m, 2H), 1.88-1.70 (m, 2H), 1.65-1.48 (m, 2H), 1.32-1.07 (m, 3H), 0.95-0.89 (m, 1H). LCMS (ES, m/z): 457 [M+H]$^+$.

Method 24: Preparation of Compounds 170 and 171: 5-chloro-6-methoxy-4'-((R)-6-((R)-tetrahydrofuran-2-carbonyl)-6-azaspiro[2.5]octan-1-yl)-[1,1'-biphenyl]-3-carboxylic Acid and 5-chloro-6-methoxy-4'-((S)-6-((R)-tetrahydrofuran-2-carbonyl)-6-azaspiro[2.5]octan-1-yl)-[1,1'-biphenyl]-3-carboxylic Acid

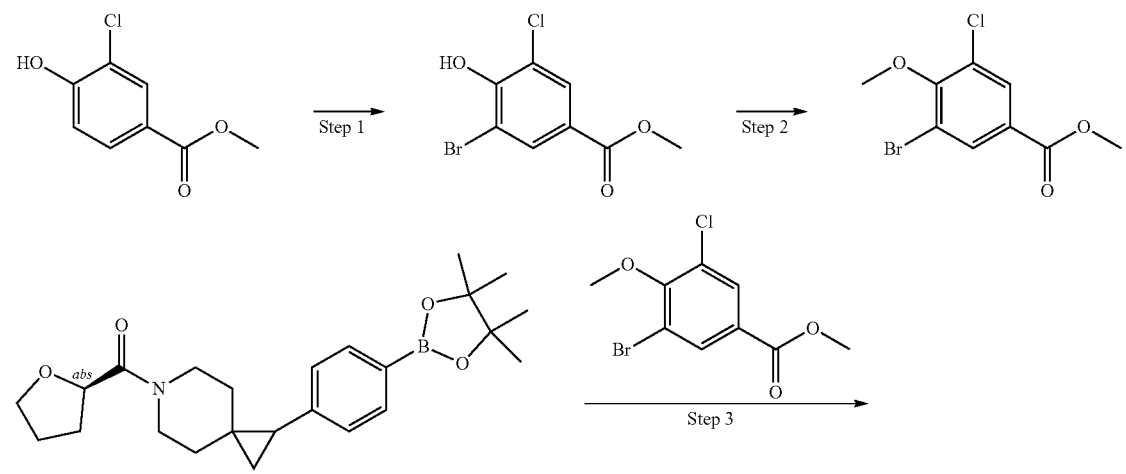

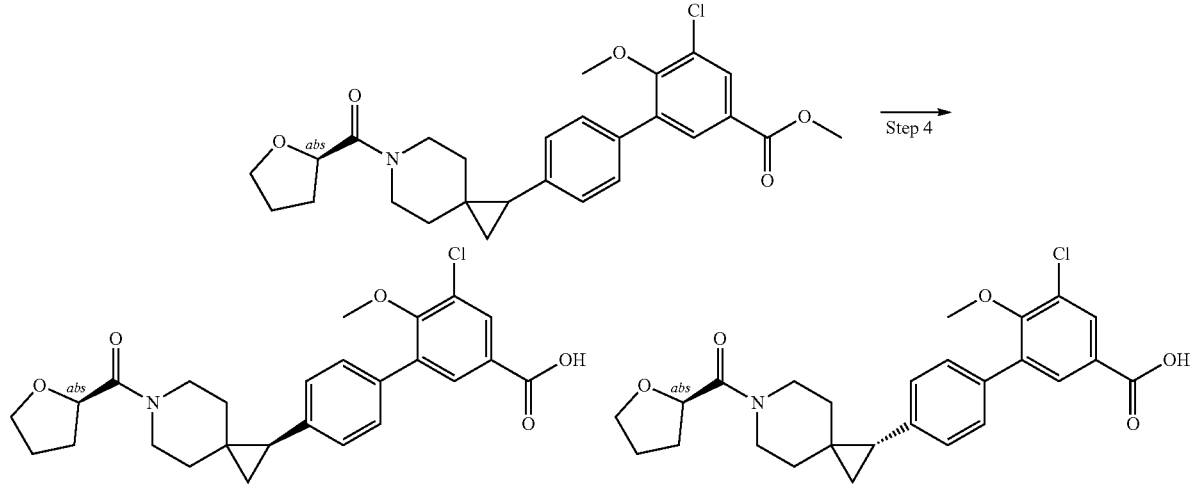

Step 1. methyl 3-bromo-5-chloro-4-hydroxybenzoate

To a stirred solution of methyl 3-chloro-4-hydroxybenzoate (5.25 g, 28.2 mmol) in acetic acid glacial (20 mL) and dichloromethane (20 mL) was added bromine (1.6 mL, 31.27 mmol) dropwise at 0° C. The resulting mixture was stirred overnight at room temperature. The reaction was quenched with water (100 mL). The resulting mixture was extracted with dichloromethane (3×100 mL). The combined organic layers were washed with brine (100 mL), dried over anhydrous sodium sulfate, filtered and concentrated under reduced pressure. The crude was purified by silica gel column chromatography, eluted with petroleum ether/ethyl acetate (2:1) to afford methyl 3-bromo-5-chloro-4-hydroxybenzoate (7.2 g, 87%) as a yellow oil. LCMS (ES, m/z): 265,267 [M+H]$^+$.

Step 2. methyl 3-bromo-5-chloro-4-methoxybenzoate

A mixture of methyl 3-bromo-5-chloro-4-hydroxy benzoate (6.7 g, 25.2 mmol), potassium carbonate (10.5 g, 75.7 mmol), iodomethane (2.4 mL, 16.6 mmol) in N,N-Dimethylformamide (30 mL) was stirred for 2 h at 60° C. under nitrogen atmosphere. The reaction was cooled to room temperature and quenched by water (100 mL). The mixture was extracted with ethyl acetate (3×100 mL). The combined organic layers were washed with brine (3×100 mL), dried over anhydrous sodium sulfate, filtered and concentrated under reduced pressure. The crude was purified by silica gel column chromatography, eluted with petroleum ether/ethyl acetate (4:1) to afford methyl 3-bromo-5-chloro-4-methoxybenzoate (7 g, 89%) as a yellow oil. LCMS (ES, m/z): 279,281 [M+H]$^+$.

Step 3 methyl 5-chloro-6-methoxy-4'-(6-((R)-tetrahydrofuran-2-carbonyl)-6-azaspiro[2.5]octan-1-yl)-[1,1'-biphenyl]-3-carboxylate A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (514 mg, 1.25 mmol), methyl 3-bromo-5-chloro-4-methoxy benzoate (419 mg, 1.50 mmol), bis(di-tert-butyl(4-dimethylaminophenyl)phosphine)dichloropalladium (88.5 mg, 0.125 mmol) and potassium phosphate (530 mg, 2.50 mmol) in dioxane (10 mL) and water (3 mL) was stirred for 2 h at 90° C. under nitrogen atmosphere. The resulting mixture was cooled to room temperature and concentrated under vacuum. The residue was purified by silica gel column chromatography, eluted with petroleum ether/ethyl acetate (5:1) to afford methyl methyl 5-chloro-6-methoxy-4'-(6-((R)-tetrahydrofuran-2-carbonyl)-6-azaspiro[2.5]octan-1-yl)-[1,1'-biphenyl]-3-carboxylate (450 mg, 67%) as a yellow oil. LCMS (ES, m/z): 484 [M+H]$^+$

Step 4. 5-chloro-6-methoxy-4'-((R)-6-((R)-tetrahydrofuran-2-carbonyl)-6-azaspiro[2.5]octan-1-yl)-[1,1'-biphenyl]-3-carboxylic Acid and 5-chloro-6-methoxy-4'-((S)-6-((R)-tetrahydrofuran-2-carbonyl)-6-azaspiro[2.5]octan-1-yl)-[1,1'-biphenyl]-3-carboxylic Acid A mixture of methyl 5-chloro-6-methoxy-4'-(6-((R)-tetrahydrofuran-2-carbonyl)-6-azaspiro[2.5]octan-1-yl)-[1,1'-biphenyl]-3-carboxylate (450 mg, 0.93 mmol), lithium hydroxide (89 mg, 3.72 mmol), water (2 mL) and methanol (2 mL) in tetrahydrofuran (6 mL) was stirred for 2 h at room temperature. The mixture was acidified to pH 6 with hydrochloric (1M). The mixture was extracted with ethyl acetate (3×30 mL). The organic layers were combined, dried over sodium sulfate, filtered and concentrated under vacuum. The crude was purified by reverse phase column chromatography with water (containing 10 mmol/L NH$_4$HCO$_3$) and ACN (20% to 65% over 30 min). The product was separated by Chiral HPLC with the following conditions: Column: CHIRAL ART Cellulose-SB S—5 μm, 2×25 cm, 5 μm; mobile phase: Hexanes (0.1% FA) and EtOH (hold 30% EtOH in 11 min); Detector: UV254 nm to afford the first eluting peak as Compound 170 (140.3 mg, 31%) and the second eluting peak as Compound 171 (122.6 mg, 28%) as a white solid.

Compound 170

$^1$H-NMR (CD$_3$OD, 400 MHz) δ (ppm): 8.10-7.96 (m, 1H), 7.95-7.68 (m, 1H), 7.51 (d, J=8.0 Hz, 2H), 7.40-7.19 (m, 2H), 4.81-4.53 (m, 1H), 4.10-3.60 (m, 4H), 3.58-3.49 (m, 3H), 3.40-3.35 (m, 2H), 2.31-2.10 (m, 2H), 2.05-1.83

(m, 3H), 1.78-1.51 (m, 2H), 1.41-1.19 (m, 2H), 1.18-1.03 (m, 1H), 1.02-0.82 (m, 1H). LCMS (ES, m/z): 470 [M+H]$^+$.

Compound 171

$^1$HNMR (CD$_3$OD, 400 MHz) δ (ppm): 8.10-8.01 (m, 1H), 8.00-7.88 (m, 1H), 7.51 (d, J=8.4 Hz, 2H), 7.48-7.25 (m, 2H), 4.80-4.62 (m, 1H), 4.02-3.60 (m, 4H), 3.58-3.52 (m, 3H), 3.50-3.39 (m, 2H), 2.32-2.10 (m, 2H), 2.05-1.85 (m, 3H), 1.78-1.52 (m, 2H), 1.50-1.21 (m, 2H), 1.20-1.11 (m, 1H), 1.08-0.90 (m, 1H). LCMS (ES, m/z): 470 [M+H]$^+$.

Method 25: Preparation of Compounds 172 and 173 5-fluoro-6-methoxy-4'-((S)-6-((R)-tetrahydrofuran-2-carbonyl)-6-azaspiro[2.5]octan-1-yl)-[1,1'-biphenyl]-3-carboxylic Acid and 5-fluoro-6-methoxy-4'-((R)-6-((R)-tetrahydrofuran-2-carbonyl)-6-azaspiro[2.5]octan-1-yl)-[1,1'-biphenyl]-3-carboxylic Acid quenched with water (100 mL). The resulting mixture was extracted with dichloromethane (3×100 mL). The combined organic layers were washed with brine (100 mL), dried over anhydrous sodium sulfate, filtered and concentrated under reduced pressure. The crude was purified by silica gel column chromatography eluting with petroleum ether/ethyl acetate (2:1) to afford methyl 3-bromo-5-fluoro-4-hydroxybenzoate (3.7 g, 90%) as a yellow oil. LCMS (ES, m/z): 249,251 [M+H]$^+$ Step 2. methyl 3-bromo-5-fluoro-4-methoxybenzoate A mixture of methyl 3-bromo-5-fluoro-4-hydroxy benzoate (3.7 g, 14.86 mmol), potassium carbonate (6.2 g, 44.57 mmol), iodomethane (3.2 g, 22.26 mmol,) in N,N-Dimethylformamide (25 mL) was stirred for 2 h at 60° C. under nitrogen atmosphere. The reaction was cooled to room temperature and quenched by water (100 mL). The mixture was extracted with ethyl acetate (3×100 mL). The combined

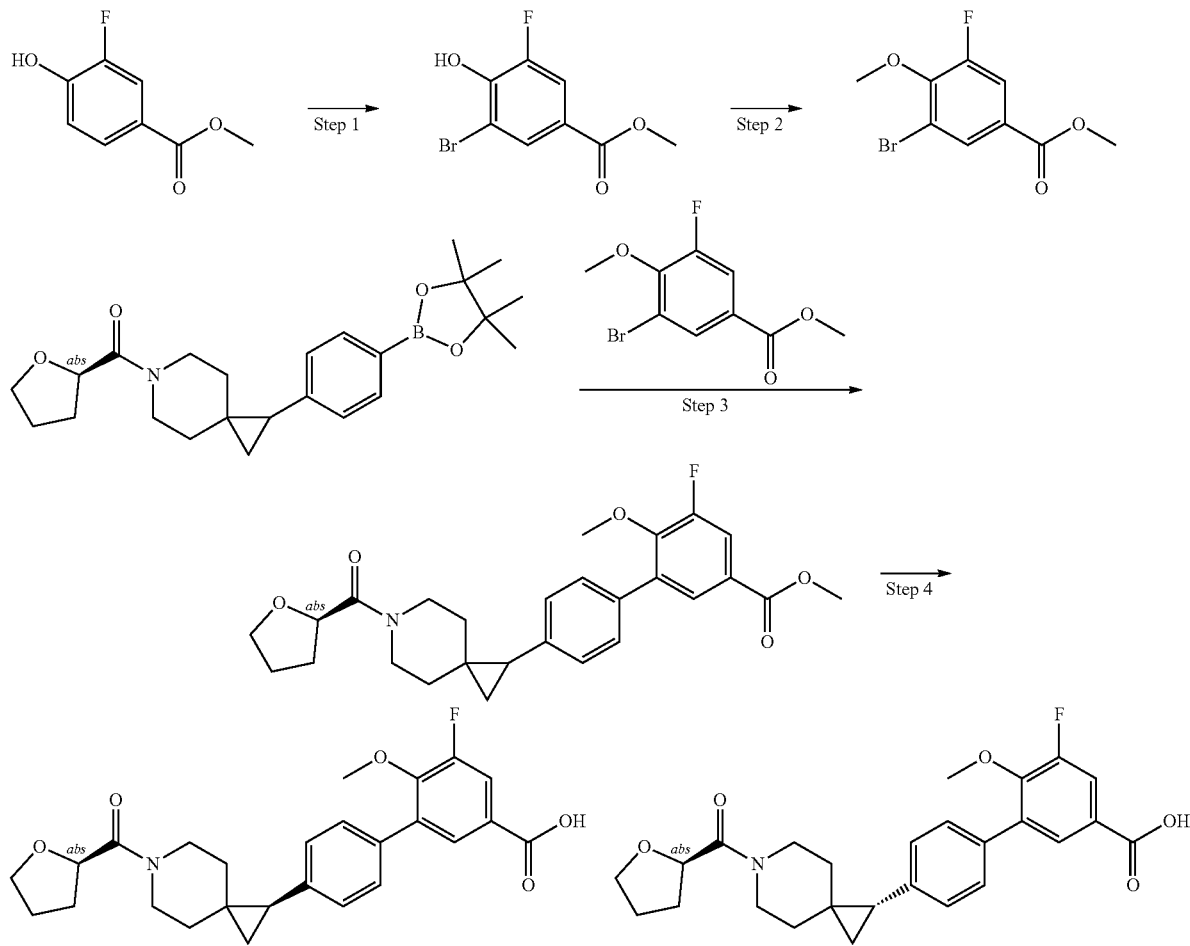

Step 1. methyl 3-bromo-5-fluoro-4-hydroxybenzoate

To a stirred solution of methyl 3-fluoro-4-hydroxybenzoate (2.4 g, 14.11 mmol) in glacial acetic acid (20 mL) and dichloromethane (10 mL) was added bromine (0.8 mL, 15.61 mmol) dropwise at 0° C. The resulting mixture was stirred overnight at room temperature. The reaction was organic layers were washed with brine (3×100 mL), dried over anhydrous sodium sulfate, filtered and concentrated under reduced pressure. The crude was purified by silica gel column chromatography, eluted with petroleum ether/ethyl acetate (4:1) to afford methyl 3-bromo-5-chloro-4-methoxybenzoate (2.7 g, 59%) as a yellow oil. LCMS (ES, m/z): 263, 265 [M+H]$^+$.

Step 3. methyl 5-fluoro-6-methoxy-4'-(6-((R)-tetra-hydrofuran-2-carbonyl)-6-azaspiro[2.5]octan-1-yl)-[1,1'-biphenyl]-3-carboxylate A mixture of 6((R)-tetrahydrofuran-2-yl)(1-(4-(4,4,5,5-tetramethyl-1,3,2-dioxaborolan-2-yl)phenyl)-6-azaspiro [2.5]octan-6-yl)methanone (720 mg, 1.75 mmol), methyl 3-bromo-5-fluoro-4-methoxy benzoate (553 mg, 2.10 mmol), bis(di-tert-butyl(4-dimethylaminophenyl)phosphine)dichloropalladium (124 mg, 0.18 mmol) and potassium phosphate (743 mg, 3.50 mmol) in dioxane (15 mL) and water (5 mL) was stirred for 2 h at 90° C. under nitrogen atmosphere. The resulting mixture was cooled to room temperature and concentrated under vacuum. The residue was purified by silica gel column chromatography, eluted with petroleum ether/ethyl acetate (3:1) to afford methyl 5-fluoro-6-methoxy-4'-(6-((R)-tetrahydrofuran-2-carbonyl)-6-azaspiro[2.5]octan-1-yl)-[1,1'-biphenyl]-3-carboxylate (580 mg, 64%) as a yellow oil. LCMS (ES, m/z): 468 [M+H]+.

Step 4. 5-fluoro-6-methoxy-4'-((S)-6-((R)-tetrahydrofuran-2-carbonyl)-6-azaspiro[2.5]octan-1-yl)-[1, 1'-biphenyl]-3-carboxylic Acid and 5-fluoro-6-methoxy-4'-((R)-6-((R)-tetrahydrofuran-2-carbonyl)-6-azaspiro[2.5]octan-1-yl)-[1,1'-biphenyl]-3-carboxylic Acid A mixture of methyl 5-fluoro-6-methoxy-4'-(6-((R)-tetrahydrofuran-2-carbonyl)-6-azaspiro[2.5]octan-1-yl)-[1,1'-biphenyl]-3-carboxylate (580 mg, 1.24 mmol), lithium hydroxide (119 mg, 4.96 mmol), water (2 mL) and methanol (2 mL) in tetrahydrofuran (6 mL) was stirred for 2 h at room temperature. The mixture was acidified to pH 6 with hydrochloric (1M). The mixture was extracted with ethyl acetate (3×30 mL). The organic layers were combined, dried over sodium sulfate, filtered and concentrated under vacuum. The crude was purified by reverse phase column chromatography with water (containing 10 mmol/L NH4HCO3) and ACN (20% to 65% over 35 min). The product was separated by Chiral HPLC with the following conditions: Column: CHIRALPAK IG, 20×250 mm, 5 μm; mobile phase: hexanes (0.1% FA) and EtOH (hold 50% EtOH in 16 min); Detector: UV254 nm to afford the first eluting peak as Compound 172 (103.8 mg, 18%) and the second eluting peak as Compound 173 (106.9 mg, 19%) as a white solid. LCMS (ES, m/z): 454 [M+H]+.

Compound 172

1H-NMR (CD3OD, 400 MHz) δ (ppm): 7.82 (s, 1H), 7.79-7.70 (m, 1H), 7.48 (d, J=8.0 Hz, 2H), 7.41-7.28 (m, 2H), 4.82-4.62 (m, 1H), 4.00-3.90 (m, 1H), 3.90-3.61 (m, 6H), 3.53-3.38 (m, 1H), 3.30-3.24 (m, 1H), 2.30-2.09 (m, 2H), 2.09-1.81 (m, 3H), 1.78-1.52 (m, 2H), 1.48-1.22 (m, 2H), 1.22-1.09 (m, 1H), 1.03-0.90 (m, 1H). LCMS (ES, m/z): 454 [M+H]+.

Compound 173

1H-NMR (CD3OD, 400 MHz) δ (ppm): 7.82 (s, 1H), 7.79-7.70 (m, 1H), 7.48 (d, J=8.0 Hz, 2H), 7.35 (d, J=8.4 Hz, 2H), 4.82-4.62 (m, 1H), 4.00-3.78 (m, 5H), 3.78-3.61 (m, 2H), 3.58-3.48 (m, 1H), 3.48-3.38 (m, 1H), 2.32-2.11 (m, 2H), 2.11-1.83 (m, 3H), 1.80-1.53 (m, 2H), 1.41-1.20 (m, 2H), 1.20-1.11 (m, 1H), 1.02-0.90 (m, 1H) LCMS (ES, m/z): 454 [M+H]+.

Method 26: Preparation of Compounds 216 and 217 4-hydroxy-6-methoxy-4'-((S)-6-((R)-tetrahydrofuran-2-carbonyl)-6-azaspiro[2.5]octan-1-yl)-[1,1'-biphenyl]-3-carboxylic Acid and 4-hydroxy-6-methoxy-4'-((R)-6-((R)-tetrahydrofuran-2-carbonyl)-6-azaspiro[2.5]octan-1-yl)-[1,1'-biphenyl]-3-carboxylic Acid

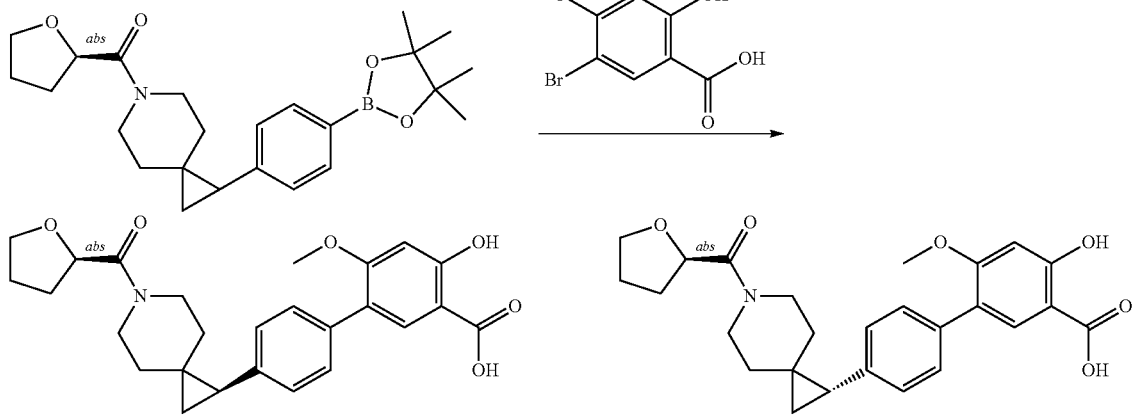

A mixture of ((R)-tetrahydrofuran-2-yl)(1-(4-(4,4,5,5-tetramethyl-1,3,2-dioxaborolan-2-yl)phenyl)-6-azaspiro[2.5] octan-6-yl)methanone (500 mg, 1.22 mmol), 5-bromo-2-hydroxy-4-methoxybenzoic acid (300 mg, 1.22 mmol), bis (di-tert-butyl(4-dimethylaminophenyl)phosphine) dichloropalladium (86 mg, 0.12 mmol) and potassium phosphate (516 mg, 2.43 mmol) in dioxane (15 mL) and water (5 mL) was stirred for 2 h at 90° C. under nitrogen atmosphere. The resulting mixture was cooled to room temperature and concentrated under vacuum. The residue was purified by reverse flash chromatography with the following conditions: water (0.1% FA)/ACN (30% to 60% in 25 min). The product was purified by Chiral HPLC with the following conditions: Column: CHIRALPAK IG, 2×25 cm, 5 μm; mobile phase: hexanes (0.1% FA) and EtOH (hold 30% EtOH in 23 min); Detector: UV 254 nm to afford the first eluting peak as Compound 216 (89 mg, 16%) as a white solid and the second eluting peak as Compound 217 (98.5 mg, 18%) as a white solid.

Compound 216

¹H-NMR (CD₃OD, 400 MHz) δ (ppm): 7.74 (s, 1H), 7.37 (d, J=7.6 Hz, 2H), 7.24 (d, J=7.6 Hz, 2H), 6.60 (s, 1H), 4.90-4.65 (m, 1H), 3.97-3.87 (m, 1H), 3.82-3.65 (m, 6H), 3.45-3.32 (m, 1H), 3.29-3.29 (m, 1H), 2.16-2.04 (m, 2H), 2.11-1.89 (m, 3H), 1.89-1.55 (m, 2H), 1.36-1.25 (m, 2H), 1.11-1.07 (m, 1H), 0.99-0.91 (m, 1H). LCMS (ES, n/z): 452 [M+H]⁺.

Compound 217

¹H-NMR (CD₃OD, 400 MHz) δ (ppm): 7.75 (s, 1H), 7.37 (d, J=8.0 Hz, 2H), 7.25 (d, J=8.0 Hz, 2H), 6.60 (s, 1H), 4.80-4.62 (m, 1H), 4.05-3.91 (m, 1H), 3.89-3.80 (m, 4H), 3.78-3.61 (m, 2H), 3.58-3.25 (m, 2H), 2.28-2.05 (m, 2H), 2.04-1.86 (m, 3H), 1.76-1.49 (m, 2H), 1.38-1.28 (m, 2H), 1.16-1.10 (m, 1H), 0.95-0.88 (m, 1H). LCMS (ES, m/z): 452 [M+H]⁺.

Method 27: Preparation of Compounds 174 and 175: 4'-((S)-6-((R)-tetrahydrofuran-2-carbonyl)-6-azaspiro[2.5]octan-1-yl)-6-(trifluoromethoxy)-[1,1'-biphenyl]-3-carboxylic Acid and 4'-((R)-6-((R)-tetrahydrofuran-2-carbonyl)-6-azaspiro[2.5]octan-1-yl)-6-(trifluoromethoxy)-[1,1'-biphenyl]-3-carboxylic Acid 4'-((S)-6-((R)-tetrahydrofuran-2-carbonyl)-6-azaspiro[2.5]octan-1-yl)-6-(trifluoromethoxy)-[1,1'-biphenyl]-3-carboxylic Acid and 4'-((R)-6-((R)-tetrahydrofuran-2-carbonyl)-6-azaspiro[2.5]octan-1-yl)-6-(trifluoromethoxy)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (600 mg, 1.46 mmol), 3-bromo-4-(trifluoromethoxy)benzoic acid (416 mg, 1.46 mmol), bis(di-tert-butyl(4-dimethylaminophenyl)phosphine)dichloropalladium (103 mg, 0.15 mmol) and potassium phosphate (619 mg, 2.92 mmol) in dioxane (15 mL) and water (5 mL) was stirred for 2 h at 90° C. under nitrogen atmosphere. The resulting mixture was cooled to room temperature and concentrated under vacuum. The residue was purified by reverse flash chromatography with the following conditions: water (0.1% FA)/ACN (10% to 50% in 30 min). The product was purified by Chiral HPLC with the following conditions: Column: CHIRALPAK AS-H, 2.0 cm×25 cm (5 μm); mobile phase: CO2 and MeOH (0.1% FA) (10% to 50% in 4.0 min, hold 2.0 min at 50%); Detector: UV 254 nm to afford the first eluting peak as Compound 174 (141.6 mg, 20%) and the second eluting peak as Compound 175 (157.7 mg, 22%) as a white solid.

Compound 174

¹H-NMR (CD₃OD, 400 MHz) δ (ppm): 8.27-7.98 (m, 2H), 7.50 (d, J=8.4 Hz, 1H), 7.46-7.33 (m, 4H), 4.81-4.63 (m, 1H), 4.00-3.60 (m, 4H), 3.53-3.30 (m, 2H), 2.29-1.83 (m, 5H), 1.80-1.53 (m, 2H), 1.41-1.22 (m, 2H), 1.20-1.14 (m, 1H), 0.99-0.91 (m, 1H). LCMS (ES, m/z): 490 [M+H]⁺.

Compound 175

¹H-NMR (CD₃OD, 400 MHz) δ (ppm): 8.21-8.05 (m, 2H), 7.50 (d, J=8.4 Hz, 1H), 7.45-7.32 (m, 4H), 4.82-4.65

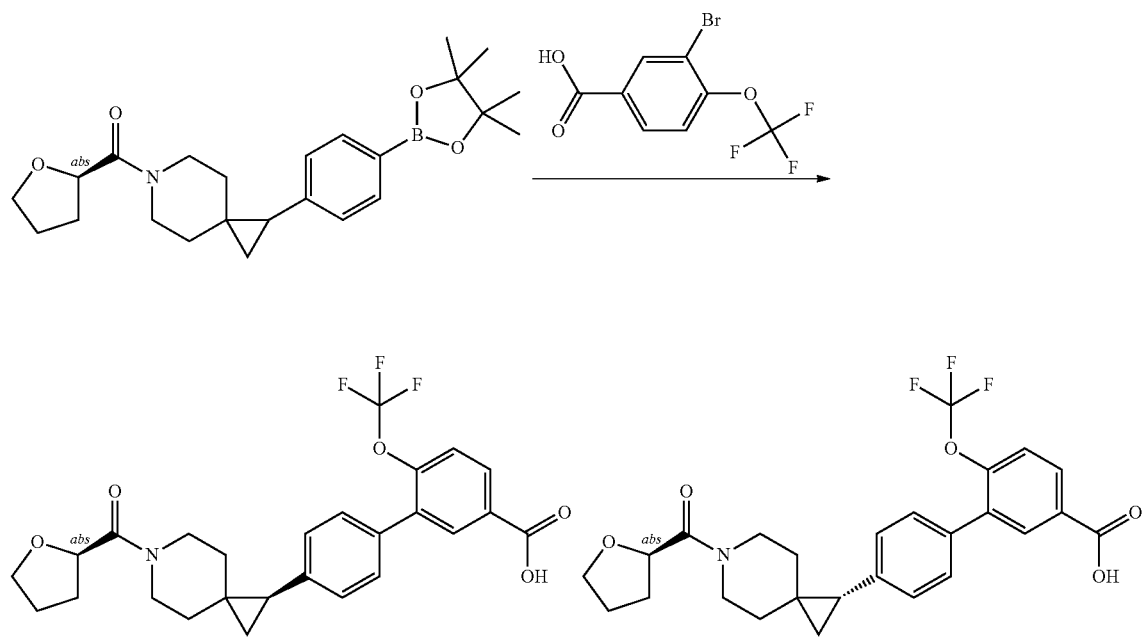

(m, 1H), 4.01-3.62 (m, 4H), 3.59-3.25 (m, 2H), 2.29-2.11 (m, 2H), 2.09-1.85 (m, 3H), 1.79-1.51 (m, 2H), 1.40-1.17 (m, 2H), 1.15-1.10 (m, 1H), 1.02-0.98 (m, 1H). LCMS (ES, m/z): 490 [M+H]+.

Method 28: Preparation of Compounds 190 and 191: 6-(difluoromethyl)-4'-((S)-6-((R)-tetrahydrofuran-2-carbonyl)-6-azaspiro[2.5]octan-1-yl)-[1,1'-biphenyl]-3-carboxylic Acid and 6-(difluoromethyl)-4'-((R)-6-((R)-tetrahydrofuran-2-carbonyl)-6-azaspiro[2.5]octan-1-yl)-[1,1'-biphenyl]-3-carboxylic Acid was purified by reverse flash chromatography with the following conditions: water (0.1% FA)/ACN (10% to 55% in 35 min). The product was purified by Chiral HPLC with the following conditions: Column: CHIRALPAK IG, 20×250 mm, 5 μm; mobile phase: Hexanes (0.1% FA) and EtOH (hold 40% EtOH in 14 min); Detector: UV254 nm to afford the first eluting peak as Compound 190 (100 mg, 15%) as an off-white solid and the second eluting peak as Compound 191 (77 mg, 11%) as an off-white solid.

Compound 190

¹H-NMR (CD₃OD, 400 MHz) δ (ppm): 8.16 (d, J=8.0 Hz, 1H), 7.99 (s, 1H), 7.87 (d, J=8.0 Hz, 1H), 7.43-7.26 (m, 4H),

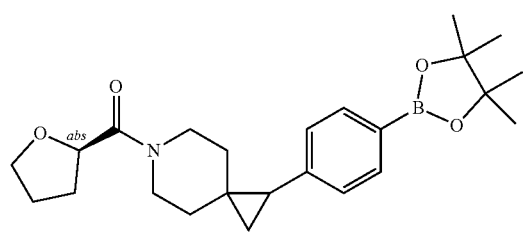
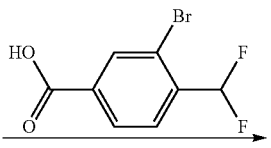

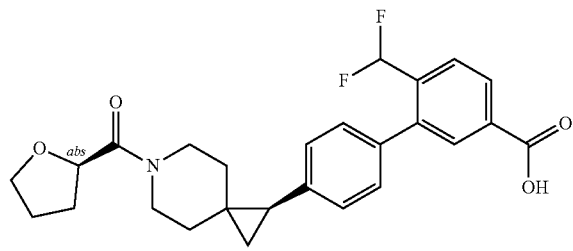
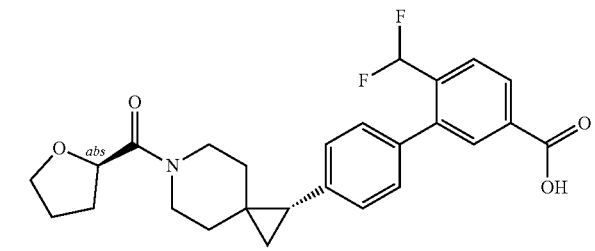

6-(difluoromethyl)-4'-((S)-6-((R)-tetrahydrofuran-2-carbonyl)-6-azaspiro[2.5]octan-1-yl)-[1,1'-biphenyl]-3-carboxylic Acid and 6-(difluoromethyl)-4'-((R)-6-((R)-tetrahydrofuran-2-carbonyl)-6-azaspiro[2.5]octan-1-yl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (600 mg, 1.46 mmol), 3-bromo-4-(difluoromethyl)benzoic acid (366 mg, 1.46 mmol), bis(di-tert-butyl(4-dimethylaminophenyl)phosphine)dichloropalladium (103 mg, 0.15 mmol) and potassium phosphate (619 mg, 2.92 mmol) in dioxane (15 mL) and water (5 mL) was stirred for 2 h at 90° C. under nitrogen atmosphere. The resulting mixture was cooled to room temperature and concentrated under vacuum. The residue 6.81-6.50 (m, 1H), 4.85-4.68 (m, 1H), 3.98-3.90 (m, 1H), 3.89-3.62 (m, 3H), 3.53-3.36 (m, 2H), 2.26-2.12 (m, 2H), 2.10-1.85 (m, 3H), 1.82-1.50 (m, 2H), 1.46-1.21 (m, 2H), 1.19-1.11 (m, 1H), 1.02-0.92 (m, 1H). LCMS (ES, m/z): 456 [M+H]+.

Compound 191

¹H-NMR (CD₃OD, 400 MHz) δ (ppm): 8.15 (d, J=8.0 Hz, 1H), 8.00 (s, 1H), 7.87 (d, J=8.4 Hz, 1H), 7.42-7.27 (m, 4H), 6.81-6.60 (m, 1H), 4.85-4.68 (m, 1H), 3.99-3.64 (m, 4H), 3.55-3.35 (m, 2H), 2.28-2.12 (m, 2H), 2.10-1.85 (m, 3H), 1.76-1.55 (m, 2H), 1.52-1.22 (m, 2H), 1.20-1.12 (m, 1H), 1.09-0.98 (m, 1H). LCMS (ES, m/z): 456 [M+H]+.

Method 28: Preparation 162 and 163: 5-methoxy-4'-((S)-6-((R)-tetrahydrofuran-2-carbonyl)-6-azaspiro[2.5]octan-1-yl)-[1,1'-biphenyl]-3-carboxylic Acid and 5-methoxy-4'-((R)-6-((R)-tetrahydrofuran-2-carbonyl)-6-azaspiro[2.5]octan-1-yl)-[1,1'-biphenyl]-3-carboxylic Acid

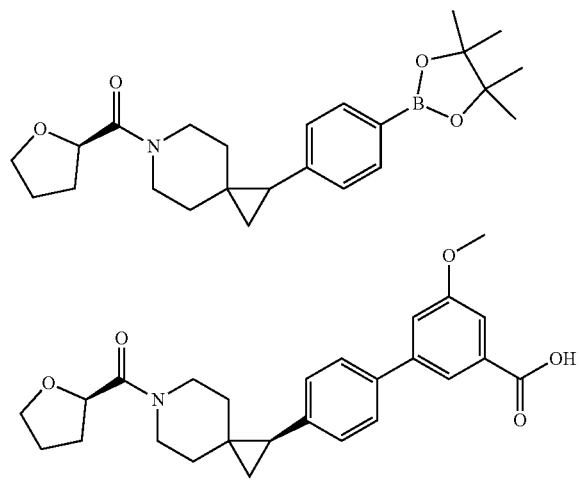

5-methoxy-4'-((S)-6-((R)-tetrahydrofuran-2-carbonyl)-6-azaspiro[2.5]octan-1-yl)-[1,1'-biphenyl]-3-carboxylic Acid and 5-methoxy-4'-((R)-6-((R)-tetrahydrofuran-2-carbonyl)-6-azaspiro[2.5]octan-1-yl)-[1,1'-biphenyl]-3-carboxylic Acid A solution of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (500 mg, 1.09 mmol), bis(di-tert-butyl(4-dimethylaminophenyl)phosphine)dichloropalladium (110 mg, 0.124 mmol), potassium phosphate (900 mg, 4.03 mmol) and 3-bromo-5-methoxybenzoic acid (450 mg, 1.85 mmol) in dioxane (10 mL) and water (3 mL) was stirred for 2 h at 90° C. under nitrogen atmosphere. The mixture was cooled to room temperature and concentrated under vacuum. The crude product was purified by reverse flash chromatography with water (containing 0.1% ammonium bicarbonate) and acetonitrile (5% to 40% over 60 min). The product was separated by Chiral HPLC with the following conditions: column: CHIRALPAK AS-3 (3×100 mm, 3 μm); mobile phase: A, CO₂ and B, MeOH (20 mM NH₃) (10% to 50% in 4 min, hold 2 min at 50%); detector: UV 254/220 nm to afford the first eluting peak as Compound 162 (140.6 mg, 28%) as a white solid and the second eluting peak as Compound 163 (134.4 mg, 27%) as a white solid.

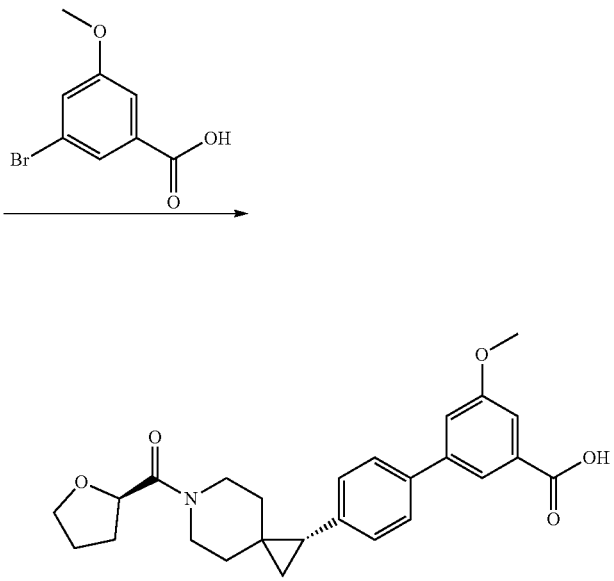

Compound 162

$^1$H-NMR (CD$_3$OD, 400 MHz) δ (ppm): 7.87 (s, 1H), 7.60 (d, J=8.0 Hz, 2H), 7.54 (s, 1H), 7.41-7.26 (m, 3H), 4.85-4.61 (m, 1H), 4.01-3.89 (m, 4H), 3.89-3.62 (m, 3H), 3.52-3.41 (m, 1H), 3.31-3.21 (m, 1H), 2.35-2.09 (m, 2H), 2.09-1.81 (m, 3H), 1.81-1.52 (m, 2H), 1.45-1.21 (m, 2H), 1.21-1.09 (m, 1H), 1.02-0.91 (m, 1H). LCMS: (ES, m/z): 436 [M+H]$^+$.

Compound 163

$^1$H-NMR (CD$_3$OD, 400 MHz) δ (ppm): 7.87 (s, 1H), 7.60 (d, J=8.0 Hz, 2H), 7.54 (s, 1H), 7.41-7.31 (m, 3H), 4.81-4.60 (m, 1H), 4.02-3.81 (m, 5H), 3.81-3.62 (m, 2H), 3.54-3.47 (m, 1H), 3.31-3.23 (m, 1H), 2.35-2.11 (m, 2H), 2.11-1.82 (m, 3H), 1.82-1.57 (m, 2H), 1.45-1.19 (m, 2H), 1.19-1.09 (m, 1H), 1.02-0.91 (m, 1H). LCMS: (ES, m/z): 436 [M+H]$^+$.

Method 29: Preparation of Compounds 224 and 225: 6-fluoro-5-methoxy-4'-((S)-6-((R)-tetrahydrofuran-2-carbonyl)-6-azaspiro[2.5]octan-1-yl)-[1,1'-biphenyl]-3-carboxylic Acid and 6-fluoro-5-methoxy-4'-((R)-6-((R)-tetrahydrofuran-2-carbonyl)-6-azaspiro[2.5]octan-1-yl)-[1,1'-biphenyl]-3-carboxylic Acid

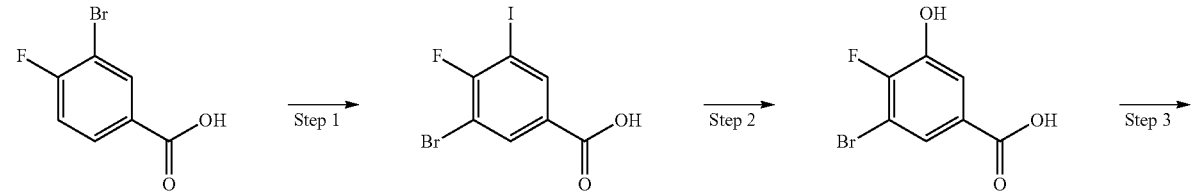

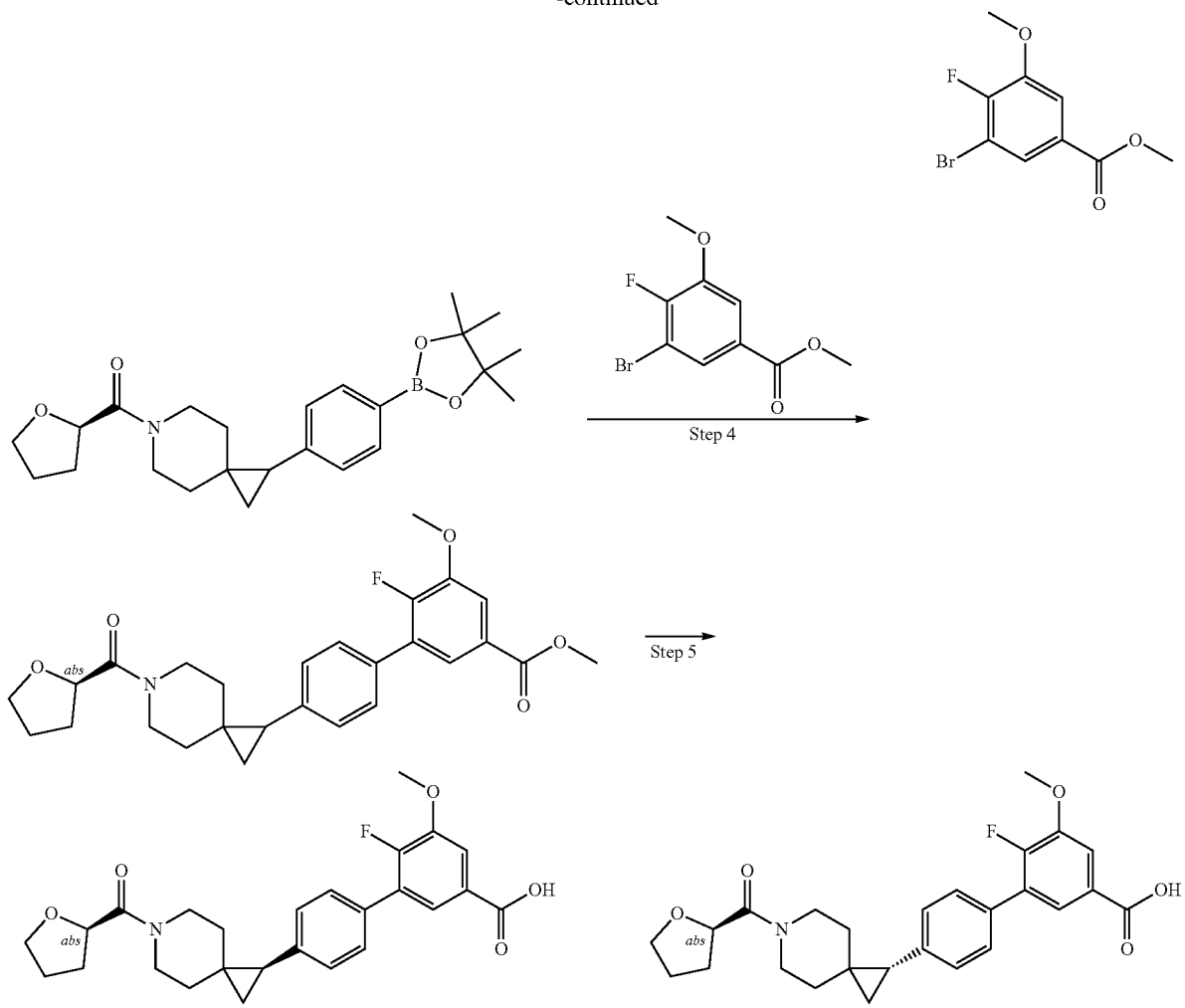

Step 1. 3-bromo-4-fluoro-5-iodobenzoic Acid

To a stirred solution of 3-bromo-4-fluorobenzoic acid (5 g, 22.8 mmol) in sulfuric acid (150 mL) was added N-iodosuccinimide (5.34 g, 23.74 mmol) in portions at 0° C. The resulting mixture was stirred for 2 h at room temperature. The reaction was quenched with ice-water (200 mL) at 0° C. The precipitated solids were collected by filtration and washed with water to yield 3-bromo-4-fluoro-5-iodo benzoic acid (8 g, crude) as a pink solid which was used in the next step directly without further purification. LCMS: (ES, m/z): 345, 347 [M+H]+.

Step 2. 3-bromo-4-fluoro-5-hydroxybenzoic Acid

A mixture of 3-bromo-4-fluoro-5-iodo benzoic acid (500 mg, 1.45 mmol), copper oxide (25 mg, 0.18 mmol) and sodium hydroxide (300 mg, 7.49 mmol) in water (5 mL) was stirred for 16 h at 100° C. The mixture was cooled to room temperature. The resulting mixture was filtered, and the filtrate was acidified to pH 5 with hydrochloric acid (5 M). The resulting mixture was extracted with ethyl acetate (3×50 mL). The combined organic layers were washed with brine (2×50 mL), dried over anhydrous sodium sulfate, filtered and concentrated under vacuum. The residue was purified by silica gel column chromatography, eluted with petroleum ether/ethyl acetate (1:1) to afford 3-bromo-4-fluoro-5-hydroxybenzoic acid (250 mg, 73%) as a pink solid. LCMS: (ES, m/z): 235, 237 [M+H]+.

Step 3. methyl 3-bromo-4-fluoro-5-methoxybenzoate

A mixture of 3-bromo-4-fluoro-5-hydroxybenzoic acid (500 mg, 1.70 mmol), potassium carbonate (1.17 g, 8.04 mmol) and methyl iodide (724 mg, 4.85 mmol) in N,N-Dimethylformamide (15 mL) was stirred for 2 h at 60° C. under nitrogen atmosphere. The mixture was cooled to room temperature and diluted with water (30 mL). The resulting mixture was extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with PE/EtOAc (4:1) to afford methyl 3-bromo-4-fluoro-5-methoxy benzoate (280 mg, 58%) as a yellow solid. LCMS: (ES, m/z): 263, 265 [M+H]+.

Step 4. methyl 6-fluoro-5-methoxy-4'-(6-((R)-tetrahydrofuran-2-carbonyl)-6-azaspiro[2.5]octan-1-yl)-[1,1'-biphenyl]-3-carboxylate A mixture of methyl 3-bromo-4-fluoro-5-methoxybenzoate (290 mg, 0.88 mmol), bis(di-tert-butyl(4-dimethylaminophenyl)phosphine)dichloropalladium (78 mg, 0.094 mmol), potassium phosphate (704 mg, 3.15 mmol) and ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (500 mg, 0.97 mmol) in dioxane (8 mL) and water (2 mL) was stirred for 2 h at 80° C. under nitrogen atmosphere. The mixture was cooled to room temperature and concentrated. The residue was purified by silica gel column chromatography, eluted with PE/EtOAc (1:1) to afford methyl 6-fluoro-5-methoxy-4'-(6-((R)-tetrahydrofuran-2-carbonyl)-6-azaspiro[2.5]octan-1-yl)-[1,1'-biphenyl]-3-carboxylate (400 mg, 78%) as a white solid. LCMS: (ES, m/z): 468 [M+H]$^+$.

Step 5. 6-fluoro-5-methoxy-4'-((S)-6-((R)-tetrahydrofuran-2-carbonyl)-6-azaspiro[2.5]octan-1-yl)-[1,1'-biphenyl]-3-carboxylic Acid and 6-fluoro-5-methoxy-4'-((R)-6-((R)-tetrahydrofuran-2-carbonyl)-6-azaspiro[2.5]octan-1-yl)-[1,1'-biphenyl]-3-carboxylic Acid A mixture of methyl 6-fluoro-5-methoxy-4'-(6-((R)-tetrahydrofuran-2-carbonyl)-6-azaspiro[2.5]octan-1-yl)-[1,1'-biphenyl]-3-carboxylate (390 mg, 0.67 mmol), lithium hydroxide (62 mg, 2.20 mmol) in tetrahydrofuran (6 mL), water (3 mL) and methanol (3 mL) was stirred for 2 h at room temperature. The resulting mixture was concentrated under vacuum. The crude product was purified by reverse flash chromatography with water (containing 0.1% FA) and acetonitrile (10% to 60% over 40 min). The product was separated by Chiral HPLC with the following conditions: column: Chiralart Cellulose-SB (0.46×10 cm, 3 μm); mobile phase: A, Hexanes (0.1% FA) and B, EtOH (hold 50% EtOH in 10 min); detector: UV 254 to afford the first eluting peak as Compound 224 (106.5 mg, 33%) as a white solid and the second eluting peak as Compound 225 (105.4 mg, 33%) as a white solid.

Compound 224

$^1$H-NMR (CD$_3$OD, 400 MHz) δ (ppm): 7.88-7.65 (m, 2H), 7.50 (d, J=7.6 Hz, 2H), 7.37 (d, J=8.0 Hz, 2H), 4.81-4.58 (m, 1H), 3.98 (s, 3H), 3.97-3.65 (m, 4H), 3.59-3.34 (m, 2H), 2.39-1.81 (m, 5H), 1.81-1.57 (m, 2H), 1.48-1.21 (m, 2H), 1.21-1.09 (m, 1H), 1.01-0.88 (m, 1H). LCMS: (ES, m/z): 454 [M+H]$^+$.

Compound 225

$^1$H-NMR (CD$_3$OD, 400 MHz) δ (ppm): 7.91-7.61 (m, 2H), 7.50 (d, J=7.2 Hz, 2H), 7.43-7.25 (m, 2H), 4.81-4.61 (m, 1H), 3.98 (s, 3H), 3.97-3.58 (m, 4H), 3.48-3.41 (m, 1H), 3.31-3.23 (m, 1H), 2.35-1.89 (m, 5H), 1.82-1.51 (m, 2H), 1.49-1.21 (m, 2H), 1.19-1.13 (m, 1H), 1.01-0.91 (m, 1H). LCMS: (ES, m/z): 454 [M+H]$^+$.

Method 30: Preparation of Compounds 56 and 57: 3-(4-((R)-6-((R)-tetrahydrofuran-2-carbonyl)-6-azaspiro[2.5]octan-1-yl)phenyl)quinoline-8-carboxylic Acid and 3-(4-((S)-6-((R)-tetrahydrofuran-2-carbonyl)-6-azaspiro[2.5]octan-1-yl)phenyl)quinoline-8-carboxylic Acid

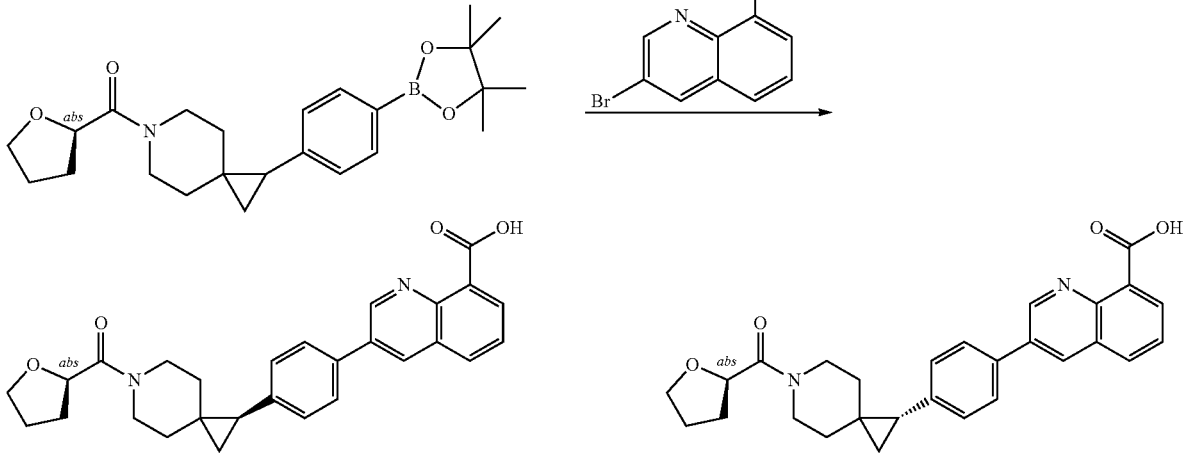

3-(4-((R)-6-((R)-tetrahydrofuran-2-carbonyl)-6-azaspiro[2.5]octan-1-yl)phenyl)quinoline-8-carboxylic Acid and 3-(4-((S)-6-((R)-tetrahydrofuran-2-carbonyl)-6-azaspiro[2.5]octan-1-yl)phenyl)quinoline-8-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (680 mg, 1.65 mmol) and 3-bromoquinoline-8-carboxylic acid (500 mg, 1.98 mmol), bis(di-tert-butyl(4-dimethylaminophenyl)phosphine)dichloropalladium (117 mg, 0.17 mmol) and potassium phosphate (702 mg, 3.31 mmol) in dioxane (10 mL) and water (2 mL) was stirred for 2 h at 80° C. under nitrogen atmosphere. The resulting mixture was extracted with EtOAc (2×20 mL). The mixture was cooled to room temperature and concentrated. The crude product was purified by Prep-HPLC with water (0.1% FA) and ACN (40% up to 55% in 20 min). The product was separated by Chiral HPLC with the following conditions: Column: CHIRALPAK IG, 20×250 mm, 5 μm; mobile phase: MTBE (0.1% FA) and EtOH (hold 50% EtOH in 30 min); Detector: UV254 nm to afford the first eluting peak as Compound 56 (66 mg, 7%) and the second eluting peak as Compound 57 (61.9 mg, 7%) as a white solid.

Compound 56

¹H-NMR (CD₃OD, 400 MHz) δ (ppm): 9.39 (s, 1H), 8.86 (s, 1H), 7.70 (d, J=6.8 Hz, 1H), 7.38 (d, J=7.6 Hz, 1H), 7.92-7.73 (m, 3H), 7.48 (d, J=8.0 Hz, 2H), 4.82-4.61 (m, 1H), 4.02-3.68 (m, 4H), 3.60-3.48 (m, 1H), 3.47-3.40 (m, 1H), 2.35-2.11 (m, 2H), 2.10-1.85 (m, 3H), 1.79-1.55 (m, 2H), 1.43-1.25 (m, 2H), 1.24-1.10 (m, 1H), 1.05-0.91 (m, 1H). LCMS (ES, m/z): 457 [M+H]⁺.

Compound 57

¹H-NMR (CD₃OD, 400 MHz) δ (ppm): 9.38 (s, 1H), 8.85 (s, 1H), 7.69 (d, J=7.2 Hz, 1H), 7.37 (d, J=7.2 Hz, 1H), 7.97-7.69 (m, 3H), 7.47 (s, 2H), 4.82-4.64 (m, 1H), 4.05-3.61 (m, 4H), 3.60-3.38 (m, 2H), 2.32-1.81 (m, 5H), 1.79-1.57 (m, 2H), 1.52-1.12 (m, 3H), 1.09-0.91 (m, 1H). LCMS (ES, m/z): 457 [M+H]⁺.

Method 31: Preparation of Compounds 222 and 223: 6-chloro-5-methoxy-4'-((S)-6-((R)-tetrahydrofuran-2-carbonyl)-6-azaspiro[2.5]octan-1-yl)-[1,1'-biphenyl]-3-carboxylic Acid and 6-chloro-5-methoxy-4'-((R)-6-((R)-tetrahydrofuran-2-carbonyl)-6-azaspiro[2.5]octan-1-yl)-[1,1'-biphenyl]-3-carboxylic Acid

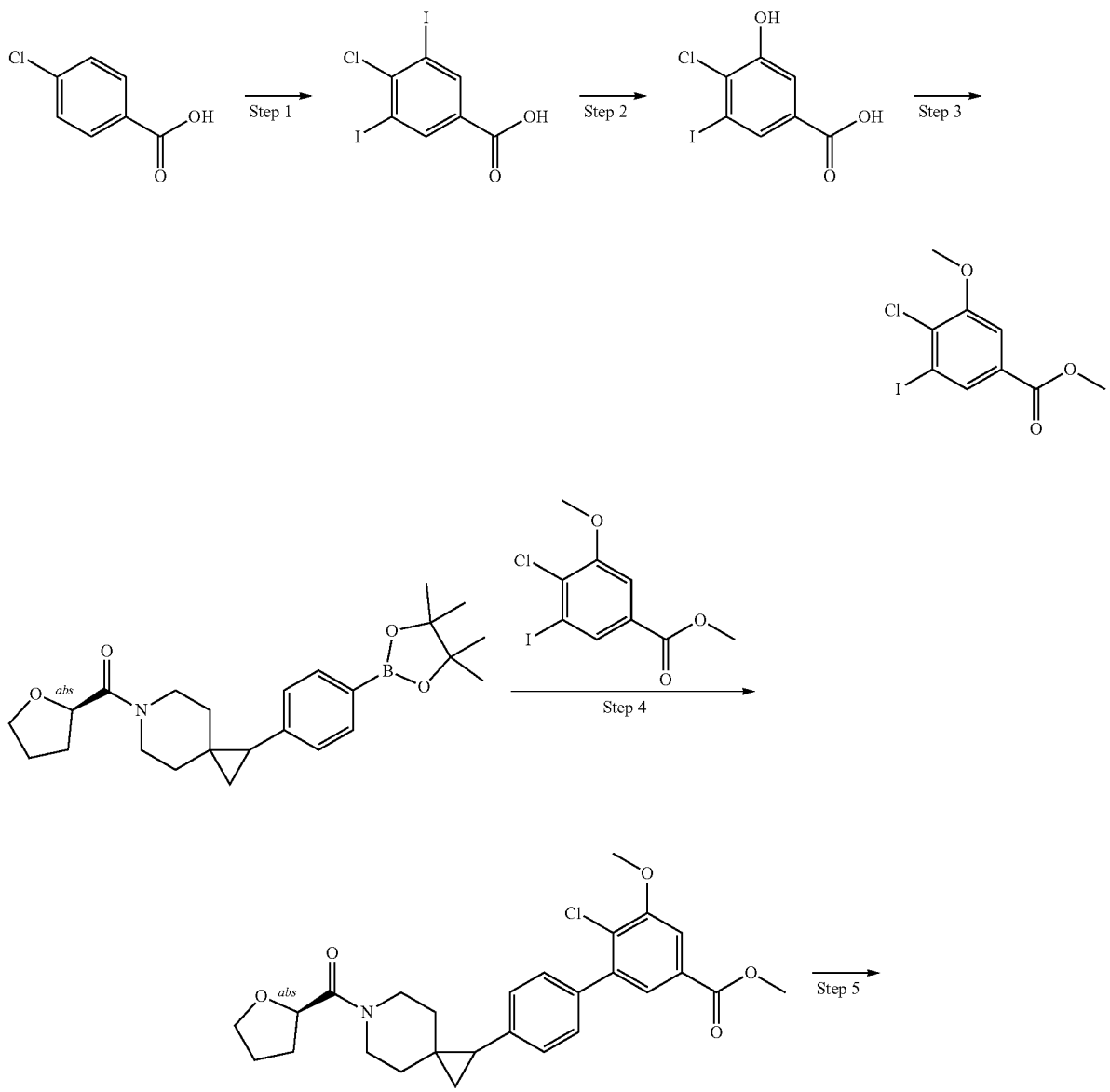

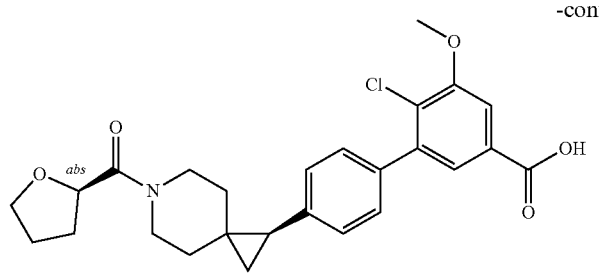 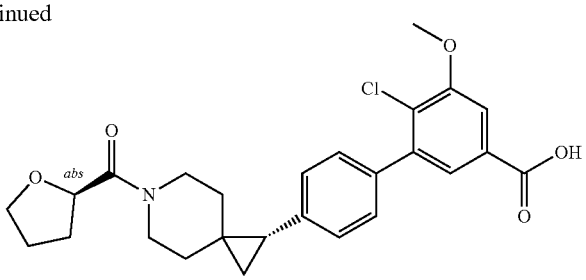

Step 1. 4-chloro-3,5-diiodobenzoic Acid

A mixture of iodine (6.20 g, 24.41 mmol) trioxochromium (2.44 g, 24.40 mmol) in sulfuric acid (150 mL) was stirred for 30 min at room temperature under nitrogen atmosphere. To the above was added 4-chlorobenzoic acid (3.00 g, 18.78 mmol). The resulting mixture was stirred overnight at room temperature and then diluted with water (200 mL). The precipitated solids were collected by filtration and washed with water (3×50 mL) to afford 4-chloro-3,5-diiodobenzoic acid (5 g, 62%) as a white solid. The crude product was used in the next step directly without further purification. LCMS (ES, m/z): 409[M+H]$^+$.

Step 2. 4-chloro-3-hydroxy-5-iodobenzoic Acid

To a stirred mixture of 4-chloro-3,5-diiodobenzoic acid (5.0 g, 11.61 mmol) and copper oxide (0.21 g, 1.40 mmol) in water (50 mL) was added sodium hydroxide (2.8 g, 69.82 mmol) at room temperature. The resulting mixture was stirred for 2 h at 80° C. under nitrogen atmosphere. The mixture was acidified to pH 6 with hydrochloric acid (2M). The mixture was extracted with dichloromethane (3×50 mL). The organic layer was washed with brine (100 mL), dried over sodium sulfate, filtered and concentrated under reduced pressure. The crude product was purified by silica gel column: eluted with petroleum ether/ethyl acetate (1:1) to afford 4-chloro-3-hydroxy-5-iodobenzoic acid (3.1 g, 42%) as a yellow solid. LCMS (ES, m/z): 299[M+H]$^+$.

Step 3. methyl 4-chloro-3-iodo-5-methoxybenzoate

A mixture of 4-chloro-3-hydroxy-5-iodobenzoic acid (1.00 g, 3.28 mmol), potassium carbonate (1.93 g, 13.17 mmol) and iodomethane (1.47 g, 9.85 mmol) in N,N-dimethylformamide (10 mL) was stirred for 1 h at 90° C. under nitrogen atmosphere. The resulting mixture was diluted with water (50 mL). The aqueous layer was extracted with ethyl acetate (3×50 mL). The resulting mixture was concentrated under reduced pressure. The organic layers were combined, washed with brine (100 mL), dried over sodium sulfate, filtered and concentrated under reduced pressure. The residue was purified by silica gel column chromatography, eluted with petroleum ether/ethyl acetate (5:1) to afford methyl 4-chloro-3-iodo-5-methoxybenzoate (250 mg, 22%) as a yellow solid. LCMS (ES, m/z): 327 [M+H]$^+$.

Step 4. methyl 6-chloro-5-methoxy-4'-(6-((R)-tetrahydrofuran-2-carbonyl)-6-azaspiro[2.5]octan-1-yl)-[1,1'-biphenyl]-3-carboxylate A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (470 mg, 1.08 mmol), methyl 4-chloro-3-iodo-5methoxybenzoate (250 mg, 0.78 mmol), bis(di-tert-butyl(4-dimethylaminophenyl)phosphine)dichloropalladium (108 mg, 0.15 mmol) and potassium phosphate (487 mg, 2.20 mmol) in dioxane (15 mL) and water (3 mL) was stirred for 1 h at 80° C. under nitrogen atmosphere. The resulting mixture was concentrated under reduced pressure. The residue was purified by silica gel column chromatography, eluted with petroleum ether/ethyl acetate (1:1) to afford methyl 6-chloro-5-methoxy-4'-(6-((R)-tetrahydrofuran-2-carbonyl)-6-azaspiro[2.5]octan-1-yl)-[1,1'-biphenyl]-3-carboxylate (350 mg, 63%) as a yellow solid. LCMS (ES, m/z): 484 [M+H]$^+$

Step 5. 6-chloro-5-methoxy-4'-((S)-6-((R)-tetrahydrofuran-2-carbonyl)-6-azaspiro[2.5]octan-1-yl)-[1,1'-biphenyl]-3-carboxylic Acid and 6-chloro-5-methoxy-4'-((R)-6-((R)-tetrahydrofuran-2-carbonyl)-6-azaspiro[2.5]octan-1-yl)-[1,1'-biphenyl]-3-carboxylic Acid A mixture of methyl 6-chloro-5-methoxy-4'-(6-((R)-tetrahydrofuran-2-carbonyl)-6-azaspiro[2.5]octan-1-yl)-[1,1'-biphenyl]-3-carboxylate (200 mg, 0.37 mmol) and lithium hydroxide (45 mg, 1.86 mmol) in water (3 mL) and tetrahydrofuran (10 mL) was stirred for 2 h at room temperature. The resulting mixture was concentrated under reduced pressure. The residue was purified by reverse flash chromatography with water (0.1% FA) and ACN (15% up to 55% in 25 min). The product was separated by Chiral HPLC (Column: CHIRAL ART Cellulose-SB, 2×25 cm, 5 μm; mobile phase: hexanes (0.1% FA) and IPA (hold 30% IPA in 30 min); Detector: UV254 to afford the first eluting peak as Compound 222 (42.5 mg, 48%) as a white solid and the second eluting peak as Compound 223 (34 mg, 39%) as a white solid.

Compound 222

$^1$H-NMR (CD$_3$OD, 400 MHz) δ (ppm): 7.68 (s, 1H), 7.61 (s, 1H), 7.42-7.25 (m, 4H), 4.85-3.67 (m, 1H), 3.97 (s, 3H), 3.96-3.91 (m, 1H), 3.90-3.69 (m, 3H), 3.58-3.35 (m, 2H), 2.28-2.11 (m, 2H), 2.10-1.85 (m, 3H), 1.80-1.49 (m, 2H), 1.42-1.22 (m, 2H), 1.20-1.05, (m, 1H), 1.01-0.92 (m, 1H). LCMS: (ES, m/z): 470 [M+H]$^+$.

Compound 223

$^1$H-NMR (CD$_3$OD, 400 MHz) δ (ppm): 7.70 (s, 1H), 7.60 (s, 1H), 7.41-7.25 (m, 4H), 4.82-4.67 (m, 1H), 3.98 (s, 3H), 3.97-3.90 (m, 1H), 3.90-3.60 (m, 3H), 3.58-3.35 (m, 2H), 2.28-2.10 (m, 2H), 2.10-1.85 (m, 3H), 1.80-1.49 (m, 2H), 1.42-1.22 (m, 2H), 1.19-1.05 (m, 1H), 1.02-0.92 (m, 1H).
LCMS: (ES, m/z): 470 [M+H]⁺.
Method 32: Preparation of Compounds 212 and 213: 3-(4-((S)-6-((R)-tetrahydrofuran-2-carbonyl)-6-azaspiro[2.5]octan-1-yl)phenyl)isoquinoline-8-carboxylic Acid and 3-(4-((R)-6-((R)-tetrahydrofuran-2-carbonyl)-6-azaspiro[2.5]octan-1-yl)phenyl)isoquinoline-8-carboxylic Acid
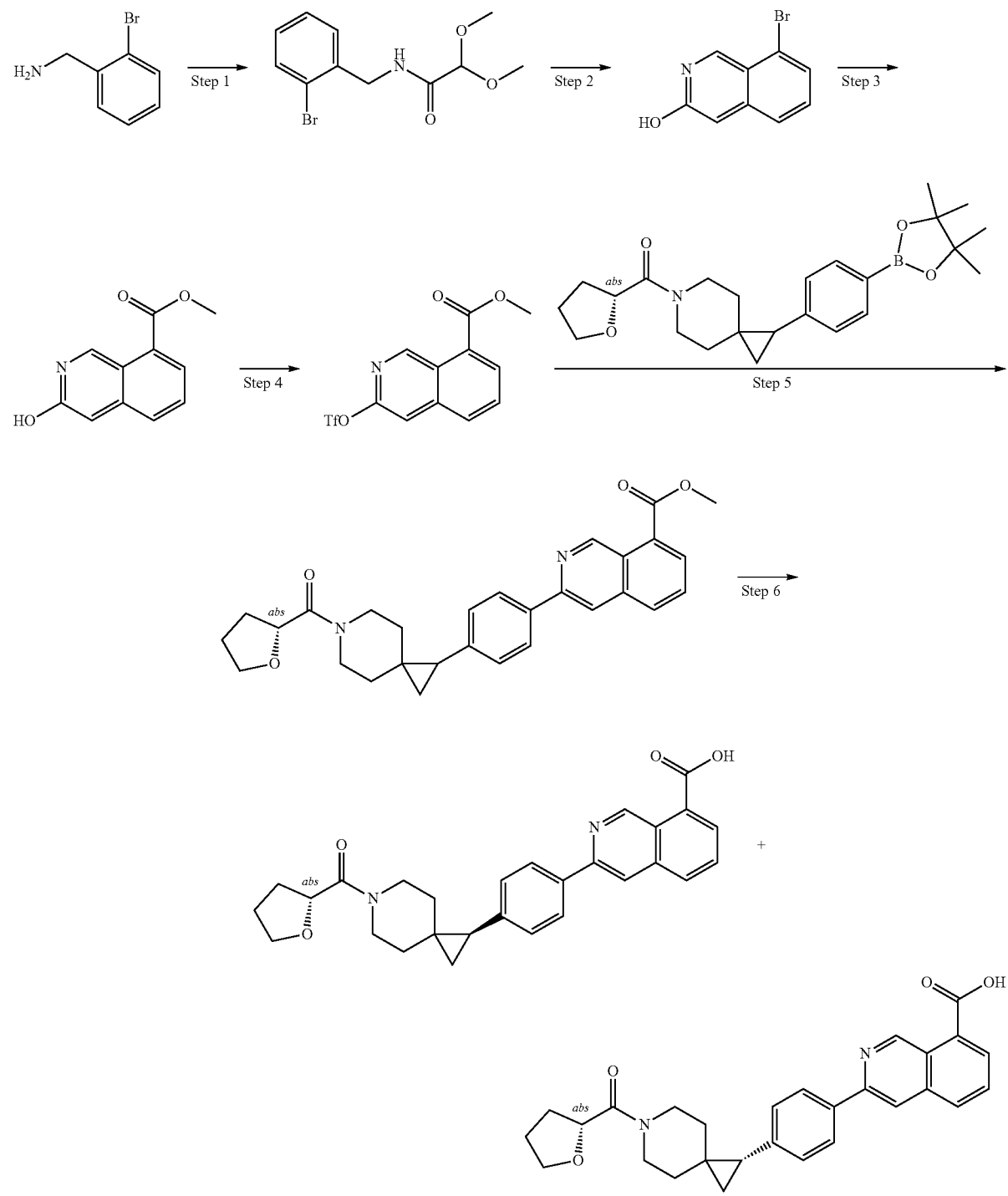

Step 1. N-[(2-bromophenyl)methyl]-2,2-dimethoxyacetamide

A mixture of 1-(2-bromophenyl)methanamine (4 g, 21.5 mmol) and methyl 2,2-dimethoxyacetate (3.60 g, 26.8 mmol) was stirred for 1 h at 80° C. under nitrogen atmosphere. The mixture was cooled to room temperature and extracted with ethyl acetate (3×200 mL). The combined organic layers were dried over sodium sulfate, filtered and concentrated under reduced pressure. The residue was purified by silica gel column chromatography, eluted with petroleum ether/ethyl acetate (1:1) to afford N-[(2-bromophenyl)methyl]-2,2-dimethoxyacetamide as a yellow solid (3 g, 48%). LCMS (ES, m/z): 288,290 [M+H]$^+$.

Step 2. 8-bromoisoquinolin-3-ol

A mixture of N-[(2-bromophenyl)methyl]-2,2-dimethoxyacetamide (3.0 g, 10.4 mmol) in sulfuric acid (6 mL) was stirred for 16 h at room temperature. The reaction was quenched by the addition of water/ice (100 mL). The mixture was basified to pH 8 with saturated sodium carbonate solution. The precipitated solids were collected by filtration and washed with methanol (2×30 mL) to afford 8-bromoisoquinolin-3-ol (2.0 g, crude) as a yellow solid. LCMS (ES, m/z): 224,226 [M+H]$^+$.

Step 3. methyl 3-hydroxyisoquinoline-8-carboxylate

A solution of 8-bromoisoquinolin-3-ol (1.00 g, 4.46 mmol), palladium acetate (0.10 g, 0.45 mmol) and 1,3-bis(diphenylphosphino)propane (0.37 g, 0.89 mmol) in methanol (10.00 mL) and N,N-dimethylformamide (10.00 mL) was stirred for 16 h at 100° C. under nitrogen atmosphere. The resulting mixture was cooled to room temperature and concentrated under reduced pressure. The crude product was purified by Prep-HPLC with water (0.1% FA) and ACN (25% up to 55% in 35 min) to afford methyl 3-hydroxyisoquinoline-8-carboxylate (500 mg, 52%) as a yellow solid. LCMS (ES, m/z): 204 [M+H]$^+$.

Step 4. methyl 3-(trifluoromethanesulfonyloxy)isoquinoline-8-carboxylate

A solution of methyl 3-hydroxyisoquinoline-8-carboxylate (500 mg, 2.46 mmol) pyrazine (0.4 mL, 4.92 mmol) and trifluoromethanesulfonic anhydride (0.62 mL, 3.69 mmol) in dichloromethane (20.00 mL) was stirred for 2 h at room temperature under nitrogen atmosphere. The mixture was acidified to pH 6 with saturated ammonium chloride. The resulting mixture was extracted with dichloromethane (3×200 mL). The combined organic layers were dried over anhydrous magnesium sulfate, filtered and concentrated under reduced pressure. The residue was purified by silica gel column chromatography, eluted with petroleum ether/ethyl acetate (1:1) to afford to afford methyl 3-(trifluoromethanesulfonyloxy)isoquinoline-8-carboxylate as a yellow solid (480 mg, 55%) as a yellow solid. LCMS (ES, m/z): 336 [M+H]$^+$.

Step 5. methyl 3-(4-(6-((R)-tetrahydrofuran-2-carbonyl)-6-azaspiro[2.5]octan-1-yl)phenyl)isoquinoline-8-carboxylate A solution of methyl 3-(trifluoromethanesulfonyloxy)isoquinoline-8-carboxylate (480 mg, 1.43 mmol), ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (883 mg, 2.15 mmol), bis(di-tert-butyl(4-dimethylaminophenyl)phosphine)dichloropalladium (101 mg, 0.14 mmol) and potassium phosphate (608 mg, 2.86 mmol) in 1,4-dioxane (20.00 mL) and water (4.00 mL) was stirred for 2 h at 80° C. under nitrogen atmosphere. The mixture was cooled to room temperature and concentrated under reduced pressure. The residue was purified by silica gel column chromatography, eluted with petroleum ether/ethyl acetate (1:5) to afford to afford to afford methyl 3-(4-(6-((R)-tetrahydrofuran-2-carbonyl)-6-azaspiro[2.5]octan-1-yl)phenyl)isoquinoline-8-carboxylate (450 mg, 64%) as a yellow solid. LCMS (ES, m/z): 471 [M+H]$^+$.

Step 6. 3-(4-((S)-6-((R)-tetrahydrofuran-2-carbonyl)-6-azaspiro[2.5]octan-1-yl)phenyl)isoquinoline-8-carboxylic Acid and 3-(4-((R)-6-((R)-tetrahydrofuran-2-carbonyl)-6-azaspiro[2.5]octan-1-yl)phenyl)isoquinoline-8-carboxylic Acid A mixture of methyl 3-(4-(6-((R)-tetrahydrofuran-2-carbonyl)-6-azaspiro[2.5]octan-1-yl)phenyl)isoquinoline-8-carboxylate (450 mg, 0.99 mmol) and lithium hydroxide (69 mg, 2.87 mmol) in tetrahydrofuran (10 mL) and water (3 mL) was stirred for 2 h at room temperature. The reaction mixture was acidified to pH 6 with hydrochloric acid (1M). The resulting mixture was extracted with ethyl acetate (3×100 mL). The combined organic layers were dried over anhydrous sodium anhydrous sulfate, filtered and concentrated under reduced pressure. The crude product was purified by Prep-HPLC with water (0.1% FA) and ACN (25% up to 55% in 7 min). The product was separated by SFC-Prep-HPLC with the following conditions: Column: CHIRAL-PAK AS-H(03), 2×25 cm, 5 μm; mobile phase: dichloromethane (containing 0.2% diethylamine) and methanol (hold 50% Methanol in 16 min); Detector: uv 254 to afford the first eluting peak as Compound 212 (149 mg, 31%) as a yellow solid and the second eluting peak as Compound 213 (148 mg, 31%) as a yellow solid.

Compound 212

$^1$H NMR (400 MHz, DMSO-d6) δ (ppm): 13.56 (br, 1H), 10.24 (s, 1H), 8.50 (s, 1H), 8.27-8.15 (m, 4H), 7.86 (t, J=7.6 Hz, 1H), 7.41 (d, J=8.0 Hz, 2H), 4.69-4.56 (m, 1H), 3.82-3.49 (m, 4H), 3.45-3.38 (m, 1H), 3.20-3.17 (m, 1H), 2.13-2.10 (m, 1H), 2.08-1.69 (m, 4H), 1.59-1.46 (m, 2H), 1.37-1.02 (m, 3H), 0.93-0.89 (m, 1H). LCMS: (ES, m/z): 457 [M+H]$^+$.

Compound 213

$^1$H NMR (400 MHz, DMSO-d6) δ (ppm): 13.56 (br, 1H), 10.24 (s, 1H), 8.50 (s, 1H), 8.29-8.14 (m, 4H), 7.86 (t, J=7.6 Hz, 1H), 7.41 (d, J=8.0 Hz, 2H), 4.68-4.56 (m, 1H), 3.82-3.55 (m, 4H), 3.43-3.39 (m, 1H), 3.24-3.03 (m, 1H), 2.13-2.10 (m, 1H), 2.08-1.70 (m, 4H), 1.65-1.47 (m, 2H), 1.32-1.03 (m, 3H), 0.93-0.89 (m, 1H). LCMS: (ES, m/z): 457 [M+H]$^+$.

Method 33: Preparation of Compounds 168 and 169: 2-fluoro-4'-((S)-6-((R)-tetrahydrofuran-2-carbonyl)-6-azaspiro[2.5]octan-1-yl)-[1,1'-biphenyl]-3-carboxylic Acid and 2-fluoro-4'-((R)-6-((R)-tetrahydrofuran-2-carbonyl)-6-azaspiro[2.5]octan-1-yl)-[1,1'-biphenyl]-3-carboxylic Acid

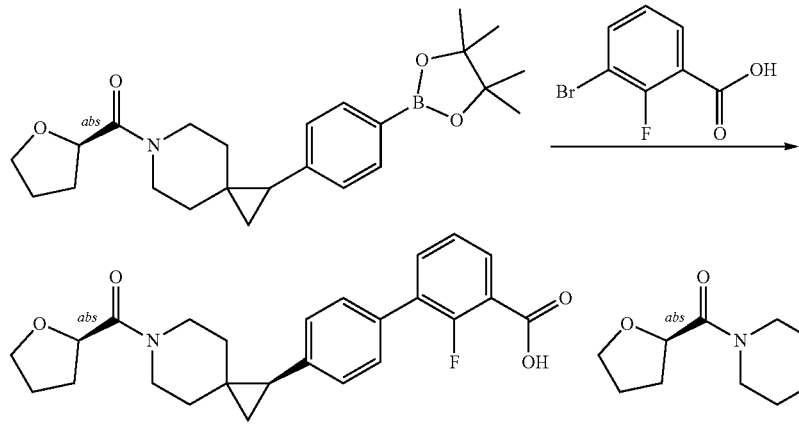

2-fluoro-4'-((S)-6-((R)-tetrahydrofuran-2-carbonyl)-6-azaspiro[2.5]octan-1-yl)-[1,1'-biphenyl]-3-carboxylic Acid and 2-fluoro-4'-((R)-6-((R)-tetrahydrofuran-2-carbonyl)-6-azaspiro[2.5]octan-1-yl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (1.47 g, 3.56 mmol), 3-bromo-2-fluorobenzoic acid (600 mg, 2.74 mmol), bis(di-tert-butyl(4-dimethylaminophenyl)phosphine)dichloropalladium (194 mg, 0.27 mmol) and potassium phosphate (1.16 mg, 5.48 mmol) in 1,4-dioxane (20 mL) and water (4 mL) was stirred at 80° C. for 2 h under nitrogen atmosphere. The mixture was cooled to room temperature and concentrated under reduced pressure. The residue was purified by reverse flash chromatography with water (0.1% FA) and ACN (30% to 50% in 20 min). The product was separated by Chiral HPLC with the following conditions: Column: CHIRALPAK IG, 20×250 mm, 5 μm; mobile phase: (Hexanes and DCM 3:1)(0.3% FA) and EtOH (hold 50% EtOH in 11 min); Detector: UV254 nm to afford the first eluting peak as Compound 168 (104.5 mg, 9%) as an off-white solid and the second eluting peak as Compound 169 (129.1 mg, 11%) as an off-white solid.

Compound 168

$^1$H NMR (CD$_3$OD, 400 MHz) δ (ppm): 7.92-7.88 (m, 1H), 7.69-7.65 (m, 1H), 7.48 (d, J=7.6 Hz, 2H), 7.37-7.30 (m, 3H), 4.89-4.60 (m, 1H), 4.01-3.57 (m, 4H), 3.52-3.40 (m, 1H), 3.32-3.23 (m, 1H), 2.33-1.78 (m, 5H), 1.78-1.50 (m, 2H), 1.45-1.21 (m, 2H), 1.15-1.13 (m, 1H), 0.98-0.95 (m, 1H). LCMS (ES, m/z): 424 [M+H]$^+$.

Compound 169

$^1$H NMR (CD$_3$OD, 400 MHz) δ (ppm): 7.92-7.87 (m, 1H), 7.68-7.66 (m, 1H), 7.56-7.43 (m, 2H), 7.42-7.25 (m, 3H), 4.89-4.72 (m, 1H), 4.03-3.63 (m, 4H), 3.59-3.34 (m, 2H), 2.26-2.13 (m, 2H), 2.05-1.85 (m, 3H), 1.76-1.50 (m, 2H), 1.39-1.20 (m, 2H), 1.16-1.13 (m, 1H), 0.99-0.95 (m, 1H). LCMS (ES, m/z): 424 [M+H]$^+$.

Method 34: Preparation of Compounds 176 and 177: 4'-((S)-6-((R)-tetrahydrofuran-2-carbonyl)-6-azaspiro[2.5]octan-1-yl)-6-(trifluoromethyl)-[1,1'-biphenyl]-3-carboxylic Acid and 4'-((R)-6-((R)-tetrahydrofuran-2-carbonyl)-6-azaspiro[2.5]octan-1-yl)-6-(trifluoromethyl)-[1,1'-biphenyl]-3-carboxylic Acid

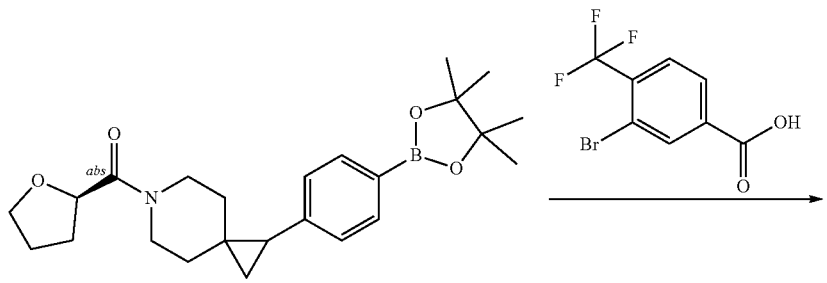

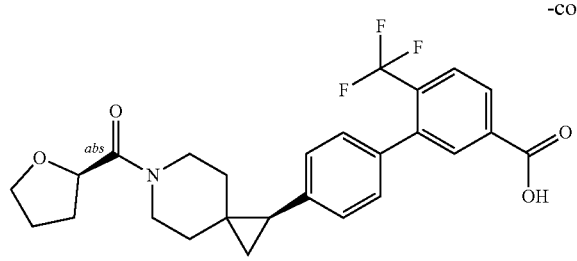
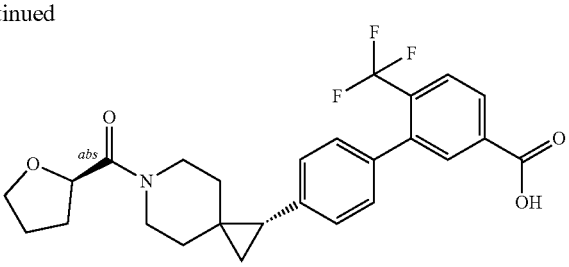

4'-((S)-6-((R)-tetrahydrofuran-2-carbonyl)-6-azaspiro[2.5]octan-1-yl)-6-(trifluoromethyl)-[1,1'-biphenyl]-3-carboxylic Acid and 4'-((R)-6-((R)-tetrahydrofuran-2-carbonyl)-6-azaspiro[2.5]octan-1-yl)-6-(trifluoromethyl)-[1,1'-biphenyl]-3-carboxylic Acid A mixture of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (713 mg, 1.73 mmol), 3-bromo-4-(trifluoromethyl)benzoic acid (311 mg, 1.16 mmol), bis(di-tert-butyl(4-dimethylaminophenyl)phosphine) dichloropalladium (82 mg, 0.12 mmol) and potassium phosphate (491 mg, 2.31 mmol) in 1,4-dioxane (20 mL) and water (4 mL) was stirred at 100° C. under nitrogen atmosphere for 2 h. The mixture was cooled to room temperature and concentrated under reduced pressure. The residue was purified by reverse flash chromatography with water (0.1% FA) and ACN (10% to 50% in 20 min); detector: UV 254 nm. The product was separated by Chiral HPLC with the following conditions: Column: CHIRALPAK IG, 20×250 mm, 5 μm; mobile phase: Hexanes (0.1% FA) and EtOH (hold EtOH 20% in 17 min); Detector: UV254 nm to afford the first eluting peak as Compound 176 (83 mg, 15%) as a grey solid and the second eluting peak as Compound 177 (52 mg, 9%) as a grey solid.

Compound 176

$^1$H NMR (CD$_3$OD, 400 MHz) δ (ppm): 8.14 (d, J=8.8 Hz, 1H), 7.96-7.86 (m, 2H), 7.34-7.26 (m, 4H), 4.80-4.64 (m, 1H), 4.00-3.55 (m, 4H), 3.52-3.36 (m, 2H), 2.24-1.83 (m, 5H), 1.80-1.49 (m, 2H), 1.42-0.88 (m, 4H). LCMS (ES, m/z): 474 [M+H]$^+$.

Compound 177

$^1$H NMR (CD$_3$OD, 400 MHz) δ (ppm): 8.10 (d, J=8.0 Hz, 1H), 7.94 (d, J=4.4 Hz, 1H), 7.83 (d, J=8.0 Hz, 1H), 7.32-7.25 (m, 4H), 4.80-4.67 (m, 1H), 3.98-3.65 (m, 4H), 3.56-3.37 (m, 2H), 2.28-2.12 (m, 2H), 2.09-1.83 (m, 3H), 1.74-1.55 (m, 2H), 1.38-1.20 (m, 2H), 1.16-1.12 (m, 1H), 0.99-0.94 (m, 1H). LCMS (ES, m/z): 474 [M+H]$^+$.

Method 35: Preparation of Compounds 120 and 121: 3-(4-((S)-6-((R)-tetrahydrofuran-2-carbonyl)-6-azaspiro[2.5]octan-1-yl)phenyl)quinoline-7-carboxylic Acid and 3-(4-((R)-6-((R)-tetrahydrofuran-2-carbonyl)-6-azaspiro[2.5]octan-1-yl)phenyl)quinoline-7-carboxylic Acid

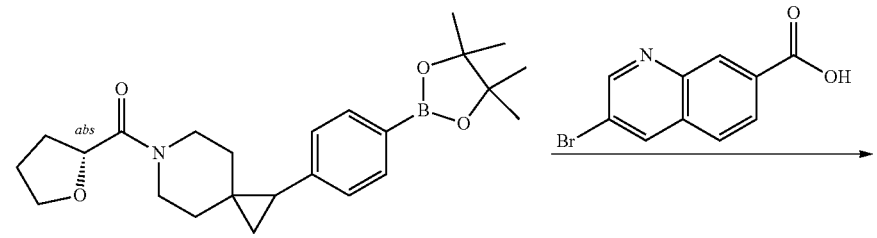

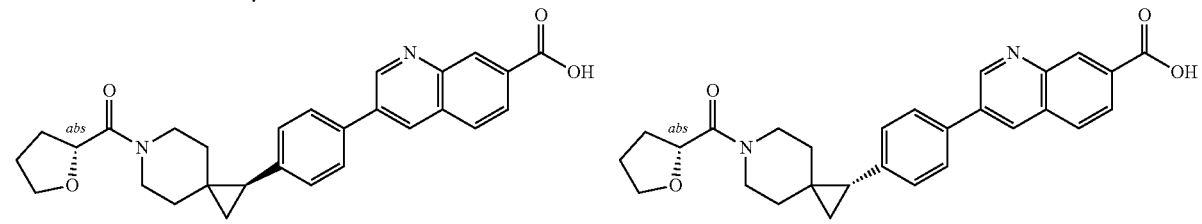

3-(4-((S)-6-((R)-tetrahydrofuran-2-carbonyl)-6-azaspiro[2.5]octan-1-yl)phenyl)quinoline-7-carboxylic Acid and 3-(4-((R)-6-((R)-tetrahydrofuran-2-carbonyl)-6-azaspiro[2.5]octan-1-yl)phenyl)quinoline-7-carboxylic Acid A solution of ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (450 mg, 1.10 mmol), 3-bromoquinoline-7-carboxylic acid (689 mg, 2.74 mmol), [1,1'-Bis(diphenylphosphino)ferrocene]dichloropalladium (89.3 mg, 0.11 mmol) and potassium phosphate (702 mg, 3.31 mmol) in 1,4-dioxane (15 mL) and water (3 mL) was stirred for 2 h at 80° C. under a nitrogen atmosphere. The mixture was cooled to room temperature and concentrated under reduced pressure. The crude product was purified by Prep-HPLC with water (0.1% FA) and ACN (40.0% up to 60.0% in 10 min). The product was separated by Chiral HPLC with the following conditions: Column: CHIRALPAK IF, 0.46×5 cm, 3 μm; mobile phase: hexanes (containing 0.1% formic acid):dichloromethane (3:1) and Methanol (hold 50% Methanol in 15 min); Detector: UV 254 nm to afford the first eluting peak as Compound 120 (119.2 mg, 24%) as a yellow solid and the second eluting peak as Compound 121 (119.3 mg, 34%) as a white solid.

Compound 120

$^1$H NMR (400 MHz, DMSO-d$_6$) δ (ppm): 13.30 (br, 1H), 9.39-9.38 (m, 1H), 8.74 (s, 1H), 8.60 (s, 1H), 8.15-8.08 (m, 2H), 7.86 (d, J=8.4 Hz, 2H), 7.45 (d, J=8.4 Hz, 2H), 4.72-4.55 (m, 1H), 3.78-3.59 (m, 6H), 2.15-2.10 (m, 1H), 2.04-1.73 (m, 4H), 1.68-1.42 (m, 2H), 1.28-0.88 (m, 4H). LCMS (ES, m/z): 457 [M+H]$^+$.

Compound 121

$^1$H NMR (400 MHz, DMSO-d$_6$) δ (ppm): 13.33 (br, 1H), 9.39 (s, 1H), 8.76 (s, 1H), 8.60 (s, 1H), 8.17-8.09 (m, 2H), 7.87 (d, J=8.0 Hz, 2H), 7.45 (d, J=8.4 Hz, 2H), 4.70-4.58 (m, 1H), 3.78-3.61 (m, 4H), 3.27-3.18 (m, 2H), 2.16-1.71 (m, 5H), 1.68-1.47 (m, 2H), 1.28-0.90 (m, 4H). LCMS (ES, m/z): 457 [M+H]$^+$.

Method 36: Preparation of Compounds 218 and 219: ((S)-tetrahydrofuran-2-yl)(1-(4-(4,4,5,5-tetramethyl-1,3,2-dioxaborolan-2-yl)phenyl)-6-azaspiro[2.5]octan-6-yl)methanone and ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone

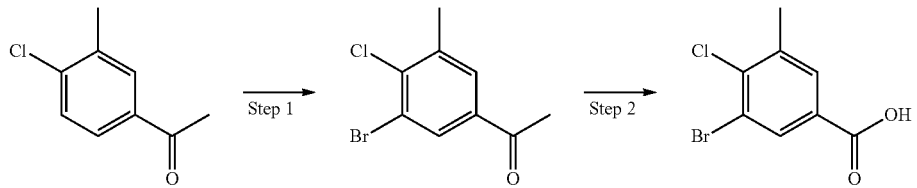

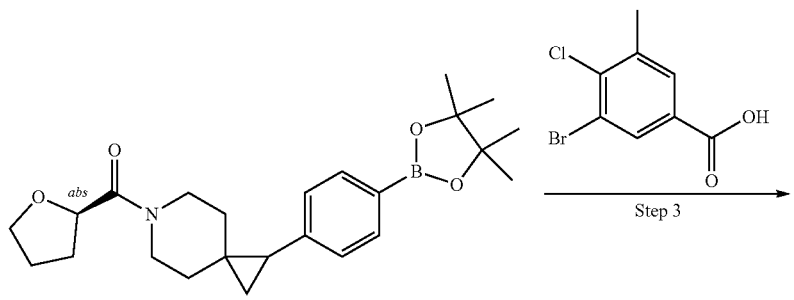

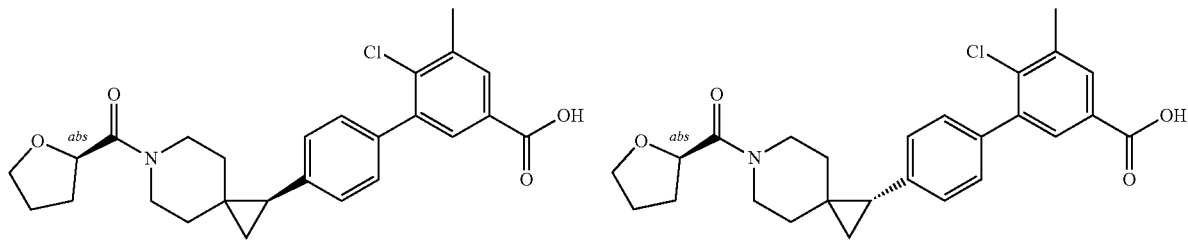

Step 1.
1-(3-bromo-4-chloro-5-methylphenyl)ethan-1-one

To a stirred mixture of 1-(4-chloro-3-methylphenyl) ethan-1-one (5 g, 29.65 mmol) and aluminum chloride (11.9 g, 88.95 mmol) was added bromine (5.45 g, 34.1 mmol). The resulting mixture was stirred for 2 h at 80° C. under nitrogen atmosphere. The reaction was quenched with water/ice (100 mL) and was extracted with ethyl acetate (3×300 mL). The combined organic layers were washed with brine (3×100 mL), dried over anhydrous sodium sulfate, filtered and concentrated under reduced pressure. The residue was purified by silica gel column chromatography, eluted with petroleum ether/ethyl acetate (1:1) to afford to afford 1-(3-bromo-4-chloro-5-methylphenyl) ethan-1-one (2.2 g, 28%) as a yellow solid. LCMS (ES, m/z): 247, 249 [M+H]+.

Step 2. 3-bromo-4-chloro-5-methylbenzoic Acid

A mixture of 1-(3-bromo-4-chloro-5-methylphenyl) ethan-1-one (1.00 g, 4.04 mmol) in sodium hypochlorite (15 mL) was stirred for 16 h at 40° C. under nitrogen atmosphere. The mixture was cooled to room temperature and diluted with water (20 mL) and was acidified to pH 5 with hydrochloric acid (2M). The resulting mixture was extracted with ethyl acetate (3×100 mL). The combined organic layers were dried over anhydrous sodium sulfate, filtered and concentrated under reduced pressure. The crude product was purified by Prep-HPLC with water (0.1% FA) and ACN (35% ACN up to 45% in 7 min) to afford 3-bromo-4-chloro-5-methylbenzoic acid (600 mg, 57%) as a white solid. LCMS (ES, m/z): 249, 251 [M+H]+.

Step 3. 6-chloro-5-methyl-4'-((S)-6-((R)-tetrahydrofuran-2-carbonyl)-6-azaspiro[2.5]octan-1-yl)-[1,1'-biphenyl]-3-carboxylic Acid and 6-chloro-5-methyl-4'-((R)-6-((R)-tetrahydrofuran-2-carbonyl)-6-azaspiro[2.5]octan-1-yl)-[1,1'-biphenyl]-3-carboxylic Acid A mixture of 3-bromo-4-chloro-5-methylbenzoic acid (550 mg, 2.20 mmol), ((R)-tetrahydrofuran-2-yl)(1-(4-(4,4,5,5-tetramethyl-1,3,2-dioxaborolan-2-yl)phenyl)-6-azaspiro[2.5]octan-6-yl)methanone (1.36 g, 3.31 mmol), potassium phosphate (941 mg, 4.43 mmol) and bis(di-tert-butyl(4-dimethylaminophenyl)phosphine)dichloropalladium (156 mg, 0.22 mmol) in 1,4-dioxane (15 mL) and water (3 mL) was stirred for 2.5 h at 80° C. under a nitrogen atmosphere. The mixture was cooled to room temperature and concentrated under reduced pressure. The residue was purified by reverse flash chromatography with water (0.1% formic acid) and acetonitrile (30% to 60% in 15 min). The product was separated by Chiral HPLC with the following conditions: Column: CHIRALPAK IC, 2×25 cm, 5 μm; mobile phase: Hexanes (containing 0.1% Formic acid) and ethanol (hold 40% ethanol in 16 min); Detector: UV 254 nm to afford the first eluting peak as Compound 218 (135.5 mg, 34%) as a yellow solid and the second eluting peak as Compound 219 (136.4 mg, 34%) as a yellow solid.

Compound 218

$^1$H NMR (400 MHz, Methanol-d$_4$) δ (ppm): 7.94 (s, 1H), 7.80 (s, 1H), 7.38-7.34 (m, 4H), 4.89-4.67 (m, 1H), 4.01-3.65 (m, 4H), 3.47-3.43 (m, 2H), 2.51 (s, 3H), 2.26-1.86 (m, 5H), 1.77-1.60 (m, 2H), 1.49-1.24 (m, 2H), 1.18-1.12 (m, 1H), 1.00-0.96 (m, 1H). LCMS (ES, m/z): 454 [M+H]+.

Compound 219

$^1$H NMR (400 MHz, Methanol-d$_4$) δ (ppm): 7.94 (s, 1H), 7.80 (s, 1H), 7.38-7.33 (m, 4H), 4.82-4.63 (m, 1H), 3.98-3.62 (m, 4H), 3.60-3.35 (m, 2H), 2.51 (s, 3H), 2.32-2.13 (m, 2H), 2.10-1.89 (m, 3H), 1.75-1.66 (m, 2H), 1.52-1.24 (m, 2H), 1.18-1.12 (m, 1H), 1.04-0.88 (m, 1H). LCMS (ES, m/z): 454 [M+H]+.

Method 37: Preparation of Compound 118: 4'-((S)-6-((R)-tetrahydrofuran-2-carbonyl)-6-azaspiro[2.5]octan-1-yl)-2-(trifluoromethyl)-[1,1'-biphenyl]-4-carboxylic acid

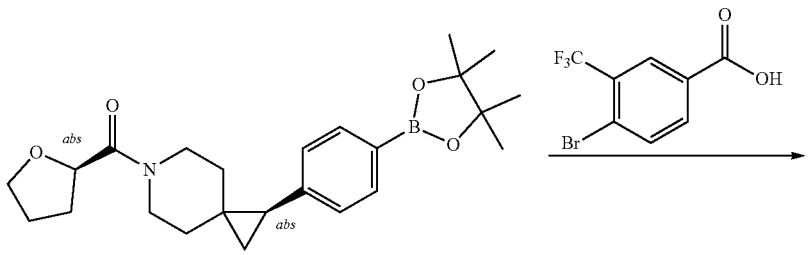

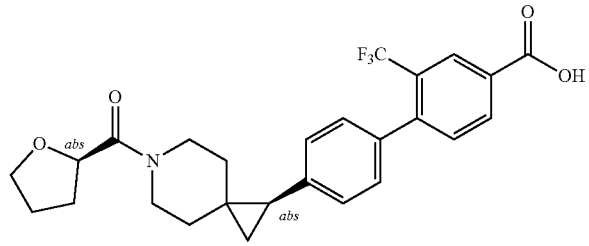

4'-((S)-6-((R)-tetrahydrofuran-2-carbonyl)-6-azaspiro[2.5]octan-1-yl)-2-(trifluoromethyl)-[1,1'-biphenyl]-4-carboxylic Acid A mixture of ((S)-tetrahydrofuran-2-yl)((R)-1-(4-(4,4,5,5-tetramethyl-1,3,2-dioxaborolan-2-yl)phenyl)-6-azaspiro[2.5]octan-6-yl)methanone (300 mg, 0.73 mmol), 4-bromo-3-(trifluoromethyl)benzoic acid (294 mg, 1.09 mmol), bis(di-tert-butyl(4-dimethylaminophenyl)phosphine)dichloropalladium (51.6 mg, 0.073 mmol) and potassium phosphate (310 mg, 1.46 mmol) in 1,4-dioxane (20 mL) and water (4 mL) was stirred for 2 h at 80° C. under nitrogen atmosphere. The resulting mixture was cooled to room temperature and concentrated under vacuum. The crude product was purified by Prep-HPLC with water (containing 0.1% Formic acid) and acetonitrile (60% acetonitrile up to 85% in 7 min) to afford 4'-((S)-6-((R)-tetrahydrofuran-2-carbonyl)-6-azaspiro[2.5]octan-1-yl)-2-(trifluoromethyl)-[1,1'-biphenyl]-4-carboxylic acid (Compound 118) (108 mg, 31%) as a white solid. 1H NMR (400 MHz, DMSO-d6) δ (ppm): 8.28 (s, 1H), 8.22 (d, J=8.0 Hz, 1H), 7.58-7.54 (m, 1H), 7.36-7.33 (m, 2H), 7.28-7.25 (m, 2H), 4.70-4.58 (m, 1H), 3.83-3.49 (m, 4H), 3.27-3.15 (m, 2H), 2.12-1.77 (m, 5H), 1.64-1.42 (m, 2H), 1.33-1.00 (m, 3H), 0.97-0.82 (m, 1H). LCMS (ES, m/z): 474 [M+H]$^+$.

Method 38: Preparation of Compound 119: 4'-((R)-6-((R)-tetrahydrofuran-2-carbonyl)-6-azaspiro[2.5]octan-1-yl)-2-(trifluoromethyl)-[1,1'-biphenyl]-4-carboxylic Acid

4'-((R)-6-((R)-tetrahydrofuran-2-carbonyl)-6-azaspiro[2.5]octan-1-yl)-2-(trifluoromethyl)-[1,1'-biphenyl]-4-carboxylic Acid A mixture of ((R)-tetrahydrofuran-2-yl)((R)-1-(4-(4,4,5,5-tetramethyl-1,3,2-dioxaborolan-2-yl)phenyl)-6-azaspiro[2.5]octan-6-yl)methanone (200 mg, 0.49 mmol), 4-bromo-3-(trifluoromethyl)benzoic acid (196 mg, 0.73 mmol), bis(di-tert-butyl(4-dimethylaminophenyl)phosphine)dichloropalladium (34.4 mg, 0.05 mmol) and potassium phosphate (206 mg, 0.97 mmol) in 1,4-dioxane (15 mL) and water (3 mL) was stirred for 2 h at 80° C. under nitrogen atmosphere. The resulting mixture was concentrated under vacuum. The crude product was purified by Prep-HPLC with water (containing 0.1% Formic acid) and acetonitrile (60% acetonitrile up to 85% in 7 min) to afford 4'-((R)-6-((R)-tetrahydrofuran-2-carbonyl)-6-azaspiro[2.5]octan-1-yl)-2-(trifluoromethyl)-[1,1'-biphenyl]-4-carboxylic acid (Compound 119) (48.3 mg, 21%) as a white solid. $^1$H NMR (400 MHz, DMSO-d6) (ppm): 13.55 (br, 1H), 8.24 (s, 1H), 8.23-8.21 (m, 1H), 7.57 (d, J=8.0 Hz, 1H), 7.36-7.33 (m, 2H), 7.28-7.25 (m, 2H), 4.70-4.58 (m, 1H), 3.78-3.53 (m, 4H), 3.25-3.07 (m, 2H), 2.13-1.76 (m, 5H), 1.57-1.44 (m, 2H), 1.23-1.00 (m, 3H), 0.92-0.87 (m, 1H). LCMS (ES, m/z): 474 [M+H]$^+$.

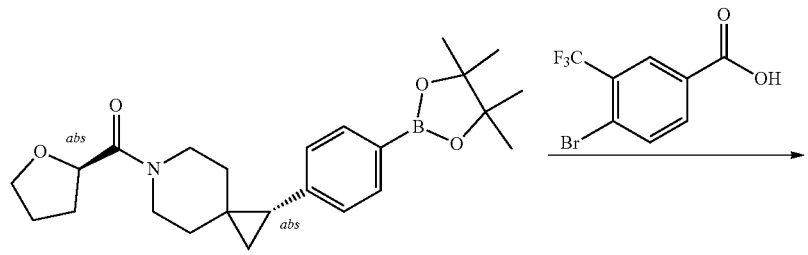

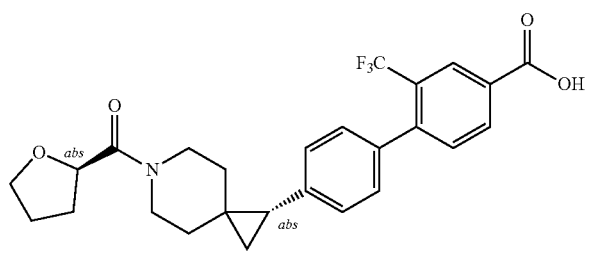

Method 38: Preparation of Compounds 44 and 45: 4-{4-[(1S)-6-(1-hydroxycyclopropanecarbonyl)-6-azaspiro[2.5]octan-1-yl]phenyl}-3-methylbenzoic Acid (44) and 4-{4-[(1R)-6-(1-hydroxycyclopropanecarbonyl)-6-azaspiro[2.5]octan-1-yl]phenyl}-3-methylbenzoic Acid (45)
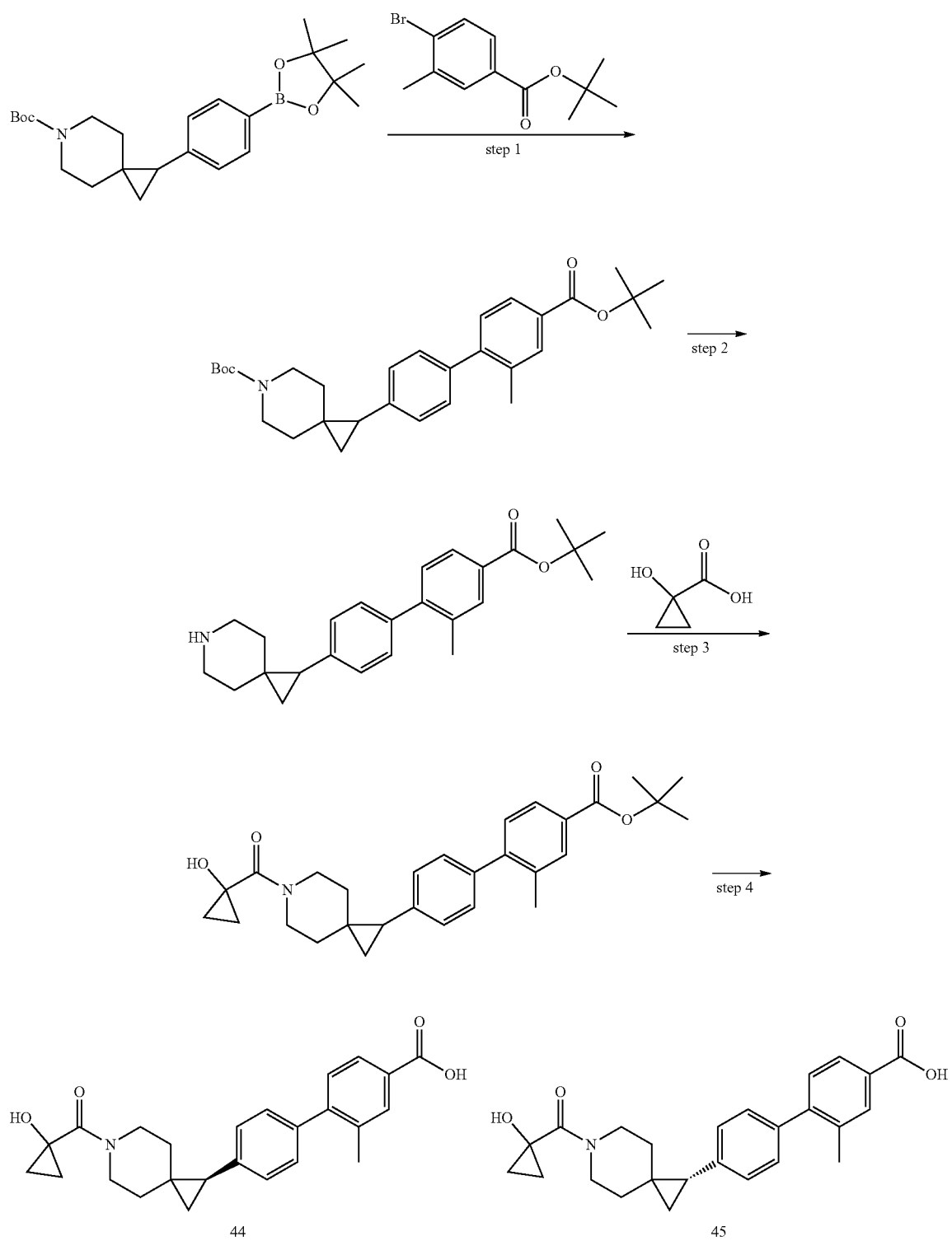

Step 1. tert-butyl 1-[4-[(tert-butoxy)carbonyl]-2-methyl-[1,1-biphenyl]-4-yl]-6-azaspiro[2.5]octane-6-carboxylate To a stirred solution of tert-butyl 1-[4-(4,4,5,5-tetramethyl-1,3,2-dioxaborolan-2-yl)phenyl]-6-azaspiro[2.5]octane-6-carboxylate (5.5 g, 13.32 mmol) and tert-butyl 4-bromo-3-methylbenzoate (3 g, 11.07 mmol) in dioxane (20 mL) and water (5 mL) were added bis(di-tert-butyl(4-dimethylaminophenyl)phosphine)dichloropalladium (784 mg, 1.12 mmol) and potassium phosphate (4.69 g, 22.14 mmol). The resulting mixture was stirred or 2 h at 80° C. under nitrogen atmosphere. The resulting mixture was extracted with ethyl acetate (3×100 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (5:1) to afford tert-butyl 1-[4-[(tert-butoxy)carbonyl]-2-methyl-[1,1-biphenyl]-4-yl]-6-azaspiro[2.5]octane-6-carboxylate (5.7 g, 97%) as a yellow oil. LCMS (ES, m/z): 478 [M+H]$^+$.

Step 2. tert-butyl 4-[6-azaspiro[2.5]octan-1-yl]-2-methyl-[1,1-biphenyl]-4-carboxylate A mixture of tert-butyl 1-[4-[(tert-butoxy)carbonyl]-2-methyl-[1,1-biphenyl]-4-yl]-6-azaspiro[2.5]octane-6-carboxylate (5.7 g, 11.93 mmol) and trifluoroacetic acid (10 mL) in dichloromethane (80 mL) was stirred at 0° C. for 0.5 h. The mixture was basified to pH 8 with saturated sodium bicarbonate. The resulting mixture was extracted with ethyl acetate (3×100 mL). The combined organic layers were washed with brine (2×100 mL), dried over anhydrous sodium sulfate, filtered and concentrated to yield tert-butyl 4-[6-azaspiro[2.5]octan-1-yl]-2-methyl-[1,1-biphenyl]-4-carboxylate (3.9 g, 78%) as a yellow oil. LCMS (ES, m/z): 378 [M+H]$^+$

Step 3. tert-butyl 4-[6-(1-hydroxycyclopropanecarbonyl)-6-azaspiro[2.5]octan-1-yl]-2-methyl-[1,1-biphenyl]-4-carboxylate A mixture of 1-hydroxycyclopropane-1-carboxylic acid (307 mg, 3.00 mmol), 1-hydroxybenzotriazole (406 mg, 3.00 mmol), 1-ethyl-3-(3-dimethyl aminopropyl)carbodiimide hydrochloride (720 mg, 3.76 mmol), tert-butyl 4-[6-azaspiro[2.5]octan-1-yl]-2-methyl-[1,1-biphenyl]-4-carboxylate (567 mg, 1.50 mmol) and N,N-dimethylformamide (10 mL) was stirred for 2 h at room temperature. The resulting mixture was diluted with water (50 mL) and was extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (3:1) to afford tert-butyl 4-[6-(1-hydroxycyclopropanecarbonyl)-6-azaspiro[2.5]octan-1-yl]-2-methyl-[1,1-biphenyl]-4-carboxylate (520 mg, 68%) as a yellow oil. LCMS (ES, m/z): 462 [M+H]$^+$

Step 4. 4-{4-[(1S)-6-(1-hydroxycyclopropanecarbonyl)-6-azaspiro[2.5]octan-1-yl]phenyl}-3-methylbenzoic acid (44) and 4-{4-[(1R)-6-(1-hydroxycyclopropanecarbonyl)-6-azaspiro[2.5]octan-1-yl]phenyl}-3-methylbenzoic Acid (45)

A mixture of tert-butyl 4-[6-(1-hydroxycyclopropanecarbonyl)-6-azaspiro[2.5] octan-1-yl]-2-methyl-[1,1-biphenyl]-4-carboxylate (500 mg, 1.08 mmol) and trifluoroacetic acid (3 mL) in dichloromethane (10 mL) was stirred for 2 h at room temperature. The resulting mixture was concentrated under vacuum. The crude product was purified by Prep-HPLC with water (containing 0.1% formic acid) and acetonitrile (20% acetonitrile up to 55% in 10 min) The product was separated by Chiral HPLC with the following conditions: Column: CHIRALPAK IA, 2×25 cm, 5 μm; mobile phase: Hexanes: (0.1% FA) and EtOH (hold 10% EtOH in 20 min); Detector: UV 254 nm to afford the first eluting peak as Compound 44 (129.5 mg, 29%) and the second eluting peak as Compound 45 (133 mg, 30%) as a white solid.

Compound 44

$^1$H-NMR (CD$_3$OD, 400 MHz) δ (ppm): 7.95 (s, 1H), 7.89 (d, J=8.0 Hz, 1H), 7.44-7.20 (m, 5H), 4.20-3.38 (m, 4H), 2.32 (s, 3H), 2.23-2.04 (m, 1H), 1.89-1.51 (m, 2H), 1.41-1.25 (m, 2H), 1.21-1.09 (m, 1H), 1.08-0.95 (m, 3H), 0.93-0.79 (m, 2H). LCMS (ES, m/z): 406 [M+H]$^+$.

Compound 45

$^1$H-NMR (CD$_3$OD, 400 MHz) δ (ppm): 7.95 (s, 1H), 7.89 (d, J=8.0 Hz, 1H), 7.40-7.20 (m, 5H), 4.18-3.39 (m, 4H), 2.32 (s, 3H), 2.23-2.10 (m, 1H), 1.85-1.48 (m, 2H), 1.47-1.22 (m, 2H), 1.20-1.10 (m, 1H), 1.09-0.95 (m, 3H), 0.94-0.69 (m, 2H). LCMS (ES, m/z): 406 [M+H]$^+$.

Method 39: Preparation of Compounds 196 and 197 (S)-4'-(6-(1H-1,2,3-triazole-5-carbonyl)-6-azaspiro[2.5]octan-1-yl)-6-methoxy-1,2,3,4,5,6-hexahydro-[1,1'-biphenyl]-3-carboxylic Acid and (R)-4'-(6-(1H-1,2,3-triazole-5-carbonyl)-6-azaspiro[2.5]octan-1-yl)-6-methoxy-1,2,3,4,5,6-hexahydro-[1,1'-biphenyl]-3-carboxylic Acid

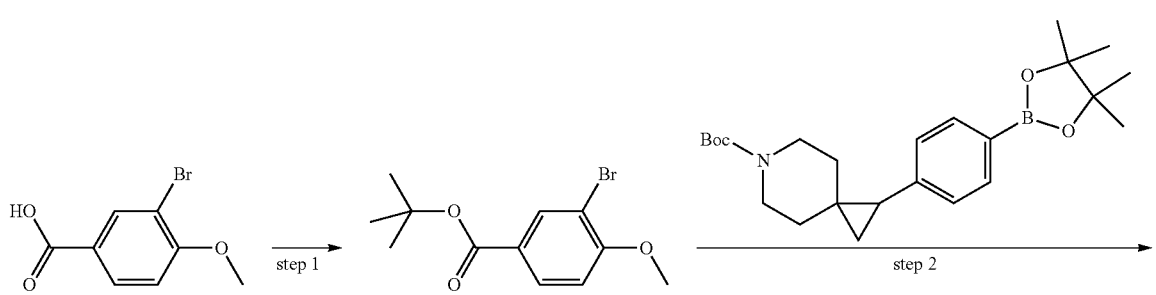

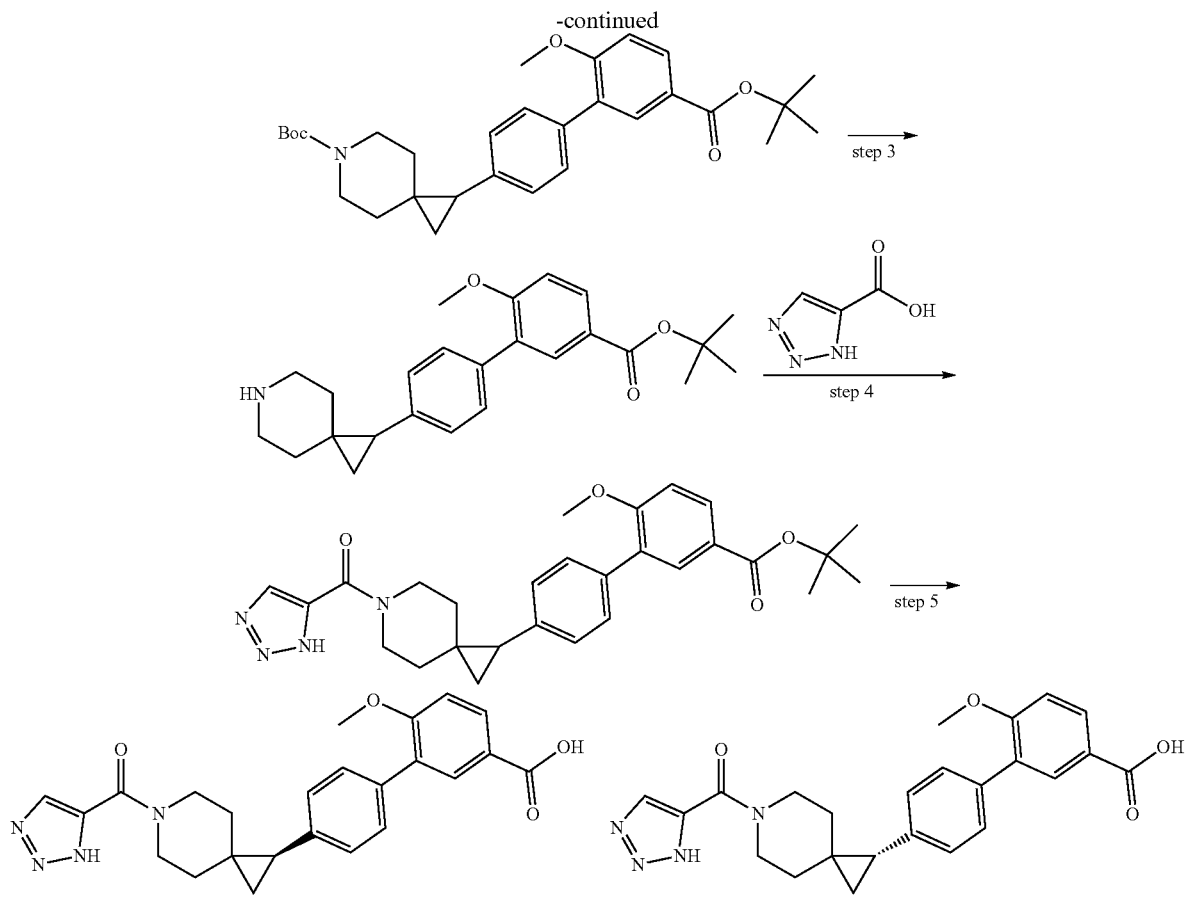

Step 1. tert-butyl 3-bromo-4-methoxybenzoate

To a stirred solution of 3-bromo-4-methoxybenzoic acid (5 g, 21.65 mmol) and 4-dimethylaminopyridine (1.3 g, 10.82 mmol) in tert-butanol (100 mL) was added di-tert-butyl dicarbonate (9.0 g, 41.28 mmol) in portions. The resulting mixture was stirred overnight at 50° C. under nitrogen atmosphere. The mixture was cooled to room temperature and concentrated. The residue was purified by silica gel column chromatography, eluted with petroleum ether/ethyl acetate (5:1) to afford tert-butyl 3-bromo-4-methoxybenzoate (1.6 g, 24%) as a white solid. LCMS: (ES, m/z): 287, 289 [M+H]+.

Step 2. tert-butyl 1-[5-[(tert-butoxy)carbonyl]-2-methoxy-[1,1-biphenyl]-4-yl]-6-azaspiro[2.5]octane-6-carboxylate To a stirred solution of tert-butyl 3-bromo-4-methoxybenzoate (1.6 g, 5.02 mmol), tert-butyl 1-[4-(4,4,5,5-tetramethyl-1,3,2-dioxaborolan-2-yl)phenyl]-6-azaspiro[2.5]octane-6-carboxylate (2.76 g, 6.34 mmol), bis(di-tert-butyl(4-dimethylaminophenyl)phosphine)dichloropalladium (320 mg, 0.45 mmol) and potassium phosphate (3.55 g, 15.89 mmol) in dioxane (25 mL) and water (5 mL) was stirred at 80° C. for 2 h under nitrogen atmosphere. The resulting mixture was cooled to room temperature and concentrated under reduced pressure. The residue was purified by silica gel column chromatography, eluted with petroleum ether/ethyl acetate (3:1) to afford tert-butyl 1-[5-[(tert-butoxy)carbonyl]-2-methoxy-[1,1-biphenyl]-4-yl]-6-azaspiro[2.5]octane-6-carboxylate (2.68 g, 85%) as a white solid. LCMS: (ES, m/z): 494 [M+H]+.

Step 3. tert-butyl 4-[6-azaspiro[2.5]octan-1-yl]-6-methoxy-[1,1-biphenyl]-3-carboxylate To a stirred solution of tert-butyl 1-[5-[(tert-butoxy)carbonyl]-2-methoxy-[1,1-biphenyl]-4-yl]-6-azaspiro[2.5]octane-6-carboxylate (2 g, 3.44 mmol) in dichloromethane (25 mL) was added trifluoroacetic acid (3 mL) dropwise. The mixture was stirred at 0° C. for 0.5 h. The mixture was basified to pH 8 with saturated sodium bicarbonate. The resulting mixture was extracted with ethyl acetate (3×50 mL). The combined organic layers were washed with brine (2×50 mL), dried over anhydrous sodium sulfate, filtered and concentrated to yield tert-butyl 4-[6-azaspiro[2.5]octan-1-yl]-6-methoxy-[1,1-biphenyl]-3-carboxylate (1.28 g, 80%) as a white solid. LCMS: (ES, m/z): 394 [M+H]+.

Step 4. tert-butyl 4'-(6-(1H-1,2,3-triazole-5-carbonyl)-6-azaspiro[2.5]octan-1-yl)-6-methoxy-[1,1'-biphenyl]-3-carboxylate To a mixture of 1H-1,2,3-triazole-5-carboxylic acid (253 mg, 2.13 mmol), N-(3-Dimethylaminopropyl)-N'-ethylcarbodiimide hydrochloride (439 mg, 2.18 mmol), 1-hydroxybenzotriazole (227 mg, 1.60 mmol), tert-butyl 6-methoxy-4'-(6-azaspiro[2.5]octan-1-yl)-[1,1'-biphenyl]-3-carboxylate (450 mg, 1.15 mmol) and 4-Methylmorpholine (339 mg, 3.35 mmol) in N,N-dimethylformamide (10 mL) was stirred for 2 h at room temperature. The crude product was purified by reverse flash chromatography with water (containing 0.1% FA) and ACN (15% to 50% over 40 min) to yield tert-butyl 4'-(6-(1H-1,2,3-triazole-5-carbonyl)-6-azaspiro[2.5]octan-1-yl)-6-methoxy-[1,1'-biphenyl]-3-carboxylate (400 mg, 69%) as a white solid. LCMS: (ES, m/z): 489 [M+H]$^+$.

Step 5. (S)-4'-(6-(1H-1,2,3-triazole-5-carbonyl)-6-azaspiro[2.5]octan-1-yl)-6-methoxy-1,2,3,4,5,6-hexahydro-[1,1'-biphenyl]-3-carboxylic acid and (R)-4'-(6-(1H-1,2,3-triazole-5-carbonyl)-6-azaspiro[2.5]octan-1-yl)-6-methoxy-1,2,3,4,5,6-hexahydro-[1,1'-biphenyl]-3-carboxylic Acid A mixture of tert-butyl 4'-(6-(1H-1,2,3-triazole-5-carbonyl)-6-azaspiro[2.5]octan-1-yl)-6-methoxy-[1,1'-biphenyl]-3-carboxylate (430 mg, 0.75 mmol) and trifluoroacetic acid (3 mL) in dichloromethane (10 mL) was stirred for 1 h at room temperature. The mixture was concentrated under vacuum. The crude product was purified by reverse flash chromatography with water (containing 0.1% FA) and acetonitrile (20% to 60% over 40 min). The product was separated by Chiral HPLC with the following conditions: column: CHIRALPAK IG-3 (0.46×5 cm, 3 µm); mobile phase: A: hexanes (0.1% FA) and B, EtOH (hold 40% EtOH in 12 min); Detector: UV 254 nm to afford the first eluting peak as Compound 196 (44.8 mg, 13%) as a white solid and the second eluting peak as Compound 197 (46 mg, 14%) as a white solid.

Compound 196

$^1$H-NMR (CD$_3$OD, 400 MHz) δ (ppm): 8.31-8.09 (m, 1H), 8.02 (d, J=8.4 Hz, 1H), 7.99-7.91 (m, 1H), 7.61-7.39 (m, 2H), 7.39-7.22 (m, 2H), 7.22-7.05 (m, 1H), 4.24-4.01 (m, 1H), 4.01-3.78 (m, 4H), 3.78-3.62 (m, 1H), 3.61-3.41 (m, 1H), 2.26-2.11 (m, 1H), 1.73 (s, 2H), 1.51-1.29 (m, 2H), 1.28-1.04 (m, 1H), 1.04-0.89 (m, 1H). LCMS: (ES, m/z): 433 [M+H]$^+$.

Compound 197

$^1$H-NMR (CD$_3$OD, 400 MHz) δ (ppm): 8.29-8.04 (m, 1H), 8.02 (d, J=8.8 Hz, 1H), 7.99-7.89 (m, 1H), 7.54-7.39 (m, 2H), 7.39-7.22 (m, 2H), 7.22-7.08 (m, 1H), 4.21-4.00 (m, 1H), 4.00-3.76 (m, 4H), 3.76-3.61 (m, 1H), 3.61-3.44 (m, 1H), 2.29-2.09 (m, 1H), 1.71 (s, 2H), 1.53-1.25 (m, 2H), 1.25-1.08 (m, 1H), 1.08-0.91 (m, H). LCMS: (ES, m/z): 433 [M+H]$^+$.

Method 40: Preparation of Compounds 194 and 195: (S)-4'-(6-(1H-pyrazole-5-carbonyl)-6-azaspiro[2.5]octan-1-yl)-6-methoxy-1,2,3,4,5,6-hexahydro-[1,1'-biphenyl]-3-carboxylic Acid and (R)-4'-(6-(1H-pyrazole-5-carbonyl)-6-azaspiro[2.5]octan-1-yl)-6-methoxy-1,2,3,4,5,6-hexahydro-[1,1'-biphenyl]-3-carboxylic Acid

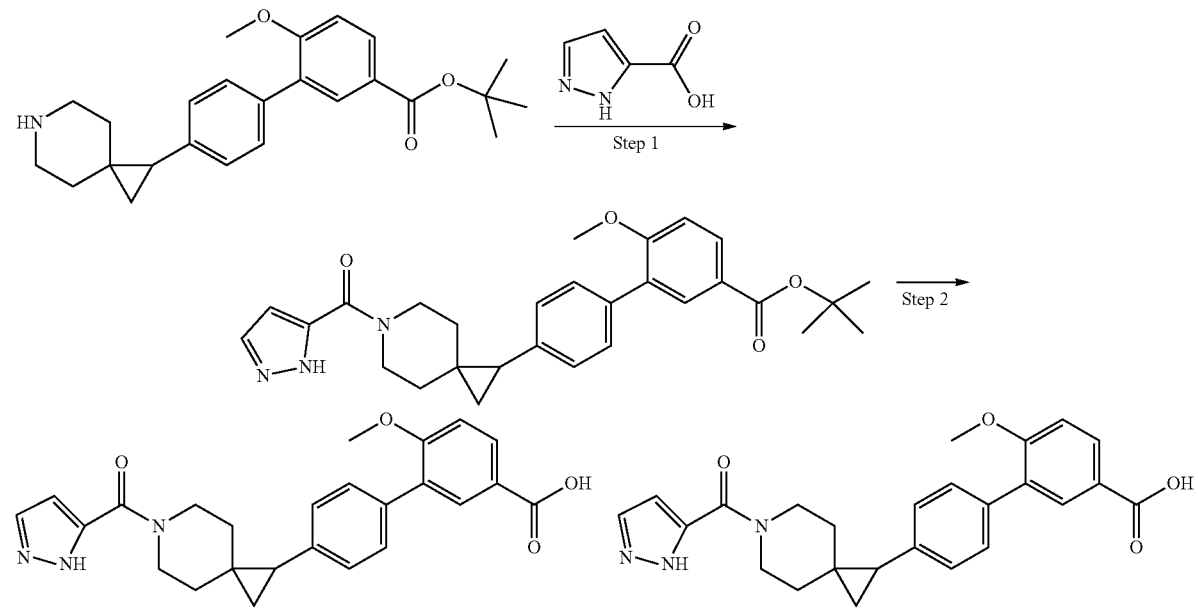

Step 1. tert-butyl 4'-(6-(1H-pyrazole-5-carbonyl)-6-azaspiro[2.5]octan-1-yl)-6-methoxy-[1,1'-biphenyl]-3-carboxylate To a stirred solution of 1H-pyrazole-5-carboxylic acid (160 mg, 1.43 mmol), N-(3-Dimethylaminopropyl)-N'-ethylcarbodiimide hydrochloride (624 mg, 3.25 mmol) and 1-hydroxybenzotriazole (352 mg, 2.60 mmol) in dichloromethane (10 mL) were added N-Methylmorpholine (395 mg, 3.91 mmol) and tert-butyl 4-[6-azaspiro[2.5]octan-1-yl]-6-methoxy-[1,1-biphenyl]-3-carboxylate (512.2 mg, 1.302 mmol) dropwise. The resulting mixture was stirred for 2 h at room temperature. The resulting mixture was diluted with water (30 mL) and was extracted with dichloromethane (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:1) to afford tert-butyl 4'-(6-(1H-pyrazole-5-carbonyl)-6-azaspiro[2.5]

octan-1-yl)-6-methoxy-[1,1'-biphenyl]-3-carboxylate (400 mg, 57%) as a yellow oil. LCMS (ES, m/z): 488 [M+H]$^+$.

Step 2. (S)-4'-(6-(1H-pyrazole-5-carbonyl)-6-azaspiro[2.5]octan-1-yl)-6-methoxy-1,2,3,4,5,6-hexahydro-[1,1'-biphenyl]-3-carboxylic Acid and (R)-4'-(6-(1H-pyrazole-5-carbonyl)-6-azaspiro[2.5]octan-1-yl)-6-methoxy-1,2,3,4,5,6-hexahydro-[1,1'-biphenyl]-3-carboxylic Acid A solution of tert-butyl 6-methoxy-4-[6-(1H-pyrazole-5-carbonyl)-6-azaspiro[2.5]octan-1-yl]-[1,1-biphenyl]-3-carboxylate (400 mg, 0.820 mmol) and trifluoroacetic acid (4 mL) in dichloromethane (12 mL) was stirred at room temperature for 2 h. The resulting mixture was concentrate under vacuum. The crude product was purified by Prep-HPLC with water (containing 0.1% FA) and acetonitrile (10% to 50% over 45 min). The product was separated by Chiral HPLC with the following conditions: Column: CHIRALPAK IE, 2×5 cm, 5 μm; mobile phase: Hexanes (0.1% FA) and EtOH (hold 40% EtOH in 23 min); Detector: UV254 nm to afford the first eluting peak as Compound 194 (58.3 mg, 16%) and the second eluting peak as Compound 195 (62.8 mg, 17%) as a white solid.

Compound 194

$^1$H-NMR (CD$_3$OD, 400 MHz) δ (ppm): 8.10-7.89 (m, 2H), 7.82-7.62 (m, 1H), 7.62-7.39 (m, 2H), 7.39-7.23 (m, 2H), 7.16 (d, J=8.0 Hz, 1H), 6.72-6.26 (m, 1H), 4.09-3.80 (m, 5H), 3.80-3.40 (m, 2H), 2.25-2.05 (m, 1H), 1.91-1.60 (m, 2H), 1.48-1.28 (m, 2H), 1.22-1.07 (m, 1H), 1.07-0.85 (m, 1H). LCMS (ES, m/z): 432 [M+H]$^+$.

Compound 195

$^1$H-NMR (CD$_3$OD, 400 MHz) δ (ppm): 8.11-7.89 (m, 2H), 7.78-7.58 (m, 1H), 7.52-7.40 (m, 2H), 7.40-7.23 (m, 2H), 7.16 (d, J=7.2 Hz, 1H), 6.72-6.49 (m, 1H), 4.09-3.78 (m, 5H), 3.78-3.43 (m, 2H), 2.28-2.05 (m, 1H), 1.80-1.55 (m, 2H), 1.46-1.23 (m, 2H), 1.19-1.08 (m, 1H), 1.08-0.88 (m, 1H). LCMS (ES, m/z): 432 [M+H]$^+$.

Method 41: Preparation of Compounds 142 and 143: (S)-4'-(6-(1H-1,2,3-triazole-5-carbonyl)-6-azaspiro[2.5]octan-1-yl)-2-methyl-[1,1'-biphenyl]-4-carboxylic Acid and (R)-4'-(6-(1H-1,2,3-triazole-5-carbonyl)-6-azaspiro[2.5]octan-1-yl)-2-methyl-[1,1'-biphenyl]-4-carboxylic Acid

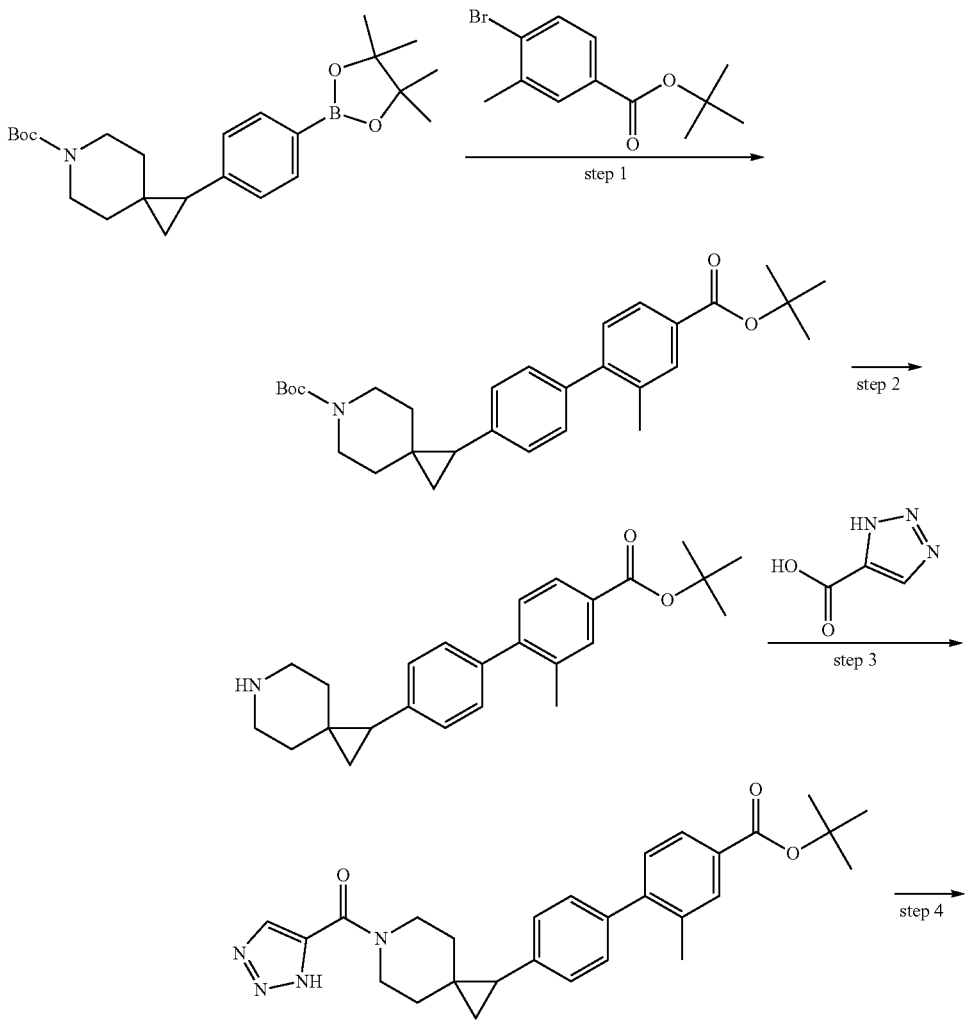

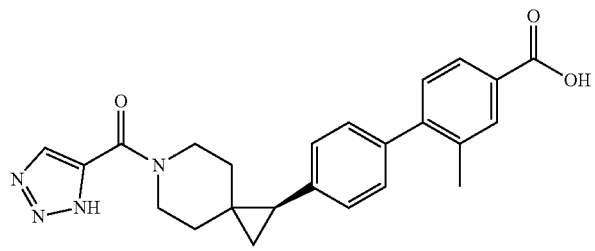 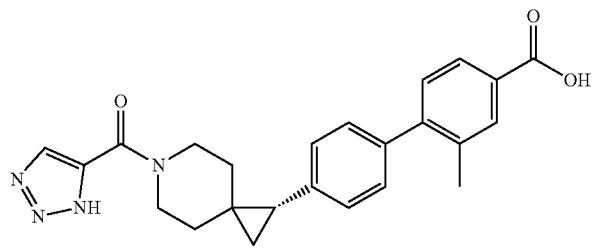

Step 1. tert-butyl 1-(4'-(tert-butoxycarbonyl)-2'-methyl-[1,1'-biphenyl]-4-yl)-6-azaspiro[2.5]octane-6-carboxylate To a stirred solution of tert-butyl 1-[4-(4,4,5,5-tetramethyl-1,3,2-dioxaborolan-2-yl)phenyl]-6-azaspiro[2.5]octane-6-carboxylate (5.5 g, 13.32 mmol) and tert-butyl 4-bromo-3-methylbenzoate (3 g, 11.07 mmol) in dioxane (30 mL) and water (6 mL) were added bis(4-(di-tert-butylphosphanyl)-N,N-dimethylaniline)dichloropalladium (784 mg, 1.11 mmol) and potassium phosphate (4.69 g, 22.14 mmol). The resulting mixture was stirred for 2 h at 80° C. under nitrogen atmosphere. The resulting mixture was extracted with ethyl acetate (3×100 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (5:1) to afford tert-butyl 1-(4'-(tert-butoxycarbonyl)-2'-methyl-[1,1'-biphenyl]-4-yl)-6-azaspiro[2.5]octane-6-carboxylate (5.7 g, 97%) as a yellow oil. LCMS (ES, m/z): 478 [M+H]$^+$

Step 2. tert-butyl 2-methyl-4'-(6-azaspiro[2.5]octan-1-yl)-[1,1'-biphenyl]-4-carboxylate To a stirred solution of tert-butyl 1-[4-[(tert-butoxy)carbonyl]-2-methyl-[1,1-biphenyl]-4-yl]-6-azaspiro[2.5]octane-6-carboxylate (5.7 g, 11.93 mmol) in dichloromethane (100 mL) were added trifluoroacetic acid (10 mL) dropwise. The mixture was stirred at 0° C. for 0.5 h. The mixture was basified to pH 8 with saturated sodium bicarbonate. The resulting mixture was extracted with dichloromethane (3×100 mL). The combined organic layers were washed with brine (100 mL), dried over anhydrous sodium sulfate, filtered and concentrated under reduced pressure to yield tert-butyl 2-methyl-4'-(6-azaspiro[2.5]octan-1-yl)-[1,1'-biphenyl]-4-carboxylate (3.9 g, 78%) as a yellow oil. LCMS (ES, m/z): 378 [M+H]$^+$

Step 3. tert-butyl 4'-(6-(1H-1,2,3-triazole-5-carbonyl)-6-azaspiro[2.5]octan-1-yl)-2-methyl-[1,1'-biphenyl]-4-carboxylate A mixture of 1H-1,2,3-triazole-5-carboxylic acid (250 mg, 2.10 mmol), N-(3-Dimethylaminopropyl)-N'-ethylcarbodiimide hydrochloride (500 mg, 2.48 mmol) and 1-hydroxybenzotriazole (250 mg, 1.76 mmol), N-Methylmorpholine (400 mg, 3.76 mmol) and tert-butyl 4-[6-azaspiro[2.5]octan-1-yl]-2-methyl-[1,1-biphenyl]-4-carboxylate (500 mg, 1.19 mmol) in N,N-Dimethylformamide (10 mL) was stirred for 1 h at room temperature. The resulting mixture was diluted with water (30 mL). The resulting mixture was extracted with ethyl acetate (3×30 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:1) to afford tert-butyl 4'-(6-(1H-1,2,3-triazole-5-carbonyl)-6-azaspiro[2.5]octan-1-yl)-2-methyl-[1,1'-biphenyl]-4-carboxylate (500 mg, 80%) as a yellow oil. LCMS (ES, m/z): 473 [M+H]$^+$

Step 4. (S)-4'-(6-(1H-1,2,3-triazole-5-carbonyl)-6-azaspiro[2.5]octan-1-yl)-2-methyl-[1,1'-biphenyl]-4-carboxylic acid and (R)-4'-(6-(1H-1,2,3-triazole-5-carbonyl)-6-azaspiro[2.5]octan-1-yl)-2-methyl-[1,1'-biphenyl]-4-carboxylic Acid A mixture of tert-butyl 4'-(6-(1H-1,2,3-triazole-5-carbonyl)-6-azaspiro[2.5]octan-1-yl)-2-methyl-[1,1'-biphenyl]-4-carboxylate (400 mg, 0.77 mmol) and trifluoroacetic acid (3 mL) in dichloromethane (10 mL) was stirred for 1 h at room temperature. The resulting mixture was concentrated under vacuum. The crude product was purified by reverse phase chromatography with water (containing 0.1% FA) and ACN (5% to 50% over 50 min). The product was separated by Chiral HPLC (Column: CHIRALPAK IG, 20×250 mm, 5 µm; Mobile Phase A: Hexanes (containing 0.1% FA) and B: EtOH (hold 50% EtOH in 23 min); Detector: UV254 nm to afford the first eluting peak as Compound 142 (134.4 mg, 83%) as a white solid and the second eluting peak as Compound 143 (128.0 mg, 79%) as a white solid.

Compound 142

$^1$H-NMR (CD$_3$OD, 400 MHz) δ (ppm): 8.41-8.01 (m, 1H), 8.01-7.93 (m, 1H), 7.93-7.75 (m, 1H), 7.49-7.18 (m, 5H), 4.21-4.02 (m, 1H), 4.02-3.83 (m, 1H), 3.83-3.48 (m, 2H), 2.31 (s, 3H), 2.26-2.12 (m, 1H), 1.88-1.63 (m, 2H), 1.45-1.33 (m, 2H), 1.21-1.12 (m, 1H), 1.05-0.97 (m, 1H). LCMS (ES, m/z): 417 [M+H]$^+$

Compound 143

$^1$H-NMR (CD$_3$OD, 400 MHz) δ (ppm): 8.38-8.02 (m, 1H), 8.02-7.93 (m, 1H), 7.93-7.76 (m, 1H), 7.49-7.17 (m, 5H), 4.21-4.02 (m, 1H), 4.02-3.85 (m, 1H), 3.85-3.70 (m, 1H), 3.70-3.50 (m, 1H), 2.32 (s, 3H), 2.22-2.06 (m, 1H), 1.82-1.61 (m, 2H), 1.49-1.31 (m, 2H), 1.27-1.08 (m, 1H), 1.08-0.88 (m, 1H). LCMS (ES, m/z): 417 [M+H]$^+$.

Method 42: Preparation of Compounds 134 and 135: 3-methyl-4-{4-[(1S)-6-(1,3-oxazole-2-carbonyl)-6-azaspiro[2.5]octan-1-yl]phenyl}benzoic Acid and 3-methyl-4-{4-[(1R)-6-(1,3-oxazole-2-carbonyl)-6-azaspiro[2.5]octan-1-yl]phenyl}benzoic Acid

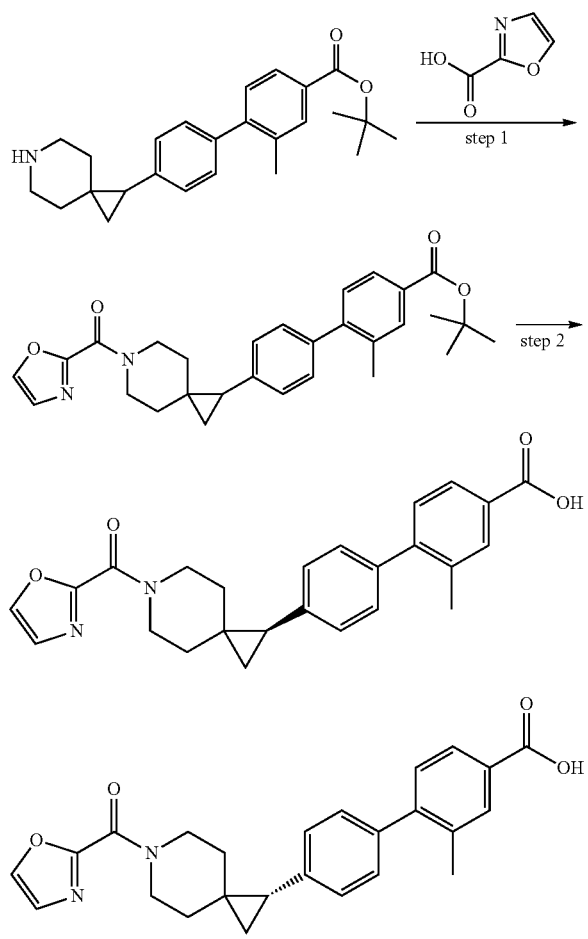

Step 1. tert-butyl 2-methyl-4'-(6-(oxazole-2-carbonyl)-6-azaspiro[2.5]octan-1-yl)-[1,1'-biphenyl]-4-carboxylate A solution of 1,3-oxazole-2-carboxylic acid (250 mg, 2.10 mmol), N-(3-Dimethylaminopropyl)-N'-ethylcarbodiimide hydrochloride (500 mg, 2.48 mmol) and 1-hydroxybenzotriazole (250 mg, 1.76 mmol), N-methylmorpholine (400 mg, 3.76 mmol) and tert-butyl 4-[6-azaspiro[2.5]octan-1-yl]-2-methyl-[1,1-biphenyl]-4-carboxylate (500 mg, 1.19 mmol) in N,N-dimethylformamide (10 mL) was stirred for 1 h at room temperature. The resulting mixture was diluted with water (30 mL). The resulting mixture was extracted with ethyl acetate (3×30 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:1) to afford tert-butyl 2-methyl-4-[6-(1,3-oxazole-2-carbonyl)-6-azaspiro[2.5]octan-1-yl]-[1,1-biphenyl]-4-carboxylate (510 mg, 81%) as a yellow oil. LCMS (ES, m/z): 473 [M+H]$^+$.

Step 2. 3-methyl-4-{4-[(1S)-6-(1,3-oxazole-2-carbonyl)-6-azaspiro[2.5]octan-1-yl]phenyl}benzoic Acid and 3-methyl-4-{4-[(1R)-6-(1,3-oxazole-2-carbonyl)-6-azaspiro[2.5]octan-1-yl]phenyl}benzoic Acid A solution of tert-butyl 2-methyl-4-[6-(1,3-oxazole-2-carbonyl)-6-azaspiro[2.5]octan-1-yl]-[1,1-biphenyl]-4-carboxylate (320 mg, 0.61 mmol) and trifluoroacetic acid (3 mL) in dichloromethane (10 mL) was stirred for 1 h at room temperature. The resulting mixture was concentrated under vacuum. The crude product was purified by reverse phase chromatography (Column: C18; Mobile phase: A: water (containing 0.1% FA) and B: ACN (5% to 40% over 60 min); Detector: UV 254 nm). The product was separated by Chiral HPLC (Column: CHIRALPAK IG, 20×250 mm, 5 µm; Mobile Phase A: Hexanes (containing 0.1% FA) and B: EtOH (hold 50% in 23 min); Detector: UV 254 nm to afford the first eluting peak as Compound 134 (91.2 mg, 71%) as an off-white solid and the second eluting peak as Compound 135 (86.7 mg, 68%) as a white solid.

Compound 134

$^1$H-NMR (CD$_3$OD, 400 MHz) δ (ppm): 8.12-8.02 (m, 1H), 8.01-7.92 (m, 1H), 7.92-7.82 (m, 1H), 7.43-7.23 (m, 6H), 4.21-4.05 (m, 1H), 3.98-3.44 (m, 3H), 2.31 (s, 3H), 2.26-2.12 (m, 1H), 1.88-1.63 (m, 2H), 1.45-1.33 (m, 2H), 1.21-1.12 (m, 1H), 1.05-0.97 (m, 1H). LCMS (ES, m/z): 417[M+H]$^+$.

Compound 135

$^1$H-NMR (CD$_3$OD, 400 MHz) δ (ppm): 8.12-8.02 (m, 1H), 7.99-7.92 (m, 1H), 7.92-7.82 (m, 1H), 7.42-7.22 (m, 6H), 4.21-4.03 (m, 1H), 4.03-3.73 (m, 2H), 3.73-3.50 (m, 1H), 2.32 (s, 3H), 2.26-2.12 (m, 1H), 1.83-1.63 (m, 2H), 1.47-1.31 (m, 2H), 1.24-1.12 (m, 1H), 1.07-0.95 (m, 1H). LCMS (ES, m/z): 417[M+H]$^+$.

Method 43: Preparation of Compounds 182 and 183 (S)-(1-(3'-(2H-tetrazol-5-yl)-[1,1'-biphenyl]-4-yl)-6-azaspiro[2.5]octan-6-yl)(cyclopropyl)methanone and (R)-(1-(3'-(2H-tetrazol-5-yl)-[1,1'-biphenyl]-4-yl)-6-azaspiro[2.5]octan-6-yl)(cyclopropyl)methanone

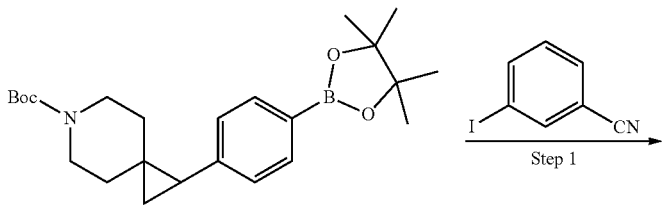

-continued

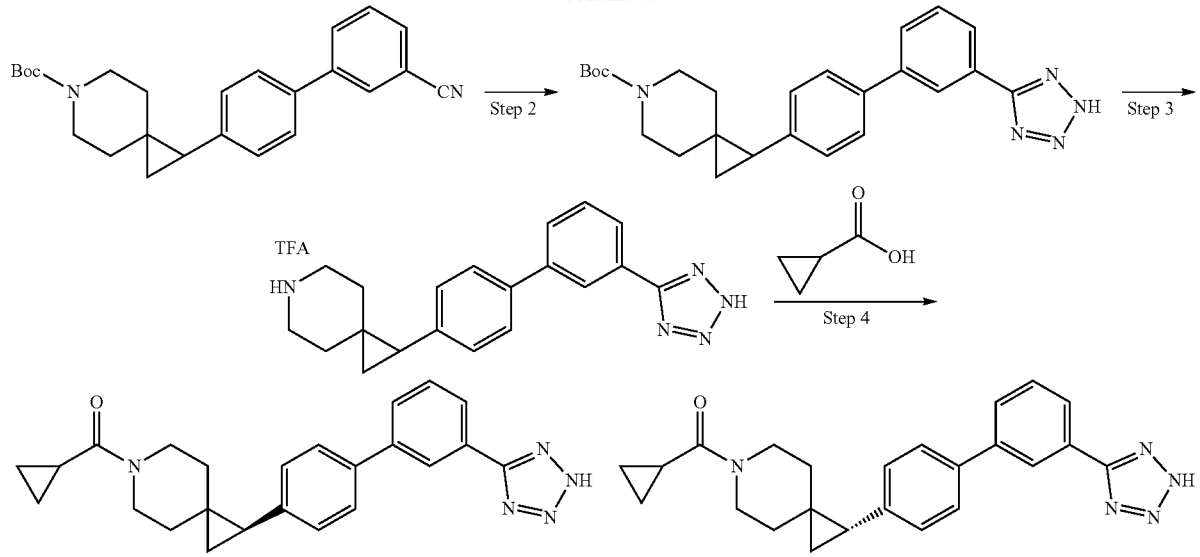

Step 1. tert-butyl 1-(3'-cyano-[1,1'-biphenyl]-4-yl)-6-azaspiro[2.5]octane-6-carboxylate A mixture of tert-butyl 1-[4-(4,4,5,5-tetramethyl-1,3,2-dioxaborolan-2-yl)phenyl]-6-azaspiro[2.5]octane-6-carboxylate (1.50 g, 3.63 mmol), 3-iodobenzonitrile (832 mg, 3.63 mmol), potassium phosphate (2.30 g, 10.89 mmol) and bis(di-tert-butyl(4-dimethylaminophenyl)phosphine)dichloropalladium (91 mg, 0.103 mmol) in water (3 mL) and dioxane (15 mL) was stirred for 2 h at 80° C. under nitrogen atmosphere. The mixture was cooled to room temperature and concentrated under vacuum. The residue was purified by silica gel column chromatography, eluted with petroleum ether/ethyl acetate (1:1) to afford tert-butyl 1-(3'-cyano-[1,1'-biphenyl]-4-yl)-6-azaspiro[2.5]octane-6-carboxylate (1.67 g, 93%) as a white solid. LCMS (ES, m/z): 389 [M+H]$^+$.

Step 2. tert-butyl 1-(3'-(2H-tetrazol-5-yl)-[1,1'-biphenyl]-4-yl)-6-azaspiro[2.5]octane-6-carboxylate A solution of tert-butyl 1-(3'-cyano-[1,1'-biphenyl]-4-yl)-6-azaspiro[2.5]octane-6-carboxylate (1.67 g, 4.30 mmol), sodium azide (840 mg, 12.92 mmol), zinc chloride (877 mg, 6.45 mmol) and water (4 mL) in tert-Butanol (18 mL) was stirred for 16 h at 90° C. under nitrogen atmosphere. The reaction was cooled to room temperature and quenched with saturated sodium bicarbonate (100 mL) at room temperature. The resulting mixture was extracted with dichloromethane/methanol (10:1) (2×100 mL). The combined organic layers were washed with brine (100 mL), dried over anhydrous sodium sulfate, filtered and concentrated under reduced pressure. The residue was purified by silica gel column chromatography, eluted with dichloromethane/methanol (10:1) to afford tert-butyl 1-(3'-(2H-tetrazol-5-yl)-[1,1'-biphenyl]-4-yl)-6-azaspiro[2.5]octane-6-carboxylate (700 mg, 38%) as a white solid. LCMS (ES, m/z): 432 [M+H]$^+$.

Step 3. 1-(3'-(2H-tetrazol-5-yl)-[1,1'-biphenyl]-4-yl)-6-azaspiro[2.5]octane trifluoroacetate A solution of tert-butyl 1-(3'-(2H-tetrazol-5-yl)-[1,1'-biphenyl]-4-yl)-6-azaspiro[2.5]octane-6-carboxylate (700 mg, 1.62 mmol) and trifluoroacetic acid (2 mL) in dichloromethane (10 mL) was stirred for 1 h at room temperature. The resulting mixture was concentrated under vacuum to afford 1-(3'-(2H-tetrazol-5-yl)-[1,1'-biphenyl]-4-yl)-6-azaspiro[2.5]octane trifluoroacetate (530 mg, crude) as a yellow solid, which was used in next step without further purification. LCMS (ES, m/z): 332 [M+H]$^+$.

Step 4. (S)-(1-(3'-(2H-tetrazol-5-yl)-[1,1'-biphenyl]-4-yl)-6-azaspiro[2.5]octan-6-yl)(cyclopropyl)methanone and (R)-(1-(3'-(2H-tetrazol-5-yl)-[1,1'-biphenyl]-4-yl)-6-azaspiro[2.5]octan-6-yl)(cyclopropyl)methanone A solution of 1-[3-(2H-1,2,3,4-tetrazol-5-yl)-[1,1-biphenyl]-4-yl]-6-azaspiro[2.5]octane trifluoroacetate (265 mg, 0.80 mmol), cyclopropane carboxylic acid (122 mg, 1.42 mmol), N-(3-dimethylaminopropyl)-N'-ethylcarbodiimide hydrochloride (385 mg, 2.01 mmol), 1-hydroxybenzotriazole (212 mg, 1.61 mmol) and 4-Methylmorpholine (0.45 ml, 4.01 mmol) in dichloromethane (10 mL) was stirred for 1 h at room temperature. The resulting mixture was diluted with water (50 mL) and was extracted with ethyl acetate (2×50 mL). Then the combined organic layers were washed with brine (2×50 mL), dried over anhydrous sodium sulfate, filtered and concentrated under reduced pressure. The residue was purified by reverse flash chromatography with water (0.1% FA) and ACN (10% to 50% in 10 min). The crude product was purified by Chiral HPLC with the following conditions: Column: CHIRALPAK IG-3, 0.46×5 mm, 3 um; mobile phase: hexanes (0.1% FA):EtOH 50:50 (hold 50% EtOH in 19 min), Detector: UV254 nm to afford the first eluting peak as Compound 182 (86.2 mg, 35%) as a white solid and the second eluting peak as Compound 183 (82 mg, 33%).

Compound 182

$^1$H NMR (CD$_3$OD, 400 MHz) δ (ppm): 8.31 (s, 1H), 8.00 (d, J=7.6 Hz, 1H), 7.87 (d, J=8.0 Hz, 1H), 7.80-7.62 (m, 3H), 7.45-7.33 (m, 2H), 3.92-3.85 (m, 1H), 3.78-3.73 (m, 2H), 3.59-3.45 (m, 1H), 2.18-2.12 (m, 1H), 2.11-1.80 (m, 1H), 1.74-1.50 (m, 2H), 1.44-1.21 (m, 2H), 1.17-1.12 (m, 1H), 1.01-0.93 (m, 1H), 0.91-0.68 (m, 4H). LCMS (ES, m/z): 400 [M+H]+.

Compound 183

1H NMR (CD3OD, 400 MHz) δ (ppm): 8.31 (s, 1H), 8.00 (d, J=8.0 Hz, 1H), 7.87 (d, J=8.0 Hz, 1H), 7.70-7.61 (m, 3H), 7.45-7.33 (m, 2H), 3.94-3.88 (m, 1H), 3.82-3.60 (m, 2H), 3.59-3.43 (m, 1H), 2.19-2.16 (m, 1H), 2.07-1.81 (m, 1H), 1.72-1.59 (m, 2H), 1.45-1.23 (m, 2H), 1.19-1.11 (m, 1H), 1.00-0.98 (m, 1H), 0.94-0.67 (m, 4H). LCMS (ES, m/z): 400 [M+H]+.

Method 44: Preparation of Compounds 210 and 211: (S)-4'-(6-(1-aminocyclopropane-1-carbonyl)-6-azaspiro[2.5]octan-1-yl)-[1,1'-biphenyl]-4-carboxylic Acid and (R)-4'-(6-(1-aminocyclopropane-1-carbonyl)-6-azaspiro[2.5]octan-1-yl)-[1,1'-biphenyl]-4-carboxylic Acid

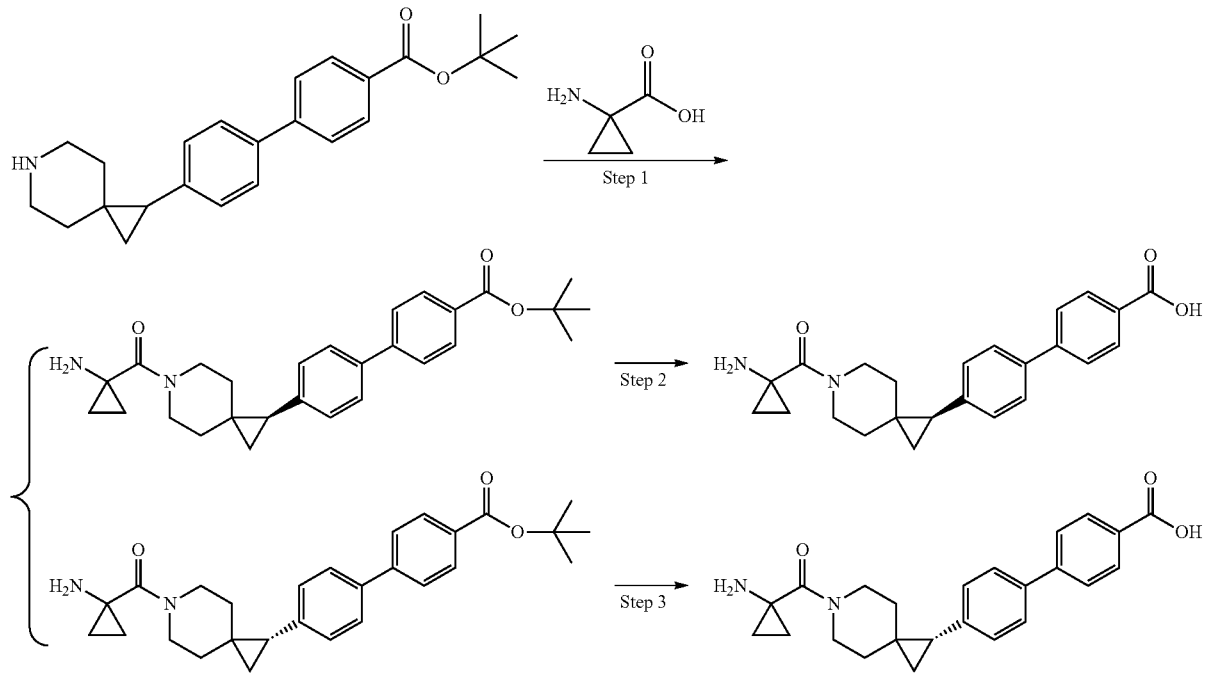

Step 1. tert-butyl (S)-4'-(6-(1-aminocyclopropane-1-carbonyl)-6-azaspiro[2.5]octan-1-yl)-[1,1'-biphenyl]-4-carboxylate and tert-butyl (R)-4'-(6-(1-aminocyclopropane-1-carbonyl)-6-azaspiro[2.5]octan-1-yl)-[1,1'-biphenyl]-4-carboxylate To a stirred mixture of tert-butyl 4'-(6-azaspiro[2.5]octan-1-yl)-[1,1'-biphenyl]-4-carboxylate and 1-aminocyclopropane-1-carboxylic acid (0.83 g, 8.24 mmol) in N,N-dimethylformamide (20 mL) were added 1-hydroxybenzotriazole (1.12 g, 8.36 mmol), N'-(ethylcarbonimidoyl)-N,N-dimethyl hydrochloride (2.37 g, 12.35 mmol) and N-methylmorpholine (2.09 g, 20.65 mmol). The resulting mixture was stirred for 2 h at room temperature. The reaction was quenched with water (120 mL) and extracted with ethyl acetate (3×150 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (1:1). The product was separated by Prep-Chiral HPLC with the following conditions: Column: CHIRALPAK IA-3, 0.46×5 cm; 3 μm; mobile phase: A, Hexanes (0.1% FA) and B, EtOH (hold EtOH 70% for 14 min); Detector: UV 254 nm to afford the first eluting peak as Compound I-210 (180 mg, 12.2%) as a white solid and the second eluting peak as Compound I-211 (180 mg, 12%). LCMS (ES, m/z): 447[M+H]+.

Step 2. Compound 210—4'-(6-(1-aminocyclopropane-1-carbonyl)-6-azaspiro[2.5]octan-1-yl)-[1,1'-biphenyl]-4-carboxylic Acid To a stirred mixture of Compound I-210 (120 mg, 0.27 mmol) and trifluoroacetic acid (4 mL) in dichloromethane (10 mL) was stirred at room temperature for 1 h. The resulting mixture was concentrated under vacuum. The crude product was purified by Prep-HPLC with water (0.1% FA) and ACN (23% ACN up to 32% in 7 min) to afford Compound 210 (107 mg, 94%) as a white solid. The crude product was purified by Prep-HPLC with water (0.1% FA) and ACN (23% ACN up to 32% in 7 min) to afford (S)-4'-(6-(1-aminocyclopropane-1-carbonyl)-6-azaspiro [2.5]octan-1-yl)-[1,1'-biphenyl]-4-carboxylic acid (107 mg, 94%) as a white solid. 1H-NMR (400 MHz, CD3OD) δ (ppm): 8.10 (d, J=8.4 Hz, 2H), 7.74 (d, J=8.4 Hz, 2H), 7.64 (d, J=8.0 Hz, 2H), 7.38 (d, J=8.4 Hz, 2H), 3.87-3.50 (m, 2H), 3.45-3.40 (m, 1H), 3.34-3.32 (m, 1H), 2.21-2.17 (m, 1H), 1.70-1.68 (m, 2H), 1.41-1.29 (m, 2H), 1.19-1.16 (m, 3H), 1.16-0.99 (m, 3H). LCMS (ES, m/z): 391[M+H]+.

Step 3 Compound 211—4'-(6-(1-aminocyclopropane-1-carbonyl)-6-azaspiro[2.5]octan-1-yl)-[1,1'-biphenyl]-4-carboxylate To a stirred mixture of tert-butyl Compound I-211 (120 mg, 0.27 mmol) and trifluoroacetic acid (4 mL) in dichloromethane (10 mL) was stirred at room temperature for 1 h. The resulting mixture was concentrated under vacuum. The crude product was purified by Prep-HPLC with water (0.1% FA) and ACN (23% ACN up to 32% in 7 min) to afford (R)-4'-(6-(1-aminocyclopropane-1-carbonyl)-6-azaspiro[2.5]octan-1-yl)-[1,1'-biphenyl]-4-carboxylate (Compound 211) as a white solid. The crude product was purified by Prep-HPLC with water (0.1% FA) and ACN (23% ACN up to 32% in 7 min) to afford (R)-4'-(6-(1-aminocyclopropane-1-carbonyl)-6-azaspiro[2.5]octan-1-yl)-[1,1'-biphenyl]-4-carboxylate (114 mg, 94%) as a white solid. $^1$H NMR (CD$_3$OD, 400 MHz) δ (ppm): 8.10 (d, J=8.4 Hz, 2H), 7.74 (d, J=8.0 Hz, 2H), 7.65 (d, J=8.4 Hz, 2H), 7.38 (d, J=8.0 Hz, 2H), 3.84-3.59 (m, 2H), 3.57-3.54 (m, 1H), 3.45-3.32 (m, 1H), 2.20-2.17 (m, 1H), 1.70-1.68 (m, 2H), 1.38-1.30 (m, 2H), 1.19-1.05 (m, 3H), 1.01-0.96 (m, 3H). LCMS (ES, m/z): 391[M+H]$^+$.

Method 45: Preparation of Compounds 108 and 109: (S)-2-(4-(6-(1-hydroxycyclopropane-1-carbonyl)-6-azaspiro[2.5]octan-1-yl)phenyl)benzo[d]oxazole-6-carboxylic acid and (R)-2-(4-(6-(1-hydroxycyclopropane-1-carbonyl)-6-azaspiro[2.5]octan-1-yl)phenyl)benzo[d]oxazole-6-carboxylic Acid

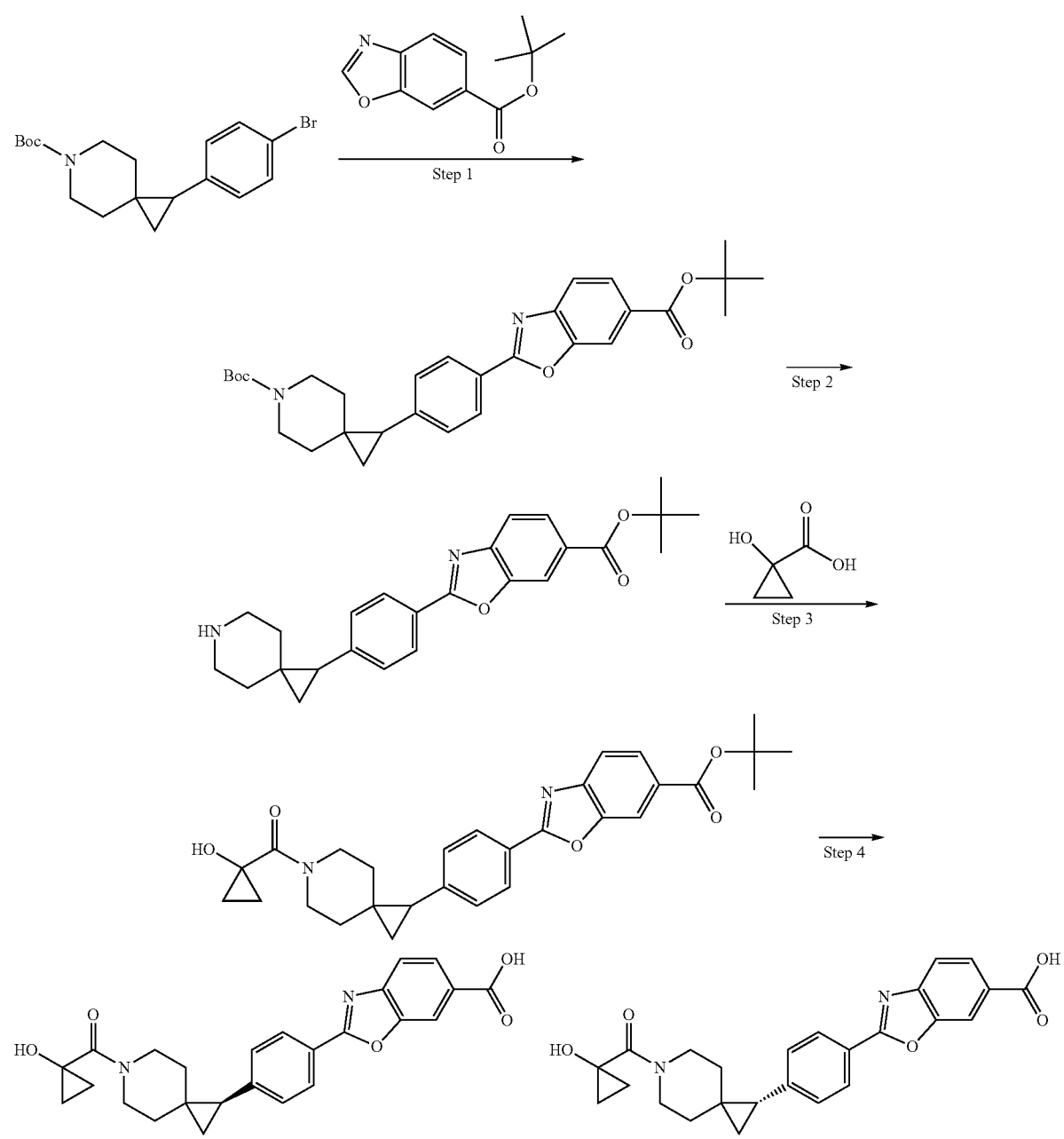

Step 1. tert-butyl 2-(4-(6-(tert-butoxycarbonyl)-6-azaspiro[2.5]octan-1-yl)phenyl)benzo[d]oxazole-6-carboxylate A mixture of tert-butyl 1-(4-bromophenyl)-6-azaspiro[2.5]octane-6-carboxylate (600 mg, 1.56 mmol), tert-butyl 1,3-benzoxazole-6-carboxylate (409 mg, 1.87 mmol), palladium acetate (18 mg, 0.072 mmol), copper iodide (59 mg, 0.21 mmol), XantPhos (180 mg, 0.31 mmol) and cesium carbonate (1.27 mg, 3.84 mmol) in toluene (15 mL) was stirred for 1 h at 110° C. under nitrogen atmosphere. The mixture was cooled to room temperature and concentrated under vacuum. The residue was purified by silica gel column chromatography, eluted with petroleum ether/ethyl acetate (1:1) to afford tert-butyl 2-(4-(6-(tert-butoxycarbonyl)-6-azaspiro[2.5]octan-1-yl)phenyl)benzo[d]oxazole-6-carboxylate (370 mg, 4544.765%) as a yellow solid. LCMS (ES, m/z): 505[M+H]$^+$.

Step 2. tert-butyl 2-(4-(6-azaspiro[2.5]octan-1-yl)phenyl)benzo[d]oxazole-6-carboxylate A mixture of tert-butyl 2-(4-(6-(tert-butoxycarbonyl)-6-azaspiro[2.5]octan-1-yl)phenyl)benzo[d]oxazole-6-carboxylate (370 mg, 0.70 mmol) and trifluoroacetic acid (3 mL) in dichloromethane (25 mL) was stirred for 0.5 h at 0° C. The pH of the mixture was adjusted to pH 7 with saturated sodium bicarbonate and the reaction was extracted with dichloromethane (3×50 mL). The combined organic layers were washed with brine (100 mL), dried over anhydrous sodium sulfate, filtered and concentrated under reduced pressure to afford tert-butyl 2-(4-(6-azaspiro[2.5]octan-1-yl)phenyl)benzo[d]oxazole-6-carboxylate (310 mg, 95%) as a yellow solid. LCMS (ES, m/z): 405[M+H]$^+$.

Step 3. tert-butyl 2-(4-(6-(1-hydroxycyclopropane-1-carbonyl)-6-azaspiro[2.5]octan-1-yl)phenyl)benzo[d]oxazole-6-carboxylate To a stirred mixture of 1-hydroxycyclopropane-1-carboxylic acid (138 mg, 1.02 mmol) 1-hydroxybenzotriazole (1.12 g, 8.36 mmol), N'-(ethylcarbonimidoyl)-N,N-dimethyl-monohydrochloride (261 mg, 1.36 mmol) in N,N-dimethylformamide (10 mL) were added tert-butyl 2-(4-(6-azaspiro[2.5]octan-1-yl)phenyl)benzo[d]oxazole-6-carboxylate (290 mg, 0.68 mmol) and N-methyl morpholine (206 mg, 2.04 mmol). The resulting mixture was stirred for 2 h at room temperature. The reaction was quenched by the addition of water/ice (50 mL) and extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (2:1) to afford tert-butyl 2-(4-(6-(1-hydroxycyclopropane-1-carbonyl)-6-azaspiro[2.5]octan-1-yl)phenyl)benzo[d]oxazole-6-carboxylate (300 mg, 86%). LCMS (ES, m/z): 489[M+H]$^+$.

Step 4. (S)-2-(4-(6-(1-hydroxycyclopropane-1-carbonyl)-6-azaspiro[2.5]octan-1-yl)phenyl)benzo[d]oxazole-6-carboxylic Acid and (R)-2-(4-(6-(1-hydroxycyclopropane-1-carbonyl)-6-azaspiro[2.5]octan-1-yl)phenyl)benzo[d]oxazole-6-carboxylic Acid To a stirred mixture of tert-butyl 2-(4-(6-(1-hydroxycyclopropane-1-carbonyl)-6-azaspiro[2.5]octan-1-yl)phenyl)benzo[d]oxazole-6-carboxylate (300 mg, 0.583 mmol) and trifluoroacetic acid (3 mL) in dichloromethane (10 mL) was stirred for 1 h at room temperature. The mixture was concentrated under reduced pressure. The crude product separated by Chiral HPLC (Column: (R, R) Whelk-01, 21.1×250 mm, 5 µm; mobile phase: Hexanes (0.1% FA):IPA 1:1 (hold 50% IPA in 30 min); Detector: UV 254 nm to afford the first eluting peak as Compound 108 as a white solid (36.9 mg, 2928.79%) and the second eluting peak as Compound 109 (30.1 mg, 23%).

Compound 108

$^1$H-NMR (CD$_3$OD, 400 MHz) δ (ppm): 8.31 (s, 1H), 8.23 (d, J=8.4 Hz, 2H), 8.13 (d, J=8.4 Hz, 1H), 7.79 (d, J=8.0 Hz, 1H), 7.51 (d, J=8.0 Hz, 2H), 4.21-3.35 (m, 4H), 2.27-2.22 (m, 1H), 1.85-1.51 (m, 2H), 1.43-1.24 (m, 3H), 1.13-0.99 (m, 3H), 0.98-0.77 (m, 2H). LCMS (ES, m/z): 433[M+H]$^+$.

Compound 109

$^1$H-NMR (CD$_3$OD, 400 MHz) δ (ppm): 8.32 (s, 1H), 8.23 (d, J=8.4 Hz, 2H), 8.14 (d, J=8.0 Hz, 1H), 7.81 (d, J=8.4 Hz, 1H), 7.51 (d, J=8.4 Hz, 2H), 4.20-3.38 (m, 4H), 2.29-2.19 (m, 1H), 1.82-1.55 (m, 2H), 1.41-1.25 (m, 3H), 1.10-0.95 (m, 3H), 0.95-0.75 (m, 2H). LCMS (ES, m/z): 433[M+H]$^+$.

Method 46: Preparation of Compounds 140 and 141: 3-methyl-4-{4-[(1S)-6-propanoyl-6-azaspiro[2.5]octan-1-yl]phenyl}benzoic Acid and 3-methyl-4-{4-[(1R)-6-propanoyl-6-azaspiro[2.5]octan-1-yl]phenyl}benzoic Acid

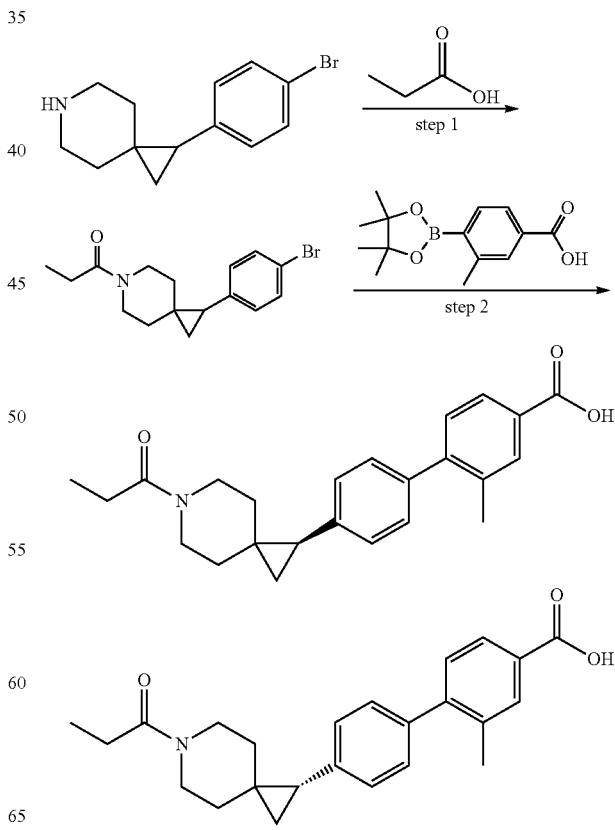

Step 1. 1-(1-(4-bromophenyl)-6-azaspiro[2.5]octan-6-yl)propan-1-one

A mixture of propanoic acid (419 mg, 5.65 mmol), N-(3-dimethylaminopropyl)-N'-ethylcarbodiimide hydrochloride (742 mg, 3.87 mmol), 1-hydroxybenzotriazole (383 mg, 2.84 mmol), 1-(4-bromophenyl)-6-azaspiro[2.5]octane (500 mg, 1.88 mmol) and 4-Methylmorpholine (572 mg, 5.66 mmol) in N,N-dimethylformamide (10 mL) was stirred for 2 h at room temperature. The resulting mixture was diluted with water (30 mL) and was extracted with dichloromethane (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:1) to afford 1-(1-(4-bromophenyl)-6-azaspiro[2.5]octan-6-yl)propan-1-one (440 mg, 62%) as a white solid. LCMS (ES, m/z): 322,324 [M+H]$^+$.

Step 2. 3-methyl-4-{4-[(1S)-6-propanoyl-6-azaspiro[2.5]octan-1-yl]phenyl}benzoic Acid and 3-methyl-4-{4-[(1R)-6-propanoyl-6-azaspiro[2.5]octan-1-yl]phenyl}benzoic Acid A mixture of 3-methyl-4-(4,4,5,5-tetramethyl-1,3,2-dioxaborolan-2-yl)benzoic acid (370 mg, 1.34 mmol), 1-[1-(4-bromophenyl)-6-azaspiro[2.5]octan-6-yl]butan-1-one (412 mg, 1.10 mmol), bis(di-tert-butyl(4-dimethylaminophenyl)phosphine)dichloropalladium (91 mg, 0.103 mmol) and potassium phosphate (816 mg, 3.65 mmol) in dioxane (10 mL) and water (2.5 mL) was stirred at 80° C. for 3 h under nitrogen atmosphere. The mixture was cooled to room temperature and concentrated under reduced pressure. The crude product was purified by reverse flash chromatography with water (containing 0.1% FA) and acetonitrile (20% to 60% over 40 min). The product was separated by Chiral HPLC with the following conditions: column: CHIRALPAK IG-3 (0.46×5 cm, 3 μm); mobile phase: A: Hexanes (0.1% FA) and B, EtOH (hold 30% EtOH in 14 mine); Detector: UV 254 to afford the first eluting peak as Compound 140 (139.9 mg, 3231.932%) as a white solid and the second eluting peak as Compound 141 (137.9 mg, 31%) as a white solid.

Compound 140

$^1$H-NMR (CD$_3$OD, 400 MHz) δ (ppm): 7.95 (s, 1H), 7.89 (d, J=8.0 Hz, 1H), 7.39-7.25 (m, 5H), 3.83-3.58 (m, 2H), 3.54-3.35 (m, 2H), 2.50-2.42 (m, 1H), 2.42-2.34 (m, 1H), 2.34-2.28 (m, 3H), 2.20-2.10 (m, 1H), 1.73-1.53 (m, 2H), 1.39-1.21 (m, 2H), 1.19-1.05 (m, 4H), 1.01-0.92 (m, 1H). LCMS (ES, m/z): 378 [M+H]$^+$

Compound 141

$^1$H-NMR (CD$_3$OD, 400 MHz) δ (ppm): 7.97 (s, 1H), 7.89 (d, J=8.0 Hz, 1H), 7.42-7.21 (m, 5H), 3.83-3.58 (m, 2H), 3.53-3.33 (m, 2H), 2.51-2.42 (m, 1H), 2.42-2.33 (m, 1H), 2.33-2.28 (m, 3H), 2.22-2.11 (m, 1H), 1.71-1.54 (m, 2H), 1.38-1.21 (m, 2H), 1.21-1.07 (m, 4H), 1.06-0.91 (m, 1H). LCMS (ES, m/z): 378 [M+H]$^+$

Method 47: Preparation of Compounds 158 and 159: [(1S)-6-cyclobutanecarbonyl-6-azaspiro[2.5]octan-1-yl]-6-methoxy-[1,1-biphenyl]-3-carboxylic Acid and 4-[(1R)-6-cyclobutanecarbonyl-6-azaspiro[2.5]octan-1-yl]-6-methoxy-[1,1-biphenyl]-3-carboxylic Acid

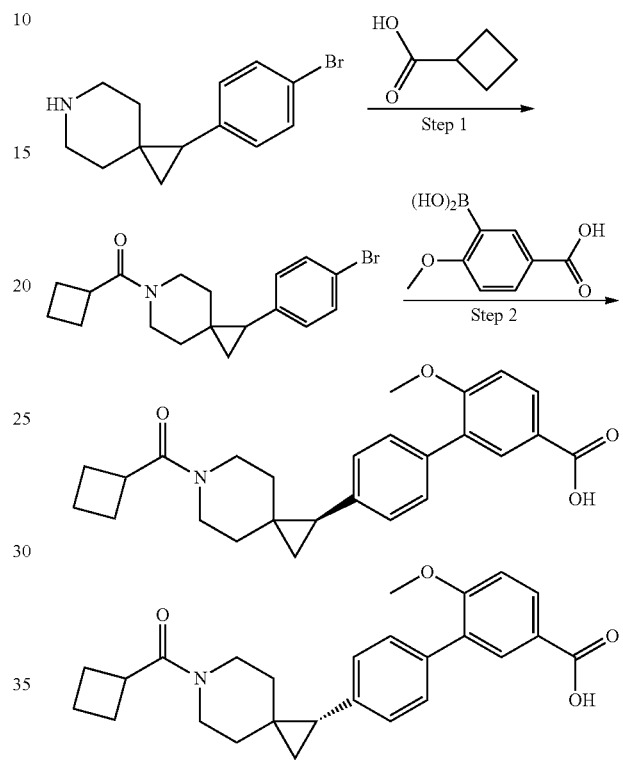

Step 1. (1-(4-bromophenyl)-6-azaspiro[2.5]octan-6-yl)(cyclobutyl)methanone

A mixture of 1-(4-bromophenyl)-6-azaspiro[2.5]octane (700 mg, 2.63 mmol) and cyclobutanecarboxylic acid (395 mg, 3.94 mmol), 1-hydroxybenzotriazole (711 mg, 5.26 mmol), N-(3-dimethylaminopropyl)-N'-ethylcarbodiimide hydrochloride (1.51 g, 7.89 mmol) in N,N-dimethylformamide (20 mL) was stirred for 2 h at room temperature. The reaction was quenched with ice water (100 mL). The resulting mixture was extracted with ethyl acetate (3×150 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (1:1) to afford 1-(4-bromophenyl)-6-cyclobutanecarbonyl-6-azaspiro[2.5]octane (450 mg, 47%) as a white solid. LCMS (ES, m/z): 348, 350 [M+H]$^+$.

Step 2. (S)-4'-(6-(cyclobutanecarbonyl)-6-azaspiro[2.5]octan-1-yl)-6-methoxy-[1,1'-biphenyl]-3-carboxylic Acid To a stirred solution of 1-(4-bromophenyl)-6-cyclobutanecarbonyl-6-azaspiro[2.5]octane (500 mg, 1.44 mmol) and 3-(dihydroxyboranyl)-4-methoxybenzoic acid (365.74 mg, 1.87 mmol) in 1,4-dioxane (15 mL) and water (3 mL) were added bis(di-tert-butyl(4-dimethylaminophenyl)phosphine) dichloropalladium (101 mg, 0.14 mmol) and potassium phosphate (609 mg, 2.87 mmol). The mixture was at 80° C. under nitrogen atmosphere for 2 h. The mixture was cooled to room temperature and concentrated under reduced pressure. The residue was purified by reverse flash chromatography with water (0.1% FA) and ACN (20% to 60% in 25 min). The product was purified by Chiral HPLC with the following conditions: Column: CHIRALPAK IG, 20×250 mm, 5 μm; mobile phase: Hexanes (0.1% FA) and IPA (hold 30% IPA in 27 min); Detector: UV 254 nm to afford the first eluting peak as Compound 158 (83 mg, 14%) as a white solid and the second eluting peak as Compound 159 (52 mg, 98.559%) as a white solid.

Compound 158

$^1$H-NMR (CD$_3$OD, 400 MHz) δ (ppm): 8.04-8.01 (m, 1H), 7.96-7.94 (m, 1H), 7.44 (d, J=8.4 Hz, 2H), 7.38 (d, J=6.8 Hz, 2H), 7.16 (d, J=8.8 Hz, 1H), 3.90 (s, 3H), 3.79-3.66 (m, 1H), 3.58-3.37 (m, 3H), 3.30-3.16 (m, 1H), 2.29-1.93 (m, 6H), 1.89-1.76 (m, 1H), 1.62-1.57 (m, 2H), 1.31-1.26 (m, 2H), 1.12-1.06 (m, 1H), 0.93-0.88 (m, 1H). LCMS (ES, m/z): 420 [M+H]$^+$.

Compound 159

$^1$H-NMR (400 MHz, CD$_3$OD) δ (ppm): 8.04 (d, J=2.4 Hz, 1H), 8.03 (d, J=2.0 Hz, 1H), 7.44 (d, J=8.4 Hz, 2H), 7.28 (d, J=7.2 Hz, 2H), 7.15 (d, J=8.8 Hz, 1H), 3.89 (s, 3H), 3.82-3.63 (m, 1H), 3.47-3.45 (m, 1H), 3.33-3.32 (m, 1H), 3.32-3.24 (m, 1H), 3.24-3.16 (m, 1H), 2.30-2.22 (m, 3H), 2.21-2.15 (m, 2H), 2.13-2.10 (m, 1H), 2.10-1.61 (m, 1H), 1.61-1.57 (m, 2H), 1.29-1.26 (m, 2H), 1.12-1.09 (m, 1H), 0.95-0.92 (m, 1H). LCMS (ES, m/z): 420 [M+H]$^+$.

Method 48: Preparation of Compounds 144 and 145: (S)-4'-(6-Acetyl-6-azaspiro[2.5]octan-1-yl)-6-methoxy-[1,1'-biphenyl]-3-carboxylic Acid and (R)-4'-(6-Acetyl-6-azaspiro[2.5]octan-1-yl)-6-methoxy-[1,1'-biphenyl]-3-carboxylic Acid

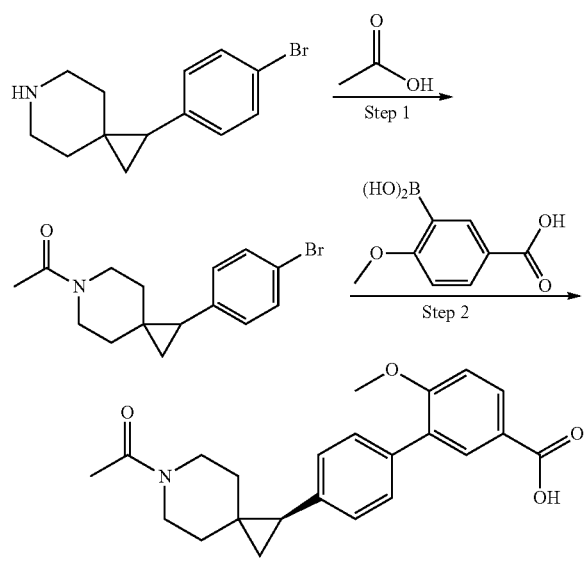

Step 1. 1-(1-(4-Bromophenyl)-6-azaspiro[2.5]octan-6-yl)ethan-1-one

A mixture of acetic acid (120 mg, 1.97 mmol), 1-(4-bromophenyl)-6-azaspiro[2.5]octane (350 mg, 1.37 mmol), 1H-benzo[d][1,2,3]triazol-1-ol hydrate (213 mg, 3.16 mmol) and N-(3-dimethylaminopropyl)-N'-ethylcarbodiimide hydrochloride (303 mg, 1.08 mmol) in N,N-dimethylformamide (10 mL) was stirred for 2 h at room temperature. The reaction was quenched with ice water (100 mL). The resulting mixture was extracted with ethyl acetate (3×150 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (1:1) to afford 1-[1-(4-bromophenyl)-6-azaspiro[2.5]octan-6-yl]ethan-1-one (340 mg, 80%) as a yellow oil. LCMS (ES, m/z): 308, 310 [M+H]$^+$.

Step 2. (S)-4'-(6-Acetyl-6-azaspiro[2.5]octan-1-yl)-6-methoxy-[1,1'-biphenyl]-3-carboxylic Acid and (R)-4'-(6-Acetyl-6-azaspiro[2.5]octan-1-yl)-6-methoxy-[1,1'-biphenyl]-3-carboxylic Acid A mixture of 1-[1-(4-bromophenyl)-6-azaspiro[2.5]octan-6-yl]ethan-1-one (340 mg, 1.10 mmol), 3-(dihydroxyboranyl)-4-methoxybenzoic acid (324.27 mg, 1.66 mmol), potassium phosphate (468 mg, 2.21 mmol) and bis(di-tert-butyl (4-dimethylaminophenyl)phosphine)dichloropalladium (78 mg, 0.11 mmol) in 1,4-dioxane (10 mL) and water (3 mL) was stirred for 2 h at 80° C. under nitrogen atmosphere. The mixture was cooled to room temperature and concentrated under reduced pressure. The residue was purified by reverse flash chromatography with water (0.1% FA) and ACN (40% to 70% in 15 min). The product was purified by Chiral HPLC with the following conditions: Column: CHIRALPAK IE, 2×25 cm, 5 μm; mobile phase: Hexanes (containing 0.1% Formic acid) and ethanol (hold 30% ethanol in 28 min); Detector: UV 254 nm to afford the first eluting peak as Compound 144 (102.7 mg, 24%) as a white solid and the second eluting peak as Compound 145 (71.4 mg, 17%) as a white solid.

Compound 144

$^1$H NMR (400 MHz, DMSO-d6) δ (ppm): 12.70 (br, 1H), 7.97-7.90 (m, 1H), 7.85-7.79 (m, 1H), 7.42 (d, J=8.0 Hz, 2H), 7.33-7.26 (m, 2H), 7.23-7.20 (m, 1H), 3.85 (s, 3H), 3.61-3.45 (m, 2H), 3.31-3.07 (m, 2H), 2.13-2.04 (m, 1H), 1.94 (s, 3H), 1.55-1.46 (m, 2H), 1.29-1.03 (m, 3H), 0.92-0.82 (m, 1H). LCMS (ES, m/z): 380 [M+H]$^+$.

Compound 145

$^1$H NMR (400 MHz, DMSO-d6) δ (ppm): 12.70 (br, 1H), 8.01-7.89 (m, 1H), 7.86-7.77 (m, 1H), 7.42 (d, J=8.0 Hz, 2H), 7.34-7.27 (m, 2H), 7.28-7.20 (m, 1H), 3.85 (s, 3H), 3.65-3.44 (m, 2H), 3.34-3.13 (m, 2H), 2.13-2.04 (m, 1H), 1.94 (s, 3H), 1.56-1.44 (m, 2H), 1.27-1.03 (m, 3H), 0.89-0.86 (m, 1H). LCMS (ES, m/z): 380 [M+H]$^+$.

Method 49: Preparation of Compounds 146 and 147: (S)-6-Methoxy-4'-(6-propionyl-6-azaspiro[2.5]octan-1-yl)-[1,1'-biphenyl]-3-carboxylic acid and (R)-6-Methoxy-4'-(6-propionyl-6-azaspiro[2.5]octan-1-yl)-[1,1'-biphenyl]-3-carboxylic Acid

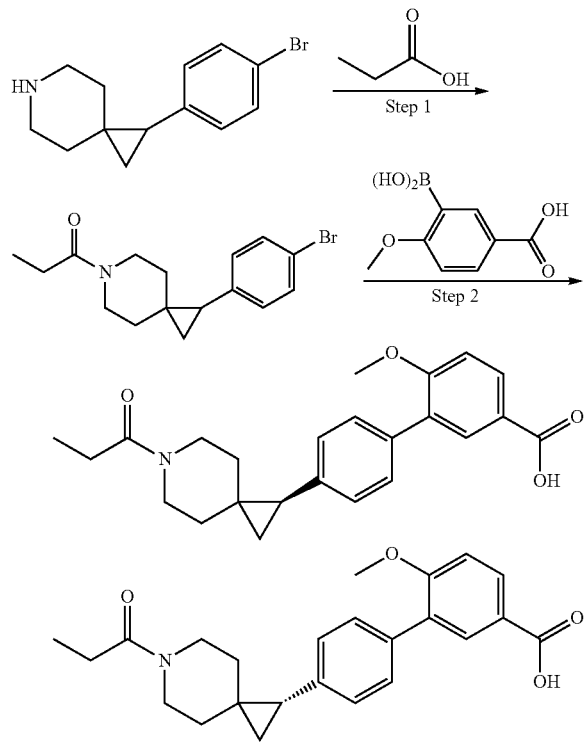

Step 1. 1-(1-(4-Bromophenyl)-6-azaspiro[2.5]octan-6-yl)propan-1-one

A mixture of propanoic acid (125 mg, 1.69 mmol), N-(3-dimethylaminopropyl)-N'-ethylcarbodiimide hydrochloride (259 mg, 1.35 mmol), 1-hydroxybenzotriazole (183 mg, 1.35 mmol) and 1-(4-bromophenyl)-6-azaspiro[2.5]octane (300 mg, 1.13 mmol) in N,N-dimethylformamide (10 mL) was stirred for additional 1 h at room temperature. The reaction was quenched with water (50 mL) at room temperature. The resulting mixture was extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:1) to afford 1-[1-(4-bromophenyl)-6-azaspiro[2.5]octan-6-yl]propan-1-one (300 mg, 78%) as a yellow oil. LCMS (ES, m/z): 322, 324 [M+H]$^+$.

Step 2. (S)-6-Methoxy-4'-(6-propionyl-6-azaspiro[2.5]octan-1-yl)-[1,1'-biphenyl]-3-carboxylic Acid and (R)-6-Methoxy-4'-(6-propionyl-6-azaspiro[2.5]octan-1-yl)-[1,1'-biphenyl]-3-carboxylic Acid A mixture of 1-[1-(4-bromophenyl)-6-azaspiro[2.5]octan-6-yl]propan-1-one (300.00 mg, 0.93 mmol), (4-bromo-2-methoxyphenyl) boronic acid (322 mg, 1.40 mmol), potassium phosphate (395.23 mg, 1.86 mmol) and bis(4-(di-tert-butylphosphanyl)-N,N-dimethylaniline) (65.92 mg, 0.093 mmol) in dioxane (10 mL) and water (3 mL) was stirred for 2 h at 80° C. under a nitrogen atmosphere. The mixture was cooled to room temperature and concentrated under reduced pressure. The residue was purified by reverse flash chromatography with water (0.05% TFA) and ACN (30% to 70% in 20 min). The product was separated by Chiral HPLC with the following conditions: Column: CHIRALPAK IE, 0.46×5 cm, 3 μm; mobile phase: Hexanes (containing 0.1% Formic acid) and IPA (hold 30% IPA in 21 min); Detector: UV 254 nm to afford the first eluting peak as Compound 146 (107.2 mg, 29%) as a white solid and the second eluting peak as Compound 147 (88.3 mg, 24.02%).

Compound 146

$^1$H NMR (400 MHz, DMSO-d6) δ 12.72 (br, 1H), 7.95-7.91 (m, 1H), 7.83 (s, 1H), 7.42 (d, J=8.0 Hz, 2H), 7.32-7.26 (m, 2H), 7.21 (d, J=8.8 Hz, 1H), 3.85 (s, 3H), 3.59-3.51 (m, 2H), 3.29-3.17 (m, 2H), 2.35-2.22 (m, 2H), 2.08-2.03 (m, 1H), 1.56-1.41 (m, 2H), 1.25-1.06 (m, 3H), 1.02-0.94 (m, 3H), 0.88-0.82 (m, 1H). LCMS (ES, m/z): 394 [M+H]$^+$.

Compound 147

$^1$H NMR (400 MHz, DMSO-d6) δ 12.72 (br, 1H), 7.95-7.91 (m, 1H), 7.83 (s, 1H), 7.42 (d, J=8.0 Hz, 2H), 7.32-7.26 (m, 2H), 7.21 (d, J=8.8 Hz, 1H), 3.85 (s, 3H), 3.61-3.51 (m, 2H), 3.27-3.14 (m, 2H), 2.35-2.22 (m, 2H), 2.08-2.03 (m, 1H), 1.55-1.43 (m, 2H), 1.25-1.06 (m, 3H), 1.02-0.93 (m, 3H), 0.89-0.82 (m, 1H). LCMS (ES, m/z): 394 [M+H]$^+$.

Method 50: Preparation of Compounds 148 and 149: 4-[(1S)-6-cyclopropanecarbonyl-6-azaspiro[2.5]octan-1-yl]-6-methoxy-[1,1-biphenyl]-3-carboxylic Acid and 4-[(1R)-6-cyclopropanecarbonyl-6-azaspiro[2.5]octan-1-yl]-6-methoxy-[1,1-biphenyl]-3-carboxylic Acid

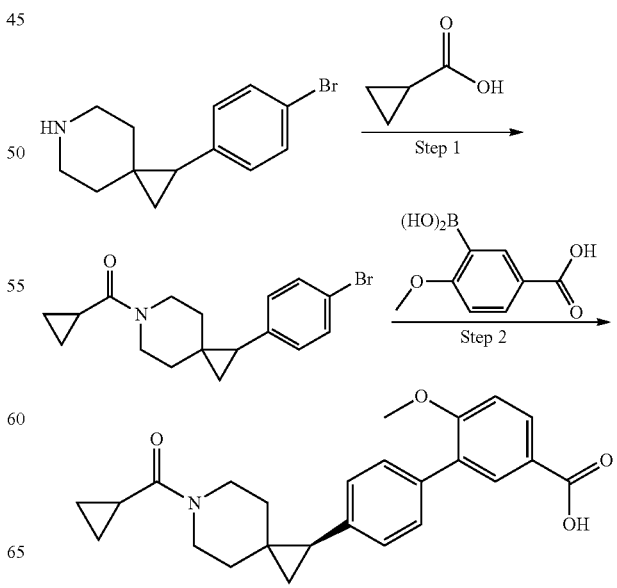

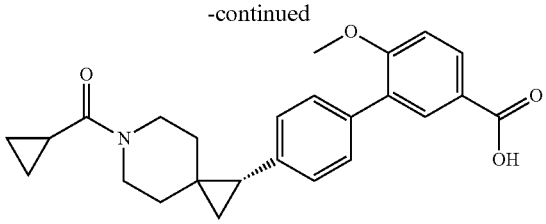

Step 1. 1-(4-bromophenyl)-6-cyclopropanecarbonyl-6-azaspiro[2.5]octane

A mixture of cyclopropane carboxylic acid (252 mg, 2.93 mmol), 1-(3-dimethylaminopropyl)-3-ethylcarbodiimide hydrochloride (1.12 g, 5.86 mmol), 1-hydroxybenzotriazole (528 mg, 3.91 mmol), 1-(4-bromophenyl)-6-azaspiro[2.5]octane (520 mg, 1.95 mmol) and 4-methylmorpholine (1.58 g, 15.63 mmol) in N,N-dimethylformamide (15 mL) was stirred for 2 h at room temperature. The reaction was quenched with water (80 mL) and was extracted with ethyl acetate (3×100 mL). The combined organic layers were washed with brine (2×100 mL), dried over anhydrous sodium sulfate, filtered and concentrated under reduced pressure. The residue was purified by silica gel column chromatography, eluted with petroleum ether/ethyl acetate (3:1) to afford 1-(4-bromophenyl)-6-cyclopropanecarbonyl-6-azaspiro[2.5]octane (580 mg, 84%) as a yellow oil. LCMS (ES, m/z): 334, 336 [M+H]$^+$.

Step 2. 4-[(1S)-6-cyclopropanecarbonyl-6-azaspiro[2.5]octan-1-yl]-6-methoxy-[1,1-biphenyl]-3-carboxylic Acid and 4-[(1R)-6-cyclopropanecarbonyl-6-azaspiro[2.5]octan-1-yl]-6-methoxy-[1,1-biphenyl]-3-carboxylic Acid A mixture of 1-(4-bromophenyl)-6-cyclopropanecarbonyl-6-azaspiro[2.5]octane (580 mg, 1.74 mmol), 3-(dihydroxyboranyl)-4-methoxybenzoic acid (340 mg, 1.74 mmol), potassium phosphate (737 mg, 3.47 mmol) and bis(di-tert-butyl(4-dimethylaminophenyl)phosphine)dichloropalladium(123 mg, 0.17 mmol) in dioxane (20 mL) and water (4 mL) was stirred for 2 h at 80° C. under nitrogen atmosphere. The mixture was cooled to room temperature and concentrated under reduced pressure. The residue was purified by reverse flash chromatography with water (0.1% FA) and ACN (10% to 70% in 25 min). The product was separated by Chiral HPLC with the following conditions: Column: CHIRAL ART Cellulose-SB S—5 μm, 2×25 cm, 5 μm; mobile phase: hexanes (0.1% FA) and EtOH (hold EtOH 30% in 13 min); Detector: UV 254 nm to afford the first eluting peak as Compound 148 (109.1 mg, 15%) as a white solid and the second eluting peak as Compound 149 (106.8 mg, 15.03%) as a white solid.

Compound 148

$^1$H NMR (CD$_3$OD, 400 MHz) δ (ppm): 8.03-8.00 (m, 1H), 7.95 (s, 1H), 7.48-7.45 (m, 2H), 7.31-7.26 (m, 2H), 7.16-7.13 (m, 1H), 3.92-3.87 (m, 4H), 3.83-3.59 (m, 2H), 3.55-3.50 (m, 1H), 2.16-2.13 (m, 1H), 2.07-1.83 (m, 1H), 1.69-1.59 (m, 2H), 1.36-1.26 (m, 2H), 1.13-1.12 (m, 1H), 0.95 (s, 1H), 0.87-0.76 (m, 4H). LCMS (ES, m/z): 406 [M+H]$^+$.

Compound 149

$^1$H NMR (CD$_3$OD, 400 MHz) δ (ppm): 8.03-8.00 (m, 1H), 7.95 (s, 1H), 7.48-7.45 (m, 2H), 7.31-7.26 (m, 2H), 7.16-7.13 (m, 1H), 3.95-3.83 (m, 4H), 3.80-3.60 (m, 2H), 3.52-3.50 (m, 1H), 2.17-2.13 (m, 1H), 2.01-1.90 (m, 1H), 1.69-1.59 (m, 2H), 1.37-1.27 (m, 2H), 1.15-1.12 (m, 1H), 0.97-0.94 (m, 1H), 0.91-0.73 (m, 4H). LCMS (ES, m/z): 406 [M+H]$^+$.

Method 51: Preparation of Compounds 251 and 252: (1S)-6-(1-hydroxycyclopropanecarbonyl)-1-[4-(quinolin-7-yl)phenyl]-6-azaspiro[2.5]octane-1-carboxylic Acid (251) and (1R)-6-(1-hydroxycyclopropanecarbonyl)-1-[4-(quinolin-7-yl)phenyl]-6-azaspiro[2.5]octane-1-carboxylic Acid (252)

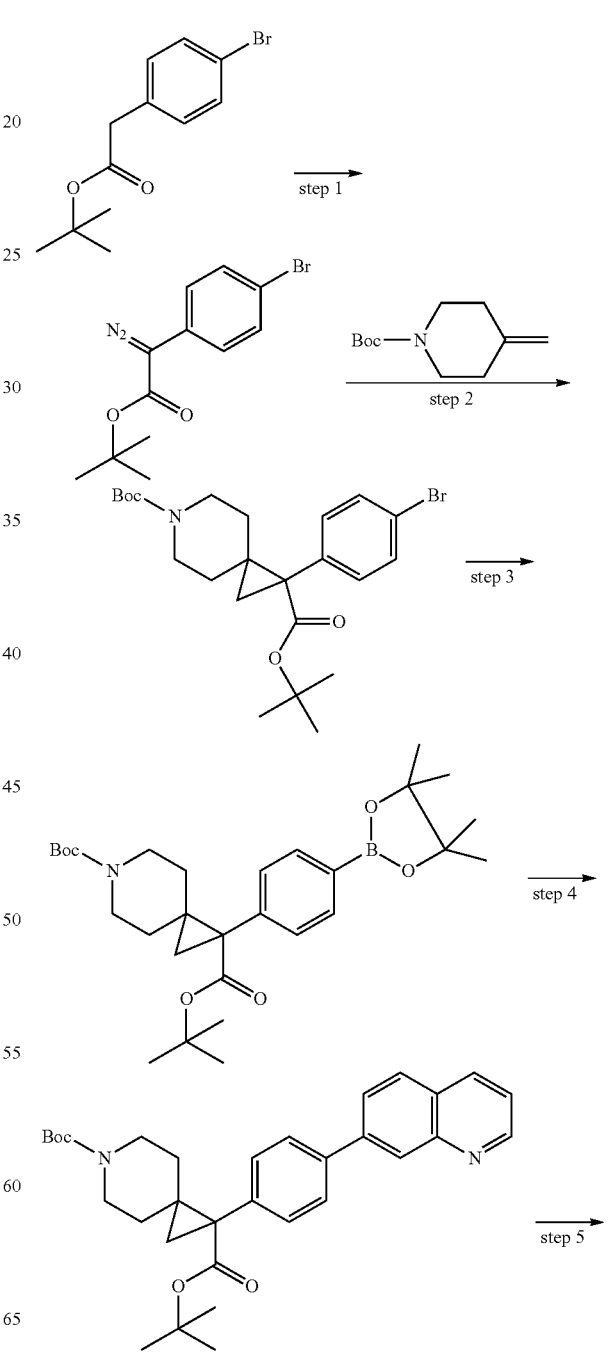

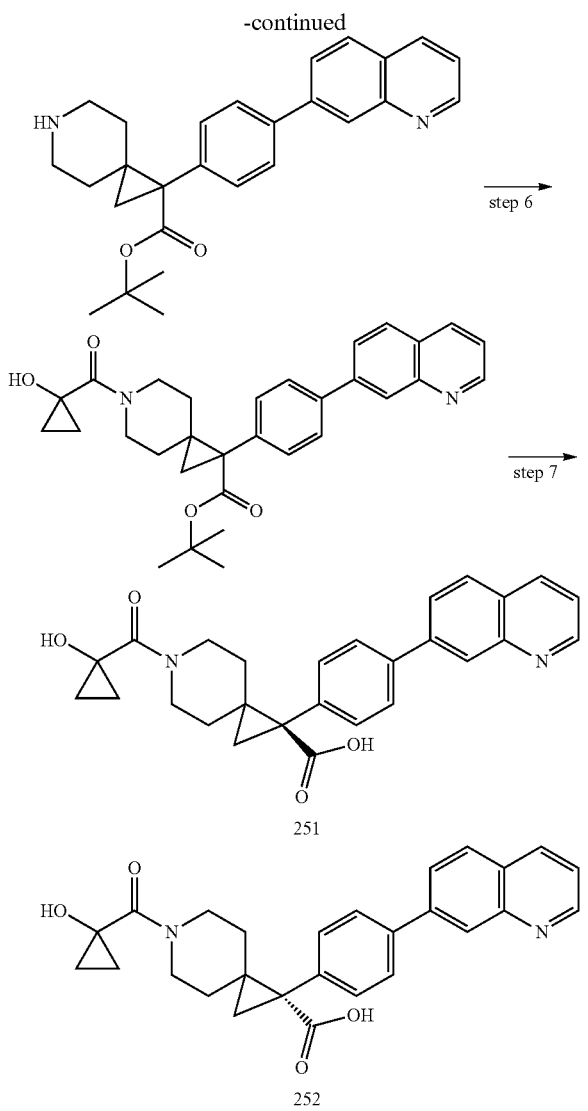

Step 1. tert-butyl 2-(4-bromophenyl)-2-diazoacetate

To a stirred solution of 4-methylbenzenesulfonyl azide (26.2 g, 66.42 mmol, 50% in ethyl acetate) and tert-butyl 2-(4-bromophenyl)acetate (15.0 g, 55.35 mmol) in acetonitrile (200 mL) was added 1,8-diazabicyclo[5.4.0]undec-7-ene (42.0 g, 83.02 mmol,) dropwise at 0° C. The resulting mixture was stirred for overnight at room temperature and concentrated under reduced pressure. The residue was purified by silica gel column chromatography, eluted with ethyl acetate/petroleum ether (1:10) to afford tert-butyl 2-(4-bromophenyl)-2-diazoacetate as a yellow solid (13.5 g, 82.3%). LCMS (ES, m/z): 297, 299 [M+H]$^+$

Step 2. 1,6-di-tert-butyl 1-(4-bromophenyl)-6-azaspiro[2.5]octane-1,6-dicarboxylate To a stirred solution of rhodium acetate dimer (1.40 g, 1.39 mmol, 46%) and tert-butyl 4-methylidenepiperidine-1-carboxylate (11.00 g, 55.80 mmol) in dichloromethane (200 mL) was added tert-butyl 2-(4-bromophenyl)-2-diazoacetate (13.50 g, 46.40 mmol). The resulting solution was stirred at 40° C. for overnight. The mixture was cooled to room temperature and concentrated under reduced pressure. The residue was purified by silica gel column chromatography, eluted with ethyl acetate/petroleum ether (1:10) to afford 1,6-di-tert-butyl 1-(4-bromophenyl)-6-azaspiro[2.5]octane-1,6-dicarboxylate as a light yellow oil (10.8 g, 49.9%). $^1$H-NMR (DMSO-d$_6$, 400 MHz) δ (ppm): δ 7.48 (d, J=8.0 Hz, 2H), 7.33 (d, J=8.0 Hz, 2H), 3.81-3.72 (m, 1H), 3.68-3.55 (m, 1H), 3.12-2.90 (m, 1H), 2.88-2.76 (m, 1H), 1.70-1.56 (m, 1H), 1.49-1.40 (m, 1H), 1.38 (s, 9H), 1.32 (s, 9H), 1.26-1.19 (m, 2H), 0.84-0.78 (m, 1H), 0.55-0.48 (m, 1H). LCMS (ES, m/z): 466, 468 [M+H]$^+$.

Step 3. 1,6-di-tert-butyl 1-[4-(4,4,5,5-tetramethyl-1,3,2-dioxaborolan-2-yl)phenyl]-6-azaspiro[2.5]octane-1,6-dicarboxylate To a stirred mixture of 4,4,5,5-tetramethyl-2-(4,4,5,5-tetramethyl-1,3,2-dioxaborolan-2-yl)-1,3,2-dioxaborolane (2.37 g, 8.87 mmol) and 1,6-di-tert-butyl 1-(4-bromophenyl)-6-azaspiro[2.5]octane-1,6-dicarboxylate (3 g, 5.92 mmol) in dioxane (30 mL) was added potassium acetate (1.83 g, 17.75 mmol) and [1,1'-Bis(diphenylphosphino)ferrocene]dichloropalladium (0.46 g, 0.59 mmol). The resulting mixture was stirred for 1 h at 80° C. under nitrogen atmosphere. The resulting mixture was concentrated under reduced pressure. The residue was purified by silica gel column chromatography, eluted with petroleum ether/ethyl acetate (4:1) to afford 1,6-di-tert-butyl 1-[4-(4,4,5,5-tetramethyl-1,3,2-dioxaborolan-2-yl)phenyl]-6-azaspiro[2.5]octane-1,6-dicarboxylate (3.1 g, 93.86%) as a yellow oil. LCMS (ES, m/z): 514[M+H]$^+$.

Step 4. 1,6-di-tert-butyl 1-[4-(quinolin-7-yl)phenyl]-6-azaspiro[2.5]octane-1,6-dicarboxylate A mixture of 1,6-di-tert-butyl 1-[4-(4,4,5,5-tetramethyl-1,3,2-dioxaborolan-2-yl)phenyl]-6-azaspiro[2.5]octane-1,6-dicarboxylate (1.6 g, 2.80 mmol), 7-bromoquinoline (714 mg, 3.26 mmol) potassium phosphate (1.98 g, 8.86 mmol) and bis(di-tert-butyl(4-dimethylaminophenyl)phosphine)dichloropalladium (221 mg, 0.31 mmol) in 1,4-dioxane (20 mL) and water (5 mL) was stirred for 1 h at 70° C. The resulting mixture was cooled to room temperature and concentrated under reduced pressure. The residue was purified by silica gel chromatography, eluted with ethyl acetate/petroleum ether (1:2) to afford 1,6-di-tert-butyl 1-[4-(quinolin-7-yl)phenyl]-6-azaspiro[2.5]octane-1,6-dicarboxylate (1.3 g, 81.06%) as a yellow solid. LCMS (ES, m/z): 515 [M+H]$^+$.

Step 5. bis(tert-butyl 1-[4-(quinolin-7-yl)phenyl]-6-azaspiro[2.5]octane-1-carboxylate)

A solution of bis(1,6-di-tert-butyl 1-[4-(quinolin-7-yl)phenyl]-6-azaspiro[2.5]octane-1,6-dicarboxylate) (1.3 g, 1.14 mmol) and trifluoroacetic acid (2 mL) in dichloromethane (20 mL) was stirred for 1 h at 0° C. The residue was basified to pH=8 with saturated sodium bicarbonate. The resulting mixture was extracted with dichloromethane (3×50 mL). The combined organic layers were washed with brine (2×60 mL), dried over anhydrous sodium sulfate filtered and concentrated under reduced pressure to afford bis(tert-butyl 1-[4-(quinolin-7-yl)phenyl]-6-azaspiro[2.5]octane-1-carboxylate) (1.0 g, 95.50%) as a yellow oil. LCMS (ES, m/z): 415 [M+H]$^+$.

Step 6. tert-butyl 6-(1-hydroxycyclopropanecarbonyl)-1-[4-(quinolin-7-yl)phenyl]-6-azaspiro[2.5]octane-1-carboxylate A solution of 1-hydroxycyclopropane-1-carboxylic acid (185 mg, 1.72 mmol), N-(3-Dimethylaminopropyl)-N'-ethyl carbodiimide hydrochloride (473 mg, 2.34 mmol), 1H-Benzo[d][1,2,3]triazol-1-ol hydrate (244 mg, 1.71 mmol), 4-methylmorpholine (366 mg, 3.44 mmol) and tert-butyl 1-[4-(quinolin-7-yl)phenyl]-6-azaspiro[2.5]octane-1-carboxylate (500 mg, 1.09 mmol) in N,N-Dimethylformamide (10 mL) was stirred for 2 h at room temperature. The resulting mixture was diluted with water (50 mL) and was extracted with ethyl acetate (3×50 mL). The combined organic layers were washed with brine (2×50 mL), dried over anhydrous sodium sulfate, filtered and concentrated under reduced pressure. The residue was purified by silica gel column chromatography, eluted with petroleum ether/ethyl acetate (1:3) to afford tert-butyl 6-(1-hydroxycyclopropanecarbonyl)-1-[4-(quinolin-7-yl)phenyl]-6-azaspiro[2.5]octane-1-carboxylate (470 mg, 78.15%) as a yellow solid. LCMS (ES, m/z): 499 [M+H]$^+$.

Step 7. (1S)-6-(1-hydroxycyclopropanecarbonyl)-1-[4-(quinolin-7-yl)phenyl]-6-azaspiro[2.5]octane-1-carboxylic acid (example 251) and (1R)-6-(1-hydroxycyclopropanecarbonyl)-1-[4-(quinolin-7-yl)phenyl]-6-azaspiro[2.5]octane-1-carboxylic Acid (Example 252)

A solution of tert-butyl 6-(1-hydroxycyclopropanecarbonyl)-1-[4-(quinolin-7-yl)phenyl]-6-azaspiro[2.5]octane-1-carboxylate (400 mg, 0.72 mmol) and trifluoroacetic acid (4 mL) in dichloromethane (10 mL) was stirred for 1 h at room temperature. The resulting mixture was concentrated under vacuum. The crude product was purified by reverse phase chromatography (Column: C18; Mobile phase, A: water (containing 10 mmol/L NH$_4$HCO$_3$) and B: ACN (5% to 40% over 60 min). The product was separated by Chiral-Prep-HPLC with the following condition: Column: (R, R) Whelk-01, 21.1×250 mm, 5 um; Mobile Phase A: Hex (containing 0.1% FA) and B: EtOH (hold 50% in 30 min); Flow rate: 20 mL/min; Detector, UV 254 nm). The product fractions were concentrated to compound 251 (114.1 mg, 70.71%) as a light yellow solid and compound 252 (120.6 mg, 74.74%) as a light yellow solid.

Compound 251

$^1$H-NMR (CD$_3$OD, 400 MHz) δ (ppm): 8.99-8.81 (m, 1H), 8.51-8.31 (m, 1H), 8.31-8.17 (m, 1H), 8.11-7.88 (m, 2H), 7.82-7.63 (m, 2H), 7.63-7.42 (m, 3H), 4.68-3.87 (m, 2H), 3.72-3.39 (m, 1H), 3.25-2.89 (m, 1H), 2.14-1.76 (m, 3H), 1.74-1.52 (m, 1H), 1.45-1.33 (m, 1H), 1.12-0.97 (m, 2H), 0.97-0.77 (m, 3H). LCMS (ES, m/z): 443 [M+H]$^+$.

Compound 252

$^1$H-NMR (CD$_3$OD, 400 MHz) δ (ppm): 8.99-8.81 (m, 1H), 8.51-8.31 (m, 1H), 8.31-8.17 (m, 1H), 8.09-8.02 (m, 1H), 8.02-7.86 (m, 1H), 7.83-7.69 (m, 2H), 7.66-7.44 (m, 3H), 4.62-4.02 (m, 2H), 3.67-3.42 (m, 1H), 3.29-2.91 (m, 1H), 2.08-1.91 (m, 1H), 1.91-1.72 (m, 2H), 1.72-1.52 (m, 1H), 1.46-1.37 (m, 1H), 1.18-0.99 (m, 2H), 0.99-0.78 (m, 3H). LCMS (ES, m/z): 443 [M+H]$^+$.

Method 52: Preparation of Compound 280: 2-methoxy-4-[7-[(2R)-oxolane-2-carbonyl]-7-azaspiro[3.5]nonan-2-yl]-[1,1-biphenyl]-4-carboxylic Acid

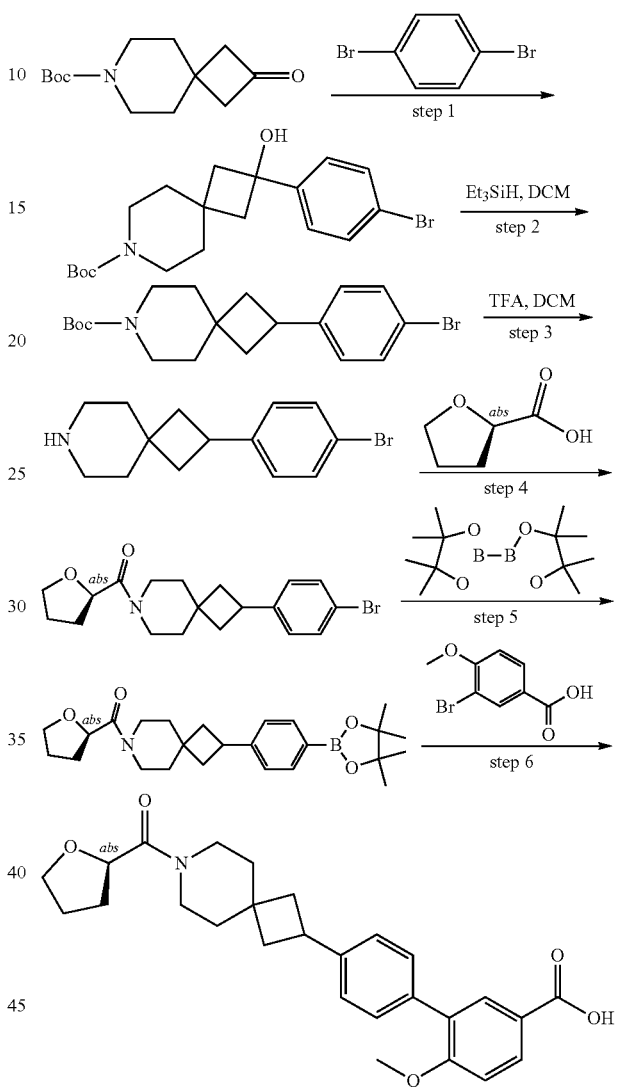

Step 1. tert-butyl 2-(4-bromophenyl)-2-hydroxy-7-azaspiro[3.5]nonane-7-carboxylate To a stirred solution of dibromobenzene (5 g, 21.2 mmol) in tetrahydrofuran (20 mL) was added n-Butyllithium (10 mL, 2.5 mol/L) dropwise at −78° C. under nitrogen atmosphere. To the above was added tert-butyl 2-oxo-7-azaspiro[3.5]nonane-7-carboxylate (6 g, 25.4 mmol) in tetrahydrofuran (20 mL) dropwise over 10 min at −78° C. The resulting mixture was stirred for overnight at room temperature. The reaction was quenched by the addition of water/ice (200 mL). The resulting mixture was extracted with ethyl acetate (3×100 mL). The combined organic layers were washed with brine (2×100 mL), dried over anhydrous sodium sulfate, filtered and concentrated under reduced pressure. The residue was purified by silica gel column chromatography (eluting with 2:1 ethyl acetate/petroleum ether) to afford tert-butyl 2-(4-bromophenyl)-2-hydroxy-7-azaspiro[3.5]nonane-7-carboxylate (6 g, 57.14%) as a yellow solid. LCMS (ES, m/z): 396,398 [M+H]+.

Step 2. tert-butyl 2-(4-bromophenyl)-7-azaspiro[3.5]nonane-7-carboxylate

To a stirred solution of tert-butyl 2-(4-bromophenyl)-2-hydroxy-7-azaspiro[3.5]nonane-7-carboxylate (2.80 g, 7.065 mmol) in dichloromethane (10 mL) were added triethylsilane (2.80 mL, 17.53 mmol) and $BF_3 \cdot Et_2O$ (4.68 mL, 36.93 mmol) dropwise at −70° C. under nitrogen atmosphere. The resulting mixture was stirred for 2.5 h from at −20° C. The reaction was quenched by the addition of saturated sodium carbonate (300 mL). The resulting mixture was extracted with dichloromethane (3×100 mL). The combined organic layers were dried over anhydrous sodium sulfate, filtered and concentrated under reduced pressure. The residue was purified by silica gel column chromatography (eluting with 1:3 ethyl acetate/petroleum ether) to afford tert-butyl 2-(4-bromophenyl)-7-azaspiro[3.5]nonane-7-carboxylate (680 mg, 24.04%) as a white solid. LCMS (ES, m/z): 380,382 [M+H]+.

Step 3. 2-(4-bromophenyl)-7-azaspiro[3.5]nonane

A solution of tert-butyl 2-(4-bromophenyl)-7-azaspiro[3.5]nonane-7-carboxylate (400 mg, 1.05 mmol) and trifluoroacetic acid (2 mL) in dichloromethane (10 mL) was stirred for 1 h at 0° C. The mixture was basified to pH 8 with saturated sodium carbonate. The resulting mixture was extracted with dichloromethane (3×50 mL). The combined organic layers were washed with brine (2×100 mL), dried over anhydrous sodium sulfate, filtered and concentrated under reduced pressure to afford 2-(4-bromophenyl)-7-azaspiro[3.5]nonane (350 mg, crude) as a yellow solid. LCMS (ES, m/z): 280,282 [M+H]+.

Step 4. 2-(4-bromophenyl)-7-[(2R)-oxolane-2-carbonyl]-7-azaspiro[3.5]nonane

A mixture of 2-(4-bromophenyl)-7-azaspiro[3.5]nonane (330 mg, 1.18 mmol), (2R)-oxolane-2-carboxylic acid (165 mg, 1.42 mmol) in N,N-dimethylformamide (10 mL) were added 1-(3-dimethylaminopropyl)-3-ethylcarbodiimide (364 mg, 2.35 mmol), 1-hydroxybenzotriazole (231 mg, 1.71 mmol), 4-methylmorpholine (347 mg, 3.43 mmol) was stirred for 1 h at room temperature. The resulting mixture was diluted with ice/water (50 mL). The resulting mixture was extracted with ethyl acetate (3×50 mL). The combined organic layers were washed with brine (2×100 mL), dried over anhydrous sodium sulfate, filtered and concentrated under reduced pressure. The residue was purified by silica gel column chromatography (eluting with 3:1 ethyl acetate/petroleum ether) to afford 2-(4-bromophenyl)-7-[(2R)-oxolane-2-carbonyl]-7-azaspiro[3.5]nonane (400 mg, 84.9%) as a yellow oil. LCMS (ES, m/z): 378,380 [M+H]+.

Step 5. 7-[(2R)-oxolane-2-carbonyl]-2-[4-(4,4,5,5-tetramethyl-1,3,2-dioxaborolan-2-yl)phenyl]-7-azaspiro[3.5]nonane A mixture of 2-(4-bromophenyl)-7-[(2R)-oxolane-2-carbonyl]-7-azaspiro[3.5]nonane (380 mg, 1.00 mmol), bis(pinacolato)diboron (382 mg, 1.50 mmol), 1,1-bis(diphenylphosphino)ferrocene-palladium(II) dichloride dichloromethane complex (164 mg, 0.20 mmol) and potassium acetate (296 mg, 3.02 mmol) in 1,4-dioxane (10 mL) was stirred for 2 h at 80° C. under nitrogen atmosphere. The mixture was allowed to cool down to room temperature. The solids were filtered out. The filter cake was washed with dichloromethane (3×10 mL). The filtrate was concentrated under reduced pressure. The residue was purified by silica gel column chromatography (eluting with 3:1 ethyl acetate/petroleum ether) to afford 7-[(2R)-oxolane-2-carbonyl]-2-[4-(4,4,5,5-tetramethyl-1,3,2-dioxaborolan-2-yl)phenyl]-7-azaspiro[3.5]nonane (350 mg, 73.72%) as a yellow solid. LCMS (ES, m/z): 426 [M+H]+.

Step 6. 2-methoxy-4-[7-[(2R)-oxolane-2-carbonyl]-7-azaspiro[3.5]nonan-2-yl]-[1,1-biphenyl]-4-carboxylic Acid (280)

A mixture 3-bromo-4-methoxybenzoic acid (196 mg, 0.85 mmol), 7-[(2R)-oxolane-2-carbonyl]-2-[4-(4,4,5,5-tetramethyl-1,3,2-dioxaborolan-2-yl)phenyl]-7-azaspiro[3.5]nonane (300 mg, 0.71 mmol), potassium phosphate (450 mg, 2.12 mmol) and chloro(2-dicyclohexylphosphino-2',4',6'-triisopropyl-1,1'-biphenyl)[2-(2'-aMino-1,1'-biphenyl)]palladium(II) (50 mg, 0.07 mmol) in 1,4-dioxane (12 mL) and water (3 mL) was stirred for 2 h at 100° C. under nitrogen atmosphere. The reaction was allowed to cool down to room temperature. The resulting mixture was concentrated under reduced pressure. The residue was purified by reverse flash chromatography with the following conditions: column, C18 silica gel; mobile phase, A: water (5% NH4HCO3) and B: ACN (30% ACN to 70% in 20 min); detector, UV 254 nm to afford compound 280 (132.5 mg, 40.54%) as an off-white solid.

Compound 280

1H-NMR (400 MHz, CD3OD) δ (ppm): 8.08-7.99 (m, 1H), 7.95 (s, 1H), 7.45 (d, J=8.0 Hz, 2H), 7.30 (d, J=8.4 Hz, 2H), 7.13 (d, J=8.4 Hz, 1H), 4.84-4.61 (m, 1H), 4.12-3.95 (m, 1H), 3.95-3.78 (m, 4H), 3.74-3.38 (m, 5H), 2.44-2.34 (m, 2H), 2.31-2.18 (m, 1H), 2.08-1.92 (m, 5H), 1.92-1.78 (m, 2H), 1.78-1.57 (m, 2H). LCMS (ES, m/z): 450 [M+H]+.

Method 53: Preparation of compounds 282, 283, 284, 285: 6-methoxy-4-[(1R,3R)-5-[(2r)-oxolane-2-carbonyl]-5-azaspiro[2.4]heptan-1-yl]-[1,1-biphenyl]-3-carboxylic acid (282), 6-methoxy-4-[(1S,3R)-5-[(2r)-oxolane-2-carbonyl]-5-azaspiro[2.4]heptan-1-yl]-[1,1-biphenyl]-3-carboxylic Acid (283), 6-methoxy-4-[(1R,3S)-5-[(2R)-oxolane-2-carbonyl]-5-azaspiro[2.4]heptan-1-yl]-[1,1-biphenyl]-3-carboxylic Acid (284), and 6-methoxy-4-[(1S,3S)-5-[(2R)-oxolane-2-carbonyl]-5-azaspiro[2.4]heptan-1-yl]-[1,1-biphenyl]-3-carboxylic Acid (285)

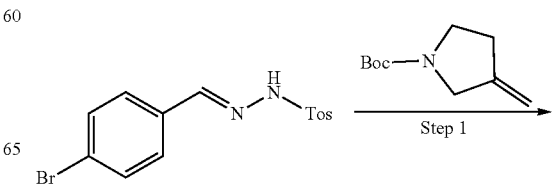

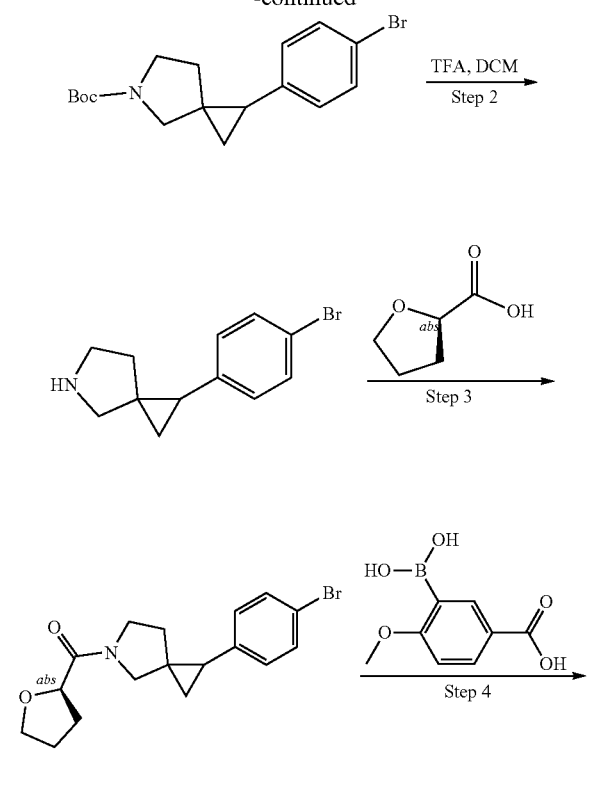

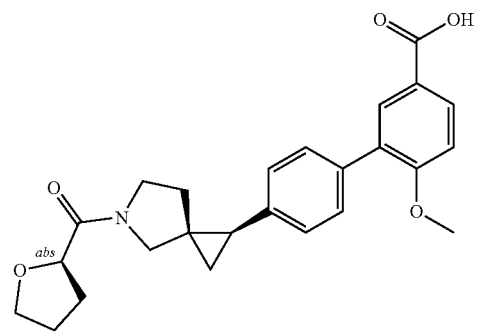

first eluting isomer
282

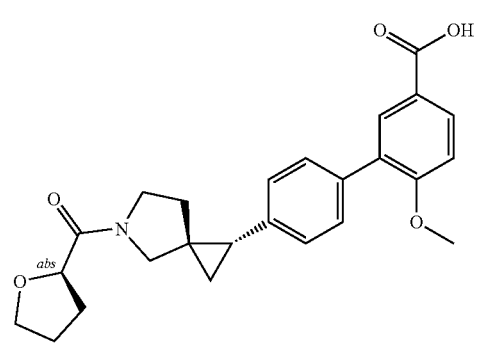

second eluting isomer
283

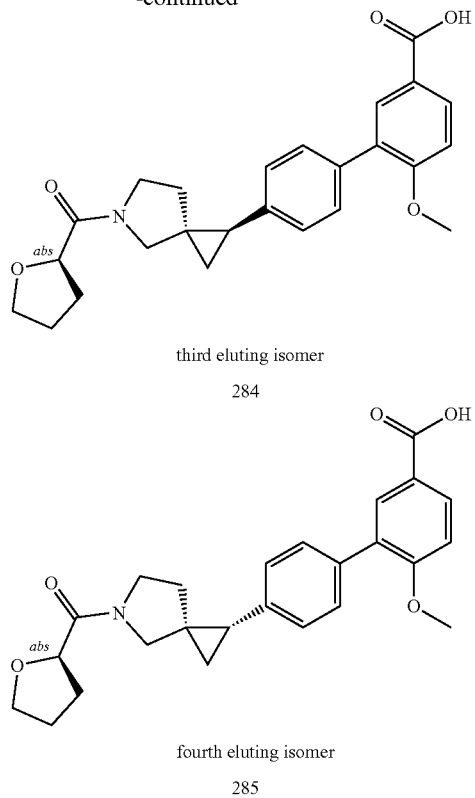

third eluting isomer
284 fourth eluting isomer
285

Step 1. Tert-butyl 1-(4-bromophenyl)-5-azaspiro[2.4]heptane-5-carboxylate

To a stirred mixture of N-[(4-bromophenyl)methylidene]-4-methylbenzenesulfonohydrazide (9.64 g, 27.29 mmol) in dichloromethane (100 mL) was added sodium hydride (2.34 g, 58.50 mmol, 60%) in portions at 0° C. under nitrogen atmosphere. To the above were added tert-butyl 3-methylidenepyrrolidine-1-carboxylate (4.00 g, 21.83 mmol) and oxo(trifluoromethanesulfonyl)silver (1.18 g, 4.58 mmol) in portions over 30 min at 0° C. The resulting mixture was stirred for 12 h at 40° C. The reaction was cooled to room temperature nd then quenched with saturated ammonium chloride (150 mL). The solids were filtered out. The filter cake was washed with ethyl acetate (3×200 mL). The filtrate was dried over sodium sulfate, filtered and concentrated under reduced pressure. The residue was purified by silica gel column chromatography (eluting with 4:1 petroleum ether/ethyl acetate to afford tert-butyl 1-(4-bromophenyl)-5-azaspiro[2.4]heptane-5-carboxylate (1.4 g, 15.31%) as a yellow oil. LCMS (ES, m/z): 352, 354[M+H]+.

Step 2. 1-(4-bromophenyl)-5-[(2R)-oxolane-2-carbonyl]-5-azaspiro[2.4]heptane 1-(4-bromophenyl)-5-azaspiro[2.4]heptane;trifluoroacetaldehyde A solution of tert-butyl 1-(4-bromophenyl)-5-azaspiro[2.4]heptane-5-carboxylate (600 mg, 1.70 mmol) in dichloromethane (15 mL) and trifluoroacetic acid (3 mL) was stirred for 2 h at room temperature. The resulting solution was concentrated under reduced pressure to afford 1-(4-bromophenyl)-5-azaspiro[2.4]heptane;trifluoroacetaldehyde (610 mg, crude), which was used in next step directly without further purification. LCMS (ES, m/z): 252, 254[M+H]$^+$.

Step 3. 1-(4-bromophenyl)-5-[(2R)-oxolane-2-carbonyl]-5-azaspiro[2.4]heptane

A mixture of (2R)-oxolane-2-carboxylic acid (345 mg, 2.97 mmol), 1H-Benzo[d][1,2,3]triazol-1-ol hydrate (322 mg, 2.38 mmol), N-(3-Dimethylaminopropyl)-N'-ethylcarbodiimide hydrochloride (456 mg, 2.38 mmol), 1-(4-bromophenyl)-5-azaspiro[2.4]heptane (500 mg, 1.98 mmol) and 4-methylmorpholine (986 mg, 9.75 mmol) in N,N-dimethylfomamide (10 mL) was stirred for 1.5 h at room temperature. The reaction was quenched by the addition of ice/water (50 mL). The resulting mixture was extracted with ethyl acetate (3×50 mL). The combined organic layers were washed with brine (50 mL), dried over anhydrous sodium anhydrous sulfate, filtered and concentrated under reduced pressure. The residue was purified by silica gel column chromatography (eluting with 1:1 petroleum ether/ethyl acetate) to afford 1-(4-bromophenyl)-5-[(2R)-oxolane-2-carbonyl]-5-azaspiro[2.4]heptane (390 mg, 50.04%) as a yellow oil. LCMS (ES, m/z): 350, 352 [M+H]$^+$.

Step 4. 6-methoxy-4-[(1R,3R)-5-[(2r)-oxolane-2-carbonyl]-5-azaspiro[2.4]heptan-1-yl]-[1,1-biphenyl]-3-carboxylic Acid (282), 6-methoxy-4-[(1S, 3R)-5-[(2r)-oxolane-2-carbonyl]-5-azaspiro[2.4] heptan-1-yl]-[1,1-biphenyl]-3-carboxylic Acid (283), 6-methoxy-4-[(1R,3S)-5-[(2R)-oxolane-2-carbonyl]-5-azaspiro[2.4]heptan-1-yl]-[1,1-biphenyl]-3-carboxylic Acid (284) and 6-methoxy-4-[(1S, 3S)-5-[(2R)-oxolane-2-carbonyl]-5-azaspiro[2.4] heptan-1-yl]-[1,1-biphenyl]-3-carboxylic Acid (285)

A mixture of 1-(4-bromophenyl)-5-[(2R)-oxolane-2-carbonyl]-5-azaspiro[2.4]heptane (360 mg, 1.03 mmol), 3-(dihydroxyboranyl)-4-methoxybenzoic acid (302 mg, 1.54 mmol), potassium phosphate (262 mg, 1.23 mmol) and bis(di-tert-butyl(4-dimethylaminophenyl)phosphine)dichloropalladium (873 mg, 1.23 mmol) in 1,4-dioxane (12 mL) and water (3 mL) was stirred for 1.5 h at 80° C. under a nitrogen atmosphere. The reaction was allowed to cool down to room temperature and diluted with ice/water (50 mL). The resulting mixture was ethyl acetate (3×50 mL). The combined organic layers were dried over sodium sulfate, filtered and concentrated under reduced pressure. The residue was purified by reverse flash chromatography with the following conditions: column, C18 silica gel; mobile phase, water (0.1% FA) and ACN (5% to 95% in 30 min); detector, UV 254/220 nm. The product was separated by Chiral-Prep-HPLC with the following conditions: Column, CHIRAL ART Cellulose-SB, 2×25 cm, 5 um; mobile phase, n-hexane (0.1% formic acid) and isopropyl alcohol (hold 50% isopropyl alcohol in 19 min); Detector, UV 254/220 nm to afford compound 282 (14.3 mg, 4.74%) as a white solid, compound 283 (6.3 mg, 2.09%), compound 284 (27.2 mg, 9.06%) and compound 285 (22.9 mg, 7.62%) as a white solid.

Compound 282

$^1$H NMR (400 MHz, DMSO-d$_6$) δ12.40 (br, 1H), 7.93 (d, J=8.8, Hz, 1H), 7.82 (s, 1H), 7.43 (d, J=8.0 Hz, 2H), 7.23-7.12 (m, 3H), 4.56-4.14 (m, 1H), 3.85 (s, 3H), 3.79-3.55 (m, 3H), 3.53-3.40 (m, 1H), 3.20-3.02 (m, 1H), 2.88-2.82 (m, 1H), 2.26-2.18 (m, 1H), 2.05-1.64 (m, 6H), 1.32-1.22 (m, 1H), 1.21-1.13 (m, 1H). LCMS (ES, m/z): 422[M+H]$^+$.

Compound 283

$^1$H NMR (400 MHz, DMSO-d$_6$) δ 12.71 (br, 1H), 7.93 (d, J=8.8, 1H), 7.884-7.78 (m, 1H), 7.45-7.41 (m, 2H), 7.24-7.16 (m, 3H), 4.54-4.04 (m, 1H), 3.85 (d, J=3.2 Hz, 3H), 3.80-3.58 (m, 3H), 3.50-3.33 (m, 2H), 2.91-2.78 (m, 1H), 2.26-2.15 (m, 1H), 2.04-1.90 (m, 2H), 1.87-1.52 (m, 3H), 1.46-1.13 (m, 3H). LCMS (ES, m/z): 422[M+H]$^+$.

Compound 284

$^1$H NMR (400 MHz, DMSO-d$_6$) δ 12.72 (br, 1H), 7.93 (d, J=8.4 Hz, 1H), 7.83 (s, 1H), 7.43 (d, J=8.0 Hz, 2H), 7.28-7.17 (m, 3H), 4.58-4.46 (m, 1H), 3.85 (s, 3H), 3.84-3.70 (m, 1H), 3.68-3.35 (m, 4H), 3.33-3.25 (m, 1H), 2.28-2.21 (m, 1H), 2.08-1.94 (m, 2H), 1.92-1.41 (m, 4H), 1.31-1.12 (m, 2H). LCMS (ES, m/z): 422[M+H]$^+$.

Compound 285

$^1$H NMR (400 MHz, DMSO-d$_6$) δ12.71 (br, 1H), 7.96-7.91 (m, 1H), 7.82 (s, 1H), 7.42 (d, J=8.0 Hz, 2H), 7.24-7.16 (m, 3H), 4.56-4.42 (m, 1H), 3.86 (s, 3H), 3.77-3.54 (m, 3H), 3.50-3.17 (m, 3H), 2.28-2.21 (m, 1H), 2.07-1.98 (m, 2H), 1.87-1.52 (m, 3H), 1.45-1.30 (m, 1H), 1.35-1.32 (m, 1H), 1.31-1.12 (m, 1H). LCMS (ES, m/z): 422[M+H]$^+$.

Method 54: Preparation of Compounds 296 and 297: 6-methoxy-4-[(2s,4s)-6-[(2R)-oxolane-2-carbonyl]-6-azaspiro[3.4]octan-2-yl]-[1,1'-biphenyl]-3-carboxylic Acid (296) and 6-methoxy-4'-[(2r,4r)-6-[(2R)-oxolane-2-carbonyl]-6-azaspiro[3.4]octan-2-yl]-[1,1-biphenyl]-3-carboxylic Acid (297)

-continued

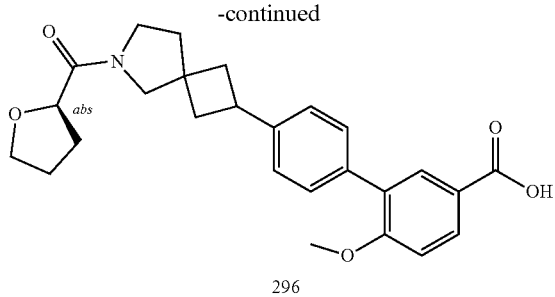

296

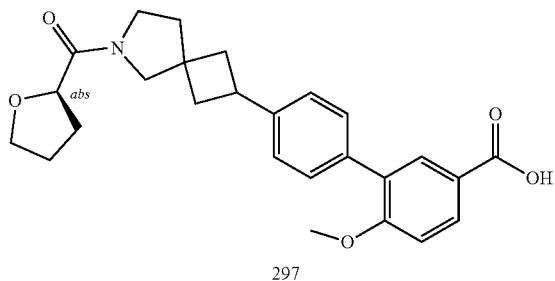

297

Step 1. tert-butyl 2-(4-bromophenyl)-2-hydroxy-6-azaspiro[3.4]octane-6-carboxylate To a stirred solution of dibromobenzene (5.70 g, 24.16 mmol) in THF (30 mL) was added n-Butyllithium (11.0 mL, 27.78 mmol, 2.5 mmol/L) dropwise at −78° C. under nitrogen atmosphere. To the above mixture was added tert-butyl 2-oxo-6-azaspiro[3.4]octane-6-carboxylate (5.00 g, 22.19 mmol) in THF (10 mL) dropwise over 10 min at −78° C. The resulting mixture was stirred for overnight at room temperature. The reaction was quenched by the addition of water/ice (100 mL). The resulting mixture was extracted with ethyl acetate (3×100 mL). The combined organic layers were washed with brine (2×100 mL), dried over anhydrous sodium sulfate, filtered and concentrated under reduced pressure. The residue was purified by silica gel column chromatography (eluting with 1:2 ethyl acetate/petroleum ether) to afford tert-butyl 2-(4-bromophenyl)-2-hydroxy-6-azaspiro[3.4]octane-6-carboxylate (3 g, 33.59%) as a yellow solid. LCMS (ES, m/z): 382,384 [M+H]$^+$

Step 2. 4-[6-(tert-butoxycarbonyl)-2-hydroxy-6-azaspiro[3.4]octan-2-yl]-6-methoxy-[1,1-biphenyl]-3-carboxylic Acid To a stirred mixture of tert-butyl 2-(4-bromophenyl)-2-hydroxy-6-azaspiro[3.4]octane-6-carboxylate (1.50 g, 3.92 mmol), 3-(dihydroxyboranyl)-4-methoxybenzoic acid (0.92 g, 4.71 mmol), chloro(2-dicyclohexylphosphino-2',4',6'-triisopropyl-1,1'-biphenyl) [2-(2'-aMino-1,1'-biphenyl)]palladium(II) (0.28 g, 0.39 mmol) and potassium phosphate (1.67 g, 7.85 mmol) in dioxane (25 mL) and water (5 mL) was stirred for 2 h at 80° C. under nitrogen atmosphere. The resulting mixture was cooled to room temperature. The reaction was diluted with ice/water (100 mL). The resulting mixture was extracted with dichloromethane (3×100 mL). The combined organic layers were washed with brine (2×100 mL), dried over anhydrous sodium sulfate, filtered and concentrated under reduced pressure. The residue was purified by reverse flash chromatography with the following conditions: column, C18 silica gel; mobile phase, A: ACN and water (0.1% FA) and B: ACN (10% ACN to 50% in 30 min); detector, UV 254 nm to afford 4-[6-(tert-butoxycarbonyl)-2-hydroxy-6-azaspiro[3.4]octan-2-yl]-6-methoxy-[1,1-biphenyl]-3-carboxylic acid (1.2 g, 67.5%) as a white solid. LCMS (ES, m/z): 454 [M+H]$^+$

Step 3. 4-[6-azaspiro[3.4]octan-2-yl]-6-methoxy-[1,1-biphenyl]-3-carboxylic Acid To a stirred solution of 4-[6-(tert-butoxycarbonyl)-2-hydroxy-6-azaspiro[3.4]octan-2-yl]-6-methoxy-[1,1-biphenyl]-3-carboxylic acid (1.20 g, 2.65 mmol) in DCM (30 mL) was added trifluoroacetic acid (5 mL) and triethylsilane (0.58 g, 4.99 mmol) at −40° C. under nitrogen atmosphere. The resulting mixture was stirred for 3 h at −10° C. under nitrogen atmosphere. The mixture was concentrated under reduced pressure. The residue was purified by reverse flash chromatography with the following conditions: column, C18 silica gel; mobile phase, water (0.1% FA) and ACN (10% ACN to 50% in 30 min); detector, UV 254 nm to afford 4-[6-azaspiro[3.4]octan-2-yl]-6-methoxy-[1,1-biphenyl]-3-carboxylic acid (800 mg, 80.65%) as a white solid. LCMS (ES, m/z): 338 [M+H]$^+$

Step 4. 6-methoxy-4-[(2s,4s)-6-[(2R)-oxolane-2-carbonyl]-6-azaspiro[3.4]octan-2-yl]-[1,1-biphenyl]-3-carboxylic Acid (296) and 6-methoxy-4-[(2r,4r)-6-[(2R)-oxolane-2-carbonyl]-6-azaspiro[3.4]octan-2-yl]-[1,1-biphenyl]-3-carboxylic Acid (297)

A mixture of (2R)-oxolane-2-carboxylic acid (165 mg, 1.42 mmol), 4-[6-azaspiro[3.4]octan-2-yl]-6-methoxy-[1,1-biphenyl]-3-carboxylic acid (400 mg, 1.19 mmol), 1-(3-dimethylaminopropyl)-3-ethylcarbodiimide (490 mg, 2.56 mmol), 1-hydroxybenzotriazole (80 mg, 0.59 mmol) and 4-methylmorpholine (360 mg, 3.56 mmol) in DMF (15 mL) was stirred for 2 h. The reaction was diluted with ice/water (50 mL). The resulting mixture was extracted with ethyl acetate (3×50 mL). The combined organic layers were washed with brine (2×50 mL), dried over anhydrous sodium sulfate, filtered and concentrated under reduced pressure. The residue was purified by reverse flash chromatography with the following conditions: column, C18 silica gel; mobile phase A: water (0.1% FA) and B: ACN (20% ACN to 50% in 30 min); detector, UV 254 nm. The product was separated by Chiral-Prep-HPLC with the following conditions: Column, CHIRAL ART Cellulose-SB, 2×25 cm, 5 um; mobile phase, Hex (0.1% FA) and IPA (hold 50% IPA in 19 min); Detector, UV 254 nm to afford compound 296 (53.9 mg, 10.23%) and compound 297 (70.8 mg, 13.44%) as a white solid.

Compound 296

$^1$H-NMR (CD$_3$OD, 400 MHz) δ (ppm): 8.08-7.99 (m, 1H), 7.95 (s, 1H), 7.545 (d, J=7.2 Hz, 2H), 7.31 (d, J=8.4 Hz, 2H), 7.15 (d, J=8.4 Hz, 1H), 4.68-4.55 (m, 1H), 4.05-3.92 (m, 1H), 3.90-3.82 (m, 4H), 3.80-3.40 (m, 5H), 2.49-2.38 (m, 2H), 2.31-2.19 (m, 4H), 2.19-2.11 (m, 1H), 2.08-1.89 (m, 3H). LCMS (ES, m/z): 436 [M+H]$^+$

Compound 297

$^1$H-NMR (CD$_3$OD, 400 MHz) δ (ppm): 8.08-7.99 (m, 1H), 7.95 (s, 1H), 7.45 (d, J=8.0 Hz, 2H), 7.31 (d, J=7.6 Hz, 2H), 7.15 (d, J=8.8 Hz, 1H), 4.72-4.59 (m, 1H), 4.08-3.97

(m, 1H), 3.97-3.82 (m, 4H), 3.75-3.42 (m, 5H), 2.58-2.39 (m, 2H), 2.38-2.19 (m, 3H), 2.18-1.86 (m, 5H). LCMS (ES, m/z): 436 [M+H]⁺.

Method 55: Preparation of compound 298: 7-(1-hydroxycyclopropanecarbonyl)-2-[4-(quinolin-7-yl)phenyl]-7-azaspiro[3.5]nonane-2-carboxylic Acid (298)

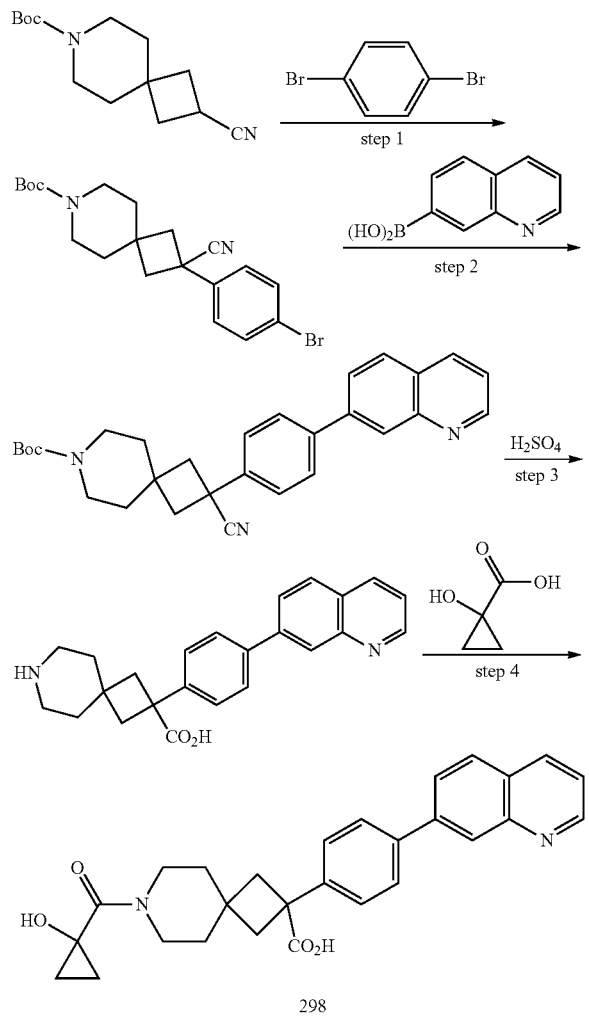

Step 1. tert-butyl 2-(4-bromophenyl)-2-cyano-7-azaspiro[3.5]nonane-7-carboxylate To a stirred solution of tert-butyl 2-cyano-7-azaspiro[3.5]nonane-7-carboxylate (1.60 g, 6.39 mmol) and dibromobenzene (3.00 g, 12.72 mmol) in methoxycyclopentane (30 mL) and tetrahydrofuran (30 mL) were added 6-Bis(diphenylphosphino)phenoxazine (388 mg, 0.70 mmol), tris(dibenzylideneacetone)dipalladium(0) (585 mg, 0.64 mmol) and lithium bis(trimethylsilyl)amide (20.00 mL, 1 mol/L). The resulting mixture was stirred for overnight at 70° C. The reaction was allowed to cool down to room temperature. The mixture was diluted with ice/water (100 mL). The resulting mixture was extracted with ethyl acetate (3×200 mL). The combined organic layers were washed with brine (2×200 mL), dried over anhydrous sodium sulfate, filtered and concentrated under reduced pressure. The residue was purified by silica gel column chromatography, eluted with petroleum ether/ethyl acetate (4:1) to afford tert-butyl 2-(4-bromophenyl)-2-cyano-7-azaspiro[3.5]nonane-7-carboxylate (1.6 g, 49.41%) as a light yellow oil. LCMS: (ES, m/z): 405, 407 [M+H]⁺.

Step 2. tert-butyl 2-cyano-2-[4-(quinolin-7-yl)phenyl]-7-azaspiro[3.5]nonane-7-carboxylate A mixture of tert-butyl 2-(4-bromophenyl)-2-cyano-7-azaspiro[3.5]nonane-7-carboxylate (1.50 g, 3.70 mmol), quinolin-7-ylboronic acid (704 mg, 4.07 mmol) and potassium phosphate (2.36 g, 11.12 mmol) and bis(di-tert-butyl(4-dimethylaminophenyl)phosphine)dichloropalladium(ii) (262.00 mg, 0.37 mmol) in dioxane (15 mL) and water (5 mL) was stirred for 2 h at 100° C. under nitrogen atmosphere. The mixture was allowed to cool down to room temperature. The resulting mixture was diluted with ice/water (50 mL). The mixture was extracted with ethyl acetate (3×50 mL). The combined organic layers were washed with brine (50 mL), dried over anhydrous sodium sulfate, filtered and concentrated under reduced pressure. The residue was purified by silica gel column chromatography, eluted with petroleum ether/ethyl acetate (1:3) to afford tert-butyl 2-cyano-2-[4-(quinolin-7-yl)phenyl]-7-azaspiro[3.5]nonane-7-carboxylate (1.6 g, 85.79%) as a yellow solid. LCMS: (ES, m/z): 454 [M+H]⁺.

Step 3. 2-[4-(quinolin-7-yl)phenyl]-7-azaspiro[3.5]nonane-2-carboxylic Acid

A mixture of tert-butyl 2-cyano-2-[4-(quinolin-7-yl)phenyl]-7-azaspiro[3.5]nonane-7-carboxylate (1.50 g, 3.31 mmol) in sulfuric acid (30% in water, 15 mL) was stirred for overnight at 100° C. The mixture was allowed to cool down to room temperature. The resulting mixture was concentrated under reduced pressure. The crude product was purified by reverse flash chromatography with the following conditions: column, C18 silica gel; mobile phase, A: water (containing 0.1% formic acid) and B: acetonitrile (5% to 30% over 20 min); detector, UV 254/220 nm to afford 2-[4-(quinolin-7-yl)phenyl]-7-azaspiro[3.5]nonane-2-carboxylic acid (1.2 g, 82.81%) as a yellow solid. LCMS: (ES, m/z): 373 [M+H]⁺.

Step 4. 7-(1-hydroxycyclopropanecarbonyl)-2-[4-(quinolin-7-yl)phenyl]-7-azaspiro[3.5]nonane-2-carboxylic Acid (298)

To a stirred mixture of 1-hydroxycyclopropane-1-carboxylic acid (134 mg, 1.31 mmol), N-(3-Dimethylaminopropyl)-N'-ethylcarbodiimide hydrochloride (418 mg, 2.18 mmol), 1H-Benzo[d][1,2,3]triazol-1-ol hydrate (222 mg, 1.64 mmol), 4-Methylmorpholine (0.6 mL, 5.46 mmol) and 2-[4-(quinolin-7-yl)phenyl]-7-azaspiro[3.5]nonane-2-carboxylic acid (400 mg, 1.07 mmol) in N,N-Dimethylformamide (5 mL) was stirred for 2 h at room temperature. The mixture was diluted with ice/water (20 mL). The resulting mixture was extracted with ethyl acetate (3×30 mL). The combined organic layers were washed with brine (50 mL), dried over anhydrous sodium sulfate, filtered and concentrated under reduced pressure. The crude product was purified by reverse flash chromatography with the following conditions: column, C18 silica gel; mobile phase, A: water (containing 0.1% formic acid) and B: acetonitrile (5% to 30% over 60 min); detector, UV 254/220 nm to afford compound 298 (126.6 mg, 23.01%) as a white solid.

Compound 298

¹H-NMR (CD₃OD, 400 MHz) δ (ppm): 8.94-8.86 (m, 1H), 8.47-8.37 (d, J=8.4 Hz, 1H), 8.27 (s, 1H), 8.06 (d, J=8.8 Hz, 1H), 8.02-7.92 (m, 1H), 7.82-7.78 (m, 2H), 7.62-7.51 (m, 3H), 3.93-3.36 (m, 4H), 2.92 (d, J=12.8 Hz, 2H), 2.52 (d, J=12.8 Hz, 2H), 1.78-1.71 (m, 2H), 1.57-1.46 (m, 2H), 1.09-0.97 (m, 2H), 0.92-0.73 (m, 2H). LCMS: (ES, m/z): 457 [M+H]⁺.

Method 56: Preparation of compound 326: 3-hydroxy-4-[6-methyl-4-[(1S)-6-[(2R)-oxolane-2-carbonyl]-6-azaspiro[2.5]octan-1-yl]-[1,1-biphenyl]-3-yl]cyclobut-3-ene-1,2-dione (326)

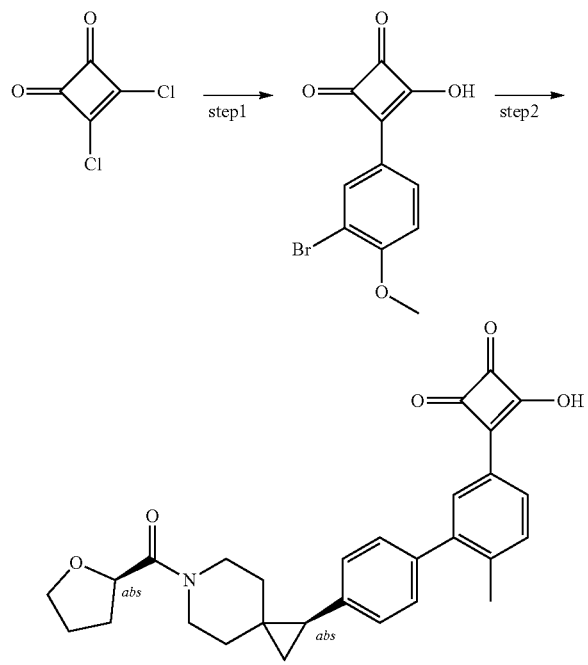

Step 1. 3-(3-bromo-4-methylphenyl)-4-hydroxycyclobut-3-ene-1,2-dione

To a stirred mixture of 3-chloro-4-hydroxycyclobut-3-ene-1,2-dione (3.00 g, 22.642 mmol) and 0-bromotoluene (3.87 g, 22.642 mmol) in CHCl3 (15.00 mL) was added aluminium chloride (3.02 g, 22.651 mmol) in portions at 0° C. The resulting mixture was stirred for 1 h at room temperature. The resulting mixture was diluted with ice/water (100 mL). The resulting mixture was extracted with DCM (3×50 mL). The combined organic layers were washed with brine (2×50 mL), dried over anhydrous Na2SO4. After filtration, the filtrate was concentrated under reduced pressure. The residue was purified by reverse flash chromatography with the following conditions: column, C18 silica gel; mobile phase, water (NH4CO3 10 m mol/L) and ACN (30% to 70% ACN in 10 min); detector, UV 254 nm. This resulted in 3-(3-bromo-4-methylphenyl)-4-hydroxycyclobut-3-ene-1,2-dione (3.1 g, 46.14%) as a yellow solid. LCMS (ES, m/z): 283,285 [M+H]⁺

Step 2. 3-hydroxy-4-[6-methyl-4-[(1S)-6-[(2R)-oxolane-2-carbonyl]-6-azaspiro[2.5]octan-1-yl]-[1,1-biphenyl]-3-yl]cyclobut-3-ene-1,2-dione (326)

To a stirred mixture of 3-(3-bromo-4-methylphenyl)-4-hydroxycyclobut-3-ene-1,2-dione (80.00 mg, 0.300 mmol) and (1S)-6-[(2R)-oxolane-2-carbonyl]-1-[4-(4,4,5,5-tetramethyl-1,3,2-dioxaborolan-2-yl)phenyl]-6-azaspiro[2.5]octane (147.00 mg, 0.357 mmol) in dioxane (2.00 mL) and H2O (0.50 mL) were added PdAMPHOS (40.00 mg, 0.056 mmol) and K3PO4 (183.00 mg, 0.862 mmol) at room temperature. The resulting mixture was stirred for 1 h at 90° C. under nitrogen atmosphere. The mixture was allowed to cool down to room temperature. The residue was purified by reverse flash chromatography with the following conditions: column, C18 silica gel; mobile phase, water (10 mmol/L NH4HCO3) and ACN (20% to 50% in 10 min); detector, UV 254 nm. This resulted in compound 326 (32.3 mg, 22.41%) as a yellow solid.

Compound 326

¹H-NMR (CD₃OD, 400 MHz) δ (ppm): 8.05 (s, 1H), 7.97 (d, J=8.0 Hz, 1H), 7.49-7.02 (m, 5H), 4.85-4.65 (m, 1H), 4.02-3.60 (m, 4H), 2.35-2.32 (m, 2H), 2.32 (s, 3H), 2.28-2.13 (m, 2H), 2.10-1.81 (m, 3H), 1.76-1.55 (m, 2H), 1.48-1.23 (m, 2H), 1.20-1.05 (m, 1H), 1.02-0.88 (m, 1H). LCMS (ES, m/z): 472 [M+H]⁺

Method 57: Preparation of compound 330: N-[4-[(1S)-6-(1-hydroxycyclopropanecarbonyl)-6-azaspiro[2.5]octan-1-yl]-6-methoxy-[1,1-biphenyl]-3-ylsulfonyl]acetamide (330)

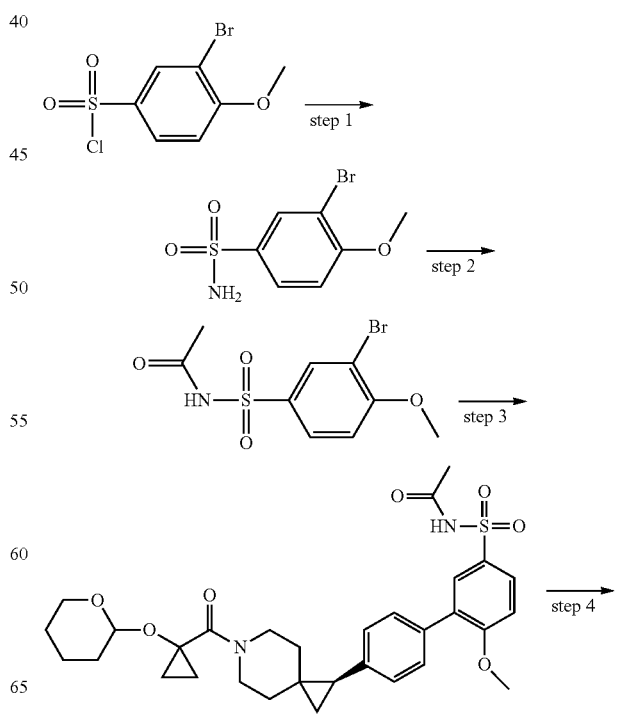

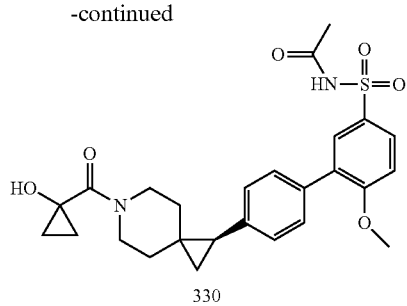

Step 1. 3-bromo-4-methoxybenzenesulfonamide

A mixture of 3-bromo-4-methoxybenzenesulfonyl chloride (3.00 g, 10.506 mmol) and $NH_3$ in MeOH (30 mL, 7 M) was stirred for 1 h at 0° C. The resulting mixture was concentrated under reduced pressure. The crude product was purified by reverse flash chromatography with the following conditions: column, C18 silica gel; mobile phase, A: water (containing 10 mM ammonium bicarbonate) and B: ACN (10% to 40% ACN over 30 min); detector, UV 254 nm to afford 3-bromo-4-methoxybenzenesulfonamide (1.5 g, 48.29%) as a yellow solid. LCMS (ES, m/z): 266, 268 [M+H]+.

Step 2. N-(3-bromo-4-methoxybenzenesulfonyl)acetamide

A solution of 3-bromo-4-methoxybenzenesulfonamide (1.80 g, 6.764 mmol), TEA (76.00 mg, 0.751 mmol) and Ac2O (690.00 mg, 6.759 mmol) in DCM (18 mL) was stirred for overnight at room temperature. The crude product was purified by reverse flash chromatography with the following conditions: column, C18 silica gel; mobile phase, A: water (containing 0.1% FA) and B: ACN (20% to 60% ACN over 60 min); detector, UV 254 nm to afford N-(3-bromo-4-methoxybenzenesulfonyl)acetamide (800 mg, 34.54%) as a white solid. LCMS (ES, m/z): 308, 310 [M+H]+.

Step 3. N-[6-methoxy-4-[(1S)-6-[1-(oxan-2-yloxy)cyclopropanecarbonyl]-6-azaspiro[2.5]octan-1-yl]-[1,1-biphenyl]-3-ylsulfonyl]acetamide A mixture of (1S)-6-[1-(oxan-2-yloxy)cyclopropanecarbonyl]-1-[4-(4,4,5,5-tetramethyl-1,3,2-dioxaborolan-2-yl)phenyl]-6-azaspiro[2.5]octane (50.00 mg, 0.104 mmol), N-(3-bromo-4-methoxybenzenesulfonyl)acetamide (35.00 mg, 0.114 mmol) bis(di-tert-butyl(4-dimethylaminophenyl)phosphine)dichloropalladium (8.00 mg, 0.011 mmol) and potassium phosphate (66.00 mg, 0.311 mmol) in dioxane (4 mL) and water (1 mL) was stirred for 1 h at 90° C. under nitrogen atmosphere. The mixture was allowed to cool down to room temperature. The resulting mixture was concentrated under reduced pressure. The crude product was purified by reverse flash chromatography with the following conditions: column, C18 silica gel; mobile phase, A: water (containing 10 mM ammonium bicarbonate) and B: ACN (20% to 50% over 30 min); detector, UV 254 nm to afford N-[6-methoxy-4-[(1S)-6-[1-(oxan-2-yloxy)cyclopropanecarbonyl]-6-azaspiro[2.5]octan-1-yl]-[1,1-biphenyl]-3-ylsulfonyl]acetamide (30 mg, 44.62%) as a white solid. LCMS (ES, m/z): 583 [M+H]+.

Step 4. N-[4-[(1S)-6-(1-hydroxycyclopropanecarbonyl)-6-azaspiro[2.5]octan-1-yl]-6-methoxy-[1,1-biphenyl]-3-ylsulfonyl]acetamide (330)

To a stirred solution of N-[6-methoxy-4-[(1S)-6-[1-(oxan-2-yloxy)cyclopropanecarbonyl]-6-azaspiro[2.5]octan-1-yl]-[1,1-biphenyl]-3-ylsulfonyl]acetamide (30.00 mg, 0.051 mmol) and TFA (0.5 mL) in DCM (3 mL) was stirred for 30 min at room temperature. The resulting mixture was concentrated under reduced pressure. The crude product was purified by reverse flash chromatography with the following conditions: column, C18 silica gel; mobile phase, A: water (containing 10 mM ammonium bicarbonate) and B: ACN (10% to 30% ACN over 30 min); detector, UV 254 nm. This resulted compound 330 (10.7 mg, 39.60%) as a white solid.

Compound 330

$^1$H-NMR (CD$_3$OD, 400 MHz) δ (ppm): 8.01-7.85 (m, 2H), 7.47 (d, J=8.0 Hz, 2H), 7.31 (d, J=8.0 Hz, 2H), 7.22 (d, J=8.8 Hz, 1H), 4.27-3.40 (m, 7H), 2.20-2.07 (m, 1H), 1.96 (s, 3H), 1.79-1.70 (m, 2H), 1.38-1.31 (m, 2H), 1.17-1.09 (m, 1H), 1.07-1.02 (m, 2H), 0.99-0.93 (m, 1H), 0.87-0.81 (m, 2H). LCMS (ES, m/z): 499 [M+H]+.

Method 58: Preparation of compound 337: 4-[(1S)-6-(1-hydroxycyclopropanecarbonyl)-6-azaspiro[2.5]octan-1-yl]-6-methyl-[1,1-biphenyl]-3-yl(methyl)phosphinic Acid (337)

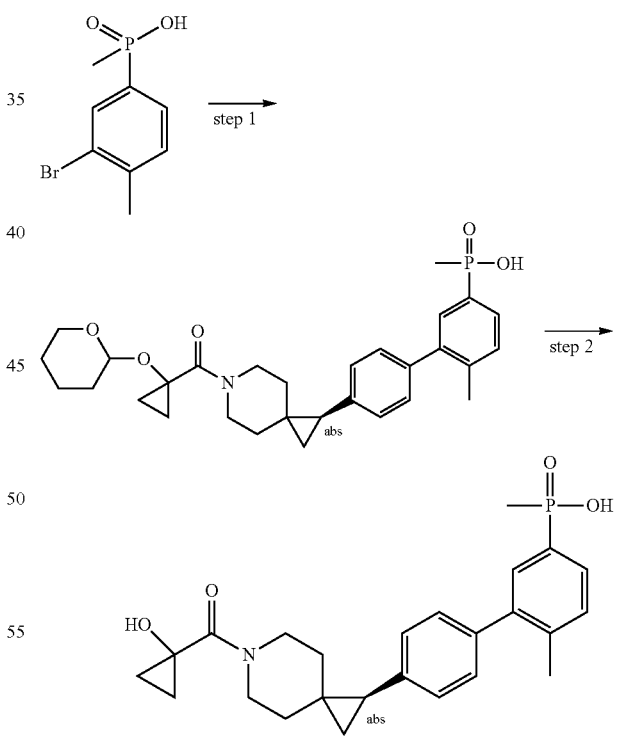

Step 1. methyl(6-methyl-4-[(1S)-6-[1-(oxan-2-yloxy)cyclopropanecarbonyl]-6-azaspiro[2.5]octan-1-yl]-[1,1-biphenyl]-3-yl)phosphinic Acid To a stirred mixture of (1S)-6-[1-(oxan-2-yloxy)cyclopropanecarbonyl]-1-[4-(4,4,5,5-tetramethyl-1,3,2-di oxaborolan-2-yl)phenyl]-6-azaspiro[2.5]octane (50.00 mg, 0.104 mmol), 3-bromo-4-methylphenyl(methyl)phosphinic acid (29.00 mg, 0.116 mmol) and K3PO4 (66.00 mg, 0.311 mmol) in dioxane (4 mL) and H2O (1 mL) was added PdAMPHOS (8.00 mg, 0.011 mmol) at room temperature under nitrogen atmosphere. The resulting mixture was stirred for 1 h at 90° C. under nitrogen atmosphere. The mixture was allowed to cool down to room temperature. The resulting mixture was concentrated under reduced pressure. The crude product was purified by reverse flash chromatography with the following conditions: column, C18 silica gel; mobile phase: A, water (containing 10 mM ammonium bicarbonate) and B, ACN (10% to 35% ACN over 30 min); detector, UV 254 nm. This resulted in methyl(6-methyl-4-[(1S)-6-[1-(oxan-2-yloxy)cyclopropanecarbonyl]-6-azaspiro[2.5]octan-1-yl]-[1,1-biphenyl]-3-yl)phosphinic acid (30 mg, 49.65%) as a light yellow oil. LCMS (ES, m/z): 534[M+H]+.

Step 2. 4-[(1S)-6-(1-hydroxycyclopropanecarbonyl)-6-azaspiro[2.5]octan-1-yl]-6-methyl-[1,1-biphenyl]-3-yl(methyl)phosphinic Acid (337)

A mixture of methyl(6-methyl-4-[(1S)-6-[1-(oxan-2-yloxy)cyclopropanecarbonyl]-6-azaspiro[2.5]octan-1-yl]-[1,1-biphenyl]-3-yl)phosphinic acid (30.00 mg, 0.057 mmol) and TFA (0.5 mL) in DCM (3 mL) was stirred for 1 h at room temperature. The crude product was purified by reverse flash chromatography with the following conditions: column, C18 silica gel; mobile phase: water (containing 10 mM ammonium bicarbonate) and ACN (10% to 30% ACN over 30 min); detector, UV 254 nm. This resulted in compound 337 (15 mg, 56.59%) as a white solid.

Compound 337

1H-NMR (CD3OD, 400 MHz) δ (ppm): 67.72-7.59 (m, 2H), 7.33-7.29 (m, 3H), 7.28-7.21 (m, 2H), 4.26-3.41 (m, 4H), 2.28 (s, 3H), 2.20-2.00 (m, 1H), 1.73-1.64 (m, 2H), 1.46-1.40 (m, 3H), 1.35-1.28 (m, 2H), 1.17-1.08 (m, 1H), 1.08-1.01 (m, 2H), 0.99-0.92 (m, 1H), 0.87-0.81 (m, 2H). LCMS (ES, m/z): 440[M+H]+.

Method 59: Preparation of Compounds 345, 346, 347, and 348: 6-methoxy-4'-[(1R,4R)-6-[(2R)-oxolane-2-carbonyl]-6-azaspiro[3.4]octan-1-yl]-[1,1'-biphenyl]-3-carboxylic Acid (345), 6-methoxy-4'-[(1S,4R)-6-[(2R)-oxolane-2-carbonyl]-6-azaspiro[3.4]octan-1-yl]-[1,1'-biphenyl]-3-carboxylic Acid (346), 6-methoxy-4'-[(1R,4S)-6-[(2R)-oxolane-2-carbonyl]-6-azaspiro[3.4]octan-1-yl]-[1,1'-biphenyl]-3-carboxylic Acid (347), and 6-methoxy-4'-[(1S,4S)-6-[(2R)-oxolane-2-carbonyl]-6-azaspiro[3.4]octan-1-yl]-[1,1'-biphenyl]-3-carboxylic Acid (348)

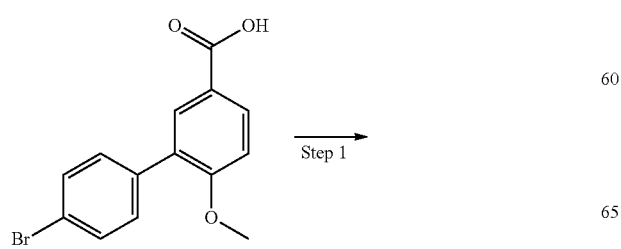

Step 1

-continued

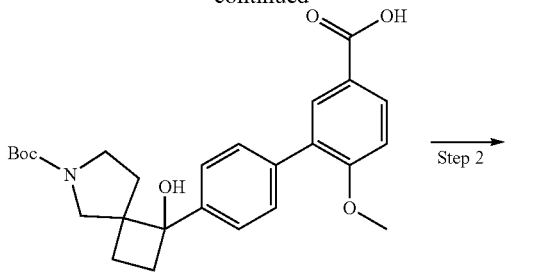

Step 2

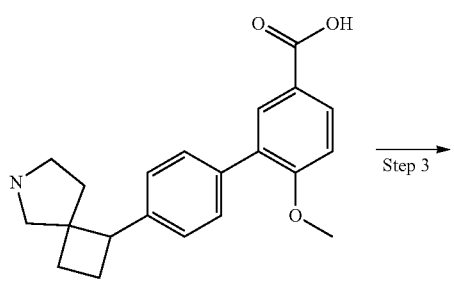

Step 3

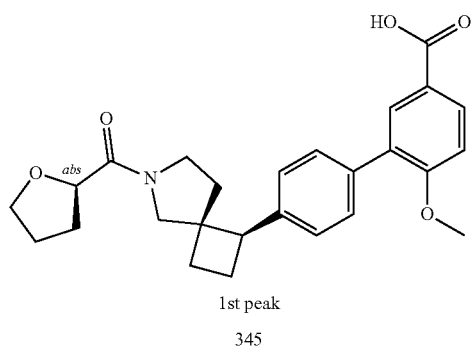

1st peak
345

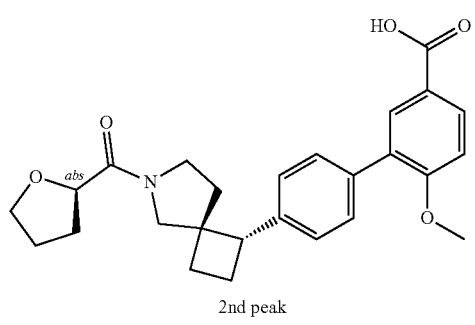

2nd peak
346

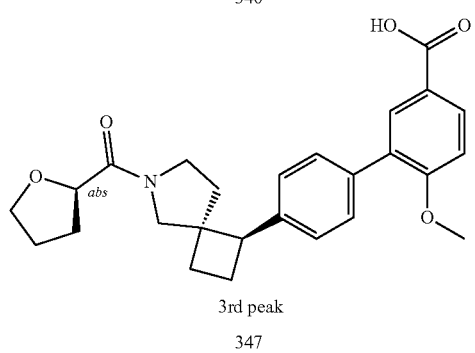

3rd peak
347

-continued

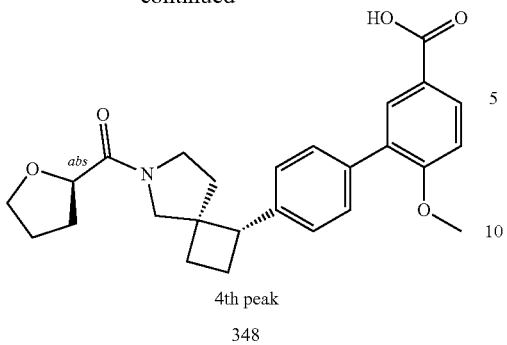

4th peak
348

Step 1. 4'-[6-(tert-butoxycarbonyl)-1-hydroxy-6-azaspiro[3.4]octan-1-yl]-6-methoxy-[1,1'-biphenyl]-3-carboxylic Acid A solution of 4-bromo-6-methoxy-[1,1-biphenyl]-3-carboxylic acid (800.00 mg, 2.605 mmol) in THF (10 mL) was added n-butyllithium (2.5 M in THF, 1.6 mL) dropwise at −78° C. under nitrogen atmosphere. The reaction mixture was stirred at −78° C. for 1 h. Then a solution of tert-butyl 1-oxo-6-azaspiro[3.4]octane-6-carboxylate (590.00 mg, 2.619 mmol) in THF (5 mL) was added dropwise. The resulting mixture was allowed to warm to room temperature and stirred for overnight. The reaction was quenched with saturated NH$_4$Cl (50 mL). The resulting mixture was extracted with EtOAc (3×30 mL). The combined organic layers were washed with brine (2×30 mL), dried over anhydrous Na$_2$SO$_4$, filtered and concentrated under reduced pressure. The crude product was purified by reverse phase chromatography with the following conditions: Column: C18; Mobile phase, A: water (containing 0.1% FA) and B: ACN (5% to 40% ACN over 30 min); Detector, UV 254 nm to afford 4-[6-(tert-butoxycarbonyl)-1-hydroxy-6-azaspiro[3.4]octan-1-yl]-6-methoxy-[1,1-biphenyl]-3-carboxylic acid (150 mg, 13%) as a yellow oil. LCMS (ES, m/z): 454 [M+H]$^+$

Step 2. 4'-[6-azaspiro[3.4]octan-1-yl]-6-methoxy-[1,1'-biphenyl]-3-carboxylic Acid A solution of 4-[6-(tert-butoxycarbonyl)-1-hydroxy-6-azaspiro[3.4]octan-1-yl]-6-methoxy-[1,1-biphenyl]-3-carboxylic acid (125.00 mg, 0.276 mmol), TFA (0.5 mL) and Et$_3$SiH (80.00 mg, 0.688 mmol) in DCM (5 mL) was stirred for 4 h at −10° C. The mixture was basified to pH 8 with saturated NaHCO$_3$. The resulting mixture was extracted with CH$_2$Cl$_2$ (3×20 mL). The combined organic layers were washed with brine (2×20 mL), dried over anhydrous Na$_2$SO$_4$, filtered and concentrated under reduced pressure. The crude product was purified by reverse phase chromatography with the following conditions: Column: C18; Mobile phase, A: water (containing 10 mmol/L NH$_4$HCO$_3$) and B: ACN (5% to 40% ACN over 60 min); Detector, UV 254 nm to afford 4-[6-azaspiro[3.4]octan-1-yl]-6-methoxy-[1,1-biphenyl]-3-carboxylic acid (50 mg, 48.39%) as a yellow oil. LCMS (ES, m/z): 338 [M+H]$^+$

Step 3. 6-methoxy-4'-[(1R,4R)-6-[(2R)-oxolane-2-carbonyl]-6-azaspiro[3.4]octan-1-yl]-[1,1'-biphenyl]-3-carboxylic Acid (345), 6-methoxy-4'-[(1S,4R)-6-[(2R)-oxolane-2-carbonyl]-6-azaspiro[3.4]octan-1-yl]-[1,1'-biphenyl]-3-carboxylic Acid (346), 6-methoxy-4'-[(1R,4S)-6-[(2R)-oxolane-2-carbonyl]-6-azaspiro[3.4]octan-1-yl]-[1,1'-biphenyl]-3-carboxylic Acid (347), and 6-methoxy-4'-[(1S,4S)-6-[(2R)-oxolane-2-carbonyl]-6-azaspiro[3.4]octan-1-yl]-[1,1'-biphenyl]-3-carboxylic Acid (348)

A mixture of (2R)-oxolane-2-carboxylic acid (20.00 mg, 0.172 mmol), 4-[6-azaspiro[3.4]octan-1-yl]-6-methoxy-[1,1-biphenyl]-3-carboxylic acid (50.00 mg, 0.148 mmol), EDCI (10.00 mg, 0.052 mmol) and HOBT (40.00 mg, 0.296 mmol) and NMM (45.00 mg, 0.445 mmol) in DMF (5 mL) was stirred for 2 h at room temperature. The reaction was quenched with water (30 mL). The resulting mixture was extracted with EtOAc (3×30 mL). The combined organic layers were washed with brine (2×30 mL), dried over anhydrous Na$_2$SO$_4$, filtered and concentrated under reduced pressure. The residue was purified by reverse flash chromatography with the following conditions: column, C18 silica gel; mobile phase, A: water (containing 0.1% FA) and B: ACN (30% to 50% ACN in 10 min); detector, UV 254 nm. Then this product was separated by Chiral-Prep-HPLC with the following conditions: Column, CHIRAL ART Cellulose-SB, 2×25 cm, 5 um; mobile phase, Hex (0.3% FA) and EtOH (hold 15% EtOH in 25 min); Detector, UV 254 nm to afford two eluting isomers. These two isomers were separated by Chiral-Prep-HPLC with the following conditions: Column, CHIRALPAK AD-H SFC, 5×25 cm, 5 um; mobile phase, Hex (0.3% FA) and EtOH (hold 30% EtOH in 19 min); Detector, UV 254 nm to afford, in order of elution, compound 345 (1.0 mg, 1.53%) as a white solid, compound 346 (1.0 mg, 1.53%) as a white solid, compound 347 (5.3 mg, 8.13%) as a white solid and compound 348 (4.4 mg, 6.75%) as a white solid.

Compound 345

$^1$H-NMR (CD$_3$OD, 400 MHz) δ (ppm): 8.03-7.99 (m, 1H), 7.96-7.92 (m, 1H), 7.49 (d, J=8.0 Hz, 2H), 7.30 (d, J=8.4 Hz, 2H), 7.15 (d, J=8.4 Hz, 1H), 4.18-4.12 (m, 1H), 3.90 (s, 3H), 3.85-3.77 (m, 1H), 3.73-3.68 (m, 1H), 3.62-3.55 (m, 1H), 3.52-3.43 (m, 2H), 3.27-3.12 (m, 2H), 2.48-2.36 (m, 1H), 2.32-2.21 (m, 2H), 2.20-1.99 (m, 3H), 1.96-1.82 (m, 1H), 1.79-1.65 (m, 2H), 1.36-1.21 (m, 1H). LCMS (ES, m/z): 436 [M+H]$^+$.

Compound 346

$^1$H NMR (400 MHz, Methanol-d$_4$) δ 8.06-7.91 (m, 2H), 7.52-7.44 (m, 2H), 7.36-7.26 (m, 2H), 7.14 (d, J=7.6 Hz, 1H), 4.48-3.97 (m, 1H), 3.91-3.86 (m, 3H), 3.85-3.65 (m, 2H), 3.63-3.36 (m, 4H), 3.22-3.14 (m, 1H), 2.50-2.30 (m, 1H), 2.29-2.08 (m, 3H), 2.08-1.91 (m, 2H), 1.88-1.71 (m, 2H), 1.70-1.59 (m, 1H), 1.41-1.34 (m, 1H). LCMS (ES, m/z): 436 [M+H]$^+$.

Compound 347

$^1$H NMR (400 MHz, Methanol-d$_4$) δ 8.06-7.99 (m, 1H), 7.96 (s, 1H), 7.49 (d, J=7.6 Hz, 2H), 7.29 (d, J=8.0 Hz, 2H), 7.15 (d, J=8.4 Hz, 1H), 4.67-4.43 (m, 1H), 4.04-3.91 (m, 1H), 3.91-3.88 (m, 3H), 3.87-3.72 (m, 1H), 3.70-3.61 (m, 2H), 3.52-3.50 (m, 1H), 3.39-3.35 (m, 1H), 3.16-3.05 (m, 1H), 2.56-2.44 (m, 1H), 2.34-2.08 (m, 3H), 2.08-1.88 (m, 4H), 1.87-1.57 (m, 2H) LCMS (ES, m/z): 436 [M+H]$^+$.

Compound 348

$^1$H NMR (400 MHz, Methanol-d$_4$) δ 8.02 (d, J=8.4 Hz, 1H), 7.96 (s, 1H), 7.49 (d, J=8.0 Hz, 2H), 7.29 (d, J=8.0 Hz, 2H), 7.17-7.12 (m, 1H), 4.70-4.44 (m, 1H), 4.05-3.94 (m, 1H), 3.91 (s, 3H), 3.88-3.78 (m, 1H), 3.72-3.56 (m, 2H), 3.55-3.41 (m, 1H), 3.28-3.19 (m, 1H), 3.16-2.93 (m, 1H), 2.57-2.44 (m, 1H), 2.32-2.07 (m, 3H), 2.06-1.81 (m, 5H), 1.80-1.61 (m, 1H). LCMS (ES, m/z): 436 [M+H]$^+$.

Method 60: Preparation of compound 384: 4-[4-[(1S)-6-(1-hydroxycyclopropanecarbonyl)-6-azaspiro[2.5]octan-1-yl]phenyl]quinoline-2-carboxylic Acid (384)

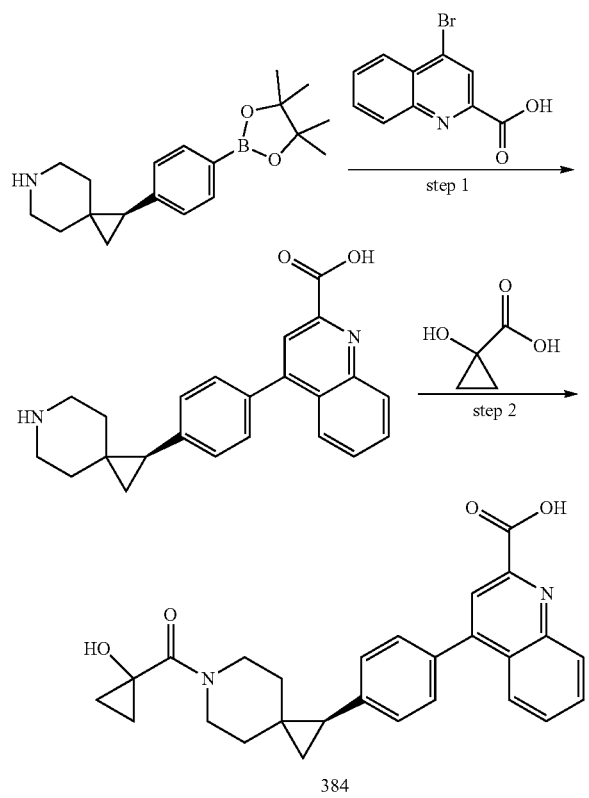

384

Step 1. 4-[4-[(1S)-6-azaspiro[2.5]octan-1-yl]phenyl]quinoline-2-carboxylic Acid

A mixture of (1S)-1-[4-(4,4,5,5-tetramethyl-1,3,2-dioxaborolan-2-yl)phenyl]-6-azaspiro[2.5]octane (200 mg, 0.638 mmol), 4-bromoquinoline-2-carboxylic acid (193.00 mg, 0.766 mmol), potassium phosphate (406.00 mg, 1.913 mmol) and bis(di-tert-butyl(4-dimethylaminophenyl)phosphine)dichloropalladium (90.00 mg, 0.127 mmol) in dioxane (5 mL) and water (1.5 mL) was stirred for 1 h at 100° C. under nitrogen atmosphere. The mixture was allowed to cool down to room temperature. The resulting mixture was concentrated under reduced pressure. The residue was purified by reverse flash chromatography with the following conditions: column, C18 silica gel; mobile phase, A: water (10 mmol/L NH$_4$HCO$_3$) and B: ACN (20% to 50% ACN in 10 min); detector, UV 254 nm to afford 4-[4-[(1S)-6-azaspiro[2.5]octan-1-yl]phenyl]quinoline-2-carboxylic acid (100 mg, 39.33%) as a white solid. LCMS (ES, m/z): 359 [M+H]$^+$ Step 2. 4-[4-[(1S)-6-(1-hydroxycyclopropanecarbonyl)-6-azaspiro[2.5]octan-1-yl]phenyl]quinoline-2-carboxylic Acid (384)

A mixture of 1-hydroxycyclopropane-1-carboxylic acid (15.00 mg, 0.147 mmol), 4-[4-[(1S)-6-azaspiro[2.5]octan-1-yl]phenyl]quinoline-2-carboxylic acid (50.00 mg, 0.139 mmol), 1H-benzo[d][1,2,3]triazol-1-ol hydrate (35.00 mg, 0.259 mmol), N-(3-dimethylaminopropyl)-N'-ethylcarbodiimide hydrochloride (65.00 mg, 0.339 mmol) and 4-methylmorpholine (40.00 mg, 0.395 mmol) in N,N-dimethylformamide (5 mL) was stirred for 3 h at room temperature. The reaction was quenched by the addition of water/ice (30 mL). The resulting mixture was extracted with ethyl acetate (3×30 mL). The combined organic layers were washed with brine (2×30 mL), dried over anhydrous sodium anhydrous sulfate, filtered and concentrated under reduced pressure. The residue was purified by reverse flash chromatography with the following conditions: column, C18 silica gel; mobile phase, A: water (0.1% FA) and B: ACN (20% to 50% ACN in 30 min); detector, UV 254 nm to afford compound 384 (15.8 mg, 25.34%) as a white solid. LCMS (ES, m/z): 443 [M+H]$^+$.

Compound 384

$^1$H-NMR (CD$_3$OD, 400 MHz) δ (ppm): 9.18-8.04 (m, 2H), 8.00 (d, J=8.0 Hz, 1H), 7.84 (t, J=7.6 Hz, 1H), 7.64 (t, J=8.0 Hz, 1H), 7.59-7.33 (m, 4H), 4.24-3.41 (m, 4H), 2.29-2.18 (m, 1H), 1.82-1.59 (m, 2H), 1.48-1.28 (m, 2H), 1.28-1.19 (m, 1H), 1.12-0.98 (m, 3H), 0.95-0.83 (m, 2H).

Example 3—FASN Biochemical Assay Protocol

The assay was performed in a final volume of 6 μL in assay buffer containing 50 mM HEPES (pH 7.5, (0.5M Hepes, pH 7.5 solution; Teknova H1575)), 50 mM NaCl, 50 mM KCl, 0.03% BGG (0.22 μM filtered, Sigma, G7516-25G), and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 25 μM to 1.3 nM, top to lowest dose, respectively. Concentration and incubation times were optimized for the maximal signal-to-background while maintaining initial velocity conditions at a fixed Substrate/Cofactors concentration. Final concentration of Enzyme (FASN) was 20 nM and Substrate/Cofactors are 40 μM NADPH, 20 uM Acetyl CoA, 20 uM Malonyl CoA. 2 μL of 2× enzyme was added to assay plates (pre-stamped with compound), preincubated for 30 minutes and then treated with 2 μL of 2× Substrate. Plates were incubated for 30 minutes at room temperature and the reaction stopped with the addition of 2 μL of detection reagent (30 μM final concentration of CPM) in 50% Ethanol. Plates were incubated for 30 minutes before fluorescence was read on the Envision (Perkin Elmer), excitation at 355 nm and emission at 535 nm. For all assay formats data were reported as percent inhibition compared with control wells based on the following equation: % inh=100*((FLU−AveLow)/(AveHigh−AveLow)) where FLU=measured Fluorescence, AveLow=average Fluorescence of no enzyme control (n=32), and AveHigh=average Fluorescence of DMSO control (n=32). IC50 values were determined by curve fitting of the standard 4 parameter logistic fitting algorithm included in the Activity Base software package: IDBS XE Designer Model 205. Data is fitted using the Levenburg Marquardt algorithm. $IC_{50}$ values are shown in FIGS. 2 and 3. As set forth in FIGS. 2 and 3, an $IC_{50}$ value of greater than or equal to 0.001 μM and less than or equal to 0.1 M is marked "A"; a value greater than 0.1 M and less than or equal to 1.0 M is marked "B"; a value greater than 1.0 M and less than or equal to 10 M is marked "C"; a value greater than 10 M and less than 25 M is marked "D"; and a value greater than or equal to 25 M is marked "E." Compounds that were not tested in a particular assay are marked "NT."

We claim:

1. A method for preparing a compound of formula (VII-A):

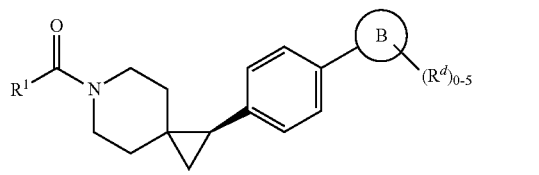

(VII-A)

or a pharmaceutically acceptable salt thereof, wherein:
Ring B is phenyl, fused bicyclic 8-10 membered aryl, or fused bicyclic 8-10 membered heteroaryl containing 1-2 heteroatoms independently selected from the group consisting of O, N, and S;
$R^1$ is 3-membered cycloalkyl optionally substituted with —OH, or 5-membered heterocyclyl containing 1-3 heteroatoms independently selected from the group consisting of O, N, and S;
each $R^d$ is independently halogen, —$CO_2H$, —$OR^3$, $SO_2NHCOR^3$, $C_{1-3}$ aliphatic, or 5-membered heteroaryl containing 1-4 heteroatoms independently selected from the group consisting of O, N, and S; and
each $R^3$ is independently hydrogen or $C_{1-3}$ alkyl;
comprising:
treating a compound of formula (A):

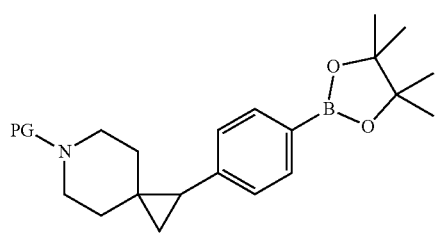

(A)

with a compound of formula (B):

Ar—X  (B)

to afford a compound of formula (C):

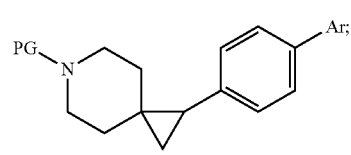

(C)

wherein:
PG is hydrogen or Boc;
X is halogen; and
Ar is a substituted phenyl, fused bicyclic 8-10 membered aryl, or fused bicyclic 8-10 membered heteroaryl containing 1-2 heteroatoms independently selected from the group consisting of O, N, and S; and
converting the compound of formula (C) to the compound of formula (VII-A), or a pharmaceutically acceptable salt thereof.

2. The method of claim 1, wherein said treating the compound of formula (A) with the compound of formula (B) is performed in the presence of a palladium catalyst and a base.

3. The method of claim 1, wherein the compound of formula (VII-A) is

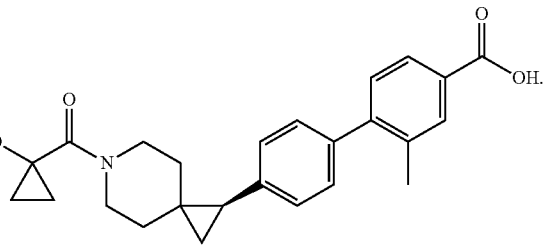

4. The method of claim 3, wherein the compound of formula (C) is

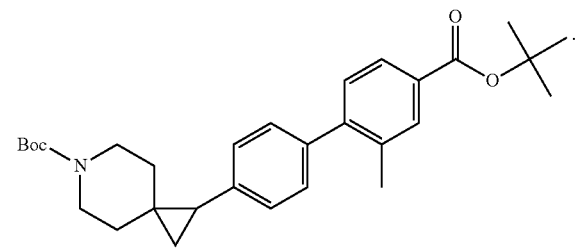 [SMILES: Cc1cc(C(=O)OC(C)(C)C)ccc1-c1ccc(C2CC23CCN(C(=O)OC(C)(C)C)CC3)cc1]

5. The method of claim 4, wherein the compound of formula (A) is

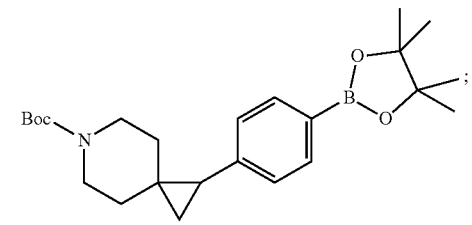 [SMILES: CC(C)(C)OC(=O)N1CCC2(CC1)CC2c1ccc(B2OC(C)(C)C(C)(C)O2)cc1]

and
the compound of formula (B) is

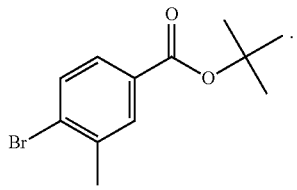

6. The method of claim 4, wherein said converting the compound of formula (C) to the compound of formula (VII-A) comprises:

treating the compound of formula (C) with trifluoroacetic acid to afford a compound of formula (D)

(D)

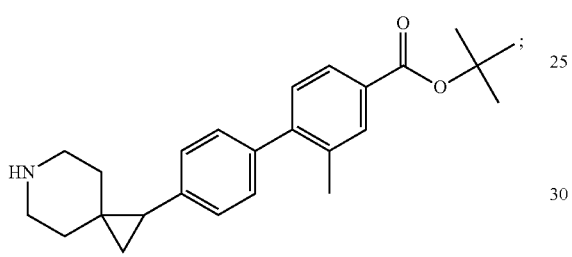

coupling the compound of formula (D) with 1-hydroxy-cyclopropane-1-carboxylic acid to afford a compound of formula (E)

(E)

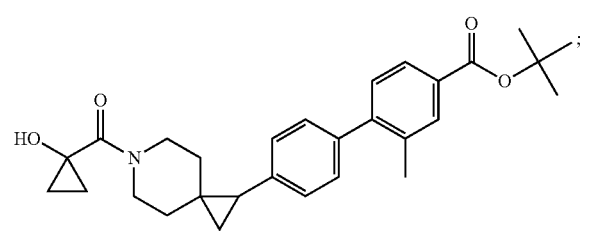

treating the compound of formula (E) with trifluoroacetic acid to afford a compound of formula (F)

(F)

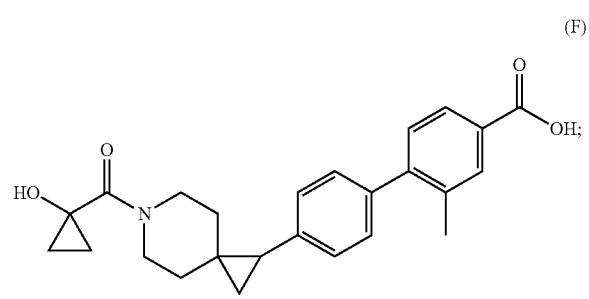 [SMILES: Cc1cc(C(=O)O)ccc1-c1ccc(C2CC23CCN(C(=O)C2(O)CC2)CC3)cc1]

and
separating enantiomers of the compound of formula (F) by chiral HPLC to afford the compound of formula (VII-A).

7. The method of claim 1, wherein the compound of formula (VII-A) is

49

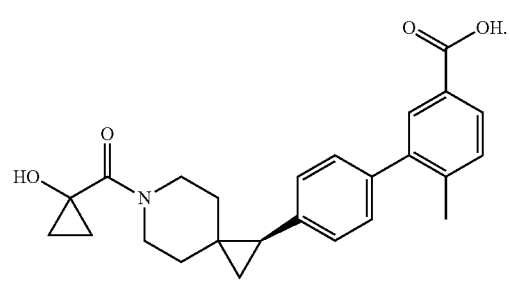

8. The method of claim 7, wherein the compound of formula (C) is

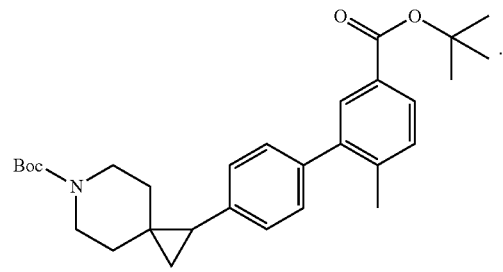 [SMILES: Cc1ccc(C(=O)OC(C)(C)C)cc1-c1ccc(C2CC23CCN(C(=O)OC(C)(C)C)CC3)cc1]

9. The method of claim 8, wherein the compound of formula (A) is

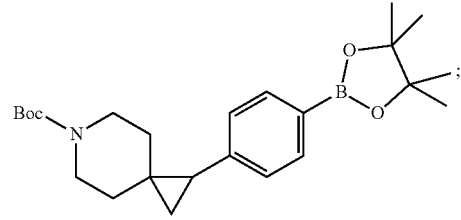 [SMILES: CC(C)(C)OC(=O)N1CCC2(CC1)CC2c1ccc(B2OC(C)(C)C(C)(C)O2)cc1]

and
the compound of formula (B) is

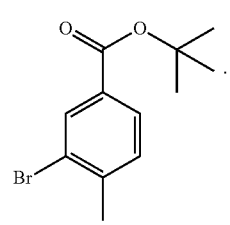

10. The method of claim 8, wherein said converting the compound of formula (C) to the compound of formula (VII-A) comprises:

treating the compound of formula (C) with trifluoroacetic acid to afford a compound of formula (D)

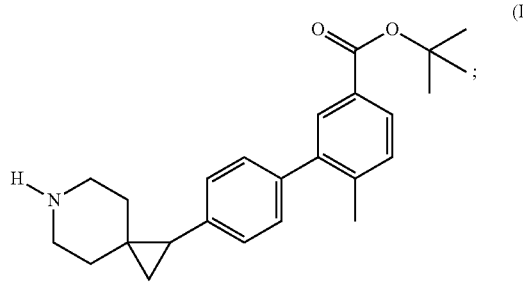
(D)

coupling the compound of formula (D) with 1-hydroxy-cyclopropane-1-carboxylic acid to afford a compound of formula (E)

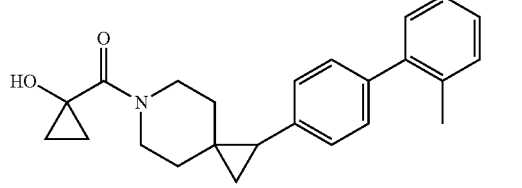
(E)

treating the compound of formula (E) with trifluoroacetic acid to afford a compound of formula (F)

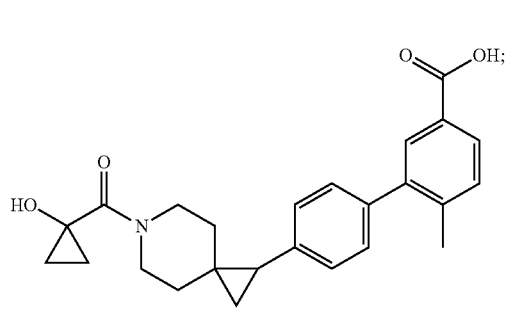
(F)

and separating enantiomers of the compound of formula (F) by chiral HPLC to afford the compound of formula (VII-A).

11. The method of claim 1, wherein the compound of formula (VII-A) is

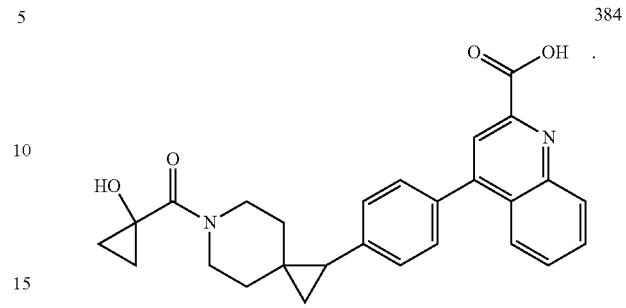

12. The method of claim 11, wherein the compound of formula (C) is

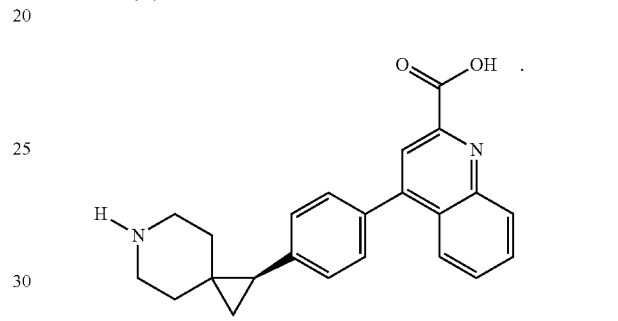

13. The method of claim 12, wherein the compound of formula (A) is

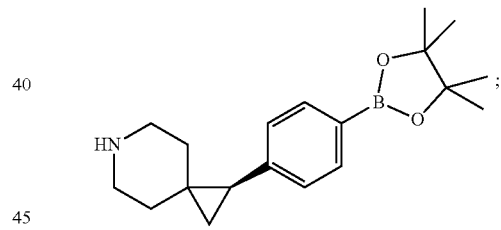

and
the compound of formula (B) is

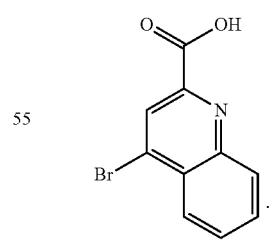

14. The method of claim 12, wherein said converting the compound of formula (C) to the compound of formula (VII-A) comprises:

coupling the compound of formula (C) with 1-hydroxy-cyclopropane-1-carboxylic acid to afford the compound of formula (VII-A).

15. The method of claim 1, wherein the compound of formula (VII-A) is

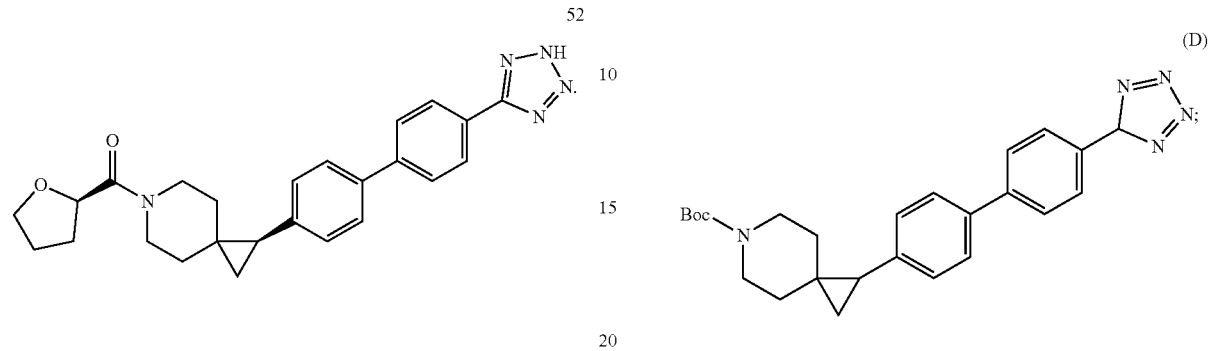

16. The method of claim 15, wherein the compound of formula (C) is

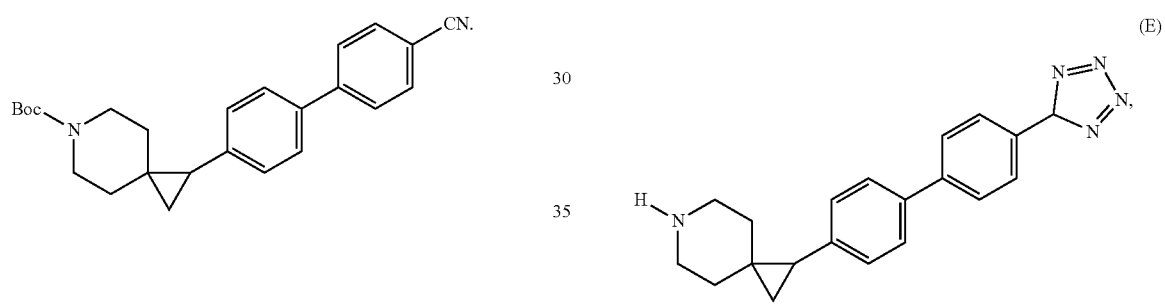

17. The method of claim 16, wherein the compound of formula (A) is

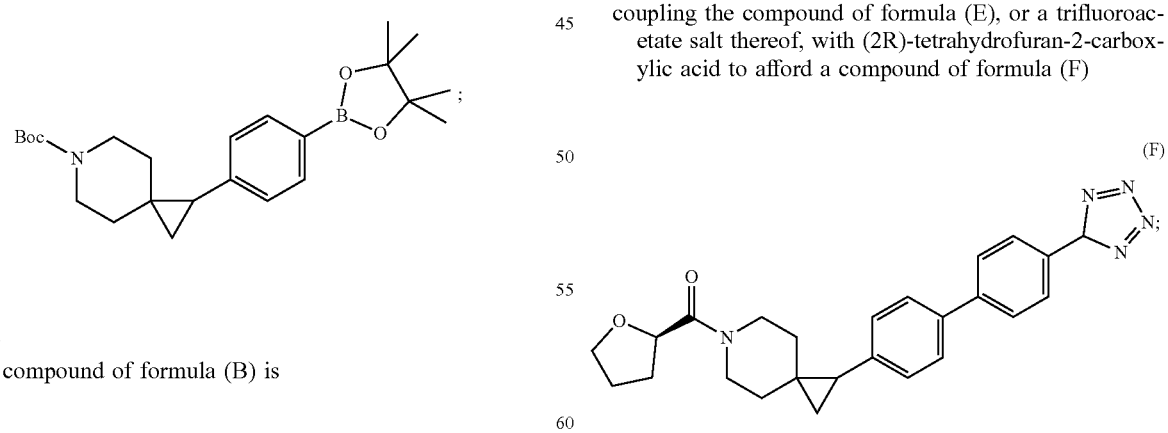

and
the compound of formula (B) is

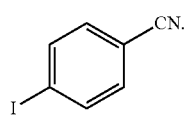

18. The method of claim 16, wherein said converting the compound of formula (C) to the compound of formula (VII-A) comprises:

treating the compound of formula (C) with sodium azide and zinc chloride to afford a compound of formula (D)

(D)

treating the compound of formula (D) with trifluoroacetic acid to afford a compound of formula (E)

(E)

or a trifluoroacetate salt thereof;

coupling the compound of formula (E), or a trifluoroacetate salt thereof, with (2R)-tetrahydrofuran-2-carboxylic acid to afford a compound of formula (F)

(F)

and separating diastereomers of the compound of formula (F) by HPLC to afford the compound of formula (VII-A).

19. The method of claim 1, wherein the compound of formula (VII-A) is

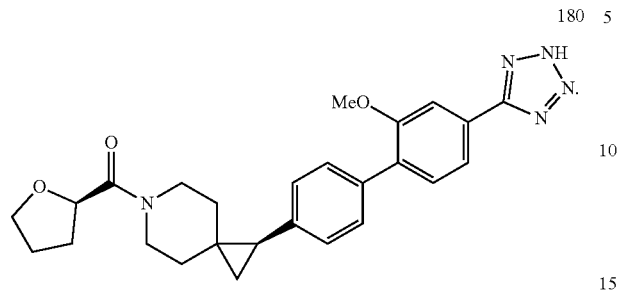

20. The method of claim 19, wherein the compound of formula (C) is

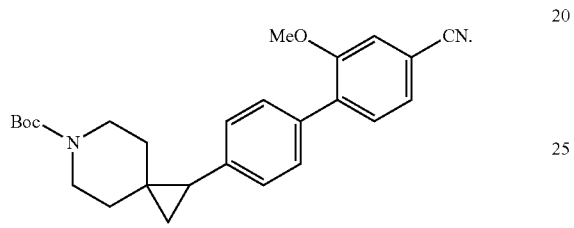

21. The method of claim 20, wherein the compound of formula (A) is

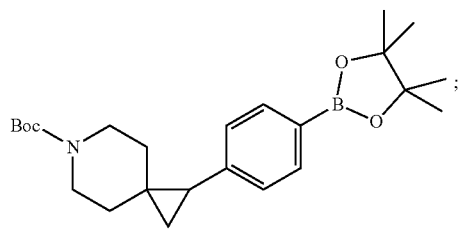 [SMILES: CC(C)(C)OC(=O)N1CCC2(CC1)CC2c1ccc(B2OC(C)(C)C(C)(C)O2)cc1]

and
the compound of formula (B) is

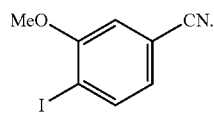

22. The method of claim 20, wherein said converting the compound of formula (C) to the compound of formula (VII-A) comprises:

treating the compound of formula (C) with sodium azide and zinc chloride to afford a compound of formula (D)

(D)

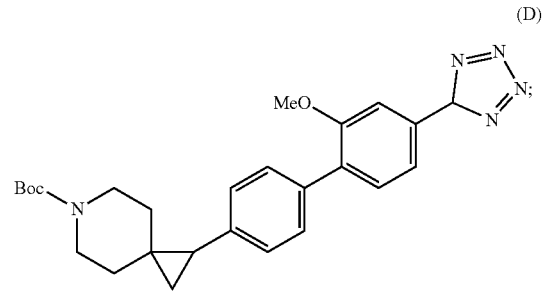 [SMILES: COc1cc(C2N=NN=N2)ccc1-c1ccc(C2CC23CCN(C(=O)OC(C)(C)C)CC3)cc1]

treating the compound of formula (D) with trifluoroacetic acid to afford a compound of formula (E)

(E)

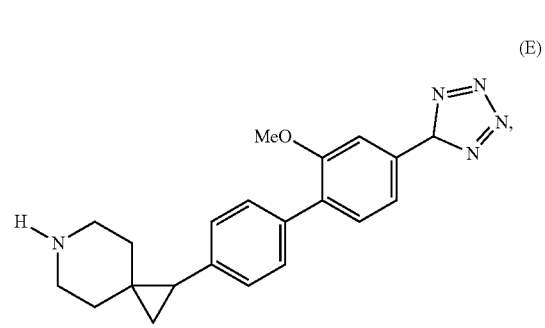 [SMILES: COc1cc(C2N=NN=N2)ccc1-c1ccc(C2CC23CCNCC3)cc1]

or a trifluoroacetate salt thereof;
coupling the compound of formula (E), or a trifluoroacetate salt thereof, with (2R)-tetrahydrofuran-2-carboxylic acid to afford a compound of formula (F)

(F)

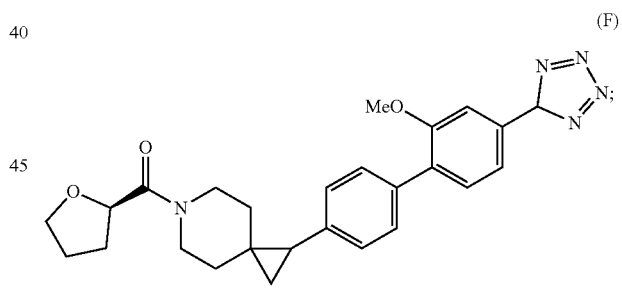

and
separating diastereomers of the compound of formula (F) by HPLC to afford the compound of formula (VII-A).

* * * * *